US012516319B2

(12) United States Patent
Prakash et al.

(10) Patent No.: US 12,516,319 B2
(45) Date of Patent: Jan. 6, 2026

(54) COMPOSITIONS AND METHODS FOR MODULATING TTR EXPRESSION

(71) Applicant: IONIS PHARMACEUTICALS, INC., Carlsbad, CA (US)

(72) Inventors: Thazha P. Prakash, Carlsbad, CA (US); Punit P. Seth, Carlsbad, CA (US); Eric E. Swayze, Encinitas, CA (US)

(73) Assignee: IONIS PHARMACEUTICALS, INC., Carlsbad, CA (US)

( * ) Notice: Subject to any disclaimer, the term of this patent is extended or adjusted under 35 U.S.C. 154(b) by 289 days.

(21) Appl. No.: 17/970,887

(22) Filed: Oct. 21, 2022

(65) Prior Publication Data

US 2023/0151365 A1 May 18, 2023

Related U.S. Application Data

(63) Continuation of application No. 16/790,557, filed on Feb. 13, 2020, now abandoned, which is a continuation of application No. 15/687,306, filed on Aug. 25, 2017, now Pat. No. 10,683,499, which is a continuation of application No. 14/822,493, filed on Aug. 10, 2015, now Pat. No. 9,932,580, which is a continuation of application No. 14/633,491, filed on Feb. 27, 2015, now Pat. No. 9,145,558, which is a continuation of application No. PCT/US2014/036463, filed on May 1, 2014.

(60) Provisional application No. 61/986,867, filed on Apr. 30, 2014, provisional application No. 61/976,991, filed on Apr. 8, 2014, provisional application No. 61/880,790, filed on Sep. 20, 2013, provisional application No. 61/871,673, filed on Aug. 29, 2013, provisional application No. 61/843,887, filed on Jul. 8, 2013, provisional application No. 61/823,826, filed on May 15, 2013, provisional application No. 61/818,442, filed on May 1, 2013.

(51) Int. Cl.

| | |
|---|---|
| ***C12N 15/113*** | (2010.01) |
| ***A61K 31/7088*** | (2006.01) |
| ***A61K 31/713*** | (2006.01) |
| ***A61K 47/54*** | (2017.01) |
| ***C07H 21/04*** | (2006.01) |
| ***C12N 15/11*** | (2006.01) |

(52) U.S. Cl.

CPC ........ *C12N 15/113* (2013.01); *A61K 31/7088* (2013.01); *A61K 31/713* (2013.01); *A61K 47/549* (2017.08); *C07H 21/04* (2013.01); *C12N 15/111* (2013.01); *C12N 2310/11* (2013.01); *C12N 2310/113* (2013.01); *C12N 2310/17* (2013.01); *C12N 2310/31* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/341* (2013.01); *C12N 2310/346* (2013.01); *C12N 2310/351* (2013.01); *C12N 2310/3511* (2013.01); *C12N 2310/3513* (2013.01); *C12N 2310/3515* (2013.01); *C12N 2310/3525* (2013.01); *C12N 2310/353* (2013.01); *C12N 2320/32* (2013.01)

(58) Field of Classification Search

CPC . C12N 15/113; C12N 15/111; C12N 2310/11; C12N 2310/113; C12N 2310/31; C12N 2310/17; C12N 2310/351; C12N 2310/3515; C12N 2310/315; A61K 31/7088; A61K 31/713; A61K 47/549; C07H 21/04

See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,458,066 | A | 7/1984 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,668,777 | A | 5/1987 | Caruthers et al. |
| 4,725,677 | A | 2/1988 | Koster et al. |
| 4,751,219 | A | 6/1988 | Kempen et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |

(Continued)

FOREIGN PATENT DOCUMENTS

| | | | |
|---|---|---|---|
| JP | WO 2015105083 | * | 7/2016 |
| WO | WO 1994/002499 | | 2/1994 |

(Continued)

OTHER PUBLICATIONS

Akinc et al., "Targeted Delivery of RNAi Therapeutics with Endogenous and Exogenous Ligand-Based Mechanisms" Molecular Therapy (2010) 18(7): 1357-1364.

(Continued)

*Primary Examiner* — Kimberly Chong

(57) ABSTRACT

Provided herein are oligomeric compounds with conjugate groups. In certain embodiments, the oligomeric compounds are conjugated to N-Acetylgalactosamine.

14 Claims, No Drawings

Specification includes a Sequence Listing.

(56) References Cited

U.S. PATENT DOCUMENTS

| | | | |
|---|---|---|---|
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,194,599 | A | 3/1993 | Froehler |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,276,019 | A | 1/1994 | Cohen et al. |
| 5,278,302 | A | 1/1994 | Caruthers et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,399,676 | A | 3/1995 | Froehler |
| 5,403,711 | A | 4/1995 | Walder et al. |
| 5,405,938 | A | 4/1995 | Sumerton et al. |
| 5,405,939 | A | 4/1995 | Suhadolnik et al. |
| 5,432,272 | A | 7/1995 | Benner |
| 5,434,257 | A | 7/1995 | Matteucci et al. |
| 5,446,137 | A | 8/1995 | Maag et al. |
| 5,453,496 | A | 9/1995 | Caruthers et al. |
| 5,455,233 | A | 10/1995 | Spielvogel et al. |
| 5,457,187 | A | 10/1995 | Gmelner et al. |
| 5,457,191 | A | 10/1995 | Cook et al. |
| 5,459,255 | A | 10/1995 | Cook et al. |
| 5,466,677 | A | 11/1995 | Baxter et al. |
| 5,466,786 | A | 11/1995 | Burh et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,491,133 | A | 2/1996 | Walder et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,555 | A | 10/1996 | Froehler et al. |
| 5,567,811 | A | 10/1996 | Mistura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,587,470 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bishofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci |
| 5,652,355 | A | 7/1997 | Metelev et al. |
| 5,652,356 | A | 7/1997 | Agrawal |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,698,685 | A | 12/1997 | Summerton et al. |
| 5,700,920 | A | 12/1997 | Altmann et al. |
| 5,700,922 | A | 12/1997 | Cook |
| 5,721,218 | A | 2/1998 | Froehler |
| 5,750,692 | A | 5/1998 | Cook et al. |
| 5,763,588 | A | 6/1998 | Matteucci et al. |
| 5,792,608 | A | 8/1998 | Swaminathan et al. |
| 5,792,847 | A | 8/1998 | Burh et al. |
| 5,801,154 | A | 9/1998 | Baracchini et al. |
| 5,808,027 | A | 9/1998 | Cook et al. |
| 5,830,653 | A | 11/1998 | Froehler et al. |
| 5,859,221 | A | 1/1999 | Cook et al. |
| 5,948,903 | A | 9/1999 | Cook et al. |
| 5,994,517 | A | 11/1999 | Ts'o et al. |
| 5,998,203 | A | 12/1999 | Matulic-Adamic |
| 6,005,087 | A | 12/1999 | Cook et al. |
| 6,005,096 | A | 12/1999 | Matteucci et al. |
| 6,166,199 | A | 12/2000 | Cook et al. |
| 6,268,490 | B1 | 7/2001 | Imanishi et al. |
| 6,300,319 | B1 | 10/2001 | Manoharan |
| 6,383,812 | B1 | 5/2002 | Chen et al. |
| 6,426,220 | B1 | 7/2002 | Bennett et al. |
| 6,525,031 | B2 | 2/2003 | Manoharan |
| 6,525,191 | B1 | 2/2003 | Ramasamy |
| 6,531,584 | B1 | 3/2003 | Cook et al. |
| 6,582,908 | B2 | 6/2003 | Fodor et al. |
| 6,600,032 | B1 | 7/2003 | Manoharan et al. |
| 6,620,916 | B1 | 9/2003 | Takahara et al. |
| 6,660,720 | B2 | 12/2003 | Manoharan et al. |
| 6,670,461 | B1 | 12/2003 | Wengel et al. |
| 6,673,661 | B1 | 1/2004 | Liu et al. |
| 6,770,748 | B2 | 8/2004 | Imanishi et al. |
| 6,794,499 | B2 | 9/2004 | Wengel et al. |
| 6,906,182 | B2 | 6/2005 | Ts'o et al. |
| 6,908,903 | B1 | 6/2005 | Theodore et al. |
| 7,015,315 | B1 | 3/2006 | Cook et al. |
| 7,034,133 | B2 | 4/2006 | Wengel et al. |
| 7,053,199 | B2 | 5/2006 | Imanishi et al. |
| 7,053,207 | B2 | 5/2006 | Wengel |
| 7,060,809 | B2 | 6/2006 | Wengel et al. |
| 7,101,993 | B1 | 9/2006 | Cook et al. |
| 7,217,805 | B2 | 5/2007 | Imanishi et al. |
| 7,262,177 | B2 | 8/2007 | Ts'o et al. |
| 7,314,923 | B2 | 1/2008 | Kaneko et al. |
| 7,399,845 | B2 | 7/2008 | Seth et al. |
| 7,427,672 | B2 | 9/2008 | Imanishi et al. |
| 7,439,043 | B2 | 10/2008 | DeFrees et al. |
| 7,491,805 | B2 | 2/2009 | Vargeese et al. |
| 7,547,684 | B2 | 6/2009 | Seth et al. |
| 7,569,686 | B1 | 8/2009 | Bhat et al. |
| 7,572,582 | B2 | 8/2009 | Wengel et al. |
| 7,582,744 | B2 | 9/2009 | Manoharan et al. |
| 7,666,854 | B2 | 2/2010 | Seth et al. |
| 7,696,344 | B2 | 4/2010 | Khvorova et al. |
| 7,696,345 | B2 | 4/2010 | Allerson et al. |

(56) References Cited

U.S. PATENT DOCUMENTS

| | | | |
|---|---|---|---|
| 7,723,509 | B2 | 5/2010 | Manoharan et al. |
| 7,741,457 | B2 | 6/2010 | Swayze et al. |
| 7,750,131 | B2 | 7/2010 | Seth et al. |
| 7,851,615 | B2 | 12/2010 | Manoharan et al. |
| 7,875,733 | B2 | 1/2011 | Bhat et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,101,743 | B2 | 1/2012 | Brown-Driver et al. |
| 8,106,022 | B2 | 1/2012 | Manoharan et al. |
| 8,124,745 | B2 | 2/2012 | Allerson et al. |
| 8,137,695 | B2 | 3/2012 | Rozema et al. |
| 8,153,365 | B2 | 4/2012 | Wengel et al. |
| 8,158,601 | B2 | 4/2012 | Chen et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,313,772 | B2 | 11/2012 | Rozema et al. |
| 8,344,125 | B2 | 1/2013 | Manoharan et al. |
| 8,349,308 | B2 | 1/2013 | Yurkovetskiy et al. |
| 8,404,862 | B2 | 3/2013 | Manoharan et al. |
| 8,435,491 | B2 | 5/2013 | Wang et al. |
| 8,440,803 | B2 | 5/2013 | Swayze et al. |
| 8,450,467 | B2 | 5/2013 | Manoharan et al. |
| 8,501,805 | B2 | 8/2013 | Seth et al. |
| 8,501,930 | B2 | 8/2013 | Rozema et al. |
| 8,530,640 | B2 | 9/2013 | Seth et al. |
| 8,541,548 | B2 | 9/2013 | Rozema |
| 8,546,556 | B2 | 10/2013 | Seth et al. |
| 8,552,163 | B2 | 10/2013 | Lee et al. |
| 8,575,123 | B2 | 11/2013 | Manoharan et al. |
| 8,604,192 | B2 | 12/2013 | Seth et al. |
| RE44,779 | E | 2/2014 | Imanishi et al. |
| 8,642,752 | B2 | 2/2014 | Swayze et al. |
| 8,697,860 | B1 | 4/2014 | Monia et al. |
| 8,809,514 | B2 | 8/2014 | Yamada et al. |
| 8,828,956 | B2 | 9/2014 | Manoharan et al. |
| 8,993,738 | B2 | 3/2015 | Prakash et al. |
| 9,005,906 | B2 | 4/2015 | Swayze et al. |
| 9,012,421 | B2 | 4/2015 | Migawa et al. |
| 9,061,044 | B2 | 6/2015 | Freier |
| 9,102,938 | B2 | 8/2015 | Rajeev et al. |
| 9,127,276 | B2 | 9/2015 | Prakash et al. |
| 9,181,549 | B2 | 11/2015 | Prakash et al. |
| 9,290,760 | B2 | 3/2016 | Rajeev et al. |
| 9,399,774 | B2 | 7/2016 | Monia et al. |
| 9,816,092 | B2 | 11/2017 | Monia et al. |
| 10,150,965 | B2 | 12/2018 | Brown et al. |
| 2001/0053519 | A1 | 12/2001 | Fodor et al. |
| 2002/0082227 | A1 | 6/2002 | Henry et al. |
| 2003/0077829 | A1 | 4/2003 | MacLachlan |
| 2003/0082807 | A1 | 5/2003 | Wengel |
| 2003/0119724 | A1 | 6/2003 | Ts'o et al. |
| 2003/0158403 | A1 | 8/2003 | Manoharan et al. |
| 2003/0170249 | A1 | 9/2003 | Hakomori et al. |
| 2003/0175906 | A1 | 9/2003 | Manoharan et al. |
| 2003/0207841 | A1 | 11/2003 | Kaneko et al. |
| 2003/0224377 | A1 | 12/2003 | Wengel et al. |
| 2003/0228597 | A1 | 12/2003 | Cowsert et al. |
| 2004/0143114 | A1 | 7/2004 | Imanishi et al. |
| 2004/0171570 | A1 | 9/2004 | Allerson et al. |
| 2004/0192918 | A1 | 9/2004 | Imanishi et al. |
| 2004/0249178 | A1 | 12/2004 | Vargeese et al. |
| 2005/0107319 | A1 | 5/2005 | Bansal |
| 2005/0130923 | A1 | 6/2005 | Bhat et al. |
| 2005/0164235 | A1 | 7/2005 | Manoharan et al. |
| 2005/0244869 | A1 | 11/2005 | Brown-Driver et al. |
| 2006/0148740 | A1 | 7/2006 | Platenburg |
| 2006/0183886 | A1 | 8/2006 | Tso et al. |
| 2007/0031844 | A1 | 2/2007 | Khvorova et al. |
| 2007/0287831 | A1 | 12/2007 | Seth et al. |
| 2008/0039618 | A1 | 2/2008 | Allerson et al. |
| 2008/0085869 | A1 | 4/2008 | Yamada et al. |
| 2008/0108801 | A1 | 5/2008 | Manoharan et al. |
| 2008/0206869 | A1 | 8/2008 | Smith et al. |
| 2008/0281041 | A1 | 11/2008 | Rozema et al. |
| 2008/0281044 | A1 | 11/2008 | Manoharan et al. |
| 2009/0012281 | A1 | 1/2009 | Swayze et al. |
| 2009/0203132 | A1 | 8/2009 | Swayze et al. |
| 2009/0203135 | A1 | 8/2009 | Forst et al. |
| 2009/0286973 | A1 | 11/2009 | Manoharan et al. |
| 2010/0093085 | A1 | 4/2010 | Yamada et al. |
| 2010/0120665 | A1 | 5/2010 | Kaleko et al. |
| 2010/0190837 | A1 | 7/2010 | Migawa et al. |
| 2010/0197762 | A1 | 8/2010 | Swayze et al. |
| 2010/0240730 | A1 | 9/2010 | Beigelman et al. |
| 2011/0077386 | A1 | 3/2011 | Lee et al. |
| 2011/0097264 | A1 | 4/2011 | Wang et al. |
| 2011/0097265 | A1 | 4/2011 | Wang et al. |
| 2011/0123520 | A1 | 5/2011 | Manoharan et al. |
| 2011/0124853 | A1 | 5/2011 | Chen et al. |
| 2011/0201798 | A1 | 8/2011 | Manoharan et al. |
| 2011/0207799 | A1 | 8/2011 | Rozema et al. |
| 2011/0269814 | A1 | 11/2011 | Manoharan et al. |
| 2011/0294868 | A1 | 12/2011 | Monia et al. |
| 2012/0035115 | A1 | 2/2012 | Manoharan et al. |
| 2012/0095075 | A1 | 4/2012 | Manoharan et al. |
| 2012/0101148 | A1 | 4/2012 | Aking et al. |
| 2012/0128760 | A1 | 5/2012 | Manoharan et al. |
| 2012/0136042 | A1 | 5/2012 | Manoharan et al. |
| 2012/0157509 | A1 | 6/2012 | Hadwiger et al. |
| 2012/0165393 | A1 | 6/2012 | Rozema et al. |
| 2012/0183602 | A1 | 7/2012 | Chen et al. |
| 2012/0225927 | A1 | 9/2012 | Sah et al. |
| 2012/0230938 | A1 | 9/2012 | Rozema et al. |
| 2013/0004427 | A1 | 1/2013 | El-Sayed et al. |
| 2013/0035366 | A1 | 2/2013 | Swayze et al. |
| 2013/0109817 | A1 | 5/2013 | Yurkovetskiy et al. |
| 2013/0121954 | A1 | 5/2013 | Wakefield et al. |
| 2013/0130378 | A1 | 5/2013 | Manoharan et al. |
| 2013/0178512 | A1 | 7/2013 | Manoharan et al. |
| 2013/0203836 | A1 | 8/2013 | Rajeev et al. |
| 2013/0236968 | A1 | 9/2013 | Manoharan et al. |
| 2014/0107184 | A1 | 4/2014 | Swayze et al. |
| 2014/0107330 | A1 | 4/2014 | Freier et al. |
| 2014/0256797 | A1 | 9/2014 | Monia et al. |
| 2014/0357701 | A1 | 12/2014 | Swayze et al. |
| 2015/0018540 | A1 | 1/2015 | Prakash et al. |
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0275212 | A1 | 10/2015 | Albaek et al. |

FOREIGN PATENT DOCUMENTS

| | | |
|---|---|---|
| WO | WO 1994/017093 | 8/1994 |
| WO | WO 1997/020563 | 6/1997 |
| WO | WO 1997/046098 | 12/1997 |
| WO | WO 1998/013381 | 4/1998 |
| WO | WO 1999/014226 | 3/1999 |
| WO | WO 2000/014048 | 3/2000 |
| WO | WO 2000/063364 | 10/2000 |
| WO | WO 2001/049687 | 7/2001 |
| WO | WO 2002/043771 | 6/2002 |
| WO | WO 2003/004602 | 1/2003 |
| WO | WO 2004/011624 | 2/2004 |
| WO | WO 2004/024757 | 3/2004 |
| WO | WO 2004/035765 | 4/2004 |
| WO | WO 2004/045543 | 6/2004 |
| WO | WO 2004/063208 | 7/2004 |
| WO | WO 2004/101619 | 11/2004 |
| WO | WO 2004/106356 | 12/2004 |
| WO | WO 2005/021570 | 3/2005 |
| WO | WO 2005/097155 | 10/2005 |
| WO | WO 2005/121371 | 12/2005 |
| WO | WO 2006/031461 | 3/2006 |
| WO | WO 2006/047842 | 5/2006 |
| WO | WO 2007/035759 | 3/2007 |
| WO | WO 2007/090071 | 8/2007 |

(56) References Cited

FOREIGN PATENT DOCUMENTS

| | | |
|---|---|---|
| WO | WO 2007/134181 | 11/2007 |
| WO | WO 2008/098788 | 8/2008 |
| WO | WO 2008/101157 | 8/2008 |
| WO | WO 2008/150729 | 12/2008 |
| WO | WO 2008/154401 | 12/2008 |
| WO | WO 2009/003009 | 12/2008 |
| WO | WO 2009/006478 | 1/2009 |
| WO | WO 2009/073809 | 6/2009 |
| WO | WO 2009/082607 | 7/2009 |
| WO | WO 2009/126933 | 10/2009 |
| WO | WO 2009/143369 | 11/2009 |
| WO | WO 2010/017509 | 2/2010 |
| WO | WO 2010/036698 | 4/2010 |
| WO | WO 2010/048549 | 4/2010 |
| WO | WO 2010/048585 | 4/2010 |
| WO | WO 2010/054406 | 5/2010 |
| WO | WO 2010/077578 | 7/2010 |
| WO | WO 2010/088537 | 8/2010 |
| WO | WO 2010/101951 | 9/2010 |
| WO | WO 2010/103204 | 9/2010 |
| WO | WO 2010/129709 | 11/2010 |
| WO | WO 2010/144740 | 12/2010 |
| WO | WO 2011/005860 | 1/2011 |
| WO | WO 2011/005861 | 1/2011 |
| WO | WO 2011/038356 | 3/2011 |
| WO | WO 2011/047312 | 4/2011 |
| WO | WO 2011/100131 | 8/2011 |
| WO | WO 2011/115818 | 9/2011 |
| WO | WO 2011/120053 | 9/2011 |
| WO | WO 2011/133871 | 10/2011 |
| WO | WO 2011/139702 | 10/2011 |
| WO | WO 2011/139917 | 11/2011 |
| WO | WO 2011/163121 | 12/2011 |
| WO | WO 2012/037254 | 3/2012 |
| WO | WO 2012/068187 | 5/2012 |
| WO | WO 2012/083046 | 6/2012 |
| WO | WO 2012/083185 | 6/2012 |
| WO | WO 2012/089352 | 7/2012 |
| WO | WO 2012/089602 | 7/2012 |
| WO | WO 2012/135736 | 10/2012 |
| WO | WO 2012/145674 | 10/2012 |
| WO | WO 2012/145697 | 10/2012 |
| WO | WO 2012/177784 | 12/2012 |
| WO | WO 2012/177947 | 12/2012 |
| WO | WO 2013/033230 | 3/2013 |
| WO | WO 2013/075035 | 5/2013 |
| WO | WO 2013/119979 | 8/2013 |
| WO | WO 2013/165816 | 11/2013 |
| WO | WO 2013/166121 | 11/2013 |
| WO | WO 2013/173789 | 11/2013 |
| WO | WO 2014/076195 | 5/2014 |
| WO | WO 2014/076196 | 5/2014 |
| WO | WO 2014/118267 | 8/2014 |
| WO | WO 2014/118272 | 8/2014 |
| WO | WO 2014/179620 | 11/2014 |
| WO | WO 2014/179625 | 11/2014 |
| WO | WO 2014/179626 | 11/2014 |
| WO | WO 2014/179627 | 11/2014 |
| WO | WO 2014/179629 | 11/2014 |
| WO | WO 2014/205451 | 12/2014 |
| WO | WO 2014/207232 | 12/2014 |
| WO | WO 2015/006740 | 1/2015 |
| WO | WO 2008/036825 | 3/2018 |

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Allshire, "RNAi and Heterochromatin—a Hushed-Up Affair" Science (2002) 297: 1818-1819.

Altmann et al., "Second generation antisense oligonucleotides—inhibition of PKC-a an c-RAF kinase expression by chimeric oligonucleotides incorporating 5'-substitute carbocyclic nucleosides and 2'-O-ethylene glycol substituted ribonucleosides." Nucleosides Nucleotides (1997) 16(7-9): 917-926.

Altmann et al., "Second Generation of Antisense Oligonucleotides: From Nuclease Resistance to Biological Efficacy in Animals" Chimia (1996) 50: 168-176.

Altmann et al., "Second-generation antisense oligonucleotides: structure-activity relationships and the design of improved signal-transduction inhibitors" Biochem. Soc. Trans. (1996) 24: 630-637.

Andre et al., "Determination of modulation of ligand properties of synthetic complex-type biantennary N-glycans by introduction of bisecting GlcNAc in silico, in vitro and in vivo" Eur. J. Biochem. (2004) 271: 118-134.

Asseline et al., "Modification of the 5' Terminus of Oligodeoxyribonucleotides for Conjugation with Ligands" in Current Protocols in Nucleic Acid Chemistry, 2001, Supplement 5, Chapter 4: Unit 4.9 (4.9.1-4.9.28); John Wiley & Sons.

Atsma et al., "Partial characterization of low density lipoprotein preparations isolated from fresh and frozen plasma after radiolabeling by seven different methods." J Lipid Res. (1991) 32(1): 173-181.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem., (1997) 272(18): 11944-12000.

Beaucage et al., "The functionalization of oligonucleotides via phosphoramidate derivatives" Tetrahedron (1993) 49(10): 1925-1963.

Biessen et al., "Novel hepatotrophic prodrugs of the antiviral nucleoside 9-(2-phosphonylmethoxyethyl)adenine with improved pharmacokinetics and antiviral activity" FASEB J. (2000) 14: 1784-1792.

Biessen et al., "Synthesis of Cluster Galactosides with High Affinity for the Hepatic Asialoglycoprotein Receptor" J. Med. Chem. (1995) 38:1538-1546.

Biessen et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852.

Braasch et al., "Locked nucleic acid (LNA): fine-tuning the recognition of DNA and RNA" Chem. Biol. (2001) 8:1-7.

Braasch et al., "Novel Antisense and Peptide Nucleic Acid Strategies for Controlling Gene Expression" Biochemistry (2002) 41(14): 4503-4510.

Branch et al., "A good antisense molecule is hard to find," TIBS (1998) 23:45-50.

Branda et al., "Amplification of antibody production by phosphorothioate oligodeoxynucleotides" J Lab Clin Med. (1996) 128(3): 329-338.

Chin "On the Preparation and Utilization of Isolated and Purified Oligonucleotides" Document purportedly located on a CD-ROM and contributed to the public collection of the Katherine R. Everett Law Library of the University of North Carolina (2002).

Coltart et al., "Principles of Mucin Architecture: Structural Studies on Synthetic Glycopeptides Bearing Clustered Mono-, Di-, Tri-, and Hexasaccharide Glycodomains" J. Am. Chem. Soc. (2002) 124: 9833-9844.

Connolly et al., "Binding and Endocytosis of Cluster Glycosides by Rabbit Hepatocytes" J Biol Chem (1982) 257: 939-945.

Costa et al., "Amyloid fibril protein related to prealbumin in familial amyloidotic polyneuropathy" PNAS (1978) 75(9): 4499-4503.

Crooke et al., "Pharmacokinetic Properties of Several Novel Oligonucleotide Analogs in mice" J. Pharmacol. Exp. Ther. (1996) 277(2):923-937.

Crooke et al., "Pharmacological Properties of 2'-O-Methoxyethyl Modified Oligonucleotides" in Antisense a Drug Technology, Chapter 10, pp. 273-303, Crooke, S.T., ed., 2008.

Crooke et al., "Toxicologic Properties of 2-O-Methoxyethyl Chimeric Antisense Inhibitors in Animals and Man" in Antisense a Drug Technology, Chapter 12, pp. 342-351, Crooke, S.T., ed., 2008.

Czech et al. "RNAi-based therapeutic strategies for metabolic disease" Nature Reviews Endocrinology (2011) 7: 473-484.

(56) References Cited

OTHER PUBLICATIONS

Dellinger et al., "Solid-Phase Chemical Synthesis of Phosphonoacetate and Thiophosphonoacetate Oligodeoxynucleotides" J. Am .Chem. Soc. (2003) 125: 940-950.
Dickson et al., "Rat Choroid Plexus Specializes in the Synthesis and the Secretion of Transthyretin" J Biol Chem (1986) 261(8): 3475-3478.
Duff et al., "Intrabody Tissue-Specific Delivery of Antisense Conjugates in Animals: Ligand-Linker-Antisense Oligomer Conjugates" Methods in Enzymology (1999) 313: 297-321.
Dupouy et al., "Watson-Crick Base-Pairing Properties of Nucleic Acid Analogues with Stereocontrolled a and b Torsion Angles (a,b-D-CNAs)" Angew. Chem. Int. Ed. (2006) 45: 3623-3627.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Elayadi et al., "Application of PNA and LNA oligomers to chemotherapy" Curr. Opinion Invens. Drugs (2001) 2:558-561.
Englisch et al., "Chemically Modified Oligonucleotides as Probes and Inhibitors" Agnew Chem. Int. Ed. Engl. (1991) 30:613-629.
Extended European Search Report for Application No. 15786214.5 dated Aug. 21, 2017.
Freier et al., "The ups and downs of nucleic acid duplex stability: structure-stability studies on chemically-modified DNA:RNA duplexes" Nucleic Acids Research (1997) 25(22):4429-4443.
Fried et al., "HBeAg and hepatitis B virus DNA as outcome predictors during therapy with peginterferon alfa-2a for HBeAg-positive chronic hepatitis B." Hepatology (2008) 47(2): 428-434.
Frieden et al., "Expanding the design horizon of antisense oligonucleotides with alpha-L-LNA" Nucleic Acids Research (2003) 31(21):6365-6372.
Ganem et al., "Hepatitis B Virus Infection—Natural History and Clinical Consequences" N Engl J Med. (2004) 350: 1118-1129.
Gautschi et al., "Activity of a novel bcl-2/bcl-xLbispecific antisense oligonucleotide against tumors of diverse histologic origins" J. Natl. Cancer Inst. (2001) 93:463-471.
Geary et al., "A nonradioisotope biomedical assay for intact oligonucleotide and its chain-shortened metabolites used for determination of exposure and elimination half-life of antisense drugs in tissue." Analytical Biochemistry (1999) 274, 241-248.
Geary et al., "Pharmacokinetic Properties of 2'-O-(2-Methoxyethyl)-Modified Oligonucleotide Analogs in Rats" The Journal of Pharmacology and Experimental Therapeutics (2001) 296:890-897.
Grossman et al., "Inhibition of the alternative complement pathway by antisense oligonucleotides targeting complement factor B improves lupus nephritis in mice" Immunobiology (2016) 221(6): 701-708.
Gu et al. "Base Pairing Properties of D- and L-Cyclohexene Nucleic Acids (CeNA)" Oligonucleotides (2003) 13(6): 479-489.
Gu et al., "Enzymatic resolution and base pairing properties of D- and L-cyclohexenyl nucleic acids (CeNA)." Nucleosides, Nucleotides & Nucleic Acids (2005) 24(5-7): 993-998.
Gu et al., "Synthesis of enantiomeric-pure cyclohexenyl nucleoside building blocks for oligonucleotide synthesis" Tetrahedron (2004) 60(9): 2111-2123.
Hall et al., "Establishment and Maintenance of a Heterochromatin Domain" Science (2002) 297: 2232-2237.
Henry et al., "Drug properties of second-generation antisense oligonucleotides: how do they measure up to their predecessors?" Curr Opin Investig Drugs (2001) 2: 1444-1449.
Hoffman et al., "'Brain-type' N-glycosylation of asialo-transferrin from human cerebrospinal fluid" FEBS Letters (1995) 359: 164-168.
Horn et al., "Chemical synthesis and characterization of branched oligodeoxyribonucleotides (bDNA) for use as signal amplifiers in nucleic acid quantification assays." Nucleic Acids Research (1997) 25: 4842-4849.
Horvath et al., "Stereoselective synthesis of (−)-ara-cyclohexenyl-adenine" Tetrahedron Letters (2007) 48: 3621-3623.
International Search Report for Application PCT/US12/52884 dated Nov. 20, 2012.
International Search Report for Application PCT/US14/36460 dated Oct. 10, 2014.
International Search Report for Application PCT/US14/36462 dated Dec. 23, 2014.
International Search Report for Application PCT/US14/36463 dated Dec. 30, 2014.
International Search Report for Application PCT/US14/36466 dated Dec. 1, 2014.
International Search Report for Application PCT/US14/43731 dated Dec. 10, 2014.
International Search Report for Application PCT/US14/56630 dated Dec. 24, 2014.
Jayaprakash et al., "Non-Nucleoside Building Blocks for Copper-Assisted and Copper-Free Click Chemistry for the Efficient Synthesis of RNA Conjugates" Organic Letters (2010) 12(23): 5410-5413.
Jenuwein "An RNA-Guided Pathway for the Epigenome" Science (2002) 297: 2215-2218.
Jiang et al., "The Design and Synthesis of Highly Branched and Spherically Symmetric Fluorinated Oils and Amphiles." Tetrahedron (2007) 63(19): 3982-3988.
Jin et al., "Use of α-N,N-bis[Carboxymethyl]lysine-Modified Peroxidase in Immunoassays" Analytical Biochemistry (1995) 229: 54-60.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Kanasty et al., "Delivery Materials for siRNA Therapeutics" Nature Materials (2013) 12: 967-977.
Kassim et al., "Gene therapy for dyslipidemia: a review of gene replacement and gene inhibition strategies" Clinical Lipidology (2010) 5(6): 793-809.
Kato et al., "N-acetylgalactosamine incorporation into a peptide containing consecutive threonine residues by UDP-N-acetyl-D-galactosaminide:polypeptide N-acetylgalactosaminyltransferases" Glyobiology (2001) 11: 821-829.
Khorev et al., "Trivalent, Gal/GalNAc-containing ligands designed for the asialoglycoprotein receptor" Bioorganic & Medicinal Chemistry (2008) 16: 5216-5231.
Kim et al., "Oligomeric Glycopeptidomimetics Bearing the Cancer Related TN-Antigen" Tetrahedron Letters (1997) 38(20): 3487-3490.
Kim et al., "Synthesis of Novel Phosphoramidite Building Blocks from Pentaerythritol" Synlett (2003) 12: 1838-1840.
Koller et al., "Mechanisms of single-stranded phosphorothioate modified antisense oligonucleotide accumulation in hepatocytes." Nucleic Acids Res. (2011) 39(11): 4795-4807.
Kornilova et al., "Development of a fluorescence polarization binding assay for asialoglycoprotein receptor" Analytical Biochemistry (2012) 425: 43-46.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Kurosawa et al., "Selective silencing of a mutant transthyretin allele by small interfering RNAs" Biochemical and Biophysical Research Communications (2005) 337 (3): 1012-1018.
Lazaris-Karatzas et al., "Malignant transformation by a eukaryotic initiation factor subunit that binds to mRNA 5' cap" Nature (1990) 345: 544-547.
Lee et al., "Antisense Technology: An Emerging Platform for Cardiovascular Disease Therapeutics" J of Cardiovasc Trans Res (2013) 6: 969-980.

(56) References Cited

OTHER PUBLICATIONS

Lee et al., "Facile Synthesis of a High-Affinity Ligand for Mammalian Hepatic Lectin Containing Three Terminal N-Acetylgalactosamine Residues" Bioconjugate Chem. (1997) 8: 762-765.
Lee et al., "New and more efficient multivalent glyco-ligands for asialoglycoprotein receptor of mammalian hepatocytes" Bioorganic & Medicinal Chemistry (2011) 19:2494-2500.
Lee et al., "New synthetic cluster ligands for galactose/N-acetylgalactosamine-specific lectin of mammalian liver" Biochem (1984) 23: 4255-4261.
Lee et al., "Preparation of Cluster Glycosides of Nacetylgalactosamine That Have Subnanomolar Binding Constants Towards the Mammalian Hepatic Gal/GalNAc-specific Receptor" Glycoconjugate J. (1987) 4: 317-328.
Lee et al., "Protein microarrays to study carbohydrate-recognition events" Bioorg Med Chem Lett (2006) 16(19): 5132-5135.
Lee et al., "Synthesis of multivalent neoglyconjugates of MUC1 by the conjugation of carbohydrate-centered, triazole-linked glycoclusters to MUC1peptides using click chemistry." J Org Chem (2012) 77: 7564-7571.
Lee et al., "Synthesis of Peptide-Based Trivalent Scaffold for Preparation of Cluster Glycosides" Methods in Enzymology (2003) 362: 38-43.
Lee et al., "Synthesis of some cluster glycosides suitable for attachment to proteins or solid matrices" Carbohydrate Research (1978) 67: 509-514.
Leeds et al., "Quantitation of phosphorothioate oligonucleotides in human plasma." Analytical Biochemistry (1996) 235, 36-43.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Liang et al., "Hepatitis B e Antigen—The Dangerous Endgame of Hepatitis B" N Engl J Med. (2002) 347: 208-210.
Link, "Pharmacological regulation of hepatic glucose production" Curr Opin Investig Drugs (2003) 4: 421-429.
Machida et al., "Postmortem findings in a patient with cerebral amyloid angiopathy actively treated with corticosteroid" Amyloid (2012) 19: 47-52.
Maher et al., "Comparative hybrid arrest by tandem antisense oligodeoxyribonucleotides or oligodeoxyribonucleoside methylphosphonates in a cell-free system" Nucl. Acid. Res. (1998) 16(8):3341-3358.
Maier et al., "Synthesis of Antisense Oligonucleotides Conjugated to a Multivalent Carbohydrate Cluster for Cellular Targeting" Bioconjugate Chem. (2003) 14: 18-29.
Maierhofer et al., "Probing multivalent carbohydrate-lectin interactions by an enzyme-linked lectin assay employing covalently immobilized carbohydrates" Bioorganic & Medicinal Chemistry (2007) 15: 7661-7676.
Manoharan et al., "Chemical Modifications to Improve Uptake and Bioavailability of Antisense Oligonucleotides" Ann. N.Y. Acad. Sci. (1992) 660: 306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "N-(2-Cyanoethoxycarbonyloxy)succinimide: A New Reagent for Protection of Amino Groups in Oligonucleotides" J. Org. Chem. (1999) 64: 6468-6472.
Manoharan et al., "Oligonucleotide Conjugates: Alteration of the Pharmacokinetic Properties of Antisense Agents" Nucleosides & Nucleotides (1995) 14(3-5): 969-973.
Manoharan, "Oligonucleotide Conjugates as Potential Antisense Drugs with Improved Uptake, Biodistribution, Targeted Delivery, and Mechanism of Action" Antisense & Nucleic Acid Drug Development (2002) 12: 103-128.
Marcaurelle et al., "Synthesis of Oxime-Linked Mucin Mimics Containing the Tumor-Related TN and Sialyl TN Antigens" Organic Letters (2001) 3(23): 3691-3694.
Martin, "Ein neuer Zugang zu 2'-O-Alkylribonucleosiden und Eigenschaften deren Oligonucleotide" Helv. Chim. Acta (1995)78: 486-504.
Merwin et al., "Targeted delivery of DNA using YEE(GalNAcAH)3, a synthetic glycopeptide ligand for the asialoglycoprotein receptor." Bioconjug Chem (1994) 5(6): 612-620.
Mishra et al., "Improved leishmanicidal effect of phosphorotioate antisense oligonucleotides by LDL-mediated delivery" Biochim. Biophys. Acta (1995) 1264:229-237.
Miura et al., "Fluorometric determination of total mRNA with oligo(dT) immobilized on microtiter plates" Clin. Chem. (1996) 42:1758-1764.
Moucari et al., "Early serum HBsAg drop: a strong predictor of sustained virological response to pegylated interferon alfa-2a in HBeAg-negative patients." Hepatology (2009) 49(4): 1151-1157.
Nair et al., "Multivalent N-Acetylgalactosamine-Conjugated siRNA Localizes in Hepatocytes and Elicits Robust RNAi-Mediated Gene Silencing" J. Am. Chem. Soc. (2014) 136(49): 16958-16961.
Nauwelaerts et al., "Cyclohexenyl nucleic acids: conformationally flexible oligonucleotides" Nucleic Acids Research (2005) 33(8): 2452-2463.
Nauwelaerts et al., "Structural Characterization and Biological Evaluation of Small Interfering RNAs Containing Cyclohexenyl Nucleosides" J. Am. Chem. Soc. (2007) 129(30): 9340-9348.
New England Biolabs 1998/99 Catalog (cover page and pp. 121 and 284).
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Ostergaard et al., "Efficient Synthesis and Biological Evaluation of 5'-GalNAc Conjugated Antisense Oligonucleotides" Bioconjug. Chem. (2015) 26(8): 1451-1455.
Pal-Bhadra et al., "Heterochromatic Silencing and HP1 Localization in *Drosophila* Are Dependent on the RNAi Machinery" Science (2004) 303: 669-672.
Palha, "Transthyretin as a Thyroid Hormone Carrier: Function Revisited" Clin Chem Lab Med (2002) 40(12): 1292-1300.
Park et al., "The asialoglycoprotein receptor clears glycoconjugates terminating with sialic acid a2,6GalNAc" PNAS (2005) 102(47): 17125-17129.
Pavia et al., "Synthetic TN glycopeptide related to human glycophorin AM. High-field proton and carbon-13 nuclear magnetic resonance study." Int J Pep Protein Res (1983) 22: 539-548.
Petrova et al., "Carrier-free cellular uptake and the gene-silencing activity of the lipophilic siRNAs is strongly affected by the length of the linker between siRNA and lipophilic group" Nucleic Acids Research (2012) 40(5): 2330-2344.
Prakash et al., "Targeted delivery of antisense oligonucleotides to hepatocytes using triantennary N-acetyl galactosamine improves potency 10-fold in mice" Nucleic Acid Research (2014) 42(13): 8796-8807.
Pujol et al., "A Sulfur Tripod Glycoconjugate that Releases a High-Affinity Copper Chelator in Hepatocytes" Angew. Chem. Int. Ed. (2012) 51: 7445-7448.
Rajeev, "Conjugation Strategies for In Vitro siRNA Delivery" 8th Annual Meeting of the Oligonucleotide Therapeutics Society (2012).
Rajur et al., "Covalent Protein-Oligonucleotide Conjugates for Efficient Delivery of Antisense Molecules" Bioconjugate Chem. (1997) 8: 935-940.

(56) References Cited

OTHER PUBLICATIONS

Raouane et al., "Synthesis, Characterization, and in Vivo Delivery of siRNA-Squalene Nanoparticles Targeting Fusion Oncogene in Papillary Thyroid Carcinoma" J. Med. Chem. (2011) 54: 4067-4076.
Rensen et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808.
Rensen et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584.
Rensen et al., "Stimulation of Liver-Directed Cholesterol Flux in Mice by Novel N-Acetylgalactosamine-Terminated Glycolipids With High Affinity for the Asialoglycoprotein Receptor" Arterioscler Thromb Vasc Biol (2006) 26: 169-175.
Reynolds et al., "Rational siRNA design for RNA interference" Nature Biotechnology (2004) 22(3):326-330.
Robeyns et al., "Oligonucleotides with cyclohexene-nucleoside building blocks: crystallization and preliminary X-ray studies of a left-handed sequence GTGT ACAC" Acta Crystallographica, Section F: Structural Biology and Crystallization Communications (2005) F61(6): 585-586.
Robeyns et al., "Structure of the Fully Modified Left-Handed Cyclohexene Nucleic Acid Sequence Gtgtacac" J. Am. Chem. Soc. (2008) 130(6): 1979-1984.
Rossenberg et al., "Stable polyplexes based on arginine-containing oligopeptides for in vivo gene delivery" Gene Therapy (2004) 11: 457-464.
Rouchaud et al., "A New and Efficient Synthesis of Derivatives of Octahydro-4H-pyrrolo[1,2-c]pyrido[1',2'-a]imidazole" Eur. J. Org. Chem. (2011) 12: 2346-2353.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sakaki et al., "Human Transthyretin (Prealbumin) Gene and Molecular Genetics of Familial Amyloidotic Polyneruopathy" Mol Biol Med. (1989) 6: 161-168.
Sanghvi et al., "Heterocyclic Base Modifications in Nucleic Acids and Their Applications in Antisense Oligonucleotides" Antisense Research and Applications (1993)273-288.
Sanghvi, Chapter 15, Antisense Research and Applications, Crooke and Lebleu ed., CRC Press (1993).
Saraiva et al., "Amyloid Fibril Protein in Familial Amyloidotic Polyneuropathy, Portuguese Type" J Clin Invest. (1984) 74: 104-119.
Sato et al., "Glycoinsulins: Dendritic Sialyloligosaccharide-Displaying Insulins Showing a Prolonged Blood-Sugar-Lowering Activity" J. Am. Chem. Soc. (2004) 126: 14013-14022.
Savige et al., "Retinal abnormalities characteristic of inherited renal disease." Journal of American Society of Nephrol. (2011) 22(8):1403-15.
Seeger et al., "Hepatitis B virus biology" Microbiol Mol Biol Rev. (2000) 64(1): 51-68.
Seth et al., "Design, Synthesis And Evaluation Of Constrained Methoxyethyl (cMOE) and Constrained Ethyl (cEt) Nucleoside Analogs" Nucleic Acids Symposium Series (2008) 52(1): 553-554.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Seth et al., "Synthesis and biophysical characterization of R-6'-Me-α-L-LNA modified oligonucleotides." Bioorg. Med. Chem. (2011) 21(4): 1122-1125.
Seth et al., "Synthesis and Biophysical Evaluation of 2',4'-Constrained 2'O-Methoxyethyl and 2',4'-Constrained 2'O-Ethyl Nucleic Acid Analogues" J Org Chem. (2010) 75(5): 1569-1581.
Shchepinov et al., "Oligonucleotide dendrimers: stable nano-structures" Nucleic Acids Research (1999) 27(15): 3035-3041.
Shchepinov et al., "Oligonucleotide dendrimers: synthesis and use as polylabelled DNA probes." Nucleic Acids Research (1997) 25(22): 4447-4454.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J. Med. Chem. (1999) 42:609-618.
Sofia et al., "Discovery of a beta-d-2'-deoxy-2'-alpha-fluoro-2'-beta-C-methyluridine Nucleotide Prodrug (PSA-7977) For the Treatment of Hepatitis C virus" J. Med. Chem. (2010) 53(19): 7202-7218.
Sousa et al., "Neurodegeneration in familial amyloid polyneuropathy: from pathology to molecular signaling" Prog Neurobiol (2003) 71: 385-400.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Swayze et al., "The Medicinal Chemistry of Oligonucleotides" Antisense Drug Technology: Principles, Strategies, and Applications, 2nd ED. (2007) 143-182.
Tanskanen et al., "Senile systemic amyloidosis affects 25% of the very aged and associates with genetic variation in alpha2-macroglobulin and tau: A population-based autopsy study" Ann Med. (2008) 40(3): 232-239.
Tober et al., "Self-Metathesis of Polyol Allyl Ethers towards Carbohydrate-Based Oligohydroxy Derivatives" Eur. J. Org. Chem. (2013) 3: 566-577.
Tomiya et al., "Liver-targeting of primaquine-(poly-c-glutamic acid) and its degradation in rat hepatocytes" Bioorganic & Medicinal Chemistry (2013) 21: 5275-5281.
Toyokuni et al., "Synthetic vaccines: I. Synthesis of multivalent Tn antigen cluster-lysyllysine conjugates" Tetrahedron Lett (1990) 31(19): 2673-2676.
Valentijn et al., "Solid-phase Synthesis of Lysine-based Cluster Galactosides with High Affinity for the Asialoglycoprotein Receptor" Tetrahedron (1997) 53(2): 759-770.
Van Rossenberg et al., "Stable polyplexes based on arginine-containing oligopeptides for in vivo gene delivery" Gene Ther (2004) 11: 457-464.
Verbeure et al., "RNase H mediated cleavage of RNA by cyclohexene nucleic acid (CeNA)" Nucleic Acids Research (2001) 29(24): 4941-4947.
Verdel et al., "RNAi-Mediated Targeting of Heterochromatin by the RITS Complex" Science (2004) 303: 672-676.
Volpe et al., "Regulation of heterochromatic silencing and histone H3 lysine-9 methylation by RNAi." Science (2002) 297(5588): 1833-1837.
Wahlestedt et al., "Potent and nontoxic antisense oligonucleotide containing locked nucleic acids" Proc. Natl. Acad. Sci. USA (2000) 97: 5633-5638.
Wang et al., "A Straightforward Stereoselective Synthesis of D- and L-5-Hydroxy-4-hydroxymethyl-2-cyclohexenylguanine" Journal of Organic Chem. (2001) 66: 8478-8482.
Wang et al., "Cyclohexene nucleic acids (CeNA) form stable duplexes with RNA and induce RNase H activity." Nucleosides, Nucleotides & Nucleic Acids (2001) 20(4-7) 785-788.
Wang et al., "Cyclohexene Nucleic Acids (CeNA): Serum Stable Oligonucleotides that Activate RNase H and Increase Duplex Stability with Complementary RNA" Journal of American Chem. (2000) 122: 8595-8602.
Wang et al., "Stereocontrolled Synthesis of Ara-Type Cyclohexenyl Nucleosides" Journal of Organic Chem.(2003) 68, 4499-4505.

(56) References Cited

OTHER PUBLICATIONS

Weber et al., "Design and synthesis of P2-P1'-linked macrocyclic human renin inhibitors" J. Med. Chem. (1991) 34(9): 2692-2701.
Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal (2004) 21: 227-241.
Woolf et al., "Specificity of antisense oligonucleotides in vivo" PNAS (1992) 89: 7305-7309.
Wu et al., "A New N-Acetylgalactosamine Containing Peptide as a Targeting Vehicle for Mammalian Hepatocytes Via Asialoglycoprotein Receptor Endocytosis" Current Drug Delivery (2004) 1: 119-127.
Zimmermann et al., "Carbohydrate conjugation to siRNA for liver-specific delivery" Hepatology (2010) 52(1): pp. 587A, Abstract No. 547, Retrieved from STN, Accession No. 0050381852 EMBASE [retrieved on Jun. 25, 2018].
Zhao et al., "Synthesis and preliminary biochemical studies with 5'-deoxy-5'-methylidyne phosphonate linked thymidine oligonucleotides" Tetrahedron Letters (1996) 37(35): 6239-6242.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Zhou et al., "Proteolytic processing in the secretory pathway." J. Biol. Chem. (1999) 274(30): 20745-20748.

* cited by examiner

SEQUENCE LISTING

```
Sequence total quantity: 55
SEQ ID NO: 1            moltype = DNA  length = 3182
FEATURE                 Location/Qualifiers
source                  1..3182
                        mol_type = other DNA
                        organism = Hepatitis B virus
SEQUENCE: 1
aattccacaa cctttcacca aactctgcaa gatcccagag tgagaggcct gtatttccct  60
gctggtggct ccagttcagg agcagtaaac cctgttccga ctactgcctc tcccttatcg  120
tcaatcttct cgaggattgg ggaccctgcg ctgaacatgg agaacatcac atcaggattc  180
ctaggacccc ttctcgtgtt acaggcgggg tttttcttgt tgacaagaat cctcacaata  240
ccgcagagtc tagactcgtg gtggacttct ctcaattttc tagggggaac taccgtgtgt  300
cttggccaaa attcgcagtc cccaacctcc aatcactcac caacctcctg tcctccaact  360
tgtcctggtt atcgctggat gtgtctgcgg cgttttatca tcttcctctt catcctgctg  420
ctatgcctca tcttcttgtt ggttcttctg gactatcaag gtatgttgcc cgtttgtcct  480
ctaattccag gatcctcaac caccagcacg ggaccatgcc gaacctgcat gactactgct  540
caaggaacct ctatgtatcc ctcctgttgc tgtaccaaac cttcggacgg aaattgcacc  600
tgtattccca tcccatcatc ctgggctttc ggaaaattcc tatgggagtg ggcctcagcc  660
cgtttctcct ggctcagttt actagtgcca tttgttcagt ggttcgtagg gctttccccc  720
actgtttggc tttcagttat atggatgatg tggtattggg ggccaagtct gtacagcatc  780
ttgagtccct ttttaccgct gttaccaatt ttcttttgtc tttgggtata catttaaacc  840
ctaacaaaac aaagagatgg ggttactctc tgaattttat gggttatgtc attggaagtt  900
atgggtcctt gccacaagaa cacatcatac aaaaaatcaa agaatgtttt agaaaacttc  960
ctattaacag gcctattgat tggaaagtat gtcaacgaat tgtgggtctt ttgggttttg  1020
ctgccccatt tacacaatgt ggttatcctg cgttaatgcc cttgtatgca tgtattcaat  1080
ctaagcaggc tttcactttc tcgccaactt acaaggcctt tctgtgtaaa caatacctga  1140
acctttaccc cgttgcccgg caacggccag gtctgtgcca agtgtttgct gacgcaaccc  1200
ccactggctg gggcttggtc atgggccatc agcgcgtgcg tggaaccttt tcggctcctc  1260
tgccgatcca tactgcggaa ctcctagccg cttgttttgc tcgcagcagg tctggagcaa  1320
acattatcgg gactgataac tctgttgtcc tctcccgcaa atatacatcg tatccatggc  1380
tgctaggctg tgctgccaac tggatcctgc gcgggacgtc ctttgtttac gtcccgtcgg  1440
cgctgaatcc tgcggacgac ccttctcggg gtcgcttggg actctctcgt ccccttctcc  1500
gtctgccgtt ccgaccgacc acggggcgca cctctcttta cgcggactcc ccgtctgtgc  1560
cttctcatct gccggaccgt gtgcacttcg cttcacctct gcacgtcgca tggagaccac  1620
cgtgaacgcc caccgaatgt tgcccaaggt cttacataag aggactcttg gactctctgc  1680
aatgtcaacg accgaccttg aggcatactt caaagactgt ttgtttaaag actgggagga  1740
gttgggggag gagattagat taaaggtctt tgtactagga ggctgtaggc ataaattggt  1800
ctgcgcacca gcaccatgca actttttcac ctctgcctaa tcatctcttg ttcatgtcct  1860
actgttcaag cctccaagct gtgccttggg tggctttggg gcatggacat cgacccttat  1920
aaagaatttg gagctactgt ggagttactc tcgtttttgc cttctgactt ctttccttca  1980
gtacgagatc ttctagatac cgcctcagct ctgtatcggg aagccttaga gtctcctgag  2040
cattgttcac ctcaccatac tgcactcagg caagcaattc tttgctgggg ggaactaatg  2100
actctagcta cctgggtggg tgttaatttg gaagatccag catctagaga cctagtagtc  2160
agttatgtca acactaatat gggcctaaag ttcaggcaac tcttgtggtt tcacatttct  2220
tgtctcactt ttggaagaga aaccgttata gagtatttgg tgtctttcgg agtgtggatt  2280
cgcactcctc cagcttatag accaccaaat gcccctatcc tatcaacact tccggaaact  2340
actgttgtta gacgacgagg caggtcccct agaagaagaa ctccctcgcc tcgcagacga  2400
```

```
aggtctcaat cgccgcgtcg cagaagatct caatctcggg aacctcaatg ttagtattcc  2460
ttggactcat aaggtgggga actttactgg tctttattct tctactgtac ctgtctttaa  2520
tcctcattgg aaaacaccat cttttcctaa tatacattta caccaagaca ttatcaaaaa  2580
atgtgaacag tttgtaggcc cacttacagt taatgagaaa agaagattgc aattgattat  2640
gcctgctagg ttttatccaa aggttaccaa atatttacca ttggataagg gtattaaacc  2700
ttattatcca gaacatctag ttaatcatta cttccaaact agacactatt tacacactct  2760
atggaaggcg ggtatattat ataagagaga aacaacacat agcgcctcat tttgtgggtc  2820
accatattct tgggaacaag atctacagca tggggcagaa tctttccacc agcaatcctc  2880
tgggattctt tcccgaccac cagttggatc cagccttcag agcaaacaca gcaaatccag  2940
attgggactt caatcccaac aaggacacct ggccagacgc caacaaggta ggagctggag  3000
cattcgggct gggtttcacc ccaccgcacg gaggcctttt ggggtggagc cctcaggctc  3060
agggcatact acaaactttg ccagcaaatc cgcctcctgc ctccaccaat cgccagacag  3120
gaaggcagcc taccccgctg tctccacctt tgagaaacac tcatcctcag gccatgcagt  3180
gg                                                                 3182

SEQ ID NO: 2            moltype = DNA  length = 938
FEATURE                 Location/Qualifiers
source                  1..938
                        mol_type = other DNA
                        organism = Homo sapiens
SEQUENCE: 2
gttgactaag tcaataatca gaatcagcag gtttgcagtc agattggcag ggataagcag  60
cctagctcag gagaagtgag tataaaagcc ccaggctggg agcagccatc acagaagtcc  120
actcattctt ggcaggatgg cttctcatcg tctgctcctc ctctgccttg ctggactggt  180
atttgtgtct gaggctggcc ctacgggcac cggtgaatcc aagtgtcctc tgatggtcaa  240
agttctagat gctgtccgag gcagtcctgc catcaatgtg gccgtgcatg tgttcagaaa  300
ggctgctgat gacacctggg agccatttgc ctctgggaaa accagtgagt ctggagagct  360
gcatgggctc acaactgagg aggaatttgt agaagggata tacaaagtgg aaatagacac  420
caaatcttac tggaaggcac ttggcatctc cccattccat gagcatgcag aggtggtatt  480
cacagccaac gactccggcc cccgccgcta caccattgcc gccctgctga gcccctactc  540
ctattccacc acggctgtcg tcaccaatcc caaggaatga gggacttctc ctccagtgga  600
cctgaaggac gagggatggg atttcatgta accaagagta ttccattttt actaaagcag  660
tgttttcacc tcatatgcta tgttagaagt ccaggcagag acaataaaac attcctgtga  720
aaggcacttt tcattccact ttaacttgat tttttaaatt cccttattgt cccttccaaa  780
aaaaagagaa tcaaaatttt acaaagaatc aaaggaattc tagaaagtat ctgggcagaa  840
cgctaggaga gatccaaatt tccattgtct tgcaagcaaa gcacgtatta aatatgatct  900
gcagccatta aaaagacaca ttctgtaaaa aaaaaaaa                          938

SEQ ID NO: 3            moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 3
gcagaggtga agcgaagtgc                                              20

SEQ ID NO: 4            moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 4
ccaatttatg cctacagcct                                              20

SEQ ID NO: 5            moltype = DNA  length = 17
FEATURE                 Location/Qualifiers
misc_feature            1..17
                        note = Synthetic oligonucleotide
source                  1..17
                        mol_type = other DNA
                        organism = synthetic construct
SEQUENCE: 5
ggcatagcag caggatg                                                 17

SEQ ID NO: 6            moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 6
aggagttccg cagtatggat                                              20

SEQ ID NO: 7            moltype = DNA  length = 20
```

```
FEATURE                 Location/Qualifiers
misc_feature            1..20
                        note = Synthetic oligonucleotide
source                  1..20
                        mol_type = other DNA
                        organism = synthetic construct
SEQUENCE: 7
gtgaagcgaa gtgcacacgg                                                       20

SEQ ID NO: 8            moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 8
gtgcagaggt gaagcgaagt                                                       20

SEQ ID NO: 9            moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 9
aggtgaagcg aagtgc                                                           16

SEQ ID NO: 10           moltype = DNA  length = 16
FEATURE                 Location/Qualifiers
misc_feature            1..16
                        note = Synthetic oligonucleotide
source                  1..16
                        mol_type = other DNA
                        organism = synthetic construct
SEQUENCE: 10
tccgcagtat ggatcg                                                           16

SEQ ID NO: 11           moltype = DNA  length = 18
FEATURE                 Location/Qualifiers
misc_feature            1..18
                        note = Synthetic oligonucleotide
source                  1..18
                        mol_type = other DNA
                        organism = synthetic construct
SEQUENCE: 11
aatttatgcc tacagcct                                                         18

SEQ ID NO: 12           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 12
tcttggttac atgaaatccc                                                       20

SEQ ID NO: 13           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 13
cttggttaca tgaaatccca                                                       20

SEQ ID NO: 14           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 14
ggaatactct tggttacatg                                                       20
```

```
SEQ ID NO: 15          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 15
tggaatactc ttggttacat                                        20

SEQ ID NO: 16          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 16
ttttattgtc tctgcctgga                                        20

SEQ ID NO: 17          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 17
gaatgtttta ttgtctctgc                                        20

SEQ ID NO: 18          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 18
aggaatgttt tattgtctct                                        20

SEQ ID NO: 19          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 19
acaggaatgt tttattgtct                                        20

SEQ ID NO: 20          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 20
agcttcttgt ccagctttat                                        20

SEQ ID NO: 21          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 21
agcttcttgt ccagctttat a                                      21

SEQ ID NO: 22          moltype = DNA  length = 14
FEATURE                Location/Qualifiers
misc_feature           1..14
                       note = Synthetic oligonucleotide
source                 1..14
                       mol_type = other DNA
                       organism = synthetic construct
SEQUENCE: 22
tcagtcatga cttc                                              14
```

```
SEQ ID NO: 23           moltype = DNA  length = 15
FEATURE                 Location/Qualifiers
misc_feature            1..15
                        note = Synthetic oligonucleotide
source                  1..15
                        mol_type = other DNA
                        organism = synthetic construct
SEQUENCE: 23
tcagtcatga cttca                                                    15

SEQ ID NO: 24           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 24
gctgattaga gagaggtccc                                               20

SEQ ID NO: 25           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 25
tcccatttca ggagacctgg                                               20

SEQ ID NO: 26           moltype = DNA  length = 15
FEATURE                 Location/Qualifiers
misc_feature            1..15
                        note = Synthetic oligonucleotide
source                  1..15
                        mol_type = other DNA
                        organism = synthetic construct
SEQUENCE: 26
atcagtcatg acttc                                                    15

SEQ ID NO: 27           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 27
cggtgcaagg cttaggaatt                                               20

SEQ ID NO: 28           moltype = DNA  length = 20
FEATURE                 Location/Qualifiers
misc_feature            1..20
                        note = Synthetic oligonucleotide
source                  1..20
                        mol_type = other DNA
                        organism = synthetic construct
SEQUENCE: 28
gcttcagtca tgacttcctt                                               20

SEQ ID NO: 29           moltype = DNA  length = 21
FEATURE                 Location/Qualifiers
misc_feature            1..21
                        note = Synthetic oligonucleotide
source                  1..21
                        mol_type = other DNA
                        organism = synthetic construct
SEQUENCE: 29
gcttcagtca tgacttcctt a                                             21

SEQ ID NO: 30           moltype = DNA  length = 21
FEATURE                 Location/Qualifiers
misc_feature            1..21
                        note = Synthetic oligonucleotide
source                  1..21
                        mol_type = other DNA
                        organism = synthetic construct
SEQUENCE: 30
```

```
agcttcagtc atgacttcct t                                        21

SEQ ID NO: 31          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 31
tggtaatcca ctttcagagg                                          20

SEQ ID NO: 32          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 32
tggtaatcca ctttcagagg a                                        21

SEQ ID NO: 33          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 33
tgcttcagtc atgacttcct t                                        21

SEQ ID NO: 34          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 34
cactgatttt tgcccaggat                                          20

SEQ ID NO: 35          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 35
cactgatttt tgcccaggat a                                        21

SEQ ID NO: 36          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 36
aagcttcttg tccagcttta t                                        21

SEQ ID NO: 37          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 37
acccaattca gaaggaagga                                          20

SEQ ID NO: 38          moltype = DNA  length = 21
FEATURE                Location/Qualifiers
misc_feature           1..21
                       note = Synthetic oligonucleotide
source                 1..21
                       mol_type = other DNA
                       organism = synthetic construct
```

```
SEQUENCE: 38
acccaattca gaaggaagga a                                              21

SEQ ID NO: 39          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 39
aacccaattc agaaggaagg a                                              21

SEQ ID NO: 40          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 40
atggtaatcc actttcagag g                                              21

SEQ ID NO: 41          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 41
tcttggttac atgaaatccc                                                20

SEQ ID NO: 42          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 42
tcttggttac atgaaatccc a                                              21

SEQ ID NO: 43          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 43
attcactttc ataatgctgg                                                20

SEQ ID NO: 44          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 44
attcactttc ataatgctgg a                                              21

SEQ ID NO: 45          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 45
atcttggtta catgaaatcc c                                              21

SEQ ID NO: 46          moltype = DNA  length = 20
FEATURE                Location/Qualifiers
misc_feature           1..20
                       note = Synthetic oligonucleotide
source                 1..20
                       mol_type = other DNA
```

```
                       organism = synthetic construct
SEQUENCE: 46
atgcatggtg atgcttctga                                                  20

SEQ ID NO: 47          moltype = DNA  length = 20
FEATURE                Location/Qualifiers
misc_feature           1..20
                       note = Synthetic oligonucleotide
source                 1..20
                       mol_type = other DNA
                       organism = synthetic construct
SEQUENCE: 47
cagctttatt agggacagca                                                  20

SEQ ID NO: 48          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 48
cagctttatt agggacagca a                                                21

SEQ ID NO: 49          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 49
acagctttat tagggacagc a                                                21

SEQ ID NO: 50          moltype = DNA  length = 16
FEATURE                Location/Qualifiers
misc_feature           1..16
                       note = Synthetic oligonucleotide
source                 1..16
                       mol_type = other DNA
                       organism = synthetic construct
SEQUENCE: 50
ttcagtcatg acttcc                                                      16

SEQ ID NO: 51          moltype = DNA  length = 18
FEATURE                Location/Qualifiers
misc_feature           1..18
                       note = Synthetic oligonucleotide
misc_feature           1..4
                       note = bases at these positions are RNA
misc_feature           15..18
                       note = bases at these positions are RNA
source                 1..18
                       mol_type = other DNA
                       organism = synthetic construct
modified_base          3..4
                       mod_base = OTHER
                       note = uracil
modified_base          16
                       mod_base = OTHER
                       note = uracil
SEQUENCE: 51
gcttcagtca tgacttcc                                                    18

SEQ ID NO: 52          moltype = DNA  length = 21
FEATURE                Location/Qualifiers
misc_feature           1..21
                       note = Synthetic oligonucleotide
source                 1..21
                       mol_type = other DNA
                       organism = synthetic construct
SEQUENCE: 52
tgctccgttg gtgcttgttc a                                                21

SEQ ID NO: 53          moltype = DNA  length = 20
FEATURE                Location/Qualifiers
misc_feature           1..20
                       note = Synthetic oligonucleotide
source                 1..20
```

```
                        mol_type = other DNA
                        organism = synthetic construct
SEQUENCE: 53
tgctccgttg gtgcttgttc                                            20

SEQ ID NO: 54           moltype = DNA  length = 20
FEATURE                 Location/Qualifiers
source                  1..20
                        mol_type = other DNA
                        organism = synthetic construct
modified_base           1
                        mod_base = OTHER
                        note = 2'-O-methoxyethyl thymidine 3'-phosphorothioate
modified_base           2
                        mod_base = OTHER
                        note = 2'-O-methoxyethyl 5-methyl cytidine 3'-phosphodiester
modified_base           3
                        mod_base = OTHER
                        note = 2'-O-methoxyethyl thymidine 3'-phosphodiester
modified_base           4
                        mod_base = OTHER
                        note = 2'-O-methoxyethyl thymidine 3'-phosphodiester
modified_base           5
                        mod_base = OTHER
                        note = 2'-O-methoxyethyl guanosine 3'-phosphodiester
modified_base           6
                        mod_base = OTHER
                        note = 2'-deoxyguanosine 3'-phosphorothioate
modified_base           7
                        mod_base = OTHER
                        note = 2'-deoxythymidine 3'-phosphorothioate
modified_base           8
                        mod_base = OTHER
                        note = 2'-deoxythymidine 3'-phosphorothioate
modified_base           9
                        mod_base = OTHER
                        note = 2'-deoxyadenosine 3'-phosphorothioate
modified_base           10
                        mod_base = OTHER
                        note = 5-methyl-2'-deoxycytidine 3'-phosphorothioate
modified_base           11
                        mod_base = OTHER
                        note = 2'-deoxyadenosine 3'-phosphorothioate
modified_base           12
                        mod_base = OTHER
                        note = 2'-deoxythymidine 3'-phosphorothioate
modified_base           13
                        mod_base = OTHER
                        note = 2'-deoxyguanosine 3'-phosphorothioate
modified_base           14
                        mod_base = OTHER
                        note = 2'-deoxyadenosine 3'-phosphorothioate
modified_base           15
                        mod_base = OTHER
                        note = 2'-deoxyadenosine 3'-phosphorothioate
modified_base           16
                        mod_base = OTHER
                        note = 2'-O-methoxyethyl adenosine 3'-phosphodiester
modified_base           17
                        mod_base = OTHER
                        note = 2'-O-methoxyethyl thymidine 3'-phosphodiester
modified_base           18
                        mod_base = OTHER
                        note = 2'-O-methoxyethyl 5-methyl cytidine
                         3'-phosphorothioate
modified_base           19
                        mod_base = OTHER
                        note = 2'-O-methoxyethyl 5-methyl cytidine
                         3'-phosphorothioate
modified_base           20
                        mod_base = OTHER
                        note = 2'-O-methoxyethyl 5-methyl cytidine
misc_feature            1..5
                        note = RNA
misc_feature            6..15
                        note = DNA
misc_feature            16..20
                        note = RNA
SEQUENCE: 54
```

-continued

```
tcttggttac atgaaatccc                                              20

SEQ ID NO: 55          moltype = DNA  length = 20
FEATURE                Location/Qualifiers
source                 1..20
                       mol_type = other DNA
                       organism = synthetic construct
modified_base          1
                       mod_base = OTHER
                       note = 2'-O-methoxyethyl thymidine 3'-phosphorothioate
                        attached to
                        trishexylamino-N-Acetylgalactosamine-6-aminohexyl
                        phosphodiester
modified_base          2
                       mod_base = OTHER
                       note = 2'-O-methoxyethyl 5-methyl cytidine 3'-phosphodiester
modified_base          3
                       mod_base = OTHER
                       note = 2'-O-methoxyethyl thymidine 3'-phosphodiester
modified_base          4
                       mod_base = OTHER
                       note = 2'-O-methoxyethyl thymidine 3'-phosphodiester
modified_base          5
                       mod_base = OTHER
                       note = 2'-O-methoxyethyl guanosine 3'-phosphodiester
modified_base          6
                       mod_base = OTHER
                       note = 2'-deoxyguanosine 3'-phosphorothioate
modified_base          7
                       mod_base = OTHER
                       note = 2'-deoxythymidine 3'-phosphorothioate
modified_base          8
                       mod_base = OTHER
                       note = 2'-deoxythymidine 3'-phosphorothioate
modified_base          9
                       mod_base = OTHER
                       note = 2'-deoxyadenosine 3'-phosphorothioate
modified_base          10
                       mod_base = OTHER
                       note = 5-methyl-2'-deoxycytidine 3'-phosphorothioate
modified_base          11
                       mod_base = OTHER
                       note = 2'-deoxyadenosine 3'-phosphorothioate
modified_base          12
                       mod_base = OTHER
                       note = 2'-deoxythymidine 3'-phosphorothioate
modified_base          13
                       mod_base = OTHER
                       note = 2'-deoxyguanosine 3'-phosphorothioate
modified_base          14
                       mod_base = OTHER
                       note = 2'-deoxyadenosine 3'-phosphorothioate
modified_base          15
                       mod_base = OTHER
                       note = 2'-deoxyadenosine 3'-phosphorothioate
modified_base          16
                       mod_base = OTHER
                       note = 2'-O-methoxyethyl adenosine 3'-phosphodiester
modified_base          17
                       mod_base = OTHER
                       note = 2'-O-methoxyethyl thymidine 3'-phosphodiester
modified_base          18
                       mod_base = OTHER
                       note = 2'-O-methoxyethyl 5-methyl cytidine
                        3'-phosphorothioate
modified_base          19
                       mod_base = OTHER
                       note = 2'-O-methoxyethyl 5-methyl cytidine
                        3'-phosphorothioate
```

-continued

| | |
|---|---|
| modified_base | 20<br>mod_base = OTHER<br>note = 2'-O-methoxyethyl 5-methyl cytidine |
| misc_feature | 1..5<br>note = RNA |
| misc_feature | 6..15<br>note = DNA |
| misc_feature | 16..20<br>note = RNA |
| SEQUENCE: 55 | |
| tcttggttac atgaaatccc | 20 |

COMPOSITIONS AND METHODS FOR MODULATING TTR EXPRESSION

COMPOSITIONS AND METHODS FOR MODULATING TTR EXPRESSION

This application is a continuation of U.S. patent application Ser. No. 16/790,557, filed on Feb. 13, 2020, now abandoned, which is a continuation of U.S. patent application Ser. No. 15/687,306, filed on Aug. 25, 2017, now issued as U.S. Pat. No. 10,683,499, which is a continuation of U.S. patent application Ser. No. 14/822,493, filed on Aug. 10, 2015, now issued as U.S. Pat. No. 9,932,580, which is a continuation of U.S. patent application Ser. No. 14/633,491, filed on Feb. 27, 2015, now issued as U.S. Pat. No. 9,145,558, which is a continuation of International Patent Application No. PCT/US2014/036463, filed May 1, 2014, said Application No. PCT/US2014/036463 claims benefit under 35 U.S.C. § 119 (e) of U.S. Provisional Application No. 61/986,867 filed Apr. 30, 2014, and U.S. Provisional Application No. 61/976,991, filed Apr. 8, 2014, and U.S. Provisional Application No. 61/880,790, filed Sep. 20, 2013, and U.S. Provisional Application No. 61/871,673, filed Aug. 29, 2013, and U.S. Provisional Application No. 61/843,887, filed Jul. 8, 2013, and U.S. Provisional Application No. 61/823,826, filed May 15, 2013, and U.S. Provisional Application No. 61/818,442, filed May 1, 2013. Each of the above listed applications is incorporated by reference herein in its entirety for all purposes.

SEQUENCE LISTING

The present application is being filed along with a Sequence Listing in electronic format. The Sequence Listing is provided as a file entitled 201181_generic_SL.xml, created on Jul. 26, 2024, which is 100,619 bytes in size. The information in the electronic format of the sequence listing is incorporated herein by reference in its entirety.

BACKGROUND OF THE INVENTION

The principle behind antisense technology is that an antisense compound hybridizes to a target nucleic acid and modulates the amount, activity, and/or function of the target nucleic acid. For example in certain instances, antisense compounds result in altered transcription or translation of a target. Such modulation of expression can be achieved by, for example, target mRNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced siliencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of diseases.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics or affinity for a target nucleic acid. In 1998, the antisense compound, Vitravene® (fomivirsen; developed by Isis Pharmaceuticals Inc., Carlsbad, CA) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

SUMMARY OF THE INVENTION

In certain embodiments, the present disclosure provides conjugated antisense compounds. In certain embodiments, the present disclosure provides conjugated antisense compounds comprising an antisense oligonucleotide complementary to a nucleic acid transcript. In certain embodiments, the present disclosure provides methods comprising contacting a cell with a conjugated antisense compound comprising an antisense oligonucleotide complementary to a nucleic acid transcript. In certain embodiments, the present disclosure provides methods comprising contacting a cell with a conjugated antisense compound comprising an antisense oligonucleotide and reducing the amount or activity of a nucleic acid transcript in a cell.

The asialoglycoprotein receptor (ASGP-R) has been described previously. See e.g., Park et al., PNAS vol. 102, No. 47, pp 17125-17129 (2005). Such receptors are expressed on liver cells, particularly hepatocytes. Further, it has been shown that compounds comprising clusters of three N-acetylgalactosamine (GalNAc) ligands are capable of binding to the ASGP-R, resulting in uptake of the compound into the cell. See e.g., Khorev et al., Bioorganic and Medicinal Chemistry, 16, 9, pp 5216-5231 (May 2008). Accordingly, conjugates comprising such GalNAc clusters have been used to facilitate uptake of certain compounds into liver cells, specifically hepatocytes. For example it has been shown that certain GalNAc-containing conjugates increase activity of duplex siRNA compounds in liver cells in vivo. In such instances, the GalNAc-containing conjugate is typically attached to the sense strand of the siRNA duplex. Since the sense strand is discarded before the antisense strand ultimately hybridizes with the target nucleic acid, there is little concern that the conjugate will interfere with activity. Typically, the conjugate is attached to the 3' end of the sense strand of the siRNA. See e.g., U.S. Pat. No. 8,106,022.

Certain conjugate groups described herein are more active and/or easier to synthesize than conjugate groups previously described.

In certain embodiments of the present invention, conjugates are attached to single-stranded antisense compounds, including, but not limited to RNase H based antisense compounds and antisense compounds that alter splicing of a pre-mRNA target nucleic acid. In such embodiments, the conjugate should remain attached to the antisense compound long enough to provide benefit (improved uptake into cells) but then should either be cleaved, or otherwise not interfere with the subsequent steps necessary for activity, such as hybridization to a target nucleic acid and interaction with RNase H or enzymes associated with splicing or splice modulation. This balance of properties is more important in the setting of single-stranded antisense compounds than in siRNA compounds, where the conjugate may simply be attached to the sense strand. Disclosed herein are conjugated single-stranded antisense compounds having improved potency in liver cells in vivo compared with the same antisense compound lacking the conjugate. Given the required balance of properties for these compounds such improved potency is surprising.

In certain embodiments, conjugate groups herein comprise a cleavable moiety. As noted, without wishing to be bound by mechanism, it is logical that the conjugate should remain on the compound long enough to provide enhancement in uptake, but after that, it is desirable for some portion or, ideally, all of the conjugate to be cleaved, releasing the parent compound (e.g., antisense compound) in its most active form. In certain embodiments, the cleavable moiety is a cleavable nucleoside. Such embodiments take advantage of endogenous nucleases in the cell by attaching the rest of the conjugate (the cluster) to the antisense oligonucleotide through a nucleoside via one or more cleavable bonds, such as those of a phosphodiester linkage. In certain embodiments, the cluster is bound to the cleavable nucleoside through a phosphodiester linkage. In certain embodiments, the cleavable nucleoside is attached to the antisense oligonucleotide (antisense compound) by a phosphodiester linkage. In certain embodiments, the conjugate group may comprise two or three cleavable nucleosides. In such embodiments, such cleavable nucleosides are linked to one another, to the antisense compound and/or to the cluster via cleavable bonds (such as those of a phosphodiester linkage). Certain conjugates herein do not comprise a cleavable nucleoside and instead comprise a cleavable bond. It is shown that that sufficient cleavage of the conjugate from the oligonucleotide is provided by at least one bond that is vulnerable to cleavage in the cell (a cleavable bond).

In certain embodiments, conjugated antisense compounds are prodrugs. Such prodrugs are administered to an animal and are ultimately metabolized to a more active form. For example, conjugated antisense compounds are cleaved to remove all or part of the conjugate resulting in the active (or more active) form of the antisense compound lacking all or some of the conjugate.

In certain embodiments, conjugates are attached at the 5' end of an oligonucleotide. Certain such 5'-conjugates are cleaved more efficiently than counterparts having a similar conjugate group attached at the 3' end. In certain embodiments, improved activity may correlate with improved cleavage. In certain embodiments, oligonucleotides comprising a conjugate at the 5' end have greater efficacy than oligonucleotides comprising a conjugate at the 3' end (see, for example, Examples 56, 81, 83, and 84). Further, 5'-attachment allows simpler oligonucleotide synthesis. Typically, oligonucleotides are synthesized on a solid support in the 3' to 5' direction. To make a 3'-conjugated oligonucleotide, typically one attaches a pre-conjugated 3' nucleoside to the solid support and then builds the oligonucleotide as usual. However, attaching that conjugated nucleoside to the solid support adds complication to the synthesis. Further, using that approach, the conjugate is then present throughout the synthesis of the oligonucleotide and can become degraded during subsequent steps or may limit the sorts of reactions and reagents that can be used. Using the structures and techniques described herein for 5'-conjugated oligonucleotides, one can synthesize the oligonucleotide using standard automated techniques and introduce the conjugate with the final (5'-most) nucleoside or after the oligonucleotide has been cleaved from the solid support.

In view of the art and the present disclosure, one of ordinary skill can easily make any of the conjugates and conjugated oligonucleotides herein. Moreover, synthesis of certain such conjugates and conjugated oligonucleotides disclosed herein is easier and/or requires few steps, and is therefore less expensive than that of conjugates previously disclosed, providing advantages in manufacturing. For example, the synthesis of certain conjugate groups consists of fewer synthetic steps, resulting in increased yield, relative to conjugate groups previously described. Conjugate groups such as GalNAc$_3$-10 in Example 46 and GalNAc$_3$-7 in Example 48 are much simpler than previously described conjugates such as those described in U.S. Pat. No. 8,106,022 or U.S. Pat. No. 7,262,177 that require assembly of more chemical intermediates. Accordingly, these and other conjugates described herein have advantages over previously described compounds for use with any oligonucleotide, including single-stranded oligonucleotides and either strand of double-stranded oligonucleotides (e.g., siRNA).

Similarly, disclosed herein are conjugate groups having only one or two GalNAc ligands. As shown, such conjugates groups improve activity of antisense compounds. Such compounds are much easier to prepare than conjugates comprising three GalNAc ligands. Conjugate groups comprising one or two GalNAc ligands may be attached to any antisense compounds, including single-stranded oligonucleotides and either strand of double-stranded oligonucleotides (e.g., siRNA).

In certain embodiments, the conjugates herein do not substantially alter certain measures of tolerability. For example, it is shown herein that conjugated antisense compounds are not more immunogenic than unconjugated parent compounds. Since potency is improved, embodiments in which tolerability remains the same (or indeed even if tolerability worsens only slightly compared to the gains in potency) have improved properties for therapy.

In certain embodiments, conjugation allows one to alter antisense compounds in ways that have less attractive consequences in the absence of conjugation. For example, in certain embodiments, replacing one or more phosphorothioate linkages of a fully phosphorothioate antisense compound with phosphodiester linkages results in improvement in some measures of tolerability. For example, in certain instances, such antisense compounds having one or more phosphodiester are less immunogenic than the same compound in which each linkage is a phosphorothioate. However, in certain instances, as shown in Example 26, that same replacement of one or more phosphorothioate linkages with phosphodiester linkages also results in reduced cellular uptake and/or loss in potency. In certain embodiments, conjugated antisense compounds described herein tolerate such change in linkages with little or no loss in uptake and potency when compared to the conjugated full-phosphorothioate counterpart. In fact, in certain embodiments, for example, in Examples 44, 57, 59, and 86, oligonucleotides comprising a conjugate and at least one phosphodiester internucleoside linkage actually exhibit increased potency in vivo even relative to a full phosphorothioate counterpart also comprising the same conjugate. Moreover, since conjugation results in substantial increases in uptake/potency a small loss in that substantial gain may be acceptable to achieve improved tolerability. Accordingly, in certain embodiments, conjugated antisense compounds comprise at least one phosphodiester linkage.

In certain embodiments, conjugation of antisense compounds herein results in increased delivery, uptake and activity in hepatocytes. Thus, more compound is delivered to liver tissue. However, in certain embodiments, that increased delivery alone does not explain the entire increase in activity. In certain such embodiments, more compound enters hepatocytes. In certain embodiments, even that increased hepatocyte uptake does not explain the entire increase in activity. In such embodiments, productive uptake of the conjugated compound is increased. For example, as shown in Example 102, certain embodiments of GalNAc-containing conjugates increase enrichment of antisense oligonucleotides in hepatocytes versus non-parenchymal cells. This enrichment is beneficial for oligonucleotides that target genes that are expressed in hepatocytes.

In certain embodiments, conjugated antisense compounds herein result in reduced kidney exposure. For example, as shown in Example 20, the concentrations of antisense oligonucleotides comprising certain embodiments of GalNAc-containing conjugates are lower in the kidney than that of antisense oligonucleotides lacking a GalNAc-containing conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly for non-kidney targets, kidney accumulation is undesired.

In certain embodiments, the present disclosure provides conjugated antisense compounds represented by the formula:

$$A—B—C—D—(E—F)_q$$

wherein
A is the antisense oligonucleotide;
B is the cleavable moiety
C is the conjugate linker
D is the branching group
each E is a tether;
each F is a ligand; and
q is an integer between 1 and 5.

In the above diagram and in similar diagrams herein, the branching group "D" branches as many times as is necessary to accommodate the number of (E-F) groups as indicated by "q". Thus, where q=1, the formula is:

A-B-C-D-E-F where q=2, the formula is:

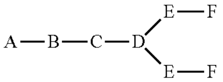

where q=3, the formula is:

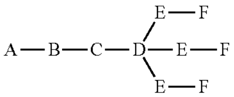

where q=4, the formula is:

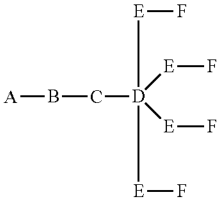

where q=5, the formula is:

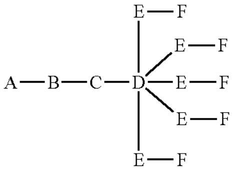

In certain embodiments, conjugated antisense compounds are provided having the structure:

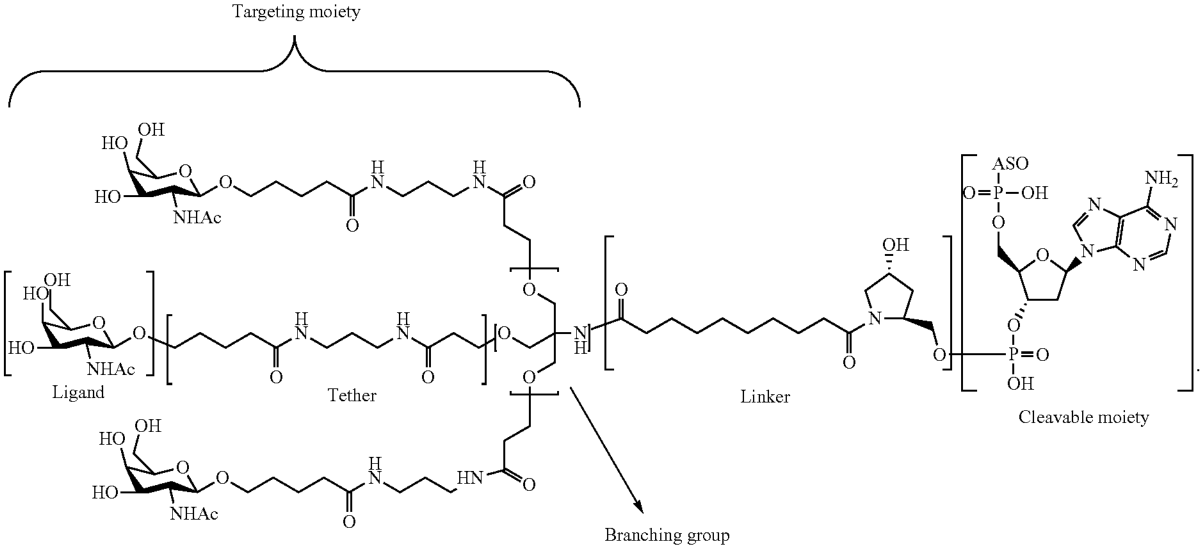

In certain embodiments, conjugated antisense compounds are provided having the structure:
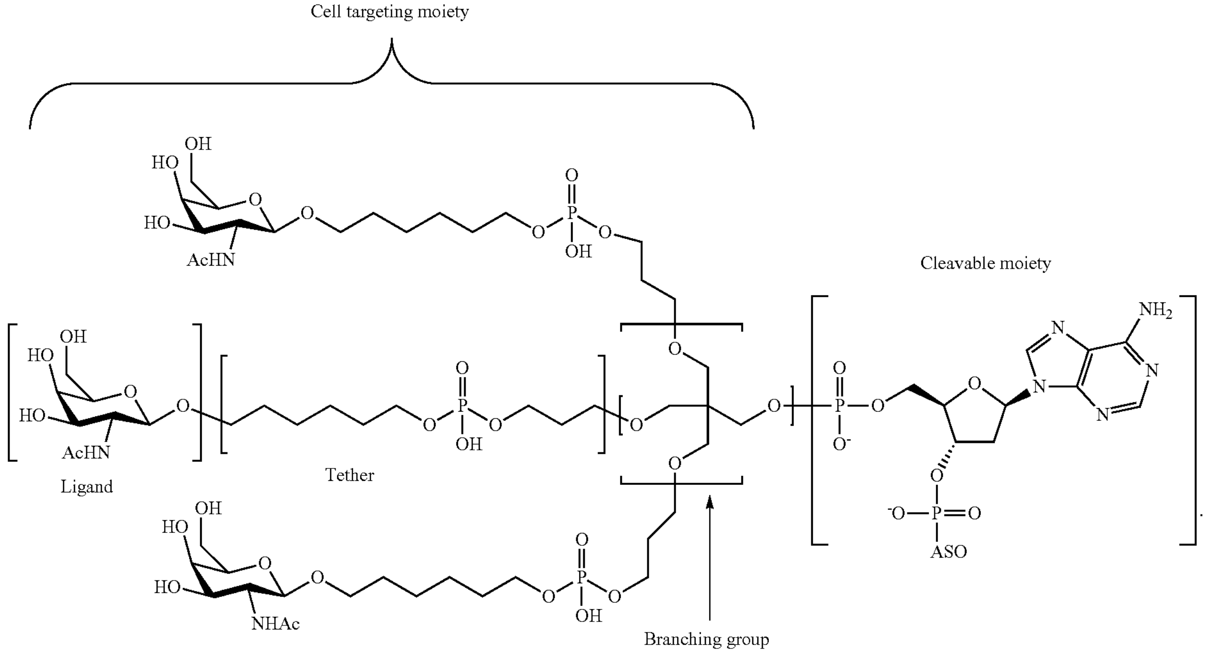
In certain embodiments, conjugated antisense compounds are provided having the structure:
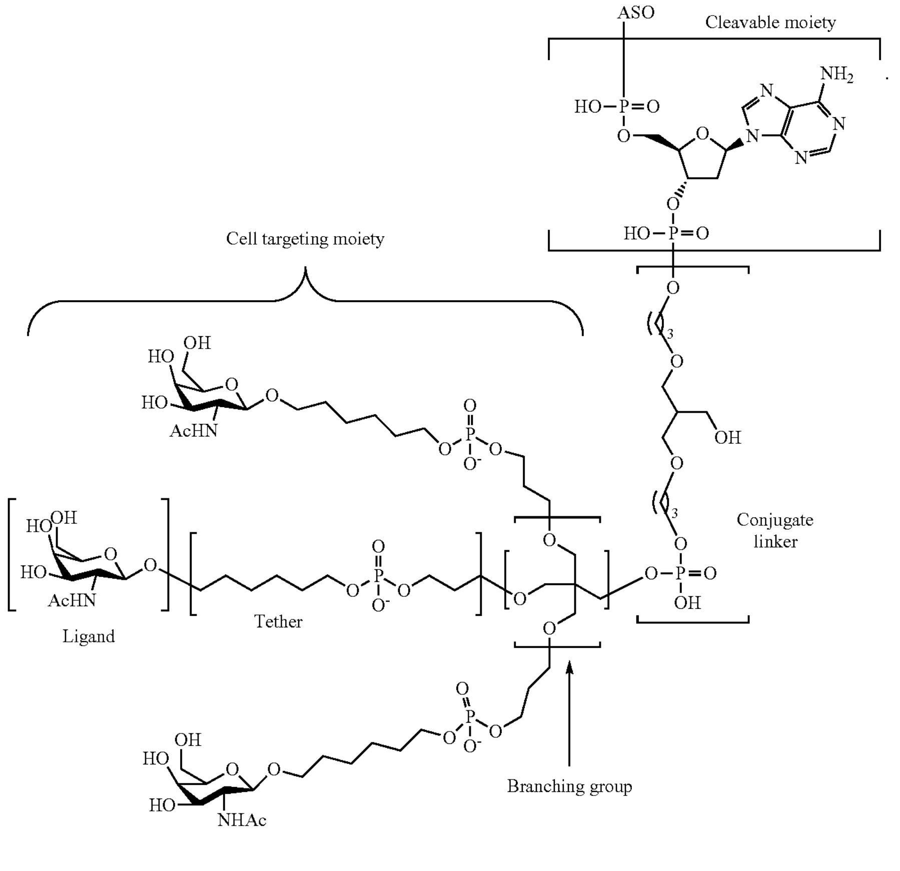

In certain embodiments, conjugated antisense compounds are provided having the structure:

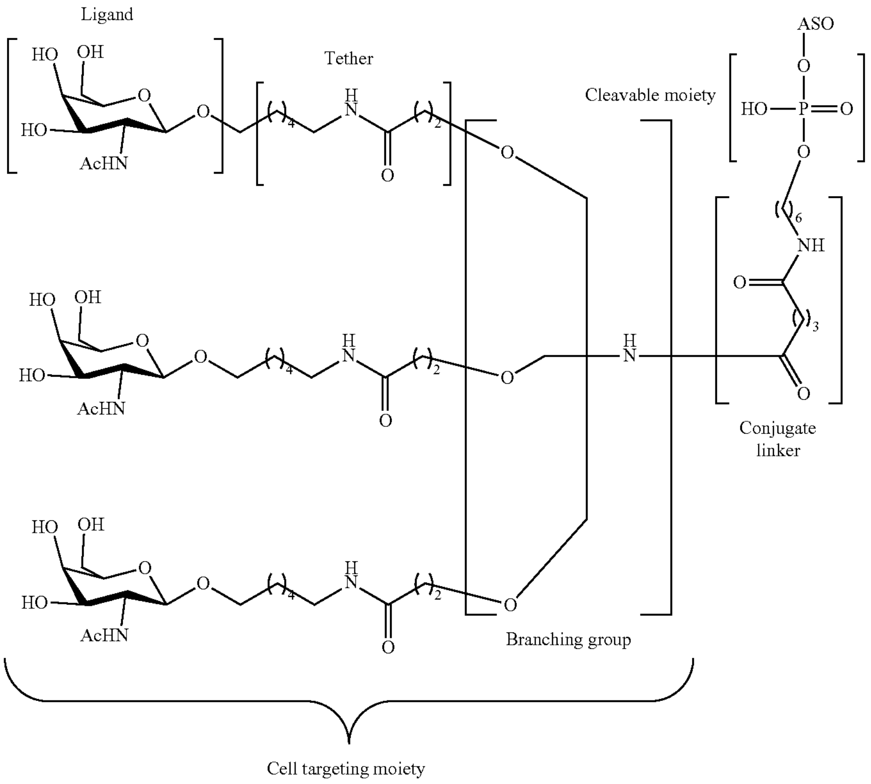

In embodiments having more than one of a particular variable (e.g., more than one "m" or "n"), unless otherwise indicated, each such particular variable is selected independently. Thus, for a structure having more than one n, each n is selected independently, so they may or may not be the same as one another.

DETAILED DESCRIPTION

It is to be understood that both the foregoing general description and the following detailed description are exemplary and explanatory only and are not restrictive of the disclosure. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Florida; and Sambrook et al., "Molecular Cloning, A laboratory Manual," 2nd Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means-$OCH_2CH_2OCH_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C)(including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'—$CH(CH_3)$—O-2'bridge.

As used herein, "locked nucleic acid nucleoside" or "LNA" means a nucleoside comprising a bicyclic sugar moiety comprising a 4'—$CH_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein, "linkage" or "linking group" means a group of atoms that link together two or more other groups of atoms.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "terminal internucleoside linkage" means the linkage between the last two nucleosides of an oligonucleotide or defined region thereof.

As used herein, "phosphorus linking group" means a linking group comprising a phosphorus atom. Phosphorus linking groups include without limitation groups having the formula:

wherein:

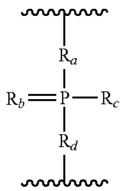

$R_a$ and $R_a$ are each, independently, O, S, $CH_2$, NH, or $NJ_1$ wherein $J_1$ is $C_1$-$C_6$ alkyl or substituted $C_1$-$C_6$ alkyl;

$R_b$ is O or S;

$R_c$ is OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $J_1$ is $R_b$ is O or S.

Phosphorus linking groups include without limitation, phosphodiester, phosphorothioate, phosphorodithioate, phosphonate, phosphoramidate, phosphorothioamidate, thionoalkylphosphonate, phosphotriesters, thionoalkylphosphotriester and boranophosphate.

As used herein, "internucleoside phosphorus linking group" means a phosphorus linking group that directly links two nucleosides.

As used herein, "non-internucleoside phosphorus linking group" means a phosphorus linking group that does not directly link two nucleosides. In certain embodiments, a non-internucleoside phosphorus linking group links a nucleoside to a group other than a nucleoside. In certain embodiments, a non-internucleoside phosphorus linking group links two groups, neither of which is a nucleoside.

As used herein, "neutral linking group" means a linking group that is not charged. Neutral linking groups include without limitation phosphotriesters, methylphosphonates, MMI ($—CH_2—N(CH_3)—O—$), amide-3 ($—CH_2—C(═O)—N(H)—$), amide-4 ($—CH_2—N(H)—C(═O)—$), formacetal ($—O—CH_2—O—$), and thioformacetal ($—S—CH_2—O—$). Further neutral linking groups include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral linking groups include nonionic linkages comprising mixed N, O, S and $CH_2$ component parts.

As used herein, "internucleoside neutral linking group" means a neutral linking group that directly links two nucleosides.

As used herein, "non-internucleoside neutral linking group" means a neutral linking group that does not directly link two nucleosides. In certain embodiments, a non-internucleoside neutral linking group links a nucleoside to a group other than a nucleoside. In certain embodiments, a non-internucleoside neutral linking group links two groups, neither of which is a nucleoside.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids. In certain embodiments, an oligomeric compound comprises a backbone of one or more linked monomeric subunits where each linked monomeric subunit is directly or indirectly attached to a heterocyclic base moiety. In certain embodiments, oligomeric compounds may also include monomeric subunits that are not linked to a heterocyclic base moiety, thereby providing abasic sites. In certain embodiments, the linkages joining the monomeric subunits, the sugar moieties or surrogates and the heterocyclic base moieties can be independently modified. In certain embodiments, the linkage-sugar unit, which may or may not include a heterocyclic base, may be substituted with a mimetic such as the monomers in peptide nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" or "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linker" or "linker" in the context of a conjugate group means a portion of a conjugate group comprising any atom or group of atoms and which covalently link (1) an oligonucleotide to another portion of the conjugate group or (2) two or more portions of the conjugate group.

Conjugate groups are shown herein as radicals, providing a bond for forming covalent attachment to an oligomeric compound such as an antisense oligonucleotide. In certain embodiments, the point of attachment on the oligomeric compound is the 3'-oxygen atom of the 3'-hydroxyl group of the 3' terminal nucleoside of the oligomeric compound. In certain embodiments the point of attachment on the oligomeric compound is the 5'-oxygen atom of the 5'-hydroxyl group of the 5' terminal nucleoside of the oligomeric compound. In certain embodiments, the bond for forming attachment to the oligomeric compound is a cleavable bond. In certain such embodiments, such cleavable bond constitutes all or part of a cleavable moiety.

In certain embodiments, conjugate groups comprise a cleavable moiety (e.g., a cleavable bond or cleavable nucleoside) and a carbohydrate cluster portion, such as a GalNAc cluster portion. Such carbohydrate cluster portion comprises: a targeting moiety and, optionally, a conjugate linker. In certain embodiments, the carbohydrate cluster portion is identified by the number and identity of the ligand. For example, in certain embodiments, the carbohydrate cluster portion comprises 3 GalNAc groups and is designated "$GalNAc_3$". In certain embodiments, the carbohydrate cluster portion comprises 4 GalNAc groups and is designated "$GalNAc_4$". Specific carbohydrate cluster portions (having specific tether, branching and conjugate linker groups) are described herein and designated by Roman numeral followed by subscript "a". Accordingly "$GalNac_3$-1a" refers to a specific carbohydrate cluster portion of a conjugate group having 3 GalNac groups and specifically identified tether, branching and linking groups. Such carbohydrate cluster fragment is attached to an oligomeric compound via a cleavable moiety, such as a cleavable bond or cleavable nucleoside.

As used herein, "cleavable moiety" means a bond or group that is capable of being split under physiological conditions. In certain embodiments, a cleavable moiety is cleaved inside a cell or sub-cellular compartments, such as a lysosome. In certain embodiments, a cleavable moiety is cleaved by endogenous enzymes, such as nucleases. In certain embodiments, a cleavable moiety comprises a group of atoms having one, two, three, four, or more than four cleavable bonds.

As used herein, “cleavable bond” means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

As used herein, “carbohydrate cluster” means a compound having one or more carbohydrate residues attached to a scaffold or linker group. (see, e.g., Maier et al., “Synthesis of Antisense Oligonucleotides Conjugated to a Multivalent Carbohydrate Cluster for Cellular Targeting,” *Bioconjugate Chemistry,* 2003, (14): 18-29, which is incorporated herein by reference in its entirety, or Rensen et al., “Design and Synthesis of Novel N-Acetylgalactosamine-Terminated Glycolipids for Targeting of Lipoproteins to the Hepatic Asiaglycoprotein Receptor,” *J. Med. Chem.* 2004, (47): 5798-5808, for examples of carbohydrate conjugate clusters).

As used herein, “carbohydrate derivative” means any compound which may be synthesized using a carbohydrate as a starting material or intermediate.

As used herein, “carbohydrate” means a naturally occurring carbohydrate, a modified carbohydrate, or a carbohydrate derivative.

As used herein “protecting group” means any compound or protecting group known to those having skill in the art. Non-limiting examples of protecting groups may be found in “Protective Groups in Organic Chemistry”, T. W. Greene, P. G. M. Wuts, ISBN 0-471-62301-6, John Wiley & Sons, Inc, New York, which is incorporated herein by reference in its entirety.

As used herein, “single-stranded” means an oligomeric compound that is not hybridized to its complement and which lacks sufficient self-complementarity to form a stable self-duplex.

As used herein, “double stranded” means a pair of oligomeric compounds that are hybridized to one another or a single self-complementary oligomeric compound that forms a hairpin structure. In certain embodiments, a double-stranded oligomeric compound comprises a first and a second oligomeric compound.

As used herein, “antisense compound” means a compound comprising or consisting of an oligonucleotide at least a portion of which is complementary to a target nucleic acid to which it is capable of hybridizing, resulting in at least one antisense activity.

As used herein, “antisense activity” means any detectable and/or measurable change attributable to the hybridization of an antisense compound to its target nucleic acid. In certain embodiments, antisense activity includes modulation of the amount or activity of a target nucleic acid transcript (e.g. mRNA). In certain embodiments, antisense activity includes modulation of the splicing of pre-mRNA.

As used herein, “RNase H based antisense compound” means an antisense compound wherein at least some of the antisense activity of the antisense compound is attributable to hybridization of the antisense compound to a target nucleic acid and subsequent cleavage of the target nucleic acid by RNase H.

As used herein, “RISC based antisense compound” means an antisense compound wherein at least some of the antisense activity of the antisense compound is attributable to the RNA Induced Silencing Complex (RISC).

As used herein, “detecting” or “measuring” means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, “detectable and/or measureable activity” means a statistically significant activity that is not zero.

As used herein, “essentially unchanged” means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, “expression” means the process by which a gene ultimately results in a protein. Expression includes, but is not limited to, transcription, post-transcriptional modification (e.g., splicing, polyadenlyation, addition of 5'-cap), and translation.

As used herein, “target nucleic acid” means a nucleic acid molecule to which an antisense compound is intended to hybridize to result in a desired antisense activity. Antisense oligonucleotides have sufficient complementarity to their target nucleic acids to allow hybridization under physiological conditions.

As used herein, “nucleobase complementarity” or “complementarity” when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, “non-complementary” in reference to nucleobases means a pair of nucleobases that do not form hydrogen bonds with one another.

As used herein, “complementary” in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "chemical motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein the term "metabolic disorder" means a disease or condition principally characterized by dysregulation of metabolism—the complex set of chemical reactions associated with breakdown of food to produce energy.

As used herein, the term "cardiovascular disorder" means a disease or condition principally characterized by impaired function of the heart or blood vessels.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein, "prodrug" means an inactive or less active form of a compound which, when administered to a subject, is metabolized to form the active, or more active, compound (e.g., drug).

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present disclosure have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl ($—C(O)R_{aa}$), carboxyl ($—C(O)O—R_{aa}$), aliphatic groups, alicyclic groups, alkoxy, substituted oxy ($—O—R_{aa}$), aryl, aralkyl, heterocyclic radical, heteroaryl, heteroarylalkyl, amino ($—N(R_{bb})(R_{cc})$), imino ($=NR_{bb}$), amido ($—C(O)N—(R_{bb})(R_{cc})$ or $—N(R_{bb})C(O)R_a$), azido ($—N_3$), nitro ($—NO_2$), cyano (—CN), carbamido ($—OC(O)N(R_b)(R_{cc})$ or $—N(R_{bb})C(O)OR_{aa}$), ureido ($—N(R_{bb})C(O)N(R_{bb})(R_{cc})$), thioureido ($—N(R_{bb})C(S)N(R_{bb})(R_{cc})$), guanidinyl ($—N(R_{bb})C(=NR_{bb})N(R_{bb})(R_{cc})$), amidinyl ($—C(=NR_{bb})N(R_{bb})(R_{cc})$ or $—N(R_{bb})C(=NR_{bb})(R_{aa})$), thiol ($—SR_{bb}$), sulfinyl ($—S(O)R_{bb}$), sulfonyl ($—S(O)2R_{bb}$) and sulfonamidyl ($—S(O)2N(R_{bb})(R_{cc})$ or $—N(R_{bb})S(O)_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula-C(O)-xwhere X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "conjugate compound" means any atoms, group of atoms, or group of linked atoms suitable for use as a conjugate group. In certain embodiments, conjugate compounds may possess or impart one or more properties, including, but not limited to pharmacodynamic, pharmacokinetic, binding, absorption, cellular distribution, cellular uptake, charge and/or clearance properties.

As used herein, unless otherwise indicated or modified, the term "double-stranded" refers to two separate oligomeric compounds that are hybridized to one another. Such double stranded compounds may have one or more or non-hybridizing nucleosides at one or both ends of one or both strands (overhangs) and/or one or more internal non-hybridizing nucleosides (mismatches) provided there is sufficient complementarity to maintain hybridization under physiologically relevant conditions.

B. Certain Compounds In certain embodiments, the invention provides conjugated antisense compounds comprising antisense oligonucleoitdes and a conjugate.

a. Certain Antisense Oligonucleotides

In certain embodiments, the invention provides antisense oligonucleotides. Such antisense oligonucleotides comprise linked nucleosides, each nucleoside comprising a sugar moiety and a nucleobase. The structure of such antisense oligonucleotides may be considered in terms of chemical features (e.g., modifications and patterns of modifications) and nucleobase sequence (e.g., sequence of antisense oligonucleotide, idenity and sequence of target nucleic acid).

i. Certain Chemistry Features

In certain embodiments, antisense oligonucleotide comprise one or more modification. In certain such embodiments, antisense oligonucleotides comprise one or more modified nucleosides and/or modified internucleoside linkages. In certain embodiments, modified nucleosides comprise a modified sugar moirty and/or modified nucleobase.

1. Certain Sugar Moieties

In certain embodiments, compounds of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substitued sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'—F, 2'—$OCH_3$ ("OMe" or "O-methyl"), and 2'-$O(CH_2)_2OCH_3$ ("MOE"). In certain embodiments, sugar substituents at the 2' position is selected from allyl, amino, azido, thio, O-allyl, O-$C_1$-$C_{10}$ alkyl, O-$C_1$-$C_{10}$ substituted alkyl; $OCF_3$, $O(CH_2)_2SCH_3$, $O(CH_2)_2$—O—$N(R_m)(R_n)$, and O—$CH_2$—C(═O)—$N(R_m)(R_n)$, where each $R_m$ and $R_n$ is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'—F-5'-methyl sugar moieties (see, e.g., PCT International Application WO 2008/101157, for additional 5', 2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, $CF_3$, $OCF_3$, O, S, or N $(R_m)$-alkyl; O, S, or N $(R_m)$-alkenyl; O, S or N $(R_m)$-alkynyl; O-alkylenyl-O-alkyl, alkynyl, alkaryl, aralkyl, O-alkaryl, O-aralkyl, $O(CH_2)_2SCH_3$, O—$(CH_2)_2$—O—$N(R_m)(R_n)$ or O—$CH_2$—C(═O)—N $(R_m)(R_n)$, where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH═$CH_2$, O—$CH_2$—CH═$CH_2$, $OCH_2CH_2OCH_3$, $O(CH_2)$ $2SCH_3$, O—$(CH_2)_2$—O—$N(R_m)(R_n)$, $O(CH_2)_2O(CH_2)_2N$ $(CH_3)_2$, and N-substituted acetamide (O—$CH_2$—C(═O)—$N(R_m)$ $(R_n)$ where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, $O(CH_2)$ $2SCH_3$, O—$(CH_2)_2$—O—$N(CH_3)_2$, —$O(CH_2)_2O(CH_2)_2N(CH_3)_2$, and O—$CH_2$—C(═O)—N(H) $CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —$[C(R_a)(R_b)]_n$—, —$[C(R_a)(R_b)]_n$—O—, —$C(R_aR_b)$—N(R)—O— or, —$C(R_aR_b)$—O—N(R)—; 4'—$CH_2$-2', 4'-$(CH_2)_2$-2', 4'-$(CH_2)_3$-2', 4'-$(CH_2)$—O-2' (LNA); 4'-$(CH_2)$-S-2'; 4'-$(CH_2)_2$-O-2' (ENA); 4'—$CH(CH_3)$—O-2' (cEt) and 4'—$CH(CH_2OCH_3)$—O-2', and analogs thereof (see, e.g., U.S. Pat. No. 7,399,845, issued on Jul. 15, 2008); 4'-$C(CH_3)(CH_3)$—O-2'and analogs thereof, (see, e.g., WO2009/006478, published Jan. 8, 2009); 4'—$CH_2$-$N(OCH_3)$-2' and analogs thereof (see, e.g., WO2008/150729, published Dec. 11, 2008); 4'—$CH_2$—O—N $(CH_3)$-2' (see, e.g., US2004/0171570, published Sep. 2, 2004); 4'—$CH_2$—O—N(R)-2', and 4'—$CH_2$—N(R)—O-2'-, wherein each R is, independently, H, a protecting group, or $C_1$-$C_{12}$ alkyl; 4'—$CH_2$—N(R)—O—$_2$', wherein R is H, $C_1$-$C_{12}$ alkyl, or a protecting group (see, U.S. Pat. No. 7,427,672, issued on Sep. 23, 2008); 4'—$CH_2$—$C(H)(CH_3)$-2' (see, e.g., Chattopadhyaya, et al., J. Org. Chem., 2009, 74, 118-134); and 4'—$CH_2$—C(═$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —$[C(R_a)(R_b)]_n$—, —$C(R_a)$═$C(R_b)$—, —$C(R_a)$═N—, —C(═$NR_a$)—, —C(═O)—, —C(═S)—, —O—, —$Si(R_a)_2$—, —$S(═O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $_0J_1$, $NJ_1J_2$, $SJ_1$, $N_3$, $COOJ_1$, acyl (C(═O)—H), substituted acyl, CN, sulfonyl ($S(═O)_2$-$J_1$), or sulfoxyl (S(═O)—$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) a-L-Methyleneoxy (4'—$CH_2$—O-2') BNA, (B) β-D-Methyleneoxy (4'—$CH_2$—O-2') BNA (also referred to as locked nucleic acid or LNA), (C) Ethyleneoxy (4'-$(CH_2)$ 2-O-2') BNA, (D) Aminooxy (4'—$CH_2$—O—N(R)-2') BNA, (E) Oxyamino (4'—$CH_2$—N(R)—O-2') BNA, (F) Methyl(methyleneoxy) (4'—$CH(CH_3)$—O-2') BNA (also referred to as constrained ethyl or cEt), (G) methylene-thio (4'—$CH_2$-S-2') BNA, (H) methylene-amino (4'—$CH_2$—N(R)-2') BNA, (I) methyl carbocyclic (4'—$CH_2$-$CH(CH_3)$-2') BNA, and (J) propylene carbocyclic (4'-$(CH_2)$ 3-2') BNA as depicted below.

(A)

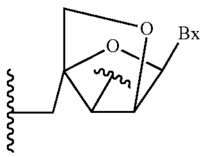

(B)

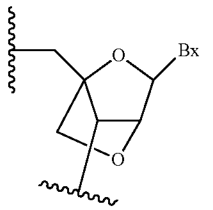

(C)

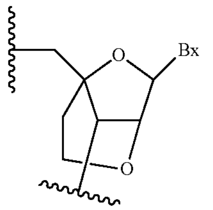

(D)

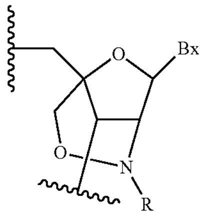

(E)

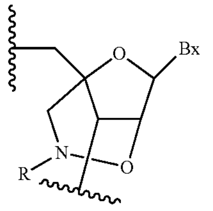

(F)

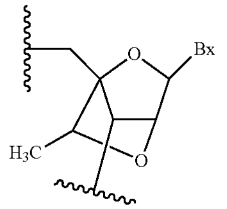

(G)

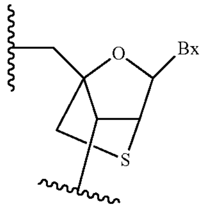

-continued (H)

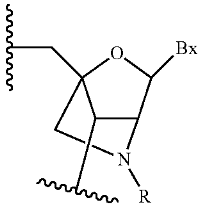

(I)

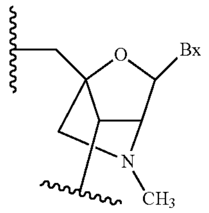

(J)

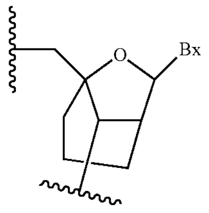

wherein Bx is a nucleobase moiety and R is, independently, H, a protecting group, or $C_1$-$C_{12}$ alkyl. Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A,* 2000, 97, 5633-5638; Kumar et al., *Bioorg. Med. Chem. Lett.,* 1998, 8, 2219-2222; Singh et al., J. Org. Chem., 1998, 63, 10035-10039; Srivastava et al., *J. Am. Chem. Soc.,* 129 (26) 8362-8379 (Jul. 4, 2007); Elayadi et al., *Curr. Opinion Invens. Drugs,* 2001, 2, 558-561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patents Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'—$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occuring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25 (22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a morphlino. Morpholino compounds and their use in oligomeric compounds has been reported in numerous patents and published articles (see for example: Braasch et al., *Biochemistry,* 2002, 41, 4503-4510; and U.S. Pat. Nos. 5,698,685; 5,166,315; 5,185,444; and 5,034,506). As used here, the term “morpholino” means a sugar surrogate having the following structure:

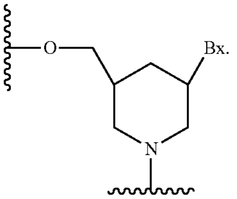

In certain embodiments, morpholinos may be modified, for example by adding or altering various substituent groups from the above morpholino structure. Such sugar surrogates are referred to herein as “modified morpholinos.”

For another example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA)(see Leumann, C J. *Bioorg. & Med. Chem.* (2002) 10:841-854), fluoro HNA (F-HNA), and those compounds having Formula VI:

VI

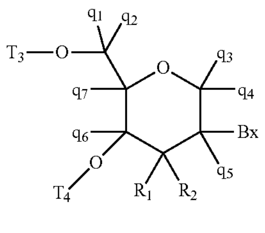

wherein independently for each of said at least one tetrahydropyran nucleoside analog of Formula VI:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, OC(=X) $J_1$, OC(=X) $NJ_1J_2$, $NJ_3C$(=X) $NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VI are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H.

In certain embodiments, at least one of $q_1$, $q_2$, $q_3$, $q_4$, $q_5$, $q_6$ and $q_7$ is methyl. In certain embodiments, THP nucleosides of Formula VI are provided wherein one of $R_1$ and $R_2$ is F. In certain embodiments, $R^1$ is fluoro and $R_2$ is H, $R_1$ is methoxy and $R_2$ is H, and $R^1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854).

Combinations of modifications are also provided without limitation, such as 2'—F-5'-methyl substituted nucleosides (see PCT International Application WO 2008/101157 Published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'—$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129 (26), 8362-8379).

In certain embodiments, the present disclosure provides oligonucleotides comprising modified nucleosides. Those modified nucleotides may include modified sugars, modified nucleobases, and/or modified linkages.

The specific modifications are selected such that the resulting oligonucleotides possess desireable characteristics. In certain embodmiments, oligonucleotides comprise one or more RNA-like nucleosides. In certain embodiments, oligonucleotides comprise one or more DNA-like nucleotides.

2. Certain Nucleobase Modifications

In certain embodiments, nucleosides of the present disclosure comprise one or more unmodified nucleobases. In certain embodiments, nucleosides of the present disclosure comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cyto-sines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2 (3H)-one), phenothiazine cytidine ([1]H-pyrimido[5,4-b][1,4]benzothiazin-2 (3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2': 4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

3. Certain Internucleoside Linkages

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (PO), phosphotriesters, methylphosphonates, phosphoramidate, and phosphorothioates (PS). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)-S—); siloxane (—O—Si (H) 2-O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or(S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'—$CH_2$—$N(CH_3)$—O-5'), amide-3 (3'—$CH_2$—C(=O)—N(H)-5'), amide-4 (3'—$CH_2$—N(H)—C(=O)-5'), formacetal (3'-O—$CH_2$—O-5'), and thioformacetal (3'-S-$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

4. Certain Motifs

In certain embodiments, antisense oligonucleotides comprise one or more modified nucleoside (e.g., nucleoside comprising a modified sugar and/or modified nucleobase) and/or one or more modified internucleoside linkage. The pattern of such modifications on an oligonucleotide is referred to herein as a motif. In certain embodiments, sugar, nucleobase, and linkage motifs are independent of one another.

a. Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

i. Certain 5'-Wings

In certain embodiments, the 5'-wing of a gapmer consists of 1 to 8 linked nucleosides. In certain embodiments, the 5'-wing of a gapmer consists of 1 to 7 linked nucleosides. In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

ii. Certain 3'-Wings

In certain embodiments, the 3'-wing of a gapmer consists of 1 to 8 linked nucleosides. In certain embodiments, the 3'-wing of a gapmer consists of 1 to 7 linked nucleosides. In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

iii. Certain Central Regions (gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)—F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleosides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

b. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides of the present disclosure comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 7 phosphorothioate internucleoside linkages. In certain embodiments, the oligonucleotide comprises at least 8 phosphorothioate internucleoside linkages. In certain embodiments, the oligonucleotide comprises at least 9 phosphorothioate internucleoside linkages. In certain embodiments, the oligonucleotide comprises at least 10 phosphorothioate internucleoside linkages. In certain embodiments, the oligonucleotide comprises at least 11 phosphorothioate internucleoside linkages. In certain embodiments, the oligonucleotide comprises at least 12 phosphorothioate internucleoside linkages. In certain embodiments, the oligonucleotide comprises at least 13 phosphorothioate internucleoside linkages. In certain embodiments, the oligonucleotide comprises at least 14 phosphorothioate internucleoside linkages.

In certain embodiments, the oligonucleotide comprises at least one block of at least 6 consecutive phosphorothioate internucleoside linkages. In certain embodiments, the oligonucleotide comprises at least one block of at least 7 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 9 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide. In certain embodiments, the oligonucleotide comprises less than 15 phosphorothioate internucleoside linkages. In certain embodiments, the oligonucleotide comprises less than 14 phosphorothioate internucleoside linkages. In certain embodiments, the oligonucleotide comprises less than 13 phosphorothioate internucleoside linkages. In certain embodiments, the oligonucleotide comprises less than 12 phosphorothioate internucleoside linkages. In certain embodiments, the oligonucleotide comprises less than 11 phosphorothioate internucleoside linkages. In certain embodiments, the oligonucleotide comprises less than 10 phosphorothioate internucleoside linkages. In certain embodiments, the oligonucleotide comprises less than 9 phosphorothioate internucleoside linkages. In certain embodiments, the oligonucleotide comprises less than 8 phosphorothioate internucleoside linkages. In certain embodiments, the oligonucleotide comprises less than 7 phosphorothioate internucleoside linkages. In certain embodiments, the oligonucleotide comprises less than 6 phosphorothioate internucleoside linkages. In certain embodiments, the oligonucleotide comprises less than 5 phosphorothioate internucleoside linkages.

c. Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

In certain embodiments, chemical modifications to nucleobases comprise attachment of certain conjugate groups to nucleobases. In certain embodiments, each purine or each pyrimidine in an oligonucleotide may be optionally modified to comprise a conjugate group.

d. Certain Overall Lengths

In certain embodiments, the present disclosure provides oligonucleotides of any of a variety of ranges of lengths. In certain embodiments, oligonucleotides consist of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the oligonucleotide may consist of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligonucleotide of a compound is limited, whether to a range or to a specific number, the compound may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugate groups, terminal groups, or other substituents.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

5. Certain Antisense Oligonucleotide Chemistry Motifs

In certain embodiments, the chemical structural features of antisense oligonucleotides are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides.

In certain embodiments, the selection of internucleoside linkage and nucleoside modification are not independent of one another.

i. Certain Sequences and Targets

In certain embodiments, the invention provides antisense oligonucleotides having a sequence complementary to a target nucleic acid. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessibility of the target region of one nucleic acid molecule compared to the other.

In certain embodiments, the present disclosure provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA: DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

In certain embodiments, a conjugate group comprises a cleavable moiety. In certain embodiments, a conjugate group comprises one or more cleavable bond. In certain embodiments, a conjugate group comprises a linker. In certain embodiments, a linker comprises a protein binding moiety. In certain embodiments, a conjugate group comprises a cell-targeting moiety (also referred to as a cell-targeting group). In certain embodiments a cell-targeting moiety comprises a branching group. In certain embodiments, a cell-targeting moiety comprises one or more tethers. In certain embodiments, a cell-targeting moiety comprises a carbohydrate or carbohydrate cluster.

ii. Certain Cleavable Moieties

In certain embodiments, a cleavable moiety is a cleavable bond. In certain embodiments, a cleavable moiety comprises a cleavable bond. In certain embodiments, the conjugate group comprises a cleavable moiety. In certain such embodiments, the cleavable moiety attaches to the antisense oligonucleotide. In certain such embodiments, the cleavable moiety attaches directly to the cell-targeting moiety. In certain such embodiments, the cleavable moiety attaches to the conjugate linker. In certain embodiments, the cleavable moiety comprises a phosphate or phosphodiester. In certain embodiments, the cleavable moiety is a cleavable nucleoside or nucleoside analog. In certain embodiments, the nucleoside or nucleoside analog comprises an optionally protected heterocyclic base selected from a purine, substituted purine, pyrimidine or substituted pyrimidine. In certain embodiments, the cleavable moiety is a nucleoside comprising an optionally protected heterocyclic base selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. In certain embodiments, the cleavable moiety is 2'-deoxy nucleoside that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester or phosphorothioate linkage. In certain embodiments, the cleavable moiety is 2'-deoxy adenosine that is attached to the 3' position of the antisense oligonucleotide by a phosphodiester linkage and is attached to the linker by a phosphodiester linkage.

In certain embodiments, the cleavable moiety is attached to the 3' position of the antisense oligonucleotide. In certain embodiments, the cleavable moiety is attached to the 5' position of the antisense oligonucleotide. In certain embodiments, the cleavable moiety is attached to a 2' position of the antisense oligonucleotide. In certain embodiments, the cleavable moiety is attached to the antisense oligonucleotide by a phosphodiester linkage. In certain embodiments, the cleavable moiety is attached to the linker by either a phosphodiester or a phosphorothioate linkage. In certain embodiments, the cleavable moiety is attached to the linker by a phosphodiester linkage. In certain embodiments, the conjugate group does not include a cleavable moiety.

In certain embodiments, the cleavable moiety is cleaved after the complex has been administered to an animal only after being internalized by a targeted cell. Inside the cell the cleavable moiety is cleaved thereby releasing the active antisense oligonucleotide. While not wanting to be bound by theory it is believed that the cleavable moiety is cleaved by one or more nucleases within the cell. In certain embodiments, the one or more nucleases cleave the phosphodiester linkage between the cleavable moiety and the linker. In certain embodiments, the cleavable moiety has a structure selected from among the following:

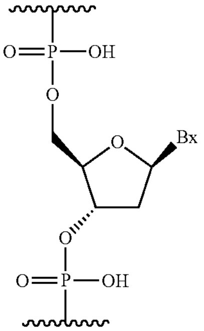

;

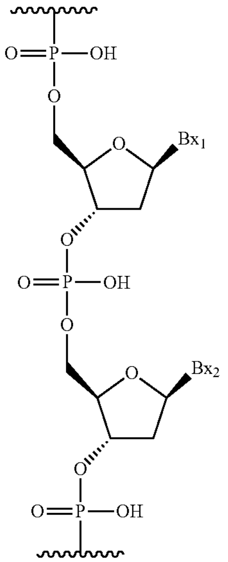

; and

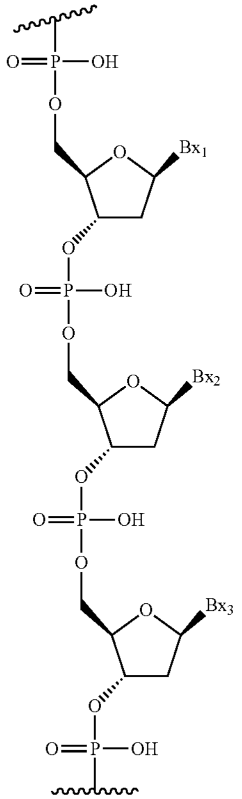

wherein each of Bx, $Bx_1$, $Bx_2$, and $Bx_3$ is independently a heterocyclic base moiety. In certain embodiments, the cleavable moiety has a structure selected from among the following:

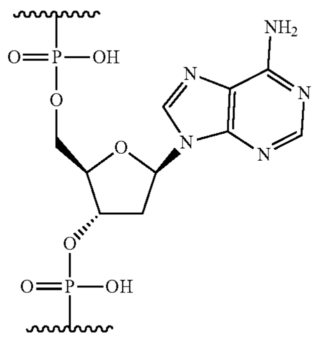 [SMILES: *P(=O)(O)OC[C@H]1O[C@@H](n2cnc3c(N)ncnc32)C[C@@H]1OP(*)(=O)O]

iii. Certain Linkers

In certain embodiments, the conjugate groups comprise a linker. In certain such embodiments, the linker is covalently bound to the cleavable moiety. In certain such embodiments, the linker is covalently bound to the antisense oligonucleotide. In certain embodiments, the linker is covalently bound to a cell-targeting moiety. In certain embodiments, the linker further comprises a covalent attachment to a solid support. In certain embodiments, the linker further comprises a covalent attachment to a protein binding moiety. In certain embodiments, the linker further comprises a covalent attachment to a solid support and further comprises a covalent attachment to a protein binding moiety. In certain embodiments, the linker includes multiple positions for attachment of tethered ligands. In certain embodiments, the linker includes multiple positions for attachment of tethered ligands and is not attached to a branching group. In certain embodiments, the linker further comprises one or more cleavable bond. In certain embodiments, the conjugate group does not include a linker.

In certain embodiments, the linker includes at least a linear group comprising groups selected from alkyl, amide, disulfide, polyethylene glycol, ether, thioether (—S—) and hydroxylamino (—O—N(H)—) groups. In certain embodiments, the linear group comprises groups selected from alkyl, amide and ether groups. In certain embodiments, the linear group comprises groups selected from alkyl and ether groups. In certain embodiments, the linear group comprises at least one phosphorus linking group. In certain embodiments, the linear group comprises at least one phosphodiester group. In certain embodiments, the linear group includes at least one neutral linking group. In certain embodiments, the linear group is covalently attached to the cell-targeting moiety and the cleavable moiety. In certain embodiments, the linear group is covalently attached to the cell-targeting moiety and the antisense oligonucleotide. In certain embodiments, the linear group is covalently attached to the cell-targeting moiety, the cleavable moiety and a solid support. In certain embodiments, the linear group is covalently attached to the cell-targeting moiety, the cleavable moiety, a solid support and a protein binding moiety. In certain embodiments, the linear group includes one or more cleavable bond.

In certain embodiments, the linker includes the linear group covalently attached to a scaffold group. In certain embodiments, the scaffold includes a branched aliphatic group comprising groups selected from alkyl, amide, disulfide, polyethylene glycol, ether, thioether and hydroxylamino groups. In certain embodiments, the scaffold includes a branched aliphatic group comprising groups selected from alkyl, amide and ether groups. In certain embodiments, the scaffold includes at least one mono or polycyclic ring system. In certain embodiments, the scaffold includes at least two mono or polycyclic ring systems. In certain embodiments, the linear group is covalently attached to the scaffold group and the scaffold group is covalently attached to the cleavable moiety and the linker. In certain embodiments, the linear group is covalently attached to the scaffold group and the scaffold group is covalently attached to the cleavable moiety, the linker and a solid support. In certain embodiments, the linear group is covalently attached to the scaffold group and the scaffold group is covalently attached to the cleavable moiety, the linker and a protein binding moiety. In certain embodiments, the linear group is covalently attached to the scaffold group and the scaffold group is covalently attached to the cleavable moiety, the linker, a protein binding moiety and a solid support. In certain embodiments, the scaffold group includes one or more cleavable bond.

In certain embodiments, the linker includes a protein binding moiety. In certain embodiments, the protein binding moiety is a lipid such as for example including but not limited to cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, 03-(oleoyl) lithocholic acid, 03-(oleoyl) cholenic acid, dimethoxytrityl, or phenoxazine), a vitamin (e.g., folate, vitamin A, vitamin E, biotin, pyridoxal), a peptide, a carbohydrate (e.g., monosaccharide, disaccharide, trisaccharide, tetrasaccharide, oligosaccharide, polysaccharide), an endosomolytic component, a steroid (e.g., uvaol, hecigenin, diosgenin), a terpene (e.g., triterpene, e.g., sarsasapogenin, friedelin, epifriedelanol derivatized lithocholic acid), or a cationic lipid. In certain embodiments, the protein binding moiety is a C16 to C22 long chain saturated or unsaturated fatty acid, cholesterol, cholic acid, vitamin E, adamantane or 1-pentafluoropropyl. 5

In certain embodiments, a linker has a structure selected from among:

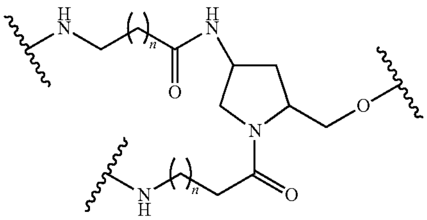
;
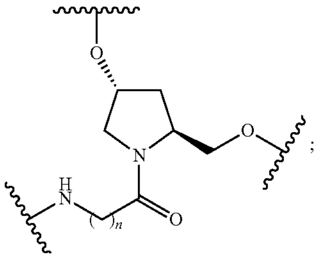
;
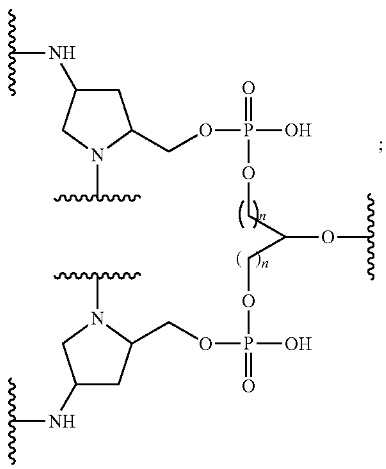
;
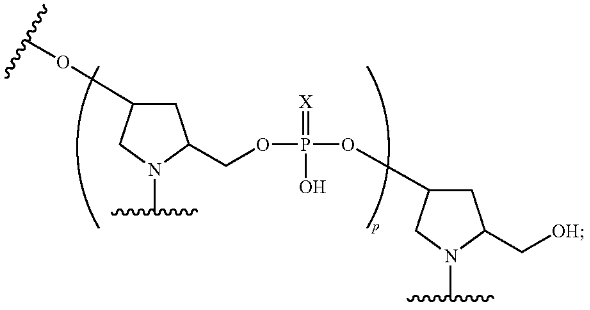
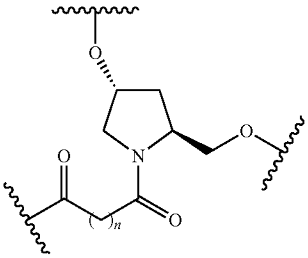
;
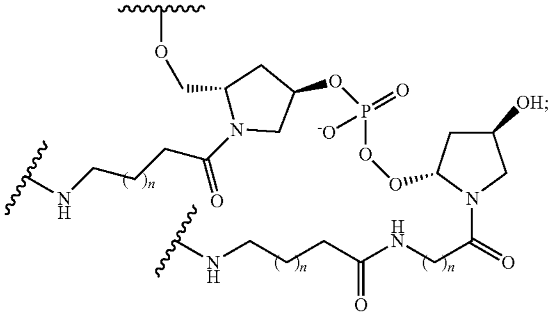
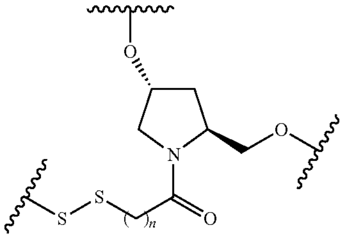
;
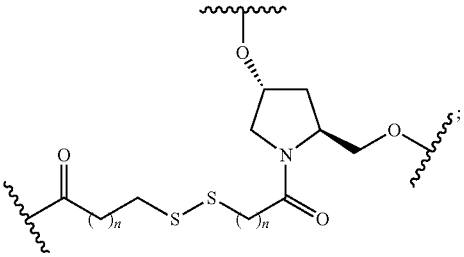
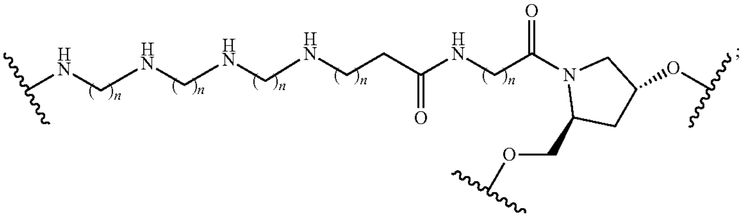

-continued
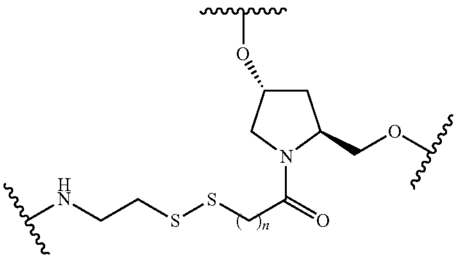
;
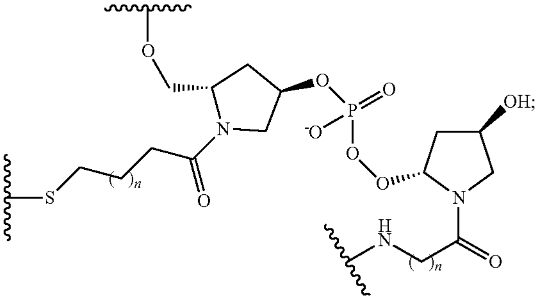
and
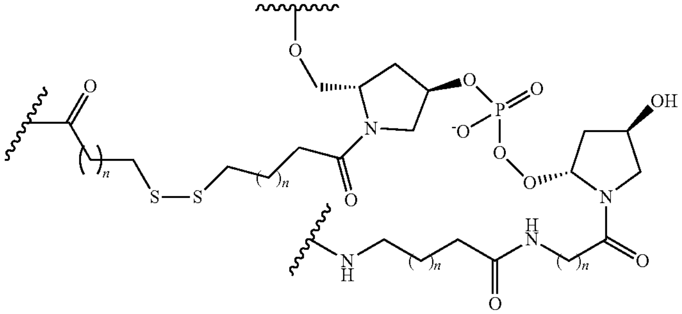
wherein each n is, independently, from 1 to 20; and p is from 1 to 6.
In certain embodiments, a linker has a structure selected from among:
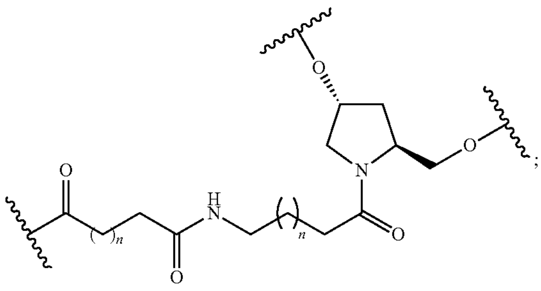
;
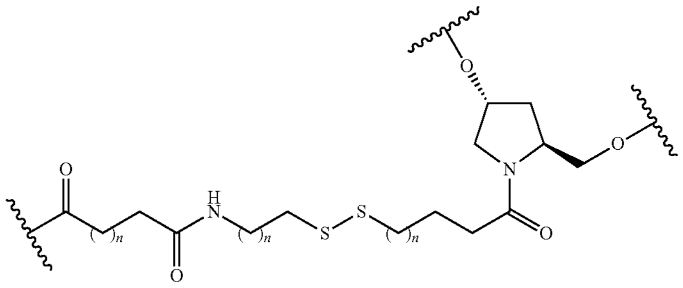
;
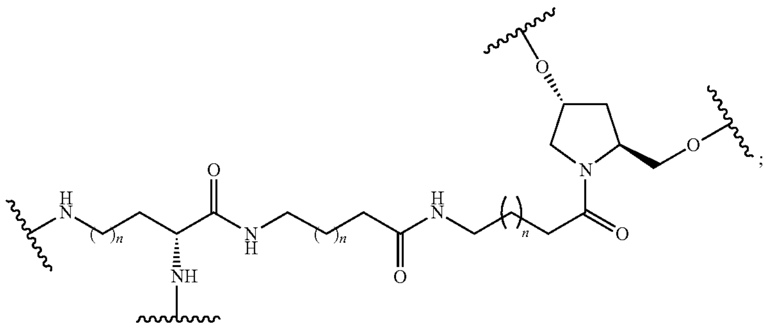
;

-continued
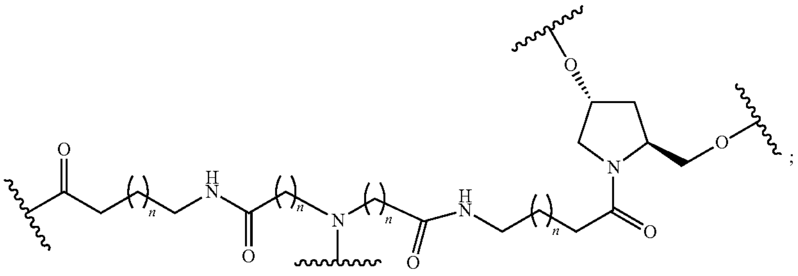
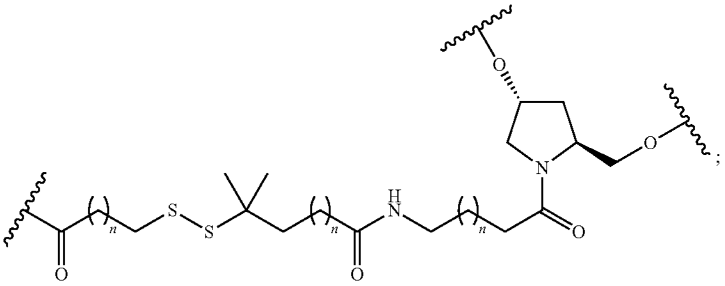
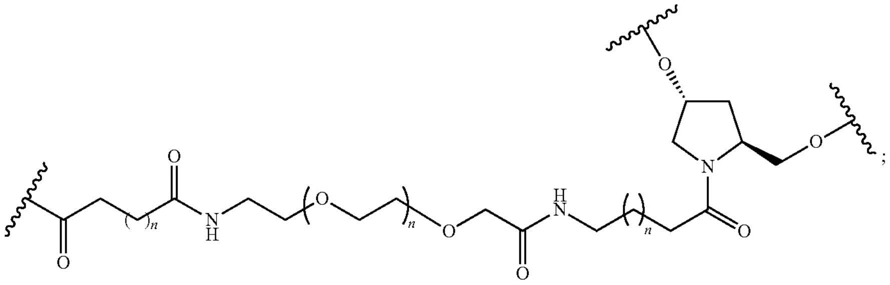
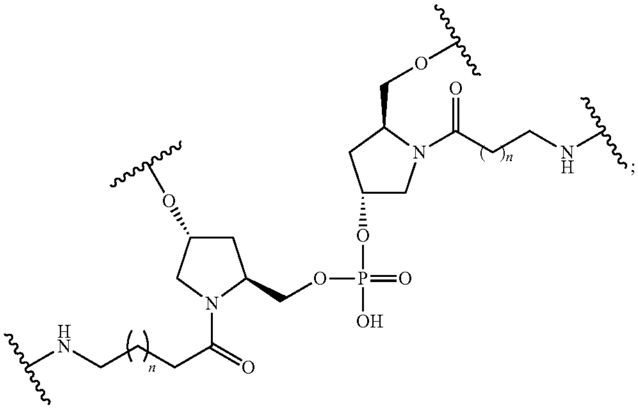
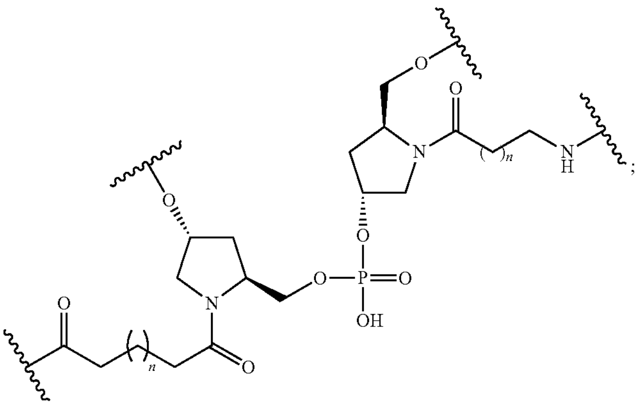
and

-continued
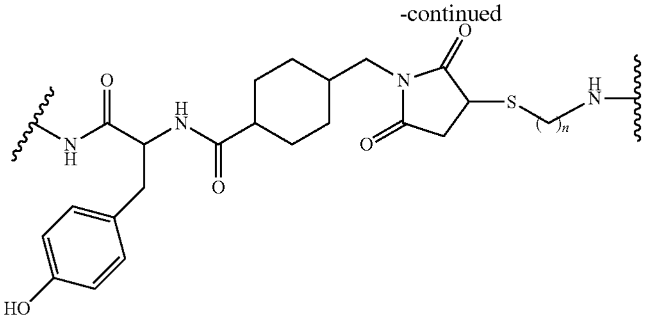
wherein each n is, independently, from 1 to 20.
In certain embodiments, a linker has a structure selected from among:
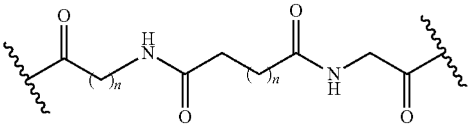
;
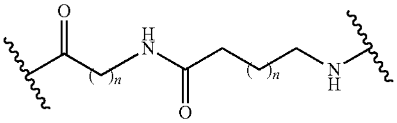
;
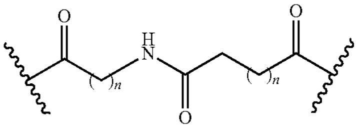
;
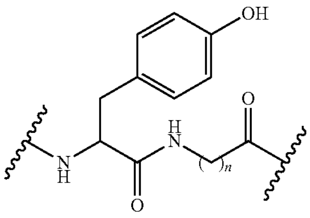
;
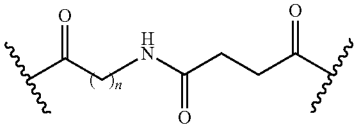
;
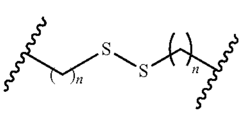
;
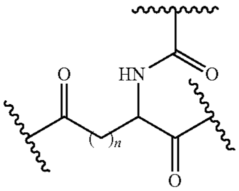
;
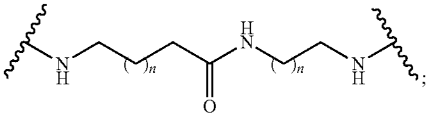
;
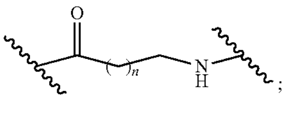
;
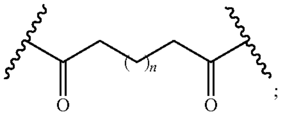
;
-continued
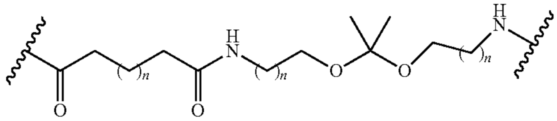
;
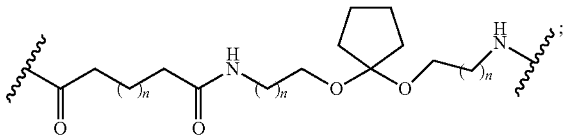
;
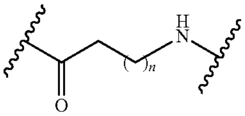
;
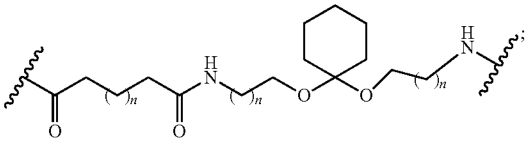
; and
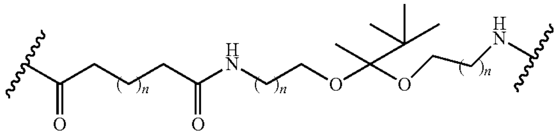
wherein n is from 1 to 20.
In certain embodiments, a linker has a structure selected from among:
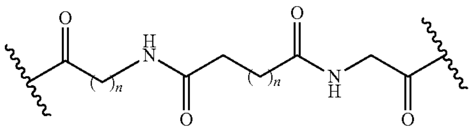
;
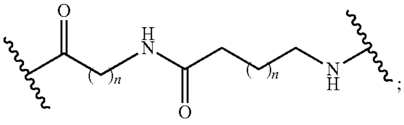
;
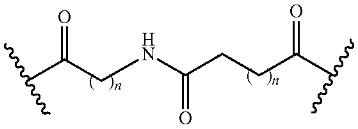
;

-continued
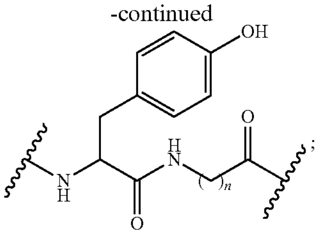
;
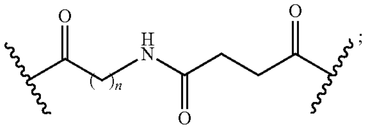
;
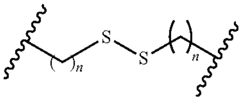
;
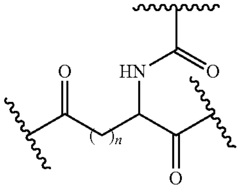
;
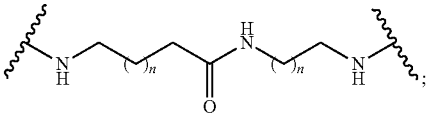
;
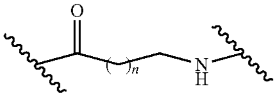
;
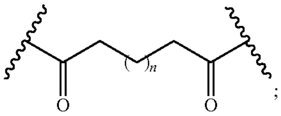
;
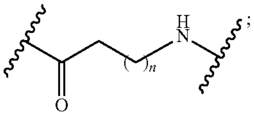
;
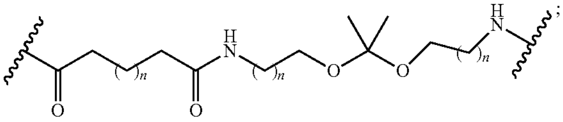
;
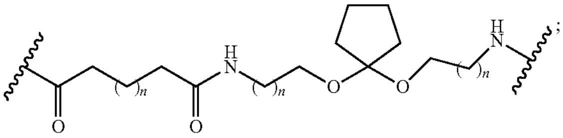
;
-continued
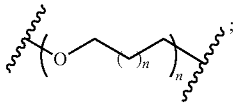
;
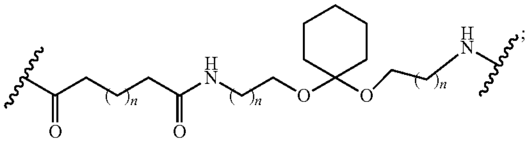
;
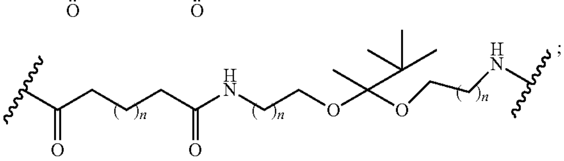
;
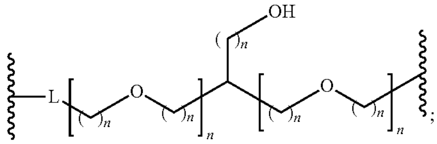
;
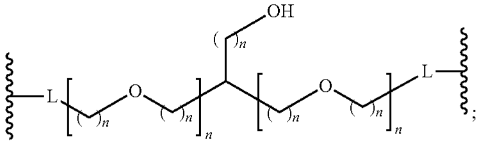
;
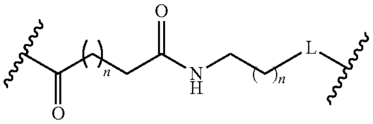
and
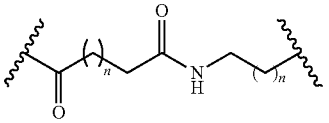
.
wherein each L is, independently, a phosphorus linking group or a neutral linking group; and
each n is, independently, from 1 to 20.
In certain embodiments, a linker has a structure selected from among:
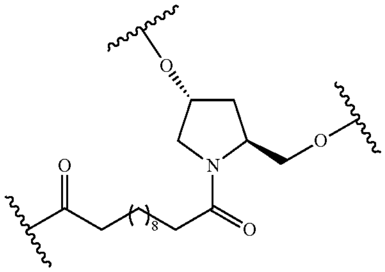
;
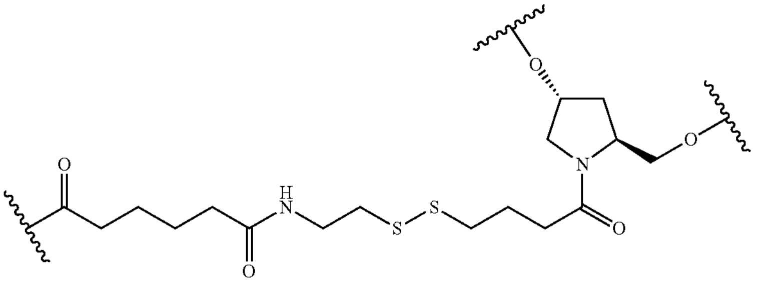
;

-continued
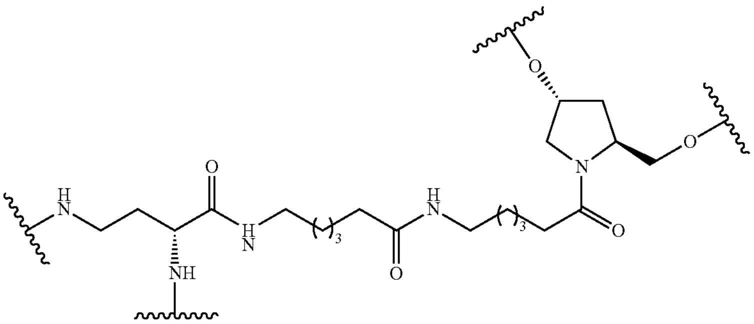
;
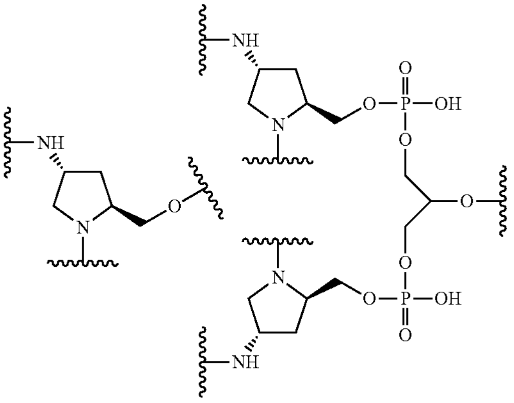
;
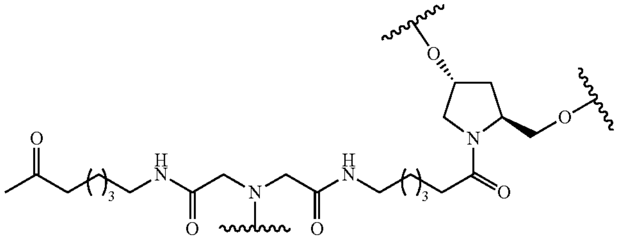
;
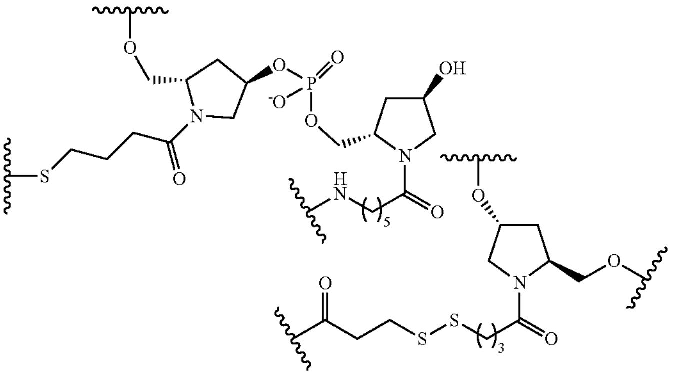
;
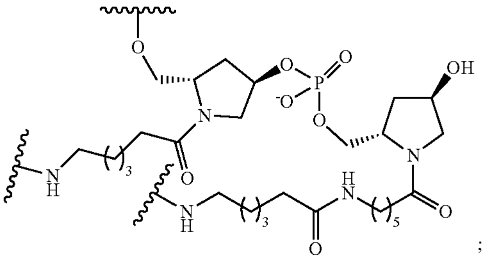
;
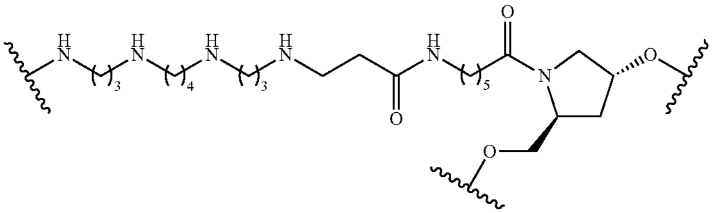
;
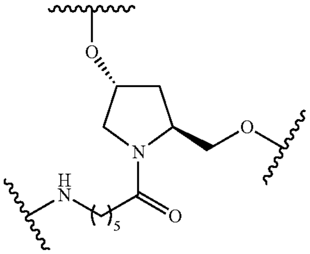
;
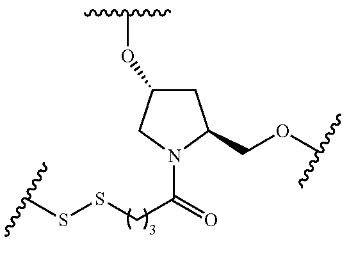
;
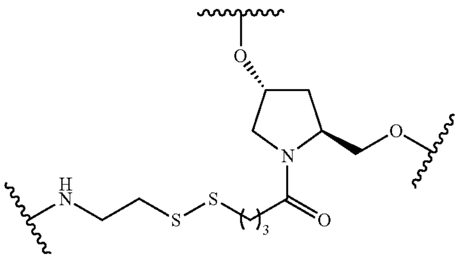
;
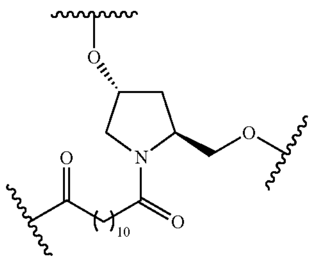
;

-continued
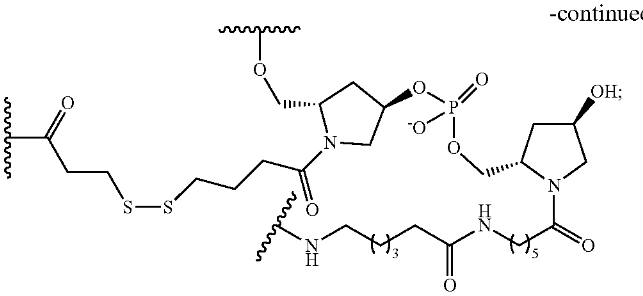
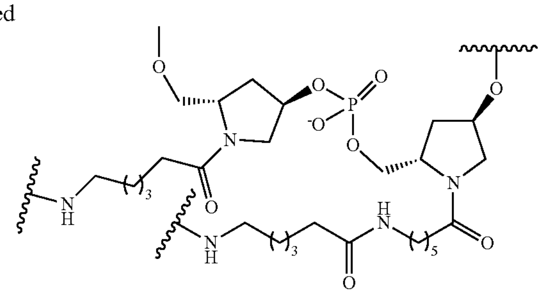
;
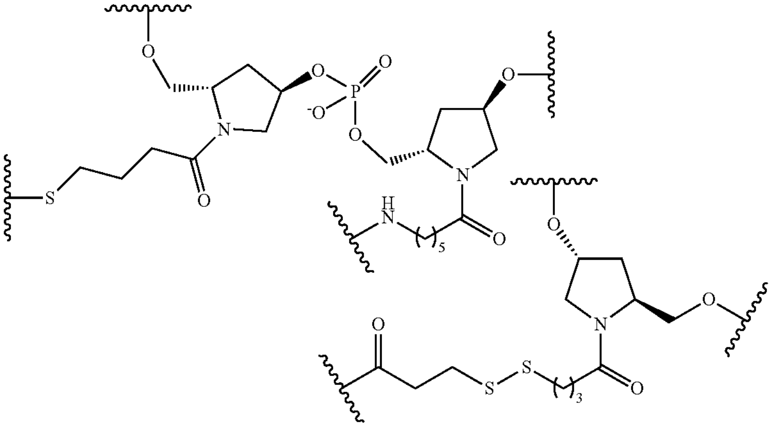
; and
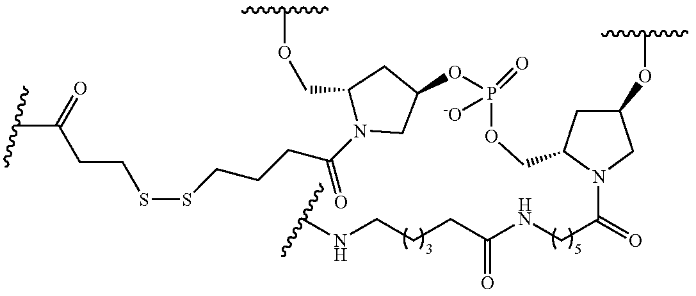
.
In certain embodiments, a linker has a structure selected from among:
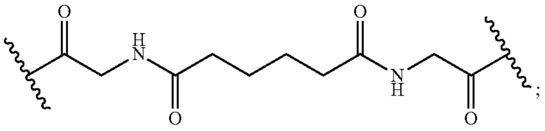
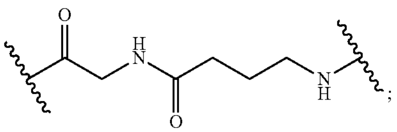
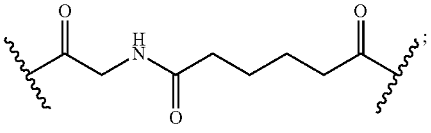
-continued
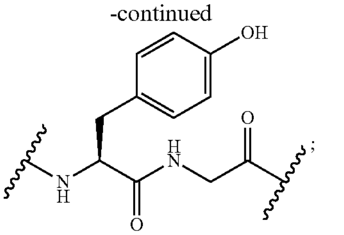
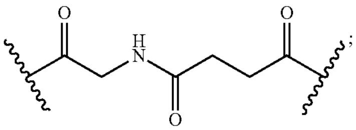
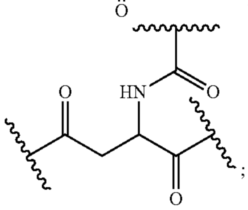
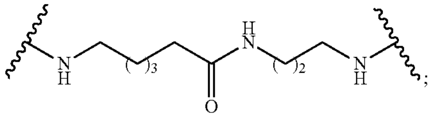

-continued
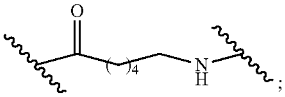
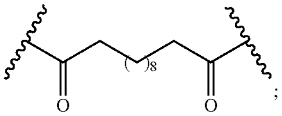
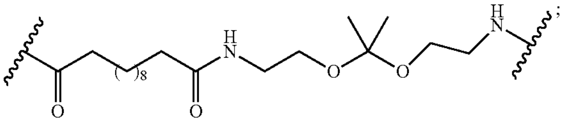
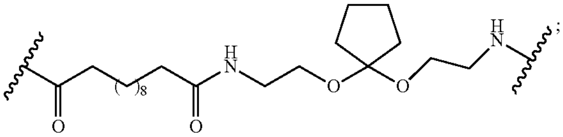
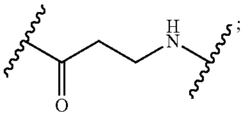
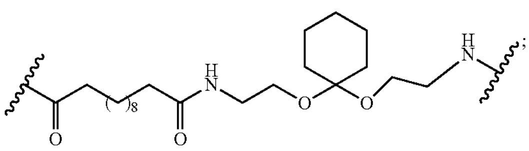
and
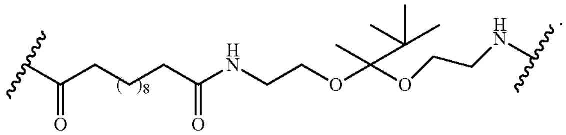
In certain embodiments, a linker has a structure selected from among:
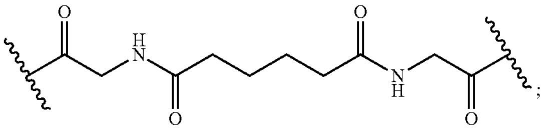
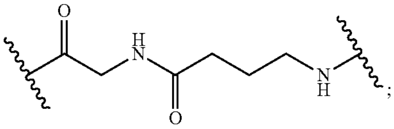
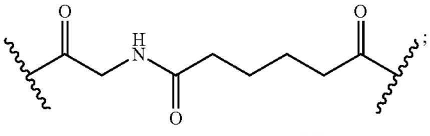
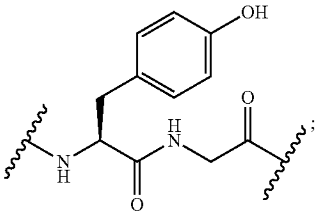
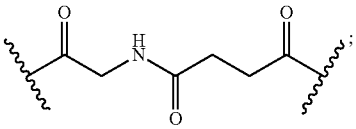
-continued
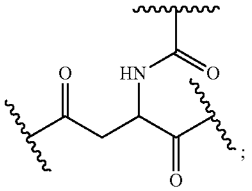
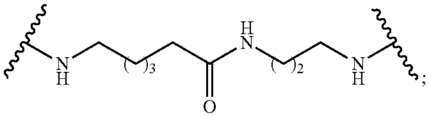
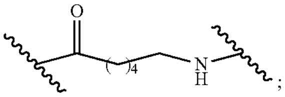
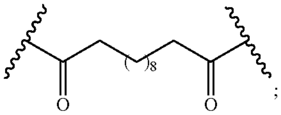
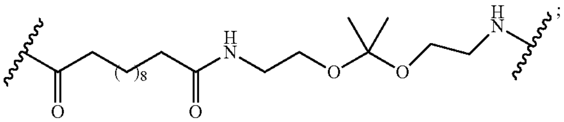
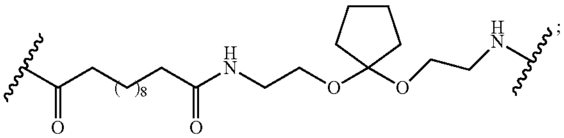
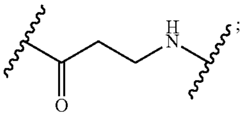
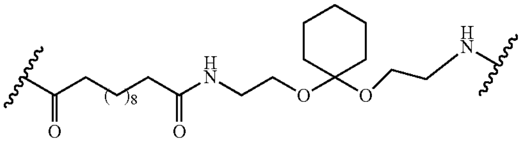
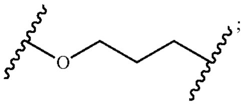
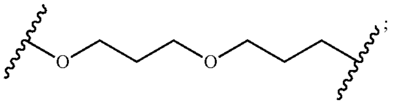
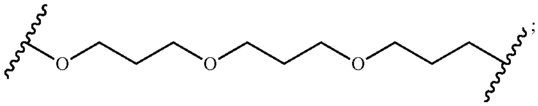
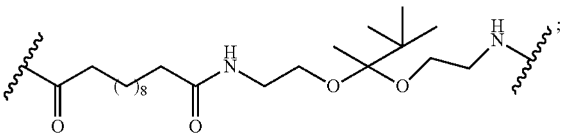
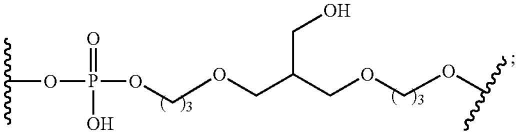
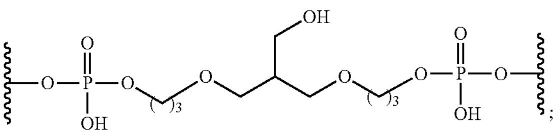

-continued

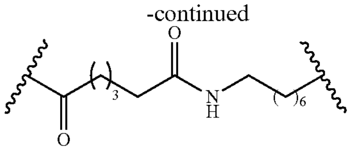

and

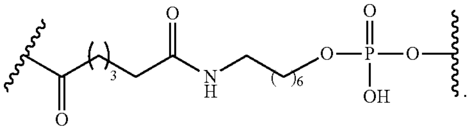

In certain embodiments, a linker has a structure selected from among:

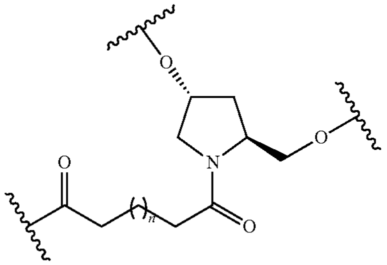

and

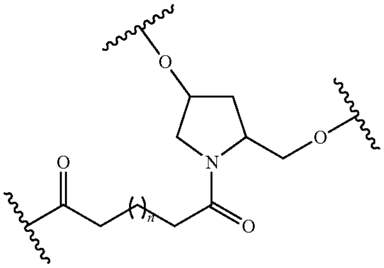

wherein n is from 1 to 20.

In certain embodiments, a linker has a structure selected from among:

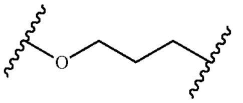

;

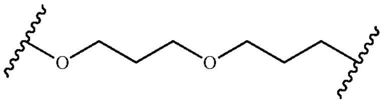

; and

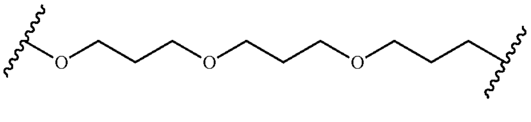

.

In certain embodiments, a linker has a structure selected from among:

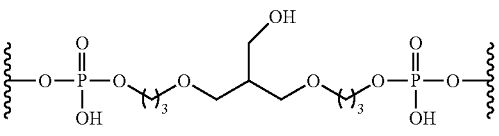

and

-continued

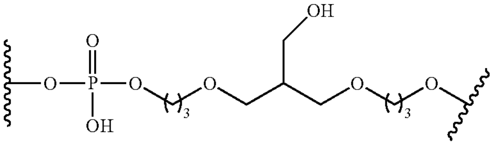

In certain embodiments, a linker has a structure selected from among:

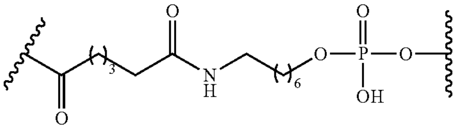

and

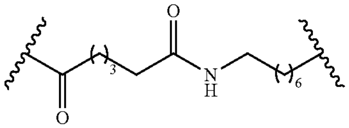

In certain embodiments, the conjugate linker has the structure:

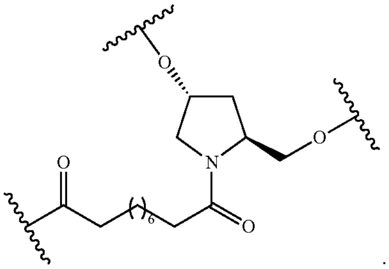

In certain embodiments, the conjugate linker has the structure:

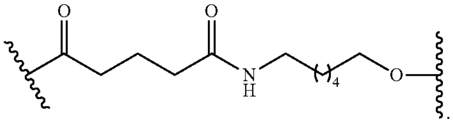

In certain embodiments, a linker has a structure selected from among:

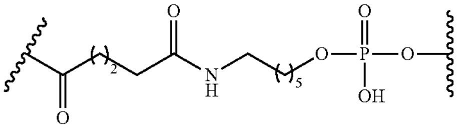

and

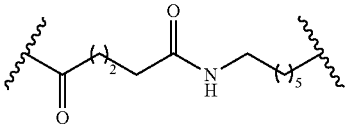

In certain embodiments, a linker has a structure selected from among:

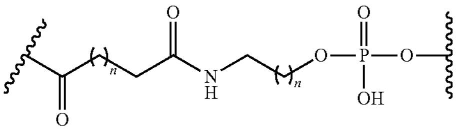

and

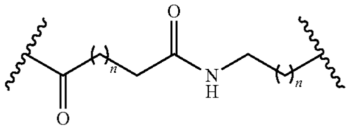

;

wherein each n is independently, 0, 1, 2, 3, 4, 5, 6, or 7.

iv. Certain Cell-Targeting Moieties

In certain embodiments, conjugate groups comprise cell-targeting moieties. Certain such cell-targeting moieties increase cellular uptake of antisense compounds. In certain embodiments, cell-targeting moieties comprise a branching group, one or more tether, and one or more ligand. In certain embodiments, cell-targeting moieties comprise a branching group, one or more tether, one or more ligand and one or more cleavable bond.

1. Certain Branching Groups

In certain embodiments, the conjugate groups comprise a targeting moiety comprising a branching group and at least two tethered ligands. In certain embodiments, the branching group attaches the conjugate linker. In certain embodiments, the branching group attaches the cleavable moiety. In certain embodiments, the branching group attaches the antisense oligonucleotide. In certain embodiments, the branching group is covalently attached to the linker and each of the tethered ligands. In certain embodiments, the branching group comprises a branched aliphatic group comprising groups selected from alkyl, amide, disulfide, polyethylene glycol, ether, thioether and hydroxylamino groups. In certain embodiments, the branching group comprises groups selected from alkyl, amide and ether groups. In certain embodiments, the branching group comprises groups selected from alkyl and ether groups. In certain embodiments, the branching group comprises a mono or polycyclic ring system. In certain embodiments, the branching group comprises one or more cleavable bond. In certain embodiments, the conjugate group does not include a branching group.

In certain embodiments, a branching group has a structure selected from among:

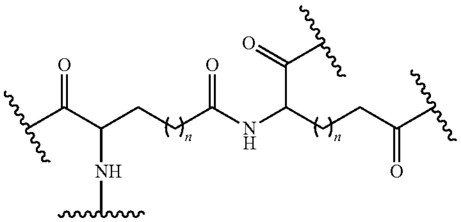

;

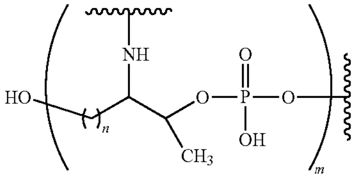

;

-continued

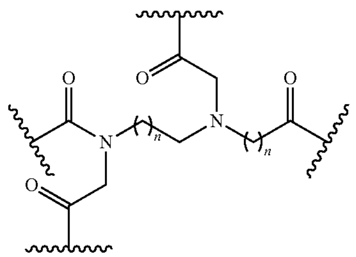

;

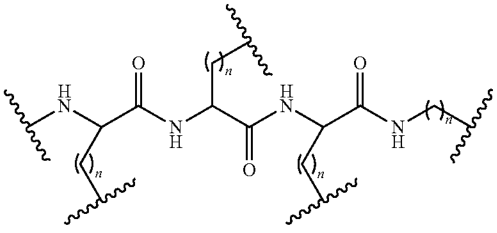

;

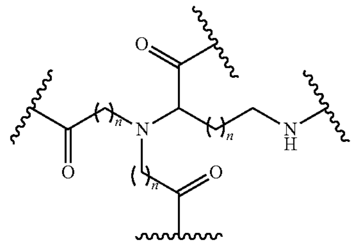

;

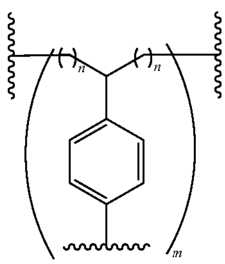

;

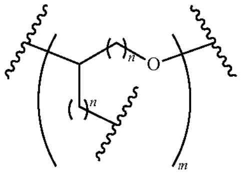

;

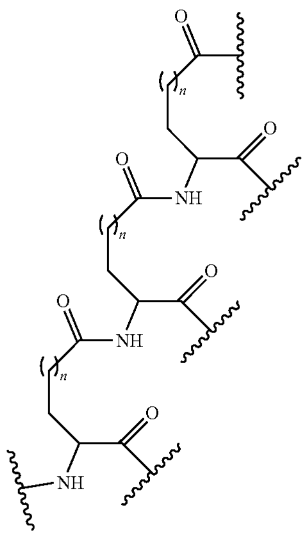

;

-continued
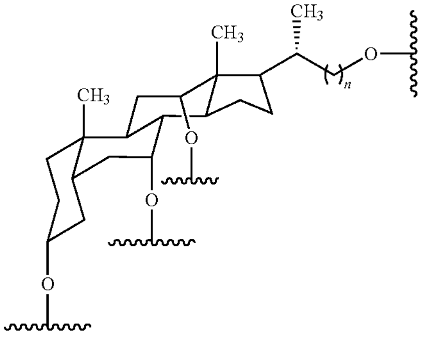
;
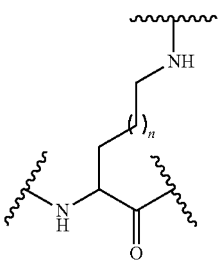
;
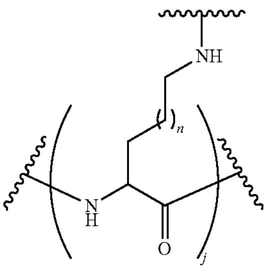
;
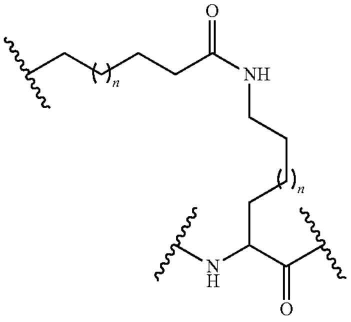
;
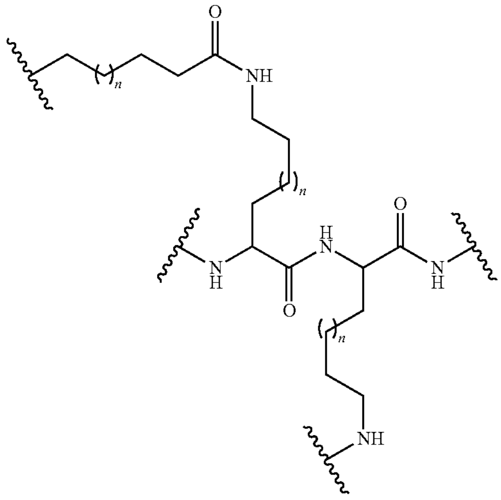
;
-continued
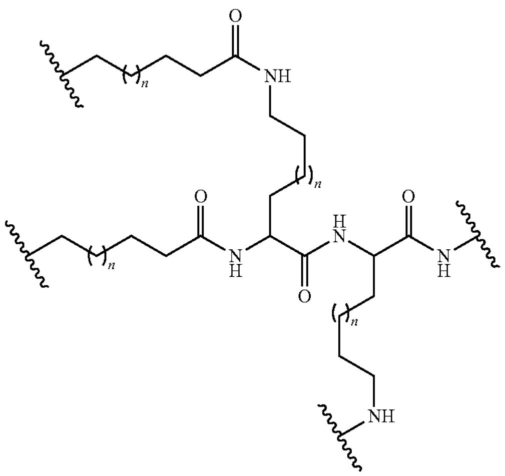
; and
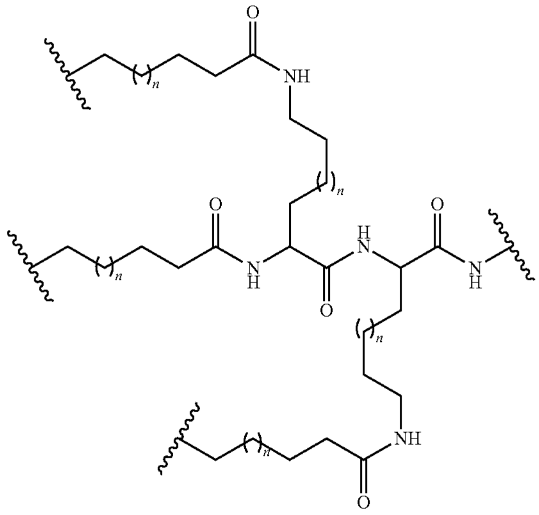
.
wherein each n is, independently, from 1 to 20;
j is from 1 to 3; and
m is from 2 to 6.
In certain embodiments, a branching group has a structure selected from among:
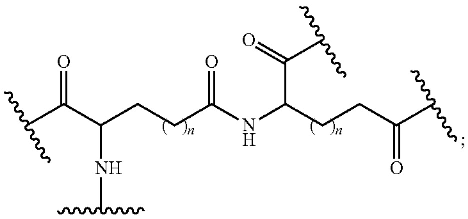
;
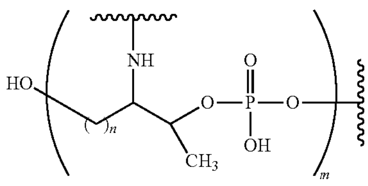
;

-continued
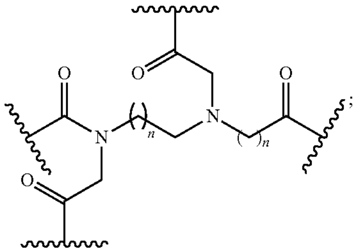
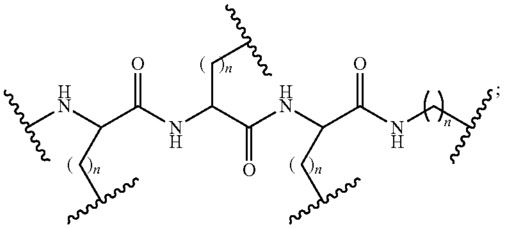
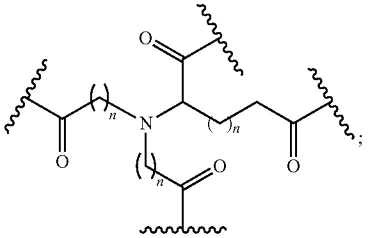
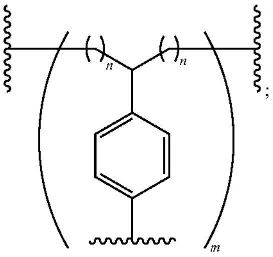
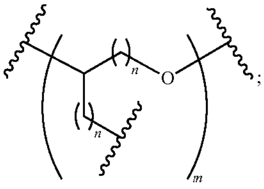
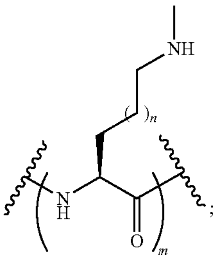
-continued
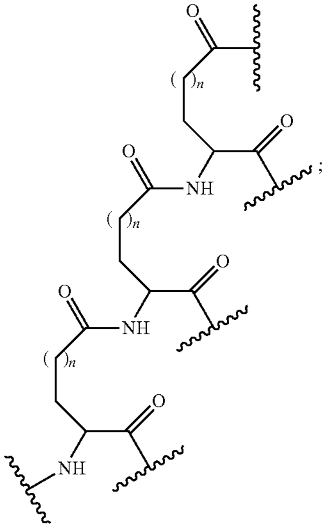
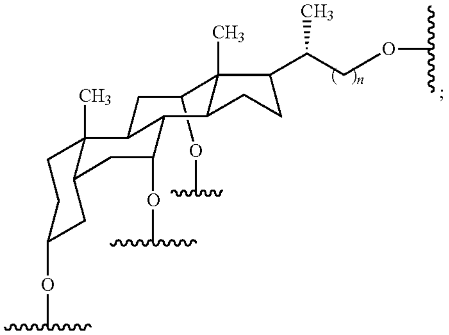
and
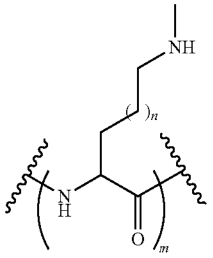
wherein each n is, independently, from 1 to 20; and
m is from 2 to 6.
In certain embodiments, a branching group has a structure selected from among:
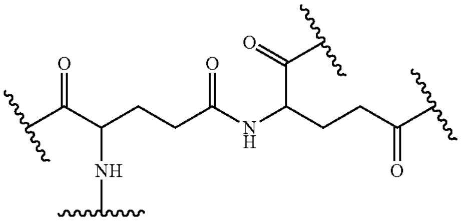
;

-continued
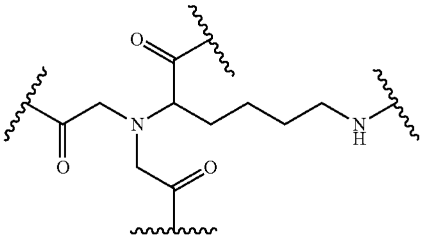
;
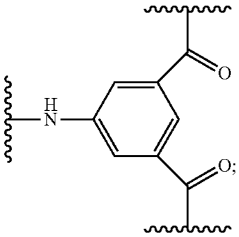
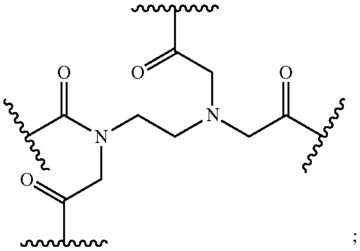
;
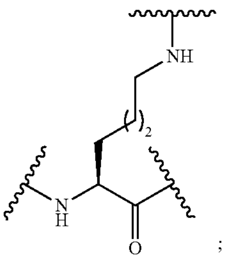
;
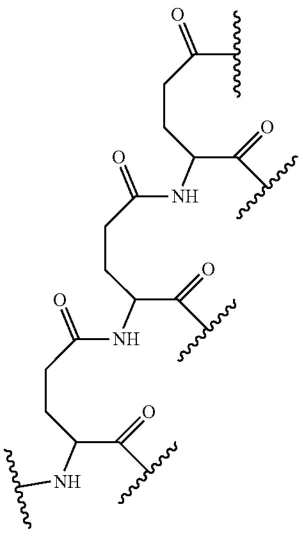
;
-continued
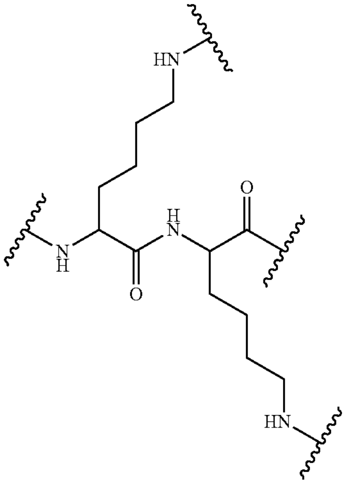
;
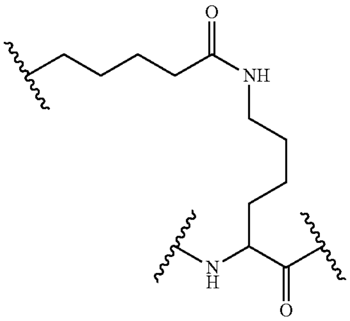
;
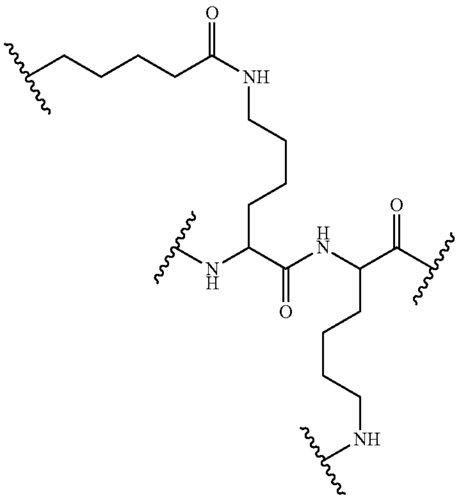
;

-continued

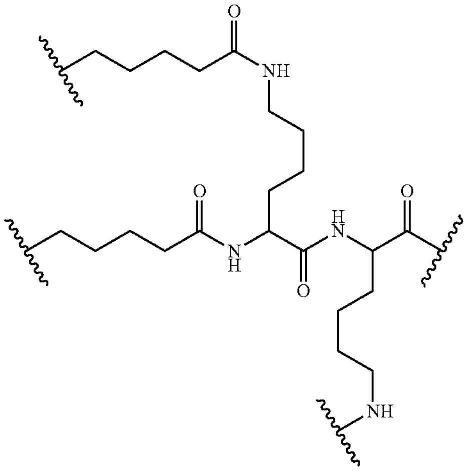

; and

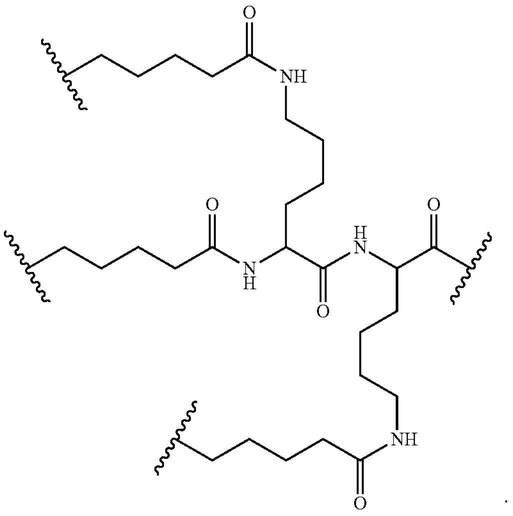

In certain embodiments, a branching group has a structure selected from among:

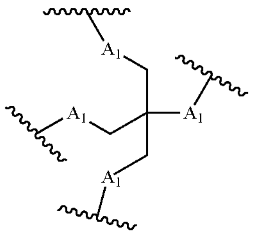

and

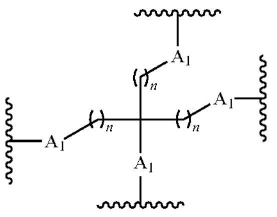

wherein each $A_1$ is independently, O, S, C═O or NH; and each n is, independently, from 1 to 20.

In certain embodiments, a branching group has a structure selected from among:

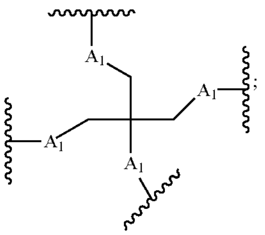

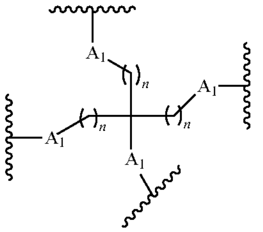

and

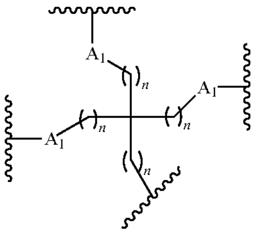

wherein each $A_1$ is independently, O, S, C═O or NH; and each n is, independently, from 1 to 20.

In certain embodiments, a branching group has a structure selected from among:

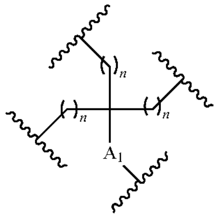

and

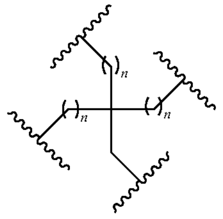

wherein $A_1$ is O, S, C═O or NH; and each n is, independently, from 1 to 20.

In certain embodiments, a branching group has a structure selected from among:

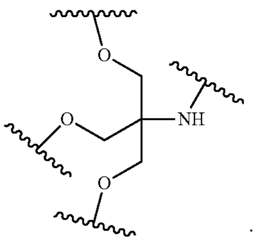 [SMILES: *NC(CO*)(CO*)CO*]

In certain embodiments, a branching group has a structure selected from among:

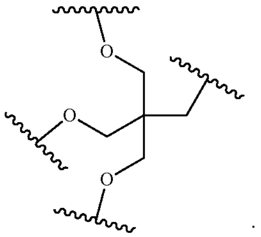 [SMILES: *CC(CO*)(CO*)CO*]

In certain embodiments, a branching group has a structure selected from among:

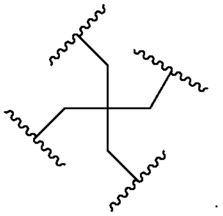 [SMILES: *CC(C*)(C*)C*]

2. Certain Tethers

In certain embodiments, conjugate groups comprise one or more tethers covalently attached to the branching group. In certain embodiments, conjugate groups comprise one or more tethers covalently attached to the linking group. In certain embodiments, each tether is a linear aliphatic group comprising one or more groups selected from alkyl, ether, thioether, disulfide, amide and polyethylene glycol groups in any combination. In certain embodiments, each tether is a linear aliphatic group comprising one or more groups selected from alkyl, substituted alkyl, ether, thioether, disulfide, amide, phosphodiester and polyethylene glycol groups in any combination. In certain embodiments, each tether is a linear aliphatic group comprising one or more groups selected from alkyl, ether and amide groups in any combination. In certain embodiments, each tether is a linear aliphatic group comprising one or more groups selected from alkyl, substituted alkyl, phosphodiester, ether and amide groups in any combination. In certain embodiments, each tether is a linear aliphatic group comprising one or more groups selected from alkyl and phosphodiester in any combination. In certain embodiments, each tether comprises at least one phosphorus linking group or neutral linking group.

In certain embodiments, the tether includes one or more cleavable bond. In certain embodiments, the tether is attached to the branching group through either an amide or an ether group. In certain embodiments, the tether is attached to the branching group through a phosphodiester group. In certain embodiments, the tether is attached to the branching group through a phosphorus linking group or neutral linking group. In certain embodiments, the tether is attached to the branching group through an ether group. In certain embodiments, the tether is attached to the ligand through either an amide or an ether group. In certain embodiments, the tether is attached to the ligand through an ether group. In certain embodiments, the tether is attached to the ligand through either an amide or an ether group. In certain embodiments, the tether is attached to the ligand through an ether group.

In certain embodiments, each tether comprises from about 8 to about 20 atoms in chain length between the ligand and the branching group. In certain embodiments, each tether group comprises from about 10 to about 18 atoms in chain length between the ligand and the branching group. In certain embodiments, each tether group comprises about 13 atoms in chain length.

In certain embodiments, a tether has a structure selected from among:

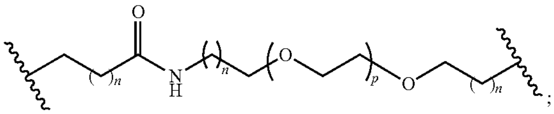;

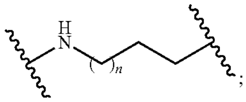; 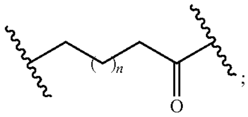;

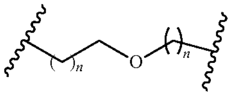;

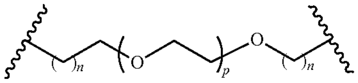;

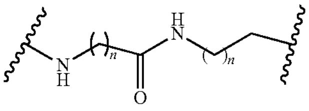;

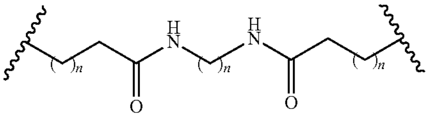;

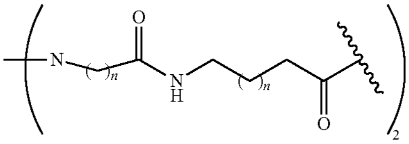;

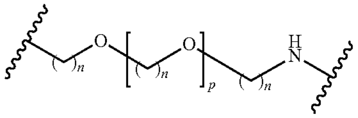;

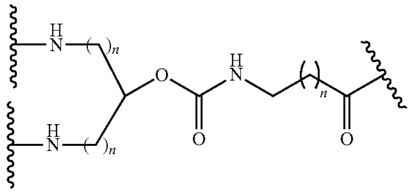;

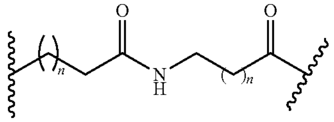;

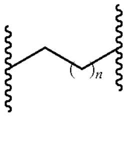; and 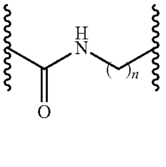

wherein each n is, independently, from 1 to 20; and each p is from 1 to about 6.

In certain embodiments, a tether has a structure selected from among:

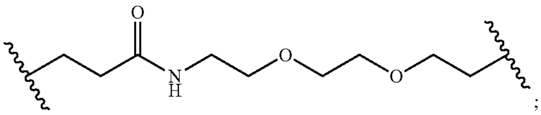
;
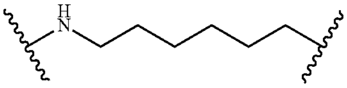
;
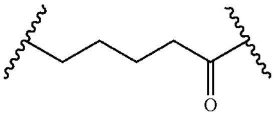
;
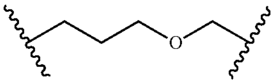
;
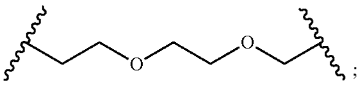
;
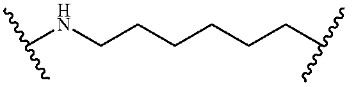
; and
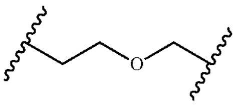
.

In certain embodiments, a tether has a structure selected from among:

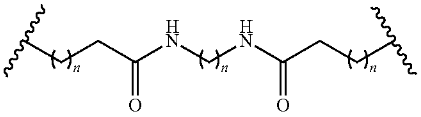

wherein each n is, independently, from 1 to 20.

In certain embodiments, a tether has a structure selected from among:

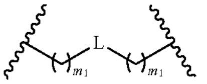
and
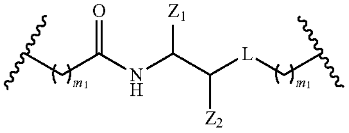

wherein L is either a phosphorus linking group or a neutral linking group;

$Z_1$ is C(=O)O—$R_2$;

$Z_2$ is H, $C_1$-$C_6$ alkyl or substituted $C_1$-$C_6$ alky;

$R_2$ is H, $C_1$-$C_6$ alkyl or substituted $C_1$-$C_6$ alky; and each $m_1$ is, independently, from 0 to 20 wherein at least one $m_1$ is greater than 0 for each tether.

In certain embodiments, a tether has a structure selected from among:

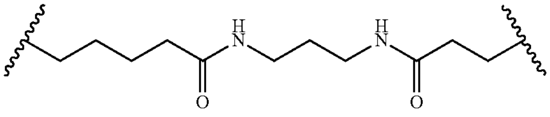
.

In certain embodiments, a tether has a structure selected from among:

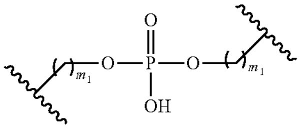
and
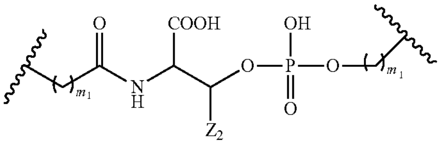

wherein $Z_2$ is H or $CH_3$; and each $m_1$ is, independently, from 0 to 20 wherein at least one $m_1$ is greater than 0 for each tether.

In certain embodiments, a tether has a structure selected from among:

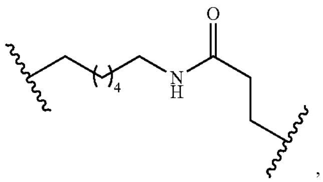
, or
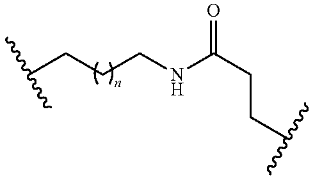
;

wherein each n is independently, 0, 1, 2, 3, 4, 5, 6, or 7.

In certain embodiments, a tether comprises a phosphorus linking group. In certain embodiments, a tether does not comprise any amide bonds. In certain embodiments, a tether comprises a phosphorus linking group and does not comprise any amide bonds.

3. Certain Ligands

In certain embodiments, the present disclosure provides ligands wherein each ligand is covalently attached to a tether. In certain embodiments, each ligand is selected to have an affinity for at least one type of receptor on a target cell. In certain embodiments, ligands are selected that have an affinity for at least one type of receptor on the surface of a mammalian liver cell. In certain embodiments, ligands are selected that have an affinity for the hepatic asialoglycoprotein receptor (ASGP-R). In certain embodiments, each ligand is a carbohydrate. In certain embodiments, each ligand is, independently selected from galactose, N-acetyl galactoseamine, mannose, glucose, glucosamone and fucose. In certain embodiments, each ligand is N-acetyl galactoseamine (GalNAc). In certain embodiments, the targeting moiety comprises 2 to 6 ligands. In certain embodiments, the targeting moiety comprises 3 ligands. In certain embodiments, the targeting moiety comprises 3 N-acetyl galactoseamine ligands.

In certain embodiments, the ligand is a carbohydrate, carbohydrate derivative, modified carbohydrate, multivalent carbohydrate cluster, polysaccharide, modified polysaccharide, or polysaccharide derivative. In certain embodiments, the ligand is an amino sugar or a thio sugar. For example, amino sugars may be selected from any number of compounds known in the art, for example glucosamine, sialic acid, α-D-galactosamine, N-Acetylgalactosamine, 2-acetamido-2-deoxy-D-galactopyranose (GalNAc), 2-Amino-3-O—[(R)-1-carboxyethyl]-2-deoxy-β-D-glucopyranose (β-muramic acid), 2-Deoxy-2-methylamino-L-glucopyranose, 4,6-Dideoxy-4-formamido-2,3-di-O-methyl-D-mannopyranose, 2-Deoxy-2-sulfoamino-D-glucopyranose and N-sulfo-D-glucosamine, and N-Glycoloyl-α-neuraminic acid. For example, thio sugars may be selected from the group consisting of 5-Thio-β-D-glucopyranose, Methyl 2,3,4-tri-O-acetyl-1-thio-6-O-trityl-α-D-glucopyranoside, 4-Thio-β-D-galactopyranose, and ethyl 3,4,6,7-tetra-O-acetyl-2-deoxy-1,5-dithio-α-D-gluco-heptopyranoside.

In certain embodiments, "GalNac" or "Gal-NAc" refers to 2-(Acetylamino)-2-deoxy-D-galactopyranose, commonly referred to in the literature as N-acetyl galactosamine. In certain embodiments, "N-acetyl galactosamine" refers to 2-(Acetylamino)-2-deoxy-D-galactopyranose. In certain embodiments, "GalNac" or "Gal-NAc" refers to 2-(Acetylamino)-2-deoxy-D-galactopyranose. In certain embodiments, "GalNac" or "Gal-NAc" refers to 2-(Acetylamino)-2-deoxy-D-galactopyranose, which includes both the β-form: 2-(Acetylamino)-2-deoxy-β-D-galactopyranose and α-form: 2-(Acetylamino)-2-deoxy-D-galactopyranose. In certain embodiments, both the β-form: 2-(Acetylamino)-2-deoxy-β-D-galactopyranose and α-form: 2-(Acetylamino)-2-deoxy-D-galactopyranose may be used interchangeably. Accordingly, in structures in which one form is depicted, these structures are intended to include the other form as well. For example, where the structure for an α-form: 2-(Acetylamino)-2-deoxy-D-galactopyranose is shown, this structure is intended to include the other form as well. In certain embodiments, In certain preferred embodiments, the β-form 2-(Acetylamino)-2-deoxy-D-galactopyranose is the preferred embodiment.

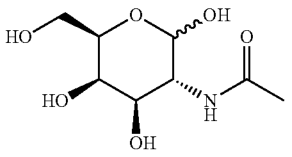

2-(Acetylamino)-2-deoxy-D-galactopyranose

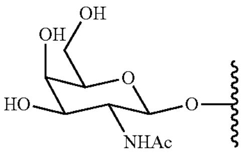

2-(Acetylamino)-2-deoxy-β-D-galactopyranose

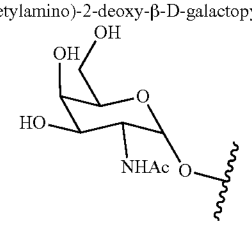

2-(Acetylamino)-2-deoxy-α-D-galactopyranose

In certain embodiments one or more ligand has a structure selected from among:

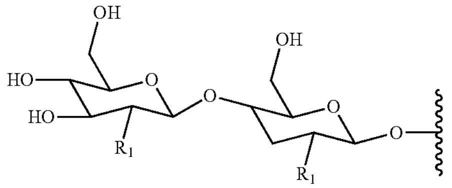

and

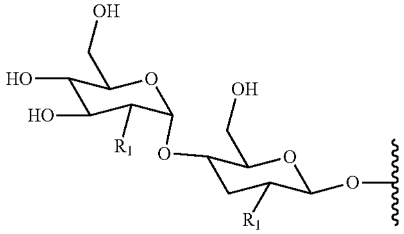

wherein each $R_1$ is selected from OH and NHCOOH.

In certain embodiments one or more ligand has a structure selected from among:

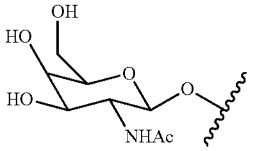

;

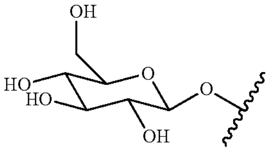

;

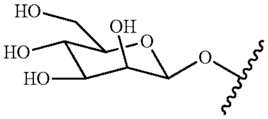

;

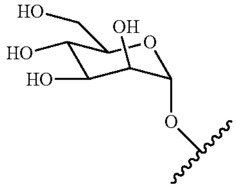

;

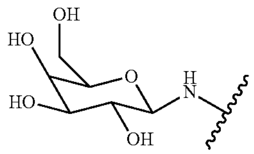

;

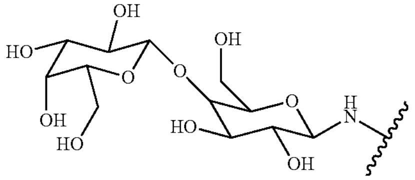

;

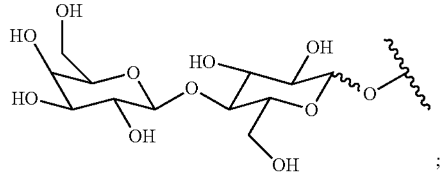

; and

-continued

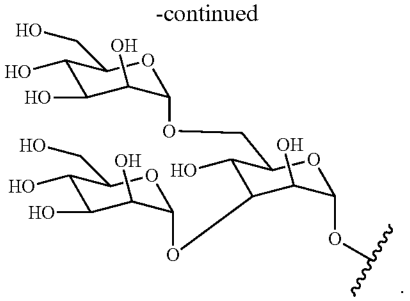

In certain embodiments one or more ligand has a structure selected from among:

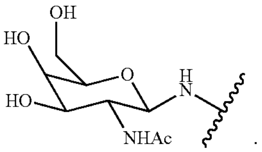 [SMILES: *NC1OC(CO)C(O)C(O)C1NC(C)=O]

In certain embodiments one or more ligand has a structure selected from among:

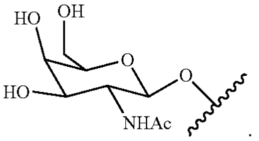 [SMILES: *OC1OC(CO)C(O)C(O)C1NC(C)=O]

i. Certain Conjugates

In certain embodiments, conjugate groups comprise the structural features above. In certain such embodiments, conjugate groups have the following structure:

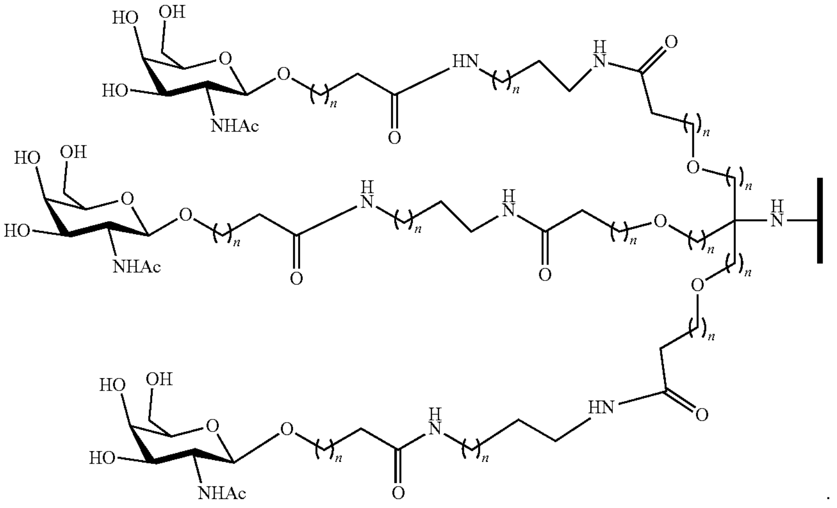

wherein each n is, independently, from 1 to 20.

In certain such embodiments, conjugate groups have the following structure:

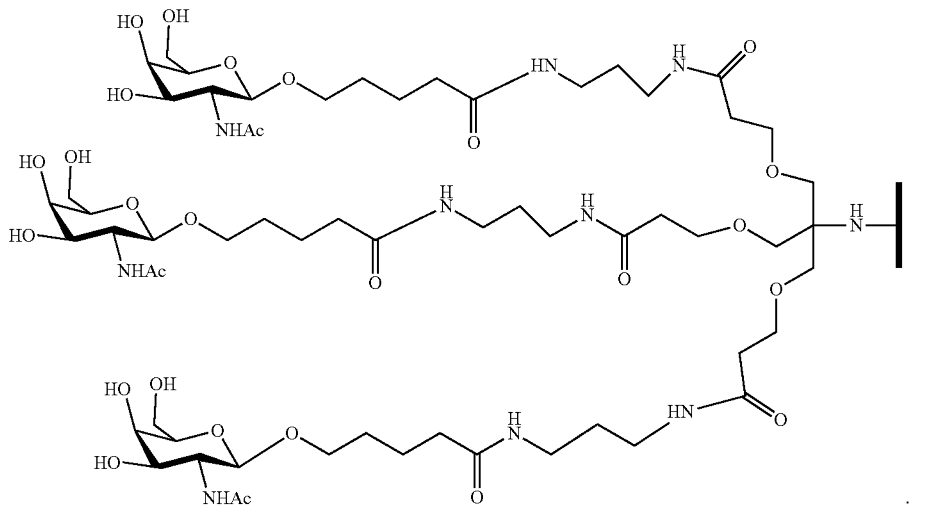
In certain such embodiments, conjugate groups have the following structure:
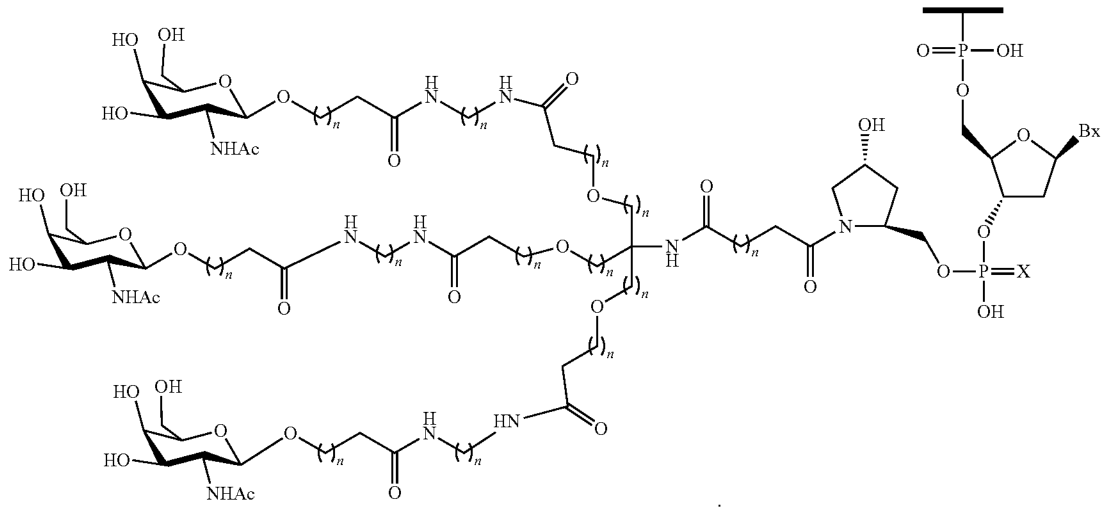
wherein each n is, independently, from 1 to 20;
Z is H or a linked solid support;
Q is an antisense compound;
X is O or S; and
Bx is a heterocyclic base moiety.
In certain such embodiments, conjugate groups have the following structure:

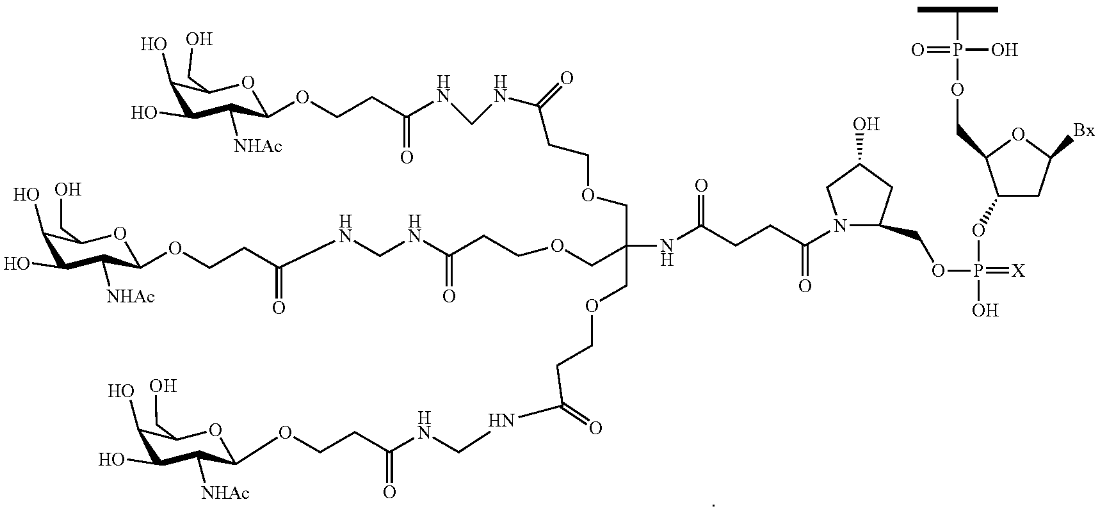
In certain such embodiments, conjugate groups have the following structure:
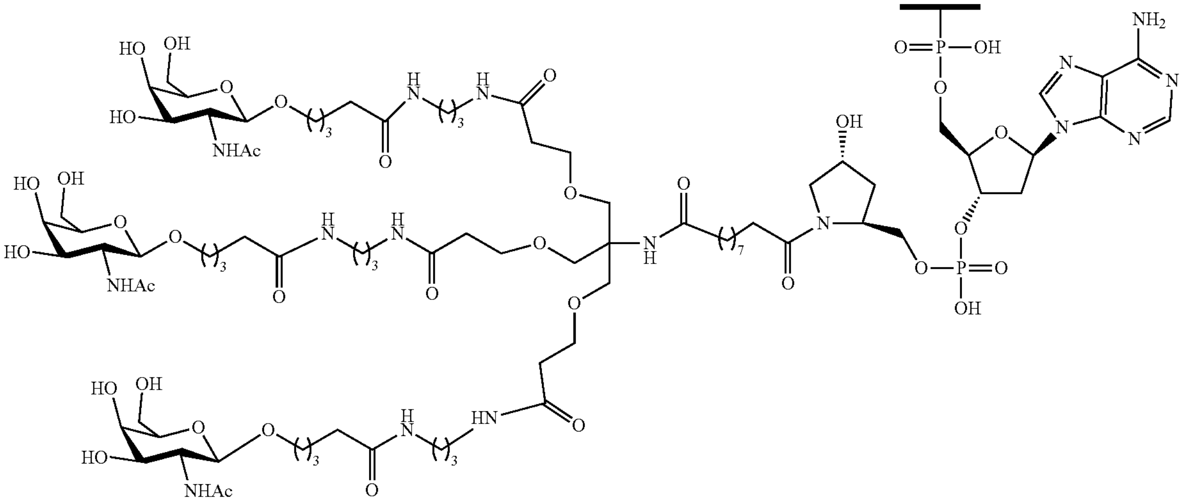
In certain such embodiments, conjugate groups have the following structure:
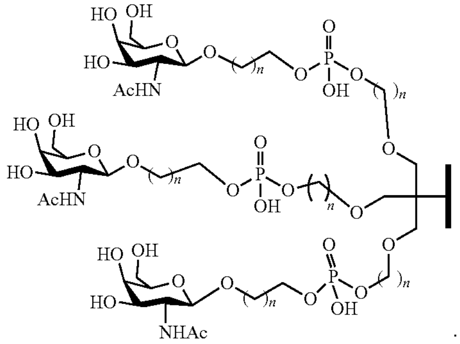

In certain such embodiments, conjugate groups have the following structure:
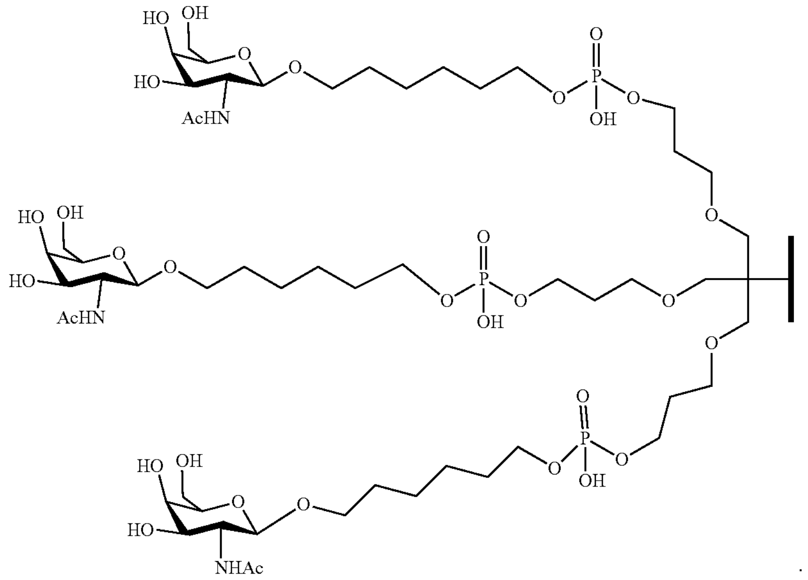
In certain such embodiments, conjugate groups have the following structure:
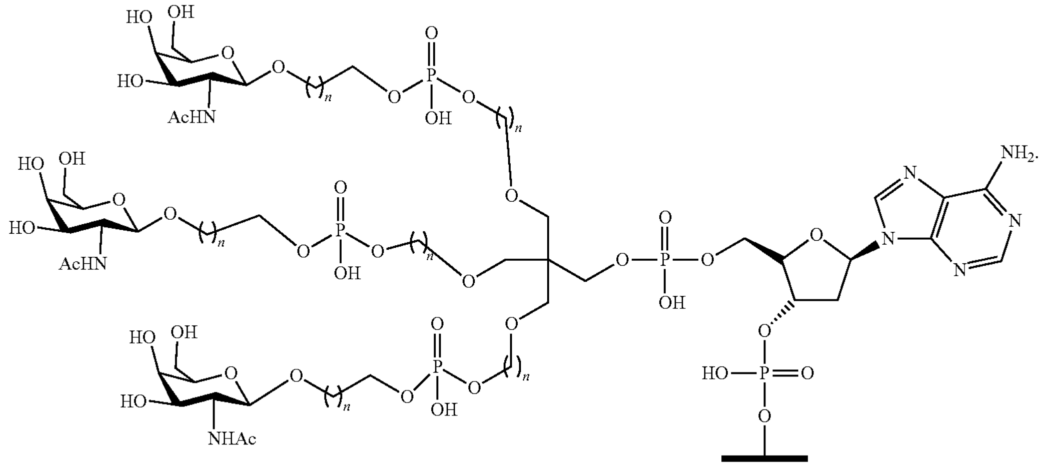
In certain such embodiments, conjugate groups have the following structure:

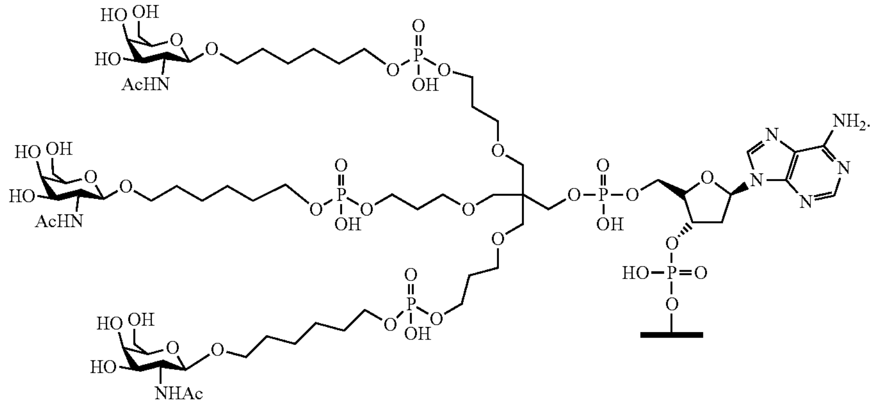
In certain such embodiments, conjugate groups have the following structure:
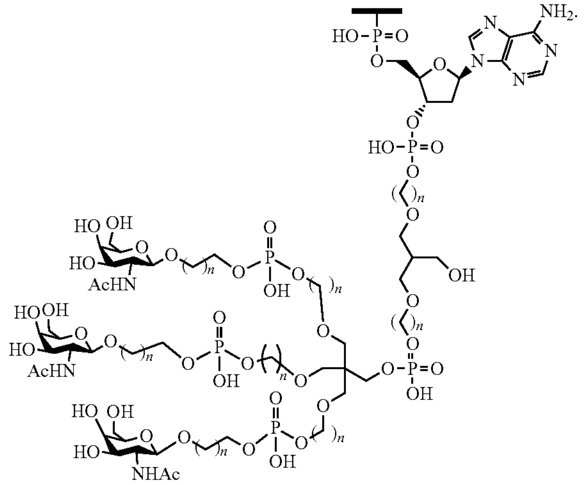
In certain such embodiments, conjugate groups have the following structure:

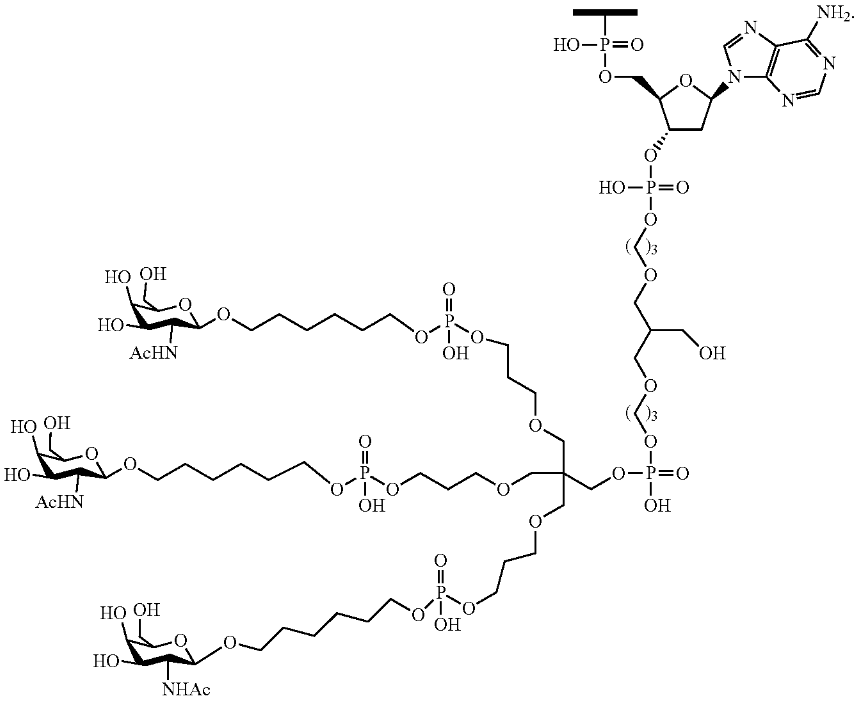
In certain embodiments, conjugates do not comprise a pyrrolidine.
In certain such embodiments, conjugate groups have the following structure:
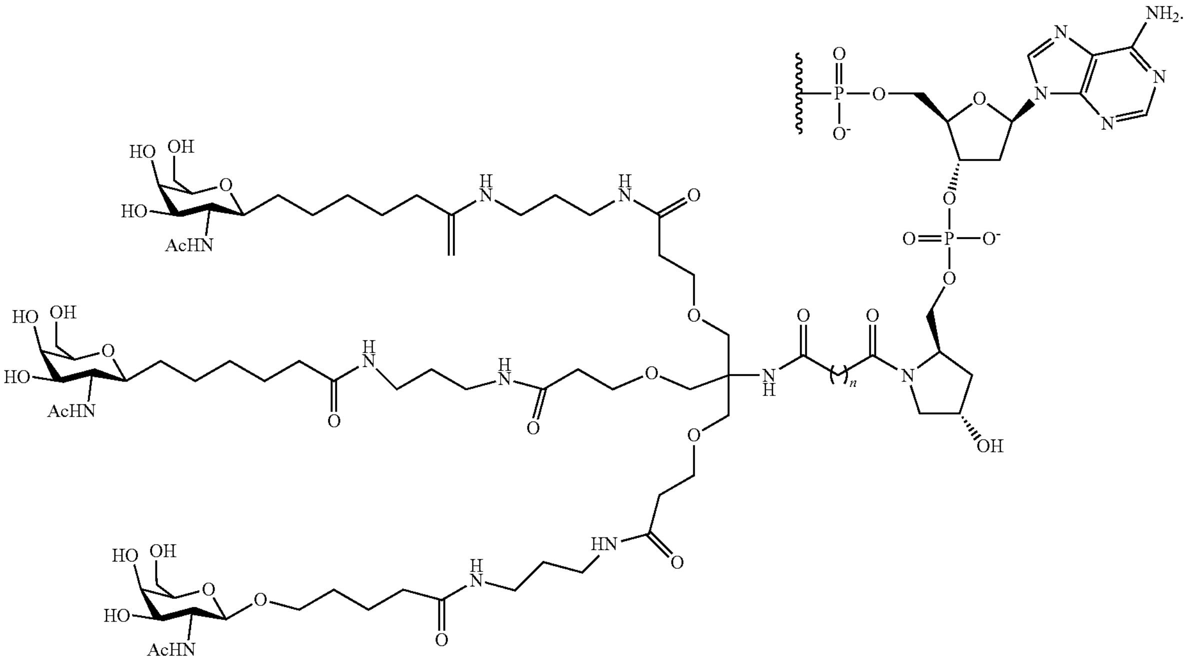
In certain such embodiments, conjugate groups have the following structure:

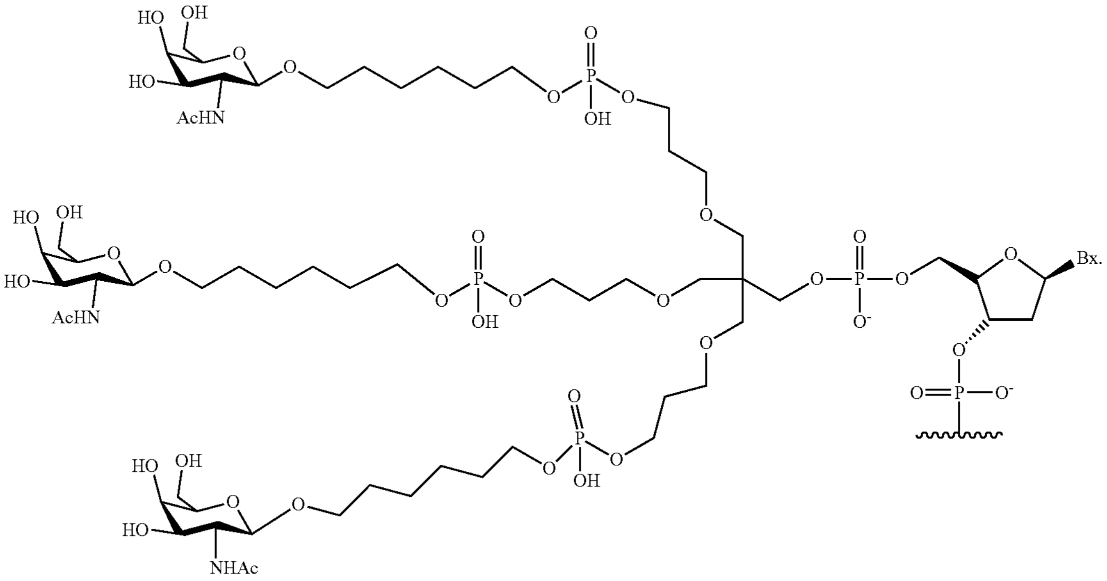
In certain such embodiments, conjugate groups have the following structure:
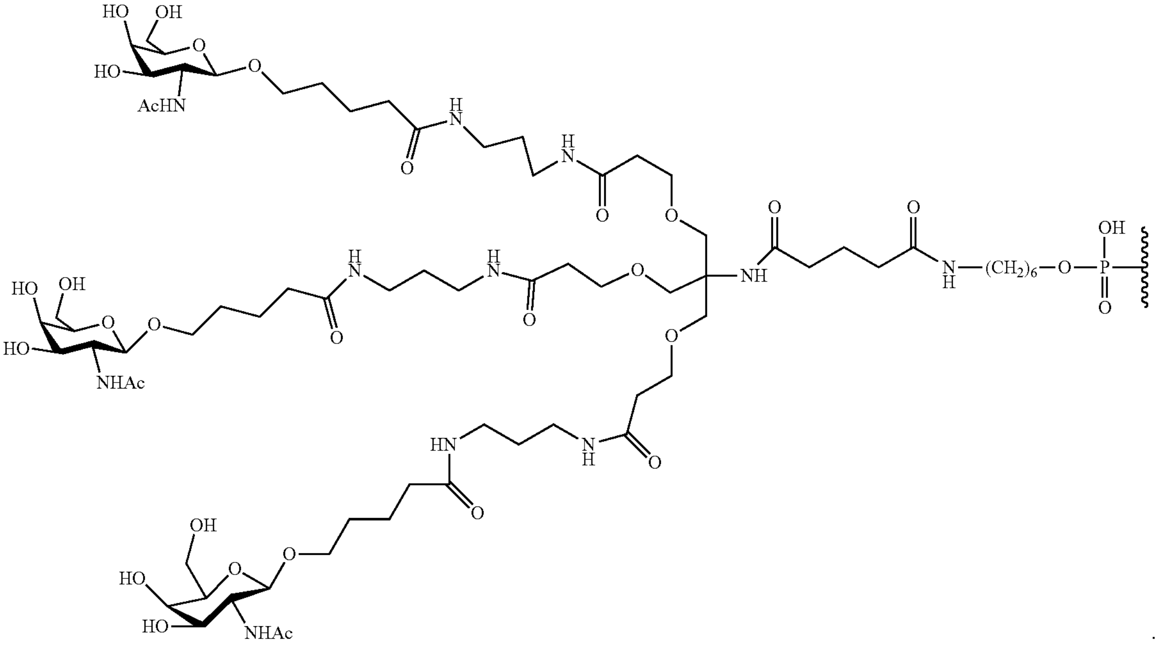
In certain such embodiments, conjugate groups have the following structure:

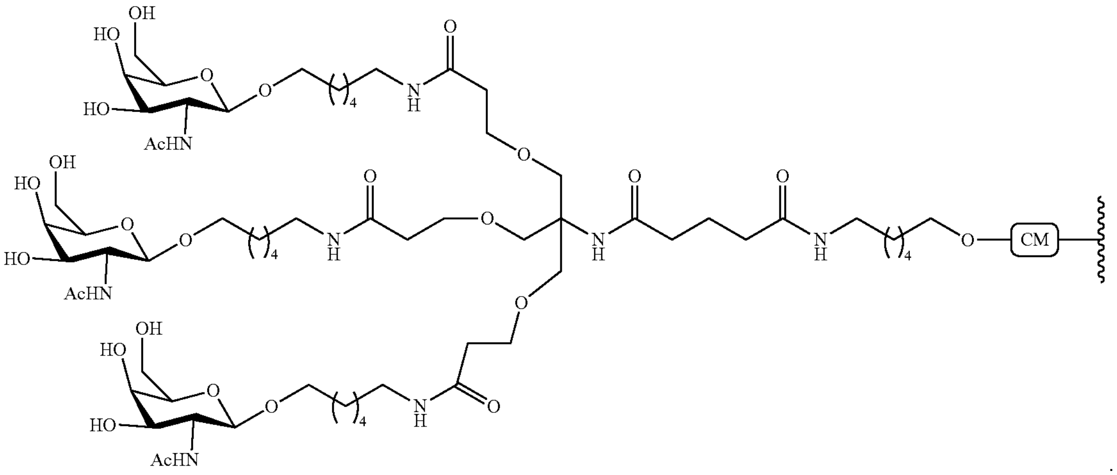
In certain such embodiments, conjugate groups have the following structure:
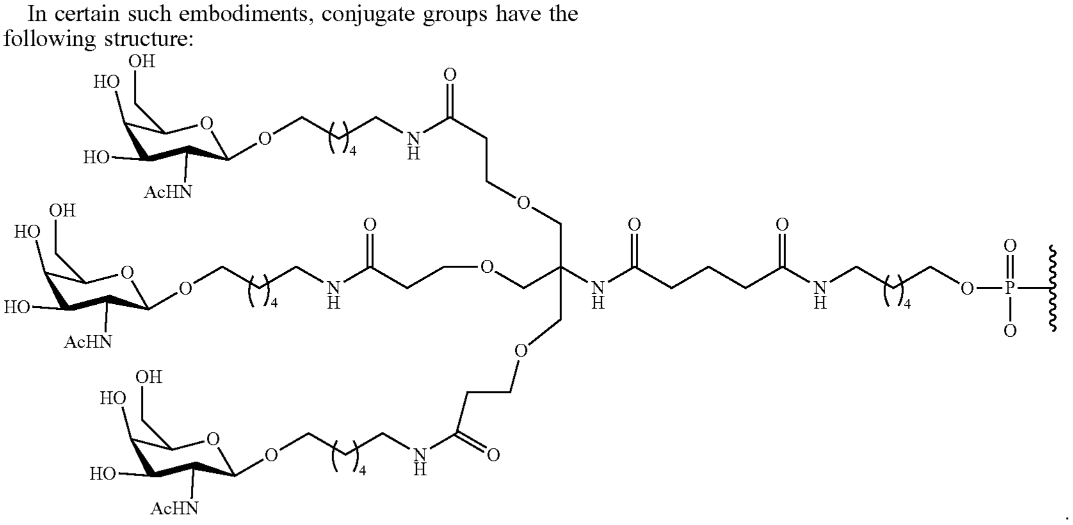
In certain such embodiments, conjugate groups have the following structure:
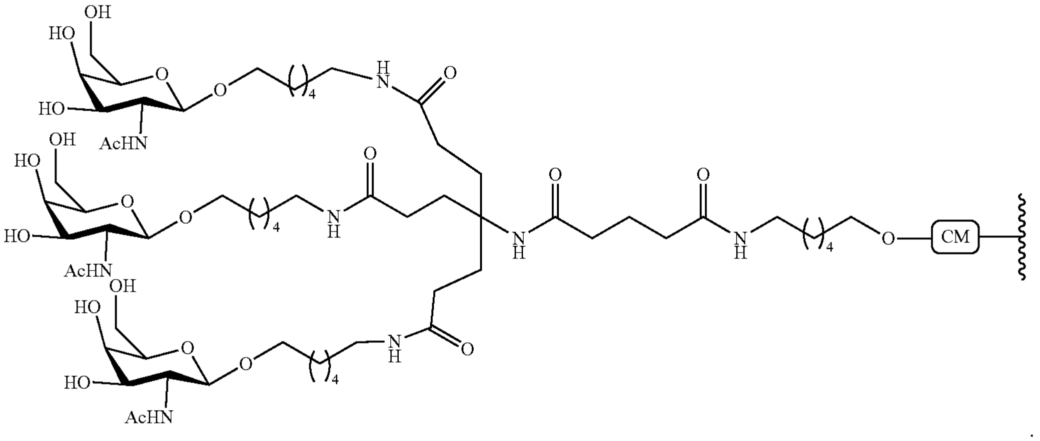
In certain such embodiments, conjugate groups have the following structure:

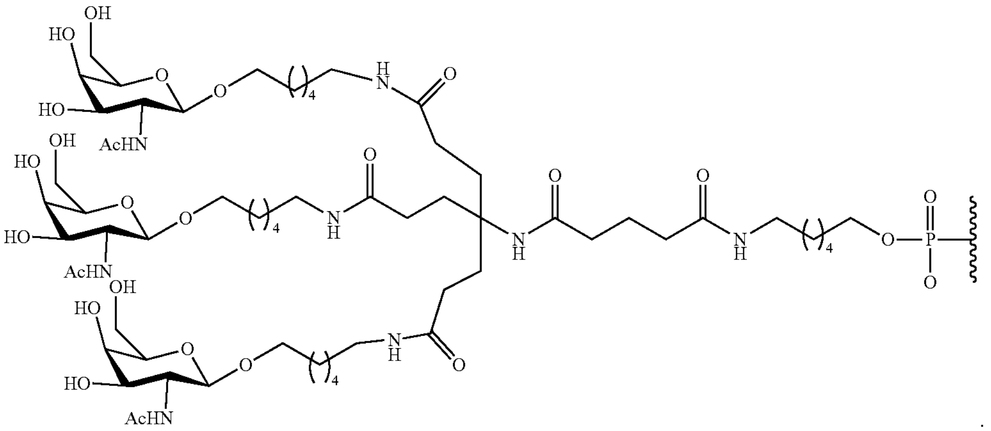
In certain such embodiments, conjugate groups have the following structure:
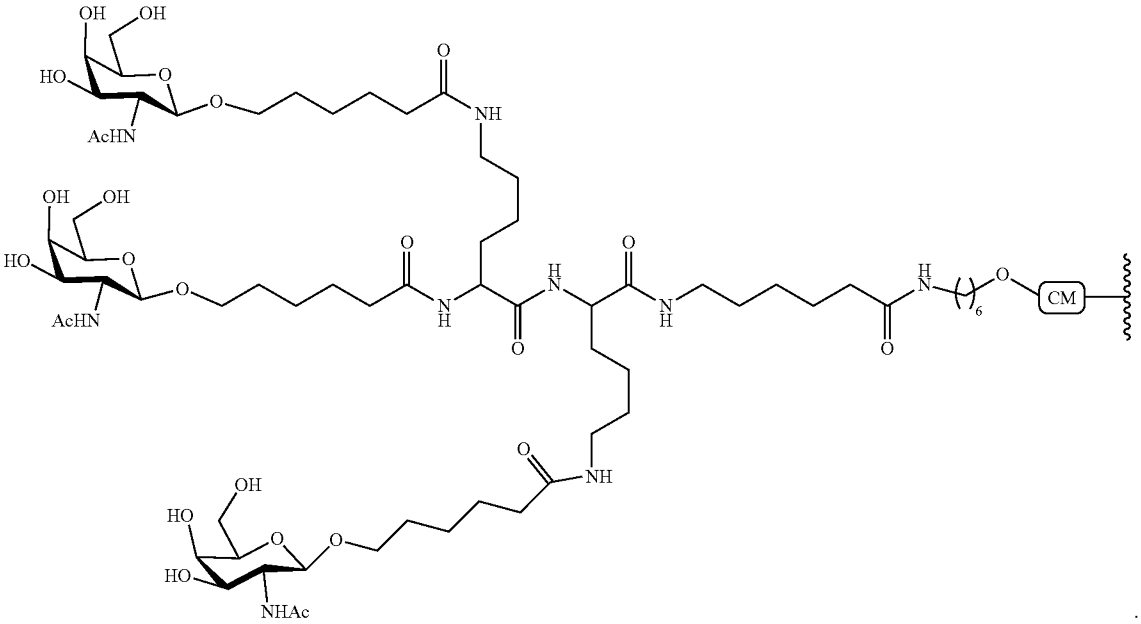
In certain such embodiments, conjugate groups have the following structure:

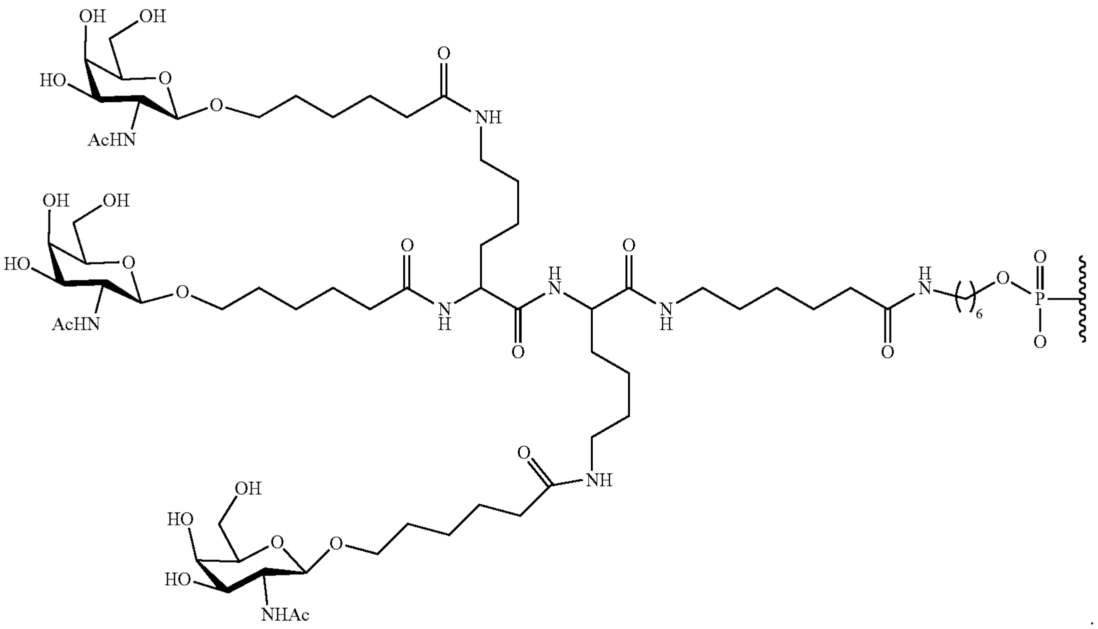
In certain such embodiments, conjugate groups have the following structure:
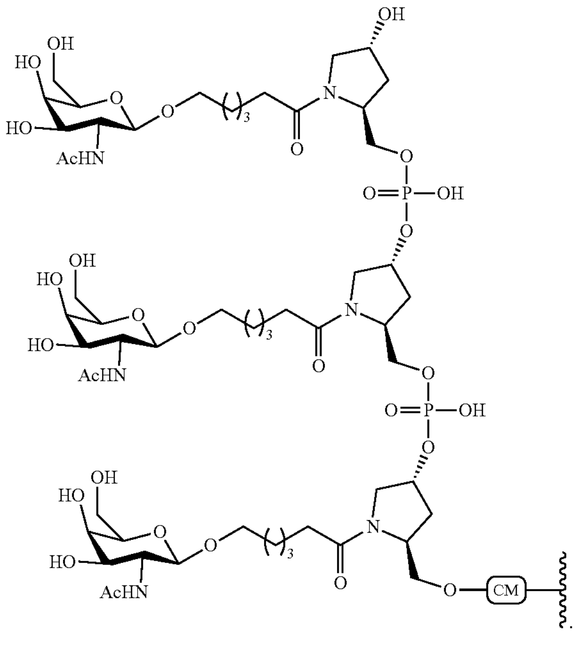
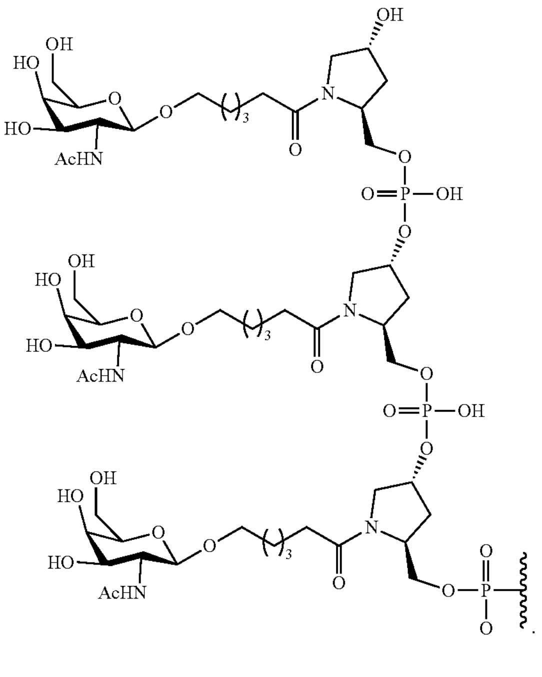
In certain such embodiments, conjugate groups have the following structure:
In certain embodiments, the cell-targeting moiety of the conjugate group has the following structure:

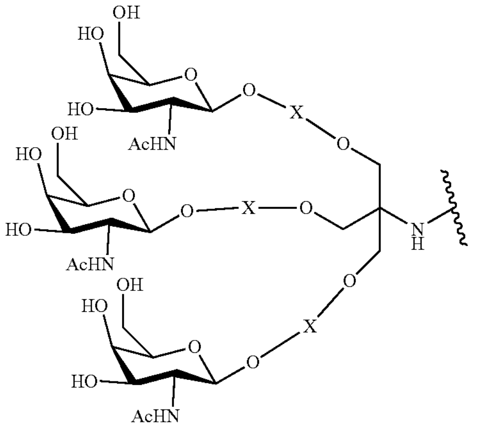

wherein X is a substituted or unsubstituted tether of six to eleven consecutively bonded atoms.

In certain embodiments, the cell-targeting moiety of the conjugate group has the following structure:

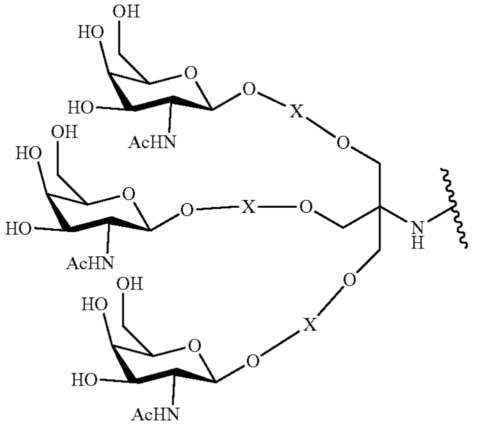

wherein X is a substituted or unsubstituted tether of ten consecutively bonded atoms.

In certain embodiments, the cell-targeting moiety of the conjugate group has the following structure:

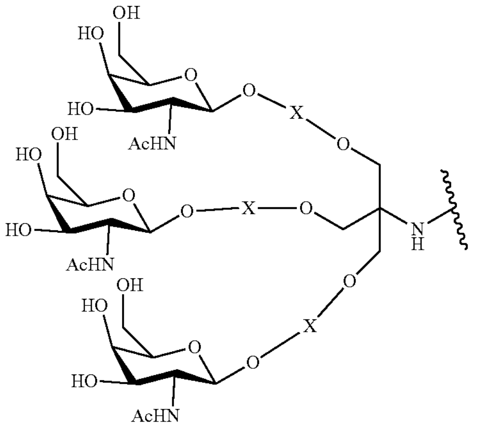

wherein X is a substituted or unsubstituted tether of four to eleven consecutively bonded atoms and wherein the tether comprises exactly one amide bond.

In certain embodiments, the cell-targeting moiety of the conjugate group has the following structure:

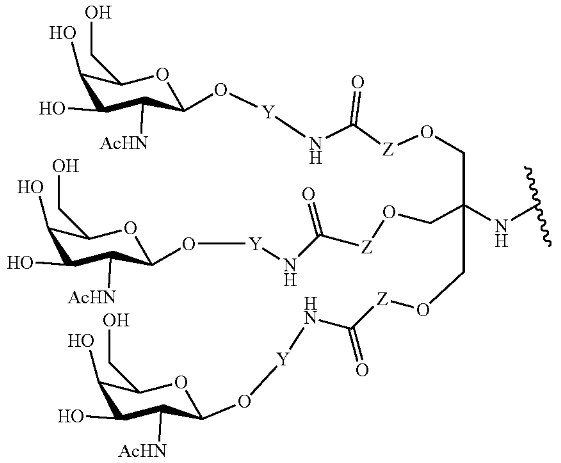

wherein Y and Z are independently selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

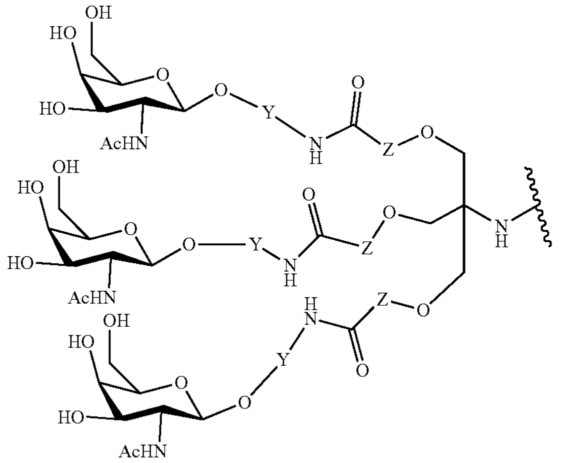

wherein Y and Z are independently selected from a $C_1$-$C_{12}$ substituted or unsubstituted alkyl group, or a group comprising exactly one ether or exactly two ethers, an amide, an amine, a piperidine, a phosphate, a phosphodiester, or a phosphorothioate.

In certain such embodiments, the cell-targeting moiety of the conjugate group has the following structure:

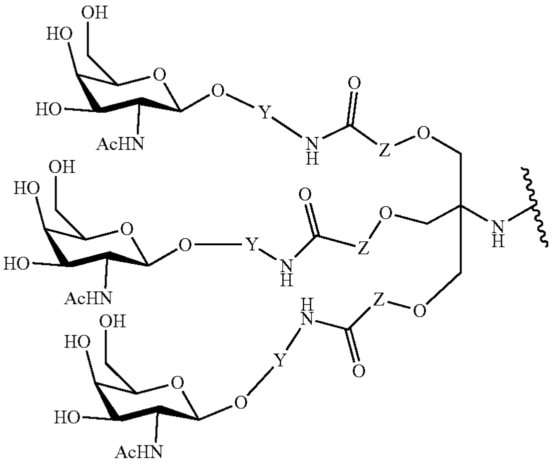

wherein Y and Z are independently selected from a $C_1$-$C_{12}$ substituted or unsubstituted alkyl group.

In certain such embodiments, the cell-targeting moiety of the conjugate group has the following structure:

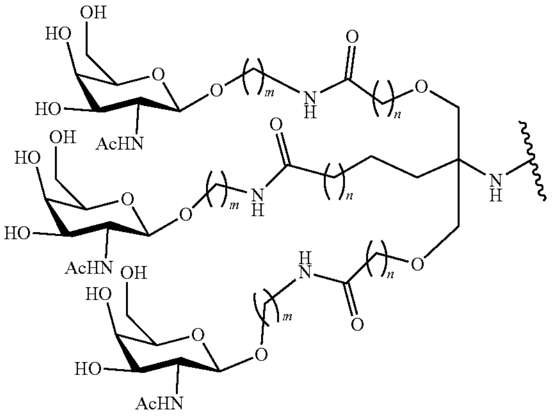

wherein m and n are independently selected from 1, 2, 3, 4, 5, 6, 7, 8, 9, 10, 11, and 12.

In certain such embodiments, the cell-targeting moiety of the conjugate group has the following structure:

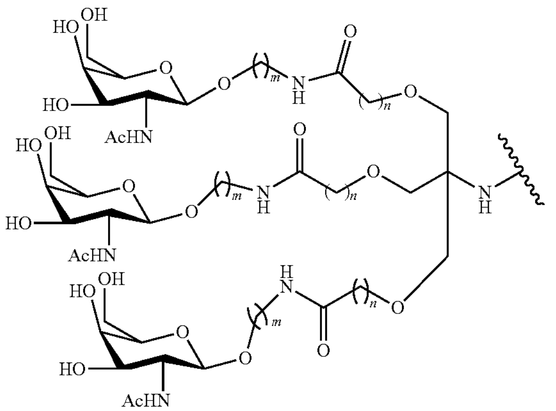

wherein m is 4, 5, 6, 7, or 8, and n is 1, 2, 3, or 4.

In certain embodiments, the cell-targeting moiety of the conjugate group has the following structure:

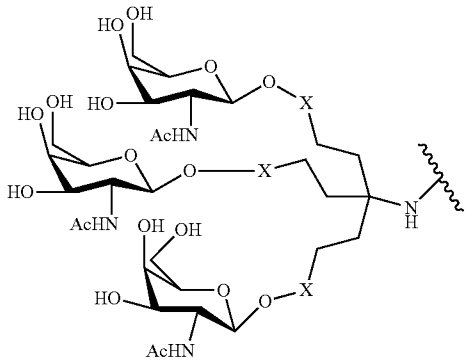

wherein X is a substituted or unsubstituted tether of four to thirteen consecutively bonded atoms, and wherein X does not comprise an ether group.

In certain embodiments, the cell-targeting moiety of the conjugate group has the following structure:

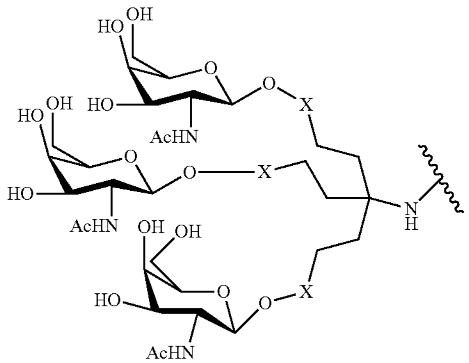

wherein X is a substituted or unsubstituted tether of eight consecutively bonded atoms, and wherein X does not comprise an ether group.

In certain embodiments, the cell-targeting moiety of the conjugate group has the following structure:

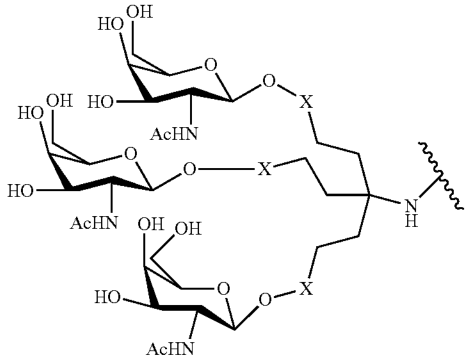

wherein X is a substituted or unsubstituted tether of four to thirteen consecutively bonded atoms, and wherein the tether comprises exactly one amide bond, and wherein X does not comprise an ether group.

In certain embodiments, the cell-targeting moiety of the conjugate group has the following structure:

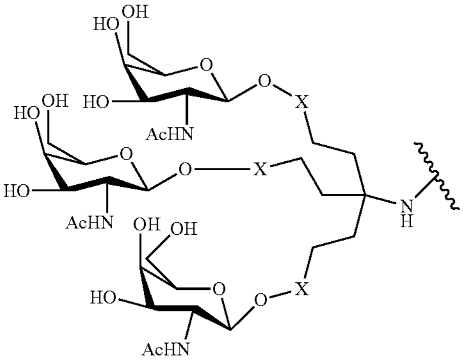

wherein X is a substituted or unsubstituted tether of four to thirteen consecutively bonded atoms and wherein the tether consists of an amide bond and a substituted or unsubstituted $C_2$-$C_{11}$ alkyl group.

In certain embodiments, the cell-targeting moiety of the conjugate group has the following structure:

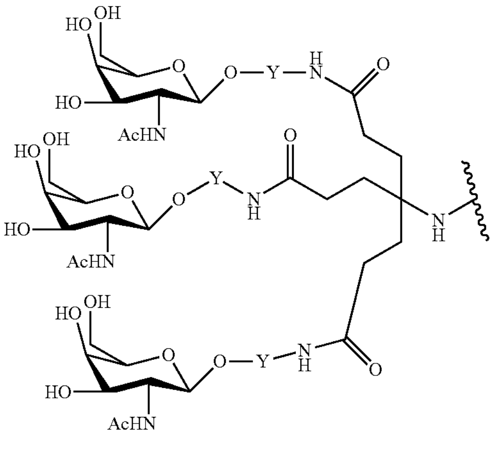

wherein Y is selected from a $C_1$-$C_{12}$ substituted or unsubstituted alkyl, alkenyl, or alkynyl group, or a group comprising an ether, a ketone, an amide, an ester, a carbamate, an amine, a piperidine, a phosphate, a phosphodiester, a phosphorothioate, a triazole, a pyrrolidine, a disulfide, or a thioether.

In certain such embodiments, the cell-targeting moiety of the conjugate group has the following structure:

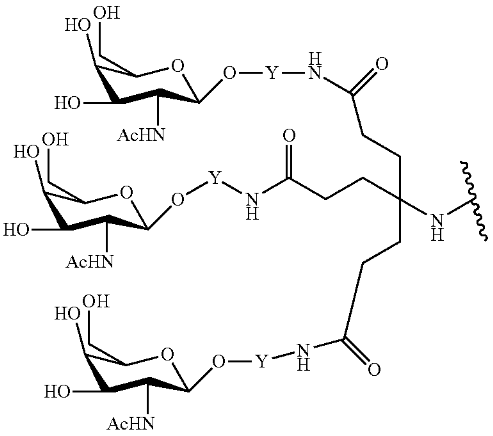

wherein Y is selected from a $C_1$-$C_{12}$ substituted or unsubstituted alkyl group, or a group comprising an ether, an amine, a piperidine, a phosphate, a phosphodiester, or a phosphorothioate.

In certain such embodiments, the cell-targeting moiety of the conjugate group has the following structure:

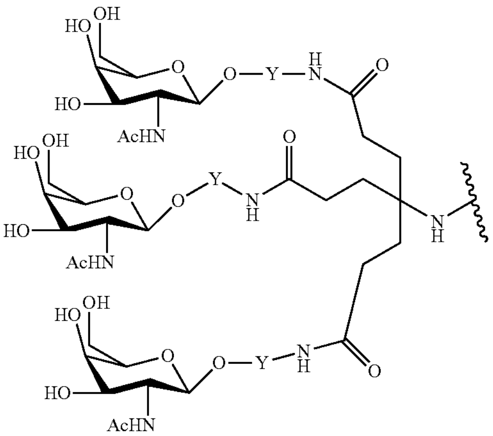

wherein Y is selected from a $C_1$-$C_{12}$ substituted or unsubstituted alkyl group.

In certain such embodiments, the cell-targeting moiety of the conjugate group has the following structure:

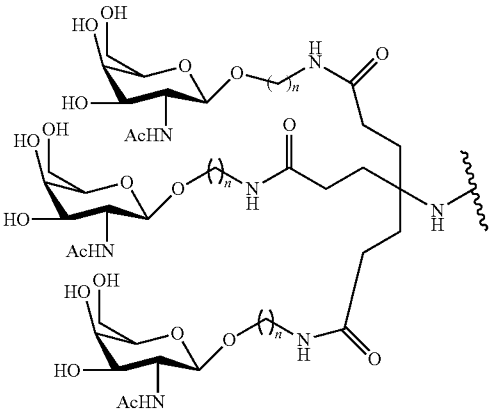

wherein n is 1, 2, 3, 4, 5, 6, 7, 8, 9, 10, 11, or 12.

In certain such embodiments, the cell-targeting moiety of the conjugate group has the following structure:

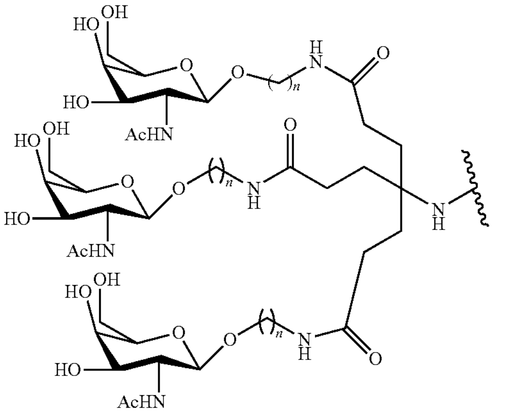

wherein n is 4, 5, 6, 7, or 8.

b. Certain Conjugated Antisense Compounds

In certain embodiments, the conjugates are bound to a nucleoside of the antisense oligonucleotide at the 2', 3', of 5' position of the nucleoside. In certain embodiments, a conjugated antisense compound has the following structure:

$$A—B—C—D—(E—F)_q$$

wherein

A is the antisense oligonucleotide;

B is the cleavable moiety

C is the conjugate linker

D is the branching group each E is a tether;

each F is a ligand; and q is an integer between 1 and 5.

In certain embodiments, a conjugated antisense compound has the following structure:

$$A—C—D—(E—F)_q$$

wherein

A is the antisense oligonucleotide;

C is the conjugate linker

D is the branching group each E is a tether;

each F is a ligand; and q is an integer between 1 and 5.

In certain such embodiments, the conjugate linker comprises at least one cleavable bond.

In certain such embodiments, the branching group comprises at least one cleavable bond.

In certain embodiments each tether comprises at least one cleavable bond.

In certain embodiments, the conjugates are bound to a nucleoside of the antisense oligonucleotide at the 2', 3', of 5' position of the nucleoside.

In certain embodiments, a conjugated antisense compound has the following structure:

$$A—B—C—(E—F)_q$$

wherein

A is the antisense oligonucleotide;

B is the cleavable moiety

C is the conjugate linker each E is a tether;

each F is a ligand; and q is an integer between 1 and 5.

In certain embodiments, the conjugates are bound to a nucleoside of the antisense oligonucleotide at the 2', 3', of 5' position of the nucleoside. In certain embodiments, a conjugated antisense compound has the following structure:

$$A—C—(E—F)_q$$

wherein

A is the antisense oligonucleotide;

C is the conjugate linker each E is a tether;

each F is a ligand; and q is an integer between 1 and 5.

In certain embodiments, a conjugated antisense compound has the following structure:

$$A—B—D—(E—F)_q$$

wherein

A is the antisense oligonucleotide;

B is the cleavable moiety

D is the branching group each E is a tether;

each F is a ligand; and q is an integer between 1 and 5.

In certain embodiments, a conjugated antisense compound has the following structure:

$$A—D—(E—F)_q$$

wherein

A is the antisense oligonucleotide;

D is the branching group each E is a tether;

each F is a ligand; and q is an integer between 1 and 5.

In certain such embodiments, the conjugate linker comprises at least one cleavable bond.

In certain embodiments each tether comprises at least one cleavable bond.

In certain embodiments, a conjugated antisense compound has a structure selected from among the following:

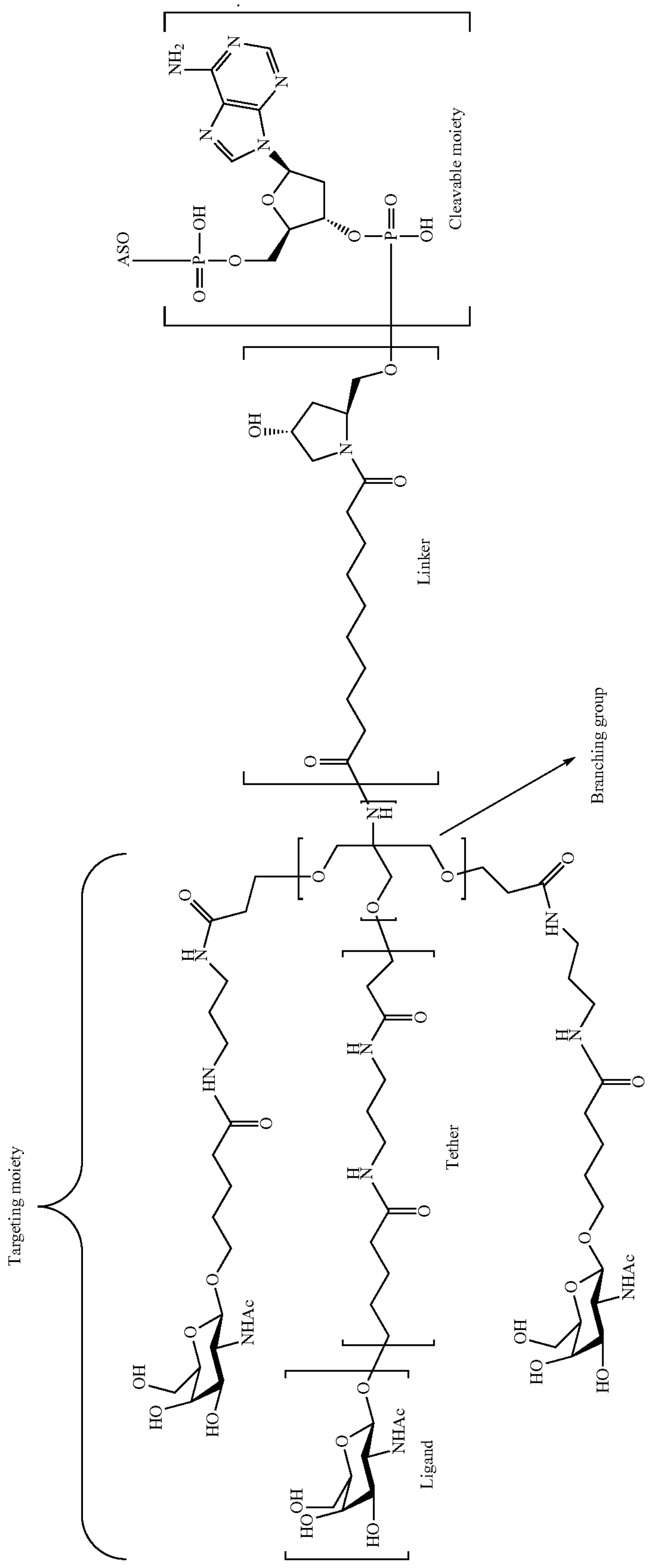
Cleavable moiety
Linker
Branching group
Targeting moiety
Tether
Ligand In certain embodiments, a conjugated antisense compound has a structure selected from among the following:
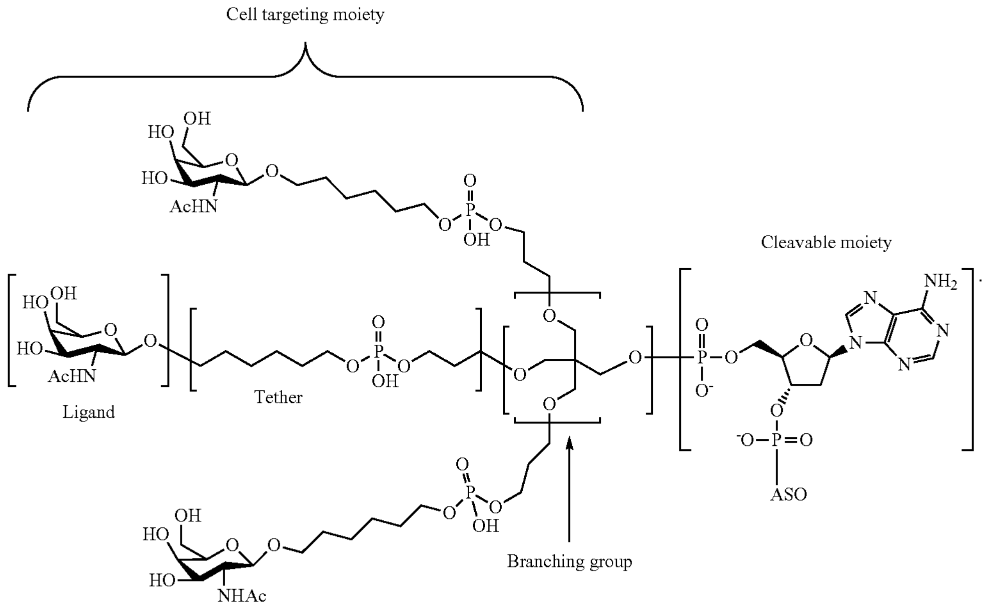
In certain embodiments, a conjugated antisense compound has a structure selected from among the following:
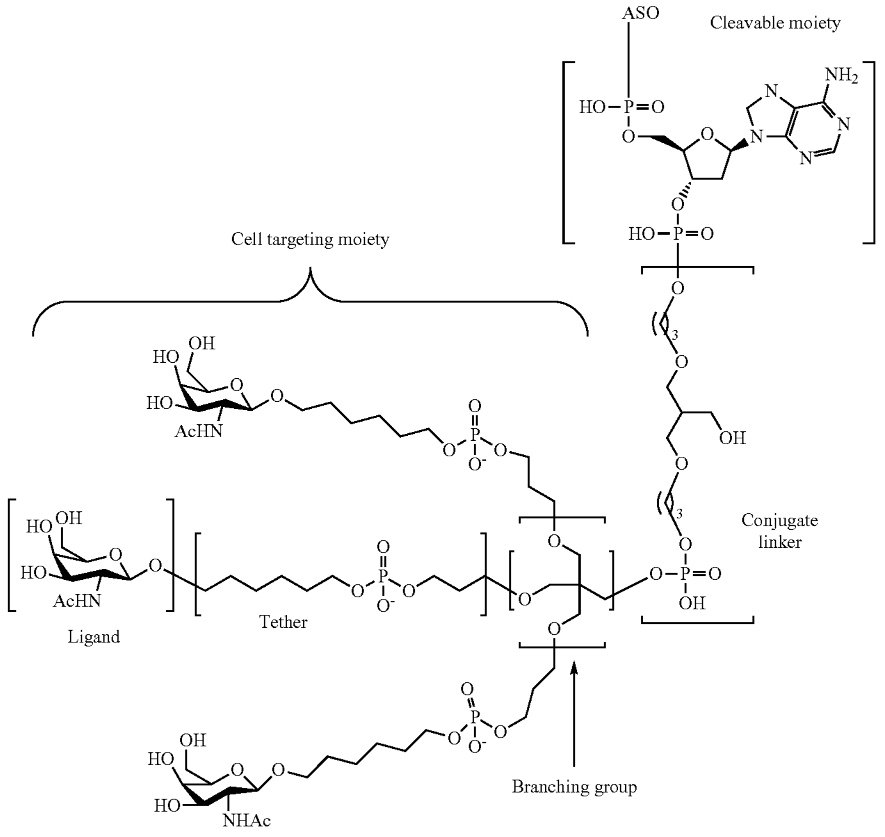

Representative United States patents, United States patent application publications, and international patent application publications that teach the preparation of certain of the above noted conjugates, conjugated antisense compounds, tethers, linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, each of which is incorporated by reference herein in its entirety.

Representative publications that teach the preparation of certain of the above noted conjugates, conjugated antisense compounds, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276 (40): 37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" *Tetrahedron,* 1997, 53 (2), 759-770, each of which is incorporated by reference herein in its entirety.

In certain embodiments, conjugated antisense compounds comprise an RNase H based oligonucleotide (such as a gapmer) or a splice modulating oligonucleotide (such as a fully modified oligonucleotide) and any conjugate group comprising at least one, two, or three GalNAc groups. In certain embodiments a conjugated antisense compound comprises any conjugate group found in any of the following references: Lee, *Carbohydr Res,* 1978, 67, 509-514; Connolly et al., *J Biol Chem,* 1982, 257, 939-945; *Pavia* et al., *Int J Pep Protein Res,* 1983, 22, 539-548; Lee et al., *Biochem,* 1984, 23, 4255-4261; Lee et al., *Glycoconjugate J,* 1987, 4, 317-328; Toyokuni et al., *Tetrahedron Lett,* 1990, 31, 2673-2676; Biessen et al., *J Med Chem,* 1995, 38, 1538-1546; Valentijn et al., *Tetrahedron,* 1997, 53, 759-770; Kim et al., *Tetrahedron Lett,* 1997, 38, 3487-3490; Lee et al., *Bioconjug Chem,* 1997, 8, 762-765; Kato et al., *Glycobiol,* 2001, 11, 821-829; Rensen et al., *J Biol Chem,* 2001, 276, 37577-37584; Lee et al., *Methods Enzymol,* 2003, 362, 38-43; Westerlind et al., *Glycoconj J,* 2004, 21, 227-241; Lee et al., *Bioorg Med Chem Lett,* 2006, 16 (19), 5132-5135; Maierhofer et al., *Bioorg Med Chem,* 2007, 15, 7661-7676; Khorev et al., *Bioorg Med Chem,* 2008, 16, 5216-5231; Lee et al., *Bioorg Med Chem,* 2011, 19, 2494-2500; Kornilova et al., *Analyt Biochem,* 2012, 425, 43-46; Pujol et al., *Angew Chemie Int Ed Engl,* 2012, 51, 7445-7448; Biessen et al., *J Med Chem,* 1995, 38, 1846-1852; Sliedregt et al., *J Med Chem,* 1999, 42, 609-618; Rensen et al., *J Med Chem,* 2004, 47, 5798-5808; Rensen et al., Arterioscler Thromb Vasc Biol, 2006, 26, 169-175; van Rossenberg et al., *Gene Ther,* 2004, 11, 457-464; Sato et al., *J Am Chem Soc,* 2004, 126, 14013-14022; Lee et al., *J Org Chem,* 2012, 77, 7564-7571; Biessen et al., FASEB J, 2000, 14, 1784-1792; Rajur et al., *Bioconjug Chem,* 1997, 8, 935-940; Duff et al., *Methods Enzymol,* 2000, 313, 297-321; Maier et al., *Bioconjug Chem,* 2003, 14, 18-29; Jayaprakash et al., *Org Lett,* 2010, 12, 5410-5413; Manoharan, Antisense Nucleic Acid Drug Dev, 2002, 12, 103-128; Merwin et al., *Bioconjug Chem,* 1994, 5, 612-620; Tomiya et al., *Bioorg Med Chem,* 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132; each of which is incorporated by reference in its entirety.

C. Certain Uses and Features

In certain embodiments, conjugated antisense compounds exhibit potent target RNA reduction in vivo. In certain embodiments, unconjugated antisense compounds accumulate in the kidney. In certain embodiments, conjugated antisense compounds accumulate in the liver. In certain embodiments, conjugated antisense compounds are well tolerated. Such properties render conjugated antisense compounds particularly useful for inhibition of many target RNAs, including, but not limited to those involved in metabolic, cardiovascular and other diseases, disorders or conditions. Thus, provided herein are methods of treating such diseases, disorders or conditions by contacting liver tissues with the conjugated antisense compounds targeted to RNAs associated with such diseases, disorders or conditions. Thus, also provided are methods for ameliorating any of a variety of metabolic, cardiovascular and other diseases, disorders or conditions with the conjugated antisense compounds of the present invention.

In certain embodiments, conjugated antisense compounds are more potent than unconjugated counterpart at a particular tissue concentration. Without wishing to be bound by any theory or mechanism, in certain embodiments, the conjugate may allow the conjugated antisense compound to enter the cell more efficiently or to enter the cell more productively. For example, in certain embodiments conjugated antisense compounds may exhibit greater target reduction as compared to its unconjugated counterpart wherein both the conjugated antisense compound and its unconjugated counterpart are present in the tissue at the same concentrations. For example, in certain embodiments conjugated antisense compounds may exhibit greater target reduction as compared to its unconjugated counterpart wherein both the conjugated antisense compound and its unconjugated counterpart are present in the liver at the same concentrations.

Productive and non-productive uptake of oligonucleotides has beed discussed previously (See e.g. Geary, R. S., E. Wancewicz, et al. (2009). "Effect of Dose and Plasma Concentration on Liver Uptake and Pharmacologic Activity of a 2'-Methoxyethyl Modified Chimeric Antisense Oligonucleotide Targeting PTEN." Biochem. Pharmacol. 78 (3): 284-91; & Koller, E., T. M. Vincent, et al. (2011). "Mechanisms of single-stranded phosphorothioate modified antisense oligonucleotide accumulation in hepatocytes." Nucleic Acids Res. 39 (11): 4795-807). Conjugate groups described herein may improve productive uptake.

In certain embodiments, the conjugate groups described herein may further improve potency by increasing the affinity of the conjugated antisense compound for a particular type of cell or tissue. In certain embodiments, the conjugate groups described herein may further improve potency by increasing recognition of the conjugated antisense compound by one or more cell-surface receptors. . . . In certain embodiments, the conjugate groups described herein may further improve potency by facilitating endocytosis of the conjugated antisense compound.

In certain embodiments, the cleavable moiety may further improve potency by allowing the conjugate to be cleaved from the antisense oligonucleotide after the conjugated antisense compound has entered the cell. Accordingly, in certain embodiments, conjugated antisense compounds can be administed at doses lower than would be necessary for unconjugated antisense oligonucleotides.

Phosphorothioate linkages have been incorporated into antisense oligonucleotides previously. Such phosphorothioate linkages are resistant to nucleases and so improve stability of the oligonucleotide. Further, phosphorothioate linkages also bind certain proteins, which results in accumulation of antisense oligonucleotide in the liver. Oligonucleotides with fewer phosphorothioate linkages accumulate less in the liver and more in the kidney (see, for example, Geary, R., "Pharmacokinetic Properties of 2'-O-(2-Methoxyethyl)-Modified Oligonucleotide Analogs in Rats," *Journal of Pharmacology and Experimental Therapeutics, Vol.* 296, *No.* 3, 890-897; & *Pharmacological Properties of* 2'-*O-Methoxyethyl Modified Oligonucleotides* in Antisense a Drug Technology, Chapter 10, Crooke, S. T., ed., 2008) In certain embodiments, oligonucleotides with fewer phosphorothioate internculeoside linkages and more phosphodiester internucleoside linkages accumulate less in the liver and more in the kidney. When treating diseases in the liver, this is undesibable for several reasons (1) less drug is getting to the site of desired action (liver); (2) drug is escaping into the urine; and (3) the kidney is exposed to relatively high concentration of drug which can result in toxicities in the kidney. Thus, for liver diseases, phosphorothioate linkages provide important benefits.

In certain embodiments, however, administration of oligonucleotides uniformly linked by phosphoro-thioate internucleoside linkages induces one or more proinflammatory reactions. (see for example: *J Lab Clin Med.* 1996 September;128 (3): 329-38. "Amplification of antibody production by phosphorothioate oligodeoxynucleotides". Branda et al.; and see also for example: *Toxicologic Properties* in Antisense a Drug Technology, Chapter 12, pages 342-351, Crooke, S. T., ed., 2008). In certain embodiments, administration of oligonucleotides wherein most of the internucleoside linkages comprise phosphorothioate internucleoside linkages induces one or more proinflammatory reactions.

In certain embodiments, the degree of proinflammatory effect may depend on several variables (e.g. backbone modification, off-target effects, nucleobase modifications, and/or nucleoside modifications) see for example: *Toxicologic Properties* in Antisense a Drug Technology, Chapter 12, pages 342-351, Crooke, S. T., ed., 2008). In certain embodiments, the degree of proinflammatory effect may be mitigated by adjusting one or more variables. For example the degree of proinflammatory effect of a given oligonucleotide may be mitigated by replacing any number of phosphorothioate internucleoside linkages with phosphodiester internucleoside linkages and thereby reducing the total number of phosphorothioate internucleoside linkages.

In certain embodiments, it would be desirable to reduce the number of phosphorothioate linkages, if doing so could be done without losing stability and without shifting the distribution from liver to kidney. For example, in certain embodiments, the number of phosphorothioate linkages may be reduced by replacing phosphorothioate linkages with phosphodiester linkages. In such an embodiment, the antisense compound having fewer phosphorothioate linkages and more phosphodiester linkages may induce less proinflammatory reactions or no proinflammatory reaction. Although the the antisense compound having fewer phosphoro-thioate linkages and more phosphodiester linkages may induce fewer proinflammatory reactions, the antisense compound having fewer phosphorothioate linkages and more phosphodiester linkages may not accumulate in the liver and may be less efficacious at the same or similar dose as compared to an antisense compound having more phosphorothioate linkages. In certain embodiments, it is therefore desirable to design an antisense compound that has a plurality of phosphodiester bonds and a plurality of phosphorothioate bonds but which also possesses stability and good distribution to the liver.

In certain embodiments, conjugated antisense compounds accumulate more in the liver and less in the kidney than unconjugated counterparts, even when some of the phospororothioate linkages are replaced with less proinflammatory phosphodiester internucleoside linkages. In certain embodiments, conjugated antisense compounds accumulate more in the liver and are not excreted as much in the urine compared to its unonjugated counterparts, even when some of the phosporothioate linkages are replaced with less proinflammatory phosphodiester internucleoside linkages. In certain embodiments, the use of a conjugate allows one to design more potent and better tolerated antisense drugs. Indeed, in certain emobidments, conjugated antisense compounds have larger therapeutic indexes than unconjugated counterparts. This allows the conjugated antisense compound to be administered at a higher absolute dose, because there is less risk of proinflammatory response and less risk of kidney toxicity. This higher dose, allows one to dose less frequently, since the clearance (metabolism) is expected to be similar. Further, because the compound is more potent, as described above, one can allow the concentration to go lower before the next dose without losing therapeutic activity, allowing for even longer periods between dosing.

In certain embodiments, the inclusion of some phosphorothioate linkages remains desirable. For example, the terminal linkages are vulnerable to exonucleoases and so in certain embodiments, those linkages are phosphorothioate or other modified linkage. Internucleoside linkages linking two deoxynucleosides are vulnerable to endonucleases and so in certain embodiments those those linkages are phosphorothioate or other modified linkage. Internucleoside linkages between a modified nucleoside and a deoxynucleoside where the deoxynucleoside is on the 5' side of the linkage deoxynucleosides are vulnerable to endonucleases and so in certain embodiments those those linkages are phosphorothioate or other modified linkage. Internucleoside linkages between two modified nucleosides of certain types and between a deoxynucleoside and a modified nucleoside of certain typ where the modified nucleoside is at the 5' side of the linkage are sufficiently resistant to nuclease digestion, that the linkage can be phosphodiester.

In certain embodiments, the antisense oligonucleotide of a conjugated antisense compound comprises fewer than 16 phosphorthioate linkages. In certain embodiments, the antisense oligonucleotide of a conjugated antisense compound comprises fewer than 15 phosphorthioate linkages. In certain embodiments, the antisense oligonucleotide of a conjugated antisense compound comprises fewer than 14 phosphorthioate linkages. In certain embodiments, the antisense oligonucleotide of a conjugated antisense compound comprises fewer than 13 phosphorthioate linkages. In certain embodiments, the antisense oligonucleotide of a conjugated antisense compound comprises fewer than 12 phosphorthioate linkages. In certain embodiments, the antisense oligonucleotide of a conjugated antisense compound comprises fewer than 11 phosphorthioate linkages. In certain embodiments, the antisense oligonucleotide of a conjugated antisense compound comprises fewer than 10 phosphorthioate linkages. In certain embodiments, the antisense oligonucleotide of a conjugated antisense compound comprises fewer than 9 phosphorthioate linkages. In certain embodiments, the antisense oligonucleotide of a conjugated antisense compound comprises fewer than 8 phosphorthioate linkages.

In certain embodiments, antisense compounds comprising one or more conjugae group described herein has increased activity and/or potency and/or tolerability compared to a parent antisense compound lacking such one or more conjugate group. Accordingly, in certain embodiments, attachment of such conjugate groups to an oligonucleotide is desirable. Such conjugate groups may be attached at the 5'-, and/or 3'-end of an oligonucleotide. In certain instances, attachment at the 5'-end is synthetically desireable. Typically, oligonucleietides are synthesized by attachment of the 3' terminal nucleoside to a solid support and sequential coupling of nucleosides from 3' to 5' using techniques that are well known in the art. Accordingly if a conjugate group is desred at the 3'-terminus, one may (1) attach the conjugate group to the 3'-terminal nucleoside and attach that conjugated nucleoside to the solid support for subsequent preparation of the oligonucleotide or (2) attach the conjugate group to the 3'-terminal nucleoside of a completed oligonucleotide after synthesis. Niether of these approaches is very efficient and thus both are costly. In particular, attachment of the conjugated nucleoside to the solid support, while demonstrated in the Examples herein, is an inefficient process. In certain embodiments, attaching a conjugate group to the 5'-terminal nucleoside is synthetically easier than attachment at the 3'-end. One may attach a non-conjugated 3' terminal nucleoside to the solid support and prepare the oligonucleotide using standard and well characterized reastions. One then needs only to attach a 5'nucleoside having a conjugate group at the final coupling step.

In certain embodiments, this is more efficient than attaching a conjugated nucleoside directly to the solid support as is typically done to prepare a 3'-conjugated oligonucleotide. The Examples herein demonstrate attachment at the 5'-end. In addition, certain conjugate groups have synthetic advantages. For Example, certain conjugate groups comprising phosphorus linkage groups are synthetically simpler and more efficiently prepared than other conjugate groups, including conjugate groups reported previously (e.g., WO/2012/037254).

In certain embodiments, conjugated antisense compounds are administered to a subject. In such embodiments, antisense compounds comprising one or more conjugae group described herein has increased activity and/or potency and/or tolerability compared to a parent antisense compound lacking such one or more conjugate group. Without being bound by mechanism, it is believed that the conjugate group helps with distribution, delivery, and/or uptake into a target cell or tissue. In certain embodiments, once inside the target cell or tissue, it is desirable that all or part of the conjugate group to be cleaved to releas the active oligonucleitde. In certain embodiments, it is not necessary that the entire conjugate group be cleaved from the oligonucleotide. For example, in Example 20 a conjugated oligonucleotide was administered to mice and a number of different chemical species, each comprising a different portion of the conjugate group remaining on the oligonucleotide, were detected (Table 10a). Thisconjugated antisense compound demonstrated good potency (Table 10). Thus, in certain embodiments, such metabolite profile of multiple partial cleavage of the conjugate group does not interfere with activity/potency. Nevertheless, in certain embodiments it is desirable that a prodrug (conjugated oligonucleotide) yield a single active compound. In certain instances, if multiple forms of the active compound are found, it may be necessary to determine relative amounts and activities for each one. In certain embodiments where regulatory review is required (e.g., USFDA or counterpart) it is desirable to have a single (or predominantly single) active species. In certain such embodiments, it is desirable that such single active species be the antisense oligonucleotide lacking any portion of the conjugate group. In certain embodiments, conjugate groups at the 5'-end are more likely to result in complete metabolism of the conjugate group. Without being bound by mechanism it may be that endogenous enzymes responsible for metabolism at the 5' end (e.g., 5' nucleases) are more active/efficient than the 3' counterparts. In certain embodiments, the specific conjugate groups are more amenable to metabolism to a single active species. In certain embodiments, certain conjugate groups are more amenable to metabolism to the oligonucleotide.

D. Antisense

In certain embodiments, oligomeric compounds of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

In certain embodiments, antisense compounds comprise a portion having a nucleobase sequence at least 70% complementary to the nucleobase sequence of a target nucleic acid. In certain embodiments, antisense compounds comprise a portion having a nucleobase sequence at least 80% complementary to the nucleobase sequence of a target nucleic acid. In certain embodiments, antisense compounds comprise a portion having a nucleobase sequence at least 90% complementary to the nucleobase sequence of a target nucleic acid. In certain embodiments, antisense compounds comprise a portion having a nucleobase sequence at least 95% complementary to the nucleobase sequence of a target nucleic acid. In certain embodiments, antisense compounds comprise a portion having a nucleobase sequence at least 98% complementary to the nucleobase sequence of a target nucleic acid. In certain embodiments, antisense compounds comprise a portion having a nucleobase sequence that is 100% complementary to the nucleobase sequence of a target nucleic acid. In certain embodiments, antisense compounds are at least 70%, 80%, 90%, 95%, 98%, or 100% complementary to the nucleobase sequence of a target nucleic acid over the entire length of the antisense compound.

Antisense mechanisms include any mechanism involving the hybridization of an oligomeric compound with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or polyadenylation of the target nucleic acid or of a nucleic acid with which the target nucleic acid may otherwise interact.

One type of antisense mechanism involving degradation of target RNA is RNase H mediated antisense. RNase H is a cellular endonuclease which cleaves the RNA strand of an RNA: DNA duplex. It is known in the art that single-stranded antisense compounds which are “DNA-like” elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms. Such mechanisms include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, oligonucleotides comprising conjugates described herein are RNAi compounds. In certain embodiments, oligomeric oligonucleotides comprising conjugates described herein are ssRNA compounds. In certain embodiments, oligonucleotides comprising conjugates described herein are paired with a second oligomeric compound to form an siRNA. In certain such embodiments, the second oligomeric compound also comprises a conjugate. In certain embodiments, the second oligomeric compound is any modified or unmodified nucleic acid. In certain embodiments, the oligonucleotides comprising conjugates described herein is the antisense strand in an siRNA compound. In certain embodiments, the oligonucleotides comprising conjugates described herein is the sense strand in an siRNA compound. In embodiments in which the conjugated oligomeric compound is double-stranded siRnA, the conjugate may be on the sense strand, the antisense strand or both the sense strand and the antisense strand.

D. Target Nucleic Acids, Regions and Segments

In certain embodiments, conjugated antisense compounds target any nucleic acid. In certain embodiments, the target nucleic acid encodes a target protein that is clinically relevant. In such embodiments, modulation of the target nucleic acid results in clinical benefit. Certain target nucleic acids include, but are not limited to, the target nucleic acids illustrated in Table 1.

TABLE 1

Certain Target Nucleic Acids

| Target | Species | GENBANK ® Accession Number | SEQ ID NO |
|---|---|---|---|
| HBV | Human | U95551.1 | 1 |
| Transthyretin (TTR) | Human | NM_000371.3 | 2 |

The targeting process usually includes determination of at least one target region, segment, or site within the target nucleic acid for the antisense interaction to occur such that the desired effect will result.

In certain embodiments, a target region is a structurally defined region of the nucleic acid. For example, in certain such embodiments, a target region may encompass a 3' UTR, a 5' UTR, an exon, an intron, a coding region, a translation initiation region, translation termination region, or other defined nucleic acid region or target segment.

In certain embodiments, a target segment is at least about an 8-nucleobase portion of a target region to which a conjugated antisense compound is targeted. Target segments can include DNA or RNA sequences that comprise at least 8 consecutive nucleobases from the 5'-terminus of one of the target segments (the remaining nucleobases being a consecutive stretch of the same DNA or RNA beginning immediately upstream of the 5'-terminus of the target segment and continuing until the DNA or RNA comprises about 8 to about 30 nucleobases). Target segments are also represented by DNA or RNA sequences that comprise at least 8 consecutive nucleobases from the 3'-terminus of one of the target segments (the remaining nucleobases being a consecutive stretch of the same DNA or RNA beginning immediately downstream of the 3'-terminus of the target segment and continuing until the DNA or RNA comprises about 8 to about 30 nucleobases). Target segments can also be represented by DNA or RNA sequences that comprise at least 8 consecutive nucleobases from an internal portion of the sequence of a target segment, and may extend in either or both directions until the conjugated antisense compound comprises about 8 to about 30 nucleobases.

In certain embodiments, antisense compounds targeted to the nucleic acids listed in Table 1 can be modified as described herein. In certain embodiments, the antisense compounds can have a modified sugar moiety, an unmodified sugar moiety or a mixture of modified and unmodified sugar moieties as described herein. In certain embodiments, the antisense compounds can have a modified internucleoside linkage, an unmodified internucleoside linkage or a mixture of modified and unmodified internucleoside linkages as described herein. In certain embodiments, the antisense compounds can have a modified nucleobase, an unmodified nucleobase or a mixture of modified and unmodified nucleobases as described herein. In certain embodiments, the antisense compounds can have a motif as described herein.

In certain embodiments, antisense compounds targeted to the nucleic acids listed in Table 1 can be conjugated as described herein.

1. Hepatitis B (HBV)

Hepatitis B is a viral disease transmitted parenterally by contaminated material such as blood and blood products, contaminated needles, sexually and vertically from infected or carrier mothers to their offspring. It is estimated by the World Health Organization that more than 2 billion people have been infected worldwide, with about 4 million acute cases per year, 1 million deaths per year, and 350-400 million chronic carriers (World Health Organization: Geographic Prevalence of Hepatitis B Prevalence, 2004. http://www.who.int/vaccines-surveillance/graphics/htmls/hepbprev.htm).

The virus, HBV, is a double-stranded hepatotropic virus which infects only humans and non-human primates. Viral replication takes place predominantly in the liver and, to a lesser extent, in the kidneys, pancreas, bone marrow and spleen (Hepatitis B virus biology. Microbiol Mol Biol Rev. 64:2000; 51-68.). Viral and immune markers are detectable in blood and characteristic antigen-antibody patterns evolve over time. The first detectable viral marker is HBsAg, followed by hepatitis B e antigen (HBeAg) and HBV DNA. Titers may be high during the incubation period, but HBV DNA and HBeAg levels begin to fall at the onset of illness and may be undetectable at the time of peak clinical illness (Hepatitis B virus infection-natural history and clinical consequences. N Engl J Med . . . 350:2004; 1118-1129). HBeAg is a viral marker detectable in blood and correlates with active viral replication, and therefore high viral load and infectivity (Hepatitis B e antigen—the dangerous end game of hepatitis B. N Engl J Med. 347:2002; 208-210). The presence of anti-HBsAb and anti-HBcAb (IgG) indicates recovery and immunity in a previously infected individual.

Currently the recommended therapies for chronic HBV infection by the American Association for the Study of Liver Diseases (AASLD) and the European Association for the Study of the Liver (EASL) include interferon alpha (INFa), pegylated interferon alpha-2a (Peg-IFN2a), entecavir, and tenofovir. The nucleoside and nucleobase therapies, entecavir and tenofovir, are successful at reducing viral load, but the rates of HBeAg seroconversion and HBsAg loss are even lower than those obtained using IFNα therapy. Other similar therapies, including lamivudine (3TC), telbivudine (LdT), and adefovir are also used, but for nucleoside/nucleobase therapies in general, the emergence of resistance limits therapeutic efficacy.

Thus, there is a need in the art to discover and develop new anti-viral therapies. Additionally, there is a need for new anti-HBV therapies capable of increasing HBeAg and HBsAg seroconversion rates. Recent clinical research has found a correlation between seroconversion and reductions in HBeAg (Fried et al (2008) Hepatology 47:428) and reductions in HBsAg (Moucari et al (2009) Hepatology 49:1151). Reductions in antigen levels may have allowed immunological control of HBV infection because high levels of antigens are thought to induce immunological tolerance. Current nucleoside therapies for HBV are capable of dramatic reductions in serum levels of HBV but have little impact on HBeAg and HBsAg levels.

Antisense compounds targeting HBV have been previously disclosed in WO2011/047312, WO2012/145674, and WO2012/145697, each herein incorporated by reference in its entirety. Clinical studies are planned to assess the effect of antisense compounds targeting HBV in patients. However, there is still a need to provide patients with additional and more potent treatment options.

Certain Conjugated Antisense Compounds Targeted to a HBV Nucleic Acid

In certain embodiments, conjugated antisense compounds are targeted to a HBV nucleic acid having the sequence of GENBANK® Accession No. U95551.1, incorporated herein as SEQ ID NO: 1. In certain such embodiments, a conjugated antisense compound targeted to SEQ ID NO: 1 is at least 90%, at least 95%, or 100% complementary to SEQ ID NO: 1.

In certain embodiments, a conjugated antisense compound targeted to SEQ ID NO: 1 comprises an at least 8 consecutive nucleobase sequence of SEQ ID NO: 3. In certain embodiments, a conjugated antisense compound targeted to SEQ ID NO: 1 comprises a nucleobase sequence of SEQ ID NO: 3.

In certain embodiments, a conjugated antisense compound targeted to SEQ ID NO: 1 comprises an at least 8 consecutive nucleobase sequence of SEQ ID NO: 4. In certain embodiments, a conjugated antisense compound targeted to SEQ ID NO: 1 comprises a nucleobase sequence of SEQ ID NO: 4.

In certain embodiments, a conjugated antisense compound targeted to SEQ ID NO: 1 comprises an at least 8 consecutive nucleobase sequence of SEQ ID NO: 5. In certain embodiments, a conjugated antisense compound targeted to SEQ ID NO: 1 comprises a nucleobase sequence of SEQ ID NO: 5.

In certain embodiments, a conjugated antisense compound targeted to SEQ ID NO: 1 comprises an at least 8 consecutive nucleobase sequence of SEQ ID NO: 6. In certain embodiments, a conjugated antisense compound targeted to SEQ ID NO: 1 comprises a nucleobase sequence of SEQ ID NO: 6.

In certain embodiments, a conjugated antisense compound targeted to SEQ ID NO: 1 comprises an at least 8 consecutive nucleobase sequence of SEQ ID NO: 7. In certain embodiments, a conjugated antisense compound targeted to SEQ ID NO: 1 comprises a nucleobase sequence of SEQ ID NO: 7.

In certain embodiments, a conjugated antisense compound targeted to SEQ ID NO: 1 comprises an at least 8 consecutive nucleobase sequence of SEQ ID NO: 8. In certain embodiments, a conjugated antisense compound targeted to SEQ ID NO: 1 comprises a nucleobase sequence of SEQ ID NO: 8.

In certain embodiments, a conjugated antisense compound targeted to SEQ ID NO: 1 comprises an at least 8 consecutive nucleobase sequence of SEQ ID NO: 9. In certain embodiments, a conjugated antisense compound targeted to SEQ ID NO: 1 comprises a nucleobase sequence of SEQ ID NO: 9.

In certain embodiments, a conjugated antisense compound targeted to SEQ ID NO: 1 comprises an at least 8 consecutive nucleobase sequence of SEQ ID NO: 10. In certain embodiments, a conjugated antisense compound targeted to SEQ ID NO: 1 comprises a nucleobase sequence of SEQ ID NO: 10.

In certain embodiments, a conjugated antisense compound targeted to SEQ ID NO: 1 comprises an at least 8 consecutive nucleobase sequence of SEQ ID NO: 11. In certain embodiments, a conjugated antisense compound targeted to SEQ ID NO: 1 comprises a nucleobase sequence of SEQ ID NO: 11.

TABLE 2

| Antisense Compounds targeted to HBV SEQ ID NO: 1 | | | | |
|---|---|---|---|---|
| ISIS No | Target Start Site | Sequence (5'-3') | Motif | SEQ ID NO |
| 505358 | 1583 | GCAGAGGTGAAGCGAAGTGC | eeeeeddddddddddeeeee | 3 |
| 509934 | 1780 | CCAATTTATGCCTACAGCCT | eeeeeddddddddddeeeee | 4 |
| 510100 | 411 | GGCATAGCAGCAGGATG | eeeddddddddddeeee | 5 |
| 552023 | 1266 | AGGAGTTCCGCAGTATGGAT | eeeeeeddddddddddeeee | 6 |
| 552024 | 1577 | GTGAAGCGAAGTGCACACGG | eeeeeeddddddddddeeee | 7 |
| 552032 | 1585 | GTGCAGAGGTGAAGCGAAGT | eeeeeeddddddddddeeee | 8 |
| 552859 | 1583 | AGGTGAAGCGAAGTGC | ekkddddddddddkke | 9 |
| 552925 | 1264 | TCCGCAGTATGGATCG | ekddddddddddkeke | 10 |
| 577119 | 1780 | AATTTATGCCTACAGCCT | kdkdkddddddddeeeee | 11 |

In certain embodiments, a compound comprises or consists of ISIS 505358 and a conjugate group. ISIS 505358 is a modified oligonucleotide having the formula: Ges mCes Aes Ges Aes Gds Gds Tds Gds Ads Ads Gds mCds Gds Ads Aes Ges Tes Ges mCe, wherein, A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 509934 and a conjugate group.

ISIS 509934 is a modified oligonucleotide having the formula: mCes mCes Aes Aes Tes Tds Tds Ads Tds Gds mCds mCds Tds Ads mCds Aes Ges mCes mCes Te, wherein, A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 510100 and a conjugate group. ISIS 510100 is a modified oligonucleotide having the formula: Ges Ges mCes Ads Tds Ads Gds mCds Ads Gds mCds Ads Gds Ges Aes Tes Ge, wherein, A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 552023 and a conjugate group. ISIS 552023 is a modified oligonucleotide having the formula: Aes Ges Ges Aes Ges Tes Tds mCds mCds Gds mCds Ads Gds Tds Ads Tds Ges Ges Aes Te, wherein, A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 552024 and a conjugate group. ISIS 552024 is a modified oligonucleotide having the formula: Ges Tes Ges Aes Aes Ges mCds Gds Ads Ads Gds Tds Gds mCds Ads mCds Aes mCes Ges Ge, wherein, A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 552032 and a conjugate group. ISIS 552032 is a modified oligonucleotide having the formula: Ges Tes Ges mCes Aes Ges Ads Gds Gds Tds Gds Ads Ads Gds mCds Gds Aes Aes Ges Te, wherein, A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 552859 and a conjugate group. ISIS 552859 is a modified oligonucleotide having the formula: Aes Gks Gks Tds Gds Ads Ads Gds mCds Gds Ads Ads Gds Tks Gks mCe, wherein, A=an adenine, mC=a 5'-methylcytosine G=a guanine, T=a thymine, e=a 2'-O-methoxyethyl modified nucleoside, k=a cEt modified nucleoside, d=a 2'-deoxynucleoside, and s=a phosphorothioate internucleoside linkage.

In certain embodiments, a compound comprises or consists of ISIS 552925 and a conjugate group. ISIS 552925 is a modified oligonucleotide having the formula: Tes mCks mCds Gds mCds Ads Gds Tds Ads Tds Gds Gds Aks Tes mCks Ge, wherein, A=an adenine, mC=a 5'-methylcytosine G=a guanine, T=a thymine, e=a 2'-O-methoxyethyl modified nucleoside, k=a cEt modified nucleoside, d=a 2'-deoxynucleoside, and s=a phosphorothioate internucleoside linkage.

s=a phosphorothioate internucleoside linkage.

In certain embodiments, a compound comprises or consists of ISIS 577119 and a conjugate group. ISIS 577119 is a modified oligonucleotide having the formula: Aks Ads Tks Tds Tks Ads Tds Gds mCds mCds Tds Ads mCds Aes Ges mCes mCes Te, wherein, A=an adenine, mC=a 5'-methylcytosine G=a guanine, T=a thymine, e=a 2'-O-methoxyethyl modified nucleoside, k=a cEt modified nucleoside, d=a 2'-deoxynucleoside, and s=a phosphorothioate internucleoside linkage.

In certain embodiments, a compound having the following chemical structure comprises or consists of ISIS 505358 with a 5'-X, wherein X is a conjugate group as described herein:

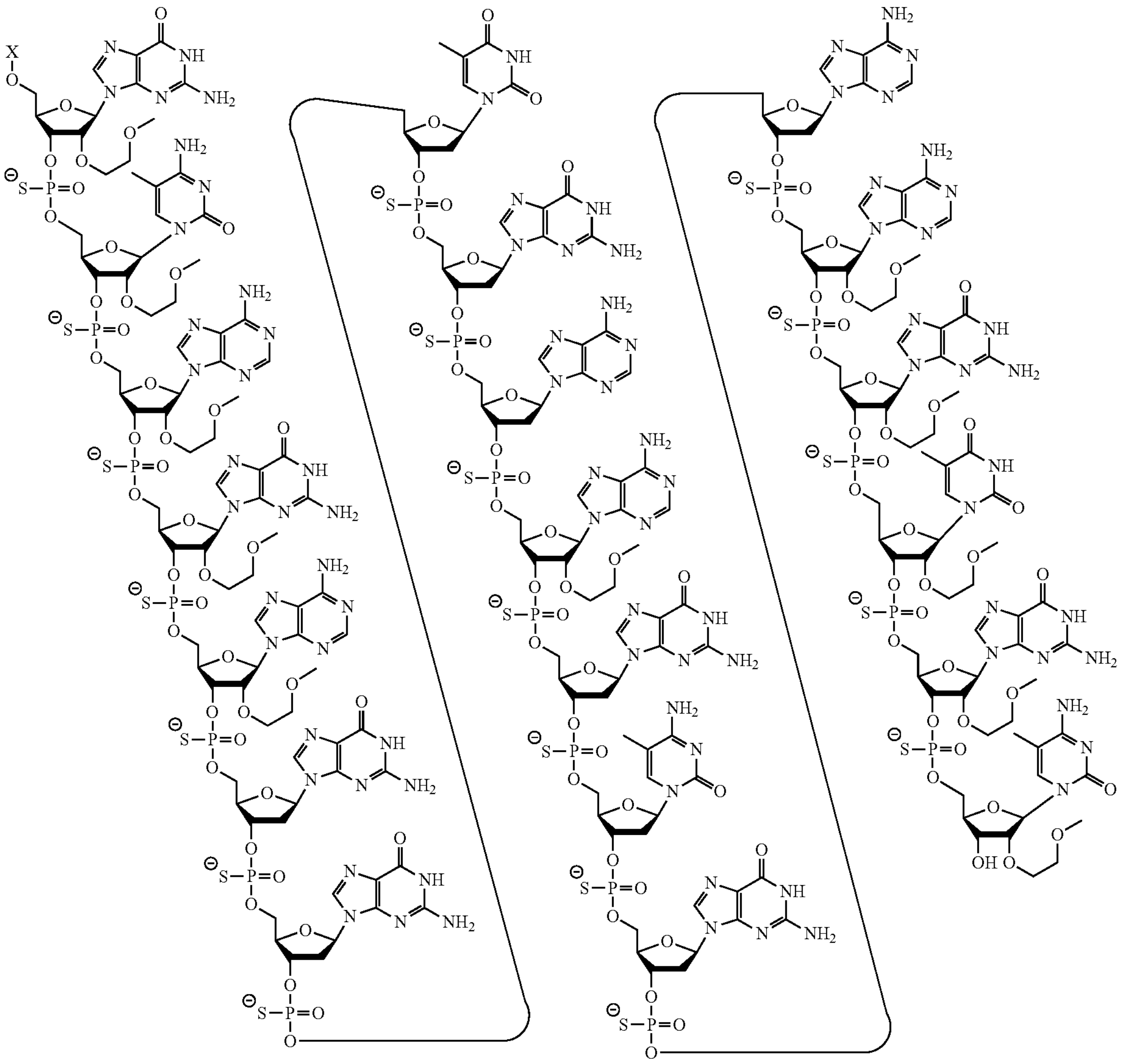

In certain embodiments, a compound comprises or consists of ISIS 712408 having the following chemical structure:
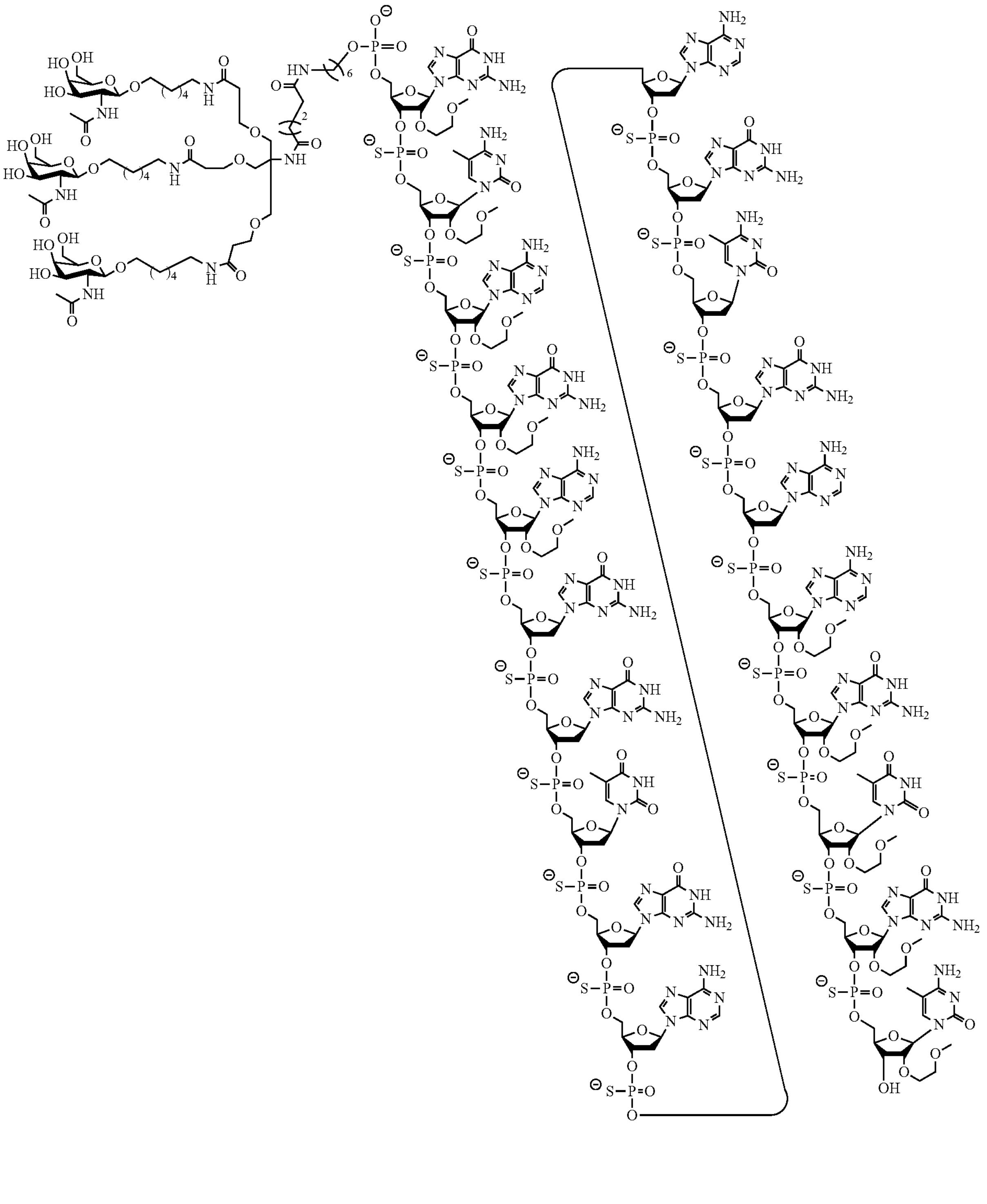
In certain embodiments, a compound comprises or consists of ISIS 695324 having the following chemical structure:

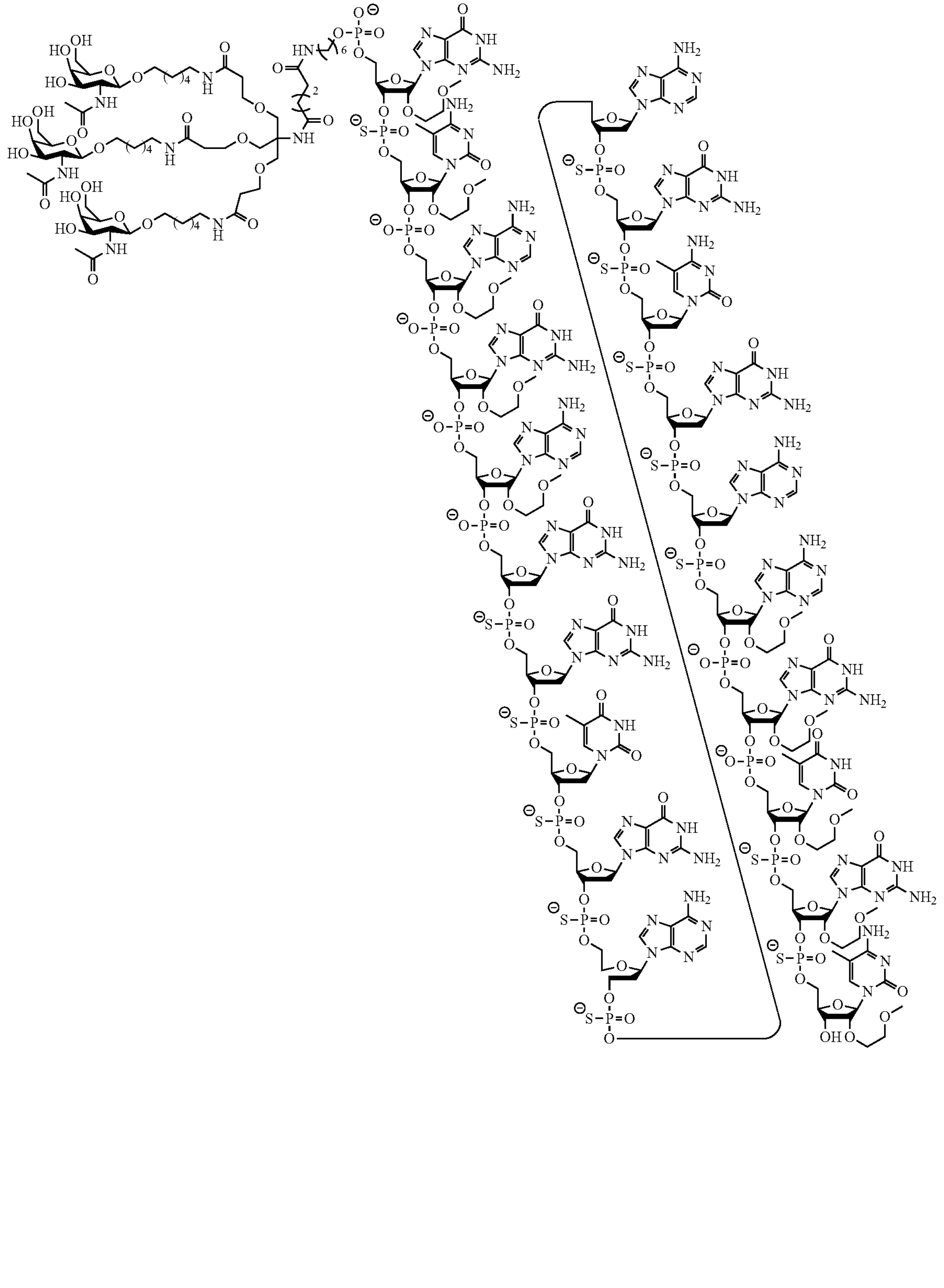
In certain embodiments, a compound comprises or consists of SEQ ID NO: 3,5'-GalNAc, and chemical modifications as represented by the following chemical structure:

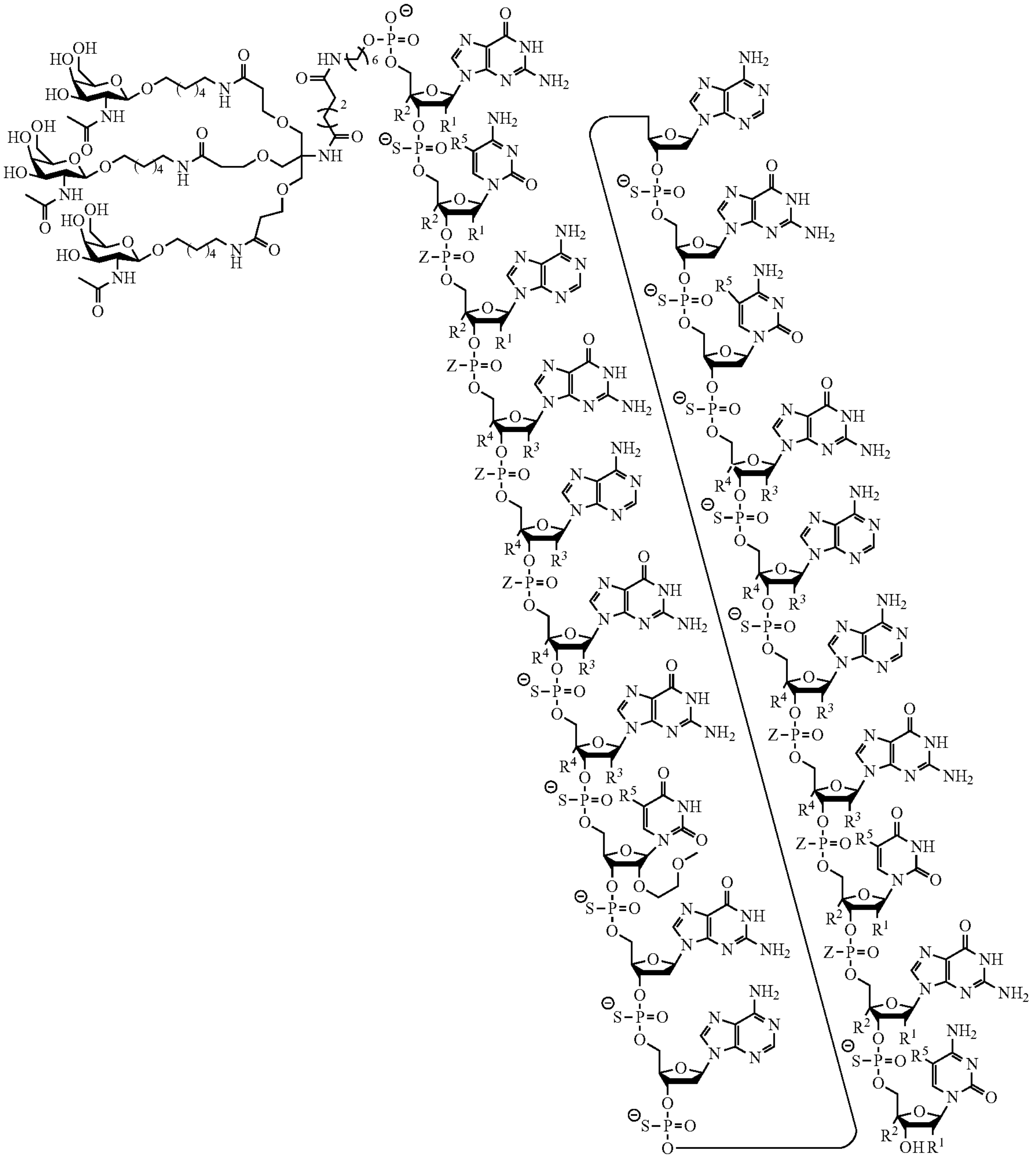

wherein either $R^1$ is —$OCH_2CH_2OCH_3$ (MOE) and $R^2$ is H; or $R^1$ and $R^2$ together form a bridge, wherein $R^1$ is —O— and $R^2$ is —$CH_2$—, —$CH(CH_3)$—, or —$CH_2CH_2$—, and $R^1$ and $R^2$ are directly connected such that the resulting bridge is selected from: —O—$CH_2$—, —O—$CH(CH_3)$—, and —O—$CH_2CH_2$—;

and for each pair of $R^3$ and $R^4$ on the same ring, independently for each ring: either $R^3$ is selected from H and —$OCH_2CH_2OCH_3$ and $R^4$ is H; or $R^3$ and $R^4$ together form a bridge, wherein $R^3$ is —O—, and $R^4$ is —$CH_2$—, —$CH(CH_3)$—, or —$CH_2CH_2$— and $R^3$ and $R^4$ are directly connected such that the resulting bridge is selected from: —O—$CH_2$—, —O—$CH(CH_3)$—, and —O—$CH_2CH_2$—;

and $R_5$ is selected from H and —$CH_3$;

and Z is selected from S- and O.

In certain embodiments, a compound comprises an antisense oligonucleotide disclosed in WO 2012/145697, which is incorporated by reference in its entirety herein, and a conjugate group described herein. In certain embodiments, a compound comprises an antisense oligonucleotide having a nucleobase sequence of any of SEQ ID NOs 5-310, 321-802, 804-1272, 1288-1350, 1364-1372, 1375, 1376, and 1379 disclosed in WO 2012/145697 and a conjugate group described herein. In certain embodiments, a compound comprises an antisense oligonucleotide disclosed in WO 2011/047312, which is incorporated by reference in its entirety herein, and a conjugate group described herein. In certain embodiments, a compound comprises an antisense oligonucleotide having a nucleobase sequence of any of SEQ ID NOs 14-22 disclosed in WO 2011/047312 and a conjugate group described herein. In certain embodiments, a compound comprises an antisense oligonucleotide disclosed in WO 2012/145674, which is incorporated by reference in its entirety herein, and a conjugate group described herein. In certain embodiments, a compound comprises an antisense oligonucleotide having a nucleobase sequence of any of SEQ ID NOs 18-35 disclosed in WO 2012/145674. In certain embodiments, a compound comprises a double-stranded oligonucleotide disclosed in WO 2013/159109, which is incorporated by reference in its entirety herein, and a conjugate group described herein. In certain embodiments, a compound comprises a double-stranded oligonucleotide in which one strand has a nucleobase sequence of any of SEQ ID NOs 30-125 disclosed in WO 2013/159109. The nucleobase sequences of all of the aforementioned referenced SEQ ID NOs are incorporated by reference herein.

HBV Therapeutic Indications In certain embodiments, the invention provides methods for using a conjugated antisense compound targeted to a HBV nucleic acid for modulating the expression of HBV in a subject. In certain embodiments, the expression of HBV is reduced.

In certain embodiments, the invention provides methods for using a conjugated antisense compound targeted to a HBV nucleic acid in a pharmaceutical composition for treating a subject. In certain embodiments, the subject has a HBV-related condition. In certain embodiments, the HBV-related condition includes, but is not limited to, chronic HBV infection, inflammation, fibrosis, cirrhosis, liver cancer, serum hepatitis, jaundice, liver cancer, liver inflammation, liver fibrosis, liver cirrhosis, liver failure, diffuse hepatocellular inflammatory disease, hemophagocytic syndrome, serum hepatitis, and HBV viremia. In certain embodiments, the HBV-related condition may have symptoms which may include any or all of the following: flu-like illness, weakness, aches, headache, fever, loss of appetite, diarrhea, jaundice, nausea and vomiting, pain over the liver area of the body, clay-or grey-colored stool, itching all over, and dark-colored urine, when coupled with a positive test for presence of a hepatitis B virus, a hepatitis B viral antigen, or a positive test for the presence of an antibody specific for a hepatitis B viral antigen. In certain embodiments, the subject is at risk for an HBV-related condition. This includes subjects having one or more risk factors for developing an HBV-related condition, including sexual exposure to an individual infected with Hepatitis B virus, living in the same house as an individual with a lifelong hepatitis B virus infection, exposure to human blood infected with the hepatitis B virus, injection of illicit drugs, being a person who has hemophilia, and visiting an area where hepatitis B is common. In certain embodiments, the subject has been identified as in need of treatment for an HBV-related condition.

Certain embodiments provide a method of reducing HBV DNA and/or HBV antigen levels in a animal infected with HBV comprising administering to the animal a conjugated antisense compound targeted to a HBV nucleic acid. In certain embodiments, the antigen is HBsAG or HBeAG. In certain embodiments, the amount of HBV antigen may be sufficiently reduced to result in seroconversion.

In certain embodiments, the invention provides methods for using a conjugated antisense compound targeted to a HBV nucleic acid in the preparation of a medicament.

In certain embodiments, the invention provides a conjugated antisense compound targeted to a HBV nucleic acid, or a pharmaceutically acceptable salt thereof, for use in therapy.

Certain embodiments provide a conjugated antisense compound targeted to a HBV nucleic acid for use in the treatment of a HBV-related condition. The HBV-related condition includes, but is not limited to, chronic HBV infection, inflammation, fibrosis, cirrhosis, liver cancer, serum hepatitis, jaundice, liver cancer, liver inflammation, liver fibrosis, liver cirrhosis, liver failure, diffuse hepatocellular inflammatory disease, hemophagocytic syndrome, serum hepatitis, and HBV viremia.

Certain embodiments provide a conjugated antisense compound targeted to a HBV nucleic acid for use in reducing HBV DNA and/or HBV antigen levels in a animal infected with HBV comprising administering to the animal a conjugated antisense compound targeted to a HBV nucleic acid. In certain embodiments, the antigen is HBsAG or HBeAG. In certain embodiments, the amount of HBV antigen may be sufficiently reduced to result in seroconversion.

It will be understood that any of the compounds described herein can be used in the aforementioned methods and uses. For example, in certain embodiments a conjugated antisense compound targeted to a HBV nucleic acid in the aforementioned methods and uses can include, but is not limited to, a conjugated antisense compound targeted to SEQ ID NO: 1 comprising an at least 8 consecutive nucleobase sequence of any of SEQ ID NOs: 3-11; a conjugated antisense compound targeted to SEQ ID NO: 1 comprising a nucleobase sequence of any of SEQ ID NOs: 3-11; a compound comprising or consisting of ISIS 505358, ISIS 509934, ISIS 510100, ISIS 552023, ISIS 552024, ISIS 552032, ISIS 552859, ISIS 552925, or ISIS 577119 and a conjugate group; a compound comprising an antisense oligonucleotide disclosed in WO 2012/145697, which is incorporated by reference in its entirety herein, and a conjugate group; a compound comprising an antisense oligonucleotide having a nucleobase sequence of any of SEQ ID NOs 5-310, 321-802, 804-1272, 1288-1350, 1364-1372, 1375, 1376, and 1379 disclosed in WO 2012/145697 and a conjugate group described herein; a compound comprising an antisense oligonucleotide having a nucleobase sequence of any of SEQ ID NOs 14-22 disclosed in WO 2011/047312 and a conjugate group described herein; a compound comprising an antisense oligonucleotide having a nucleobase sequence of any of SEQ ID NOs 18-35 disclosed in WO 2012/145674; or a compound comprising a double-stranded oligonucleotide in which one strand has a nucleobase sequence of any of SEQ ID NOs 30-125 disclosed in WO 2013/159109.

2. Transthyretin (TTR)

TTR (also known as prealbumin, hyperthytoxinemia, dysprealbuminemic, thyroxine; senile systemic amyloidosis, amyloid polyneuropathy, amyloidosis I, PALB; dystransthyretinemic, HST2651; TBPA; dysprealbuminemic euthyroidal hyperthyroxinemia) is a serum/plasma and cerebrospinal fluid protein responsible for the transport of thyroxine and retinol (Sakaki et al, Mol Biol Med. 1989, 6:161-8). Structurally, TTR is a homotetramer; point mutations and misfolding of the protein leads to deposition of amyloid fibrils and is associated with disorders, such as senile systemic amyloidosis (SSA), familial amyloid polyneuropathy (FAP), and familial amyloid cardiopathy (FAC).

TTR is synthesized primarily by the liver and the choroid plexus of the brain and, to a lesser degree, by the retina in humans (Palha, *Clin Chem Lab Med,* 2002, 40, 1292-1300). Transthyretin that is synthesized in the liver is secreted into the blood, whereas transthyretin originating in the choroid plexus is destined for the CSF. In the choroid plexus, transthyretin synthesis represents about 20% of total local protein synthesis and as much as 25% of the total CSF protein (Dickson et al., *J Biol Chem,* 1986, 261, 3475-3478).

With the availability of genetic and immunohistochemical diagnostic tests, patients with TTR amyloidosis have been found in many nations worldwide. Recent studies indicate that TTR amyloidosis is not a rare endemic disease as previously thought, and may affect as much as 25% of the elderly population (Tanskanen et al, Ann Med. 2008; 40 (3): 232-9).

At the biochemical level, TTR was identified as the major protein component in the amyloid deposits of FAP patients (Costa et al, *Proc. Natl. Acad. Sci. USA* 1978, 75:4499-4503) and later, a substitution of methionine for valine at position 30 of the protein was found to be the most common molecular defect causing the disease (Saraiva et al, *J. Clin. Invest.* 1984, 74:104-119). In FAP, widespread systemic extracellular deposition of TTR aggregates and amyloid fibrils occurs throughout the connective tissue, particularly in the peripheral nervous system (Sousa and Saraiva, *Prog. Neurobiol.* 2003, 71:385-400). Following TTR deposition, axonal degeneration occurs, starting in the unmyelinated and myelinated fibers of low diameter, and ultimately leading to neuronal loss at ganglionic sites.

Antisense compounds targeting TTR have been previously disclosed in US2005/0244869, WO2010/017509, and WO2011/139917, each herein incorporated by reference in its entirety. An antisense oligonucleobase targeting TTR, ISIS-TTRRx, is currently in Phase 2/3 clinical trials to study its effectiveness in treating subjects with Familial Amyloid Polyneuropathy. However, there is still a need to provide patients with additional and more potent treatment options.

Certain Conjugated Antisense Compounds Targeted to a TTR Nucleic Acid

In certain embodiments, conjugated antisense compounds are targeted to a TTR nucleic acid having the sequence of GENBANK® Accession No. NM_000371.3, incorporated herein as SEQ ID NO: 2. In certain such embodiments, a conjugated antisense compound targeted to SEQ ID NO: 2 is at least 90%, at least 95%, or 100% complementary to SEQ ID NO: 2.

In certain embodiments, a conjugated antisense compound targeted to SEQ ID NO: 2 comprises an at least 8 consecutive nucleobase sequence of any one of SEQ ID NOs: 12-19. In certain embodiments, a conjugated antisense compound targeted to SEQ ID NO: 2 comprises a nucleobase sequence of any one of SEQ ID NO: 12-19.

In certain embodiments, a conjugated antisense compound targeted to SEQ ID NO: 2 comprises an at least 8 consecutive nucleobase sequence of SEQ ID NO: 12. In certain embodiments, a conjugated antisense compound targeted to SEQ ID NO: 2 comprises a nucleobase sequence of SEQ ID NO: 12.

In certain embodiments, a conjugated antisense compound targeted to SEQ ID NO: 2 comprises an at least 8 consecutive nucleobase sequence of SEQ ID NO: 13. In certain embodiments, a conjugated antisense compound targeted to SEQ ID NO: 2 comprises a nucleobase sequence of SEQ ID NO: 13.

In certain embodiments, a conjugated antisense compound targeted to SEQ ID NO: 2 comprises an at least 8 consecutive nucleobase sequence of SEQ ID NO: 14. In certain embodiments, a conjugated antisense compound targeted to SEQ ID NO: 2 comprises a nucleobase sequence of SEQ ID NO: 14.

In certain embodiments, a conjugated antisense compound targeted to SEQ ID NO: 2 comprises an at least 8 consecutive nucleobase sequence of SEQ ID NO: 15. In certain embodiments, a conjugated antisense compound targeted to SEQ ID NO: 2 comprises a nucleobase sequence of SEQ ID NO: 15.

In certain embodiments, a conjugated antisense compound targeted to SEQ ID NO: 16 comprises an at least 8 consecutive nucleobase sequence of SEQ ID NO: 78. In certain embodiments, a conjugated antisense compound targeted to SEQ ID NO: 16 comprises a nucleobase sequence of SEQ ID NO: 78.

In certain embodiments, a conjugated antisense compound targeted to SEQ ID NO: 2 comprises an at least 8 consecutive nucleobase sequence of SEQ ID NO: 17. In certain embodiments, a conjugated antisense compound targeted to SEQ ID NO: 2 comprises a nucleobase sequence of SEQ ID NO: 17.

In certain embodiments, a conjugated antisense compound targeted to SEQ ID NO: 2 comprises an at least 8 consecutive nucleobase sequence of SEQ ID NO: 18. In certain embodiments, a conjugated antisense compound targeted to SEQ ID NO: 2 comprises a nucleobase sequence of SEQ ID NO: 18.

In certain embodiments, a conjugated antisense compound targeted to SEQ ID NO: 2 comprises an at least 8 consecutive nucleobase sequence of SEQ ID NO: 19. In certain embodiments, a conjugated antisense compound targeted to SEQ ID NO: 2 comprises a nucleobase sequence of SEQ ID NO: 19.

TABLE 3

Antisense Compounds targeted to TTR SEQ ID NO: 2

| ISIS No | Target Start Site | Sequence (5'-3') | Motif | SEQ ID NO |
|---|---|---|---|---|
| 420915 | 508 | TCTTGGTTACATGAAATCCC | eeeeeddddddddddeeeee | 12 |
| 304299 | 507 | CTTGGTTACATGAAATCCCA | eeeeeddddddddddeeeee | 13 |
| 420921 | 515 | GGAATACTCTTGGTTACATG | eeeeeddddddddddeeeee | 14 |
| 420922 | 516 | TGGAATACTCTTGGTTACAT | eeeeeddddddddddeeeee | 15 |
| 420950 | 580 | TTTTATTGTCTCTGCCTGGA | eeeeeddddddddddeeeee | 16 |

TABLE 3-continued

Antisense Compounds targeted to TTR SEQ ID NO: 2

| ISIS No | Target Start Site | Sequence (5'-3') | Motif | SEQ ID NO |
|---|---|---|---|---|
| 420955 | 585 | GAATGTTTTATTGTCTCTGC | eeeeeddddddddddeeeee | 17 |
| 420957 | 587 | AGGAATGTTTTATTGTCTCT | eeeeeddddddddddeeeee | 18 |
| 420959 | 589 | ACAGGAATGTTTTATTGTCT | eeeeeddddddddddeeeee | 19 |

In certain embodiments, a compound comprises or consists of ISIS 420915 and a conjugate group. ISIS 420915 is a modified oligonucleotide having the formula: Tes mCes Tes Tes Ges Gds Tds Tds Ads mCds Ads Tds Gds Ads Ads Aes Tes mCes mCes mCe, wherein A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 304299 and a conjugate group. ISIS 304299 is a modified oligonucleotide having the formula: mCes Tes Tes Ges Ges Tds Tds Ads mCds Ads Tds Gds Ads Ads Ads Tes mCes mCes mCes Ae, wherein A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 420921 and a conjugate group. ISIS 420921 is a modified oligonucleotide having the formula: Ges Ges Aes Aes Tes Ads mCds Tds mCds Tds Tds Gds Gds Tds Tds Aes mCes Aes Tes Ge, wherein A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 420922 and a conjugate group. ISIS 420922 is a modified oligonucleotide having the formula: Tes Ges Ges Aes Aes Tds Ads mCds Tds mCds Tds Tds Gds Gds Tds Tes Aes mCes Aes Te, wherein A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 420950 and a conjugate group. ISIS 420950 is a modified oligonucleotide having the formula: Tes Tes Tes Tes Aes Tds Tds Gds Tds mCds Tds mCds Tds Gds mCds mCes Tes Ges Ges Ae, wherein A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 420955 and a conjugate group. ISIS 420955 is a modified oligonucleotide having the formula: Ges Aes Aes Tes Ges Tds Tds Tds Tds Ads Tds Tds Gds Tds mCds Tes mCes Tes Ges mCe, wherein A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 420957 and a conjugate group. ISIS 420957 is a modified oligonucleotide having the formula: Aes Ges Ges Aes Aes Tds Gds Tds Tds Tds Tds Ads Tds Tds Gds Tes mCes Tes mCes Te, wherein A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound comprises or consists of ISIS 420959 and a conjugate group. ISIS 420959 is a modified oligonucleotide having the formula: Aes mCes Aes Ges Ges Ads Ads Tds Gds Tds Tds Tds Tds Ads Tds Tes Ges Tes mCes Te, wherein A=an adenine, mC=a 5'-methylcytosine G=a guanine, T=a thymine, e=a 2'-O-methoxyethyl modified nucleoside, d=a 2'-deoxynucleoside, and s=a phosphorothioate internucleoside linkage.

In certain embodiments, a compound having the following chemical structure comprises or consists of ISIS 420915 with a 5'-X, wherein X is a conjugate group as described herein:

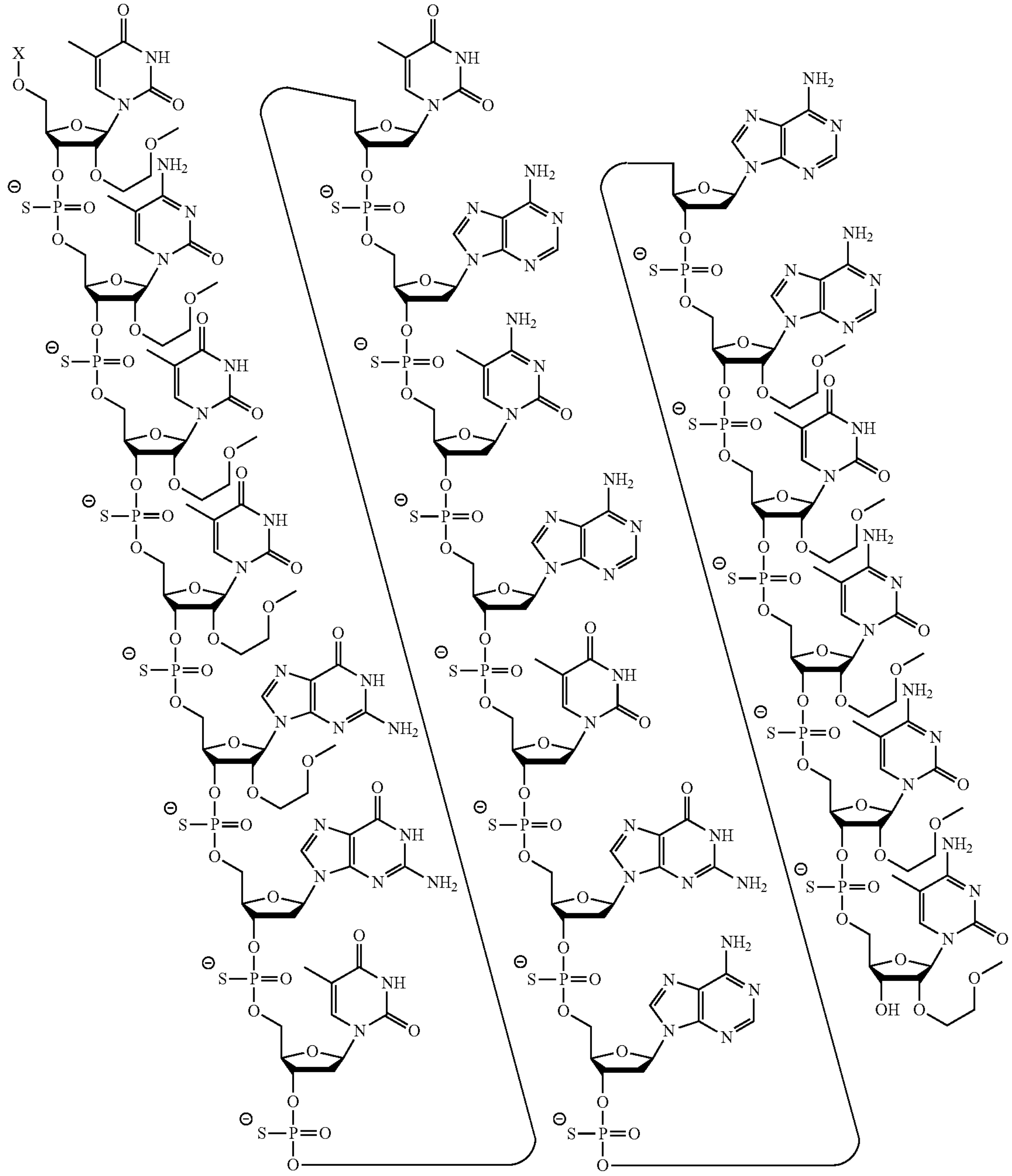
In certain embodiments, a compound comprises or consists of ISIS 682877 having the following chemical structure:

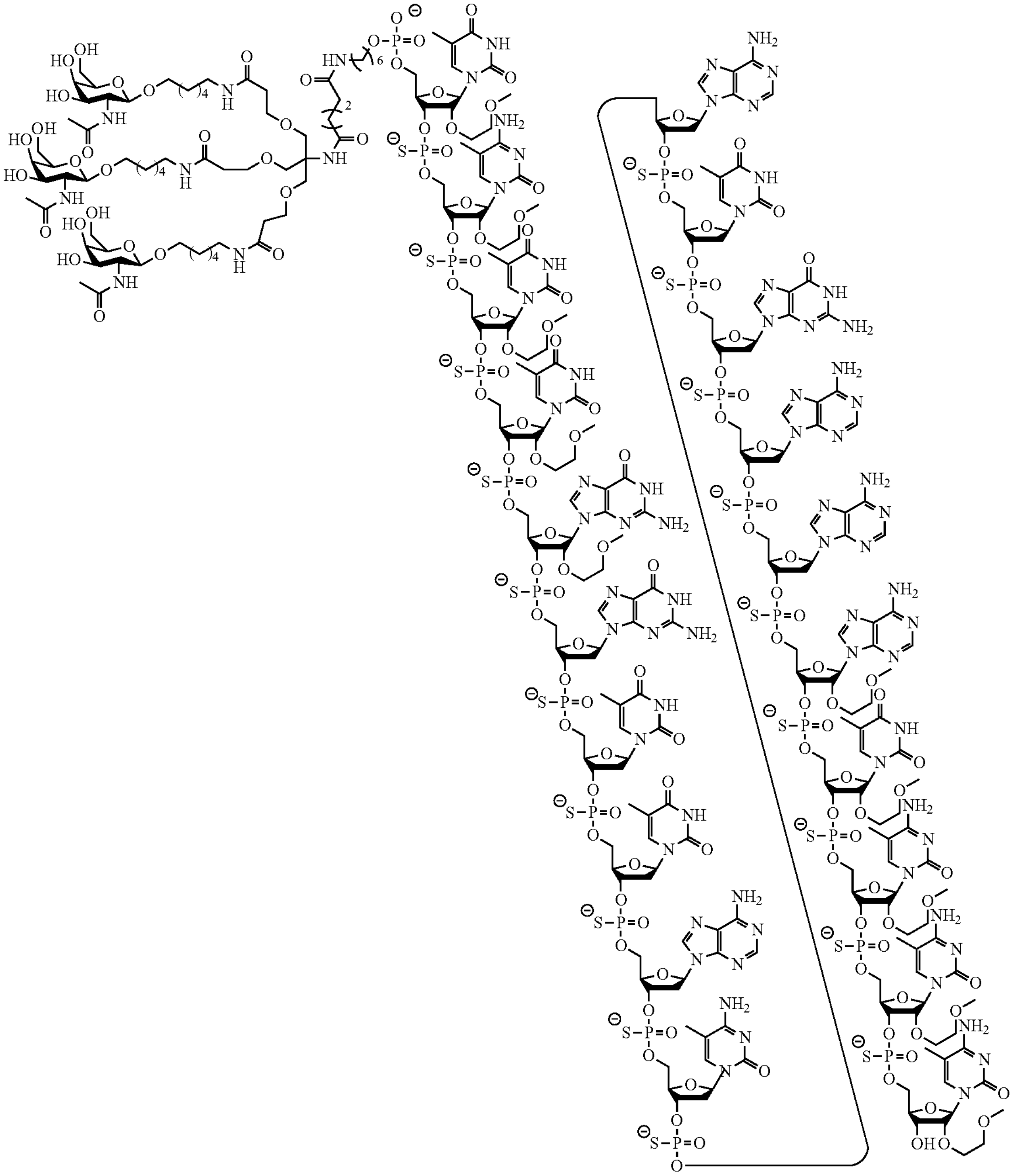
In certain embodiments, a compound comprises or consists of ISIS 682884 (SEQ ID NO: 55) having the following chemical structure:

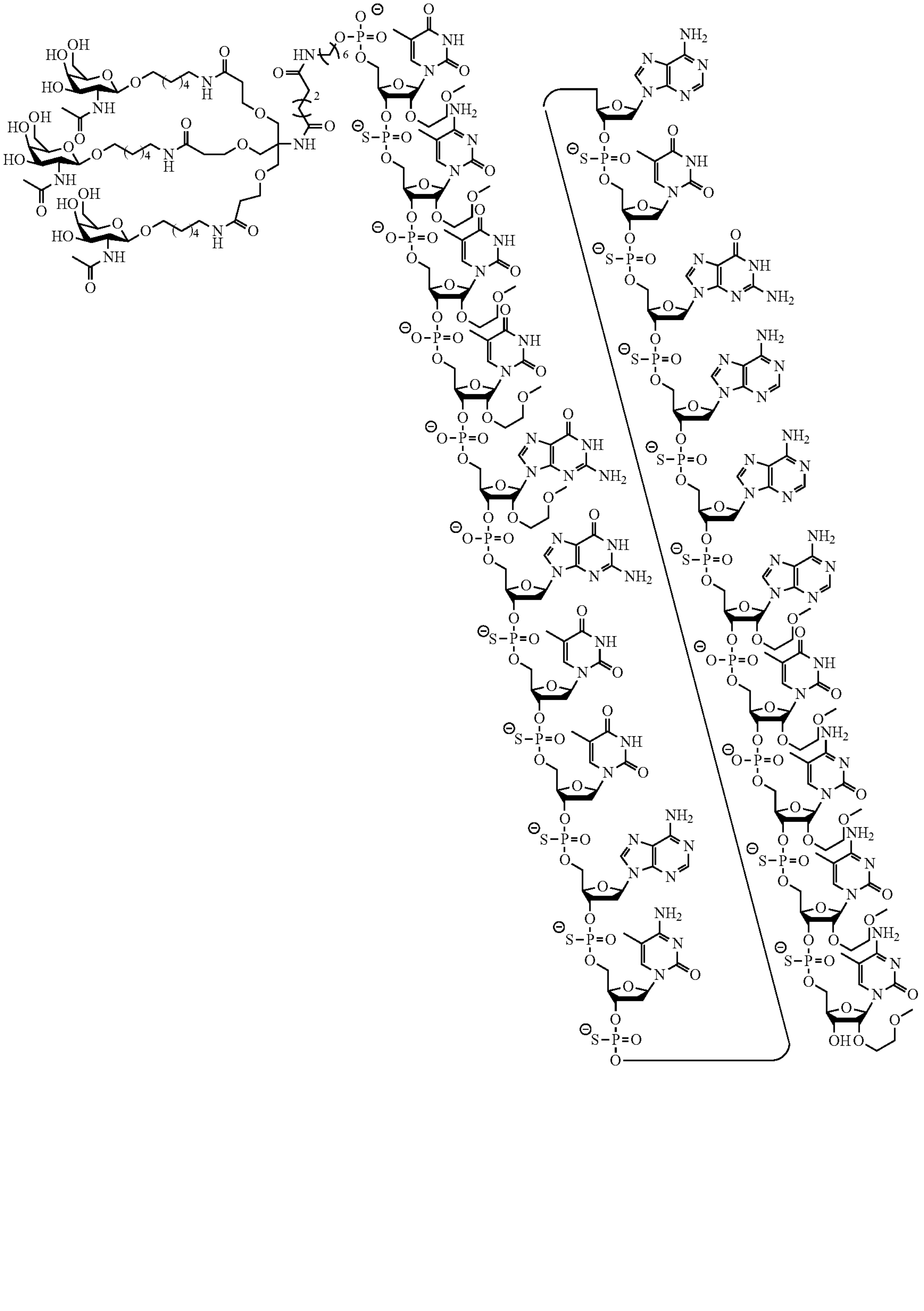
In certain embodiments, a compound comprises or consists of SEQ ID NO: 12,5'-GalNAc, and chemical modifications as represented by the following chemical structure:

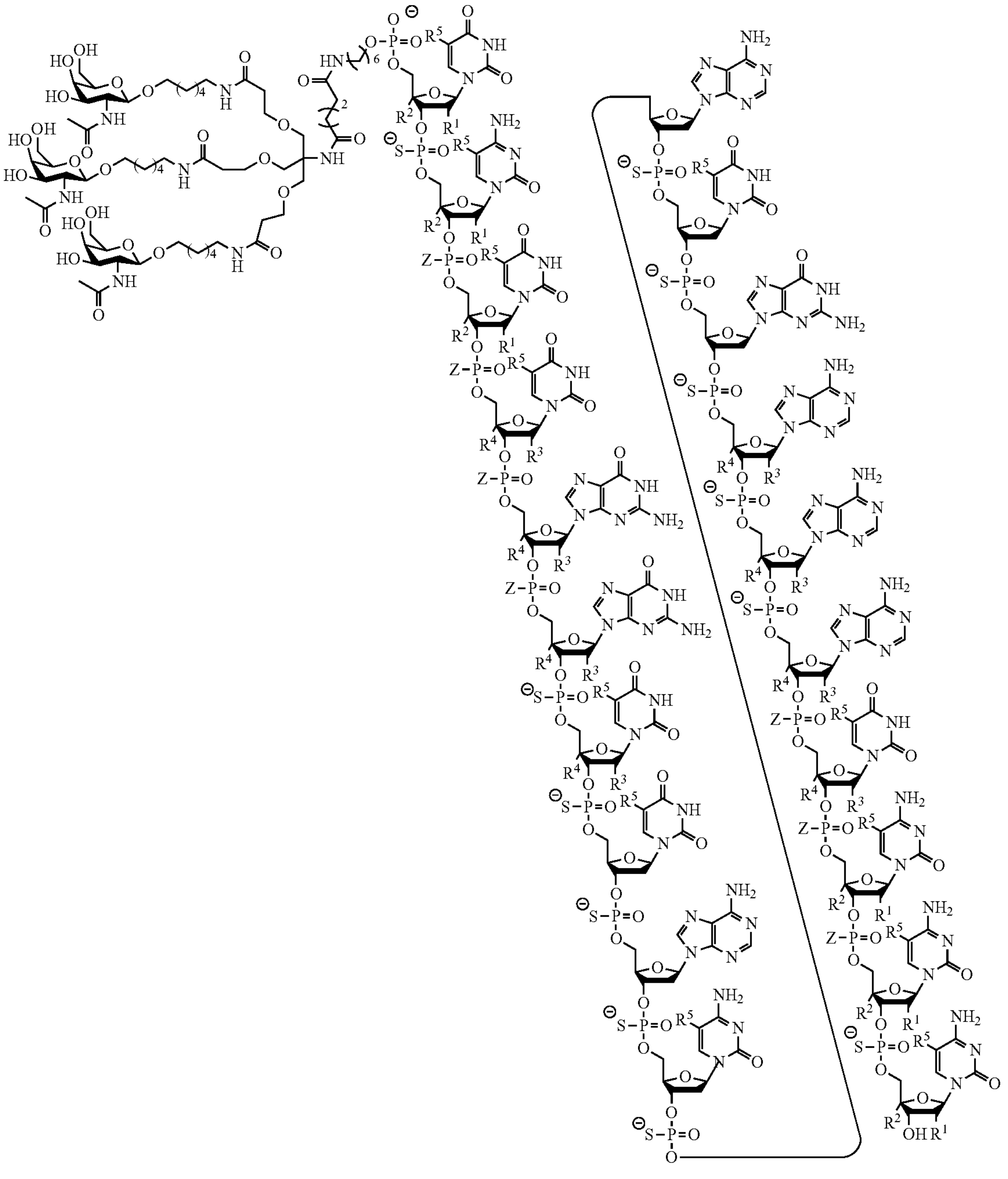

wherein either $R^1$ is —$OCH_2CH_2OCH_3$ (MOE) and $R^2$ is H; or $R^1$ and $R^2$ together form a bridge, wherein $R^1$ is —O— and $R^2$ is —$CH_2$—, —$CH(CH_3)$—, or —$CH_2CH_2$—, and $R^1$ and $R^2$ are directly connected such that the resulting bridge is selected from: —O—$CH_2$—, —O—$CH(CH_3)$—, and —O—$CH_2CH_2$-;

and for each pair of $R^3$ and $R^4$ on the same ring, independently for each ring: either $R^3$ is selected from H and —$OCH_2CH_2OCH_3$ and $R^4$ is H; or $R^3$ and $R^4$ together form a bridge, wherein $R^3$ is —O—, and $R^4$ is —$CH_2$—, —$CH(CH_3)$—, or —$CH_2CH_2$— and $R^3$ and $R^4$ are directly connected such that the resulting bridge is selected from: —O—$CH_2$—, —O—$CH(CH_3)$—, and —O—$CH_2CH_2$—;

and $R^5$ is selected from H and —$CH_3$;

and Z is selected from S- and O.

In certain embodiments, a compound comprises an antisense oligonucleotide disclosed in WO 2011/139917 or U.S. Pat. No. 8,101,743, which are incorporated by reference in their entireties herein, and a conjugate group. In certain embodiments, a compound comprises an antisense oligonucleotide having a nucleobase sequence of any of SEQ ID NOs 8-160, 170-177 disclosed in WO 2011/139917 and a conjugate group described herein. In certain embodiments, a compound comprises an antisense oligonucleotide having a nucleobase sequence of any of SEQ ID NOs 12-89 disclosed in U.S. Pat. No. 8,101,743 and a conjugate group described herein. In certain embodiments, a compound comprises an antisense oligonucleotide having a nucleobase sequence complementary to a preferred target segment of any of SEQ ID NOs 90-133 disclosed in U.S. Pat. No. 8,101,743 and a conjugate group described herein. The nucleobase sequences of all of the aforementioned referenced SEQ ID NOs are incorporated by reference herein.

TTR Therapeutic Indications

In certain embodiments, the invention provides methods for using a conjugated antisense compound targeted to a TTR nucleic acid for modulating the expression of TTR in a subject. In certain embodiments, the expression of TTR is reduced.

In certain embodiments, the invention provides methods for using a conjugated antisense compound targeted to a TTR nucleic acid in a pharmaceutical composition for treating a subject. In certain embodiments, the subject has a transthyretin related disease, disorder or condition, or symptom thereof. In certain embodiments, the transthyretin related disease, disorder or condition is transthyretin amyloidosis.

“Transthyretin-related amyloidosis” or “transthyretin amyloidosis” or “Transthyretin amyloid disease”, as used herein, is any pathology or disease associated with dysfunction or dysregulation of transthyretin that result in formation of transthyretin-containing amyloid fibrils. Transthyretin amyloidosis includes, but is not limited to, hereditary TTR amyloidosis, leptomeningeal amyloidosis, familial amyloid polyneuropathy (FAP), familial amyloid cardiomyopathy, familial oculoleptomeningeal amyloidosis, senile cardiac amyloidosis, or senile systemic amyloidosis.

In certain embodiments, the invention provides methods for using a conjugated antisense compound targeted to a TTR nucleic acid in the preparation of a medicament.

In certain embodiments, the invention provides a conjugated antisense compound targeted to a TTR nucleic acid, or a pharmaceutically acceptable salt thereof, for use in therapy.

Certain embodiments provide a conjugated antisense compound targeted to a TTR nucleic acid for use in the treatment of a transthyretin related disease, disorder or condition, or symptom thereof. In certain embodiments, the transthyretin related disease, disorder or condition is transthyretin amyloidosis.

It will be understood that any of the compounds described herein can be used in the aforementioned methods and uses. For example, in certain embodiments a conjugated antisense compound targeted to a TTR nucleic acid in the aforementioned methods and uses can include, but is not limited to, a conjugated antisense compound targeted to SEQ ID NO: 2 comprising an at least 8 consecutive nucleobase sequence of any one of SEQ ID NOs: 12-19; a conjugated antisense compound targeted to SEQ ID NO: 2 comprising a nucleobase sequence of any one of SEQ ID NO: 12-19; a compound comprising or consisting of ISIS 420915, ISIS 304299, ISIS 420921, ISIS 420922, ISIS 420950, ISIS 420955, ISIS 420957, or ISIS 420959 and a conjugate group; a compound comprising an antisense oligonucleotide disclosed in WO 2011/139917 or U.S. Pat. No. 8,101,743, which are incorporated by reference in their entireties herein, and a conjugate group; a compound comprising an antisense oligonucleotide having a nucleobase sequence of any of SEQ ID NOs 8-160, 170-177 disclosed in WO 2011/139917 and a conjugate group described herein; an antisense oligonucleotide having a nucleobase sequence of any of SEQ ID NOs 12-89 disclosed in U.S. Pat. No. 8,101,743 and a conjugate group described herein; or a compound comprising an antisense oligonucleotide having a nucleobase sequence complementary to a preferred target segment of any of SEQ ID NOs 90-133 disclosed in U.S. Pat. No. 8,101,743 and a conjugate group described herein. The nucleobase sequences of all of the aforementioned referenced SEQ ID NOs are incorporated by reference herein.

E. Certain Pharmaceutical Compositions

In certain embodiments, the present disclosure provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligonucleotide which are cleaved by endogenous nucleases within the body, to form the active antisense oligonucleotide.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present disclosure to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present disclosure provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present disclosure provides methods of administering a pharmaceutical composition comprising an oligonucleotide of the present disclosure to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Certain compounds, compositions, and methods herein are described as "comprising exactly" or "comprises exactly" a particular number of a particular element or feature. Such descriptions are used to indicate that while the compound, composition, or method may comprise additional other elements, the number of the particular element or feature is the identified number. For example, "a conjugate comprising exactly one GalNAc" is a conjugate that contains one and only one GalNAc, though it may contain other elements in addition to the one GalNAc.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "ATmeCGAUCG," wherein meC indicates a cytosine base comprising a methyl group at the 5-position.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: General Method for the Preparation of Phosphoramidites, Compounds 1,1a and 2

1

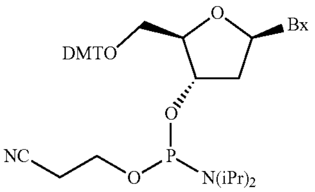

-continued

1a

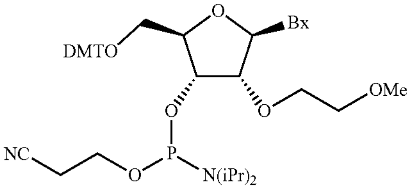

2

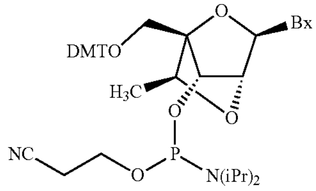

Compounds 1,1a and 2 were prepared as per the procedures well known in the art as described in the specification herein (see Seth et al., Bioorg. Med. Chem., 2011, 21 (4), 1122-1125, J. Org. Chem., 2010, 75 (5), 1569-1581, Nucleic Acids Symposium Series, 2008, 52 (1), 553-554); and also see published PCT International Applications (WO 2011/115818, WO 2010/077578, WO2010/036698, WO2009/143369, WO 2009/006478, and WO 2007/090071), and U.S. Pat. No. 7,569,686).

Example 2: Preparation of Compound 7

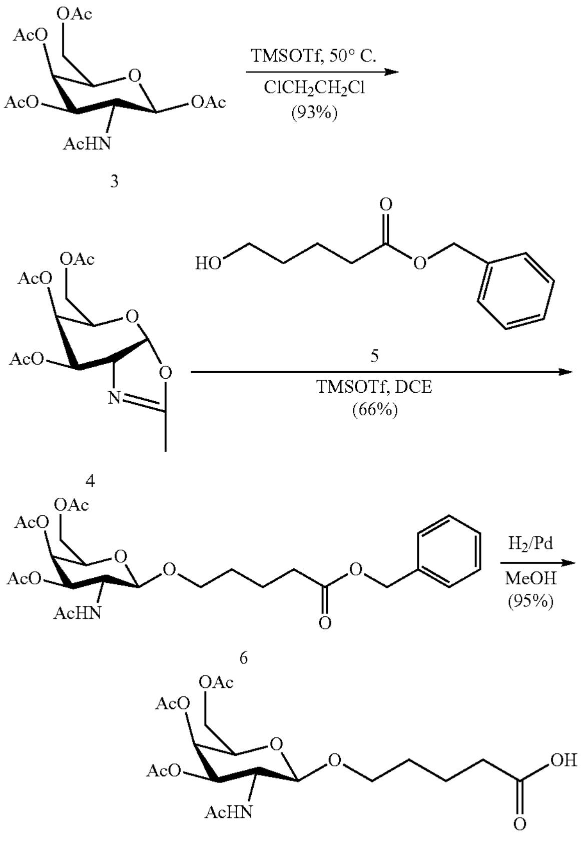

3

4

5

6

7

Compounds 3 (2-acetamido-1,3,4,6-tetra-O-acetyl-2-deoxy-β-Dgalactopyranose or galactosamine pentaacetate) is commercially available. Compound 5 was prepared according to published procedures (Weber et al., *J. Med. Chem.*, 1991, 34, 2692).
Example 3: Preparation of Compound 11
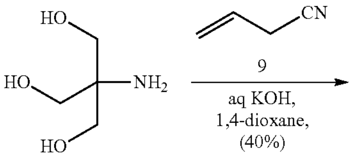
8
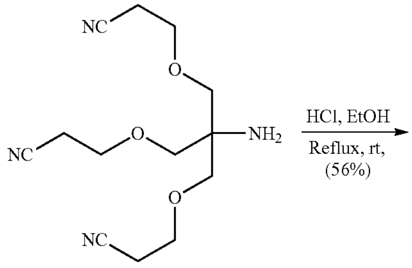
10
-continued
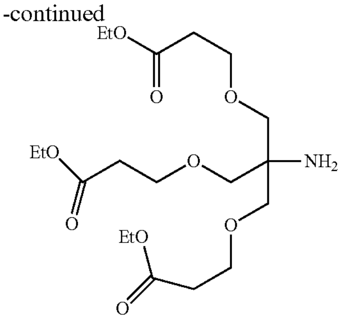
11
Compounds 8 and 9 are commercially available.
Example 4: Preparation of Compound 18
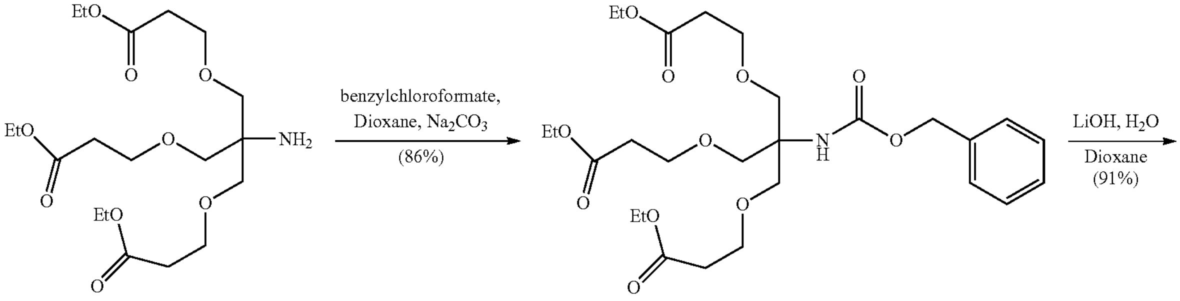
11
12
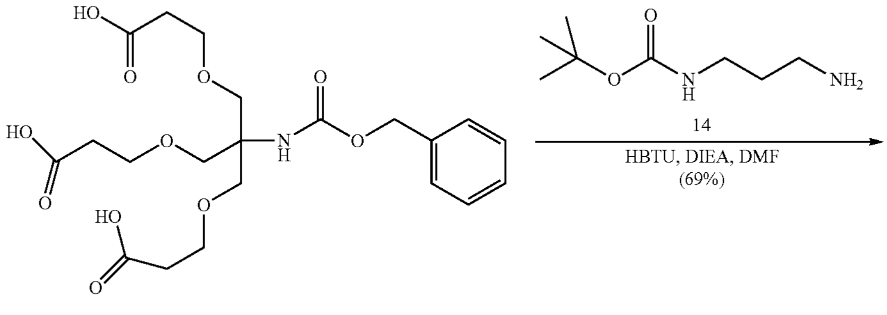
13

-continued
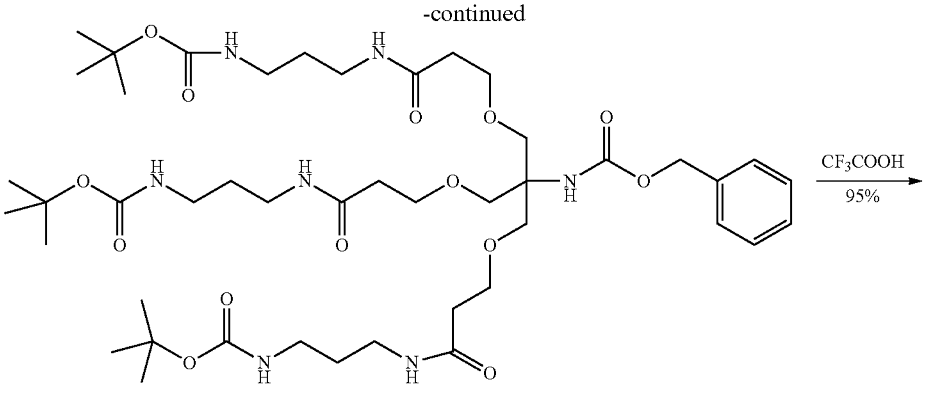
15
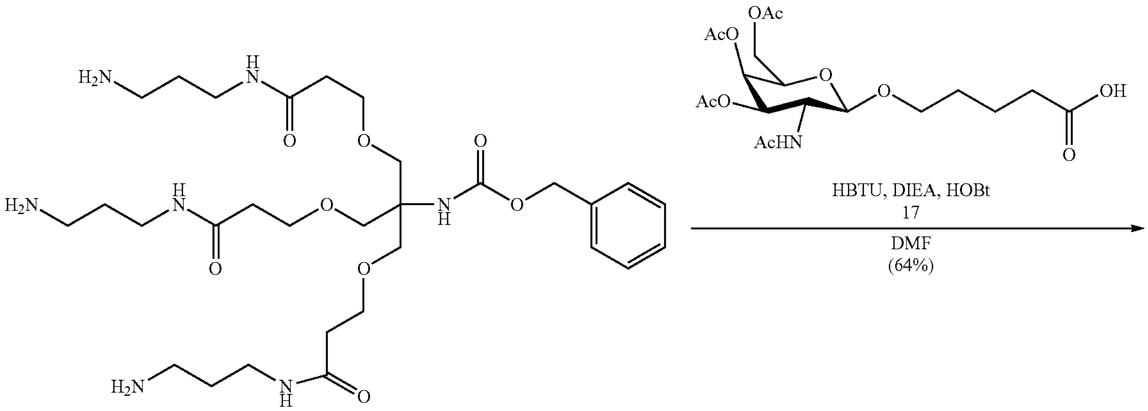
16
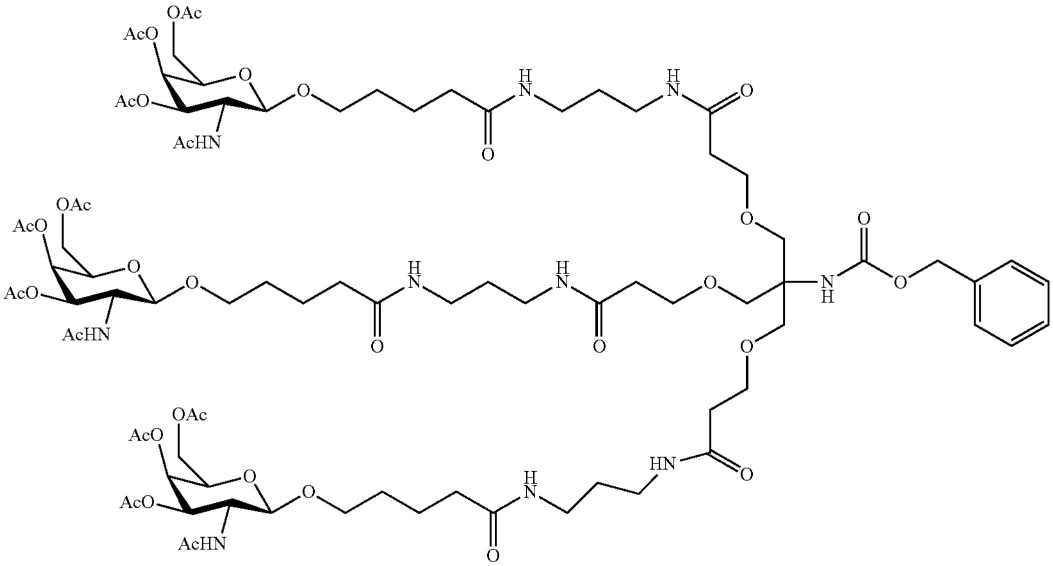
18
Compound 11 was prepared as per the procedures illustrated in Example 3. Compound 14 is commercially available. Compound 17 was prepared using similar procedures reported by Rensen et al., *J. Med. Chem.,* 2004, 47, 5798-5808.

Example 5: Preparation of Compound 23
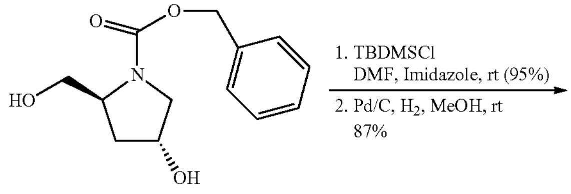
19
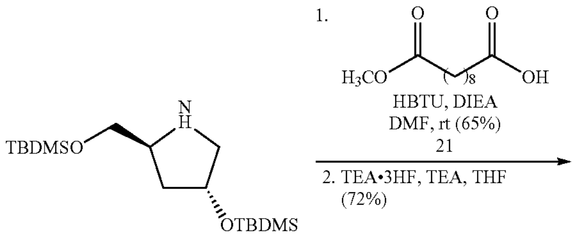
20
-continued
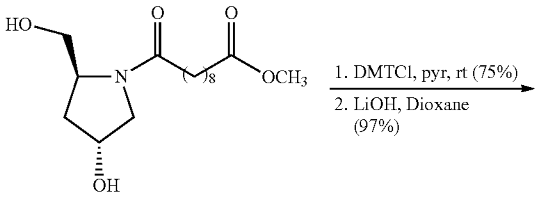
22
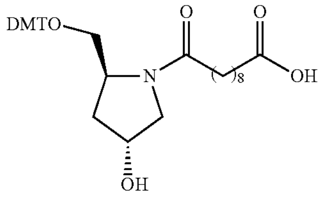
23
Compounds 19 and 21 are commercially available.
Example 6: Preparation of Compound 24
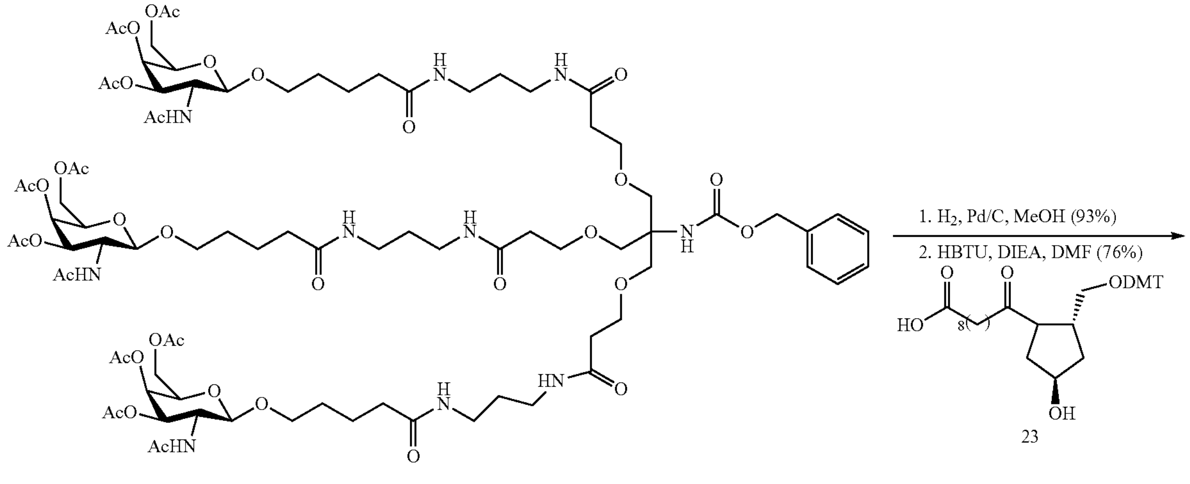
18

-continued
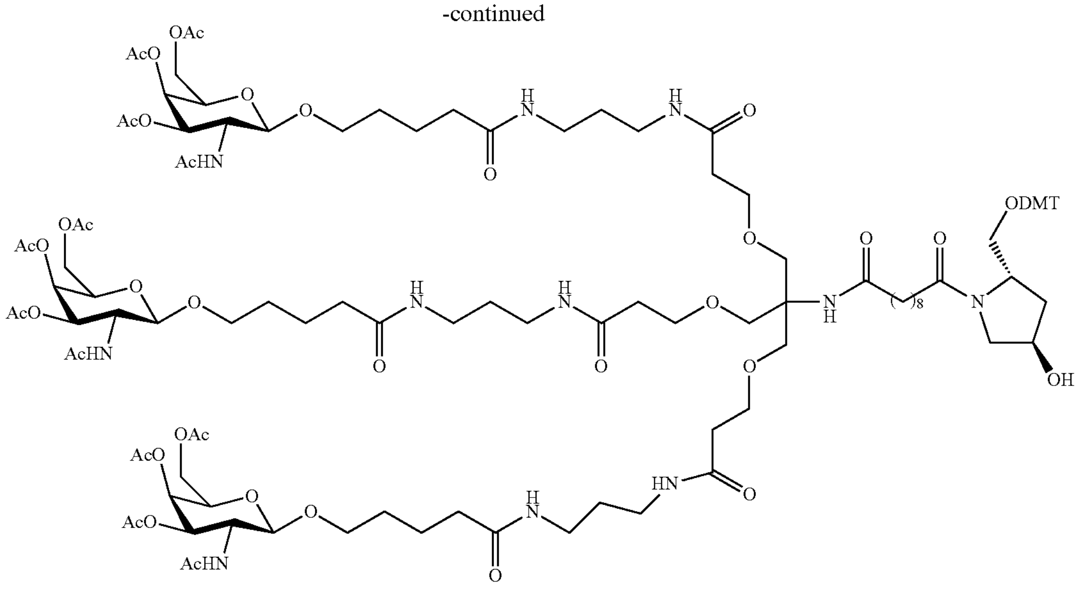
24
Compounds 18 and 23 were prepared as per the procedures illustrated in Examples 4 and 5.
Example 7: Preparation of Compound 25
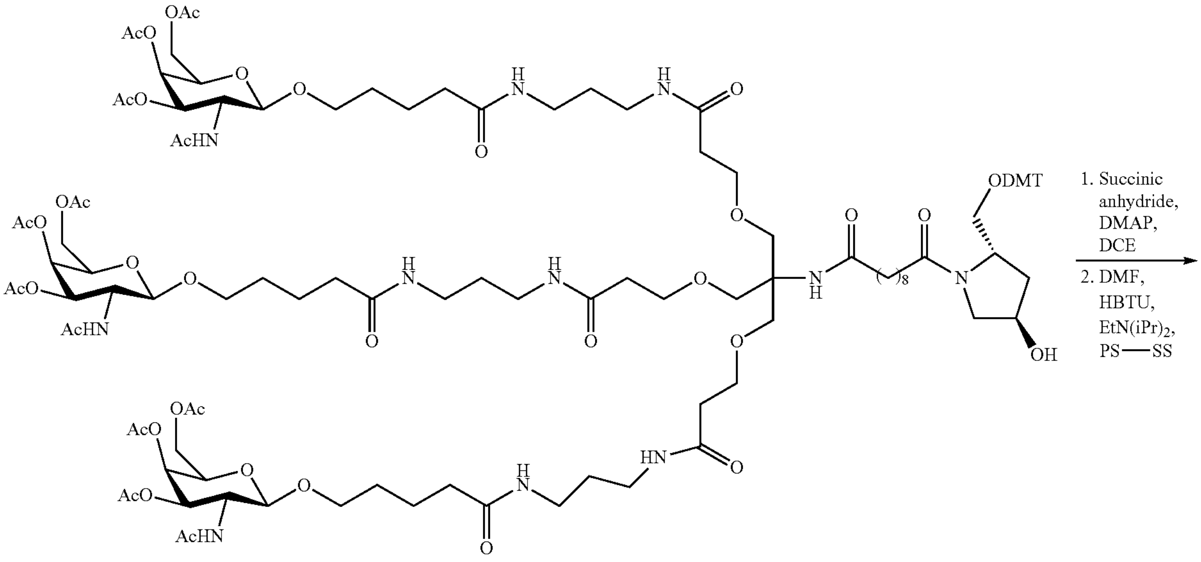
24

-continued
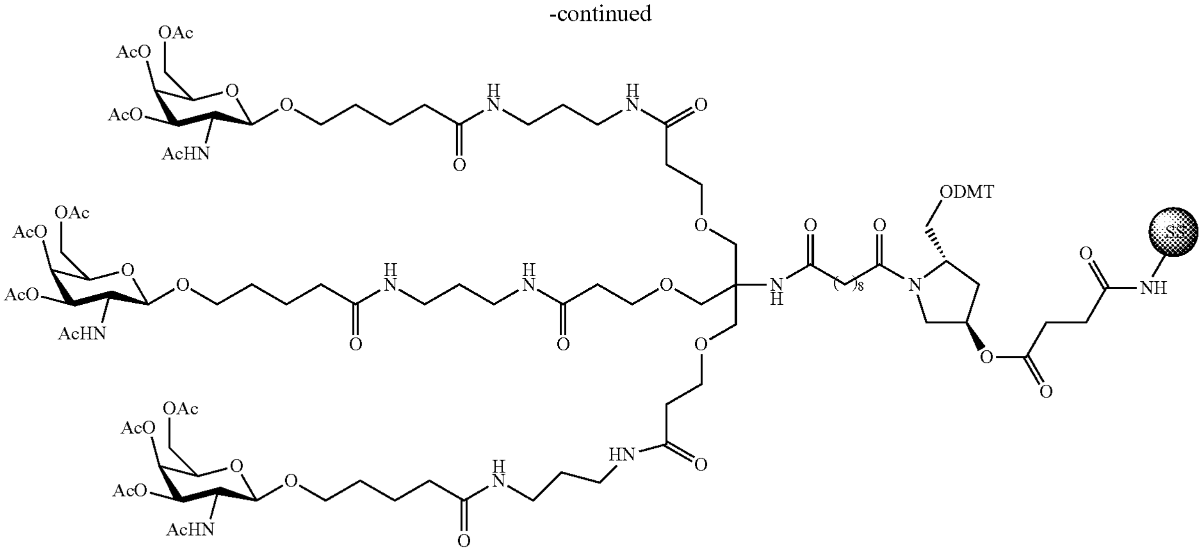
25
Compound 24 was prepared as per the procedures illustrated in Example 6.
Example 8: Preparation of Compound 26
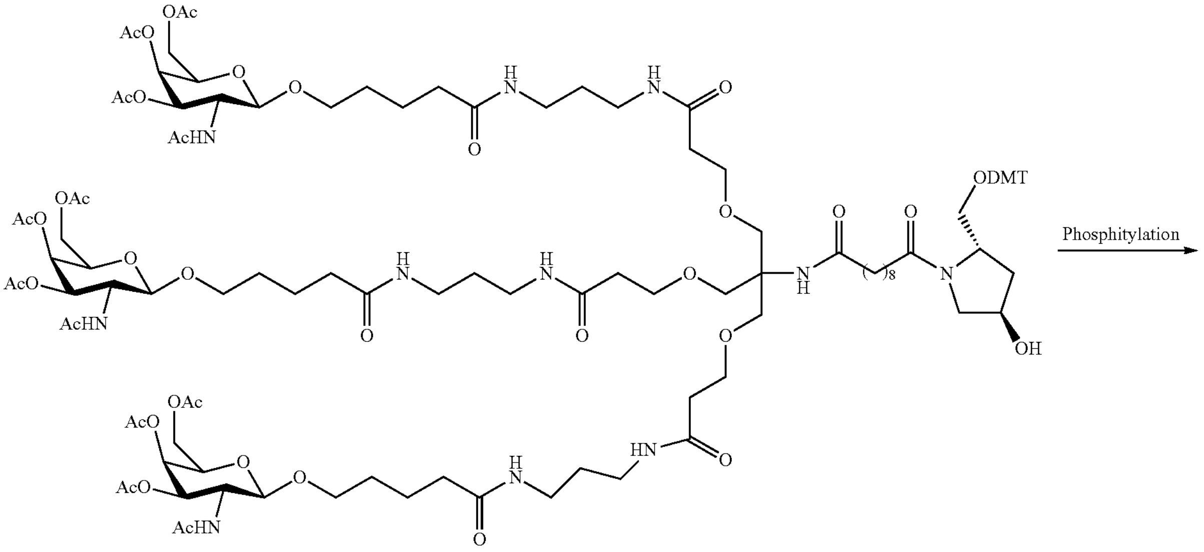
24

-continued
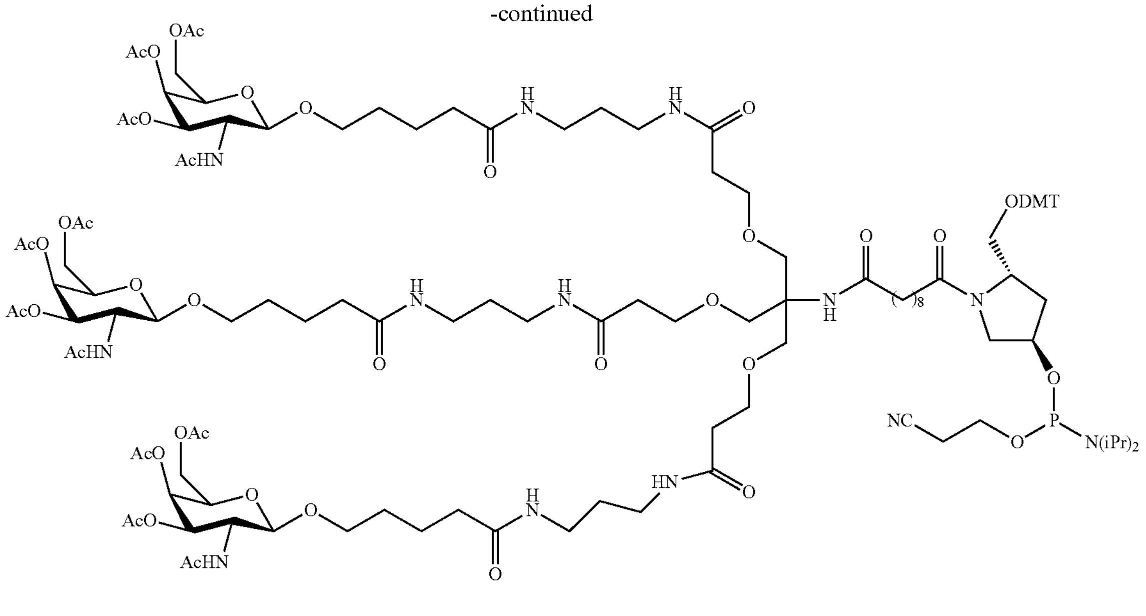
26
Compound 24 is prepared as per the procedures illustrated in Example 6.
Example 9: General preparation of conjugated ASOs comprising $GalNAc_3$-1 at the 3' terminus, Compound 29
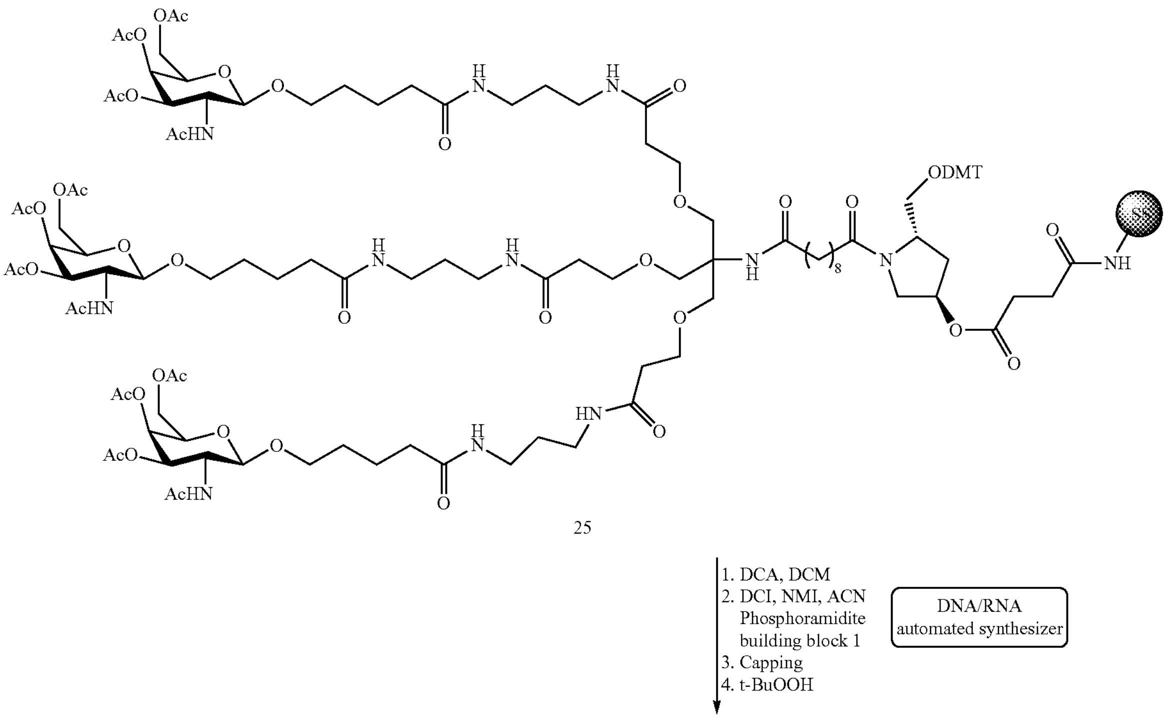
25

-continued
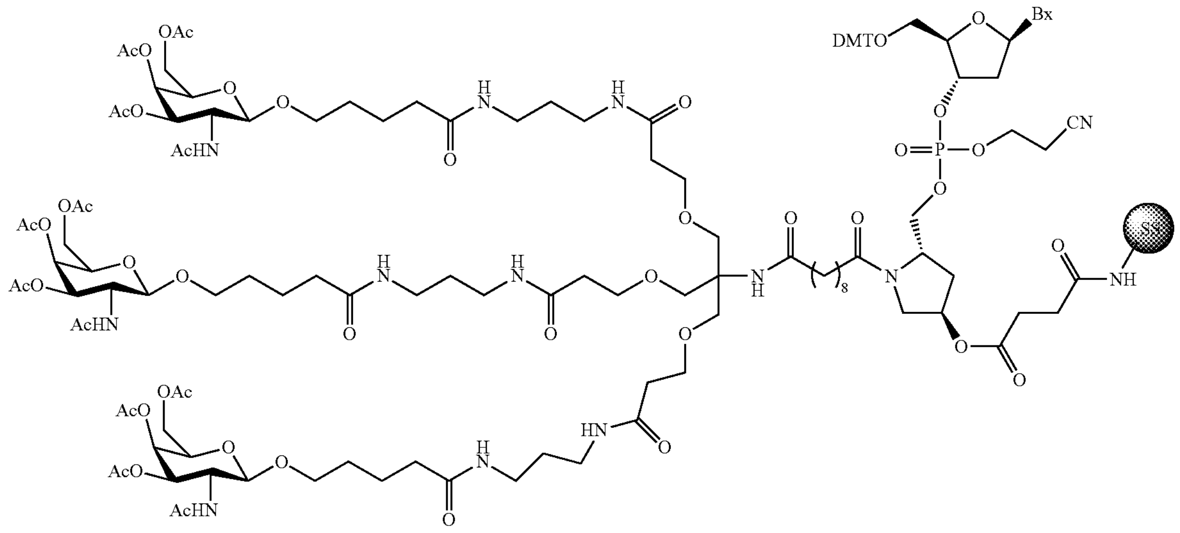
27
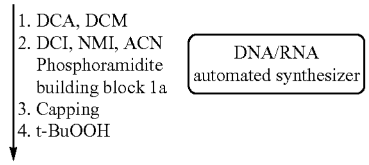
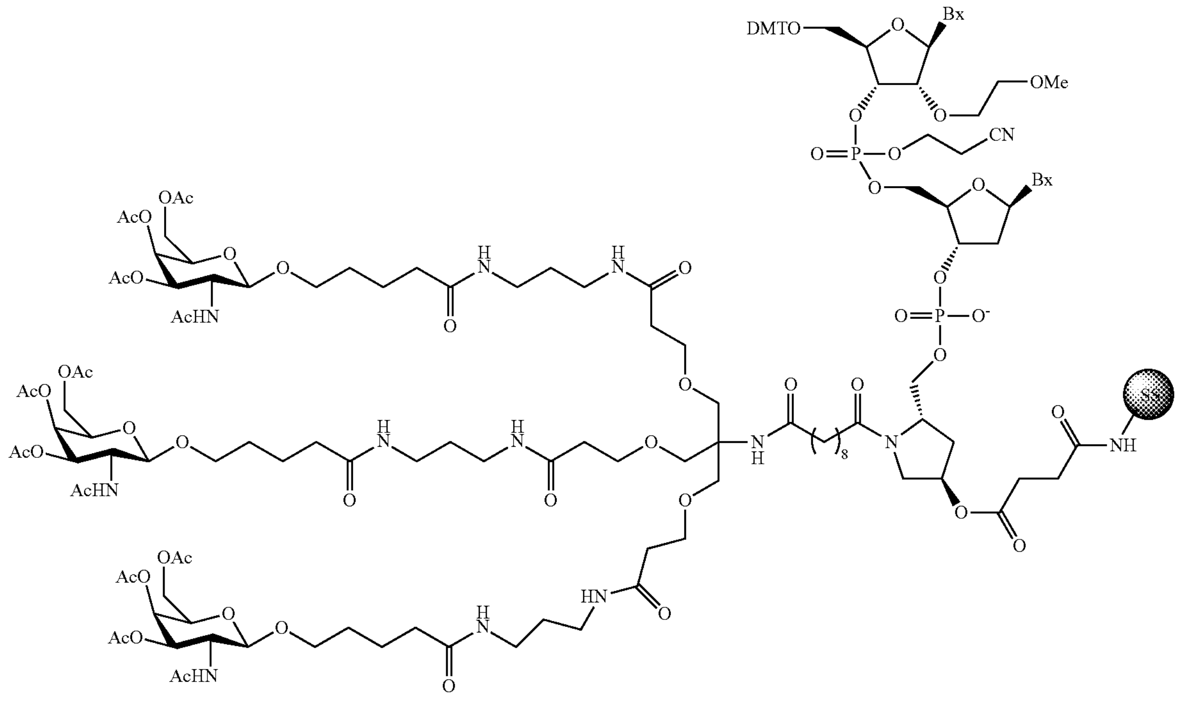
28
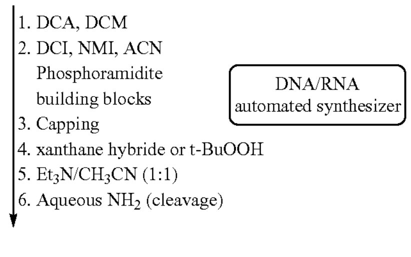

-continued
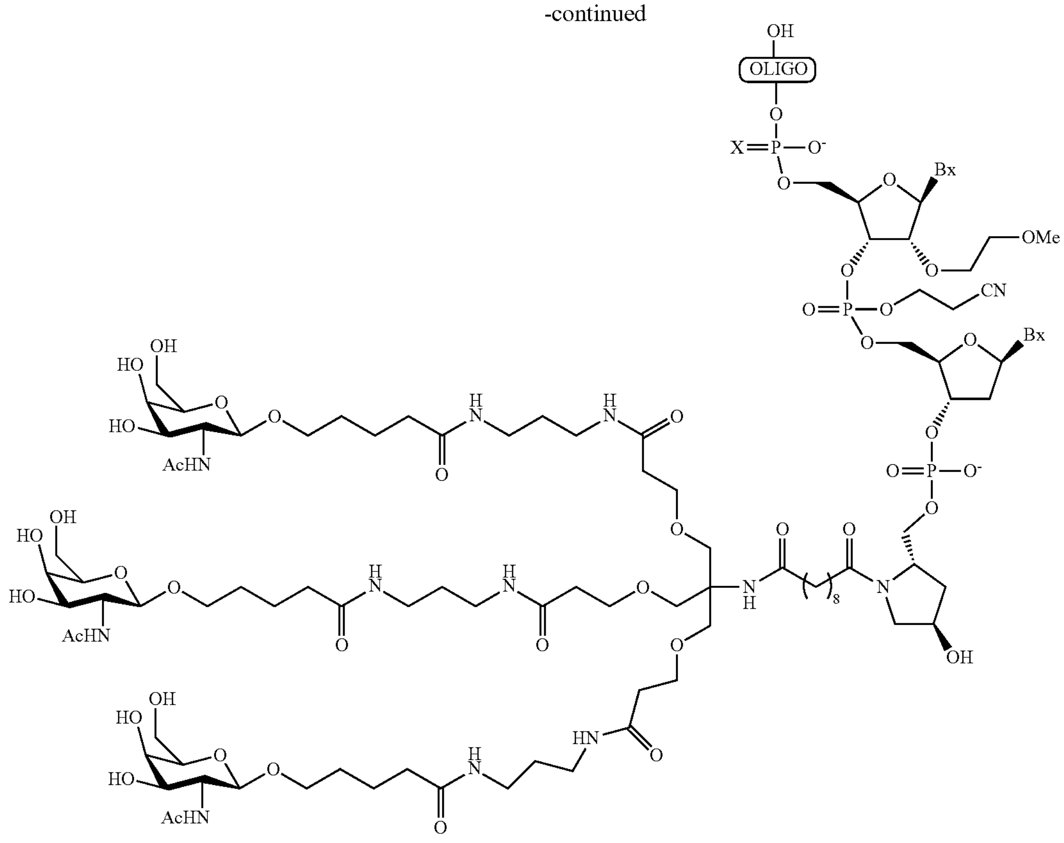
29
Bx = Heterocyclic base
X = O or S
Wherein the protected $GalNAc_3$-1 has the structure:
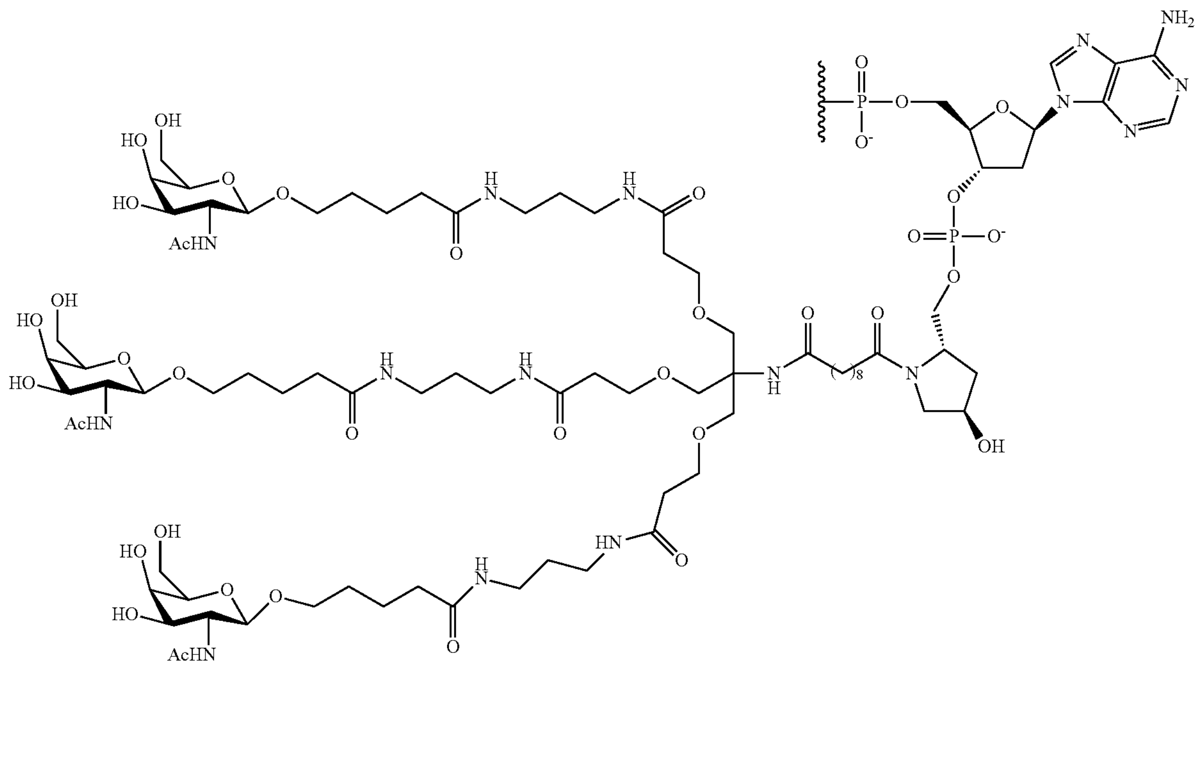

The $GalNAc_3$ cluster portion of the conjugate group $GalNAc_3$-1 ($GalNAc_3$-1a) can be combined with any cleavable moiety to provide a variety of conjugate groups. Wherein $GalNAc_3$-1a has the formula:

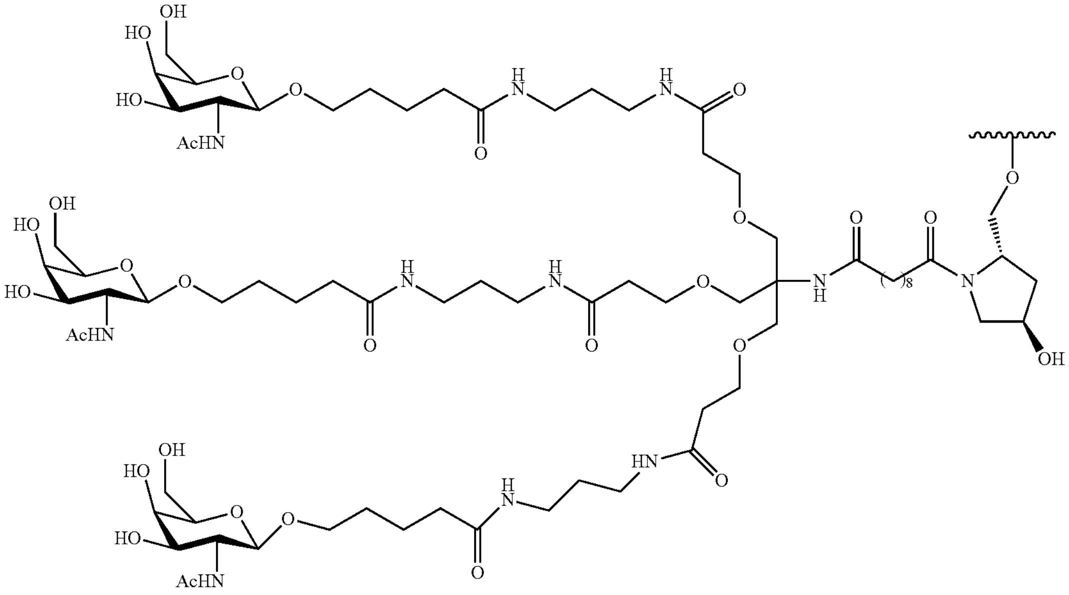

The solid support bound protected $GalNAc_3$-1, Compound 25, was prepared as per the procedures illustrated in Example 7. Oligomeric Compound 29 comprising $GalNAc_3$-1 at the 3' terminus was prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare oligomeric compounds having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 10: General Preparation Conjugated ASOs Comprising $GalNAc_3$-1 at the 5' Terminus, Compound 34

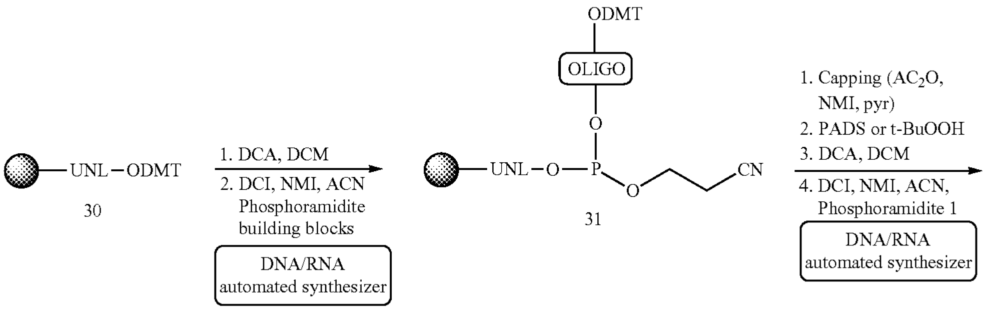

-continued
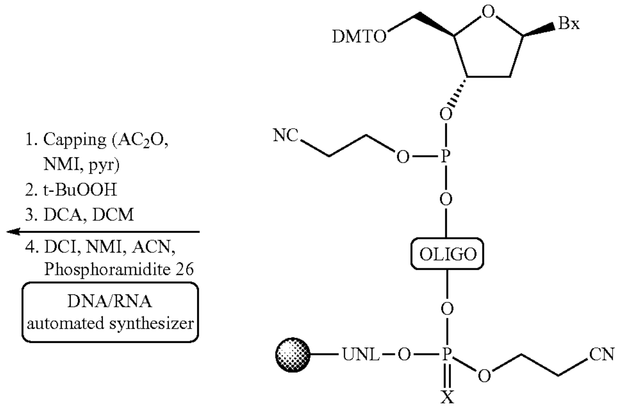
32
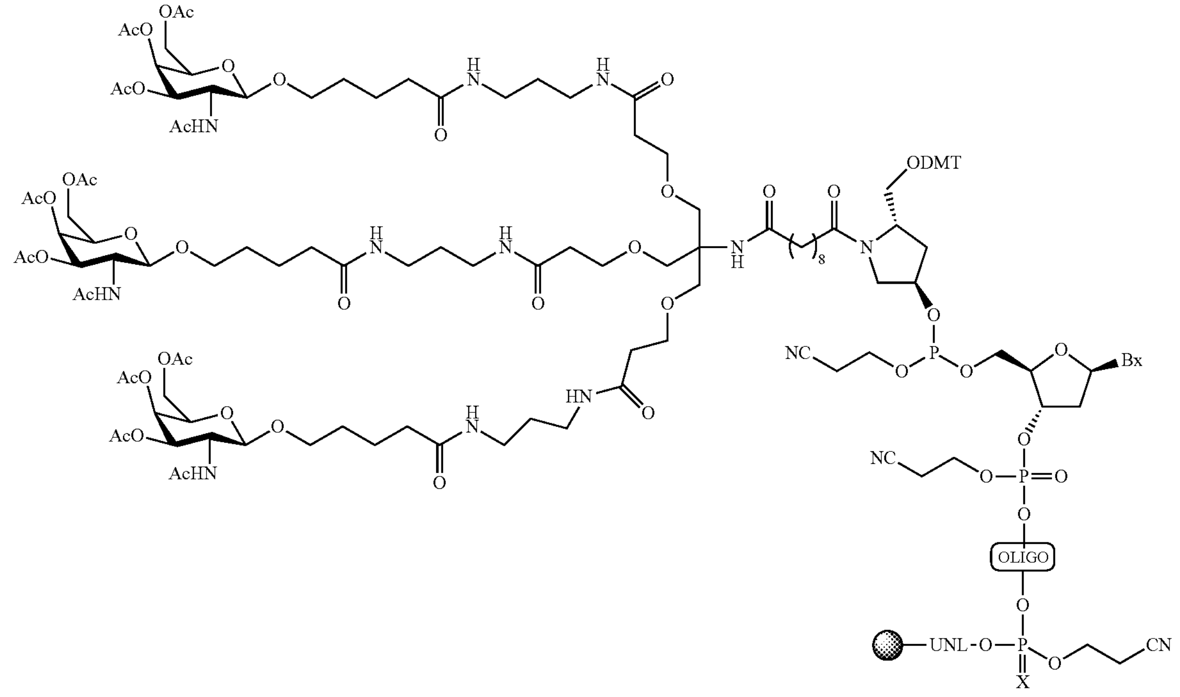
33
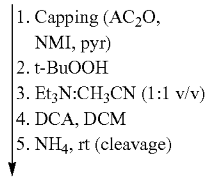

-continued

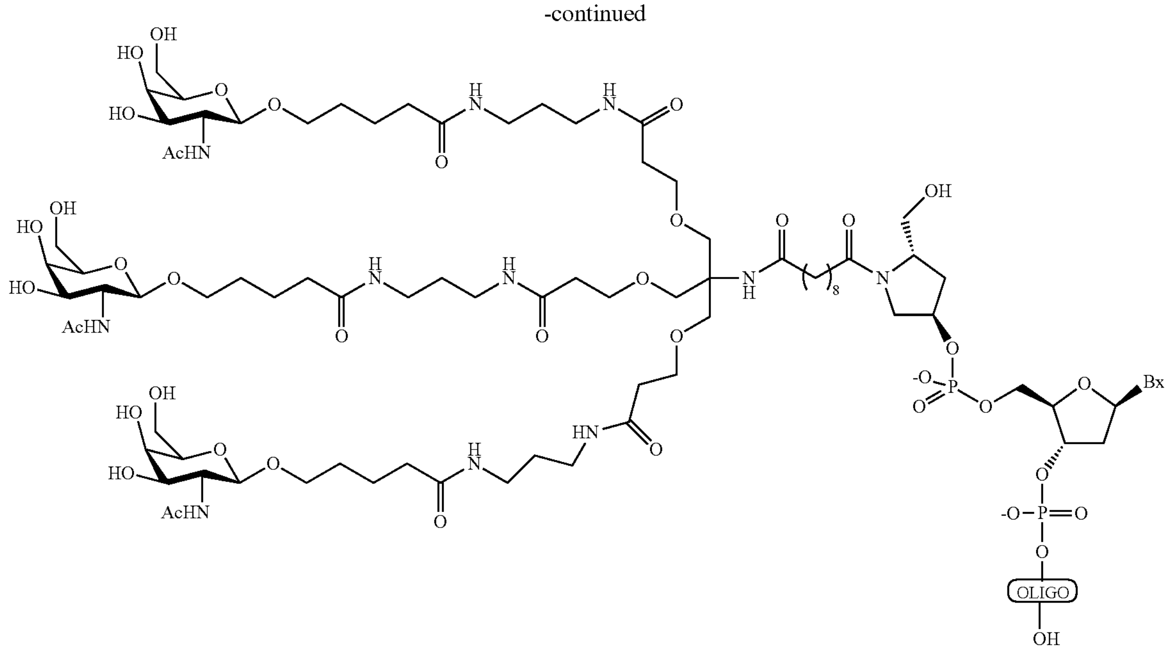

34

X = O, or S
Bx = Heterocylic base

The Unylinker™ 30 is commercially available. Oligomeric Compound 34 comprising a GalNAc$_3$-1 cluster at the 5' terminus is prepared using standard procedures in automated DNA/RNA synthesis (see Dupouy et al., *Angew. Chem. Int. Ed.*, 2006, 45, 3623-3627). Phosphoramidite building blocks, Compounds 1 and 1a were prepared as per the procedures illustrated in Example 1. The phosphoramidites illustrated are meant to be representative and not intended to be limiting as other phosphoramidite building blocks can be used to prepare an oligomeric compound having a predetermined sequence and composition. The order and quantity of phosphoramidites added to the solid support can be adjusted to prepare gapped oligomeric compounds as described herein. Such gapped oligomeric compounds can have predetermined composition and base sequence as dictated by any given target.

Example 11: Preparation of Compound 39

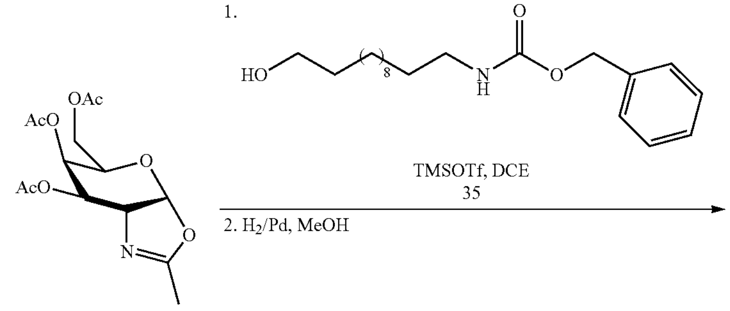

4

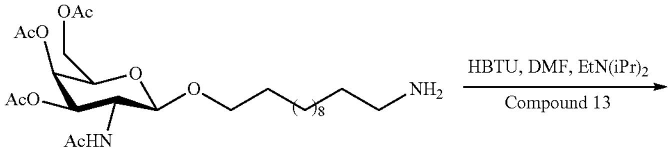

36

-continued
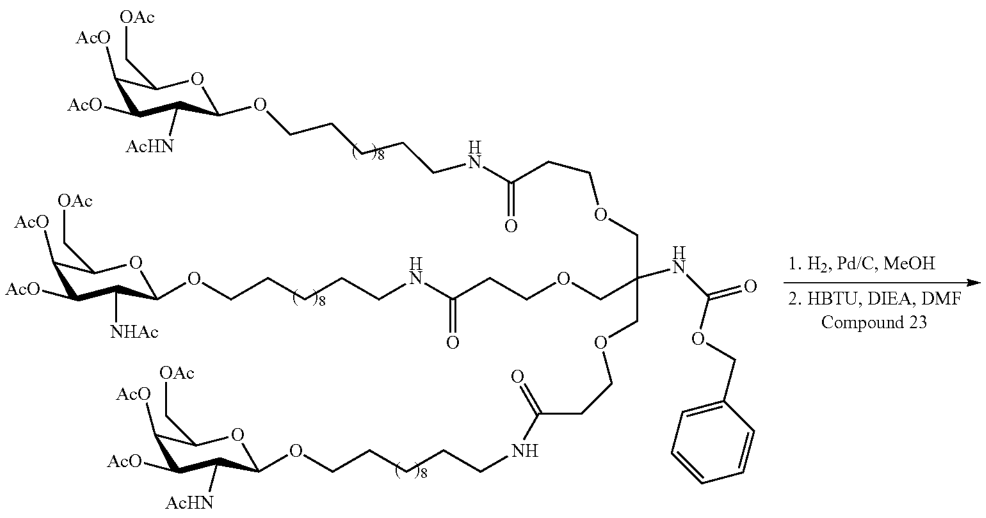
37
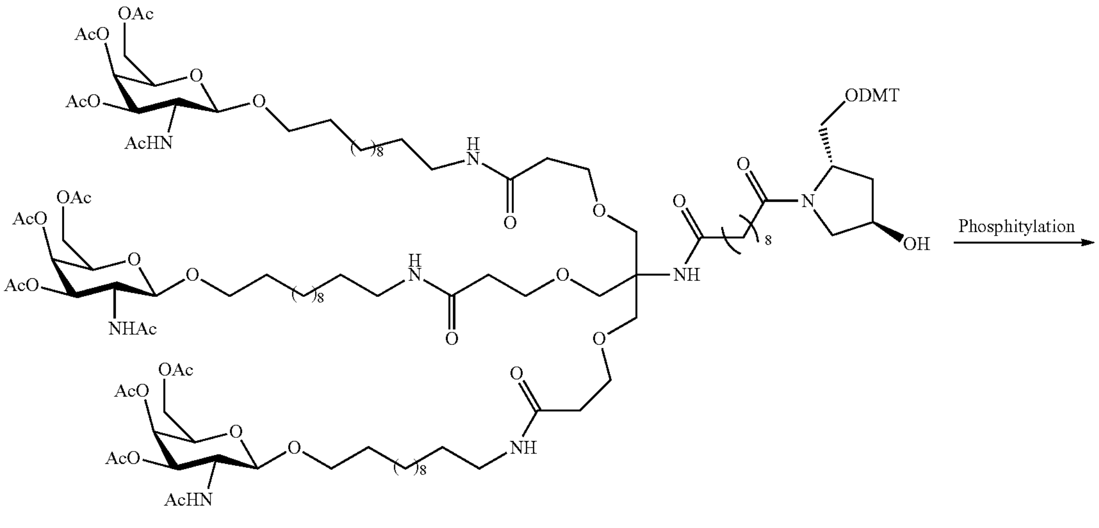
38
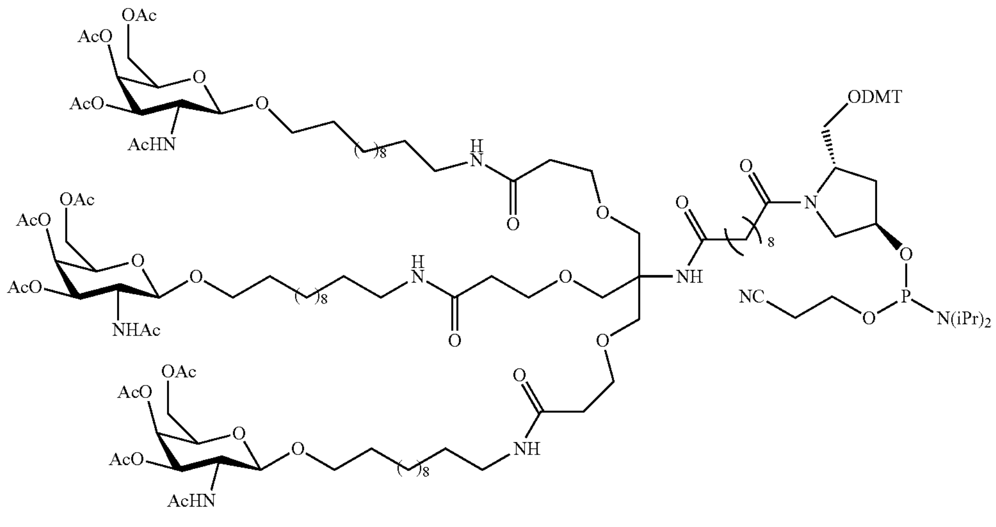
39

Compounds 4, 13 and 23 were prepared as per the procedures illustrated in Examples 2, 4, and 5. Compound 35 is prepared using similar procedures published in Rouchaud et al., *Eur. J. Org. Chem.*, 2011, 12, 2346-2353.
Example 12: Preparation of Compound 40
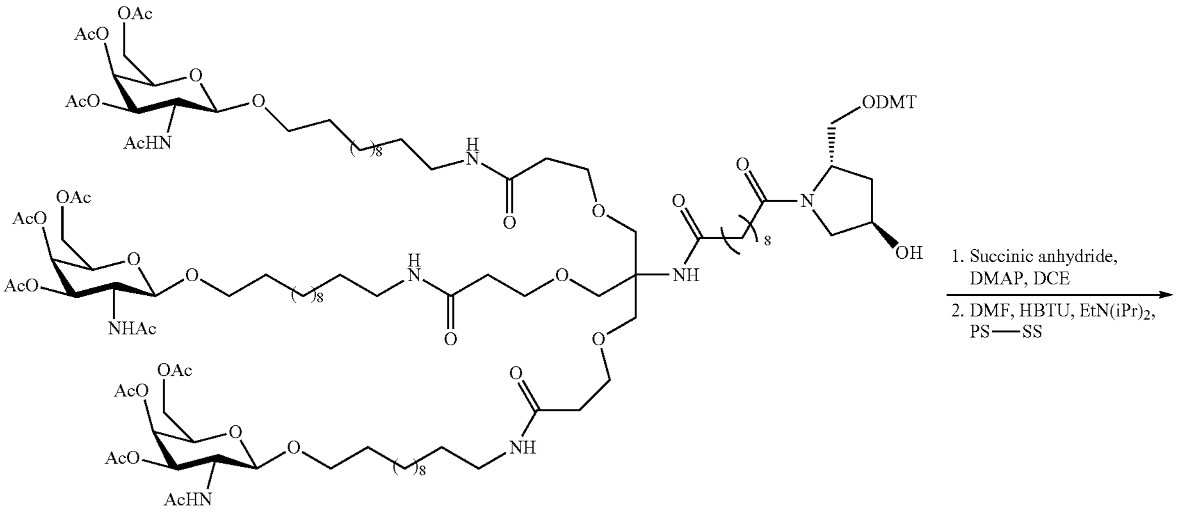
38
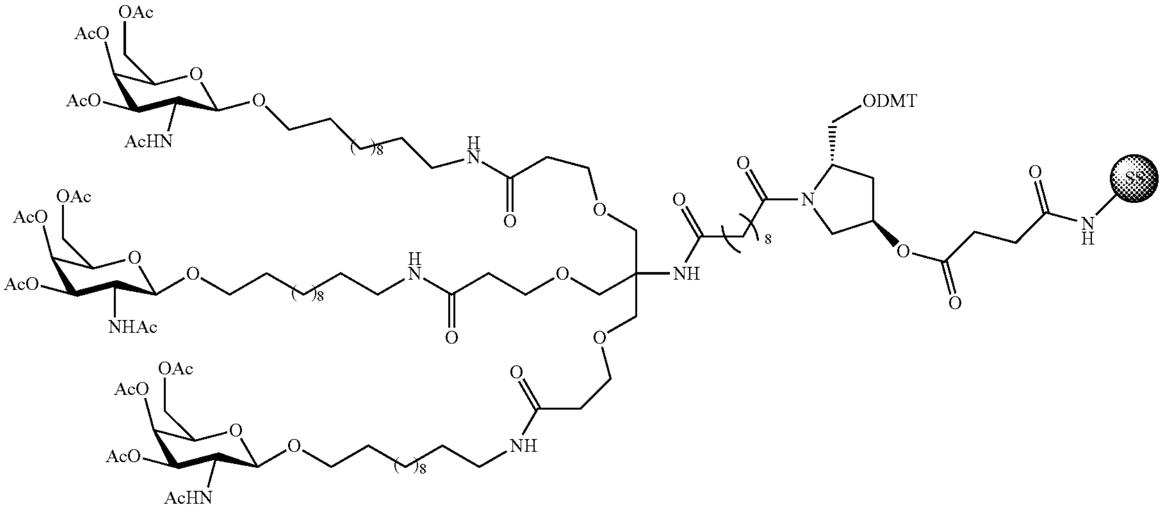
40
Compound 38 is prepared as per the procedures illustrated in Example 11.
Example 13: Preparation of Compound 44
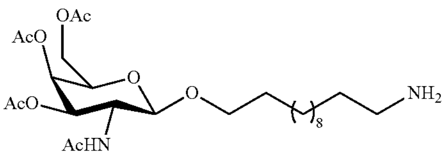
36
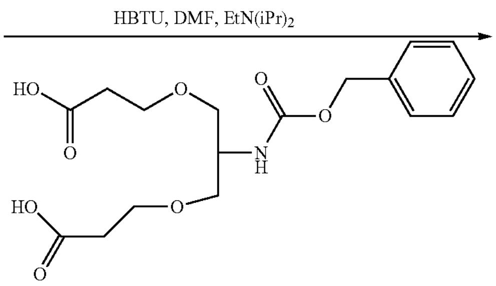
41

-continued
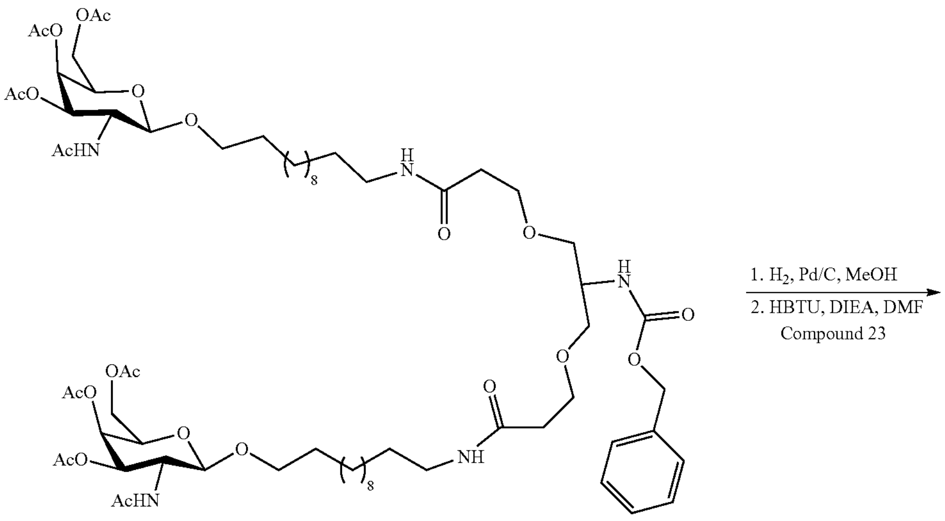
42
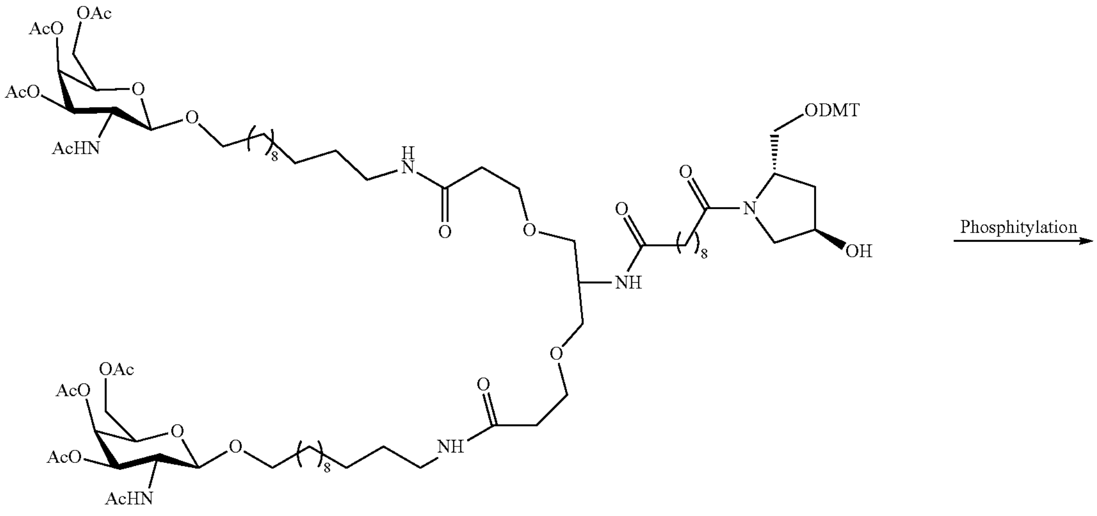
43
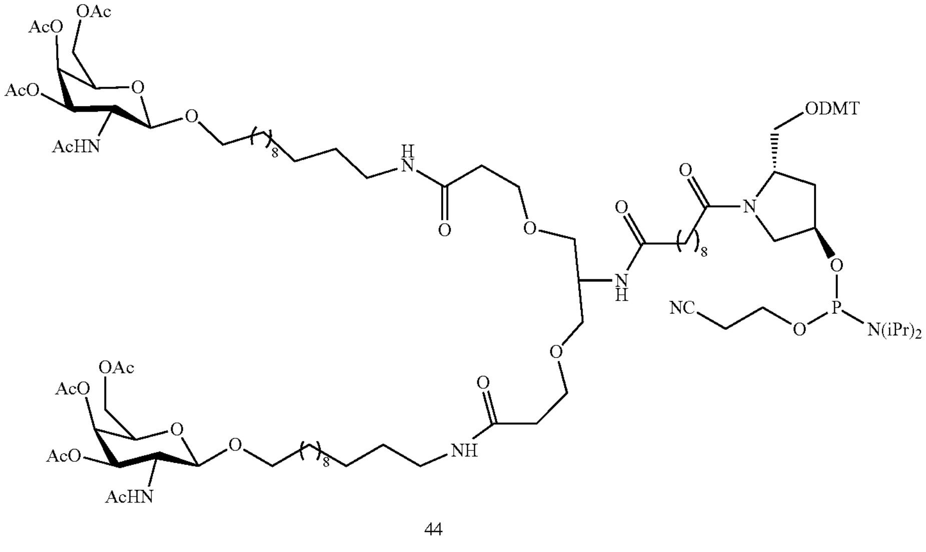
44

Compounds 23 and 36 are prepared as per the procedures illustrated in Examples 5 and 11. Compound 41 is prepared using similar procedures published in WO 2009082607.
Example 14: Preparation of Compound 45
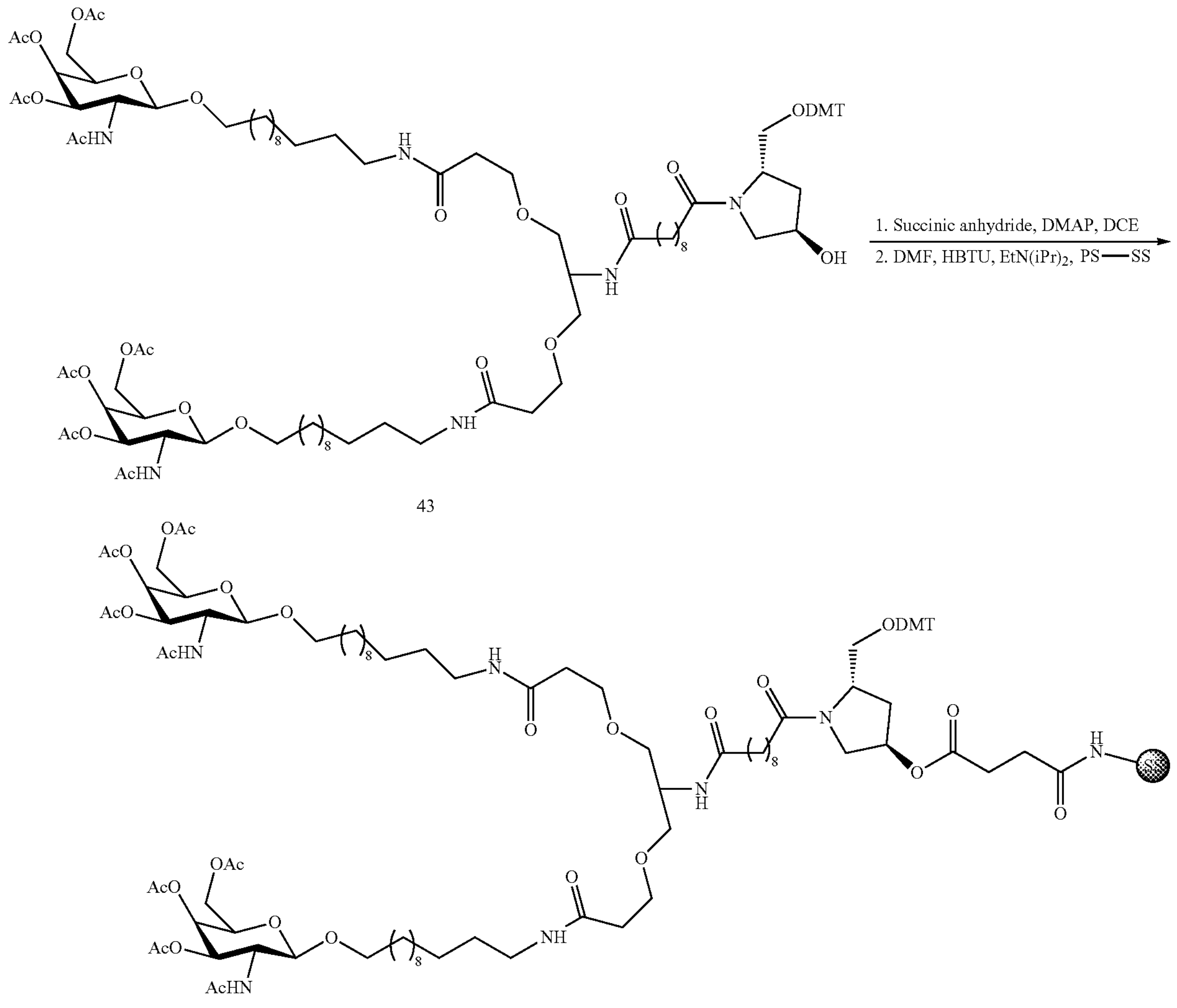
43
45
Compound 43 is prepared as per the procedures illustrated in Example 13.
Example 15: Preparation of Compound 47
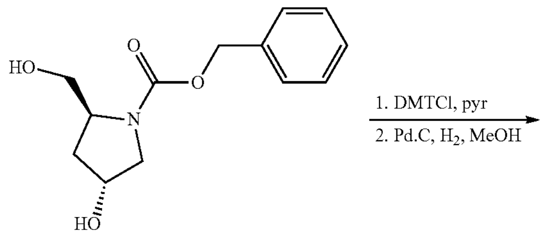
46
-continued
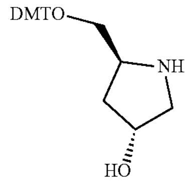
47
Compound 46 is commercially available.

Example 16: Preparation of Compound 53
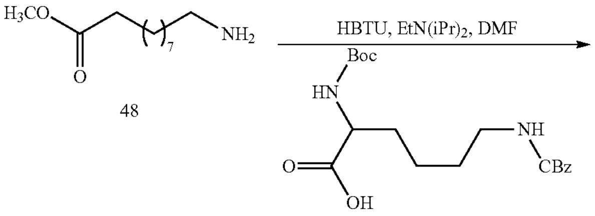
48
49
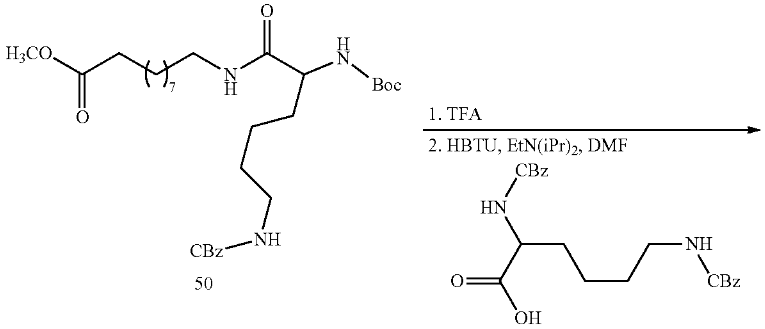
50
49
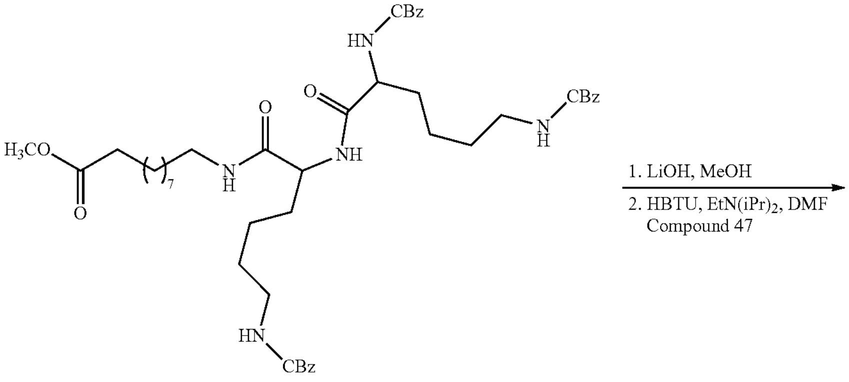
51
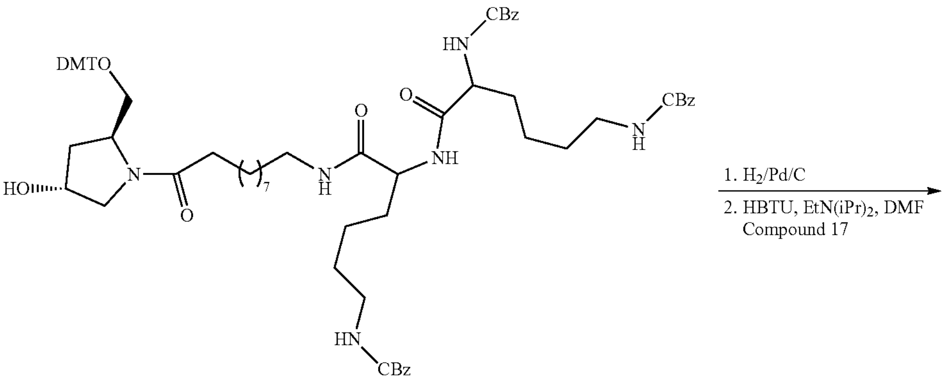
52

-continued
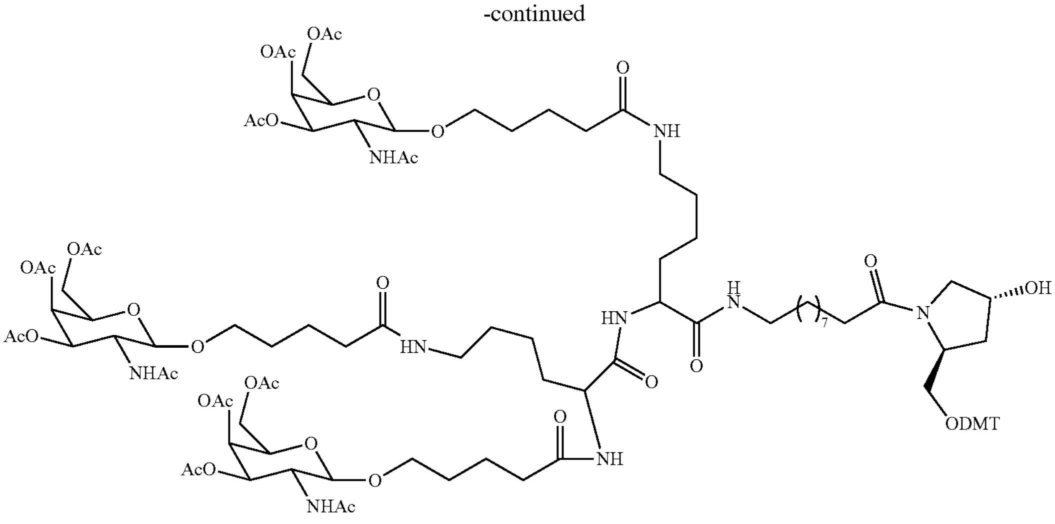
53
Compounds 48 and 49 are commercially available. Compounds 17 and 47 are prepared as per the procedures illustrated in Examples 4 and 15.
Example 17: Preparation of Compound 54
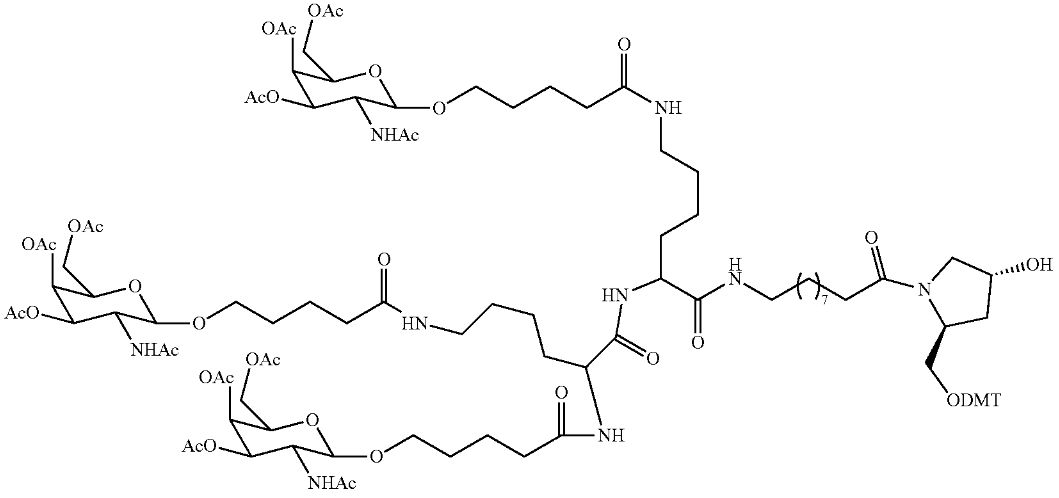
53
Phosphitylation -continued
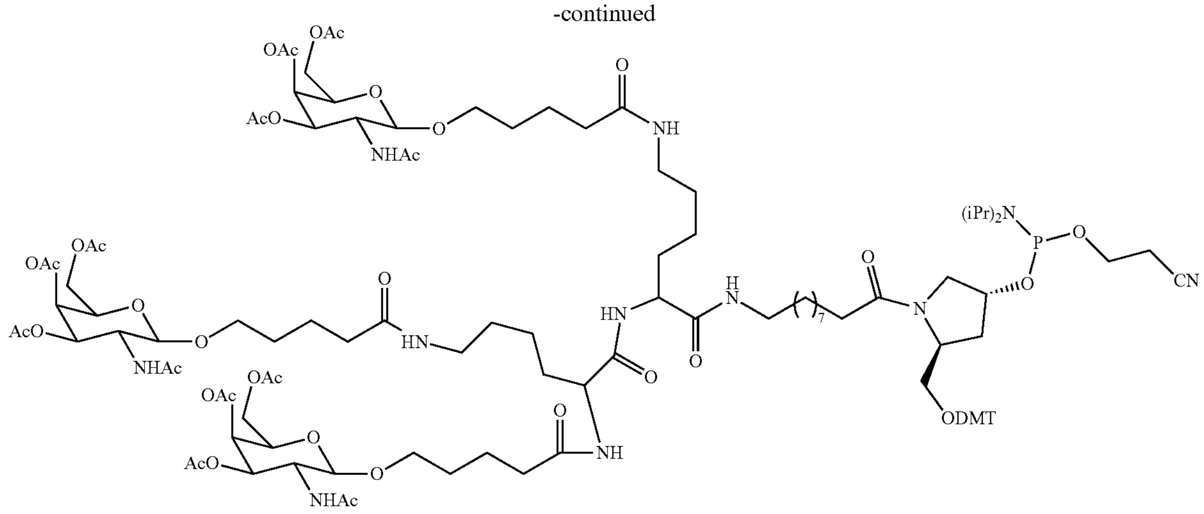
54
Compound 53 is prepared as per the procedures illustrated in Example 16.
Example 18: Preparation of Compound 55
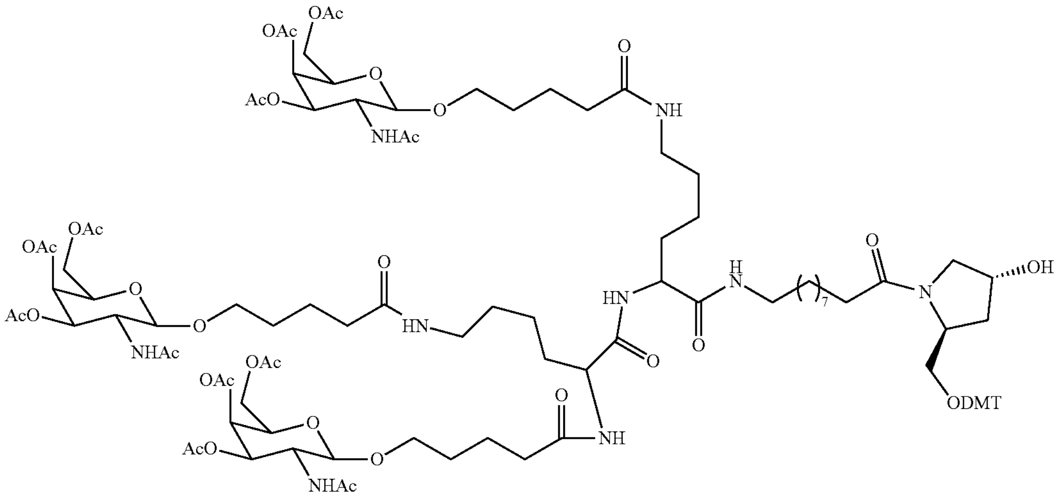
53
1. Succinic anhydride, DMAP, DCE
2. DMF, HBTU, $EtN(iPr)_2$, PS—SS -continued

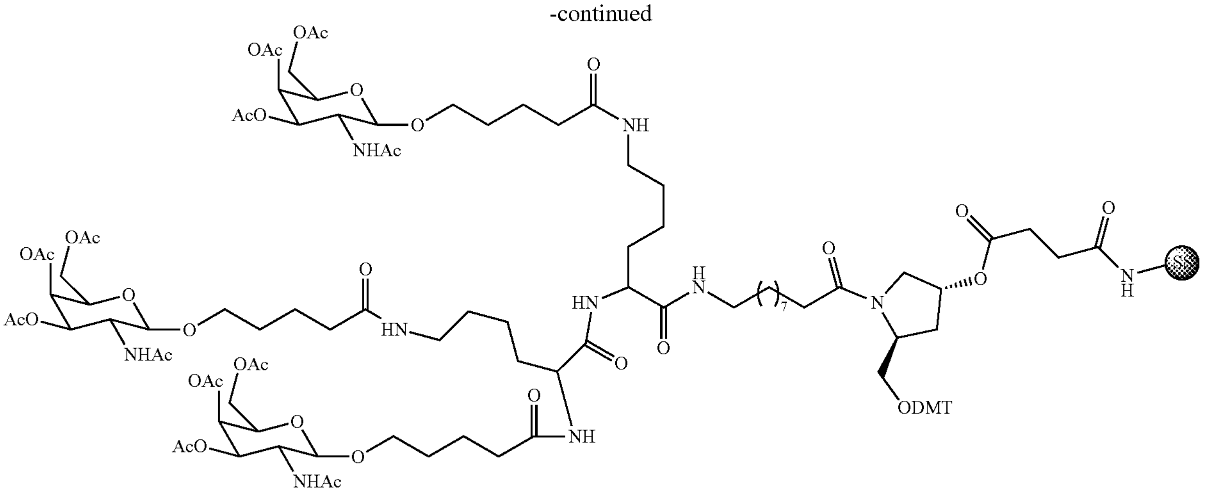

55

Compound 53 is prepared as per the procedures illustrated in Example 16.

Example 19: General Method for the Preparation of Conjugated ASOs Comprising $GalNAc_3$-1 at the 3' Position Via Solid Phase Techniques (Preparation of ISIS 647535, 647536 and 651900)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and C residues. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on an $GalNAc_3$-1 loaded VIMAD solid support (110 μmol/g, Guzaev et al., 2003) packed in the column. For the coupling step, the phosphoramidites were delivered 4 fold excess over the loading on the solid support and phosphoramidite condensation was carried out for 10 min. All other steps followed standard protocols supplied by the manufacturer. A solution of 6% dichloroacetic acid in toluene was used for removing dimethoxytrityl (DMT) group from 5'-hydroxyl group of the nucleotide. 4,5-Dicyanoimidazole (0.7 M) in anhydrous $CH_3CN$ was used as activator during coupling step. Phosphorothioate linkages were introduced by sulfurization with 0.1 M solution of xanthane hydride in 1:1 pyridine/$CH_3CN$ for a contact time of 3 minutes. A solution of 20% tert-butylhydroperoxide in $CH_3CN$ containing 6% water was used as an oxidizing agent to provide phosphodiester internucleoside linkages with a contact time of 12 minutes.

After the desired sequence was assembled, the cyanoethyl phosphate protecting groups were deprotected using a 1:1 (v/v) mixture of triethylamine and acetonitrile with a contact time of 45 minutes. The solid-support bound ASOs were suspended in aqueous ammonia (28-30 wt %) and heated at 55° C. for 6 h.

The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous $CH_3CN$, B=1.5 M NaBr in A, 0-40% of B in 60 min, flow 14 mL min-1, 2=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

Antisense oligonucleotides not comprising a conjugate were synthesized using standard oligonucleotide synthesis procedures well known in the art.

Using these methods, three separate antisense compounds targeting ApoC III were prepared. As summarized in Table 4, below, each of the three antisense compounds targeting ApoC III had the same nucleobase sequence; ISIS 304801 is a 5-10-5 MOE gapmer having all phosphorothioate linkages; ISIS 647535 is the same as ISIS 304801, except that it had a $GalNAc_3$-1 conjugated at its 3'end; and ISIS 647536 is the same as ISIS 647535 except that certain internucleoside linkages of that compound are phosphodiester linkages. As further summarized in Table 4, two separate antisense compounds targeting SRB-1 were synthesized. ISIS 440762 was a 2-10-2 cEt gapmer with all phosphorothioate internucleoside linkages; ISIS 651900 is the same as ISIS 440762, except that it included a $GalNAc_3$-1 at its 3'-end.

TABLE 4

Modified ASO targeting ApoC III and SRB-1

| ASO | Sequence (5' to 3') | Target | CalCd Mass | Observed Mass | SEQ ID No. |
|---|---|---|---|---|---|
| ISIS 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | ApoC III | 7165.4 | 7164.4 | 20 |
| ISIS 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}\mathbf{A}_{do'}$-**GalNAc$_3$-1$_a$** | ApoC III | 9239.5 | 9237.8 | 21 |
| ISIS 647536 | $A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{eo}\mathbf{A}_{do'}$-**GalNAc$_3$-1$_a$** | ApoC III | 9142.9 | 9140.8 | 21 |
| ISIS 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | SRB-1 | 4647.0 | 4646.4 | 22 |
| ISIS 651900 | $T_{ks}{}^{m}C_{ks}A_{ds}G_{ds}{}^{m}C_{ds}A_{ds}T_{ds}G_{ds}A_{ds}{}^{m}C_{ds}T_{ds}T_{ks}{}^{m}C_{ko}\mathbf{A}_{do'}$-**GalNAc$_3$-1$_a$** | SRB-1 | 6721.1 | 6719.4 | 23 |

Subscripts: "e" indicates 2'-MOE modified nucleoside; "d" indicates β-D-2'-deoxyribonucleoside; "k" indicates 6'-(S)-$CH_3$ bicyclic nucleoside (e.g. cEt); "s" indicates phosphorothioate internucleoside linkages (PS); "o" indicates phosphodiester internucleoside linkages (PO); and "o'" indicates —O—P(═O)(OH)—.
Superscript "m" indicates 5-methylcytosines.

"GalNAc$_3$-1" indicates a conjugate group having the structure shown previously in Example 9. Note that GalNAc$_3$-1 comprises a cleavable adenosine which links the ASO to remainder of the conjugate, which is designated "GalNAc$_3$-1$_a$." This nomenclature is used in the above table to show the full nucleobase sequence, including the adenosine, which is part of the conjugate. Thus, in the above table, the sequences could also be listed as ending with "GalNAc$_3$-1" with the "$\mathbf{A}_{do}$" omitted. This convention of using the subscript "a" to indicate the portion of a conjugate group lacking a cleavable nucleoside or cleavable moiety is used throughout these Examples. This portion of a conjugate group lacking the cleavable moiety is referred to herein as a "cluster" or "conjugate cluster" or "GalNAc$_3$ cluster." In certain instances it is convenient to describe a conjugate group by separately providing its cluster and its cleavable moiety.

Example 20: Dose-Dependent Antisense Inhibition of Human ApoC III in huApoC III Transgenic Mice ISIS 304801 and ISIS 647535, each targeting human ApoC III and described above, were separately tested and evaluated in a dose-dependent study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once a week for two weeks with ISIS 304801 or 647535 at 0.08, 0.25. 0.75, 2.25 or 6.75 μmol/kg or with PBS as a control. Each treatment group consisted of 4 animals. Forty-eight hours after the administration of the last dose, blood was drawn from each mouse and the mice were sacrificed and tissues were collected.

ApoC III mRNA Analysis

ApoC III mRNA levels in the mice's livers were determined using real-time PCR and RIBOGREEN® RNA quantification reagent (Molecular Probes, Inc. Eugene, OR) according to standard protocols. ApoC III mRNA levels were determined relative to total RNA (using Ribogreen), prior to normalization to PBS-treated control. The results below are presented as the average percent of ApoC III mRNA levels for each treatment group, normalized to PBS-treated control and are denoted as "% PBS". The half maximal effective dosage (ED50) of each ASO is also presented in Table 5, below.

As illustrated, both antisense compounds reduced ApoC III RNA relative to the PBS control. Further, the antisense compound conjugated to GalNAc$_3$-1 (ISIS 647535) was substantially more potent than the antisense compound lacking the GalNAc$_3$-1 conjugate (ISIS 304801).

TABLE 5

Effect of ASO treatment on ApoC III mRNA levels in human ApoC III transgenic mice

| ASO | Dose (μmol/kg) | % PBS | $ED_{50}$ (μmol/kg) | 3' Conjugate | Internucleoside Linkage/ Length | SEQ ID No. |
|---|---|---|---|---|---|---|
| PBS | 0 | 100 | — | — | — | |
| ISIS 304801 | 0.08 | 95 | 0.77 | None | PS/20 | 20 |
| | 0.75 | 42 | | | | |
| | 2.25 | 32 | | | | |
| | 6.75 | 19 | | | | |
| ISIS 647535 | 0.08 | 50 | 0.074 | GalNAc$_3$-1 | PS/20 | 21 |
| | 0.75 | 15 | | | | |
| | 2.25 | 17 | | | | |
| | 6.75 | 8 | | | | |

ApoC III Protein Analysis (Turbidometric Assay)

Plasma ApoC III protein analysis was determined using procedures reported by Graham et al, *Circulation Research*, published online before print Mar. 29, 2013.

Approximately 100 μl of plasma isolated from mice was analyzed without dilution using an Olympus Clinical Analyzer and a commercially available turbidometric ApoC III assay (Kamiya, Cat #KAI-006, Kamiya Biomedical, Seattle, WA). The assay protocol was performed as described by the vendor.

As shown in the Table 6 below, both antisense compounds reduced ApoC III protein relative to the PBS control. Further, the antisense compound conjugated to GalNAc$_3$-1 (ISIS 647535) was substantially more potent than the antisense compound lacking the GalNAc$_3$-1 conjugate (ISIS 304801).

TABLE 6

| Effect of ASO treatment on ApoC III plasma protein levels in human ApoC III transgenic mice | | | | | | |
|---|---|---|---|---|---|---|
| ASO | Dose (μmol/kg) | % PBS | $ED_{50}$ (μmol/kg) | 3' Conjugate | Inter-nucleoside Linkage/ Length | SEQ ID No. |
| PBS | 0 | 100 | — | — | — | |
| ISIS | 0.08 | 86 | 0.73 | None | PS/20 | 20 |
| 304801 | 0.75 | 51 | | | | |
| | 2.25 | 23 | | | | |
| | 6.75 | 13 | | | | |
| ISIS | 0.08 | 72 | 0.19 | $GalNAc_3$-1 | PS/20 | 21 |
| 647535 | 0.75 | 14 | | | | |
| | 2.25 | 12 | | | | |
| | 6.75 | 11 | | | | |

Plasma triglycerides and cholesterol were extracted by the method of Bligh and Dyer (Bligh, E. G. and Dyer, W. J. Can. J. Biochem. Physiol. 37:911-917, 1959)(Bligh, E and Dyer, W, *Can J Biochem Physiol,* 37, 911-917, 1959)(Bligh, E and Dyer, W, *Can J Biochem Physiol,* 37, 911-917, 1959) and measured by using a Beckmann Coulter clinical analyzer and commercially available reagents.

The triglyceride levels were measured relative to PBS injected mice and are denoted as "% PBS". Results are presented in Table 7. As illustrated, both antisense compounds lowered triglyceride levels. Further, the antisense compound conjugated to $GalNAc_3$-1 (ISIS 647535) was substantially more potent than the antisense compound lacking the $GalNAc_3$-1 conjugate (ISIS 304801).

TABLE 7

| Effect of ASO treatment on triglyceride levels in transgenic mice | | | | | | |
|---|---|---|---|---|---|---|
| ASO | Dose (μmol/kg) | % PBS | ED50 (μmol/kg) | 3' Conjugate | Inter-nucleoside Linkage/ Length | SEQ ID No. |
| PBS | 0 | 100 | — | — | — | |
| ISIS | 0.08 | 87 | 0.63 | None | PS/20 | 20 |
| 304801 | 0.75 | 46 | | | | |
| | 2.25 | 21 | | | | |
| | 6.75 | 12 | | | | |
| ISIS | 0.08 | 65 | 0.13 | $GalNAc_3$-1 | PS/20 | 21 |
| 647535 | 0.75 | 9 | | | | |
| | 2.25 | 8 | | | | |
| | 6.75 | 9 | | | | |

Plasma samples were analyzed by HPLC to determine the amount of total cholesterol and of different fractions of cholesterol (HDL and LDL). Results are presented in Tables 8 and 9. As illustrated, both antisense compounds lowered total cholesterol levels; both lowered LDL; and both raised HDL. Further, the antisense compound conjugated to $GalNAc_3$-1 (ISIS 647535) was substantially more potent than the antisense compound lacking the $GalNAc_3$-1 conjugate (ISIS 304801). An increase in HDL and a decrease in LDL levels is a cardiovascular beneficial effect of antisense inhibition of ApoC III.

TABLE 8

| Effect of ASO treatment on total cholesterol levels in transgenic mice | | | | | |
|---|---|---|---|---|---|
| ASO | Dose (μmol/kg) | Total Cholesterol (mg/dL) | 3' Conjugate | Internucleoside Linkage/Length | SEQ ID No. |
| PBS | 0 | 257 | — | — | |
| ISIS | 0.08 | 226 | None | PS/20 | 20 |
| 304801 | 0.75 | 164 | | | |
| | 2.25 | 110 | | | |
| | 6.75 | 82 | | | |
| ISIS | 0.08 | 230 | $GalNAc_3$-1 | PS/20 | 21 |
| 647535 | 0.75 | 82 | | | |
| | 2.25 | 86 | | | |
| | 6.75 | 99 | | | |

TABLE 9

| Effect of ASO treatment on HDL and LDL cholesterol levels in transgenic mice | | | | | | |
|---|---|---|---|---|---|---|
| ASO | Dose (μmol/kg) | HDL (mg/dL) | LDL (mg/dL) | 3' Conjugate | Inter-nucleoside Linkage/ Length | SEQ ID No. |
| PBS | 0 | 17 | 28 | — | — | |
| ISIS | 0.08 | 17 | 23 | None | PS/20 | 32 |
| 304801 | 0.75 | 27 | 12 | | | |
| | 2.25 | 50 | 4 | | | |
| | 6.75 | 45 | 2 | | | |
| ISIS | 0.08 | 21 | 21 | $GalNAc_3$-1 | PS/20 | 111 |
| 647535 | 0.75 | 44 | 2 | | | |
| | 2.25 | 50 | 2 | | | |
| | 6.75 | 58 | 2 | | | |

Pharmacokinetics Analysis (PK)

The PK of the ASOs was also evaluated. Liver and kidney samples were minced and extracted using standard protocols. Samples were analyzed on MSD1 utilizing IP-HPLC-MS. The tissue level (μg/g) of full-length ISIS 304801 and 647535 was measured and the results are provided in Table 10. As illustrated, liver concentrations of total full-length antisense compounds were similar for the two antisense compounds. Thus, even though the $GalNAc_3$-1-conjugated antisense compound is more active in the liver (as demonstrated by the RNA and protein data above), it is not present at substantially higher concentration in the liver. Indeed, the calculated EC50 (provided in Table 10) confirms that the observed increase in potency of the conjugated compound cannot be entirely attributed to increased accumulation. This result suggests that the conjugate improved potency by a mechanism other than liver accumulation alone, possibly by improving the productive uptake of the antisense compound into cells.

The results also show that the concentration of $GalNAc_3$-1 conjugated antisense compound in the kidney is lower than that of antisense compound lacking the GalNAc conjugate. This has several beneficial therapeutic implications. For therapeutic indications where activity in the kidney is not sought, exposure to kidney risks kidney toxicity without corresponding benefit. Moreover, high concentration in kidney typically results in loss of compound to the urine resulting in faster clearance. Accordingly, for non-kidney targets, kidney accumulation is undesired. These data suggest that $GalNAc_3$-1 conjugation reduces kidney accumulation.

TABLE 10

| PK analysis of ASO treatment in transgenic mice | | | | | | | |
|---|---|---|---|---|---|---|---|
| ASO | Dose (μmol/kg) | Liver (μg/g) | Kidney (μg/g) | Liver $EC_{50}$ (μg/g) | 3' Conjugate | Inter-nucleoside Linkage/ Length | SEQ ID No. |
| ISIS 304801 | 0.1 | 5.2 | 2.1 | 53 | None | PS/20 | 20 |
| | 0.8 | 62.8 | 119.6 | | | | |
| | 2.3 | 142.3 | 191.5 | | | | |
| | 6.8 | 202.3 | 337.7 | | | | |
| ISIS 647535 | 0.1 | 3.8 | 0.7 | 3.8 | $GalNAc_3$-1 | PS/20 | 21 |
| | 0.8 | 72.7 | 34.3 | | | | |
| | 2.3 | 106.8 | 111.4 | | | | |
| | 6.8 | 237.2 | 179.3 | | | | |

Metabolites of ISIS 647535 were also identified and their masses were confirmed by high resolution mass spectrometry analysis. The cleavage sites and structures of the observed metabolites are shown below. The relative % of full length ASO was calculated using standard procedures and the results are presented in Table 10a. The major metabolite of ISIS 647535 was full-length ASO lacking the entire conjugate (i.e. ISIS 304801), which results from cleavage at cleavage site A, shown below. Further, additional metabolites resulting from other cleavage sites were also observed. These results suggest that introducing other cleabable bonds such as esters, peptides, disulfides, phosphoramidates or acyl-hydrazones between the $GalNAc_3$-1 sugar and the ASO, which can be cleaved by enzymes inside the cell, or which may cleave in the reductive environment of the cytosol, or which are labile to the acidic pH inside endosomes and lyzosomes, can also be useful.

TABLE 10a

| Observed full length metabolites of ISIS 647535 | | | |
|---|---|---|---|
| Metabolite | ASO | Cleavage site | Relative % |
| 1 | ISIS 304801 | A | 36.1 |
| 2 | ISIS 304801 + dA | B | 10.5 |
| 3 | ISIS 647535 minus [3 GalNAc] | C | 16.1 |
| 4 | ISIS 647535 minus [3 GalNAc + 1 5-hydroxy-pentanoic acid tether] | D | 17.6 |
| 5 | ISIS 647535 minus [2 GalNAc + 2 5-hydroxy-pentanoic acid tether] | D | 9.9 |
| 6 | ISIS 647535 minus [3 GalNAc + 3 5-hydroxy-pentanoic acid tether] | D | 9.8 |

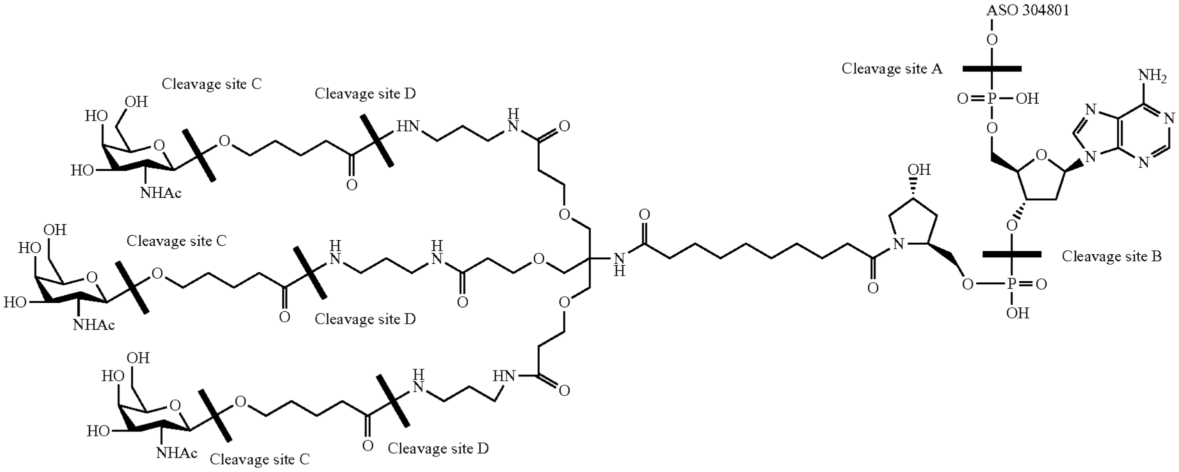

Cleavage Sites

Metabolite 1

TABLE 10a-continued
| Observed full length metabolites of ISIS 647535 | | | |
|---|---|---|---|
| Metabolite | ASO | Cleavage site | Relative % |
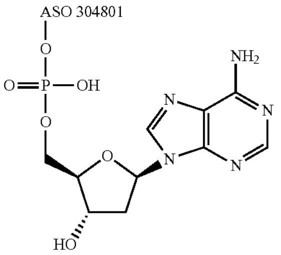
Metabolite 2
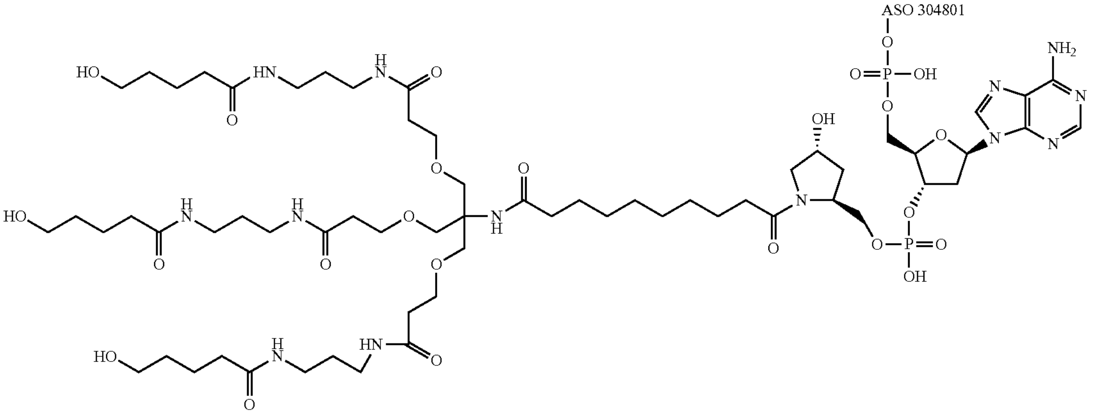
Metabolite 3
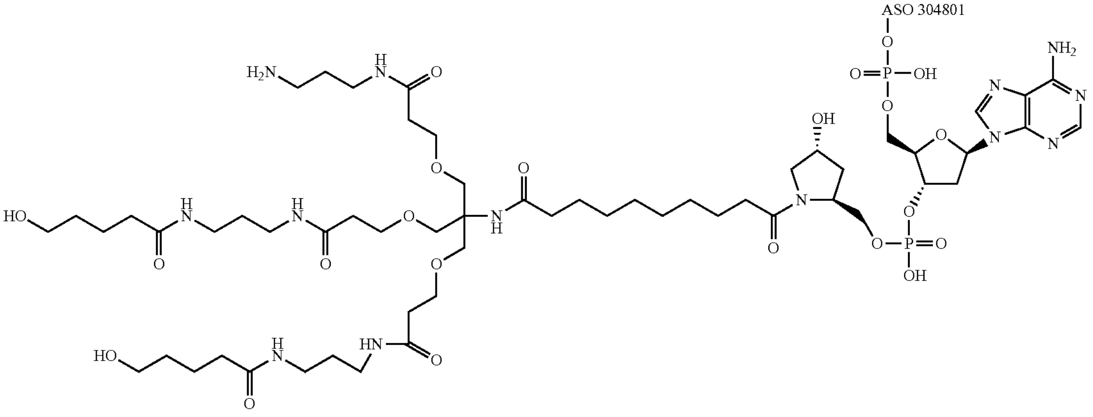
Metabolite 4

TABLE 10a-continued

Observed full length metabolites of ISIS 647535

| Metabolite | ASO | Cleavage site | Relative % |
|---|---|---|---|

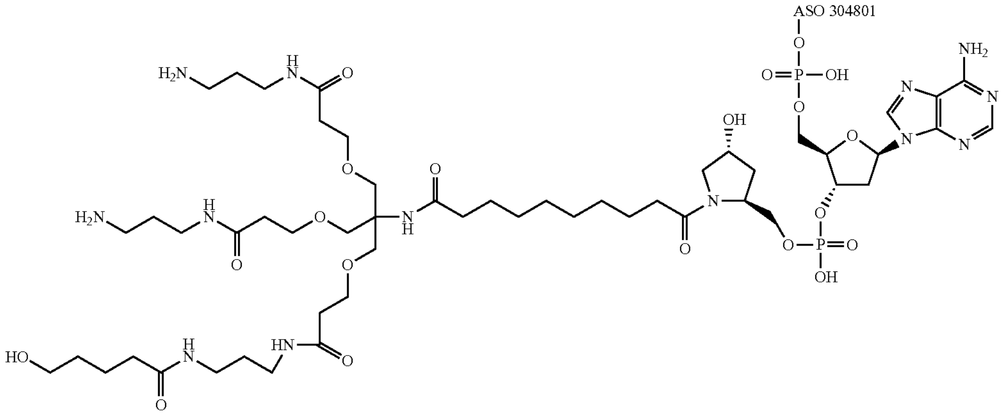

Metabolite 5

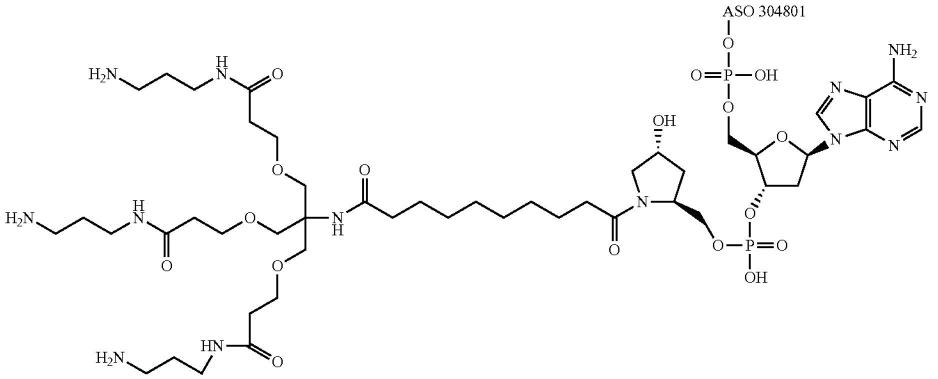

Metabolite 6

Example 21: Antisense Inhibition of Human ApoC III in Human ApoC III Transgenic Mice in Single Administration Study ISIS 304801, 647535 and 647536 each targeting human ApoC III and described in Table 4, were further evaluated in a single administration study for their ability to inhibit human ApoC III in human ApoC III transgenic mice.

Treatment

Human ApoCIII transgenic mice were maintained on a 12-hour light/dark cycle and fed ad libitum Teklad lab chow. Animals were acclimated for at least 7 days in the research facility before initiation of the experiment. ASOs were prepared in PBS and sterilized by filtering through a 0.2 micron filter. ASOs were dissolved in 0.9% PBS for injection.

Human ApoC III transgenic mice were injected intraperitoneally once at the dosage shown below with ISIS 304801, 647535 or 647536 (described above) or with PBS treated control. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III mRNA and protein levels in the liver; plasma triglycerides; and cholesterol, including HDL and LDL fractions were assessed as described above (Example 20). Data from those analyses are presented in Tables 11-15, below. Liver transaminase levels, alanine aminotransferase (ALT) and aspartate aminotransferase (AST), in serum were measured relative to saline injected mice using standard protocols. The ALT and AST levels showed that the antisense compounds were well tolerated at all administered doses.

These results show improvement in potency for antisense compounds comprising a GalNAc$_3$-1 conjugate at the 3' terminus (ISIS 647535 and 647536) compared to the antisense compound lacking a GalNAc$_3$-1 conjugate (ISIS 304801). Further, ISIS 647536, which comprises a GalNAc$_3$-1 conjugate and some phosphodiester linkages was as potent as ISIS 647535, which comprises the same conjugate and all internucleoside linkages within the ASO are phosphorothioate.

TABLE 11

Effect of ASO treatment on ApoC III mRNA levels in human ApoC III transgenic mice

| ASO | Dose (mg/kg) | % PBS | ED50 (mg/kg) | 3' Conjugate | Inter-nucleoside Linkage/ Length | SEQ ID No. |
|---|---|---|---|---|---|---|
| PBS | 0 | 99 | — | — | — | |
| ISIS | 1 | 104 | 13.2 | None | PS/20 | 20 |
| 304801 | 3 | 92 | | | | |
| | 10 | 71 | | | | |
| | 30 | 40 | | | | |
| ISIS | 0.3 | 98 | 1.9 | $GalNAc_3$-1 | PS/20 | 21 |
| 647535 | 1 | 70 | | | | |
| | 3 | 33 | | | | |
| | 10 | 20 | | | | |
| ISIS | 0.3 | 103 | 1.7 | $GalNAc_3$-1 | PS/PO/20 | 21 |
| 647536 | 1 | 60 | | | | |
| | 3 | 31 | | | | |
| | 10 | 21 | | | | |

TABLE 12

Effect of ASO treatment on ApoC III plasma protein levels in human ApoC III transgenic mice

| ASO | Dose (mg/kg) | % PBS | $ED_{50}$ (mg/kg) | 3' Conjugate | Internucleoside Linkage/Length | SEQ ID No. |
|---|---|---|---|---|---|---|
| PBS | 0 | 99 | — | — | — | |
| ISIS | 1 | 104 | 23.2 | None | PS/20 | 20 |
| 304801 | 3 | 92 | | | | |
| | 10 | 71 | | | | |
| | 30 | 40 | | | | |
| ISIS | 0.3 | 98 | 2.1 | $GalNAc_3$-1 | PS/20 | 21 |
| 647535 | 1 | 70 | | | | |
| | 3 | 33 | | | | |
| | 10 | 20 | | | | |
| ISIS | 0.3 | 103 | 1.8 | $GalNAc_3$-1 | PS/PO/20 | 21 |
| 647536 | 1 | 60 | | | | |
| | 3 | 31 | | | | |
| | 10 | 21 | | | | |

TABLE 13

Effect of ASO treatment on triglyceride levels in transgenic mice

| ASO | Dose (mg/kg) | % PBS | $ED_{50}$ (mg/kg) | 3' Conjugate | Internucleoside Linkage/Length | SEQ ID No. |
|---|---|---|---|---|---|---|
| PBS | 0 | 98 | — | — | — | |
| ISIS | 1 | 80 | 29.1 | None | PS/20 | 20 |
| 304801 | 3 | 92 | | | | |
| | 10 | 70 | | | | |
| | 30 | 47 | | | | |
| ISIS | 0.3 | 100 | 2.2 | $GalNAc_3$-1 | PS/20 | 21 |
| 647535 | 1 | 70 | | | | |
| | 3 | 34 | | | | |
| | 10 | 23 | | | | |
| ISIS | 0.3 | 95 | 1.9 | $GalNAc_3$-1 | PS/PO/20 | 21 |
| 647536 | 1 | 66 | | | | |
| | 3 | 31 | | | | |
| | 10 | 23 | | | | |

TABLE 14

Effect of ASO treatment on total cholesterol levels in transgenic mice

| ASO | Dose (mg/kg) | % PBS | 3' Conjugate | Internucleoside Linkage/Length | SEQ ID No. |
|---|---|---|---|---|---|
| PBS | 0 | 96 | — | — | |
| ISIS | 1 | 104 | None | PS/20 | 20 |
| 304801 | 3 | 96 | | | |
| | 10 | 86 | | | |
| | 30 | 72 | | | |
| ISIS | 0.3 | 93 | $GalNAc_3$-1 | PS/20 | 21 |
| 647535 | 1 | 85 | | | |
| | 3 | 61 | | | |
| | 10 | 53 | | | |
| ISIS | 0.3 | 115 | $GalNAc_3$-1 | PS/PO/20 | 21 |
| 647536 | 1 | 79 | | | |
| | 3 | 51 | | | |
| | 10 | 54 | | | |

TABLE 15

Effect of ASO treatment on HDL and LDL cholesterol levels in transgenic mice

| ASO | Dose (mg/kg) | HDL % PBS | LDL % PBS | 3' Conjugate | Internucleoside Linkage/Length | SEQ ID No. |
|---|---|---|---|---|---|---|
| PBS | 0 | 131 | 90 | — | — | |
| ISIS | 1 | 130 | 72 | None | PS/20 | 20 |
| 304801 | 3 | 186 | 79 | | | |
| | 10 | 226 | 63 | | | |
| | 30 | 240 | 46 | | | |
| ISIS | 0.3 | 98 | 86 | $GalNAc_3$-1 | PS/20 | 21 |
| 647535 | 1 | 214 | 67 | | | |
| | 3 | 212 | 39 | | | |
| | 10 | 218 | 35 | | | |
| ISIS | 0.3 | 143 | 89 | $GalNAc_3$-1 | PS/PO/20 | 21 |
| 647536 | 1 | 187 | 56 | | | |
| | 3 | 213 | 33 | | | |
| | 10 | 221 | 34 | | | |

These results confirm that the $GalNAc_3$-1 conjugate improves potency of an antisense compound. The results also show equal potency of a $GalNAc_3$-1 conjugated antisense compounds where the antisense oligonucleotides have mixed linkages (ISIS 647536 which has six phosphodiester linkages) and a full phosphorothioate version of the same antisense compound (ISIS 647535).

Phosphorothioate linkages provide several properties to antisense compounds. For example, they resist nuclease digestion and they bind proteins resulting in accumulation of compound in the liver, rather than in the kidney/urine. These are desirable properties, particularly when treating an indication in the liver. However, phosphorothioate linkages have also been associated with an inflammatory response. Accordingly, reducing the number of phosphorothioate linkages in a compound is expected to reduce the risk of inflammation, but also lower concentration of the compound in liver, increase concentration in the kidney and urine, decrease stability in the presence of nucleases, and lower overall potency. The present results show that a $GalNAc_3$-1 conjugated antisense compound where certain phosphorothioate linkages have been replaced with phosphodiester linkages is as potent against a target in the liver as a counterpart having full phosphorothioate linkages. Such compounds are expected to be less proinflammatory (See Example 24 describing an experiment showing reduction of PS results in reduced inflammatory effect).

Example 22: Effect of $GalNAc_3$-1 Conjugated Modified ASO Targeting SRB-1 In Vivo ISIS 440762 and 651900, each targeting SRB-1 and described in Table 4, were evaluated in a dose-dependent study for their ability to inhibit SRB-1 in Balb/c mice.

Treatment

Six week old male Balb/c mice (Jackson Laboratory, Bar Harbor, ME) were injected subcutaneously once at the dosage shown below with ISIS 440762, 651900 or with PBS treated control. Each treatment group consisted of 4 animals. The mice were sacrificed 48 hours following the final administration to determine the SRB-1 mRNA levels in liver using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS".

As illustrated in Table 16, both antisense compounds lowered SRB-1 mRNA levels. Further, the antisense compound comprising the $GalNAc_3$-1 conjugate (ISIS 651900) was substantially more potent than the antisense compound lacking the $GalNAc_3$-1 conjugate (ISIS 440762). These results demonstrate that the potency benefit of $GalNAc_3$-1 conjugates are observed using antisense oligonucleotides complementary to a different target and having different chemically modified nucleosides, in this instance modified nucleosides comprise constrained ethyl sugar moieties (a bicyclic sugar moiety).

TABLE 16

Effect of ASO treatment on SRB-1 mRNA levels in Balb/c mice

| ASO | Dose (mg/kg) | Liver % PBS | $ED_{50}$ (mg/kg) | 3' Conjugate | Internucleoside linkage/Length | SEQ ID No. |
|---|---|---|---|---|---|---|
| PBS | 0 | 100 | | — | — | |
| ISIS | 0.7 | 85 | 2.2 | None | PS/14 | 22 |
| 440762 | 2 | 55 | | | | |
| | 7 | 12 | | | | |
| | 20 | 3 | | | | |
| ISIS | 0.07 | 98 | 0.3 | $GalNAc_3$-1 | PS/14 | 23 |
| 651900 | 0.2 | 63 | | | | |
| | 0.7 | 20 | | | | |
| | 2 | 6 | | | | |
| | 7 | 5 | | | | |

Example 23: Human Peripheral Blood Mononuclear Cells (hPBMC) Assay Protocol

The hPBMC assay was performed using BD Vautainer CPT tube method. A sample of whole blood from volunteered donors with informed consent at US HealthWorks clinic (Faraday & El Camino Real, Carlsbad) was obtained and collected in 4-15 BD Vacutainer CPT 8 ml tubes (VWR Cat. #BD362753). The approximate starting total whole blood volume in the CPT tubes for each donor was recorded using the PBMC assay data sheet.

The blood sample was remixed immediately prior to centrifugation by gently inverting tubes 8-10 times. CPT tubes were centrifuged at rt (18-25° C.) in a horizontal (swing-out) rotor for 30 min. at 1500-1800 RCF with brake off (2700 RPM Beckman Allegra 6R). The cells were retrieved from the buffy coat interface (between Ficoll and polymer gel layers); transferred to a sterile 50 ml conical tube and pooled up to 5 CPT tubes/50 ml conical tube/donor. The cells were then washed twice with PBS (Ca++, Mg++ free; GIBCO). The tubes were topped up to 50 ml and mixed by inverting several times. The sample was then centrifuged at 330×g for 15 minutes at rt (1215 RPM in Beckman Allegra 6R) and aspirated as much supernatant as possible without disturbing pellet. The cell pellet was dislodged by gently swirling tube and resuspended cells in RPMI+10% FBS+pen/strep (~1 ml/10 ml starting whole blood volume). A 60 ul sample was pipette into a sample vial (Beckman Coulter) with 600 ul VersaLyse reagent (Beckman Coulter Cat #$A_{09777}$) and was gently vortexed for 10-15 sec. The sample was allowed to incubate for 10 min. at rt and being mixed again before counting. The cell suspension was counted on Vicell XR cell viability analyzer (Beckman Coulter) using PBMC cell type (dilution factor of 1:11 was stored with other parameters). The live cell/ml and viability were recorded. The cell suspension was diluted to $1\times10^7$ live PBMC/ml in RPMI+10% FBS+pen/strep.

The cells were plated at $5\times10^5$ in 50 μl/well of 96-well tissue culture plate (Falcon Microtest). 50 μl/well of 2× concentration oligos/controls diluted in RPMI+10% FBS+ pen/strep. was added according to experiment template (100 μl/well total). Plates were placed on the shaker and allowed to mix for approx. 1 min. After being incubated for 24 hrs at 37° C.; 5% CO2, the plates were centrifuged at 400×g for 10 minutes before removing the supernatant for MSD cytokine assay (i.e. human IL-6, IL-10, IL-8 and MCP-1).

Example 24: Evaluation of Proinflammatory Effects in hPBMC Assay for $GalNAc_3$-1 conjugated ASOs The antisense oligonucleotides (ASOs) listed in Table 17 were evaluated for proinflammatory effect in hPBMC assay using the protocol described in Example 23. ISIS 353512 is an internal standard known to be a high responder for IL-6 release in the assay. The hPBMCs were isolated from fresh, volunteered donors and were treated with ASOs at 0, 0.0128, 0.064, 0.32, 1.6, 8, 40 and 200 μM concentrations. After a 24 hr treatment, the cytokine levels were measured.

The levels of IL-6 were used as the primary readout. The EC50 and Emax was calculated using standard procedures. Results are expressed as the average ratio of Emax/EC50 from two donors and is denoted as "Emax/EC50." The lower ratio indicates a relative decrease in the proinflammatory response and the higher ratio indicates a relative increase in the proinflammatory response.

With regard to the test compounds, the least proinflammatory compound was the PS/PO linked ASO (ISIS 616468). The $GalNAc_3$-1 conjugated ASO, ISIS 647535 was slightly less proinflammatory than its non-conjugated counterpart ISIS 304801. These results indicate that incorporation of some PO linkages reduces proinflammatory reaction and addition of a $GalNAc_3$-1 conjugate does not make a compound more proinflammatory and may reduce proinflammatory response. Accordingly, one would expect that an antisense compound comprising both mixed PS/PO linkages and a $GalNAc_3$-1 conjugate would produce lower proinflammatory responses relative to full PS linked antisense compound with or without a $GalNAc_3$-1 conjugate. These results show that $GalNAc_{3-1}$ conjugated antisense compounds, particularly those having reduced PS content are less proinflammatory.

Together, these results suggest that a $GalNAc_3$-1 conjugated compound, particularly one with reduced PS content, can be administered at a higher dose than a counterpart full PS antisense compound lacking a GalNAc$_3$-1 conjugate. Since half-life is not expected to be substantially different for these compounds, such higher administration would result in less frequent dosing. Indeed such administration could be even less frequent, because the GalNAc$_3$-1 conjugated compounds are more potent (See Examples 20-22) and re-dosing is necessary once the concentration of a compound has dropped below a desired level, where such desired level is based on potency.

TABLE 17

Modified ASOs

| ASO | Sequence (5' to 3') | Target | SEQ ID No. |
| --- | --- | --- | --- |
| ISIS 104838 | $G_{es}{}^{m}C_{es}T_{es}G_{es}A_{es}T_{ds}T_{ds}A_{ds}G_{ds}A_{ds}G_{ds}A_{ds}G_{ds}A_{ds}G_{ds}G_{es}T_{es}{}^{m}C_{es}{}^{m}C_{es}{}^{m}C_{e}$ | TNFα | 24 |
| ISIS 353512 | $T_{es}{}^{m}C_{es}{}^{m}C_{es}{}^{m}C_{ds}A_{ds}T_{ds}T_{ds}T_{ds}{}^{m}C_{ds}A_{ds}G_{ds}G_{ds}A_{ds}G_{ds}A_{ds}{}^{m}C_{ds}{}^{m}C_{ds}T_{es}G_{es}G_{e}$ | CRP | 25 |
| ISIS 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | ApoC III | 20 |
| ISIS 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}\mathbf{A}_{do'}$-**GalNAc$_3$-1$_a$** | ApoC III | 21 |
| ISIS 616468 | $A_{es}G_{eo}{}^{m}C_{eo}T_{eo}T_{eo}{}^{m}C_{ds}T_{as}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{e}$ | ApoC III | 20 |

Subscripts: "e" indicates 2'-MOE modified nucleoside; "d" indicates β-D-2'-deoxyribonucleoside; "k" indicates 6'-(S)-$CH_3$ bicyclic nucleoside (e.g. cEt); "s" indicates phosphorothioate internucleoside linkages (PS); "o" indicates phosphodiester internucleoside linkages (PO); and "o'" indicates —O—P(═O)(OH)—.
Superscript "m" indicates 5-methylcytosines.
"$A_{do'}$-GalNAc$_3$-1$_a$" indicates a conjugate having the structure GalNAc$_3$-1 shown in Example 9 attached to the 3'-end of the antisense oligonucleotide, as indicated.

TABLE 18

Proinflammatory Effect of ASOs targeting ApoC III in hPBMC assay

| ASO | EC$_{50}$ (μM) | E$_{max}$ (μM) | E$_{max}$/EC$_{50}$ | 3' Conjugate | Internucleoside Linkage/Length | SEQ ID No. |
| --- | --- | --- | --- | --- | --- | --- |
| ISIS 353512 (high responder) | 0.01 | 265.9 | 26,590 | None | PS/20 | 25 |
| ISIS 304801 | 0.07 | 106.55 | 1,522 | None | PS/20 | 20 |
| ISIS 647535 | 0.12 | 138 | 1,150 | GalNAc$_3$-1 | PS/20 | 21 |
| ISIS 616468 | 0.32 | 71.52 | 224 | None | PS/PO/20 | 20 |

Example 25: Effect of GalNAc$_3$-1 Conjugated Modified ASO Targeting Human ApoC III In Vitro ISIS 304801 and 647535 described above were tested in vitro. Primary hepatocyte cells from transgenic mice at a density of 25,000 cells per well were treated with 0.03,0.08, 0.24, 0.74, 2.22, 6.67 and 20 μM concentrations of modified oligonucleotides. After a treatment period of approximately 16 hours, RNA was isolated from the cells and mRNA levels were measured by quantitative real-time PCR and the hApoC III mRNA levels were adjusted according to total RNA content, as measured by RIBOGREEN.

The IC$_{50}$ was calculated using the standard methods and the results are presented in Table 19. As illustrated, comparable potency was observed in cells treated with ISIS 647535 as compared to the control, ISIS 304801.

TABLE 19

Modified ASO targeting human ApoC III in primary hepatocytes

| ASO | IC$_{50}$ (μM) | 3' Conjugate | Internucleoside linkage/Length | SEQ ID No. |
| --- | --- | --- | --- | --- |
| ISIS 304801 | 0.44 | None | PS/20 | 20 |
| ISIS 647535 | 0.31 | GalNAc$_3$-1 | PS/20 | 21 |

In this experiment, the large potency benefits of GalNAc$_3$-1 conjugation that are observed in vivo were not observed in vitro. Subsequent free uptake experiments in primary hepatocytes in vitro did show increased potency of oligonucleotides comprising various GalNAc conjugates relative to oligonucleotides that lacking the GalNAc conjugate. (see Examples 60, 82, and 92)

Example 26: Effect of PO/PS linkages on ApoC III ASO Activity

Human ApoC III transgenic mice were injected intraperitoneally once at 25 mg/kg of ISIS 304801, or ISIS 616468 (both described above) or with PBS treated control once per week for two weeks. The treatment group consisted of 3 animals and the control group consisted of 4 animals. Prior to the treatment as well as after the last dose, blood was drawn from each mouse and plasma samples were analyzed. The mice were sacrificed 72 hours following the last administration.

Samples were collected and analyzed to determine the ApoC III protein levels in the liver as described above (Example 20). Data from those analyses are presented in Table 20, below.

These results show reduction in potency for antisense compounds with PO/PS (ISIS 616468) in the wings relative to full PS (ISIS 304801).

TABLE 20

Effect of ASO treatment on ApoC III protein levels in human ApoC III transgenic mice

| ASO | Dose (mg/kg) | % PBS | 3' Conjugate | Internucleoside linkage/Length | SEQ ID No. |
|---|---|---|---|---|---|
| PBS | 0 | 99 | — | — | |
| ISIS 304801 | 25 mg/kg/wk for 2 wks | 24 | None | Full PS | 20 |
| ISIS 616468 | 25 mg/kg/wk for 2 wks | 40 | None | 14 PS/6 PO | 20 |

Example 27: Compound 56

56

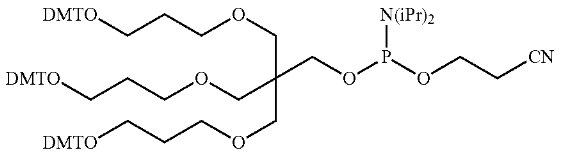

Compound 56 is commercially available from Glen Research or may be prepared according to published procedures reported by Shchepinov et al., Nucleic Acids Research, 1997, 25 (22), 4447-4454.

Example 28: Preparation of Compound 60

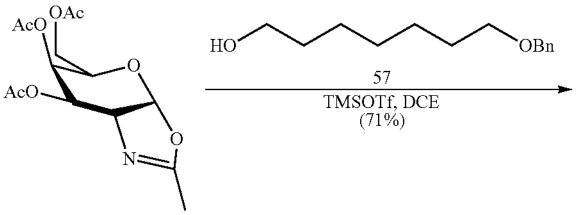

4

-continued

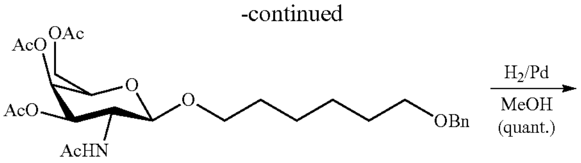

58

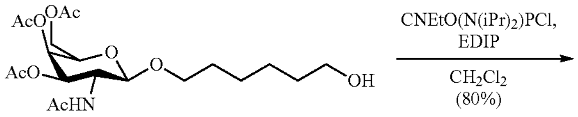

59

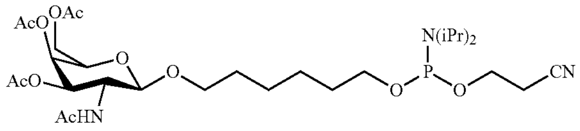

60

Compound 4 was prepared as per the procedures illustrated in Example 2. Compound 57 is commercially available. Compound 60 was confirmed by structural analysis.

Compound 57 is meant to be representative and not intended to be limiting as other monoprotected substituted or unsubstituted alkyl diols including but not limited to those presented in the specification herein can be used to prepare phosphoramidites having a predetermined composition.

Example 29: Preparation of Compound 63

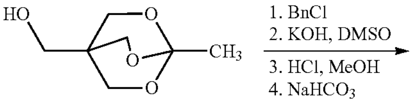

61

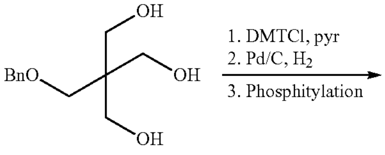

62

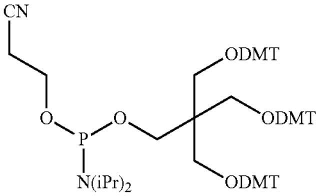

63

Compounds 61 and 62 are prepared using procedures similar to those reported by Tober et al., *Eur. J. Org. Chem.,* 2013, 3, 566-577; and Jiang et al., Tetrahedron, 2007, 63 (19), 3982-3988.

Alternatively, Compound 63 is prepared using procedures similar to those reported in scientific and patent literature by Kim et al., Synlett, 2003, 12, 1838-1840; and Kim et al., published PCT International Application, WO 2004063208.

Example 30: Preparation of Compound 63b

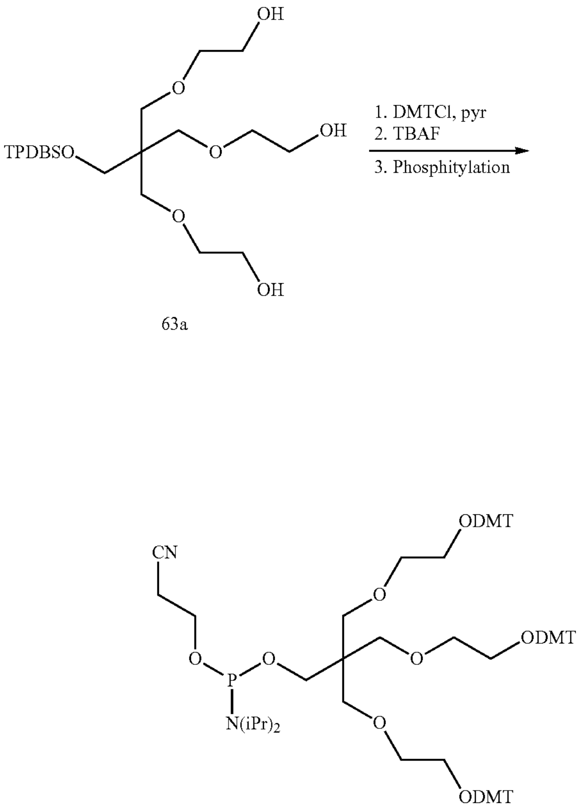
63a
63b
Compound 63a is prepared using procedures similar to those reported by Hanessian et al., *Canadian Journal of Chemistry,* 1996, 74 (9), 1731-1737.
Example 31: Preparation of Compound 63d
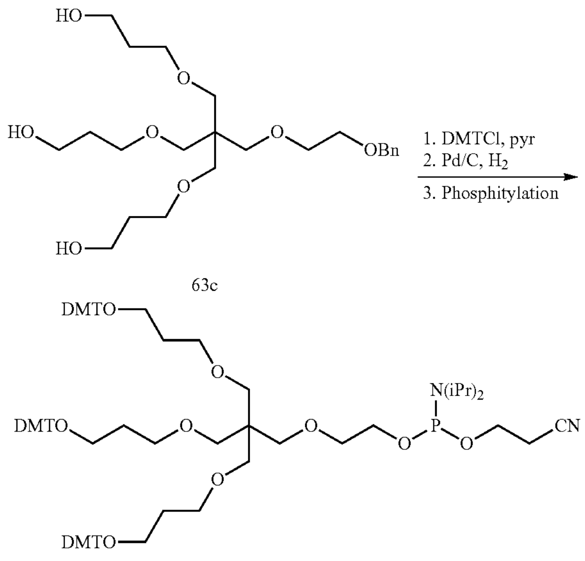
63c
63d
Compound 63c is prepared using procedures similar to those reported by Chen et al., *Chinese Chemical Letters,* 1998, 9 (5), 451-453.
Example 32: Preparation of Compound 67
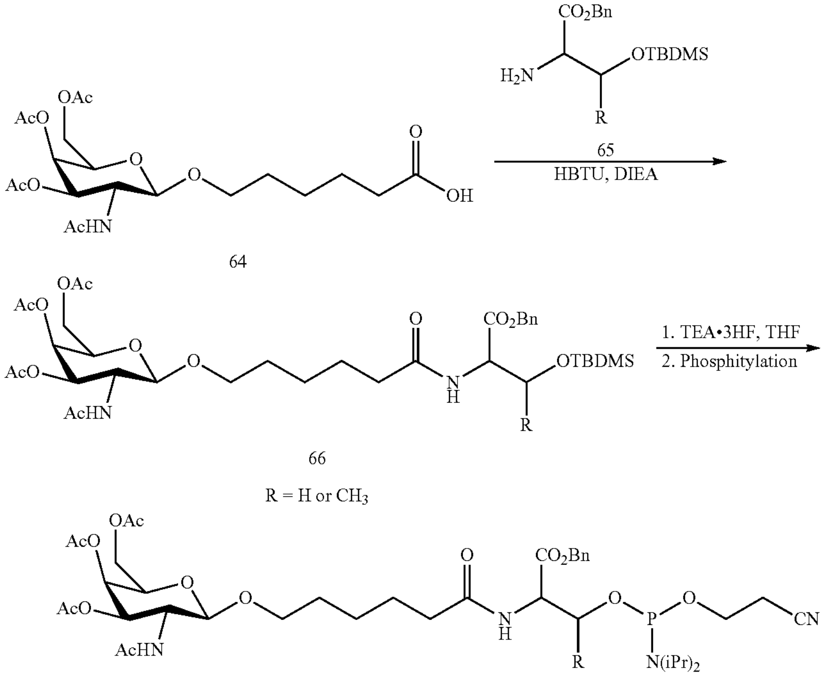
64
66
R = H or $CH_3$
67

Compound 64 was prepared as per the procedures illustrated in Example 2. Compound 65 is prepared using procedures similar to those reported by Or et al., published PCT International Application, WO 2009003009. The protecting groups used for Compound 65 are meant to be representative and not intended to be limiting as other protecting groups including but not limited to those presented in the specification herein can be used.

Example 33: Preparation of Compound 70

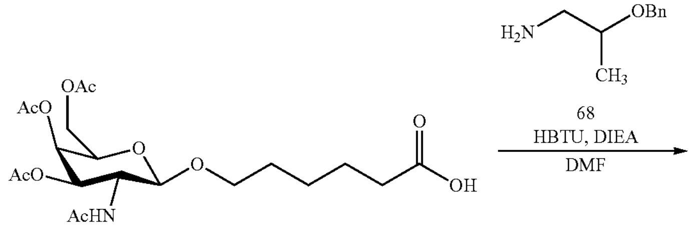

64

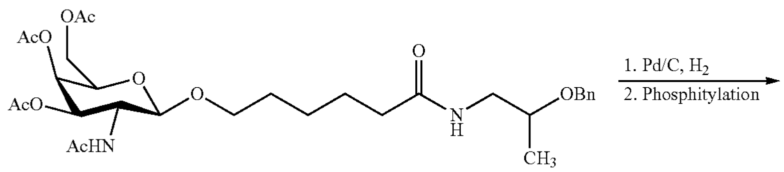

69

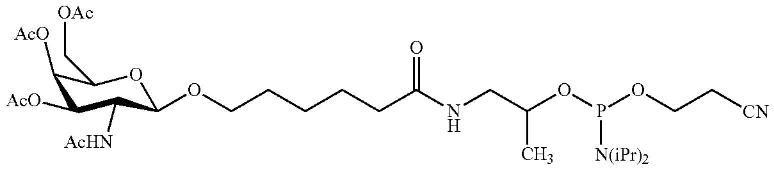

70

Compound 64 was prepared as per the procedures illustrated in Example 2. Compound 68 is commercially available. The protecting group used for Compound 68 is meant to be representative and not intended to be limiting as other protecting groups including but not limited to those presented in the specification herein can be used.

Example 34: Preparation of Compound 75a

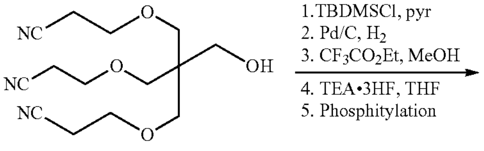

75

-continued

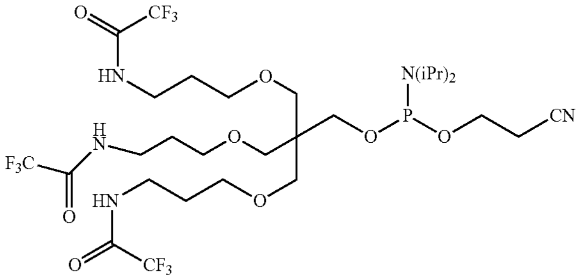

75a

Compound 75 is prepared according to published procedures reported by Shchepinov et al., Nucleic Acids Research, 1997, 25 (22), 4447-4454.

Example 35: Preparation of Compound 79
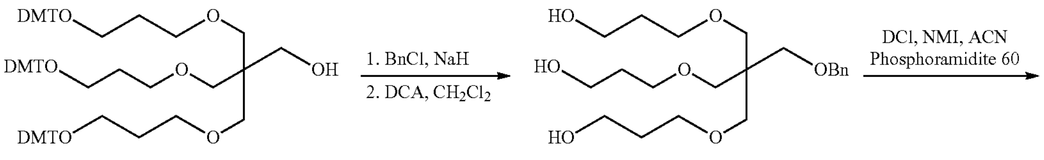
76 77
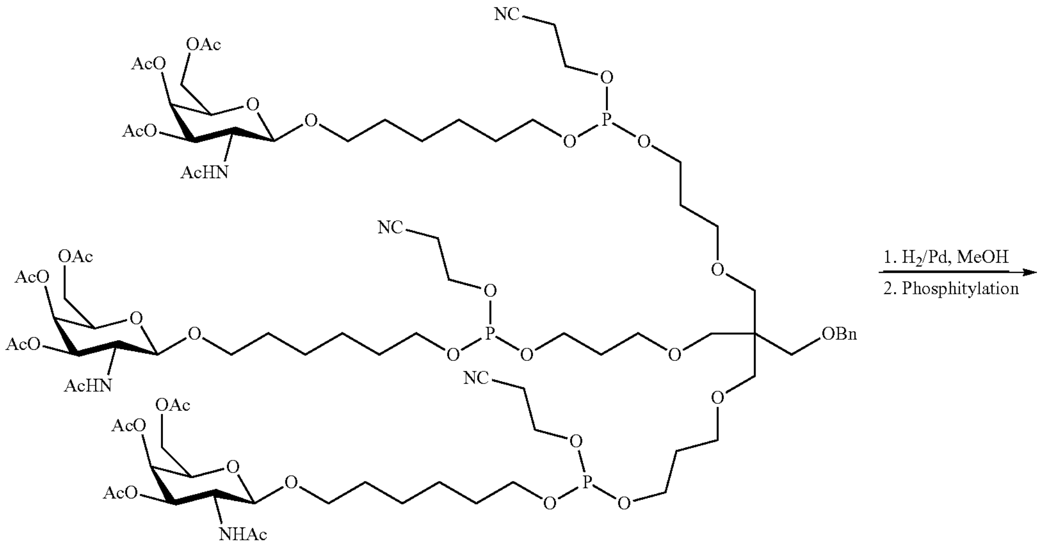
78
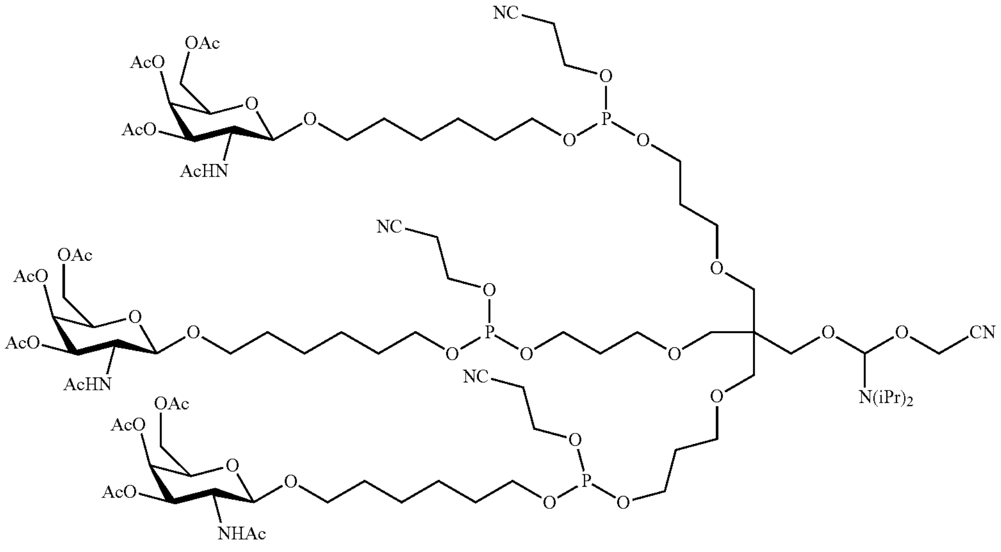
79
Compound 76 was prepared according to published procedures reported by Shchepinov et al., Nucleic Acids Research, 1997, 25 (22), 4447-4454.

Example 36: Preparation of Compound 79a
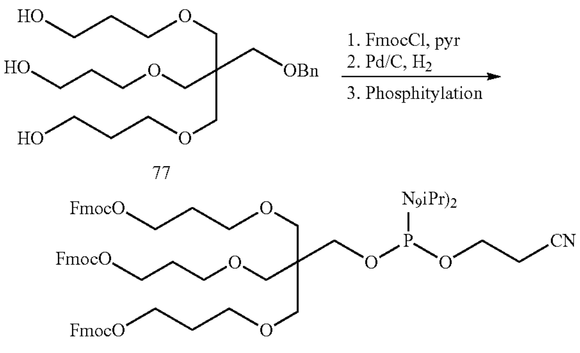
77
79a
Compound 77 is prepared as per the procedures illustrated in Example 35.
Example 37: General Method for the Preparation of Conjugated Oligomeric Compound 82 Comprising a Phosphodiester Linked GalNAc$_3$-2 Conjugate at 5' Terminus Via Solid Support (Method I)
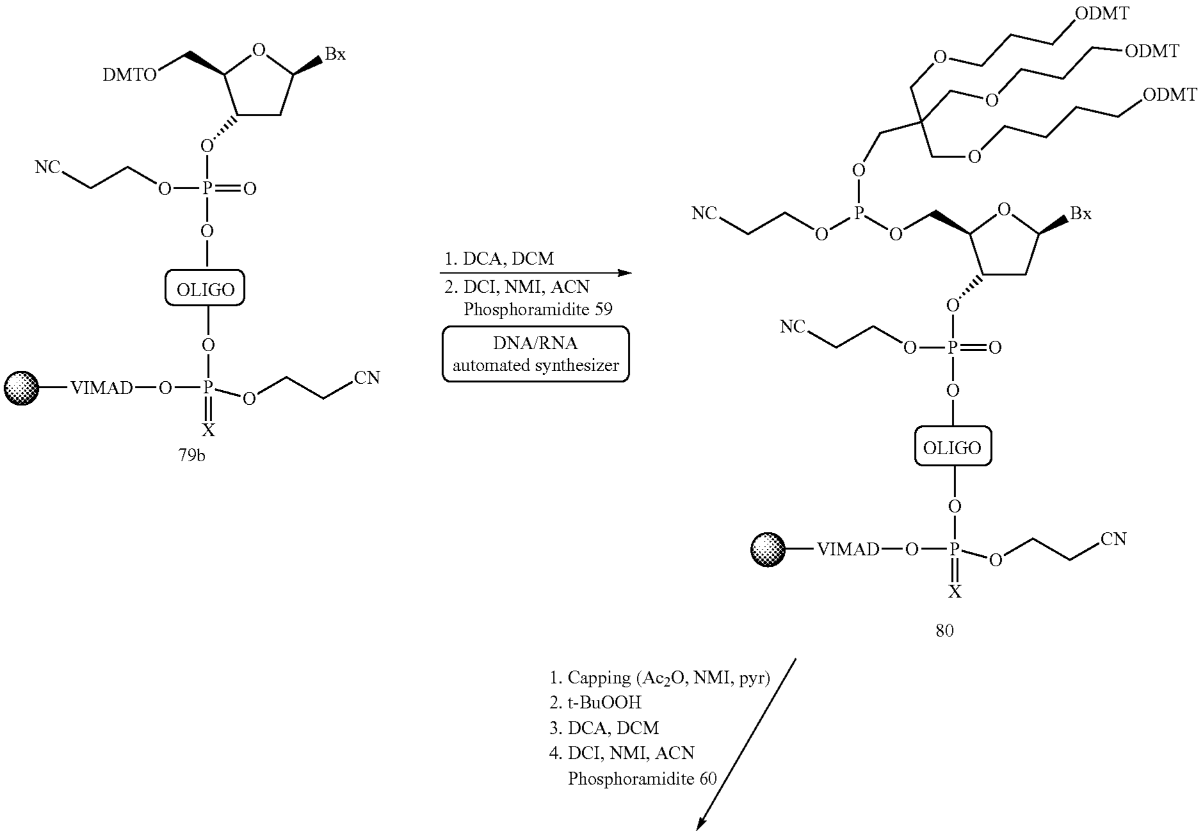
79b
80

-continued
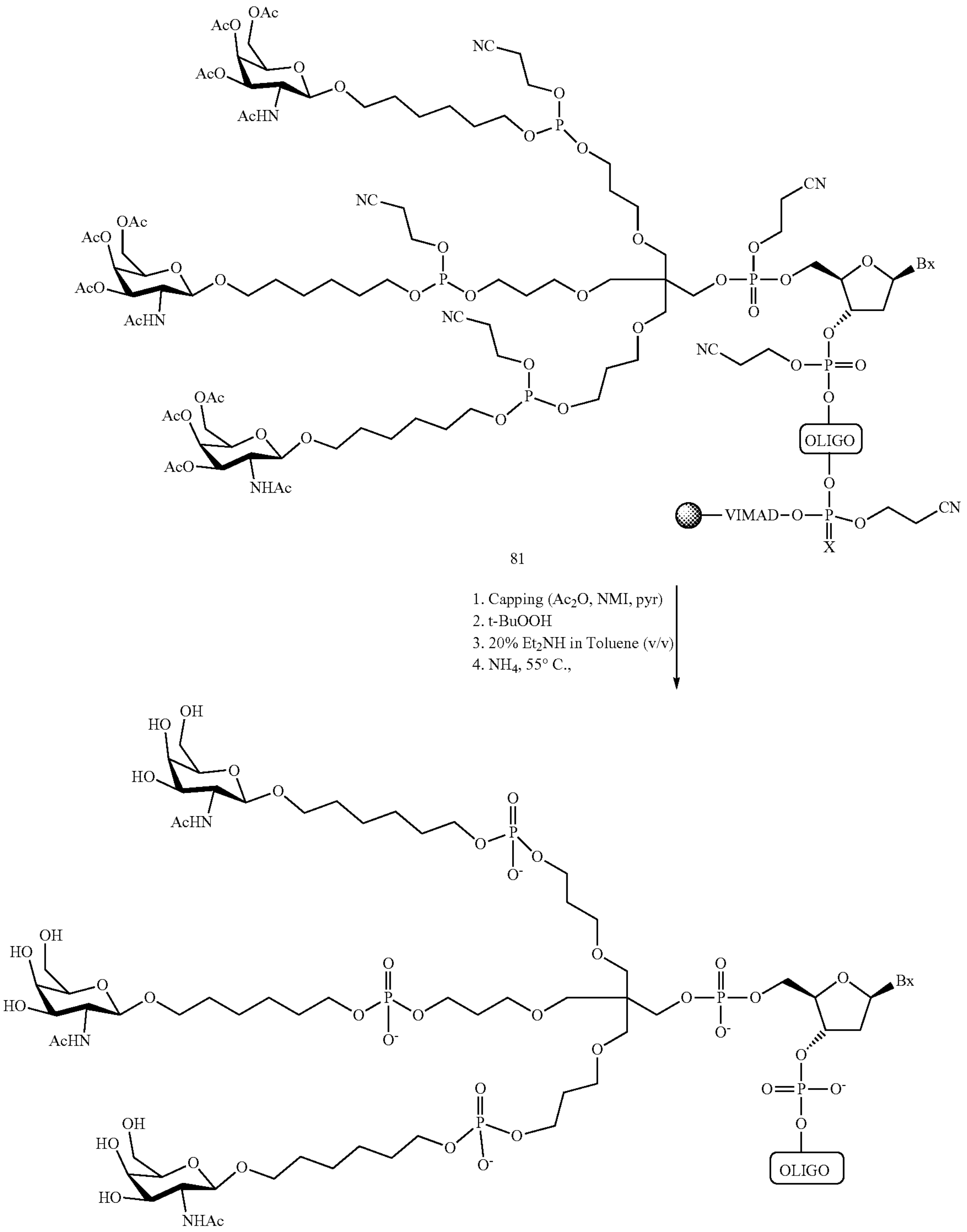
81
82
X = $S^-$ or $O^-$
Bx = Heterocylic base wherein $GalNAc_3$-2 has the structure:

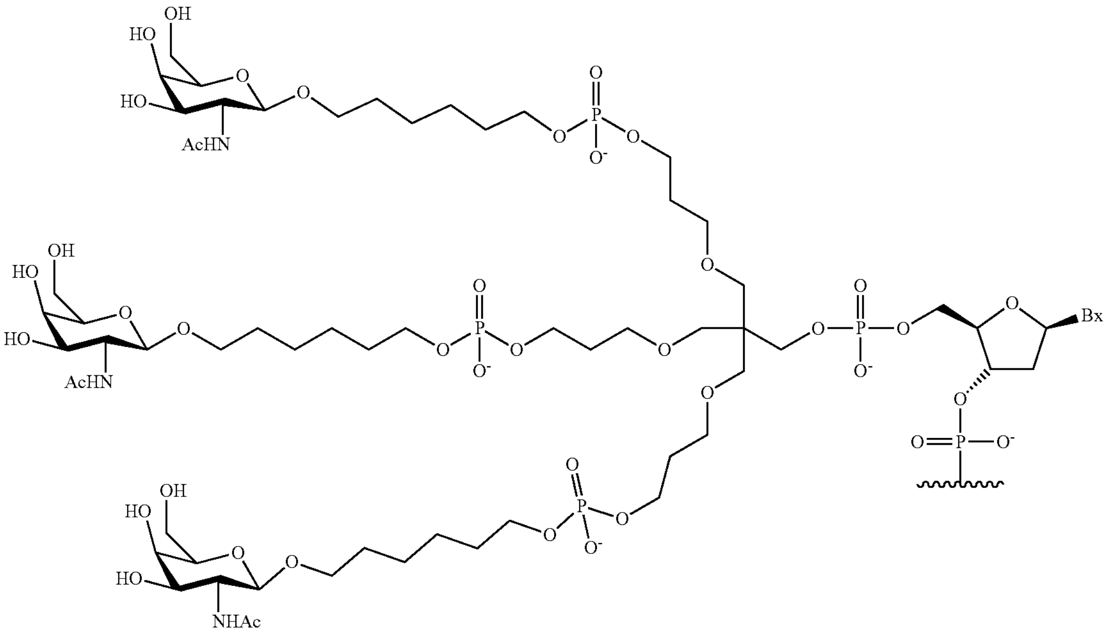

The $GalNAc_3$ cluster portion of the conjugate group $GalNAc_3$-2 ($GalNAc_3$-2a) can be combined with any cleavable moiety to provide a variety of conjugate groups. Wherein $GalNAc_3$-2a has the formula:

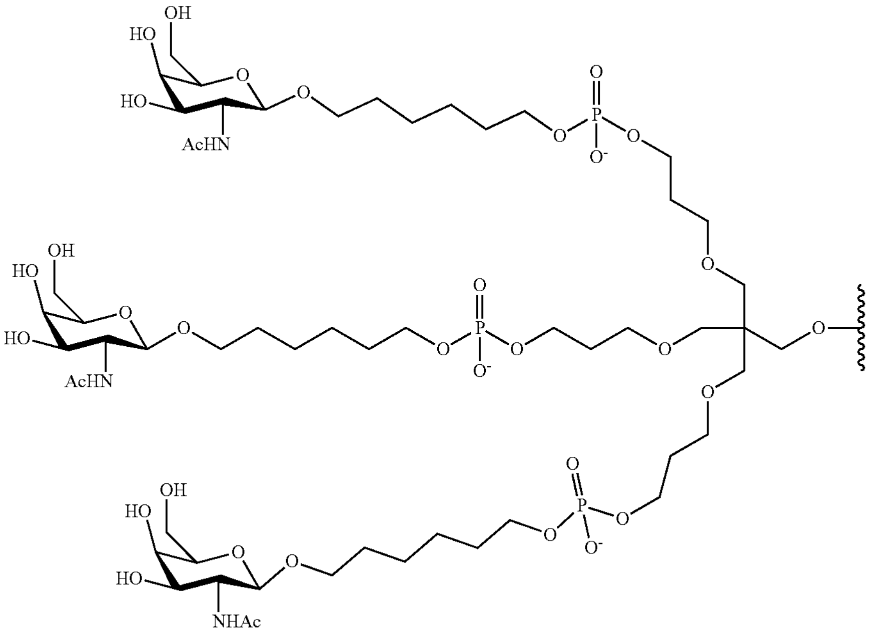

The VIMAD-bound oligomeric compound 79b was prepared using standard procedures for automated DNA/RNA synthesis (see Dupouy et al., *Angew. Chem. Int. Ed.*, 2006, 45, 3623-3627). The phosphoramidite Compounds 56 and 60 were prepared as per the procedures illustrated in Examples 27 and 28, respectively. The phosphoramidites illustrated are meant to be representative and not intended to be limiting as other phosphoramidite building blocks including but not limited those presented in the specification herein can be used to prepare an oligomeric compound having a phosphodiester linked conjugate group at the 5' terminus. The order and quantity of phosphoramidites added to the solid support can be adjusted to prepare the oligomeric compounds as described herein having any predetermined sequence and composition.

Example 38: Alternative Method for the Preparation of Oligomeric Compound 82 Comprising a Phosphodiester Linked GalNAc$_3$-2 Conjugate at 5' Terminus (Method II)

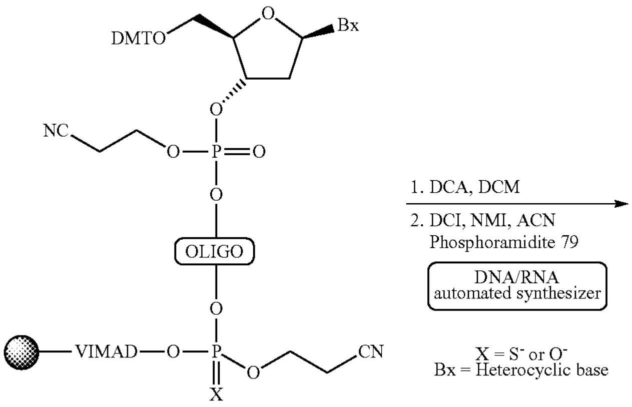

79b

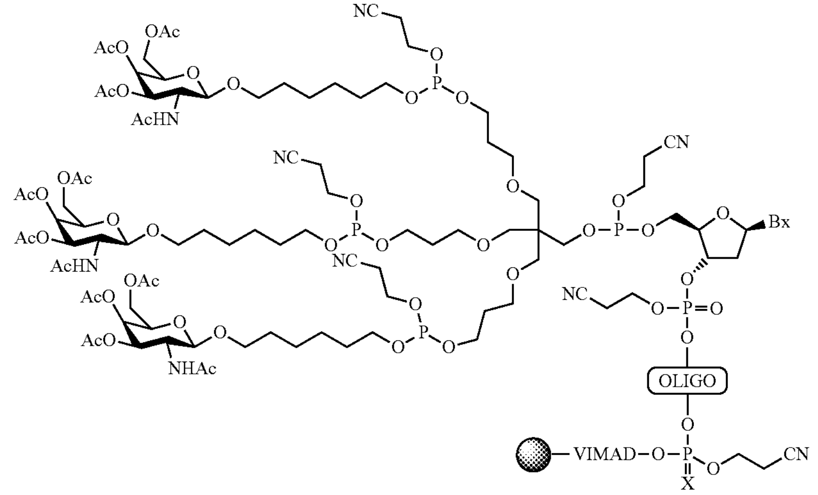

83

1. Capping
2. t-BuOOH
3. Et3N:CH3CN (1:1 v/v)
4. NH4, 55° C.

Oligomeric Compound 82

The VIMAD-bound oligomeric compound 79b was prepared using standard procedures for automated DNA/RNA synthesis (see Dupouy et al., *Angew. Chem. Int. Ed.,* 2006, 45, 3623-3627). The GalNAc$_3$-2 cluster phosphoramidite, Compound 79 was prepared as per the procedures illustrated in Example 35. This alternative method allows a one-step installation of the phosphodiester linked GalNAc$_3$-2 conjugate to the oligomeric compound at the final step of the synthesis. The phosphoramidites illustrated are meant to be representative and not intended to be limiting, as other phosphoramidite building blocks including but not limited to those presented in the specification herein can be used to prepare oligomeric compounds having a phosphodiester conjugate at the 5' terminus. The order and quantity of phosphoramidites added to the solid support can be adjusted to prepare the oligomeric compounds as described herein having any predetermined sequence and composition.

Example 39: General Method for the Preparation of Oligomeric Compound 83h Comprising a $GalNAc_3$-3 Conjugate at the 5' Terminus ($GalNAc_3$-1 Modified for 5' End Attachment) Via Solid Support
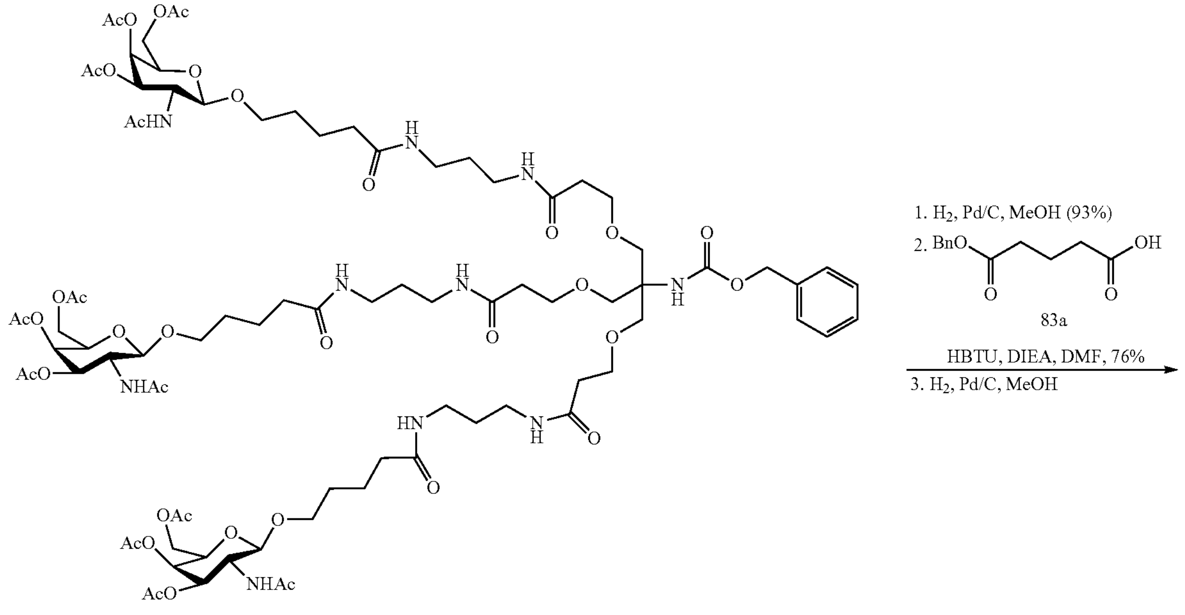
18
83b
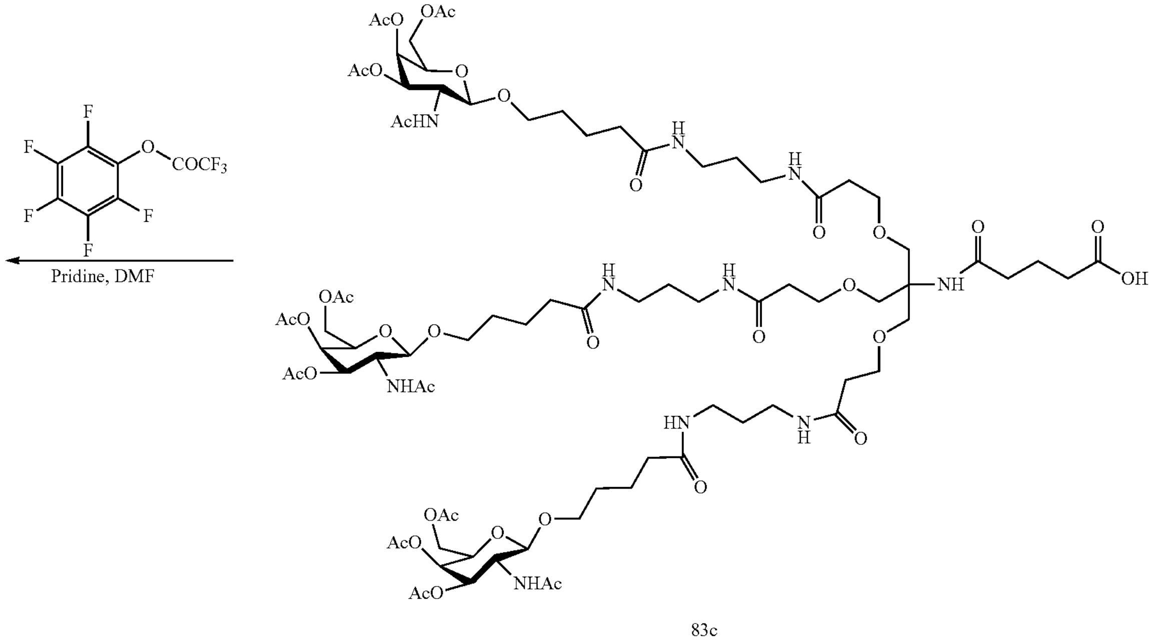
83c -continued
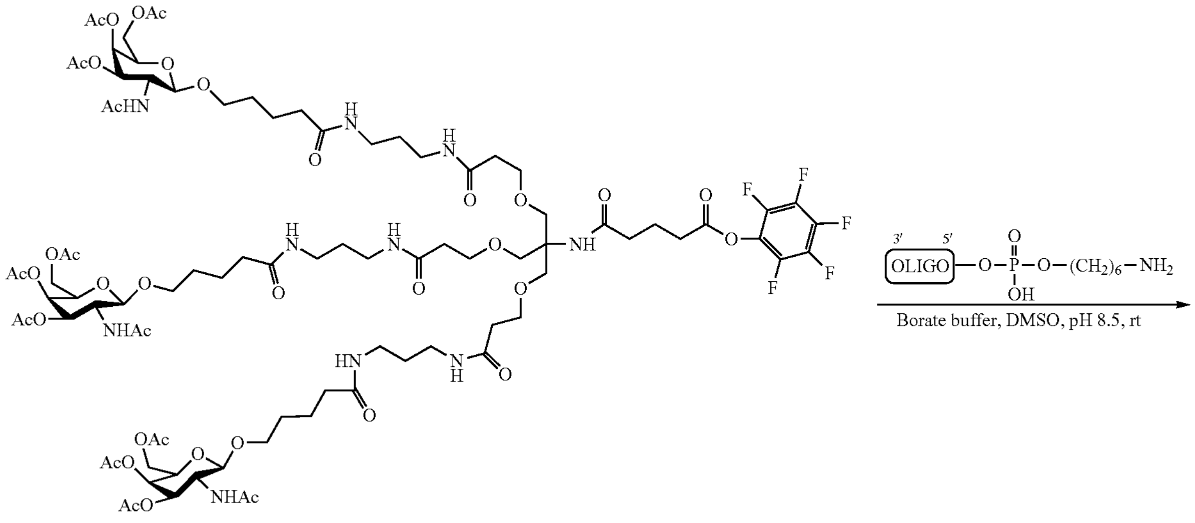
83d
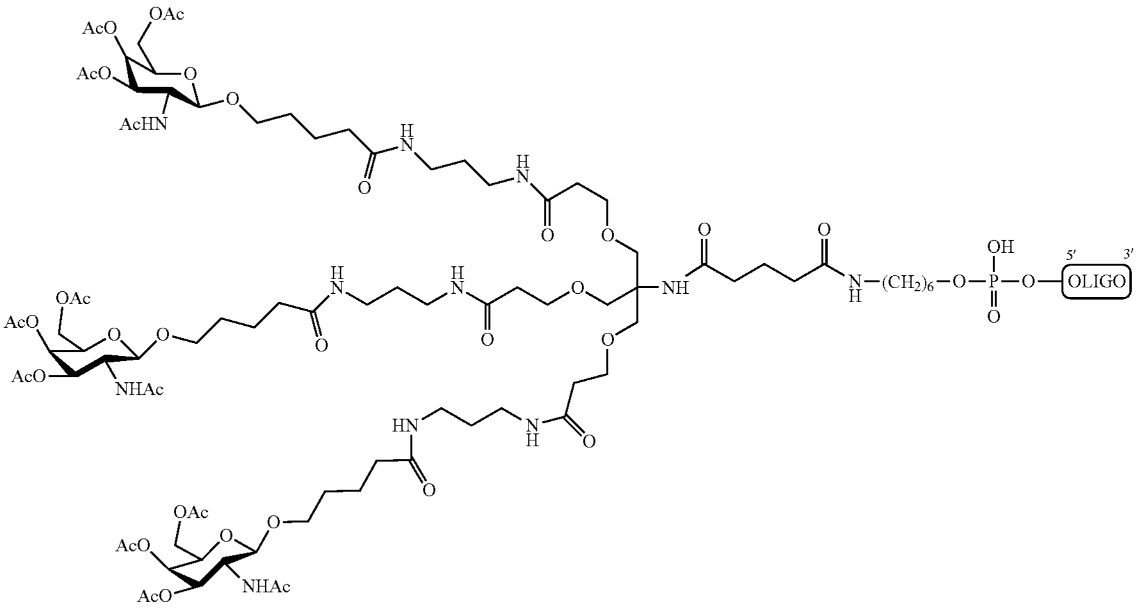
83f

-continued

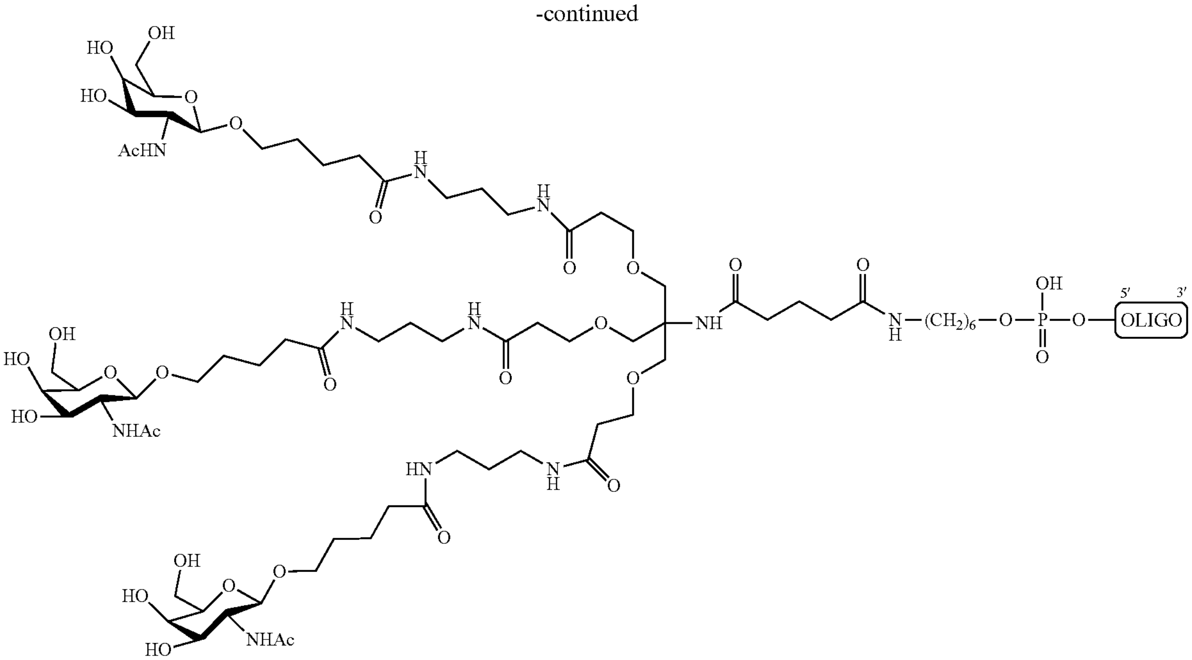

83h

Compound 18 was prepared as per the procedures illustrated in Example 4. Compounds 83a and 83b are commercially available. Oligomeric Compound 83e comprising a phosphodiester linked hexylamine was prepared using standard oligonucleotide synthesis procedures. Treatment of the protected oligomeric compound with aqueous ammonia provided the 5'-GalNAc$_3$-3 conjugated oligomeric compound (83h).

Wherein GalNAc$_3$-3 has the structure:

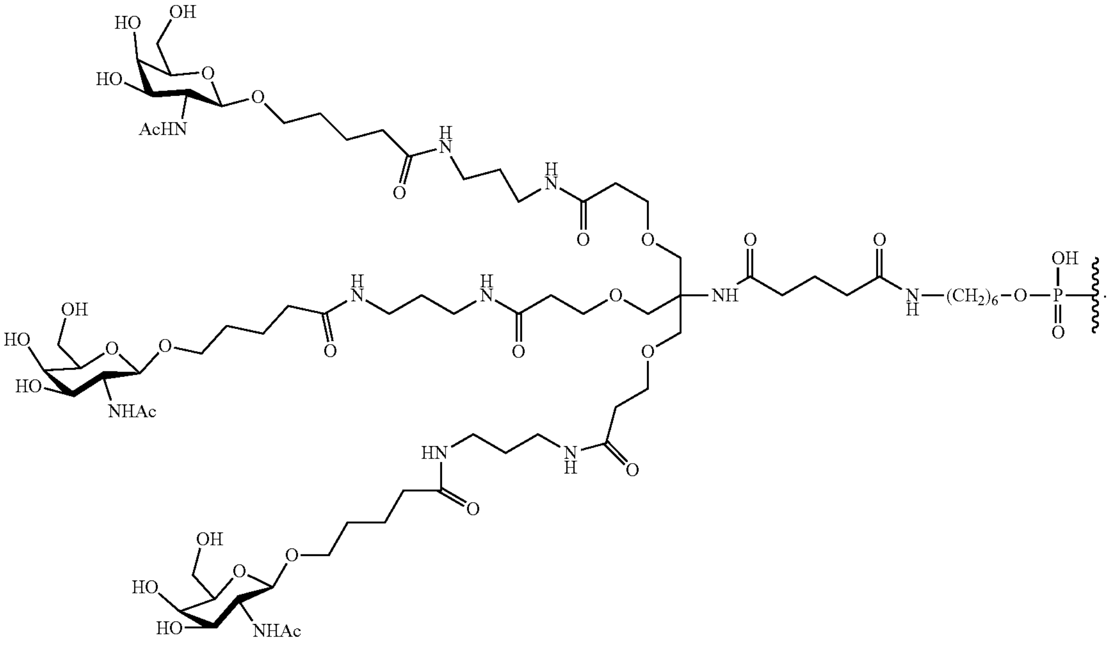

The GalNAc$_3$ cluster portion of the conjugate group GalNAc$_3$-3 (GalNAc$_3$-3a) can be combined with any cleavable moiety to provide a variety of conjugate groups. Wherein GalNAc$_3$-3a has the formula:

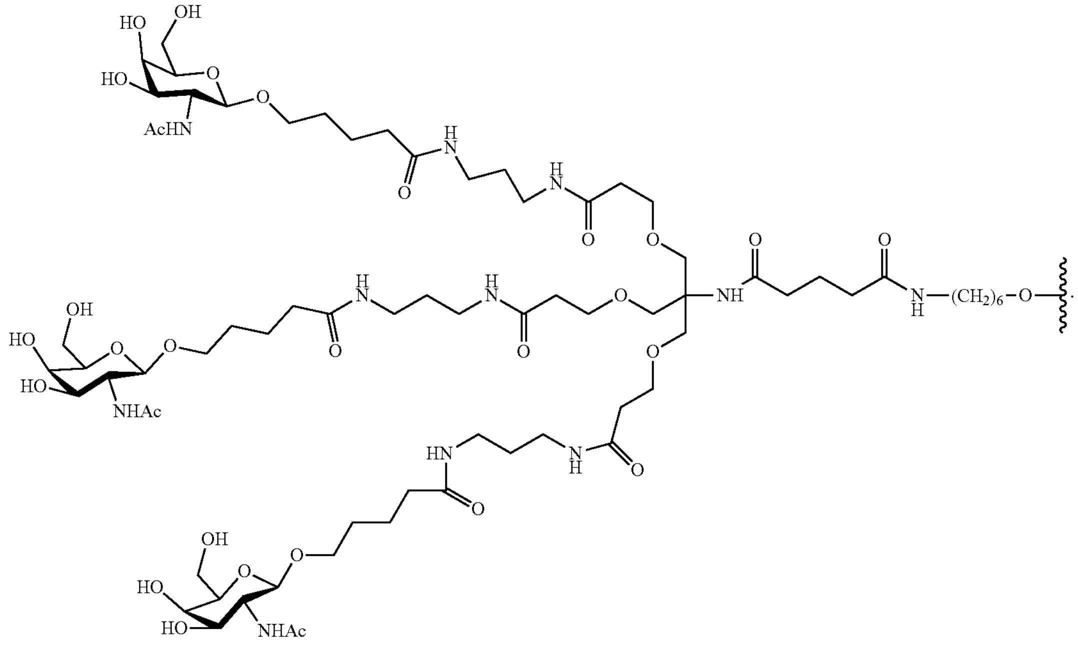
Example 40: General Method for the Preparation of Oligomeric Compound 89 Comprising a Phosphodiester Linked GalNAc$_3$-4 Conjugate at the 3' Terminus Via Solid Support
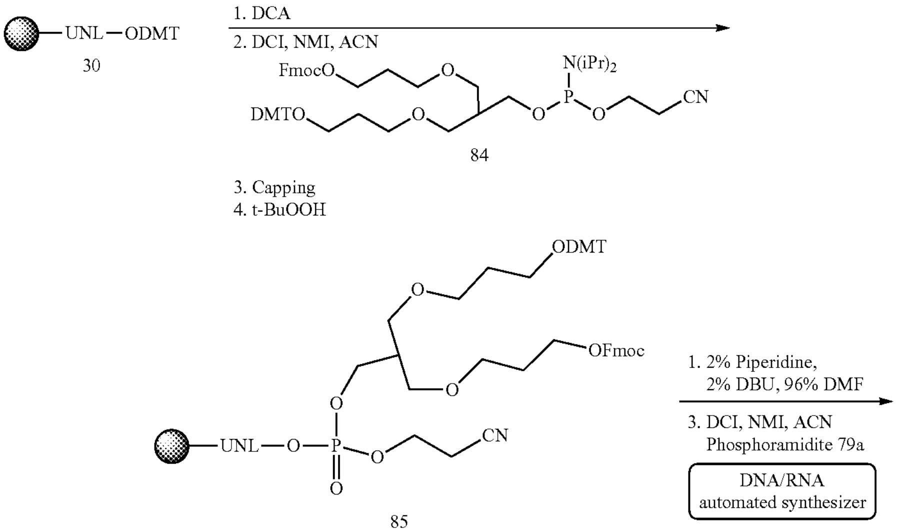
30
84
85

-continued
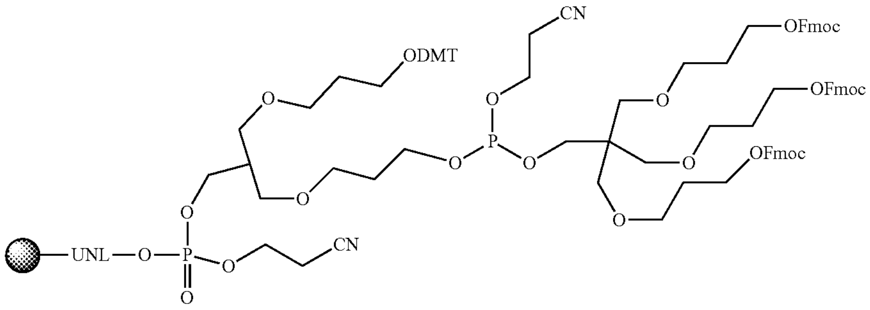
86
1. Capping
2. t-BuOOH
3. 2% Piperidine, 2% DBU, 96% DMF
4. DCI, NMI, ACN Phosphoramidite 60
DNA/RNA automated synthesizer
5. Capping
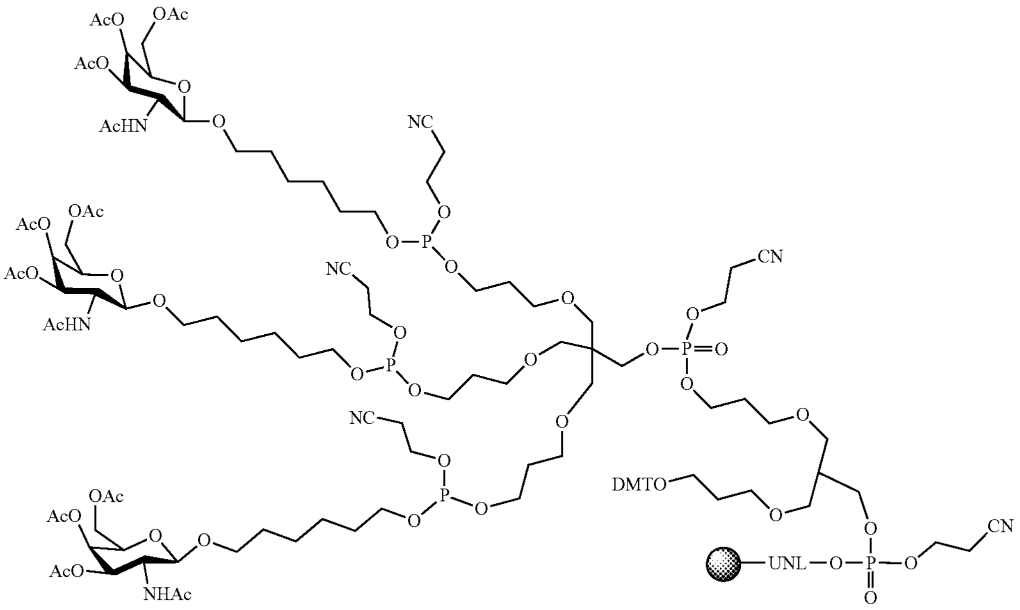
87
1. t-BuOOH
2. DCA
3. Oligo synthesis (DNA/RNA automated synthesizer)
4. Capping
5. Oxidation
6. $Et_3N$: $CH_3CN$ (1:1, v/v)

-continued
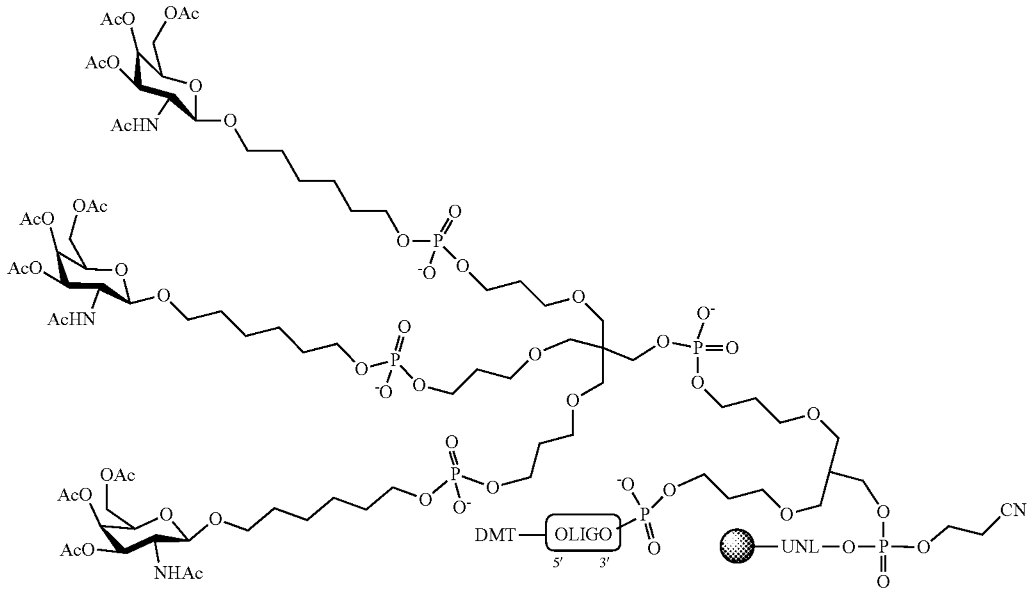
88
$NH_4$, 55° C.
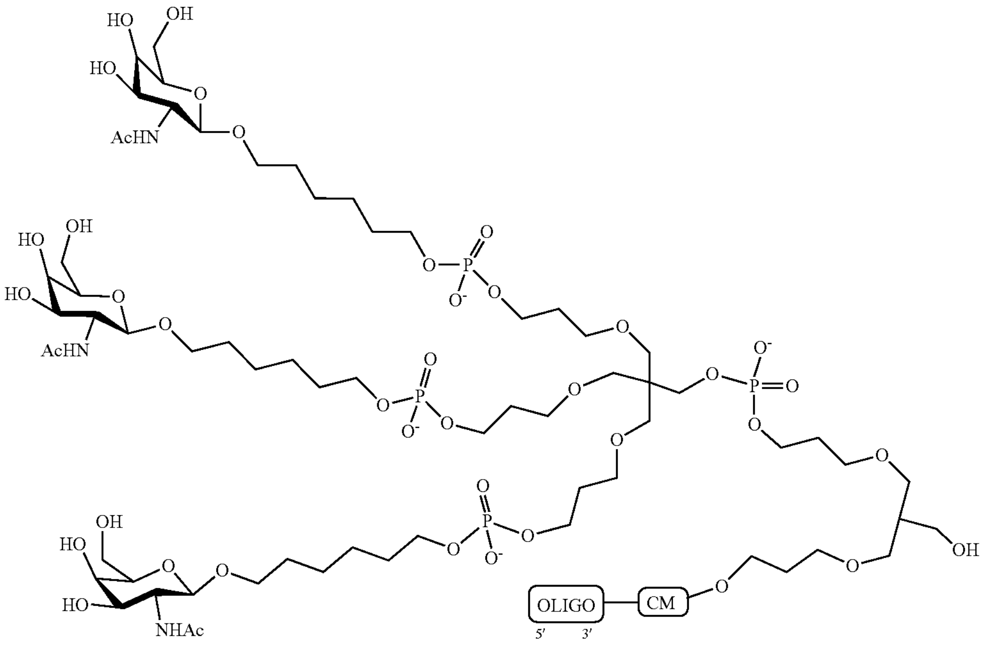
89

Wherein GalNAc$_3$-4 has the structure:
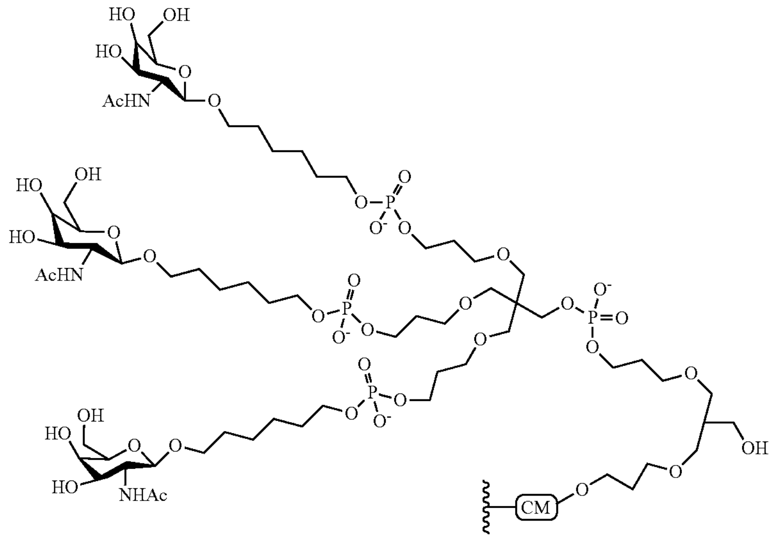
Wherein CM is a cleavable moiety. In certain embodiments, cleavable moiety is:
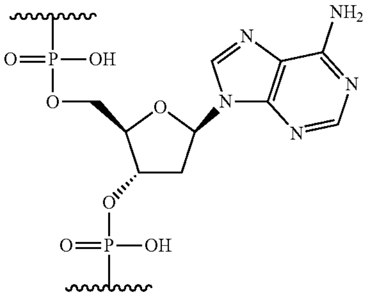 [SMILES: *P(=O)(O)OC[C@H]1O[C@@H](n2cnc3c(N)ncnc32)C[C@@H]1OP(*)(=O)O]
The GalNAc$_3$ cluster portion of the conjugate group GalNAc$_3$-4 (GalNAc$_3$-4a) can be combined with any cleavable moiety to provide a variety of conjugate groups. Wherein GalNAc$_3$-4a has the formula:
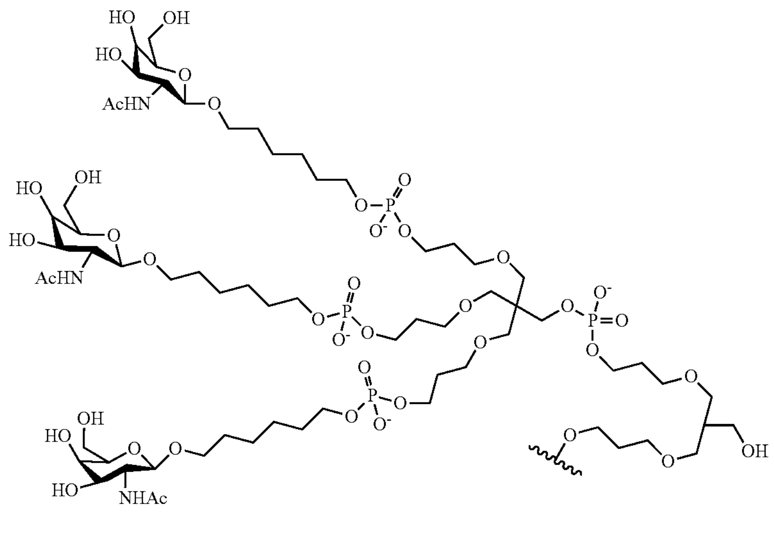

The protected Unylinker functionalized solid support Compound 30 is commercially available. Compound 84 is prepared using procedures similar to those reported in the literature (see Shchepinov et al., *Nucleic Acids Research,* 1997, 25 (22), 4447-4454; Shchepinov et al., *Nucleic Acids Research,* 1999, 27, 3035-3041; and Hornet et al., *Nucleic Acids Research,* 1997, 25, 4842-4849).

The phosphoramidite building blocks, Compounds 60 and 79a are prepared as per the procedures illustrated in Examples 28 and 36. The phosphoramidites illustrated are meant to be representative and not intended to be limiting as other phosphoramidite building blocks can be used to prepare an oligomeric compound having a phosphodiester linked conjugate at the 3' terminus with a predetermined sequence and composition. The order and quantity of phosphoramidites added to the solid support can be adjusted to prepare the oligomeric compounds as described herein having any predetermined sequence and composition.

Example 41: General Method for the Preparation of ASOs Comprising a Phosphodiester Linked GalNAc$_3$-2 (See Example 37, Bx is Adenine) Conjugate at the 5' Position Via Solid Phase Techniques (Preparation of ISIS 661134)

Unless otherwise stated, all reagents and solutions used for the synthesis of oligomeric compounds are purchased from commercial sources. Standard phosphoramidite building blocks and solid support are used for incorporation nucleoside residues which include for example T, A, G, and $^m$C residues. Phosphoramidite compounds 56 and 60 were used to synthesize the phosphodiester linked GalNAc$_3$-2 conjugate at the 5' terminus. A 0.1 M solution of phosphoramidite in anhydrous acetonitrile was used for β-D-2'-deoxyribonucleoside and 2'-MOE.

The ASO syntheses were performed on ABI 394 synthesizer (1-2 μmol scale) or on GE Healthcare Bioscience ÄKTA oligopilot synthesizer (40-200 μmol scale) by the phosphoramidite coupling method on VIMAD solid support (110 μmol/g, Guzaev et al., 2003) packed in the column. For the coupling step, the phosphoramidites were delivered at a 4 fold excess over the initial loading of the solid support and phosphoramidite coupling was carried out for 10 min. All other steps followed standard protocols supplied by the manufacturer. A solution of 6% dichloroacetic acid in toluene was used for removing the dimethoxytrityl (DMT) groups from 5'-hydroxyl groups of the nucleotide. 4,5-Dicyanoimidazole (0.7 M) in anhydrous $CH_3CN$ was used as activator during the coupling step. Phosphorothioate linkages were introduced by sulfurization with 0.1 M solution of xanthane hydride in 1:1 pyridine/$CH_3CN$ for a contact time of 3 minutes. A solution of 20% tert-butylhydroperoxide in $CH_3CN$ containing 6% water was used as an oxidizing agent to provide phosphodiester internucleoside linkages with a contact time of 12 minutes.

After the desired sequence was assembled, the cyanoethyl phosphate protecting groups were deprotected using a 20% diethylamine in toluene (v/v) with a contact time of 45 minutes. The solid-support bound ASOs were suspended in aqueous ammonia (28-30 wt %) and heated at 55° C. for 6 h. The unbound ASOs were then filtered and the ammonia was boiled off. The residue was purified by high pressure liquid chromatography on a strong anion exchange column (GE Healthcare Bioscience, Source 30Q, 30 μm, 2.54×8 cm, A=100 mM ammonium acetate in 30% aqueous $CH_3CN$, B=1.5 M NaBr in A, 0-40% of B in 60 min, flow 14 mL min-1, 2=260 nm). The residue was desalted by HPLC on a reverse phase column to yield the desired ASOs in an isolated yield of 15-30% based on the initial loading on the solid support. The ASOs were characterized by ion-pair-HPLC coupled MS analysis with Agilent 1100 MSD system.

TABLE 21

ASO comprising a phosphodiester linked GalNAc$_3$-2 conjugate at the 5' position targeting SRB-1

| ISIS No. | Sequence (5' to 3') | CalCd Mass | Observed Mass | SEQ ID No. |
|---|---|---|---|---|
| 661134 | **GalNAc$_3$-2$_a$-$_{o'}$A**$_{do}$T$_{ks}$$^m$C$_{ks}$A$_{ds}$G$_{ds}$T$_{ds}$$^m$C$_{ds}$A$_{ds}$T$_{ds}$ G$_{ds}$A$_{ds}$$^m$C$_{ds}$T$_{ds}$T$_{ks}$$^m$C$_k$ | 6482.2 | 6481.6 | 26 |

Subscripts: "e" indicates 2'-MOE modified nucleoside; "d" indicates β-D-2'-deoxyribonucleoside; "k" indicates 6'-(S)-$CH_3$ bicyclic nucleoside (e.g. cEt); "s" indicates phosphorothioate internucleoside linkages (PS); "o" indicates phosphodiester internucleoside linkages (PO); and "o'" indicates —O—P(═O)(OH)—.
Superscript "m" indicates 5-methylcytosines.

The structure of GalNAc$_3$-2$_a$ is shown in Example 37.

Example 42: General Method for the Preparation of ASOs Comprising a GalNAc$_3$-3 Conjugate at the 5' Position Via Solid Phase Techniques (Preparation of ISIS 661166)

The synthesis for ISIS 661166 was performed using similar procedures as illustrated in Examples 39 and 41.

ISIS 661166 is a 5-10-5 MOE gapmer, wherein the 5' position comprises a GalNAc$_3$-3 conjugate. The ASO was characterized by ion-pair-HPLC coupled MS analysis with Agilent 1100 MSD system.

TABLE 21a

| ASO comprising a GalNAc$_3$-3 conjugate at the 5' position via a hexylamino phosphodiester linkage targeting Malat-1 | | | | | |
|---|---|---|---|---|---|
| ISIS No. | Sequence (5' to 3') | Conjugate | Calcd Mass | Observed Mass | SEQ ID No. |
| 661166 | 5'-**GalNAc$_3$-3**$_{a-o'}$$^m$C$_{es}$G$_{es}$G$_{es}$T$_{es}$G$_{es}$ $^m$C$_{ds}$A$_{ds}$A$_{ds}$G$_{ds}$G$_{ds}$$^m$C$_{ds}$T$_{ds}$T$_{ds}$A$_{ds}$G$_{ds}$ G$_{es}$A$_{es}$A$_{es}$T$_{es}$T$_e$ | **5'-GalNAc$_3$-3** | 8992.16 | 8990.51 | 27 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(═O)(OH)—. Superscript "m" indicates 5-methylcytosines.

The structure of "5'-GalNAc$_3$-3a" is shown in Example 39.

Example 43: Dose-Dependent Study of Phosphodiester Linked GalNAc$_3$-2 (See Examples 37 and 41, Bx is Adenine) at the 5' Terminus Targeting SRB-1 In Vivo ISIS 661134 (see Example 41) comprising a phosphodiester linked GalNAc$_3$-2 conjugate at the 5' terminus was tested in a dose-dependent study for antisense inhibition of SRB-1 in mice. Unconjugated ISIS 440762 and 651900 (GalNAc$_3$-1 conjugate at 3' terminus, see Example 9) were included in the study for comparison and are described previously in Table 4.

Treatment

Six week old male Balb/c mice (Jackson Laboratory, Bar Harbor, ME) were injected subcutaneously once at the dosage shown below with ISIS 440762, 651900, 661134 or with PBS treated control. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The ED$_{50}$s were measured using similar methods as described previously and are presented below.

As illustrated in Table 22, treatment with antisense oligonucleotides lowered SRB-1 mRNA levels in a dose-dependent manner. Indeed, the antisense oligonucleotides comprising the phosphodiester linked GalNAc$_3$-2 conjugate at the 5' terminus (ISIS 661134) or the GalNAc$_3$-1 conjugate linked at the 3' terminus (ISIS 651900) showed substantial improvement in potency compared to the unconjugated antisense oligonucleotide (ISIS 440762). Further, ISIS 661134, which comprises the phosphodiester linked GalNAc$_3$-2 conjugate at the 5' terminus was equipotent compared to ISIS 651900, which comprises the GalNAc$_3$-1 conjugate at the 3' terminus.

TABLE 22

| ASOs containing GalNAc$_3$-1 or GalNAc$_3$-2 targeting SRB-1 | | | | | |
|---|---|---|---|---|---|
| ISIS No. | Dosage (mg/kg) | SRB-1 mRNA levels (% PBS) | ED$_{50}$ (mg/kg) | Conjugate | SEQ ID No. |
| PBS | 0 | 100 | — | — | |
| 440762 | 0.2 | 116 | 2.58 | No conjugate | 22 |
| | 0.7 | 91 | | | |
| | 2 | 69 | | | |
| | 7 | 22 | | | |
| | 20 | 5 | | | |
| 651900 | 0.07 | 95 | 0.26 | 3' GalNAc$_3$-1 | 23 |
| | 0.2 | 77 | | | |
| | 0.7 | 28 | | | |
| | 2 | 11 | | | |
| | 7 | 8 | | | |
| 661134 | 0.07 | 107 | 0.25 | 5' GalNAc$_3$-2 | 26 |
| | 0.2 | 86 | | | |
| | 0.7 | 28 | | | |
| | 2 | 10 | | | |
| | 7 | 6 | | | |

Structures for 3' GalNAc$_3$-1 and 5' GalNAc$_3$-2 were described previously in Examples 9 and 37.

Pharmacokinetics Analysis (PK)

The PK of the ASOs from the high dose group (7 mg/kg) was examined and evaluated in the same manner as illustrated in Example 20. Liver sample was minced and extracted using standard protocols. The full length metabolites of 661134 (5' GalNAc$_3$-2) and ISIS 651900 (3' GalNAc$_3$-1) were identified and their masses were confirmed by high resolution mass spectrometry analysis. The results showed that the major metabolite detected for the ASO comprising a phosphodiester linked GalNAc$_3$-2 conjugate at the 5' terminus (ISIS 661134) was ISIS 440762 (data not shown). No additional metabolites, at a detectable level, were observed. Unlike its counterpart, additional metabolites similar to those reported previously in Table 10a were observed for the ASO having the GalNAc$_3$-1 conjugate at the 3' terminus (ISIS 651900). These results suggest that having the phosphodiester linked GalNAc$_3$-1 or GalNAc$_3$-2 conjugate may improve the PK profile of ASOs without compromising their potency.

Example 44: Effect of PO/PS Linkages on Antisense Inhibition of ASOs Comprising GalNAc$_3$-1 Conjugate (See Example 9) at the 3' Terminus Targeting SRB-1

ISIS 655861 and 655862 comprising a GalNAc$_3$-1 conjugate at the 3' terminus each targeting SRB-1 were tested in a single administration study for their ability to inhibit SRB-1 in mice. The parent unconjugated compound, ISIS 353382 was included in the study for comparison.

The ASOs are 5-10-5 MOE gapmers, wherein the gap region comprises ten 2'-deoxyribonucleosides and each wing region comprises five 2'-MOE modified nucleosides. The ASOs were prepared using similar methods as illustrated previously in Example 19 and are described Table 23, below.

TABLE 23

Modified ASOs comprising GalNAc3-1 conjugate at the 3' terminus targeting SRB-1

| ISIS No. | Sequence (5' to 3') | Chemistry | SEQ ID No. |
|---|---|---|---|
| 353382 (parent) | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | Full PS no conjugate | 28 |
| 655861 | $G_{es}{}^{m}C_{es}T_{es}T_{es}{}^{m}C_{es}A_{ds}G_{ds}T_{ds}{}^{m}C_{ds}A_{ds}T_{as}G_{ds}A_{ds}{}^{m}C_{ds}T_{ds}T_{es}{}^{m}C_{es}{}^{m}C_{es}T_{es}T_{eo}\mathbf{A}_{do'}$**-GalNAc$_3$-1**$_a$ | Full PS with **GalNAc$_3$-1** conjugate | 29 |
| 655862 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo}\mathbf{A}_{do'}$**-GalNAc$_3$-1**$_a$ | Mixed PS/PO with **GalNAc$_3$-1** conjugate | 29 |

Subscripts: "e" indicates 2'-MOE modified nucleoside; "d" indicates β-D-2'-deoxyribonucleoside; "s" indicates phosphorothioate internucleoside linkages (PS); "o" indicates phosphodiester internucleoside linkages (PO); and "o'" indicates —O—P(═O)(OH)—. Superscript "m" indicates 5-methylcytosines.

The structure of "GalNAc$_3$-1" is shown in Example 9.

Treatment

Six week old male Balb/c mice (Jackson Laboratory, Bar Harbor, ME) were injected subcutaneously once at the dosage shown below with ISIS 353382, 655861, 655862 or with PBS treated control. Each treatment group consisted of 4 animals. Prior to the treatment as well as after the last dose, blood was drawn from each mouse and plasma samples were analyzed. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. SRB-1 mRNA levels were determined relative to total RNA (using Ribogreen), prior to normalization to PBS-treated control. The results below are presented as the average percent of SRB-1 mRNA levels for each treatment group, normalized to PBS-treated control and is denoted as "% PBS". The ED50s were measured using similar methods as described previously and are reported below.

As illustrated in Table 24, treatment with antisense oligonucleotides lowered SRB-1 mRNA levels in a dose-dependent manner compared to PBS treated control. Indeed, the antisense oligonucleotides comprising the GalNAc$_3$-1 conjugate at the 3' terminus (ISIS 655861 and 655862) showed substantial improvement in potency comparing to the unconjugated antisense oligonucleotide (ISIS 353382). Further, ISIS 655862 with mixed PS/PO linkages showed an improvement in potency relative to full PS (ISIS 655861).

TABLE 24

Effect of PO/PS linkages on antisense inhibition of ASOs comprising GalNAc$_3$-1 conjugate at 3' terminus targeting SRB-1

| ISIS No. | Dosage (mg/kg) | SRB-1 mRNA levels (% PBS) | $ED_{50}$ (mg/kg) | Chemistry | SEQ ID No. |
|---|---|---|---|---|---|
| PBS | 0 | 100 | — | — | |
| 353382 | 3 | 76.65 | 10.4 | Full PS | 28 |
| (parent) | 10 | 52.40 | | without | |
| | 30 | 24.95 | | conjugate | |
| 655861 | 0.5 | 81.22 | 2.2 | Full PS with | 29 |
| | 1.5 | 63.51 | | GalNAc$_3$-1 | |
| | 5 | 24.61 | | conjugate | |
| | 15 | 14.80 | | | |
| 655862 | 0.5 | 69.57 | 1.3 | Mixed PS/PO | 29 |
| | 1.5 | 45.78 | | with | |
| | 5 | 19.70 | | GalNAc$_3$-1 | |
| | 15 | 12.90 | | conjugate | |

Liver transaminase levels, alanine aminotransferase (ALT) and aspartate aminotransferase (AST), in serum were measured relative to saline injected mice using standard protocols. Organ weights were also evaluated. The results demonstrated that no elevation in transaminase levels (Table 25) or organ weights (data not shown) were observed in mice treated with ASOs compared to PBS control. Further, the ASO with mixed PS/PO linkages (ISIS 655862) showed similar transaminase levels compared to full PS (ISIS 655861).

TABLE 25

Effect of PO/PS linkages on transaminase levels of ASOs comprising GalNAc$_3$-1 conjugate at 3' terminus targeting SRB-1

| ISIS No. | Dosage (mg/kg) | ALT (U/L) | AST (U/L) | Chemistry | SEQ ID No. |
|---|---|---|---|---|---|
| PBS | 0 | 28.5 | 65 | — | |
| 353382 | 3 | 50.25 | 89 | Full PS | 28 |
| (parent) | 10 | 27.5 | 79.3 | without | |
| | 30 | 27.3 | 97 | conjugate | |
| 655861 | 0.5 | 28 | 55.7 | Full PS with | 29 |
| | 1.5 | 30 | 78 | GalNAc$_3$-1 | |
| | 5 | 29 | 63.5 | | |
| | 15 | 28.8 | 67.8 | | |
| 655862 | 0.5 | 50 | 75.5 | Mixed PS/PO | 29 |
| | 1.5 | 21.7 | 58.5 | with | |
| | 5 | 29.3 | 69 | GalNAc$_3$-1 | |
| | 15 | 22 | 61 | | |

Example 45: Preparation of PFP Ester, Compound 110a
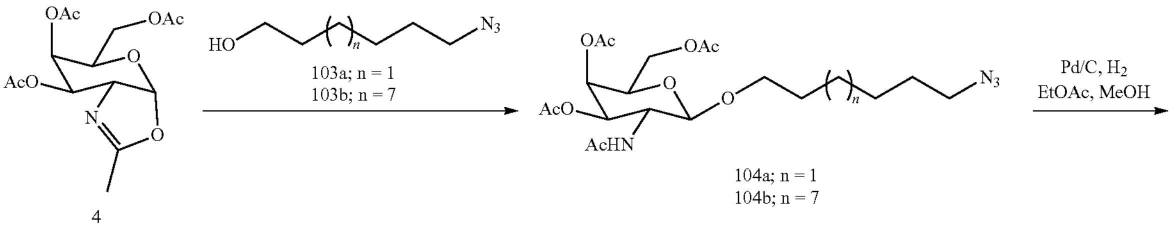
4
104a; n = 1
104b; n = 7
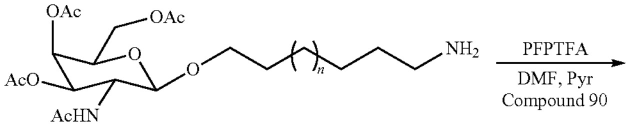
105a; n = 1
105b; n = 7
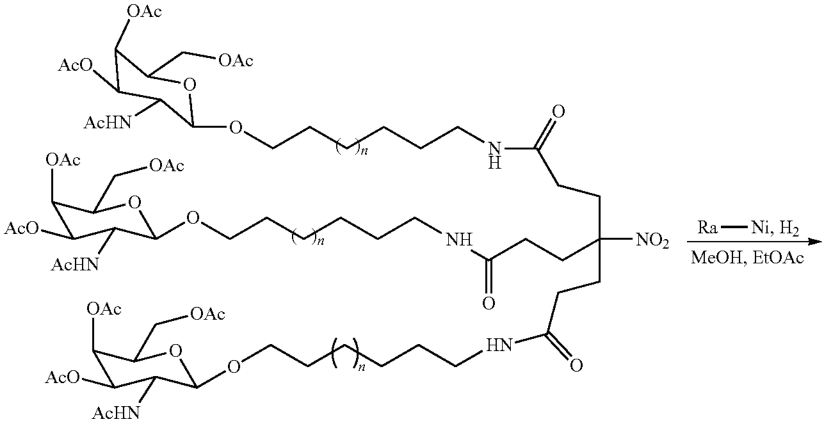
106a; n = 1
106b; n = 7
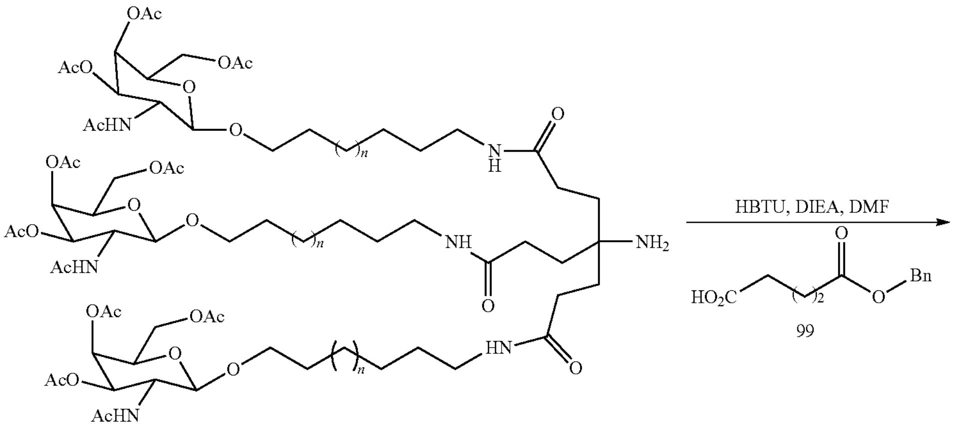
107a; n = 1
107b; n = 7

-continued
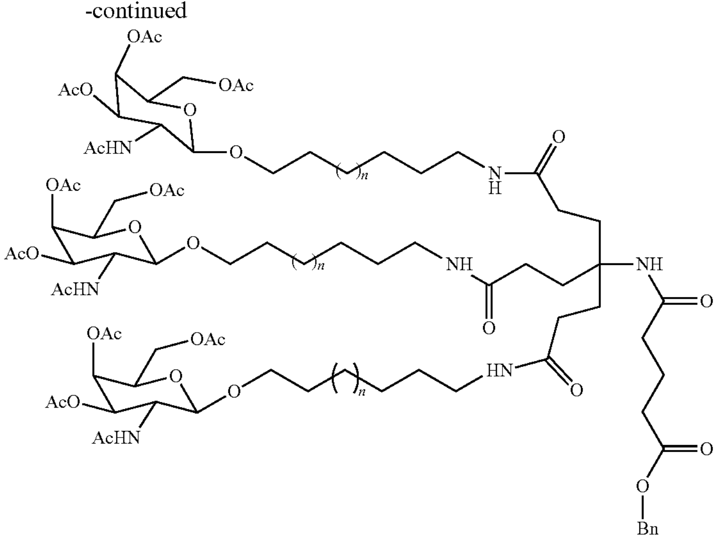
108a; n = 1
108b; n = 7
108a; n = 1
108b; n = 7
Pd/C, $H_2$,
EtOAc, MeOH
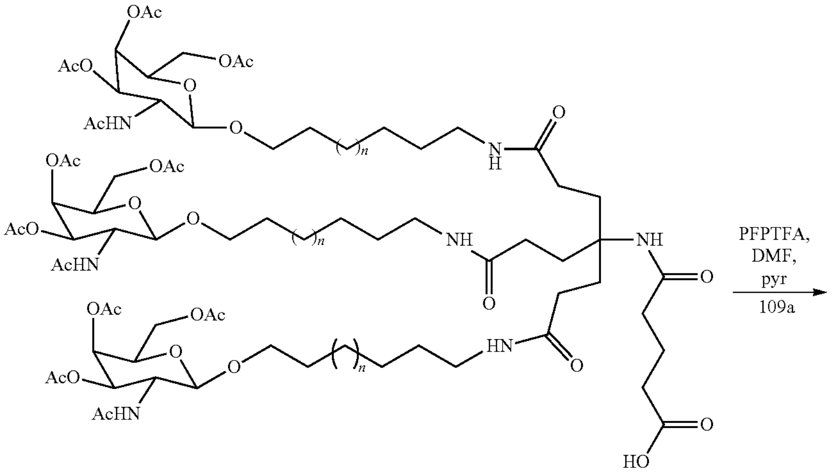
109a; n = 1
109b; n = 7

-continued

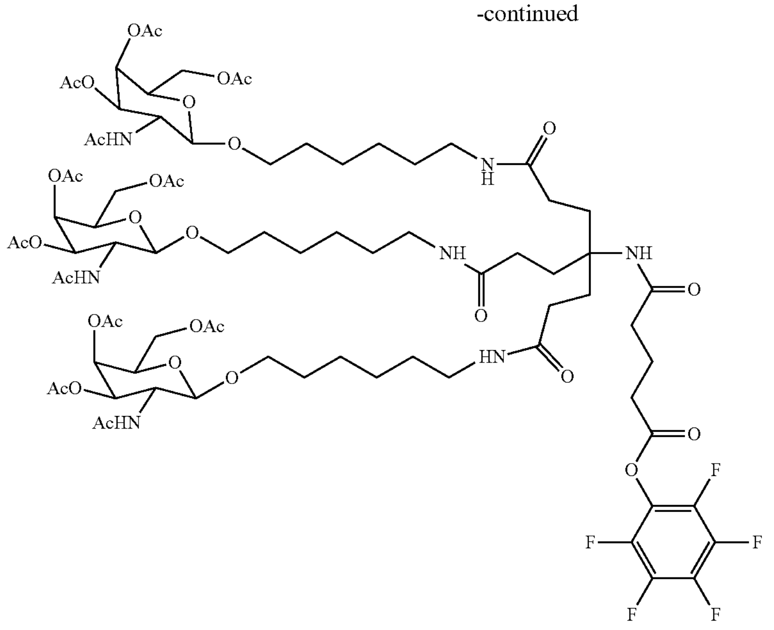

110a

Compound 4 (9.5 g, 28.8 mmoles) was treated with compound 103a or 103b (38 mmoles), individually, and TMSOTf (0.5 eq.) and molecular sieves in dichloromethane (200 mL), and stirred for 16 hours at room temperature. At that time, the organic layer was filtered thru celite, then washed with sodium bicarbonate, water and brine. The organic layer was then separated and dried over sodium sulfate, filtered and reduced under reduced pressure. The resultant oil was purified by silica gel chromatography (2%-->10% methanol/dichloromethane) to give compounds 104a and 104b in >80% yield. LCMS and proton NMR was consistent with the structure.

Compounds 104a and 104b were treated to the same conditions as for compounds 100a-d (Example 47), to give compounds 105a and 105b in >90% yield. LCMS and proton NMR was consistent with the structure.

Compounds 105a and 105b were treated, individually, with compound 90 under the same conditions as for compounds 901a-d, to give compounds 106a (80%) and 106b (20%). LCMS and proton NMR was consistent with the structure.

Compounds 106a and 106b were treated to the same conditions as for compounds 96a-d (Example 47), to give 107a (60%) and 107b (20%). LCMS and proton NMR was consistent with the structure.

Compounds 107a and 107b were treated to the same conditions as for compounds 97a-d (Example 47), to give compounds 108a and 108b in 40-60% yield. LCMS and proton NMR was consistent with the structure.

Compounds 108a (60%) and 108b (40%) were treated to the same conditions as for compounds 100α-d (Example 47), to give compounds 109a and 109b in >80% yields. LCMS and proton NMR was consistent with the structure.

Compound 109a was treated to the same conditions as for compounds 101a-d (Example 47), to give Compound 110a in 30-60% yield. LCMS and proton NMR was consistent with the structure. Alternatively, Compound 110b can be prepared in a similar manner starting with Compound 109b.

Example 46: General Procedure for Conjugation with PFP Esters (Oligonucleotide 111); Preparation of ISIS 666881 ($GalNAc_3$-10)

A 5'-hexylamino modified oligonucleotide was synthesized and purified using standard solid-phase oligonucleotide procedures. The 5'-hexylamino modified oligonucleotide was dissolved in 0.1 M sodium tetraborate, pH 8.5 (200 μL) and 3 equivalents of a selected PFP esterified $GalNAc_3$ cluster dissolved in DMSO (50 μL) was added. If the PFP ester precipitated upon addition to the ASO solution DMSO was added until all PFP ester was in solution. The reaction was complete after about 16 h of mixing at room temperature. The resulting solution was diluted with water to 12 mL and then spun down at 3000 rpm in a spin filter with a mass cut off of 3000 Da. This process was repeated twice to remove small molecule impurities. The solution was then lyophilized to dryness and redissolved in concentrated aqueous ammonia and mixed at room temperature for 2.5 h followed by concentration in vacuo to remove most of the ammonia. The conjugated oligonucleotide was purified and desalted by RP-HPLC and lyophilized to provide the $GalNAc_3$ conjugated oligonucleotide.

83e

110a

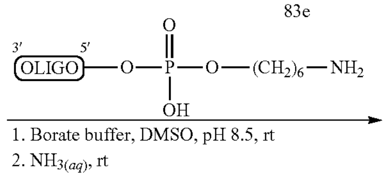

-continued

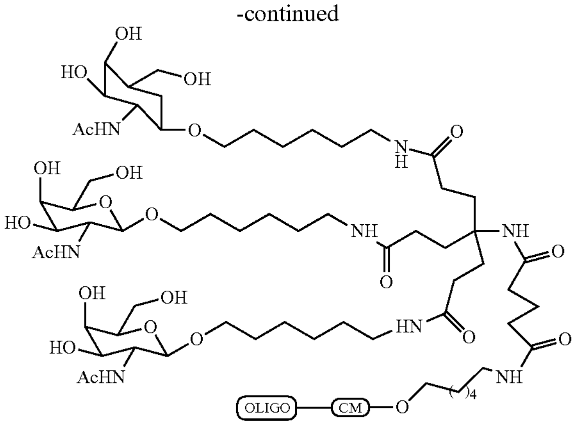

111

Oligonucleotide 111 is conjugated with $GalNAc_3$-10. The $GalNAc_3$ cluster portion of the conjugate group $GalNAc_3$-10 ($GalNAc_3$-10a) can be combined with any cleavable moiety to provide a variety of conjugate groups. In certain embodiments, the cleavable moiety is —P(═O)(OH)-Ad-P(═O)(OH)— as shown in the oligonucleotide (ISIS 666881) synthesized with $GalNAc_3$-10 below. The structure of $GalNAc_3$-10 ($GalNAc_3$-$10_a$-CM-) is shown below:

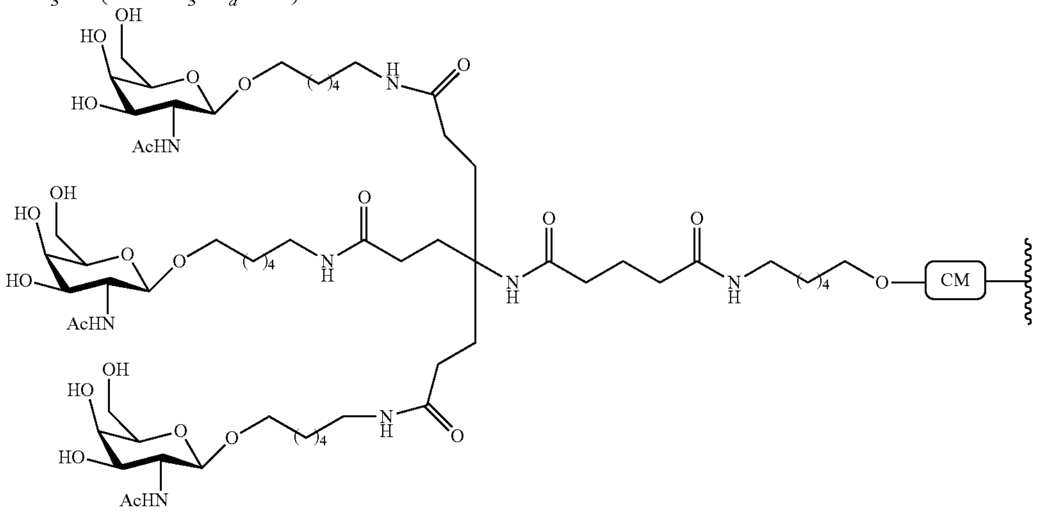

Following this general procedure ISIS 666881 was prepared. 5'-hexylamino modified oligonucleotide, ISIS 660254, was synthesized and purified using standard solid-phase oligonucleotide procedures. ISIS 660254 (40 mg, 5.2 umol) was dissolved in 0.1 M sodium tetraborate, pH 8.5 (200 μL) and 3 equivalents PFP ester (Compound 110a) dissolved in DMSO(50 μL) was added. The PFP ester precipitated upon addition to the ASO solution requiring additional DMSO(600 μL) to fully dissolve the PFP ester. The reaction was complete after 16 h of mixing at room temperature. The solution was diluted with water to 12 mL total volume and spun down at 3000 rpm in a spin filter with a mass cut off of 3000 Da. This process was repeated twice to remove small molecule impurities. The solution was lyophilized to dryness and redissolved in concentrated aqueous ammonia with mixing at room temperature for 2.5 h followed by concentration in vacuo to remove most of the ammonia. The conjugated oligonucleotide was purified and desalted by RP-HPLC and lyophilized to give ISIS 666881 in 90% yield by weight (42 mg, 4.7 umol).

| GalNAc3-10 conjugated oligonucleotide | | | |
|---|---|---|---|
| ASO | Sequence (5' to 3') | 5' group | SEQ ID No. |
| ISIS 660254 | $NH_2(CH_2)_6{-_o}A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | Hexylamine | 30 |
| ISIS 666881 | $\mathbf{GalNAc_3\text{-}10_a{-_{o'}}}A_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | **$GalNAc_3$-10** | 30 |

Capital letters indicate the nucleobase for each nucleoside and $^m$C indicates a 5-methyl cytosine.
Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—.
Conjugate groups are in bold.

Example 47: Preparation of Oligonucleotide 102 Comprising $GalNAc_3$-8

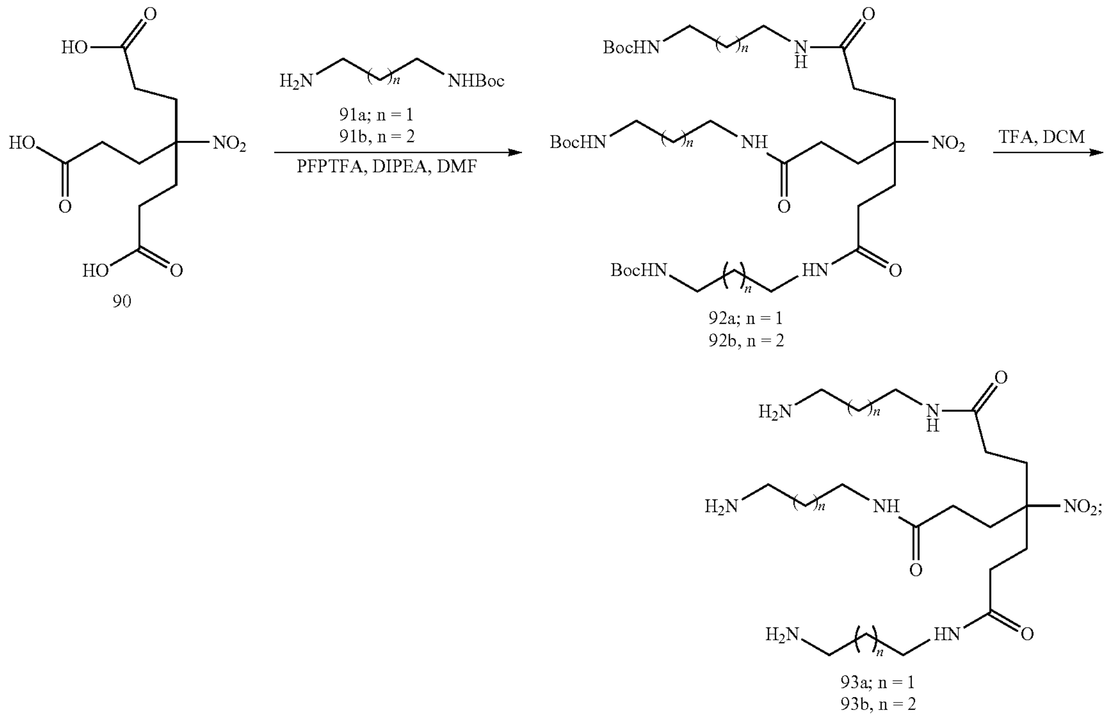

90

92a; n = 1
92b, n = 2

93a; n = 1
93b, n = 2

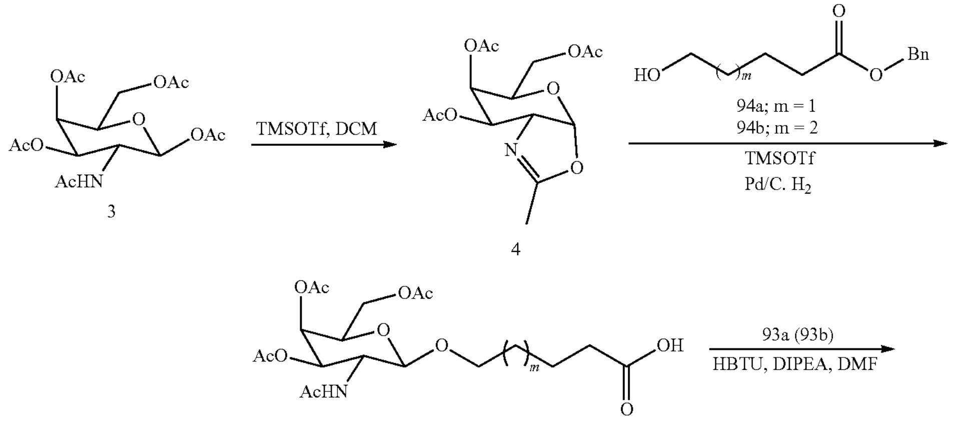

3

4

7; m = 1
64, m = 2

-continued
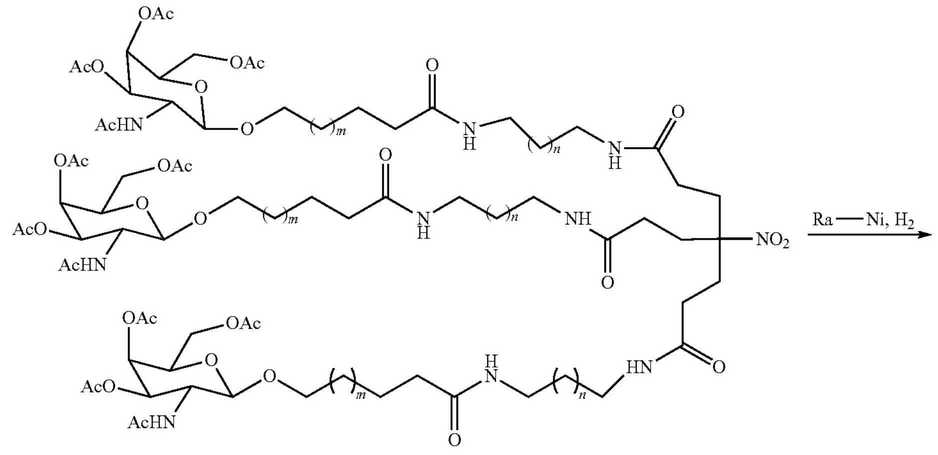
96a; n = 1, m = 1
96b; n = 1, m = 2
96c; n = 2, m = 1
96d: n = 2. m = 2
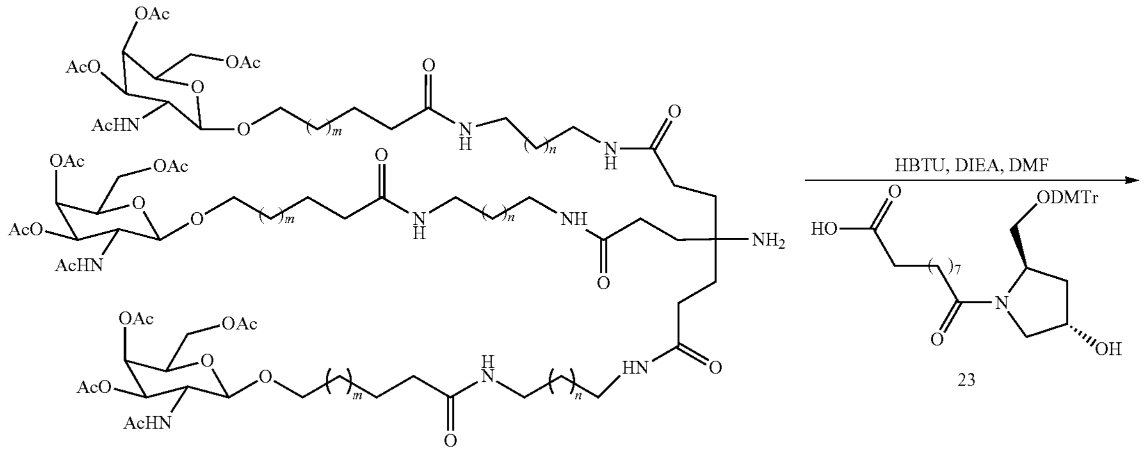
23
97a; n = 1, m = 1
97b; n = 1, m = 2
97c; n = 2, m = 1
97d: n = 2. m = 2
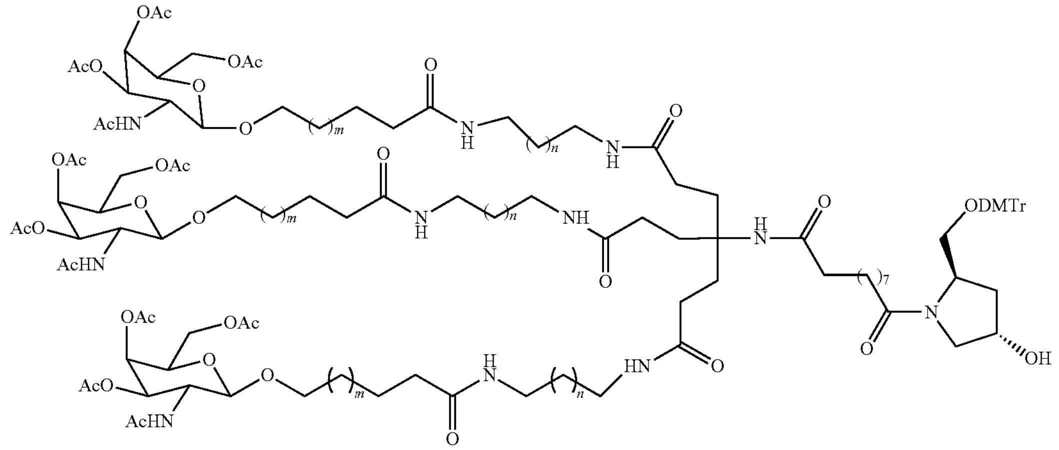
98a; n = 1, m = 1
98b; n = 1, m = 2
98c; n = 2, m = 1
98d; n = 2, m = 2

-continued
97a; n = 1, m = 1
97b; n = 1, m = 2
97c; n = 2, m = 1
97d; n = 2, m = 2
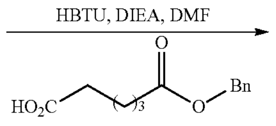
99
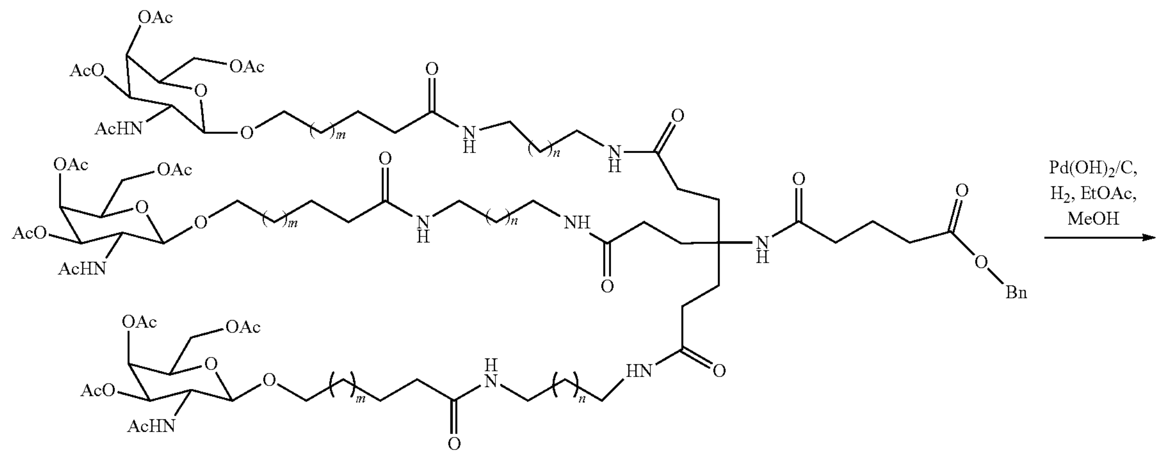
100a; n = 1, m = 1
100b; n = 1, m = 2
100c; n = 2, m = 1
100d; n = 2, m = 2
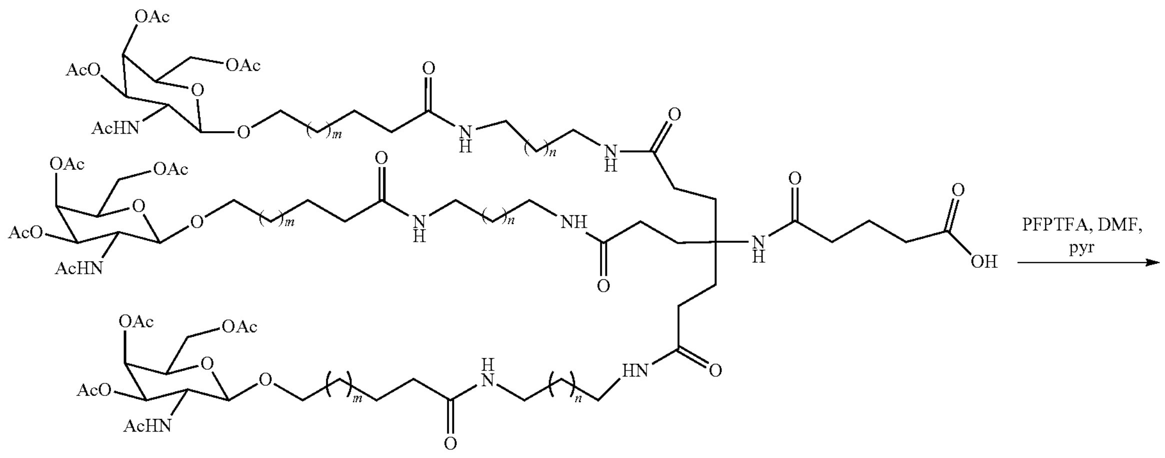
101a; n = 1, m = 1
101b; n = 1, m = 2
101c; n = 2, m = 1
101d; n = 2, m = 2

-continued

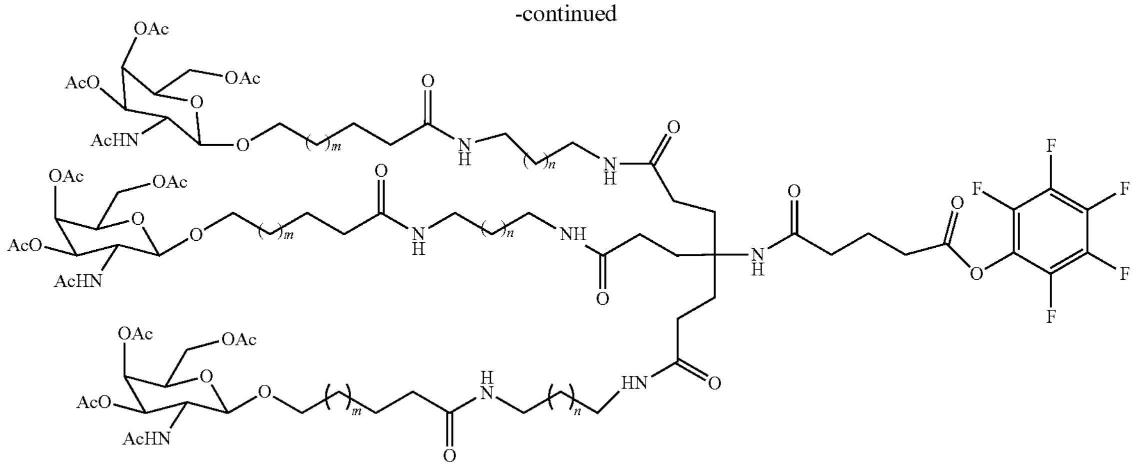

102a; n = 1, m = 1
102b; n = 1, m = 2
102c; n = 2, m = 1
102d; n = 2, m = 2

The triacid 90 (4 g, 14.43 mmol) was dissolved in DMF (120 mL) and N,N-Diisopropylethylamine (12.35 mL, 72 mmoles). Pentafluorophenyl trifluoroacetate (8.9 mL, 52 mmoles) was added dropwise, under argon, and the reaction was allowed to stir at room temperature for 30 minutes. Boc-diamine 91a or 91b (68.87 mmol) was added, along with N,N-Diisopropylethylamine (12.35 mL, 72 mmoles), and the reaction was allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%--10>10% methanol/dichloromethane) to give compounds 92a and 92b in an approximate 80% yield. LCMS and proton NMR were consistent with the structure.

Compound 92a or 92b (6.7 mmoles) was treated with 20 mL of dichloromethane and 20 mL of trifluoroacetic acid at room temperature for 16 hours. The resultant solution was evaporated and then dissolved in methanol and treated with DOWEX-OH resin for 30 minutes. The resultant solution was filtered and reduced to an oil under reduced pressure to give 85-90% yield of compounds 93a and 93b.

Compounds 7 or 64 (9.6 mmoles) were treated with HBTU (3.7 g, 9.6 mmoles) and N,N-Diisopropylethylamine (5 mL) in DMF (20 mL) for 15 minutes. To this was added either compounds 93a or 93b (3 mmoles), and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%-->20% methanol/dichloromethane) to give compounds 96a-d in 20-40% yield. LCMS and proton NMR was consistent with the structure.

Compounds 96a-d (0.75 mmoles), individually, were hydrogenated over Raney Nickel for 3 hours in Ethanol (75 mL). At that time, the catalyst was removed by filtration thru celite, and the ethanol removed under reduced pressure to give compounds 97a-d in 80-90% yield. LCMS and proton NMR were consistent with the structure.

Compound 23 (0.32 g, 0.53 mmoles) was treated with HBTU (0.2 g, 0.53 mmoles) and N,N-Diisopropylethylamine (0.19 mL, 1.14 mmoles) in DMF (30 mL) for 15 minutes. To this was added compounds 97a-d (0.38 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%-->20% methanol/dichloromethane) to give compounds 98a-d in 30-40% yield. LCMS and proton NMR was consistent with the structure.

Compound 99 (0.17 g, 0.76 mmoles) was treated with HBTU (0.29 g, 0.76 mmoles) and N,N-Diisopropylethylamine (0.35 mL, 2.0 mmoles) in DMF (50 mL) for 15 minutes. To this was added compounds 97a-d (0.51 mmoles), individually, and allowed to stir at room temperature for 16 hours. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (5%-->20% methanol/dichloromethane) to give compounds 100a-d in 40-60% yield. LCMS and proton NMR was consistent with the structure.

Compounds 100a-d (0.16 mmoles), individually, were hydrogenated over 10% Pd (OH) 2/C for 3 hours in methanol/ethyl acetate (1:1, 50 mL). At that time, the catalyst was removed by filtration thru celite, and the organics removed under reduced pressure to give compounds 101a-d in 80-90% yield. LCMS and proton NMR was consistent with the structure.

Compounds 101a-d (0.15 mmoles), individually, were dissolved in DMF (15 mL) and pyridine (0.016 mL, 0.2 mmoles). Pentafluorophenyl trifluoroacetate (0.034 mL, 0.2 mmoles) was added dropwise, under argon, and the reaction was allowed to stir at room temperature for 30 minutes. At that time, the DMF was reduced by >75% under reduced pressure, and then the mixture was dissolved in dichloromethane. The organic layer was washed with sodium bicarbonate, water and brine. The organic layer was then separated and dried over sodium sulfate, filtered and reduced to an oil under reduced pressure. The resultant oil was purified by silica gel chromatography (2%-->5% methanol/dichloromethane) to give compounds 102a-d in an approximate 80% yield. LCMS and proton NMR were consistent with the structure.

83e

102d

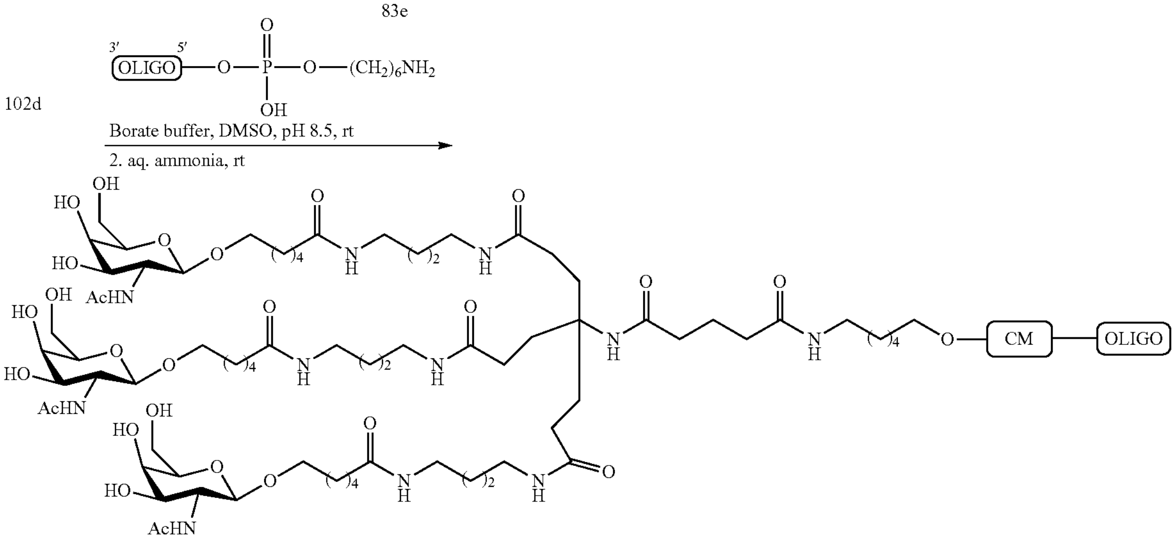

102

Oligomeric Compound 102, comprising a GalNAc$_3$-8 conjugate group, was prepared using the general procedures illustrated in Example 46. The GalNAc$_3$ cluster portion of the conjugate group GalNAc$_3$-8 (GalNAc$_3$-8$_a$) can be combined with any cleavable moiety to provide a variety of conjugate groups. In a preferred embodiment, the cleavable moiety is —P(═O)(OH)-A$_d$-P(═O)(OH)—.

The structure of GalNAc$_3$-8 (GalNAc$_3$-8$_a$-CM-) is shown below:

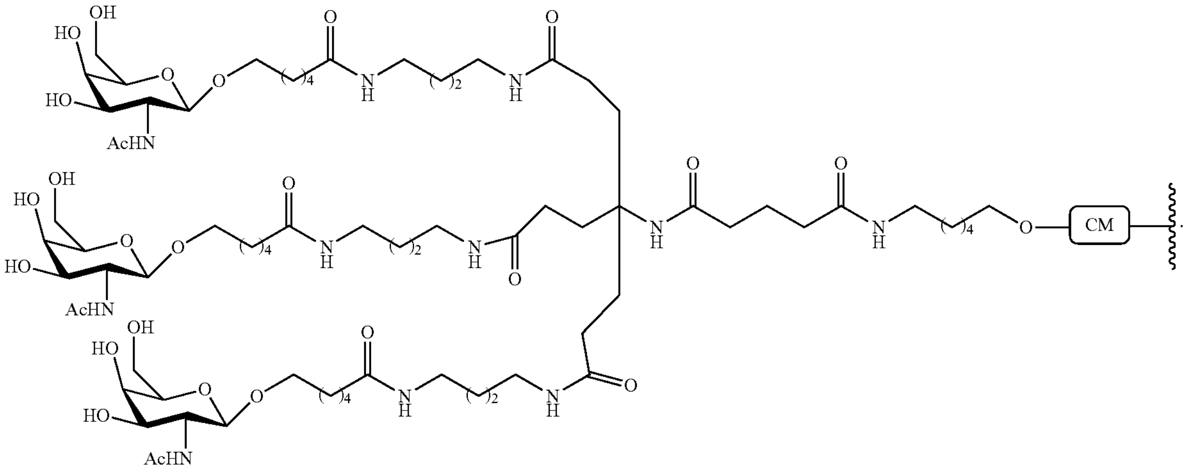

Example 48: Preparation of Oligonucleotide 119 Comprising GalNAc$_3$-7
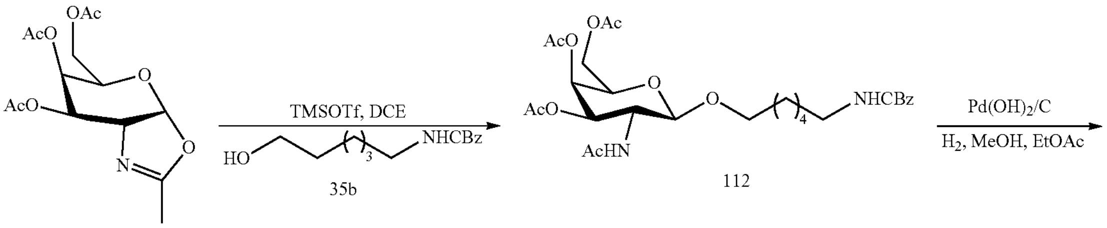
4 35b 112
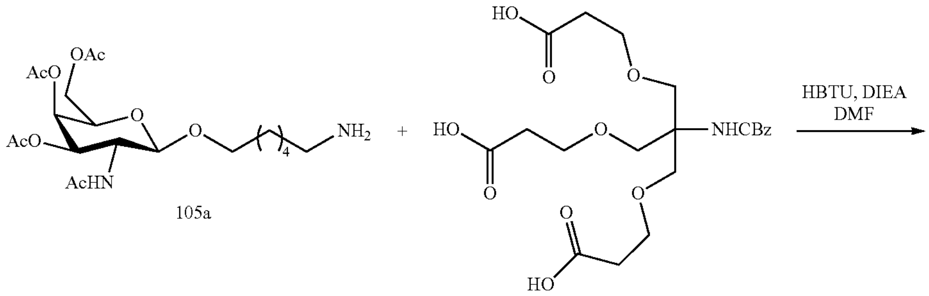
105a 113
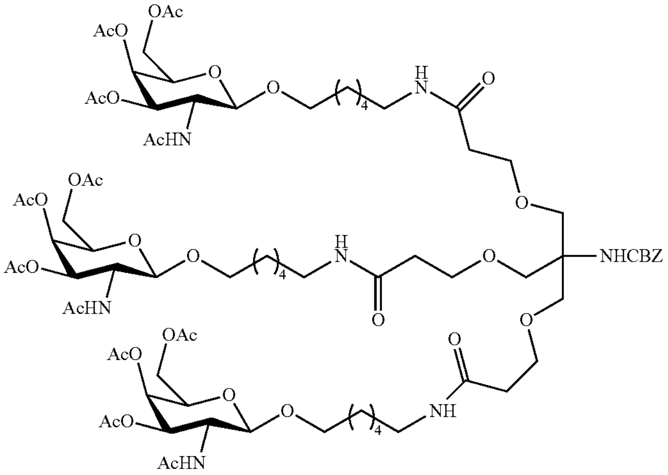
114
1114
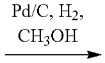

-continued

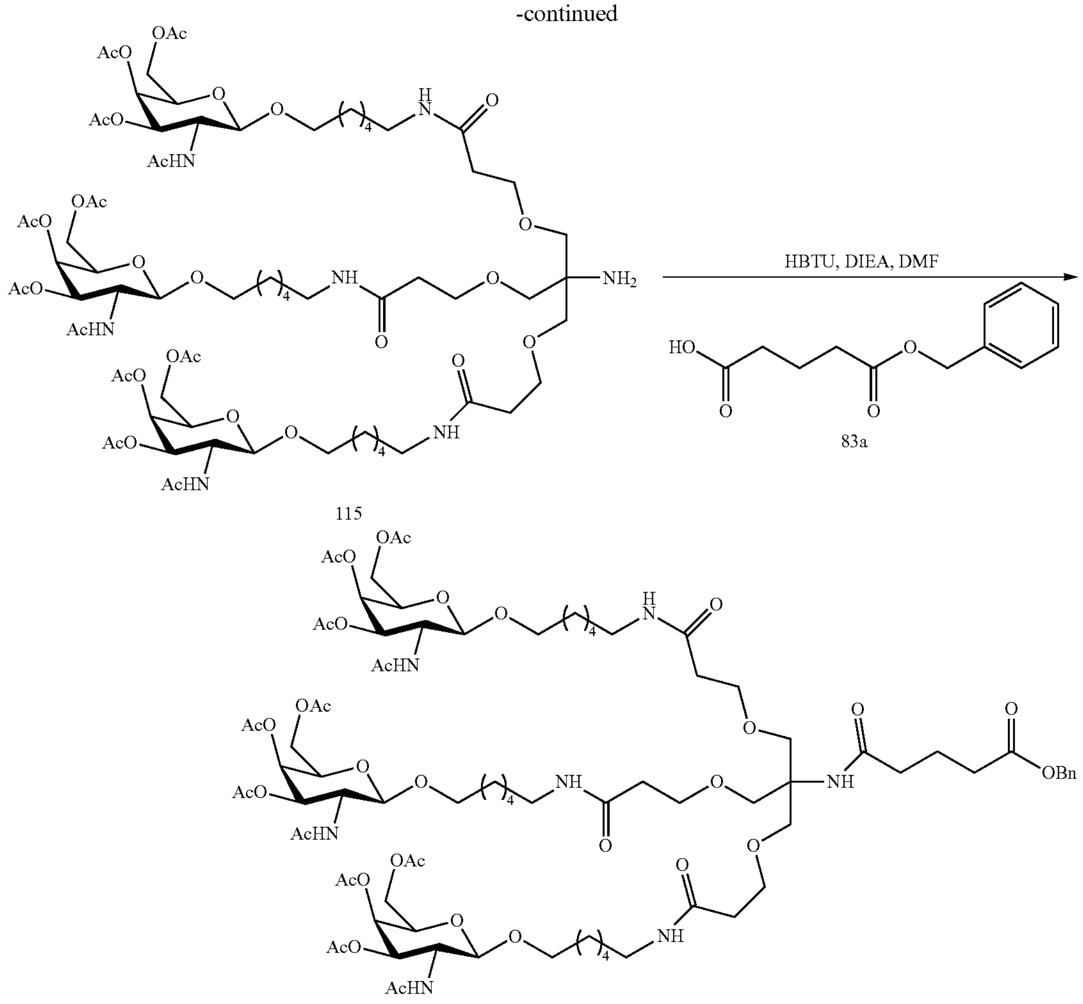

115

83a

116

Compound 112 was synthesized following the procedure described in the literature (*J. Med. Chem.* 2004, 47, 5798-5808).

Compound 112 (5 g, 8.6 mmol) was dissolved in 1:1 methanol/ethyl acetate (22 mL/22 mL). Palladium hydroxide on carbon (0.5 g) was added. The reaction mixture was stirred at room temperature under hydrogen for 12 h. The reaction mixture was filtered through a pad of celite and washed the pad with 1:1 methanol/ethyl acetate. The filtrate and the washings were combined and concentrated to dryness to yield Compound 105a (quantitative). The structure was confirmed by LCMS.

Compound 113 (1.25 g, 2.7 mmol), HBTU (3.2 g, 8.4 mmol) and DIEA (2.8 mL, 16.2 mmol) were dissolved in anhydrous DMF (17 mL) and the reaction mixture was stirred at room temperature for 5 min. To this a solution of Compound 105a (3.77 g, 8.4 mmol) in anhydrous DMF (20 mL) was added. The reaction was stirred at room temperature for 6 h. Solvent was removed under reduced pressure to get an oil. The residue was dissolved in $CH_2Cl_2$ (100 mL) and washed with aqueous saturated $NaHCO_3$ solution (100 mL) and brine (100 mL). The organic phase was separated, dried ($Na_2SO_4$), filtered and evaporated. The residue was purified by silica gel column chromatography and eluted with 10 to 20% MeOH in dichloromethane to yield Compound 114 (1.45 g, 30%). The structure was confirmed by LCMS and $^1$H NMR analysis.

Compound 114 (1.43 g, 0.8 mmol) was dissolved in 1:1 methanol/ethyl acetate (4 mL/4 mL). Palladium on carbon (wet, 0.14 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield Compound 115 (quantitative). The structure was confirmed by LCMS and $^1$H NMR analysis.

Compound 83a (0.17 g, 0.75 mmol), HBTU (0.31 g, 0.83 mmol) and DIEA (0.26 mL, 1.5 mmol) were dissolved in anhydrous DMF (5 mL) and the reaction mixture was stirred at room temperature for 5 min. To this a solution of Compound 115 (1.22 g, 0.75 mmol) in anhydrous DMF was added and the reaction was stirred at room temperature for 6 h. The solvent was removed under reduced pressure and the residue was dissolved in $CH_2Cl_2$. The organic layer was washed aqueous saturated $NaHCO_3$ solution and brine and dried over anhydrous $Na_2SO_4$ and filtered. The organic layer was concentrated to dryness and the residue obtained was purified by silica gel column chromatography and eluted with 3 to 15% MeOH in dichloromethane to yield Compound 116 (0.84 g, 61%). The structure was confirmed by LC MS and $^1$H NMR analysis.

116

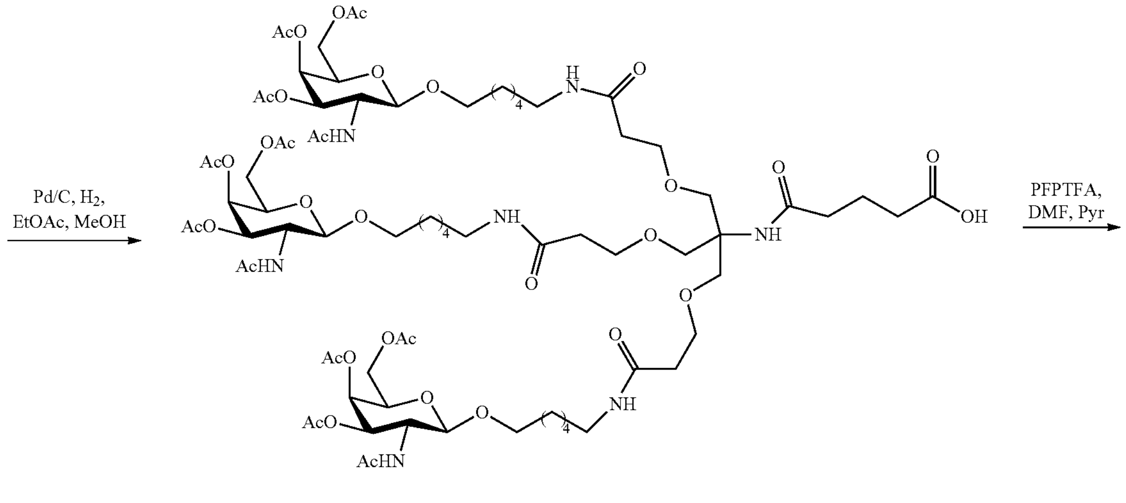

117

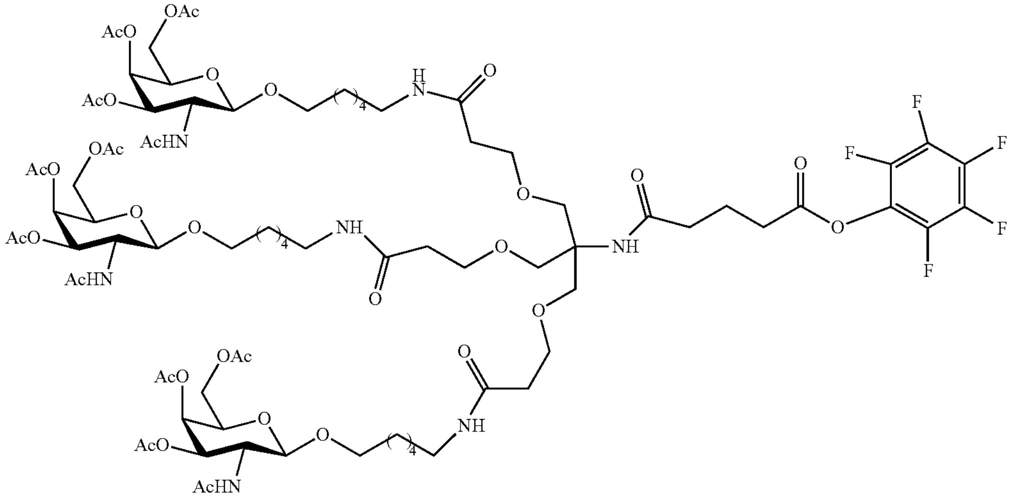

118

Compound 116 (0.74 g, 0.4 mmol) was dissolved in 1:1 methanol/ethyl acetate (5 mL/5 mL). Palladium on carbon (wet, 0.074 g) was added. The reaction mixture was flushed with hydrogen and stirred at room temperature under hydrogen for 12 h. The reaction mixture was filtered through a pad of celite. The celite pad was washed with methanol/ethyl acetate (1:1). The filtrate and the washings were combined together and evaporated under reduced pressure to yield compound 117 (0.73 g, 98%). The structure was confirmed by LCMS and $^{1}H$ NMR analysis.

Compound 117 (0.63 g, 0.36 mmol) was dissolved in anhydrous DMF (3 mL). To this solution N,N-Diisopropylethylamine (70 μL, 0.4 mmol) and pentafluorophenyl trifluoroacetate (72 μL, 0.42 mmol) were added. The reaction mixture was stirred at room temperature for 12 h and poured into a aqueous saturated $NaHCO_3$ solution. The mixture was extracted with dichloromethane, washed with brine and dried over anhydrous $Na_2SO_4$. The dichloromethane solution was concentrated to dryness and purified with silica gel column chromatography and eluted with 5 to 10% MeOH in dichloromethane to yield compound 118 (0.51 g, 79%). The structure was confirmed by LCMS and $^{1}H$ and $^{1}H$ and $^{19}F$ NMR.

83e

118

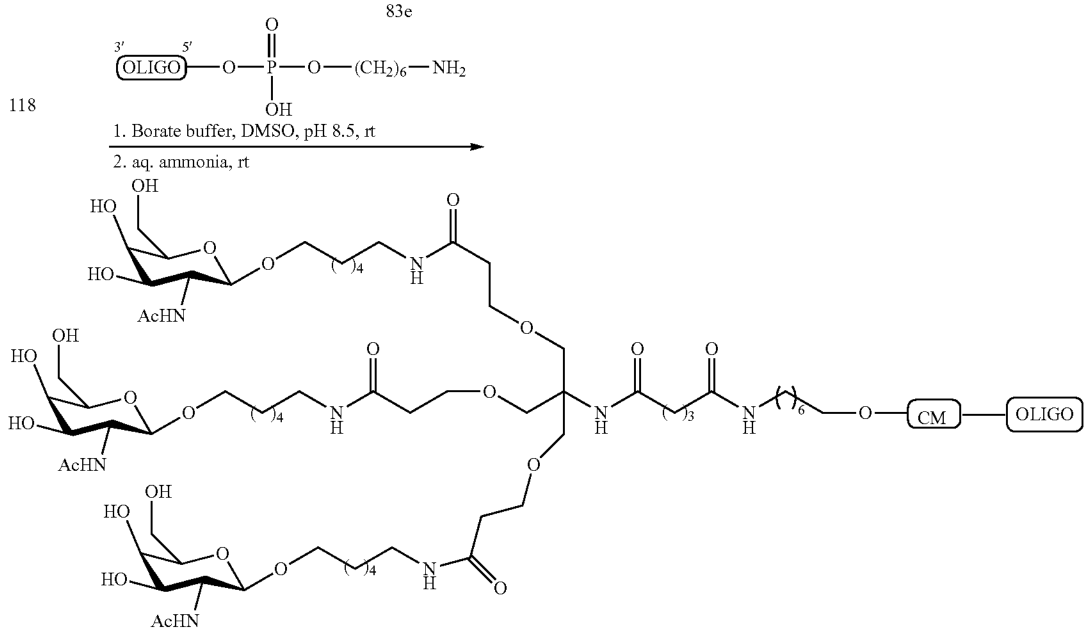

119

Oligomeric Compound 119, comprising a GalNAc$_3$-7 conjugate group, was prepared using the general procedures illustrated in Example 46. The GalNAc$_3$ cluster portion of the conjugate group GalNAc$_3$-7 (GalNAc$_3$-7$_a$) can be combined with any cleavable moiety to provide a variety of conjugate groups. In certain embodiments, the cleavable moiety is —P(═O)(OH)-A$_d$-P(═O)(OH)—.

The structure of GalNAc$_3$-7 (GalNAc$_3$-7$_a$-CM-) is shown below:

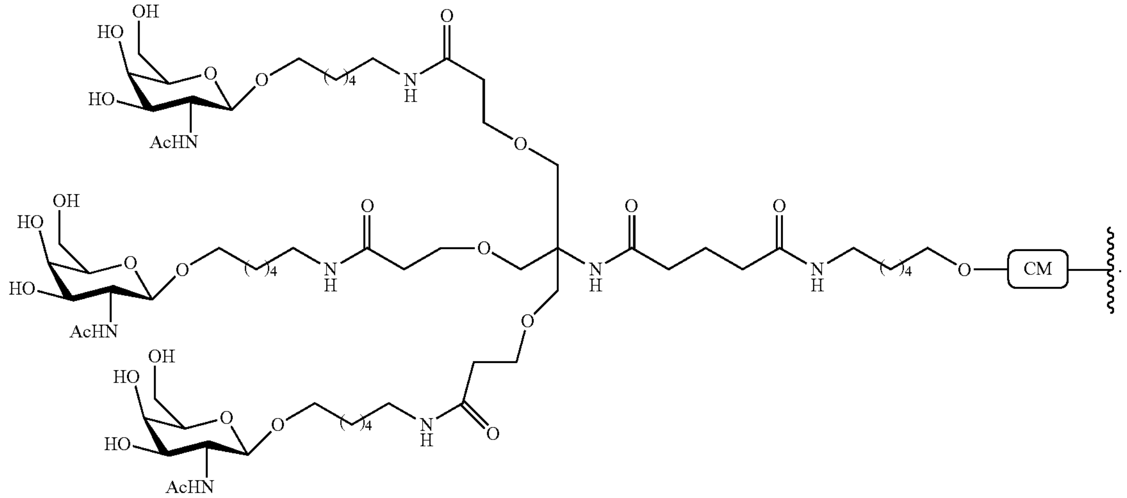

Example 49: Preparation of Oligonucleotide 132 Comprising $GalNAc_3$-5

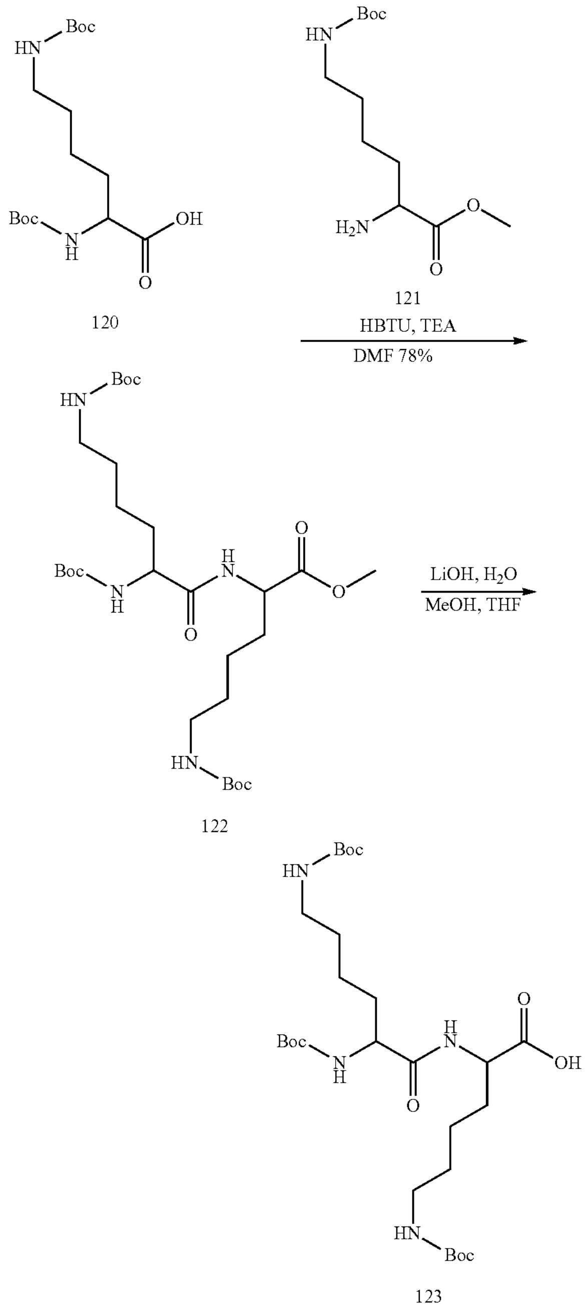

120 121 122 123

Compound 120 (14.01 g, 40 mmol) and HBTU (14.06 g, 37 mmol) were dissolved in anhydrous DMF (80 mL). Triethylamine (11.2 mL, 80.35 mmol) was added and stirred for 5 min. The reaction mixture was cooled in an ice bath and a solution of compound 121 (10 g, mmol) in anhydrous DMF (20 mL) was added. Additional triethylamine (4.5 mL, 32.28 mmol) was added and the reaction mixture was stirred for 18 h under an argon atmosphere. The reaction was monitored by TLC(ethyl acetate: hexane; 1:1; Rf=0.47). The solvent was removed under reduced pressure. The residue was taken up in EtOAc (300 mL) and washed with 1M NaHSO4 (3×150 mL), aqueous saturated $NaHCO_3$ solution (3×150 mL) and brine ($2\times10^0$ mL). Organic layer was dried with $Na_2SO_4$. Drying agent was removed by filtration and organic layer was concentrated by rotary evaporation. Crude mixture was purified by silica gel column chromatography and eluted by using 35-50% EtOAc in hexane to yield a compound 122 (15.50 g, 78.13%). The structure was confirmed by LCMS and $^1H$ NMR analysis. Mass m/z 589.3 $[M+H]^+$.

A solution of LiOH (92.15 mmol) in water (20 mL) and THF (10 mL) was added to a cooled solution of Compound 122 (7.75 g, 13.16 mmol) dissolved in methanol (15 mL). The reaction mixture was stirred at room temperature for 45 min. and monitored by TLC(EtOAc: hexane; 1:1). The reaction mixture was concentrated to half the volume under reduced pressure. The remaining solution was cooled an ice bath and neutralized by adding concentrated HCl. The reaction mixture was diluted, extracted with EtOAc (120 mL) and washed with brine (100 mL). An emulsion formed and cleared upon standing overnight. The organic layer was separated dried ($Na_2SO_4$), filtered and evaporated to yield Compound 123 (8.42 g). Residual salt is the likely cause of excess mass. LCMS is consistent with structure. Product was used without any further purification. M. W.cal: 574.36; M.W.fd: 575.3 $[M+H]^+$.

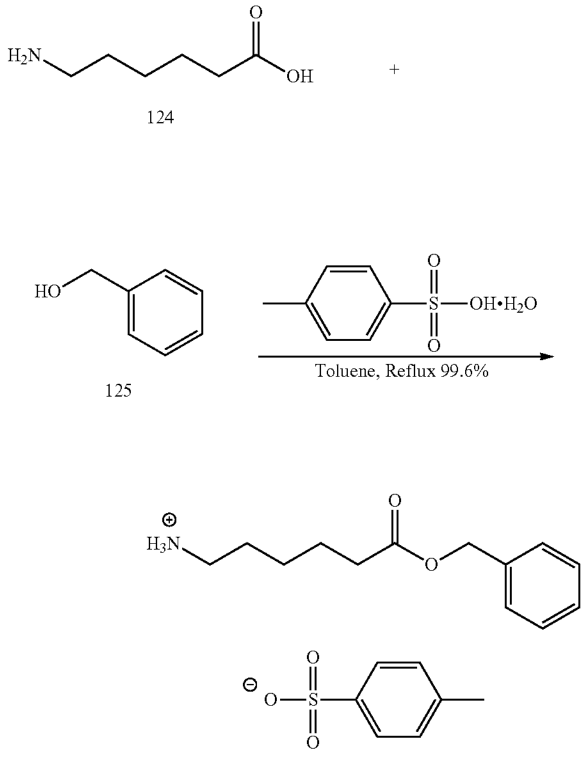

124 125 126

Compound 126 was synthesized following the procedure described in the literature (*J. Am. Chem. Soc.* 2011, 133, 958-963).

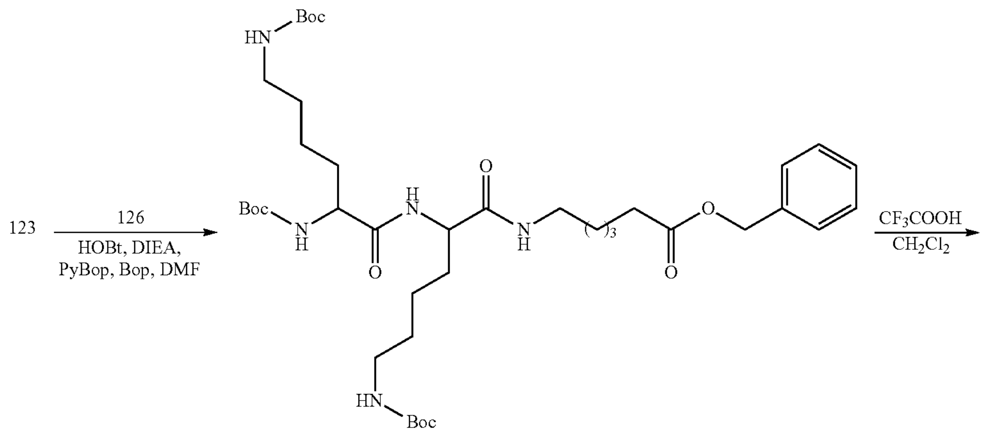
127
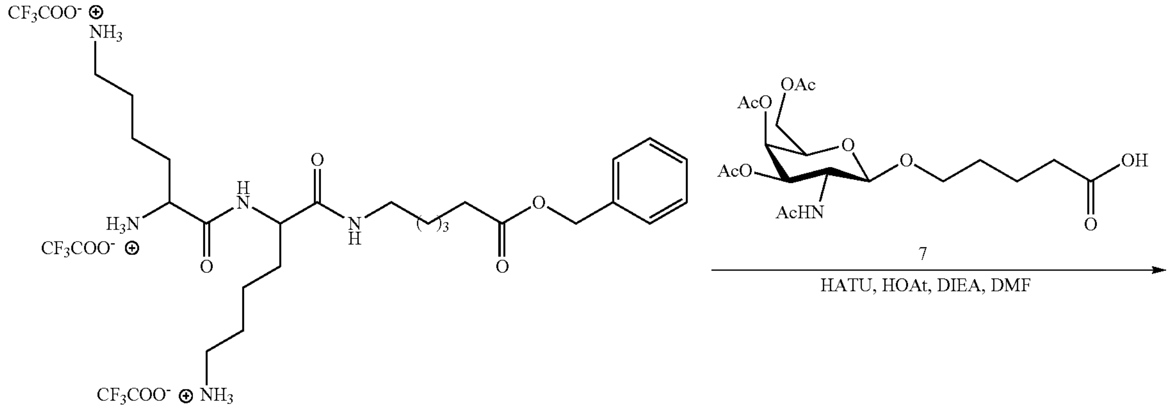
128
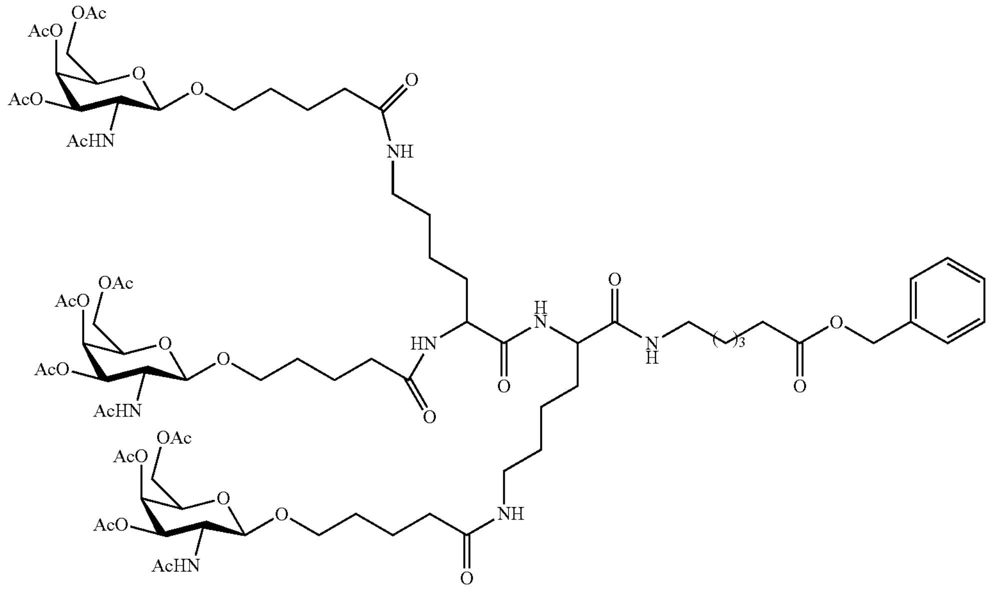
129
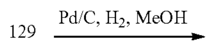

-continued

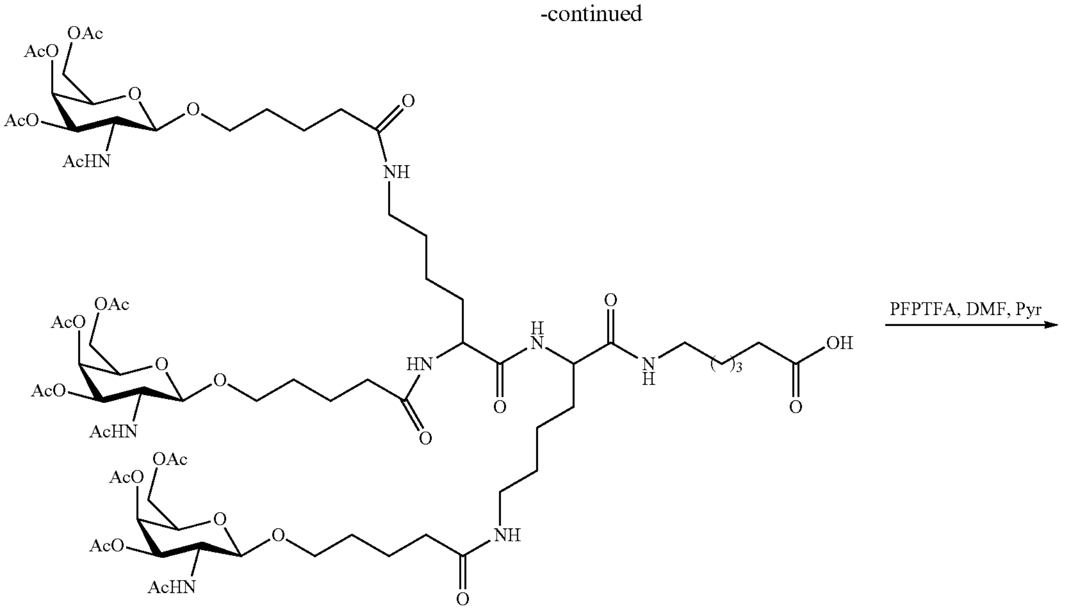

130

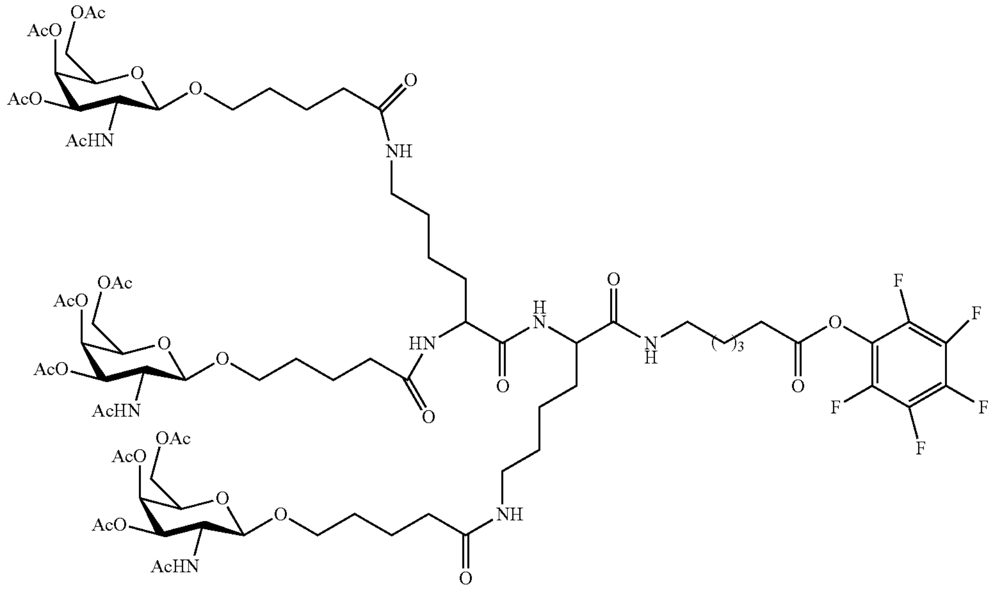

131

Compound 123 (7.419 g, 12.91 mmol), HOBt (3.49 g, 25.82 mmol) and compound 126 (6.33 g, 16.14 mmol) were dissolved in and DMF (40 mL) and the resulting reaction mixture was cooled in an ice bath. To this N,N-Diisopropylethylamine (4.42 mL, 25.82 mmol), PyBop (8.7 g, 16.7 mmol) followed by Bop coupling reagent (1.17 g, 2.66 mmol) were added under an argon atmosphere. The ice bath was removed and the solution was allowed to warm to room temperature. The reaction was completed after 1 h as determined by TLC (DCM: MeOH: AA; 89:10:1). The reaction mixture was concentrated under reduced pressure. The residue was dissolved in EtOAc (200 mL) and washed with 1 M NaHSO4 ($3\times10^0$ mL), aqueous saturated $NaHCO_3$ ($3\times10^0$ mL) and brine ($2\times10^0$ mL). The organic phase separated dried ($Na_2SO_4$), filtered and concentrated. The residue was purified by silica gel column chromatography with a gradient of 50% hexanes/EtOAC to 100% EtOAc to yield Compound 127 (9.4 g) as a white foam. LCMS and $^1$H NMR were consistent with structure. Mass m/z 778.4 $[M+H]^+$.

Trifluoroacetic acid (12 mL) was added to a solution of compound 127 (1.57 g, 2.02 mmol) in dichloromethane (12 mL) and stirred at room temperature for 1 h. The reaction mixture was co-evaporated with toluene (30 mL) under reduced pressure to dryness. The residue obtained was co-evaporated twice with acetonitrile (30 mL) and toluene (40 mL) to yield Compound 128 (1.67 g) as trifluoro acetate salt and used for next step without further purification. LCMS and $^1$H NMR were consistent with structure. Mass m/z 478.2 $[M+H]^+$.

Compound 7 (0.43 g, 0.963 mmol), HATU (0.35 g, 0.91 mmol), and HOAt (0.035 g, 0.26 mmol) were combined together and dried for 4 h over $P_2O_5$ under reduced pressure in a round bottom flask and then dissolved in anhydrous DMF (1 mL) and stirred for 5 min. To this a solution of compound 128 (0.20 g, 0.26 mmol) in anhydrous DMF (0.2 mL) and N,N-Diisopropylethylamine (0.2 mL) was added. The reaction mixture was stirred at room temperature under an argon atmosphere. The reaction was complete after 30 min as determined by LCMS and TLC(7% MeOH/DCM). The reaction mixture was concentrated under reduced pressure. The residue was dissolved in DCM (30 mL) and washed with 1 M $NaHSO_4$ (3×20 mL), aqueous saturated $NaHCO_3$ (3×20 mL) and brine (3×20 mL). The organic phase was separated, dried over $Na_2SO_4$, filtered and concentrated. The residue was purified by silica gel column chromatography using 5-15% MeOH in dichloromethane to yield Compound 129 (96.6 mg). LC MS and $^1H$ NMR are consistent with structure. Mass m/z 883.4 $[M+2H]^+$.

Compound 129 (0.09 g, 0.051 mmol) was dissolved in methanol (5 mL) in 20 mL scintillation vial. To this was added a small amount of 10% Pd/C(0.015 mg) and the reaction vessel was flushed with $H_2$ gas. The reaction mixture was stirred at room temperature under $H_2$ atmosphere for 18 h. The reaction mixture was filtered through a pad of Celite and the Celite pad was washed with methanol. The filtrate washings were pooled together and concentrated under reduced pressure to yield Compound 130 (0.08 g). LCMS and $^1H$ NMR were consistent with structure. The product was used without further purification. Mass m/z 838.3 $[M+2H]^+$.

To a 10 mL pointed round bottom flask were added compound 130 (75.8 mg, 0.046 mmol), 0.37 M pyridine/DMF (200 µL) and a stir bar. To this solution was added 0.7 M pentafluorophenyl trifluoroacetate/DMF (100 µL) drop wise with stirring. The reaction was completed after 1 h as determined by LC MS. The solvent was removed under reduced pressure and the residue was dissolved in CHCI3 (~10 mL). The organic layer was partitioned against $NaHSO_4$ (1 M, 10 mL), aqueous saturated $NaHCO_3$ (10 mL) and brine (10 mL) three times each. The organic phase separated and dried over $Na_2SO_4$, filtered and concentrated to yield Compound 131 (77.7 mg). LCMS is consistent with structure. Used without further purification. Mass m/z 921.3 $[M+2H]^+$.

83e

131

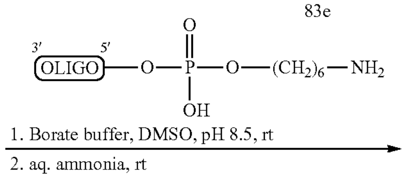

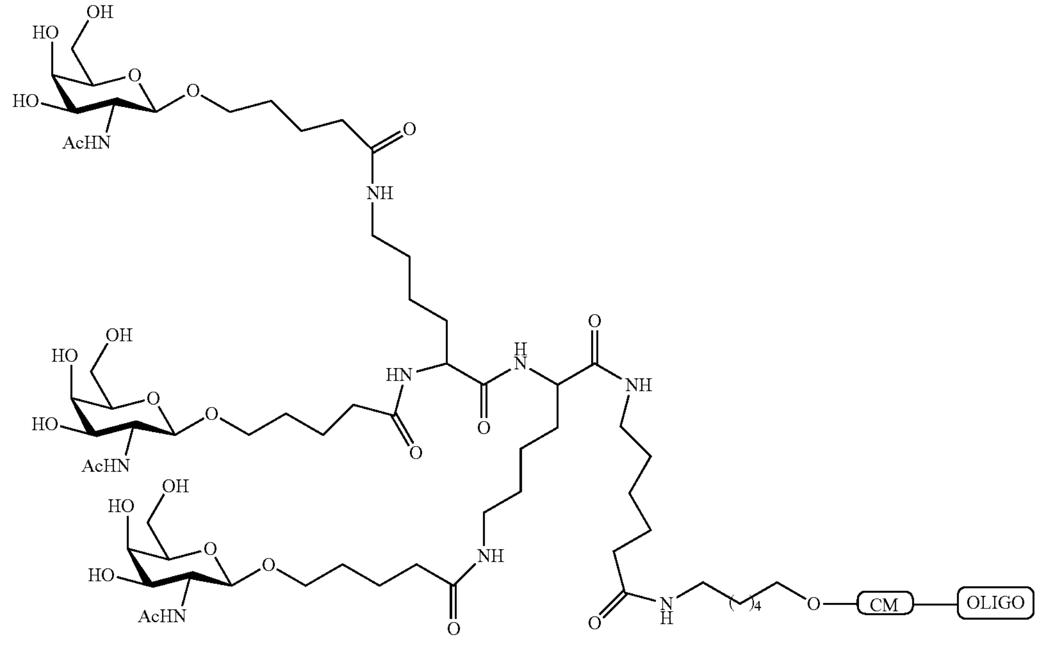

132

Oligomeric Compound 132, comprising a GalNAc$_3$-5 conjugate group, was prepared using the general procedures illustrated in Example 46. The GalNAc$_3$ cluster portion of the conjugate group GalNAc$_3$-5 (GalNAc$_3$-5$_a$) can be combined with any cleavable moiety to provide a variety of conjugate groups. In certain embodiments, the cleavable moiety is —P(═O)(OH)-Aa-P(═O)(OH)—.

The structure of GalNAc$_3$-5 (GalNAc$_3$-5$_a$-CM-) is shown below:

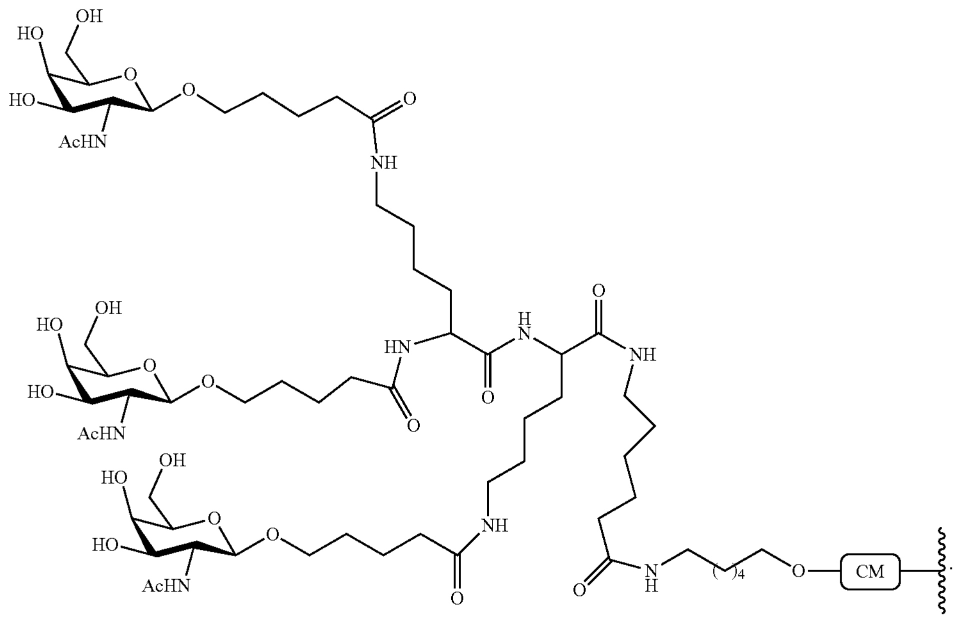

Example 50: Preparation of Oligonucleotide 144 Comprising GalNAc$_4$-11

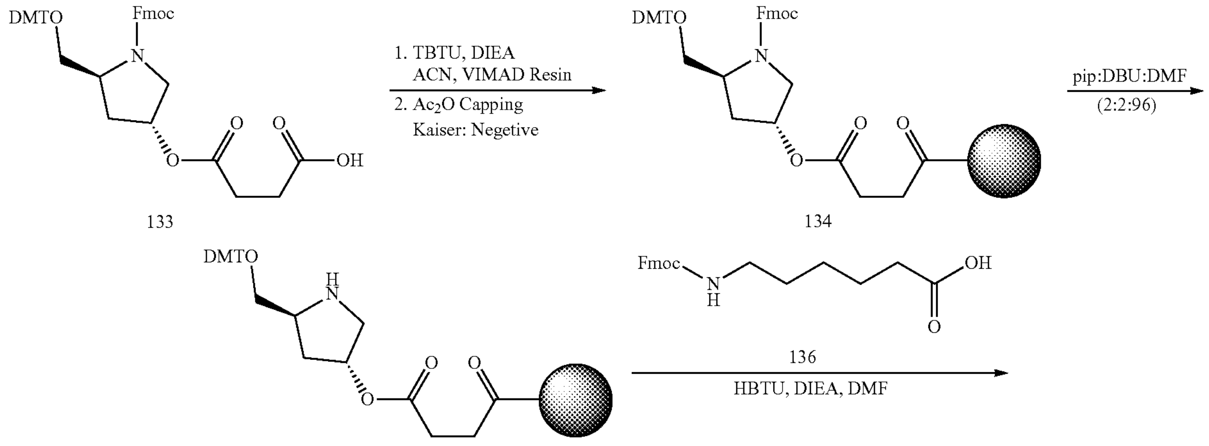

133

134

135

-continued
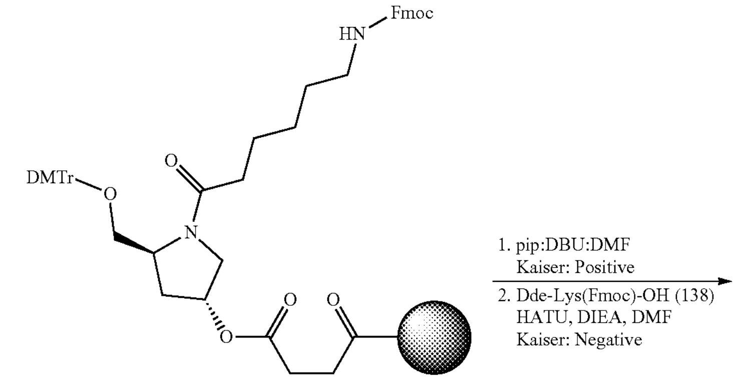
137
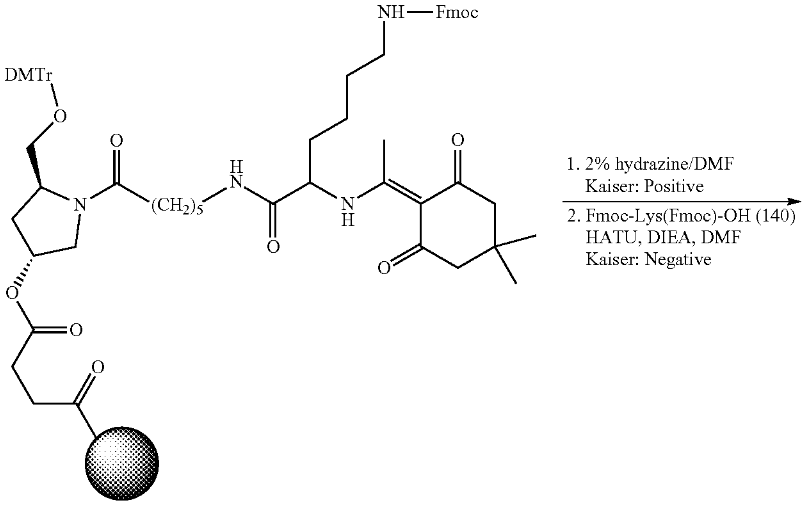
139

-continued
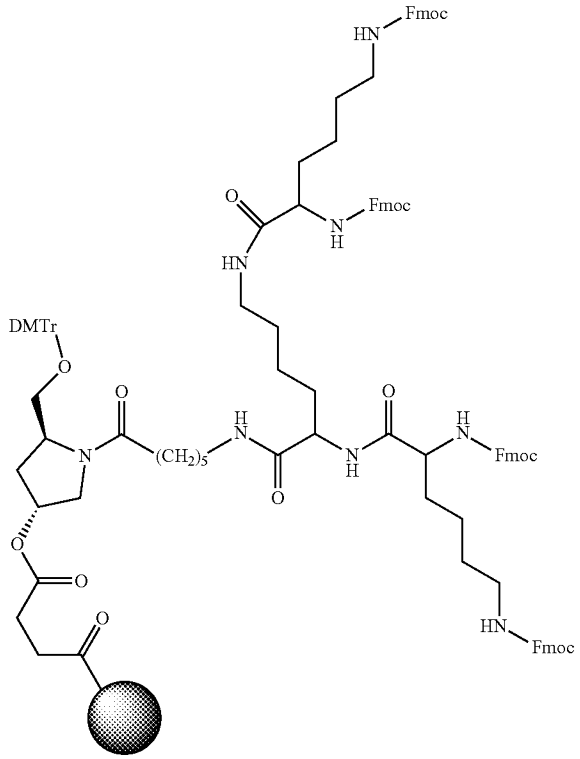
141
141
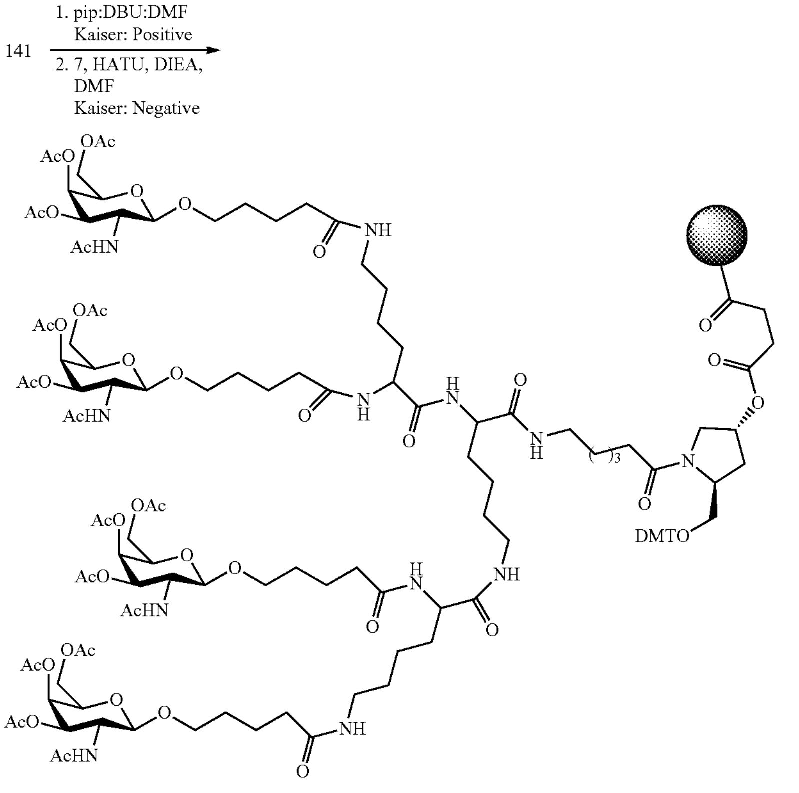
142

Synthesis of Compound 134. To a Merrifield flask was added aminomethyl VIMAD resin (2.5 g, 450 μmol/g) that was washed with acetonitrile, dimethylformamide, dichloromethane and acetonitrile. The resin was swelled in acetonitrile (4 mL). Compound 133 was pre-activated in a 100 mL round bottom flask by adding 20 (1.0 mmol, 0.747 g), TBTU (1.0 mmol, 0.321 g), acetonitrile (5 mL) and DIEA (3.0 mmol, 0.5 mL). This solution was allowed to stir for 5 min and was then added to the Merrifield flask with shaking. The suspension was allowed to shake for 3 h. The reaction mixture was drained and the resin was washed with acetonitrile, DMF and DCM. New resin loading was quantitated by measuring the absorbance of the DMT cation at 500 nm (extinction coefficient=76000) in DCM and determined to be 238 μmol/g. The resin was capped by suspending in an acetic anhydride solution for ten minutes three times.

The solid support bound compound 141 was synthesized using iterative Fmoc-based solid phase peptide synthesis methods. A small amount of solid support was withdrawn and suspended in aqueous ammonia (28-30 wt %) for 6 h. The cleaved compound was analyzed by LC-MS and the observed mass was consistent with structure. Mass m/z 1063.8 $[M+2H]^+$.

The solid support bound compound 142 was synthesized using solid phase peptide synthesis methods.

142

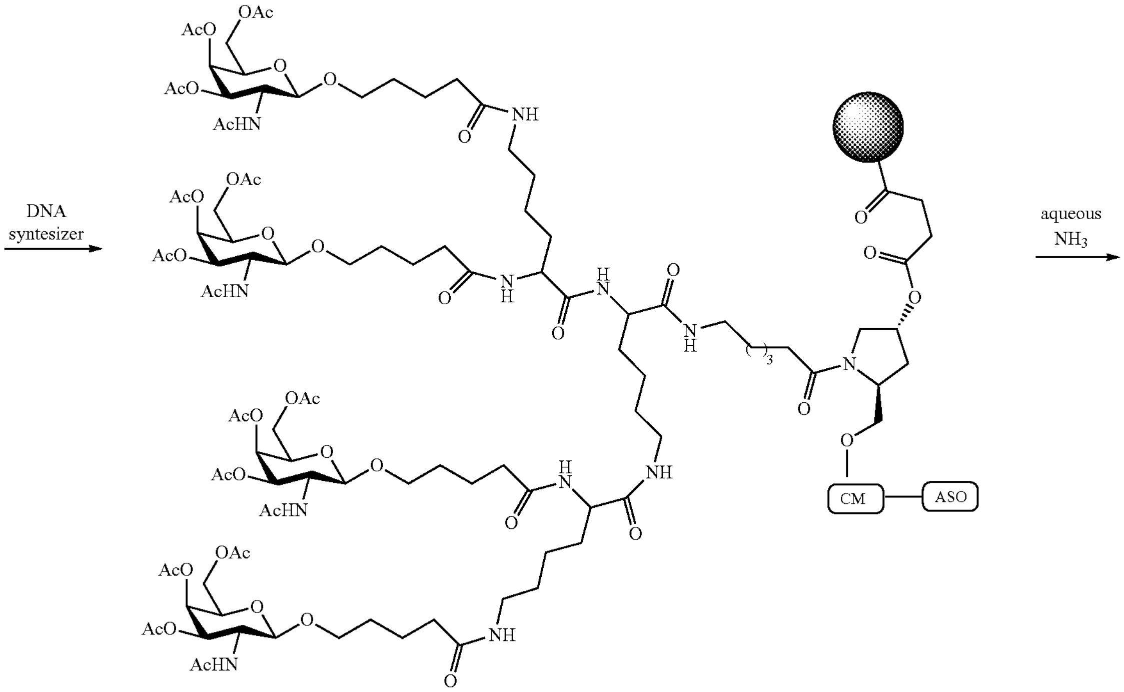

143

-continued

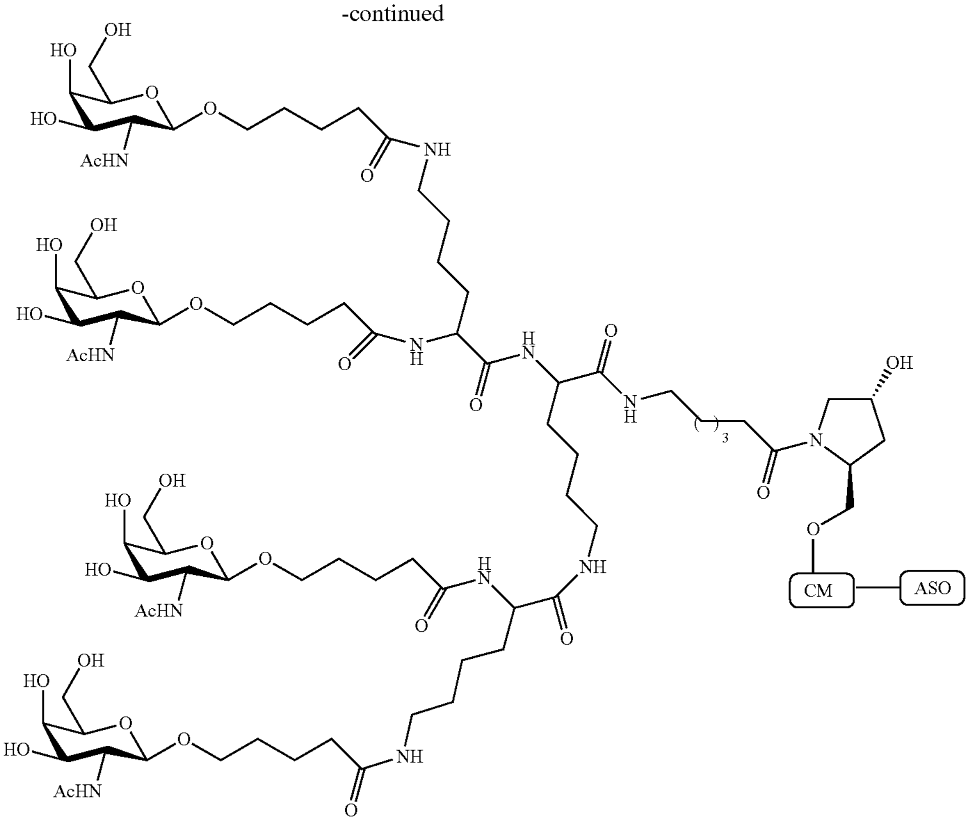

144

The solid support bound compound 143 was synthesized using standard solid phase synthesis on a DNA synthesizer.

The solid support bound compound 143 was suspended in aqueous ammonia (28-30 wt %) and heated at 55° C. for 16 h. The solution was cooled and the solid support was filtered. The filtrate was concentrated and the residue dissolved in water and purified by HPLC on a strong anion exchange column. The fractions containing full length compound 144 were pooled together and desalted. The resulting $GalNAc_4$-11 conjugated oligomeric compound was analyzed by LC-MS and the observed mass was consistent with structure.

The $GalNAc_4$ cluster portion of the conjugate group $GalNAc_4$-11 ($GalNAc_4$-$11_a$) can be combined with any cleavable moiety to provide a variety of conjugate groups. In certain embodiments, the cleavable moiety is —P(═O)(OH)-$A_d$-P(═O)(OH)—.

The structure of $GalNAc_4$-11 ($GalNAc_4$-$11_a$-CM) is shown below:

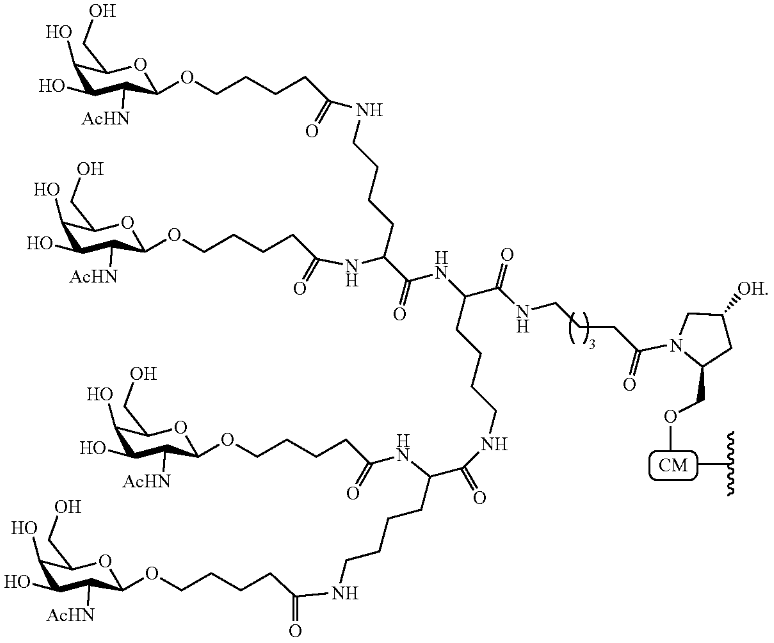
Example 51: Preparation of Oligonucleotide 155 Comprising GalNAc$_3$-6
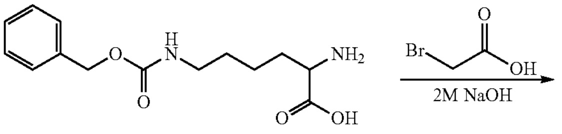
145
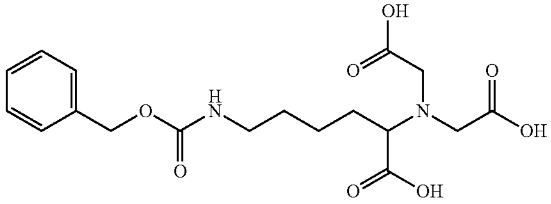
146
Compound 146 was synthesized as described in the literature (*Analytical Biochemistry* 1995, 229, 54-60).
4
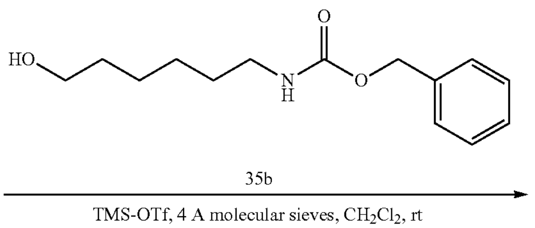

-continued

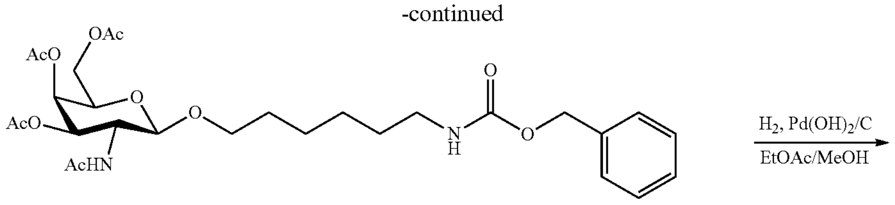

112

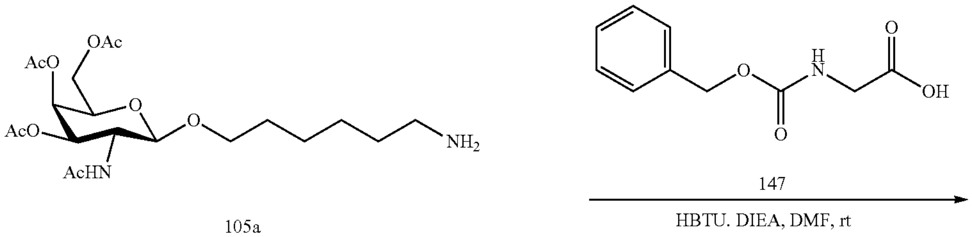

105a

147

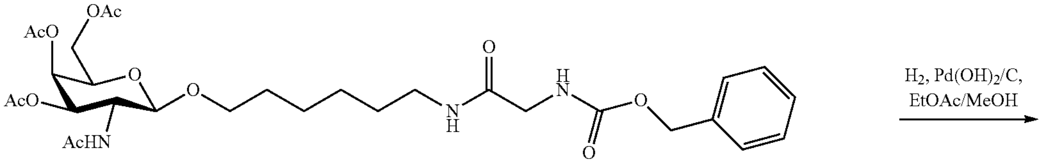

148

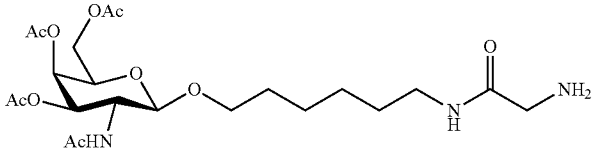

149

Compound 4 (15 g, 45.55 mmol) and compound 35b (14.3 grams, 57 mmol) were dissolved in $CH_2Cl_2$ (200 ml). Activated molecular sieves (4 Å. 2 g, powdered) were added, and the reaction was allowed to stir for 30 minutes under nitrogen atmosphere. TMS-OTf was added (4.1 ml, 22.77 mmol) and the reaction was allowed to stir at room temp overnight. Upon completion, the reaction was quenched by pouring into solution of saturated aqueous $NaHCO_3$ (500 ml) and crushed ice (~ 150 g). The organic layer was separated, washed with brine, dried over $MgSO_4$, filtered, and was concentrated to an orange oil under reduced pressure. The crude material was purified by silica gel column chromatography and eluted with 2-10% MeOH in $CH_2C_{12}$ to yield Compound 112 (16.53 g, 63%). LCMS and $^1$H NMR were consistent with the expected compound.

Compound 112 (4.27 g, 7.35 mmol) was dissolved in 1:1 MeOH/EtOAc (40 ml). The reaction mixture was purged by bubbling a stream of argon through the solution for 15 minutes. Pearlman's catalyst (palladium hydroxide on carbon, 400 mg) was added, and hydrogen gas was bubbled through the solution for 30 minutes. Upon completion (TLC 10% MeOH in $CH_2Cl_2$, and LCMS), the catalyst was removed by filtration through a pad of celite. The filtrate was concentrated by rotary evaporation, and was dried briefly under high vacuum to yield Compound 105a (3.28 g). LCMS and $^1$H NMR were consistent with desired product.

Compound 147 (2.31 g, 11 mmol) was dissolved in anhydrous DMF (100 mL). N,N-Diisopropylethylamine (DIEA, 3.9 mL, 22 mmol) was added, followed by HBTU (4 g, 10.5 mmol). The reaction mixture was allowed to stir for ~ 15 minutes under nitrogen. To this a solution of compound 105a (3.3 g, 7.4 mmol) in dry DMF was added and stirred for 2 h under nitrogen atmosphere. The reaction was diluted with EtOAc and washed with saturated aqueous $NaHCO_3$ and brine. The organics phase was separated, dried (MgSO4), filtered, and concentrated to an orange syrup. The crude material was purified by column chromatography 2-5% MeOH in $CH_2Cl_2$ to yield Compound 148 (3.44 g, 73%). LCMS and $^1$H NMR were consistent with the expected product.

Compound 148 (3.3 g, 5.2 mmol) was dissolved in 1:1 MeOH/EtOAc (75 ml). The reaction mixture was purged by bubbling a stream of argon through the solution for 15 minutes. Pearlman's catalyst (palladium hydroxide on carbon) was added (350 mg). Hydrogen gas was bubbled through the solution for 30 minutes. Upon completion (TLC 10% MeOH in DCM, and LCMS), the catalyst was removed by filtration through a pad of celite. The filtrate was concentrated by rotary evaporation, and was dried briefly under high vacuum to yield Compound 149 (2.6 g). LCMS was consistent with desired product. The residue was dissolved in dry DMF (10 ml) was used immediately in the next step.

146

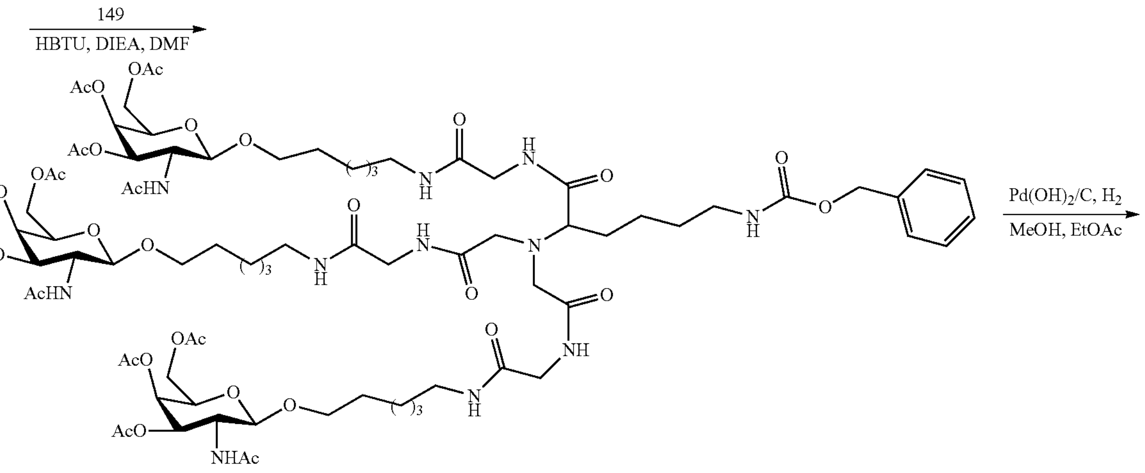

150

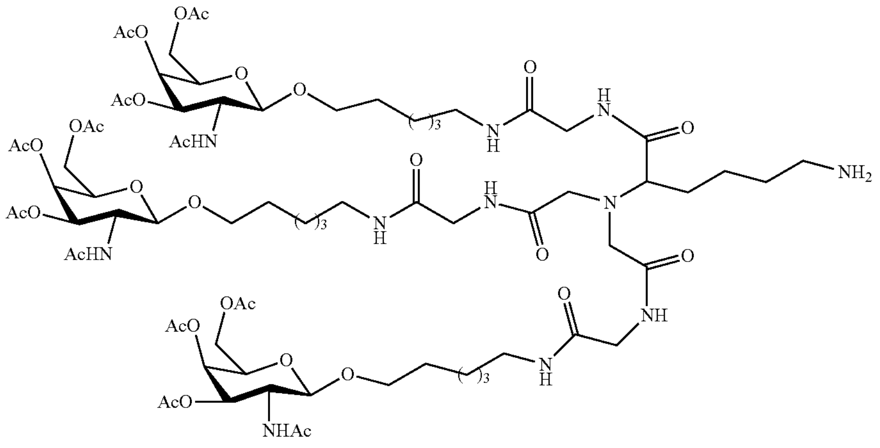

151

Compound 146 (0.68 g, 1.73 mmol) was dissolved in dry DMF (20 ml). To this DIEA (450 μL, 2.6 mmol, 1.5 eq.) and HBTU (1.96 g, 0.5.2 mmol) were added. The reaction mixture was allowed to stir for 15 minutes at room temperature under nitrogen. A solution of compound 149 (2.6 g) in anhydrous DMF (10 mL) was added. The pH of the reaction was adjusted to pH=9-10 by addition of DIEA (if necessary). The reaction was allowed to stir at room temperature under nitrogen for 2 h. Upon completion the reaction was diluted with EtOAc (100 mL), and washed with aqueous saturated aqueous $NaHCO_3$, followed by brine. The organic phase was separated, dried over $MgSO_4$, filtered, and concentrated. The residue was purified by silica gel column chromatography and eluted with 2-10% MeOH in $CH_2Cl_2$ to yield Compound 150 (0.62 g, 20%). LCMS and $^1$H NMR were consistent with the desired product.

Compound 150 (0.62 g) was dissolved in 1:1 MeOH/EtOAc (5 L). The reaction mixture was purged by bubbling a stream of argon through the solution for 15 minutes. Pearlman's catalyst (palladium hydroxide on carbon) was added (60 mg). Hydrogen gas was bubbled through the solution for 30 minutes. Upon completion (TLC 10% MeOH in DCM, and LCMS), the catalyst was removed by filtration (syringe-tip Teflon filter, 0.45 μm). The filtrate was concentrated by rotary evaporation, and was dried briefly under high vacuum to yield Compound 151 (0.57 g). The LCMS was consistent with the desired product. The product was dissolved in 4 mL dry DMF and was used immediately in the next step.

151

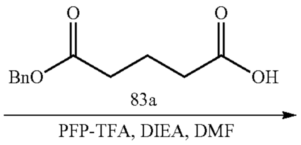

-continued

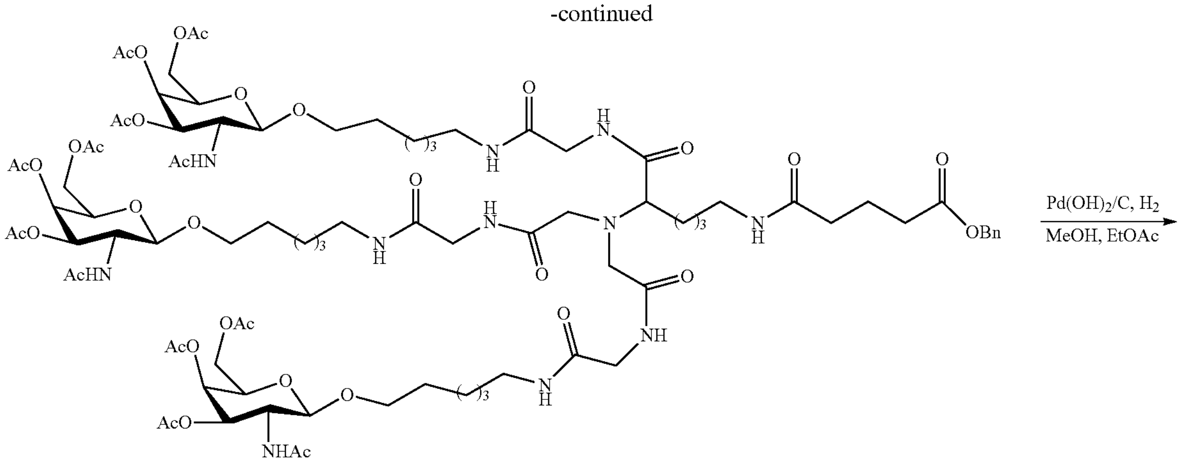

152

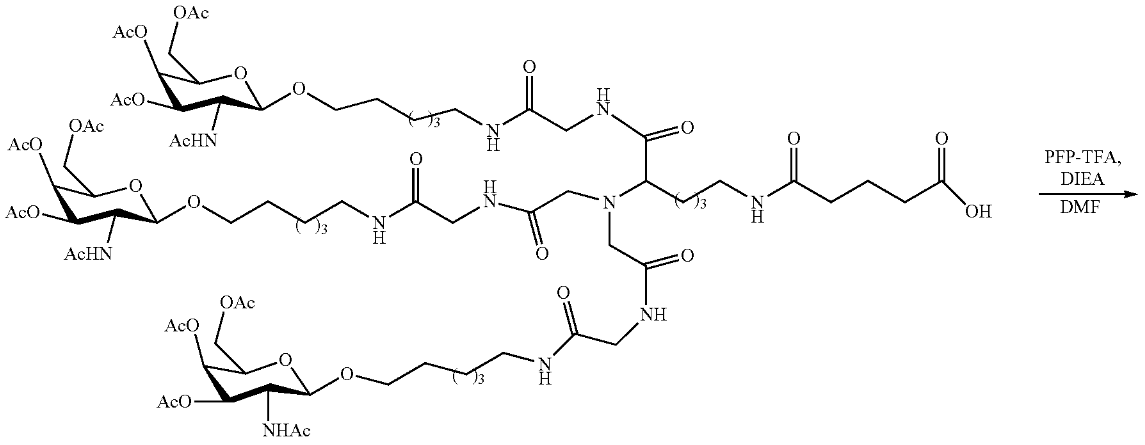

153

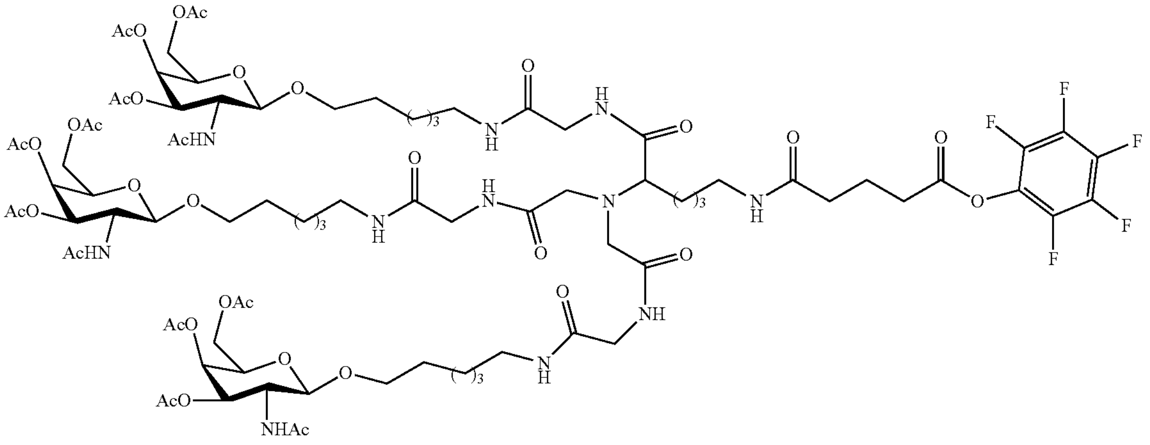

154

Compound 83a (0.11 g, 0.33 mmol) was dissolved in anhydrous DMF (5 mL) and N,N-Diisopropylethylamine (75 μL, 1 mmol) and PFP-TFA (90 μL, 0.76 mmol) were added. The reaction mixture turned magenta upon contact, and gradually turned orange over the next 30 minutes. Progress of reaction was monitored by TLC and LCMS. Upon completion (formation of the PFP ester), a solution of compound 151 (0.57 g, 0.33 mmol) in DMF was added. The pH of the reaction was adjusted to pH=9-10 by addition of N,N-Diisopropylethylamine (if necessary). The reaction mixture was stirred under nitrogen for ~ 30 min. Upon completion, the majority of the solvent was removed under reduced pressure. The residue was diluted with $CH_2Cl_2$ and washed with aqueous saturated $NaHCO_3$, followed by brine. The organic phase separated, dried over $MgSO_4$, filtered, and concentrated to an orange syrup. The residue was purified by silica gel column chromatography (2-10% MeOH in $CH_2Cl_2$) to yield Compound 152 (0.35 g, 55%). LCMS and $^1H$ NMR were consistent with the desired product.

Compound 152 (0.35 g, 0.182 mmol) was dissolved in 1:1 MeOH/EtOAc (10 mL). The reaction mixture was purged by bubbling a stream of argon thru the solution for 15 minutes. Pearlman's catalyst (palladium hydroxide on carbon) was added (35 mg). Hydrogen gas was bubbled thru the solution for 30 minutes. Upon completion (TLC 10% MeOH in DCM, and LCMS), the catalyst was removed by filtration (syringe-tip Teflon filter, 0.45 μm). The filtrate was concentrated by rotary evaporation, and was dried briefly under high vacuum to yield Compound 153 (0.33 g, quantitative). The LCMS was consistent with desired product.

Compound 153 (0.33 g, 0.18 mmol) was dissolved in anhydrous DMF (5 mL) with stirring under nitrogen. To this N,N-Diisopropylethylamine (65 μL, 0.37 mmol) and PFP-TFA (35 μL, 0.28 mmol) were added. The reaction mixture was stirred under nitrogen for ~ 30 min. The reaction mixture turned magenta upon contact, and gradually turned orange. The pH of the reaction mixture was maintained at pH=9-10 by adding more N,-Diisopropylethylamine. The progress of the reaction was monitored by TLC and LCMS. Upon completion, the majority of the solvent was removed under reduced pressure. The residue was diluted with $CH_2Cl_2$ (50 mL), and washed with saturated aqueous $NaHCO_3$, followed by brine. The organic layer was dried over MgSO4, filtered, and concentrated to an orange syrup. The residue was purified by column chromatography and eluted with 2-10% MeOH in $CH_2Cl_2$ to yield Compound 154 (0.29 g, 79%). LCMS and $^1H$ NMR were consistent with the desired product.

83e

154

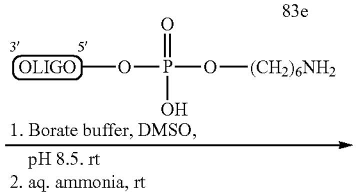

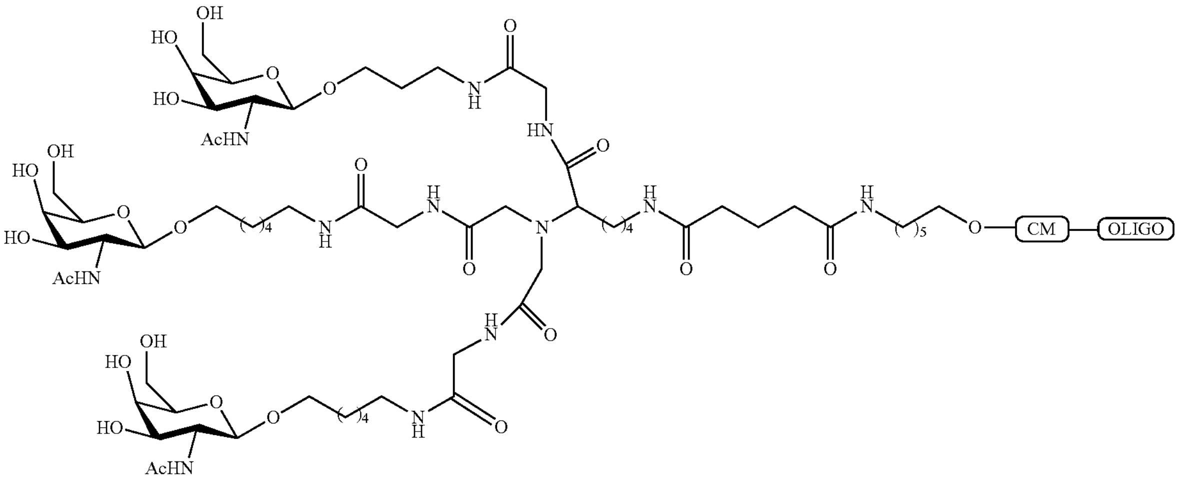

155

Oligomeric Compound 155, comprising a $GalNAc_3$-6 conjugate group, was prepared using the general procedures illustrated in Example 46. The $GalNAc_3$ cluster portion of the conjugate group $GalNAc_3$-6 ($GalNAc_3$-$6_a$) can be combined with any cleavable moiety to provide a variety of conjugate groups. In certain embodiments, the cleavable moiety is —P(═O)(OH)-$A_a$-P(═O)(OH)—.

The structure of $GalNAc_3$-6 ($GalNAc_3$-$6_a$-CM-) is shown below:

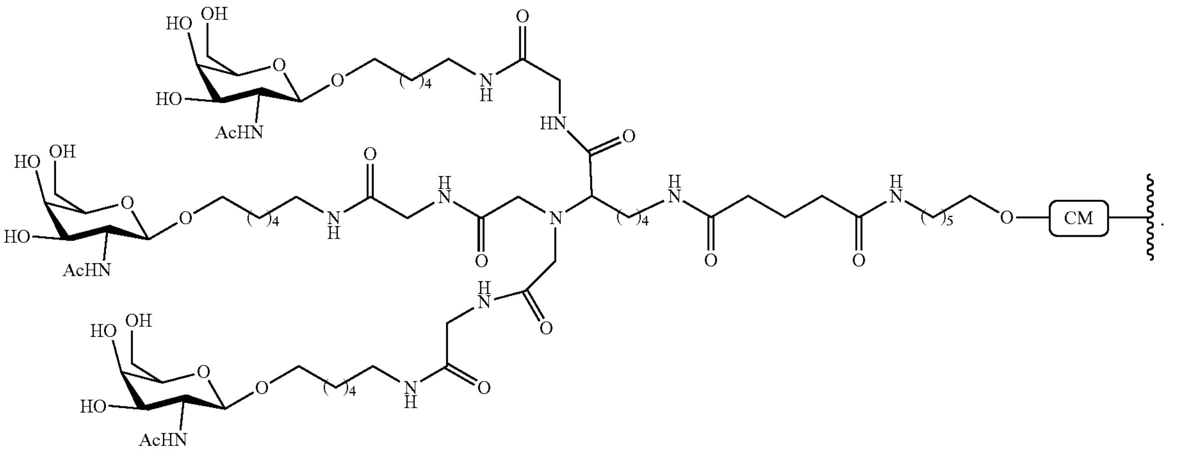

Example 52: Preparation of Oligonucleotide 160 Comprising GalNAc$_3$-9

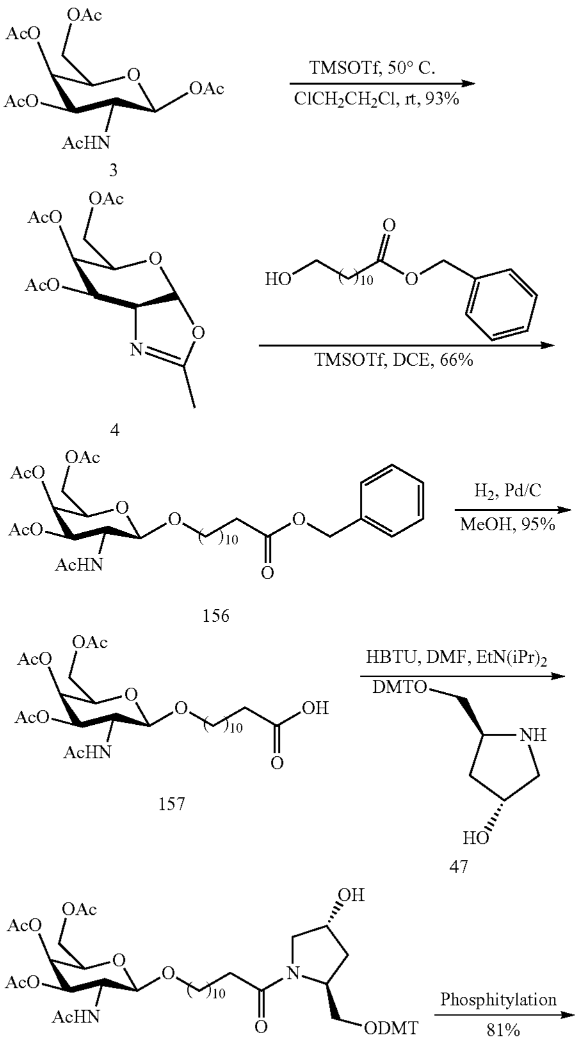

3

4

156

157

47

158

-continued

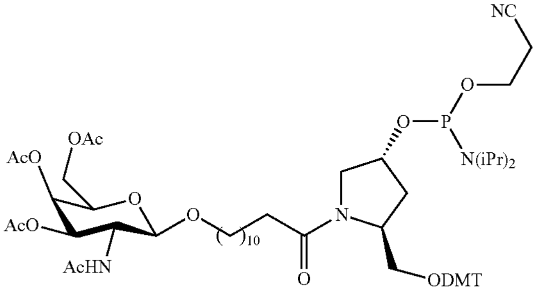

159

Compound 156 was synthesized following the procedure described in the literature (J. Med. Chem. 2004, 47, 5798-5808).

Compound 156, (18.60 g, 29.28 mmol) was dissolved in methanol (200 mL). Palladium on carbon (6.15 g, 10 wt %, loading (dry basis), matrix carbon powder, wet) was added. The reaction mixture was stirred at room temperature under hydrogen for 18 h. The reaction mixture was filtered through a pad of celite and the celite pad was washed thoroughly with methanol. The combined filtrate was washed and concentrated to dryness. The residue was purified by silica gel column chromatography and eluted with 5-10% methanol in dichloromethane to yield Compound 157 (14.26 g, 89%). Mass m/z 544.1 [M−H].

Compound 157 (5 g, 9.17 mmol) was dissolved in anhydrous DMF (30 mL). HBTU (3.65 g, 9.61 mmol) and N,N-Diisopropylethylamine (13.73 mL, 78.81 mmol) were added and the reaction mixture was stirred at room temperature for 5 minutes. To this a solution of compound 47 (2.96 g, 7.04 mmol) was added. The reaction was stirred at room temperature for 8 h. The reaction mixture was poured into a saturated $NaHCO_3$ aqueous solution. The mixture was extracted with ethyl acetate and the organic layer was washed with brine and dried ($Na_2SO_4$), filtered and evaporated. The residue obtained was purified by silica gel column chromatography and eluted with 50% ethyl acetate in hexane to yield compound 158 (8.25 g, 73.3%). The structure was confirmed by MS and $^1H$ NMR analysis.

Compound 158 (7.2 g, 7.61 mmol) was dried over $P_2O_5$ under reduced pressure. The dried compound was dissolved in anhydrous DMF (50 mL). To this $^1H$-tetrazole (0.43 g, 6.09 mmol) and N-methylimidazole (0.3 mL, 3.81 mmol) and 2-cyanoethyl-N,N,N',N'-tetraisopropyl phosphorodiamidite (3.65 mL, 11.50 mmol) were added. The reaction mixture was stirred t under an argon atmosphere for 4 h. The reaction mixture was diluted with ethyl acetate (200 mL). The reaction mixture was washed with saturated $NaHCO_3$ and brine. The organic phase was separated, dried ($Na_2SO_4$), filtered and evaporated. The residue was purified by silica gel column chromatography and eluted with 50-90% ethyl acetate in hexane to yield Compound 159 (7.82 g, 80.5%). The structure was confirmed by LCMS and 31P NMR analysis.

159 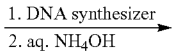

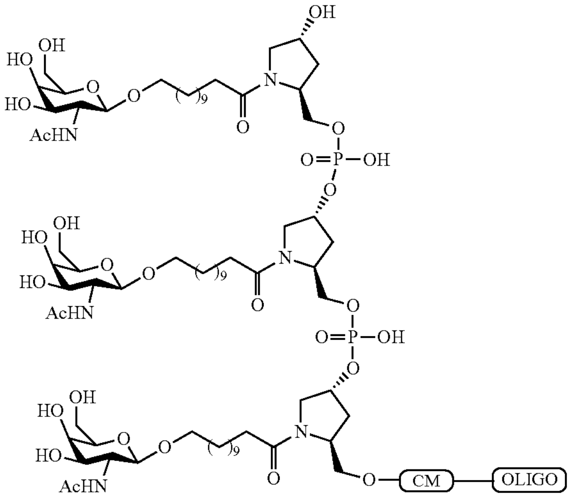

160

Oligomeric Compound 160, comprising a $GalNAc_3$-9 conjugate group, was prepared using standard oligonucleotide synthesis procedures. Three units of compound 159 were coupled to the solid support, followed by nucleotide phosphoramidites. Treatment of the protected oligomeric compound with aqueous ammonia yielded compound 160. The $GalNAc_3$ cluster portion of the conjugate group $GalNAc_3$-9 ($GalNAc_3$-$9_a$) can be combined with any cleavable moiety to provide a variety of conjugate groups. In certain embodiments, the cleavable moiety is —P(═O)(OH)-$A_d$-P(═O)(OH)—. The structure of $GalNAc_3$-9 ($GalNAc_3$-$9_a$-CM) is shown below:

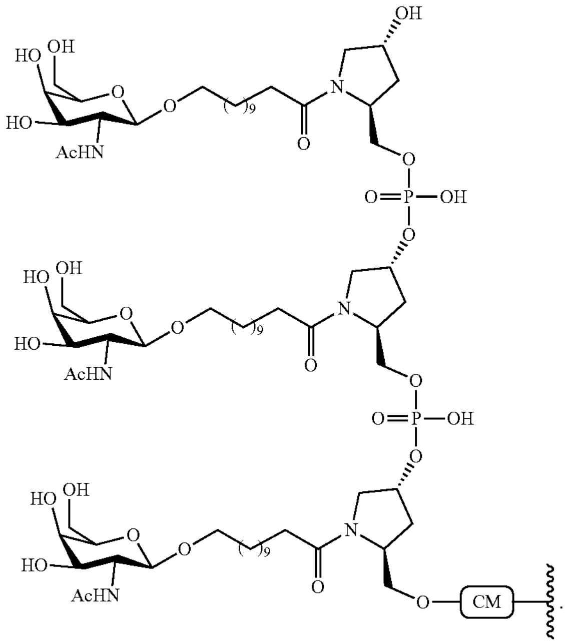

Example 53: Alternate Procedure for Preparation of Compound 18 ($GalNAc_3$-$1_a$ and $GalNAc_3$-$3_a$)

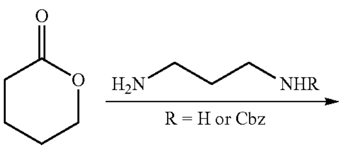

161

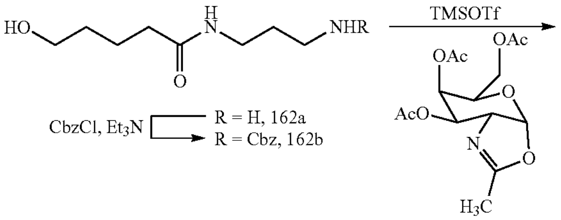

4

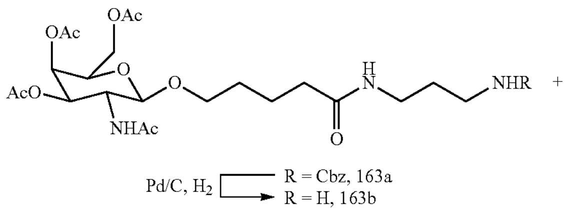

-continued

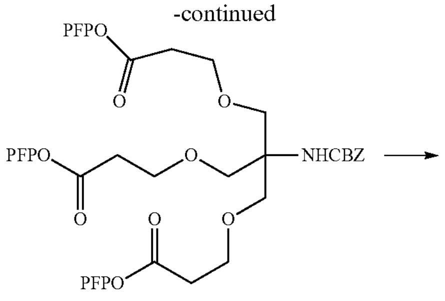

164

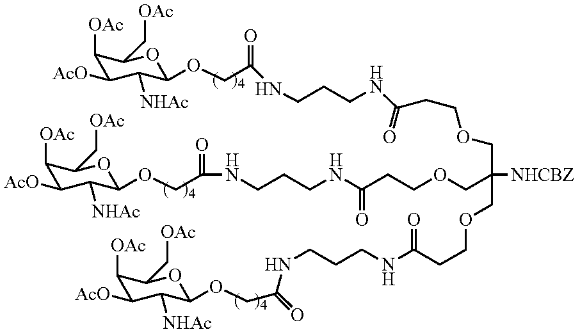

18

Lactone 161 was reacted with diamino propane (3-5 eq) or Mono-Boc protected diamino propane (1 5 eq) to provide alcohol $162_a$ or 162b. When unprotected propanediamine was used for the above reaction, the excess diamine was removed by evaporation under high vacuum and the free amino group in $162_a$ was protected using CbzCl to provide 162b as a white solid after purification by column chromatography. Alcohol 162b was further reacted with compound 4 in the presence of TMSOTf to provide $163_a$ which was converted to 163b by removal of the Cbz group using catalytic hydrogenation. The pentafluorophenyl (PFP) ester 164 was prepared by reacting triacid 113 (see Example 48) with PFPTFA (3.5 eq) and pyridine (3.5 eq) in DMF 10 (0.1 to 0.5 M). The triester 164 was directly reacted with the amine 163b (3-4 eq) and DIPEA (3-4 eq) to provide Compound 18. The above method greatly facilitates purification of intermediates and minimizes the formation of byproducts which are formed using the procedure described in Example 4.

Example 54: Alternate Procedure for Preparation of Compound 18 (GalNAc$_3$-1$_a$ and GalNAc$_3$-3$_a$)

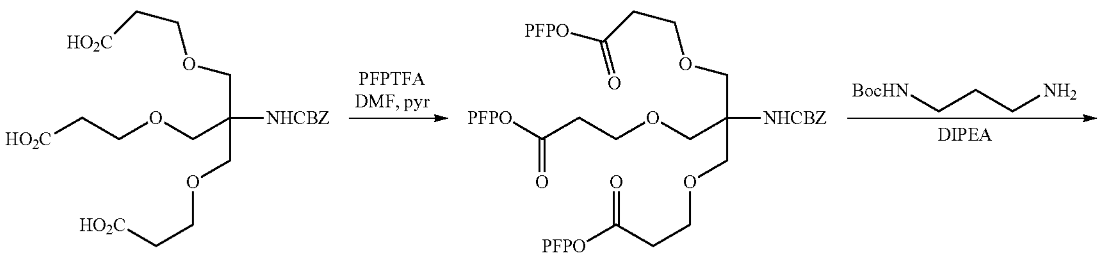

113

164

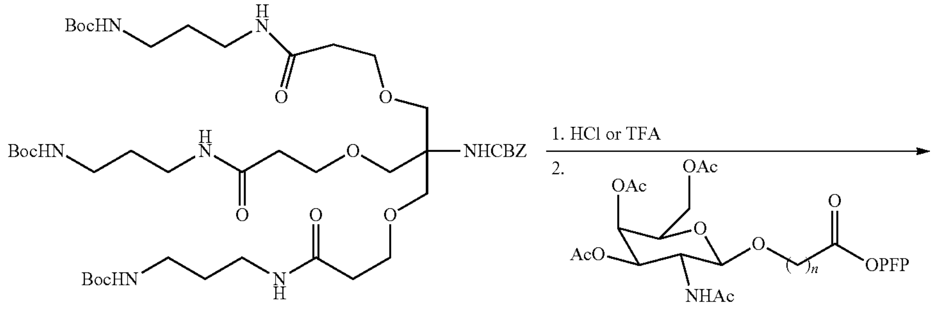

165

166

1. 1,6-hexanediol
   or 1,5-pentane-diol
   TMSOTf + compound 4
2. TEMPO
3. PFPTFA, pyr -continued

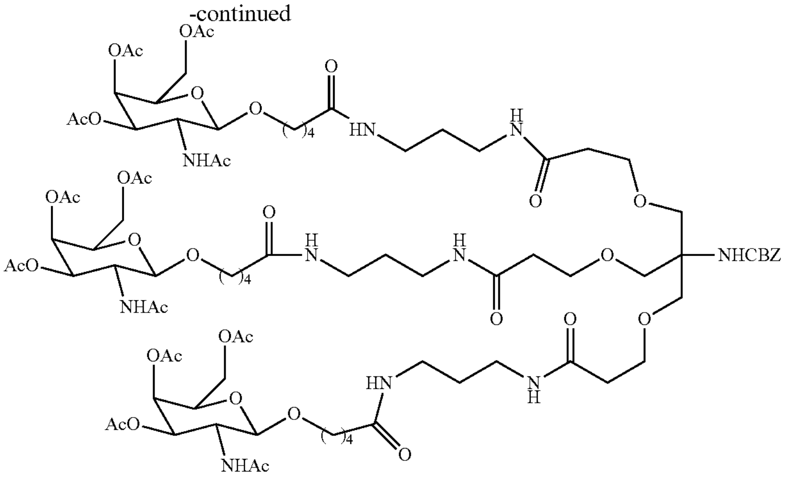

18

The triPFP ester 164 was prepared from acid 113 using the procedure outlined in example 53 above and reacted with mono-Boc protected diamine to provide 165 in essentially quantitative yield. The Boc groups were removed with hydrochloric acid or trifluoroacetic acid to provide the triamine which was reacted with the PFP activated acid 166 in the presence of a suitable base such as DIPEA to provide Compound 18.

The PFP protected Gal-NAc acid 166 was prepared from the corresponding acid by treatment with PFPTFA (1-1.2 eq) and pyridine (1-1.2 eq) in DMF. The precursor acid in turn was prepared from the corresponding alcohol by oxidation using TEMPO(0.2 eq) and BAIB in acetonitrile and water. The precursor alcohol was prepared from sugar intermediate 4 by reaction with 1,6-hexanediol (or 1,5-pentanediol or other diol for other n values)(2-4 eq) and TMSOTf using conditions described previously in example 47.

Example 55: Dose-dependent study of oligonucleotides comprising either a 3' or 5'-conjugate group (Comparison of GalNAc$_3$-1, 3, 8 and 9) Targeting SRB-1 In Vivo The oligonucleotides listed below were tested in a dose-dependent study for antisense inhibition of SRB-1 in mice. Unconjugated ISIS 353382 was included as a standard. Each of the various GalNAc$_3$ conjugate groups was attached at either the 3' or 5' terminus of the respective oligonucleotide by a phosphodiester linked 2'-deoxyadenosine nucleoside (cleavable moiety).

TABLE 26

Modified ASO targeting SRB-1

| ASO | Sequence (5' to 3') | Motif | Conjugate | SEQ ID No. |
|---|---|---|---|---|
| ISIS 353382 (parent) | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}$ ${}^{m}C_{ds}T_{ds}T_{es}{}^{m}C_{es}{}^{m}C_{es}T_{es}T_{e}$ | 5/10/5 | none | 28 |
| ISIS 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}$ ${}^{m}C_{ds}T_{ds}T_{es}{}^{m}C_{es}{}^{m}C_{es}T_{es}T_{eo}\mathbf{A}_{do'}$-**GalNAc$_3$-1**$_a$ | 5/10/5 | **GalNAc$_3$-1** | 29 |
| ISIS 664078 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}$ ${}^{m}C_{ds}T_{ds}T_{es}{}^{m}C_{es}{}^{m}C_{es}T_{es}T_{eo}\mathbf{A}_{do'}$-**GalNAc$_3$-9**$_a$ | 5/10/5 | **GalNAc$_3$-9** | 29 |
| ISIS 661161 | **GalNAc$_3$-3**$_a$-$_{o'}\mathbf{A}_{do}$ $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}$ ${}^{m}C_{ds}T_{ds}T_{es}{}^{m}C_{es}{}^{m}C_{es}T_{es}T_{e}$ | 5/10/5 | **GalNAc$_3$-3** | 30 |
| ISIS 665001 | **GalNAc$_3$-8**$_a$-$_{o'}\mathbf{A}_{do}$ $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}$ ${}^{m}C_{ds}T_{ds}T_{es}{}^{m}C_{es}{}^{m}C_{es}T_{es}T_{e}$ | 5/10/5 | **GalNAc$_3$-8** | 30 |

Capital letters indicate the nucleobase for each nucleoside and ${}^{m}C$ indicates a 5-methyl cytosine.

Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(=O)(OH)—.

Conjugate groups are in bold.

The structure of $GalNAc_3$-1a was shown previously in Example 9. The structure of $GalNAc_3$-9 was shown previously in Example 52. The structure of $GalNAc_3$-3 was shown previously in Example 39. The structure of $GalNAc_3$-8 was shown previously in Example 47.

Treatment

Six week old male Balb/c mice (Jackson Laboratory, Bar Harbor, ME) were injected subcutaneously once at the dosage shown below with ISIS 353382, 655861, 664078, 661161, 665001 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 27, treatment with antisense oligonucleotides lowered SRB-1 mRNA levels in a dose-dependent manner. Indeed, the antisense oligonucleotides comprising the phosphodiester linked $GalNAc_3$-1 and $GalNAc_3$-9 conjugates at the 3' terminus (ISIS 655861 and ISIS 664078) and the $GalNAc_3$-3 and $GalNAc_3$-8 conjugates linked at the 5' terminus (ISIS 661161 and ISIS 665001) showed substantial improvement in potency compared to the unconjugated antisense oligonucleotide (ISIS 353382). Furthermore, ISIS 664078, comprising a $GalNAc_3$-9 conjugate at the 3' terminus was essentially equipotent compared to ISIS 655861, which comprises a $GalNAc_3$-1 conjugate at the 3' terminus. The 5' conjugated antisense oligonucleotides, ISIS 661161 and ISIS 665001, comprising a $GalNAc_3$-3 or $GalNAc_3$-9, respectively, had increased potency compared to the 3' conjugated antisense oligonucleotides (ISIS 655861 and ISIS 664078).

TABLE 27

ASOs containing $GalNAc_3$-1, 3, 8 or 9 targeting SRB-1

| ISIS No. | Dosage (mg/kg) | SRB-1 mRNA (% Saline) | Conjugate |
|---|---|---|---|
| Saline | n/a | 100 | |
| 353382 | 3 | 88 | none |
| | 10 | 68 | |
| | 30 | 36 | |
| 655861 | 0.5 | 98 | $GalNac_3$-1 (3') |
| | 1.5 | 76 | |
| | 5 | 31 | |
| | 15 | 20 | |
| 664078 | 0.5 | 88 | $GalNac_3$-9 (3') |
| | 1.5 | 85 | |
| | 5 | 46 | |
| | 15 | 20 | |
| 661161 | 0.5 | 92 | $GalNac_3$-3 (5') |
| | 1.5 | 59 | |
| | 5 | 19 | |
| | 15 | 11 | |
| 665001 | 0.5 | 100 | $GalNac_3$-8 (5') |
| | 1.5 | 73 | |
| | 5 | 29 | |
| | 15 | 13 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in the table below.

TABLE 28

| ISIS No. | Dosage mg/kg | ALT | AST | Total Bilirubin | BUN | Conjugate |
|---|---|---|---|---|---|---|
| Saline | | 24 | 59 | 0.1 | 37.52 | |
| 353382 | 3 | 21 | 66 | 0.2 | 34.65 | none |
| | 10 | 22 | 54 | 0.2 | 34.2 | |
| | 30 | 22 | 49 | 0.2 | 33.72 | |
| 655861 | 0.5 | 25 | 62 | 0.2 | 30.65 | $GalNac_3$-1 (3') |
| | 1.5 | 23 | 48 | 0.2 | 30.97 | |
| | 5 | 28 | 49 | 0.1 | 32.92 | |
| | 15 | 40 | 97 | 0.1 | 31.62 | |
| 664078 | 0.5 | 40 | 74 | 0.1 | 35.3 | $GalNac_3$-9 (3') |
| | 1.5 | 47 | 104 | 0.1 | 32.75 | |
| | 5 | 20 | 43 | 0.1 | 30.62 | |
| | 15 | 38 | 92 | 0.1 | 26.2 | |
| 661161 | 0.5 | 101 | 162 | 0.1 | 34.17 | $GalNac_3$-3 (5') |
| | 1.5 g | 42 | 100 | 0.1 | 33.37 | |
| | 5 g | 23 | 99 | 0.1 | 34.97 | |
| | 15 | 53 | 83 | 0.1 | 34.8 | |
| 665001 | 0.5 | 28 | 54 | 0.1 | 31.32 | $GalNac_3$-8 (5') |
| | 1.5 | 42 | 75 | 0.1 | 32.32 | |
| | 5 | 24 | 42 | 0.1 | 31.85 | |
| | 15 | 32 | 67 | 0.1 | 31. | |

Example 56: Dose-Dependent Study of Oligonucleotides Comprising Either a 3' or 5'-Conjugate Group (Comparison of $GalNAc_3$-1, 2, 3, 5, 6, 7 and 10) Targeting SRB-1 In Vivo The oligonucleotides listed below were tested in a dose-dependent study for antisense inhibition of SRB-1 in mice. Unconjugated ISIS 353382 was included as a standard. Each of the various $GalNAc_3$ conjugate groups was attached at the 5' terminus of the respective oligonucleotide by a phosphodiester linked 2'-deoxyadenosine nucleoside (cleavable moiety) except for ISIS 655861 which had the $GalNAc_3$ conjugate group attached at the 3' terminus.

TABLE 29

Modified ASO targeting SRB-1

| ASO | Sequence (5' to 3') | Motif | Conjugate | SEQ ID No. |
|---|---|---|---|---|
| ISIS 353382 (parent) | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | no conjugate | 28 |
| ISIS 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}\mathbf{A}_{do'}$**-GalNAc**$_3$**-1**$_a$ | 5/10/5 | **GalNAc**$_3$**-1** | 29 |

TABLE 29-continued

Modified ASO targeting SRB-1

| ASO | Sequence (5' to 3') | Motif | Conjugate | SEQ ID No. |
|---|---|---|---|---|
| ISIS 664507 | $\mathbf{GalNAc_3\text{-}2}_a\text{-}_{o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-2** | 30 |
| ISIS 661161 | $\mathbf{GalNAc_3\text{-}3}_a\text{-}_{o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-3** | 30 |
| ISIS 666224 | $\mathbf{GalNAc_3\text{-}5}_a\text{-}_{o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-5** | 30 |
| ISIS 666961 | $\mathbf{GalNAc_3\text{-}6}_a\text{-}_{o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-6** | 30 |
| ISIS 666981 | $\mathbf{GalNAc_3\text{-}7}_a\text{-}_{o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-7** | 30 |
| ISIS 666881 | $\mathbf{GalNAc_3\text{-}10}_a\text{-}_{o'}\mathbf{A}_{do}G_{es}{}^{m}C_{es}T_{es}T_{es}{}^{m}C_{es}A_{ds}G_{ds}T_{ds}{}^{m}C_{ds}A_{ds}G_{ds}A_{ds}{}^{m}C_{ds}T_{ds}T_{es}{}^{m}C_{es}{}^{m}C_{es}{}^{m}C_{es}T_{es}T_{e}$ | 5/10/5 | **GalNAc$_3$-10** | 30 |

Capital letters indicate the nucleobase for each nucleoside and $^{m}C$ indicates a 5-methyl cytosine.
Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—.
Conjugate groups are in bold.

The structure of GalNAc$_3$-1a was shown previously in Example 9. The structure of GalNAc$_3$-2$_a$ was shown previously in Example 37. The structure of GalNAc$_3$-3$_a$ was shown previously in Example 39. The structure of GalNAc$_3$-5$_a$ was shown previously in Example 49. The structure of GalNAc$_3$-6$_a$ was shown previously in Example 51. The structure of GalNAc$_3$-7$_a$ was shown previously in Example 48. The structure of GalNAc$_3$-10$_a$ was shown previously in Example 46.

Treatment

Six week old male Balb/c mice (Jackson Laboratory, Bar Harbor, ME) were injected subcutaneously once at the dosage shown below with ISIS 353382, 655861, 664507, 661161, 666224, 666961, 666981, 666881 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 30, treatment with antisense oligonucleotides lowered SRB-1 mRNA levels in a dose-dependent manner. Indeed, the conjugated antisense oligonucleotides showed substantial improvement in potency compared to the unconjugated antisense oligonucleotide (ISIS 353382). The 5' conjugated antisense oligonucleotides showed a slight increase in potency compared to the 3' conjugated antisense oligonucleotide.

TABLE 30

| ISIS No. | Dosage (mg/kg) | SRB-1 mRNA (% Saline) | Conjugate |
|---|---|---|---|
| Saline | n/a | 100.0 | |
| 353382 | 3 | 96.0 | none |
| | 10 | 73.1 | |
| | 30 | 36.1 | |

TABLE 30-continued

| ISIS No. | Dosage (mg/kg) | SRB-1 mRNA (% Saline) | Conjugate |
|---|---|---|---|
| 655861 | 0.5 | 99.4 | GalNac$_3$-1 (3') |
| | 1.5 | 81.2 | |
| | 5 | 33.9 | |
| | 15 | 15.2 | |
| 664507 | 0.5 | 102.0 | GalNac$_3$-2 (5') |
| | 1.5 | 73.2 | |
| | 5 | 31.3 | |
| | 15 | 10.8 | |
| 661161 | 0.5 | 90.7 | GalNac$_3$-3 (5') |
| | 1.5 | 67.6 | |
| | 5 | 24.3 | |
| | 15 | 11.5 | |
| 666224 | 0.5 | 96.1 | GalNac$_3$-5 (5') |
| | 1.5 | 61.6 | |
| | 5 | 25.6 | |
| | 15 | 11.7 | |
| 666961 | 0.5 | 85.5 | GalNAc$_3$-6 (5') |
| | 1.5 | 56.3 | |
| | 5 | 34.2 | |
| | 15 | 13.1 | |
| 666981 | 0.5 | 84.7 | GalNAc$_3$-7 (5') |
| | 1.5 | 59.9 | |
| | 5 | 24.9 | |
| | 15 | 8.5 | |
| 666881 | 0.5 | 100.0 | GalNAc$_3$-10 (5') |
| | 1.5 | 65.8 | |
| | 5 | 26.0 | |
| | 15 | 13.0 | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 31 below.

TABLE 31

| ISIS No. | Dosage mg/kg | ALT | AST | Total Bilirubin | BUN | Conjugate |
|---|---|---|---|---|---|---|
| Saline | | 26 | 57 | 0.2 | 27 | |
| 353382 | 3 | 25 | 92 | 0.2 | 27 | none |
| | 10 | 23 | 40 | 0.2 | 25 | |
| | 30 | 29 | 54 | 0.1 | 28 | |
| 655861 | 0.5 | 25 | 71 | 0.2 | 34 | GalNac$_3$-1 (3') |
| | 1.5 | 28 | 60 | 0.2 | 26 | |
| | 5 | 26 | 63 | 0.2 | 28 | |
| | 15 | 25 | 61 | 0.2 | 28 | |
| 664507 | 0.5 | 25 | 62 | 0.2 | 25 | GalNac$_3$-2 (5') |
| | 1.5 | 24 | 49 | 0.2 | 26 | |
| | 5 | 21 | 50 | 0.2 | 26 | |
| | 15 | 59 | 84 | 0.1 | 22 | |
| 661161 | 0.5 | 20 | 42 | 0.2 | 29 | GalNac$_3$-3 (5') |
| | 1.5 g | 37 | 74 | 0.2 | 25 | |
| | 5 g | 28 | 61 | 0.2 | 29 | |
| | 15 | 21 | 41 | 0.2 | 25 | |
| 666224 | 0.5 | 34 | 48 | 0.2 | 21 | GalNac$_3$-5 (5') |
| | 1.5 | 23 | 46 | 0.2 | 26 | |
| | 5 | 24 | 47 | 0.2 | 23 | |
| | 15 | 32 | 49 | 0.1 | 26 | |
| 666961 | 0.5 | 17 | 63 | 0.2 | 26 | GalNAc$_3$-6 (5') |
| | 1.5 | 23 | 68 | 0.2 | 26 | |
| | 5 | 25 | 66 | 0.2 | 26 | |
| | 15 | 29 | 107 | 0.2 | 28 | |
| 666981 | 0.5 | 24 | 48 | 0.2 | 26 | GalNAc$_3$-7 (5') |
| | 1.5 | 30 | 55 | 0.2 | 24 | |
| | 5 | 46 | 74 | 0.1 | 24 | |
| | 15 | 29 | 58 | 0.1 | 26 | |
| 666881 | 0.5 | 20 | 65 | 0.2 | 27 | GalNAc$_3$-10 (5') |
| | 1.5 | 23 | 59 | 0.2 | 24 | |
| | 5 | 45 | 70 | 0.2 | 26 | |
| | 15 | 21 | 57 | 0.2 | 24 | |

Example 57: Duration of Action Study of Oligonucleotides Comprising a 3'-Conjugate Group Targeting ApoC III In Vivo Mice were injected once with the doses indicated below and monitored over the course of 42 days for ApoC-III and plasma triglycerides (Plasma TG) levels. The study was performed using 3 transgenic mice that express human APOC-III in each group.

TABLE 32

Modified ASO targeting ApoC III

| ASO | Sequence (5′ to 3′) | Linkages | SEQ ID No. |
|---|---|---|---|
| ISIS 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | PS | 20 |
| ISIS 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}\mathbf{A}_{do'}$-**GalNAc$_3$-1$_a$** | PS | 21 |
| ISIS 647536 | $A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{eo}\mathbf{A}_{do'}$-**GalNAc$_3$-1$_a$** | PO/PS | 21 |

Capital letters indicate the nucleobase for each nucleoside and $^{m}C$ indicates a 5-methyl cytosine.
Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—.
Conjugate groups are in bold.

The structure of GalNAc$_3$-1a was shown previously in Example 9.

TABLE 33

| ApoC III mRNA (% Saline on Day 1) and Plasma TG Levels (% Saline on Day 1) | | | | | | | |
|---|---|---|---|---|---|---|---|
| ASO | Dose | Target | Day 3 | Day 7 | Day 14 | Day 35 | Day 42 |
| Saline | 0 mg/kg | ApoC-III | 98 | 100 | 100 | 95 | 116 |
| ISIS 304801 | 30 mg/kg | ApoC-III | 28 | 30 | 41 | 65 | 74 |
| ISIS 647535 | 10 mg/kg | ApoC-III | 16 | 19 | 25 | 74 | 94 |
| ISIS 647536 | 10 mg/kg | ApoC-III | 18 | 16 | 17 | 35 | 51 |
| Saline | 0 mg/kg | Plasma TG | 121 | 130 | 123 | 105 | 109 |
| ISIS 304801 | 30 mg/kg | Plasma TG | 34 | 37 | 50 | 69 | 69 |
| ISIS 647535 | 10 mg/kg | Plasma TG | 18 | 14 | 24 | 18 | 71 |
| ISIS 647536 | 10 mg/kg | Plasma TG | 21 | 19 | 15 | 32 | 35 |

As can be seen in the table above the duration of action increased with addition of the 3'-conjugate group compared to the unconjugated oligonucleotide. There was a further increase in the duration of action for the conjugated mixed PO/PS oligonucleotide 647536 as compared to the conjugated full PS oligonucleotide 647535.

Example 58: Dose-Dependent Study of Oligonucleotides Comprising a 3'-Conjugate Group (Comparison of GalNAc$_3$-1 and GalNAc$_4$-11) Targeting SRB-1 In Vivo The oligonucleotides listed below were tested in a dose-dependent study for antisense inhibition of SRB-1 in mice. Unconjugated ISIS 440762 was included as an unconjugated standard. Each of the conjugate groups were attached at the 3' terminus of the respective oligonucleotide by a phosphodiester linked 2'-deoxyadenosine nucleoside cleavable moiety.

The structure of GalNAc$_3$-1*a* was shown previously in Example 9. The structure of GalNAc$_3$-11a was shown previously in Example 50.

Treatment

Six week old male Balb/c mice (Jackson Laboratory, Bar Harbor, ME) were injected subcutaneously once at the dosage shown below with ISIS 440762, 651900, 663748 or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 34, treatment with antisense oligonucleotides lowered SRB-1 mRNA levels in a dose-dependent manner. The antisense oligonucleotides comprising the phosphodiester linked GalNAc$_3$-1 and GalNAc$_4$-11 conjugates at the 3' terminus (ISIS 651900 and ISIS 663748) showed substantial improvement in potency compared to the unconjugated antisense oligonucleotide (ISIS 440762). The two conjugated oligonucleotides, GalNAc$_3$-1 and GalNAc$_4$-11, were equipotent.

TABLE 34

| Modified ASO targeting SRB-1 | | | | |
|---|---|---|---|---|
| ASO | Sequence (5' to 3') | Dose mg/kg | % Saline control | SEQ ID No. |
| Saline | | | 100 | |
| ISIS 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | 0.6 | 73.45 | 22 |
| | | 2 | 59.66 | |
| | | 6 | 23.50 | |
| ISIS 651900 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ko}\mathbf{A}_{do'}$-$\mathbf{GalNAc_3}$-$\mathbf{1}_a$ | 0.2 | 62.75 | 23 |
| | | 0.6 | 29.14 | |
| | | 2 | 8.61 | |
| | | 6 | 5.62 | |
| ISIS 663748 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ko}\mathbf{A}_{do'}$-$\mathbf{GalNAc_4}$-$\mathbf{11}_a$ | 0.2 | 63.99 | 23 |
| | | 0.6 | 33.53 | |
| | | 2 | 7.58 | |
| | | 6 | 5.52 | |

Capital letters indicate the nucleobase for each nucleoside and $^{m}C$ indicates a 5-methyl cytosine.
Subscripts: "e" indicates a 2'-MOE modified nucleoside; "k" indicates 6'-(S)-$CH_3$ bicyclic nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—.
Conjugate groups are in bold.

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group. ALTs, ASTs, total bilirubin and BUN values are shown in Table 35 below.

TABLE 35

| ISIS No. | Dosage mg/kg | ALT | AST | Total Bilirubin | BUN | Conjugate |
|---|---|---|---|---|---|---|
| Saline | | 30 | 76 | 0.2 | 40 | |
| 440762 | 0.60 | 32 | 70 | 0.1 | 35 | none |
| | 2 | 26 | 57 | 0.1 | 35 | |
| | 6 | 31 | 48 | 0.1 | 39 | |
| 651900 | 0.2 | 32 | 115 | 0.2 | 39 | $GalNac_3$-1 (3') |
| | 0.6 | 33 | 61 | 0.1 | 35 | |
| | 2 | 30 | 50 | 0.1 | 37 | |
| | 6 | 34 | 52 | 0.1 | 36 | |
| 663748 | 0.2 | 28 | 56 | 0.2 | 36 | $GalNac_4$-11 (3') |
| | 0.6 | 34 | 60 | 0.1 | 35 | |
| | 2 | 44 | 62 | 0.1 | 36 | |
| | 6 | 38 | 71 | 0.1 | 33 | |

Example 59: Effects of $GalNAc_3$-1 conjugated ASOs targeting FXI in vivo

The oligonucleotides listed below were tested in a multiple dose study for antisense inhibition of FXI in mice. ISIS 404071 was included as an unconjugated standard. Each of the conjugate groups was attached at the 3' terminus of the respective oligonucleotide by a phosphodiester linked 2'-deoxyadenosine nucleoside cleavable moiety.

TABLE 36

| Modified ASOs targeting FXI | | | |
|---|---|---|---|
| ASO | Sequence (5' to 3') | Linkages | SEQ ID No. |
| ISIS 404071 | $T_{es}G_{es}G_{es}T_{es}A_{es}A_{ds}T_{ds}{}^{m}C_{ds}{}^{m}C_{ds}A_{ds}{}^{m}C_{ds}T_{ds}T_{ds}T_{ds}{}^{m}C_{ds}A_{es}G_{es}A_{es}G_{es}G_{e}$ | PS | 31 |
| ISIS 656172 | $T_{es}G_{es}G_{es}T_{es}A_{es}A_{ds}T_{ds}{}^{m}C_{ds}{}^{m}C_{ds}A_{ds}{}^{m}C_{ds}T_{ds}T_{ds}T_{ds}{}^{m}C_{ds}A_{es}G_{es}A_{es}G_{es}G_{eo}\mathbf{A}_{do'}$-$\mathbf{GalNAc_3}$-$\mathbf{1}_a$ | PS | 32 |
| ISIS 656173 | $T_{es}G_{eo}G_{eo}T_{eo}A_{eo}A_{ds}T_{ds}{}^{m}C_{ds}{}^{m}C_{ds}A_{ds}{}^{m}C_{ds}T_{ds}T_{ds}T_{ds}{}^{m}C_{ds}A_{eo}G_{eo}A_{es}G_{es}G_{eo}\mathbf{A}_{do'}$-$\mathbf{GalNAc_3}$-$\mathbf{1}_a$ | PO/PS | 32 |

Capital letters indicate the nucleobase for each nucleoside and $^{m}C$ indicates a 5-methyl cytosine.
Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—.
Conjugate groups are in bold.

The structure of $GalNAc_3$-1a was shown previously in Example 9.

Treatment

Six week old male Balb/c mice (Jackson Laboratory, Bar Harbor, ME) were injected subcutaneously twice a week for 3 weeks at the dosage shown below with ISIS 404071, 656172, 656173 or with PBS treated control. Each treatment group consisted of 4 animals. The mice were sacrificed 72 hours following the final administration to determine the liver FXI mRNA levels using real-time PCR and RIBOGREEN® RNA quantification reagent (Molecular Probes, Inc. Eugene, OR) according to standard protocols. Plasma FXI protein levels were also measured using ELISA. FXI mRNA levels were determined relative to total RNA (using RIBOGREEN®), prior to normalization to PBS-treated control. The results below are presented as the average percent of FXI mRNA levels for each treatment group. The data was normalized to PBS-treated control and is denoted as "% PBS". The $ED_{50}$s were measured using similar methods as described previously and are presented below.

TABLE 37

| Factor XI mRNA (% Saline) | | | | |
|---|---|---|---|---|
| ASO | Dose mg/kg | % Control | Conjugate | Linkages |
| Saline | | 100 | none | |
| ISIS | 3 | 92 | none | PS |
| 404071 | 10 | 40 | | |
| | 30 | 15 | | |
| ISIS | 0.7 | 74 | $GalNAc_3$-1 | PS |
| 656172 | 2 | 33 | | |
| | 6 | 9 | | |
| ISIS | 0.7 | 49 | $GalNAc_3$-1 | PO/PS |
| 656173 | 2 | 22 | | |
| | 6 | 1 | | |

As illustrated in Table 37, treatment with antisense oligonucleotides lowered FXI mRNA levels in a dose-dependent manner. The oligonucleotides comprising a 3'-$GalNAc_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO(ISIS 656173).

As illustrated in Table 37a, treatment with antisense oligonucleotides lowered FXI protein levels in a dose-dependent manner. The oligonucleotides comprising a 3'-$GalNAc_3$-1 conjugate group showed substantial improvement in potency compared to the unconjugated antisense oligonucleotide (ISIS 404071). Between the two conjugated oligonucleotides an improvement in potency was further provided by substituting some of the PS linkages with PO(ISIS 656173).

TABLE 37a

| Factor XI protein (% Saline) | | | | |
|---|---|---|---|---|
| ASO | Dose mg/kg | Protein (% Control) | Conjugate | Linkages |
| Saline | | 100 | none | |
| ISIS | 3 | 127 | none | PS |
| 404071 | 10 | 32 | | |
| | 30 | 3 | | |
| ISIS | 0.7 | 70 | $GalNAc_3$-1 | PS |
| 656172 | 2 | 23 | | |
| | 6 | 1 | | |

TABLE 37a-continued

| Factor XI protein (% Saline) | | | | |
|---|---|---|---|---|
| ASO | Dose mg/kg | Protein (% Control) | Conjugate | Linkages |
| ISIS | 0.7 | 45 | $GalNAc_3$-1 | PO/PS |
| 656173 | 2 | 6 | | |
| | 6 | 0 | | |

Liver transaminase levels, alanine aminotransferase (ALT) and aspartate aminotransferase (AST), in serum were measured relative to saline injected mice using standard protocols. Total bilirubin, total albumin, CRE and BUN were also evaluated. The change in body weights was evaluated with no significant change from the saline group. ALTs, ASTs, total bilirubin and BUN values are shown in the table below.

TABLE 38

| ISIS No. | Dosage mg/kg | ALT | AST | Total Albumin | Total Bilirubin | CRE | BUN | Conjugate |
|---|---|---|---|---|---|---|---|---|
| Saline | | 71.8 | 84.0 | 3.1 | 0.2 | 0.2 | 22.9 | |
| 404071 | 3 | 152.8 | 176.0 | 3.1 | 0.3 | 0.2 | 23.0 | none |
| | 10 | 73.3 | 121.5 | 3.0 | 0.2 | 0.2 | 21.4 | |
| | 30 | 82.5 | 92.3 | 3.0 | 0.2 | 0.2 | 23.0 | |
| 656172 | 0.7 | 62.5 | 111.5 | 3.1 | 0.2 | 0.2 | 23.8 | $GalNac_3$-1 (3') |
| | 2 | 33.0 | 51.8 | 2.9 | 0.2 | 0.2 | 22.0 | |
| | 6 | 65.0 | 71.5 | 3.2 | 0.2 | 0.2 | 23.9 | |
| 656173 | 0.7 | 54.8 | 90.5 | 3.0 | 0.2 | 0.2 | 24.9 | $GalNac_3$-1 (3') |
| | 2 | 85.8 | 71.5 | 3.2 | 0.2 | 0.2 | 21.0 | |
| | 6 | 114.0 | 101.8 | 3.3 | 0.2 | 0.2 | 22.7 | |

Example 60: Effects of Conjugated ASOs Targeting SRB-1 In Vitro

The oligonucleotides listed below were tested in a multiple dose study for antisense inhibition of SRB-1 in primary mouse hepatocytes. ISIS 353382 was included as an unconjugated standard. Each of the conjugate groups were attached at the 3' or 5' terminus of the respective oligonucleotide by a phosphodiester linked 2'-deoxyadenosine nucleoside cleavable moiety.

TABLE 39

| Modified ASO targeting SRB-1 | | | | |
|---|---|---|---|---|
| ASO | Sequence (5' to 3') | Motif | Conjugate | SEQ ID No. |
| ISIS 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}T_{es}T_{e}$ | 5/10/5 | none | 28 |
| ISIS 655861 | $G_{es}{}^{m}C_{es}T_{e}ST_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}$**$A_{do'}$-$GalNAc_3$-$1_a$** | 5/10/5 | **$GalNAc_3$-1** | 29 |
| ISIS 655862 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo}$**$A_{do'}$-$GalNAc_3$-$1_a$** | 5/10/5 | **$GalNAc_3$-1** | 29 |

TABLE 39-continued

Modified ASO targeting SRB-1

| ASO | Sequence (5' to 3') | Motif | Conjugate | SEQ ID No. |
|---|---|---|---|---|
| ISIS 661161 | $\mathbf{GalNAc_3\text{-}3}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-3** | 30 |
| ISIS 665001 | $\mathbf{GalNAc_3\text{-}8}_{a\text{-}o'}\mathbf{A}_{do}G_{es}{}^{m}G_{es}T_{es}T_{e}S{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-8** | 30 |
| ISIS 664078 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}\mathbf{A}_{do'}\text{-}\mathbf{GalNAc_3\text{-}9}_{a}$ | 5/10/5 | **GalNAc$_3$-9** | 29 |
| ISIS 666961 | $\mathbf{GalNAc_3\text{-}6}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-6** | 30 |
| ISIS 664507 | $\mathbf{GalNAc_3\text{-}2}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-2** | 30 |
| ISIS 666881 | $\mathbf{GalNAc_3\text{-}10}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-10** | 30 |
| ISIS 666224 | $\mathbf{GalNAc_3\text{-}5}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-5** | 30 |
| ISIS 666981 | $\mathbf{GalNAc_3\text{-}7}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | 5/10/5 | **GalNAc$_3$-7** | 30 |

Capital letters indicate the nucleobase for each nucleoside and $^{m}$C indicates a 5-methyl cytosine.

Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—.

Conjugate groups are in bold.

The structure of GalNAc$_3$-1a was shown previously in Example 9. The structure of GalNAc$_3$-3a was shown previously in Example 39. The structure of GalNAc$_3$-8a was shown previously in Example 47. The structure of GalNAc$_3$-9a was shown previously in Example 52. The structure of GalNAc$_3$-6a was shown previously in Example 51. The structure of GalNAc$_3$-2a was shown previously in Example 37. The structure of GalNAc$_3$-10a was shown previously in Example 46. The structure of GalNAc$_3$-5a was shown previously in Example 49. The structure of GalNAc$_3$-7a was shown previously in Example 48.

Treatment

The oligonucleotides listed above were tested in vitro in primary mouse hepatocyte cells plated at a density of 25,000 cells per well and treated with 0.03, 0.08, 0.24, 0.74, 2.22, 6.67 or 20 nM modified oligonucleotide. After a treatment period of approximately 16 hours, RNA was isolated from the cells and mRNA levels were measured by quantitative real-time PCR and the SRB-1 mRNA levels were adjusted according to total RNA content, as measured by RIBOGREEN®.

The $IC_{50}$ was calculated using standard methods and the results are presented in Table 40. The results show that, under free uptake conditions in which no reagents or electroporation techniques are used to artificially promote entry of the oligonucleotides into cells, the oligonucleotides comprising a GalNAc conjugate were significantly more potent in hepatocytes than the parent oligonucleotide (ISIS 353382) that does not comprise a GalNAc conjugate.

TABLE 40

| ASO | $IC_{50}$ (nM) | Internucleoside linkages | Conjugate | SEQ ID No. |
|---|---|---|---|---|
| ISIS 353382 | 190[a] | PS | none | 28 |
| ISIS 655861 | 11[a] | PS | GalNAc$_3$-1 | 29 |
| ISIS 655862 | 3 | PO/PS | GalNAc$_3$-1 | 29 |
| ISIS 661161 | 15[a] | PS | GalNAc$_3$-3 | 30 |
| ISIS 665001 | 20 | PS | GalNAc$_3$-8 | 30 |
| ISIS 664078 | 55 | PS | GalNAc$_3$-9 | 29 |
| ISIS 666961 | 22[a] | PS | GalNAc$_3$-6 | 30 |
| ISIS 664507 | 30 | PS | GalNAc$_3$-2 | 30 |
| ISIS 666881 | 30 | PS | GalNAc$_3$-10 | 30 |
| ISIS 666224 | 30[a] | PS | GalNAc$_3$-5 | 30 |
| ISIS 666981 | 40 | PS | GalNAc$_3$-7 | 30 |

[a]Average of multiple runs.

Example 61: Preparation of oligomeric compound 175 comprising GalNAc$_3$-12

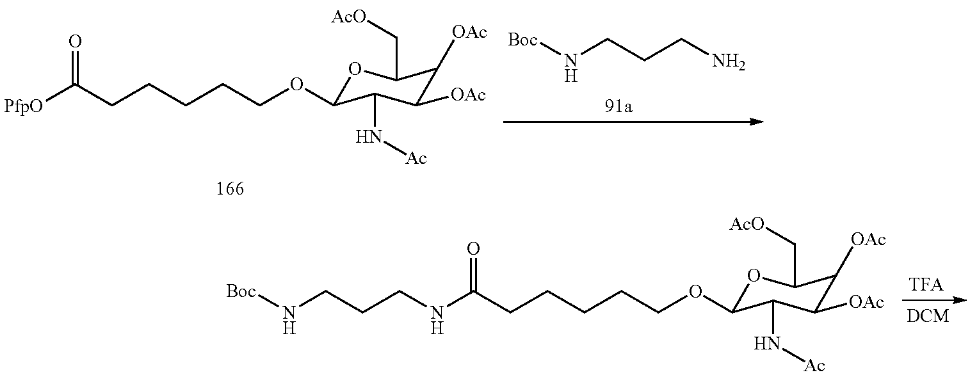

166

167

-continued
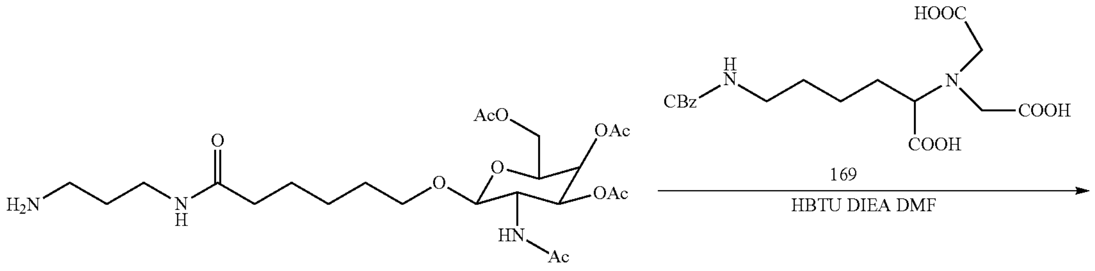
168
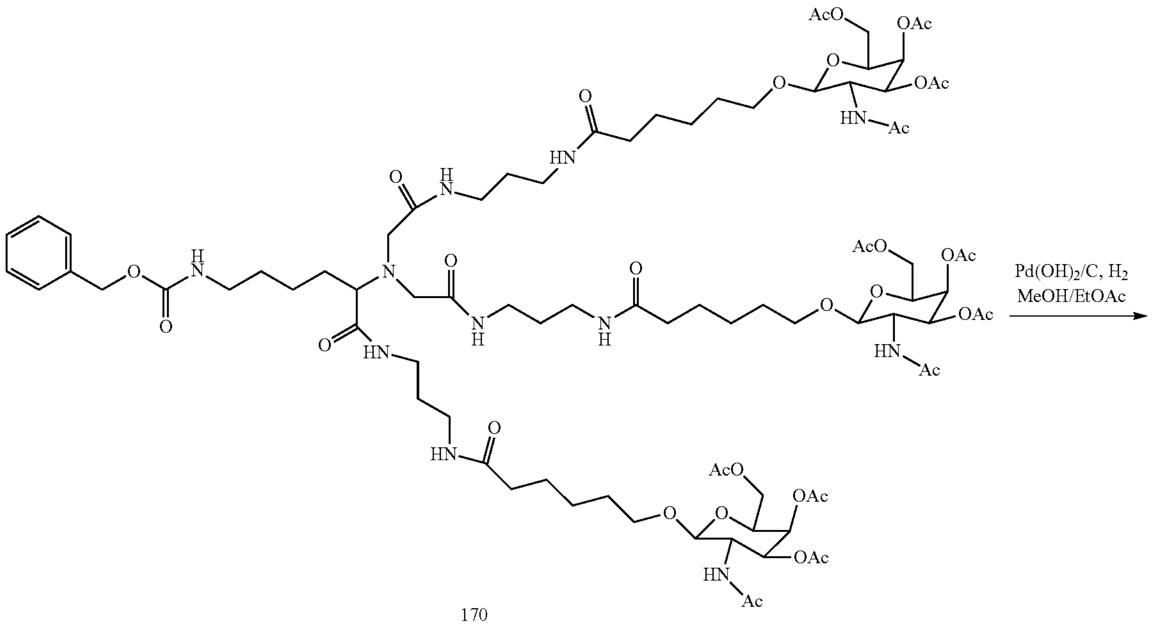
170
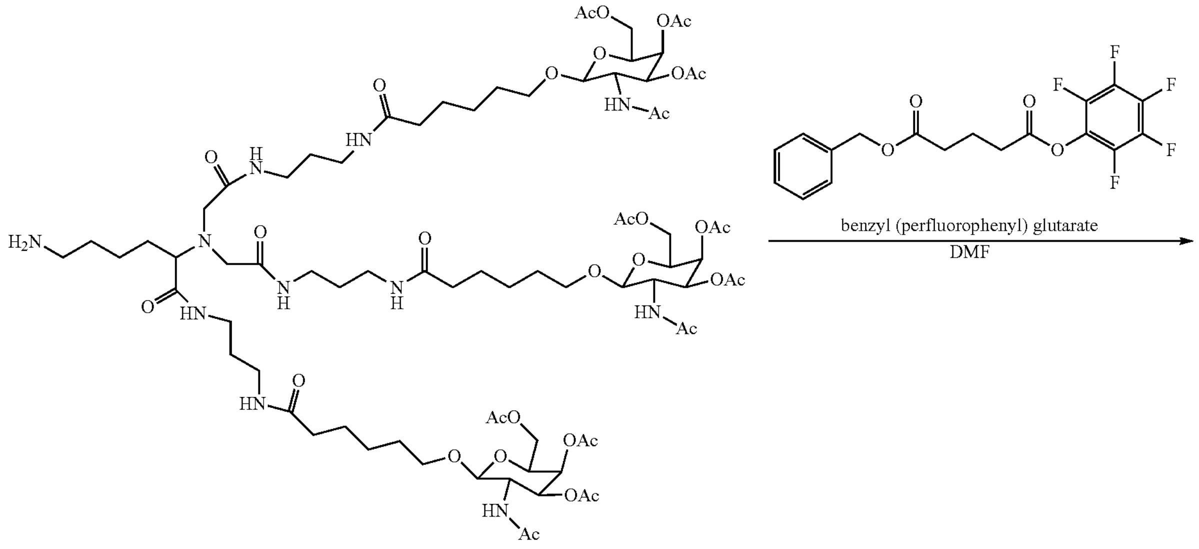
171

-continued
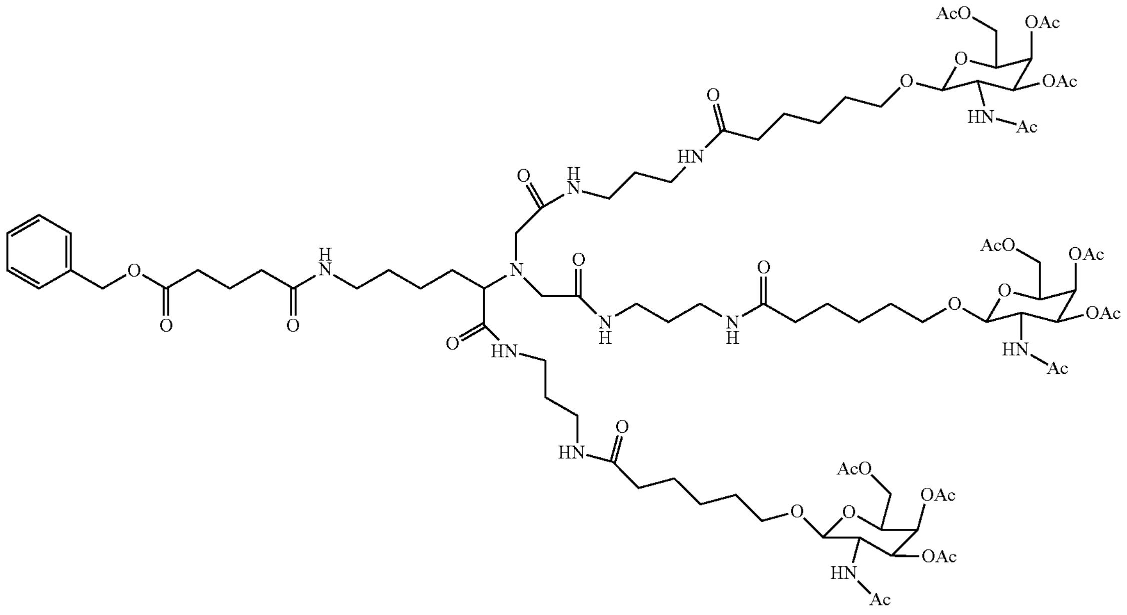
172
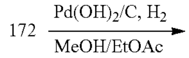
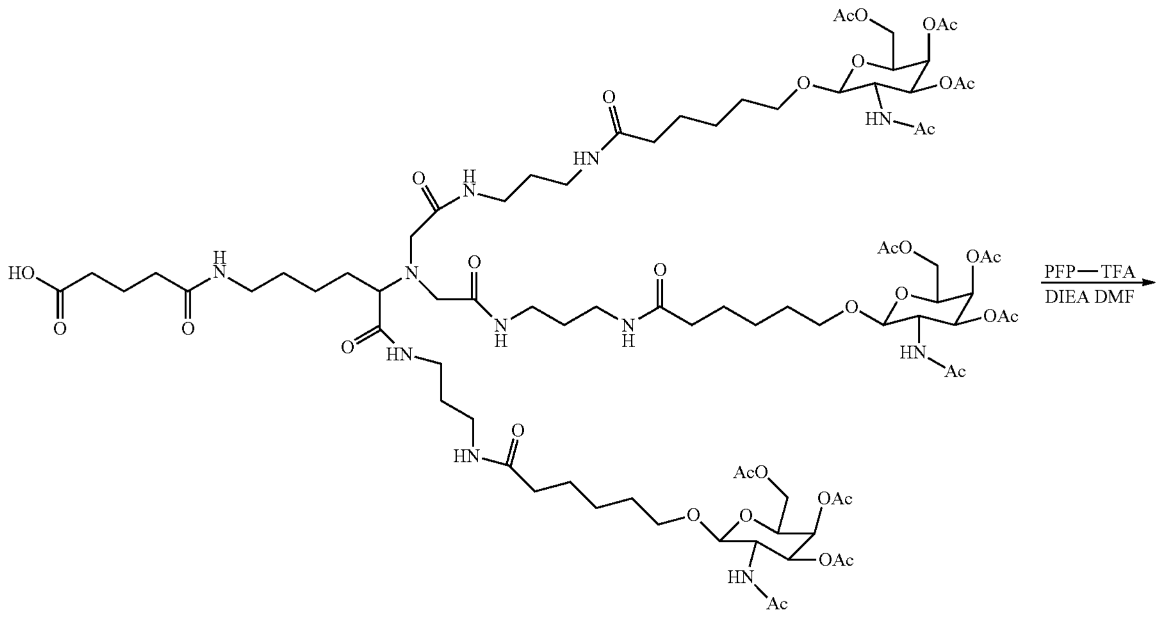
173

-continued

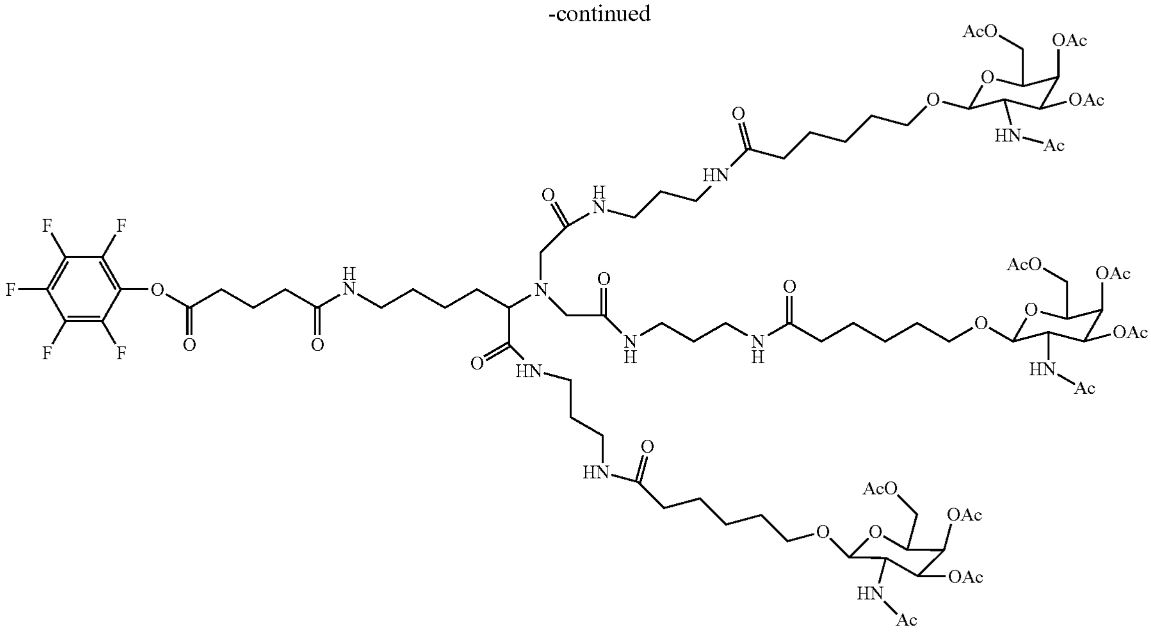

174

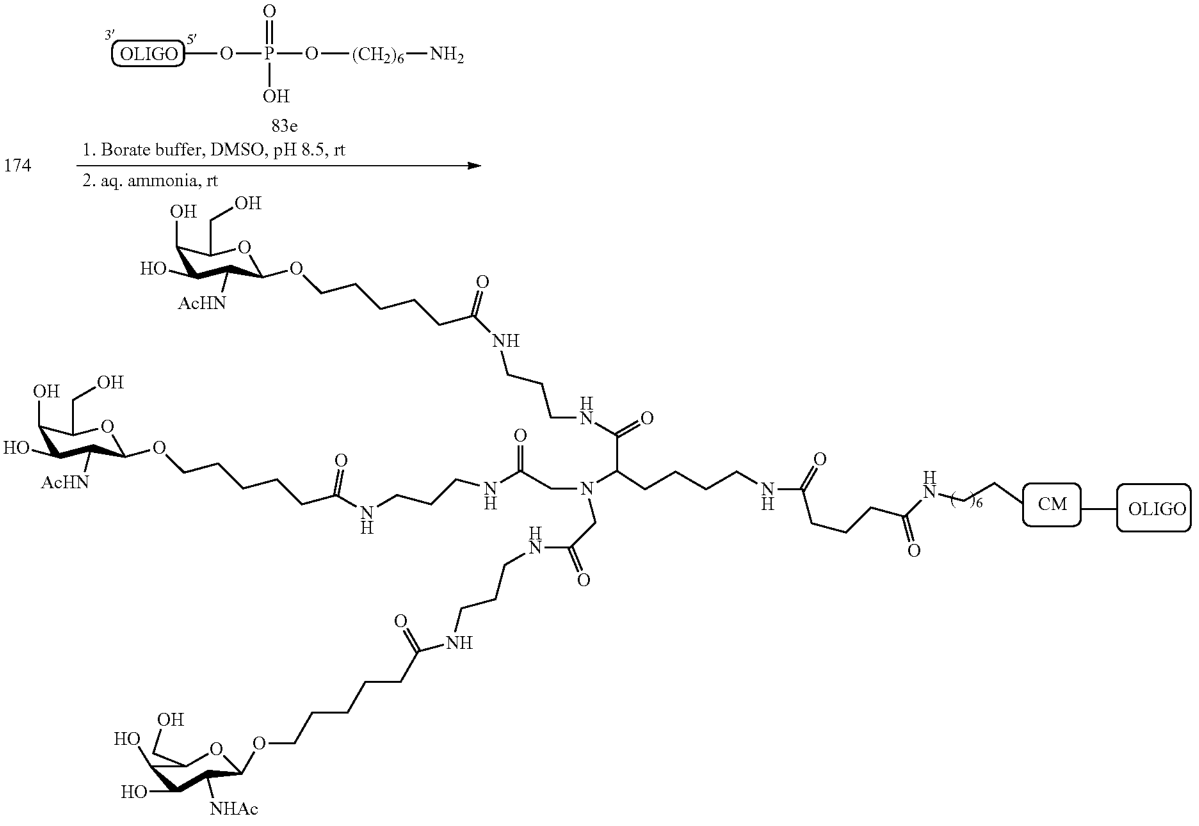

175

Compound 169 is commercially available. Compound 172 was prepared by addition of benzyl (perfluorophenyl) glutarate to compound 171. The benzyl (perfluorophenyl) glutarate was prepared by adding PFP-TFA and DIEA to 5-(benzyloxy)-5-oxopentanoic acid in DMF. Oligomeric compound 175, comprising a GalNAc$_3$-12 conjugate group, was prepared from compound 174 using the general procedures illustrated in Example 46. The GalNAc$_3$ cluster portion of the conjugate group GalNAc$_3$-12 (GalNAc$_3$-12$_a$) can be combined with any cleavable moiety to provide a variety of conjugate groups. In a certain embodiments, the cleavable moiety is —P(═O)(OH)-A$_a$-P(═O)(OH)—. The structure of GalNAc$_3$-12 (GalNAc$_3$-12$_a$-CM-) is shown below:

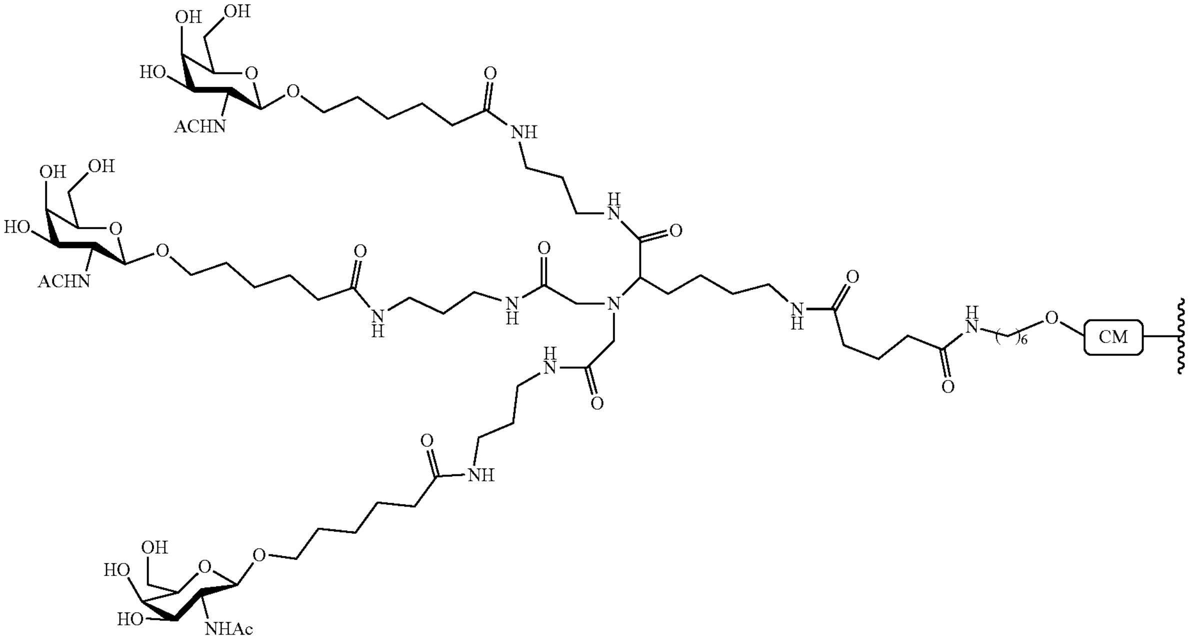
Example 62: Preparation of Oligomeric Compound 180 Comprising GalNAc$_3$-13
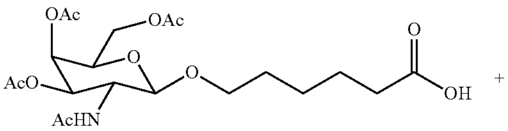
176
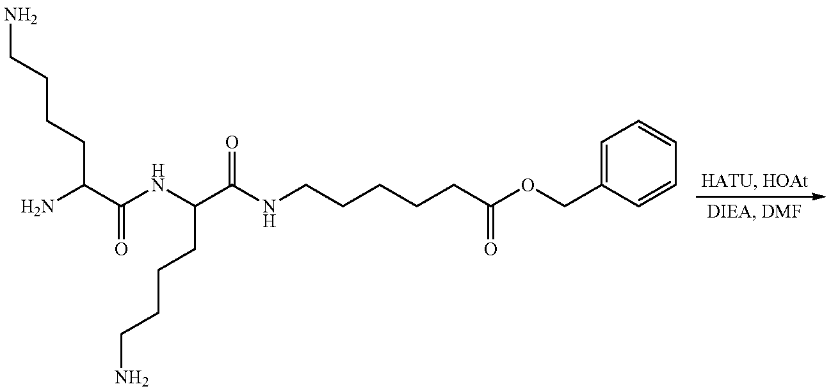
128

-continued
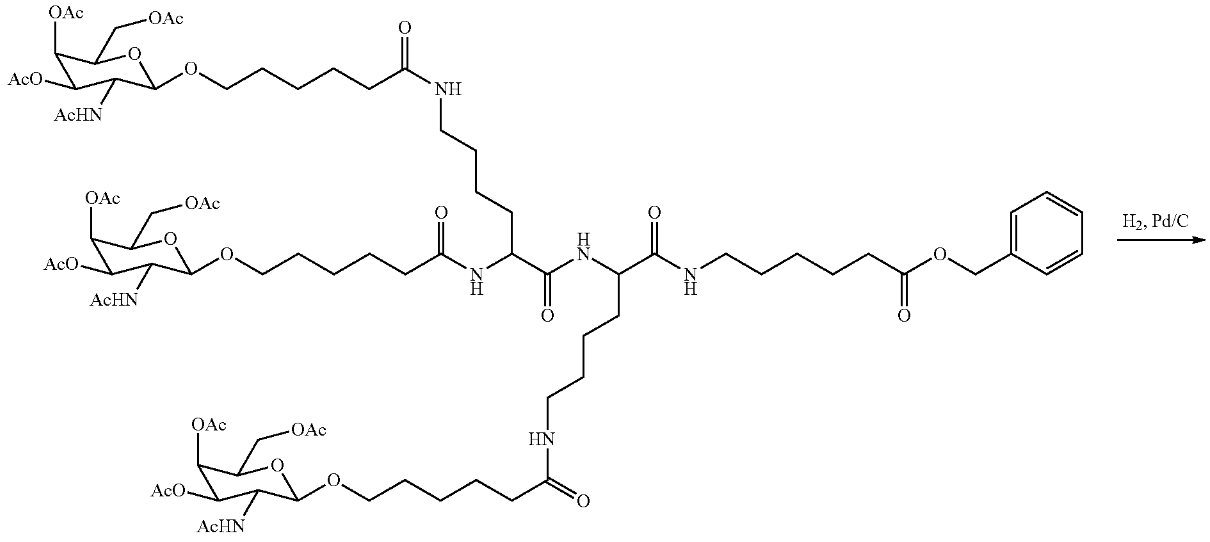
177
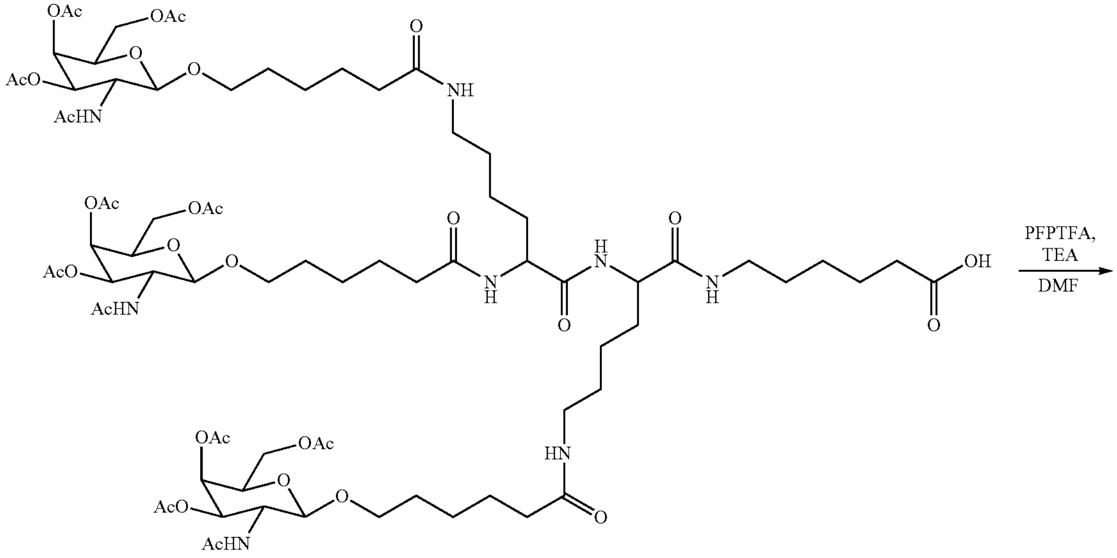
178
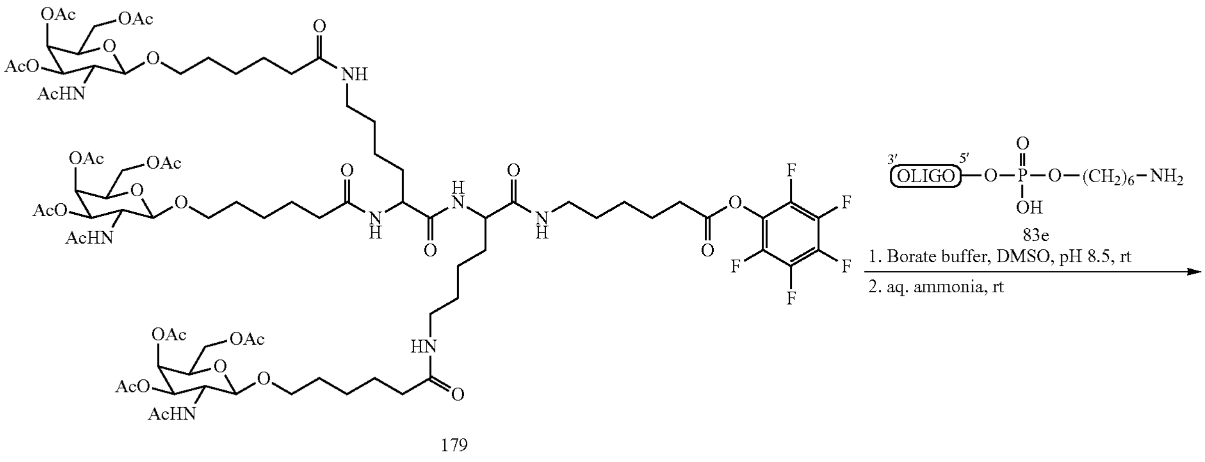
179

-continued

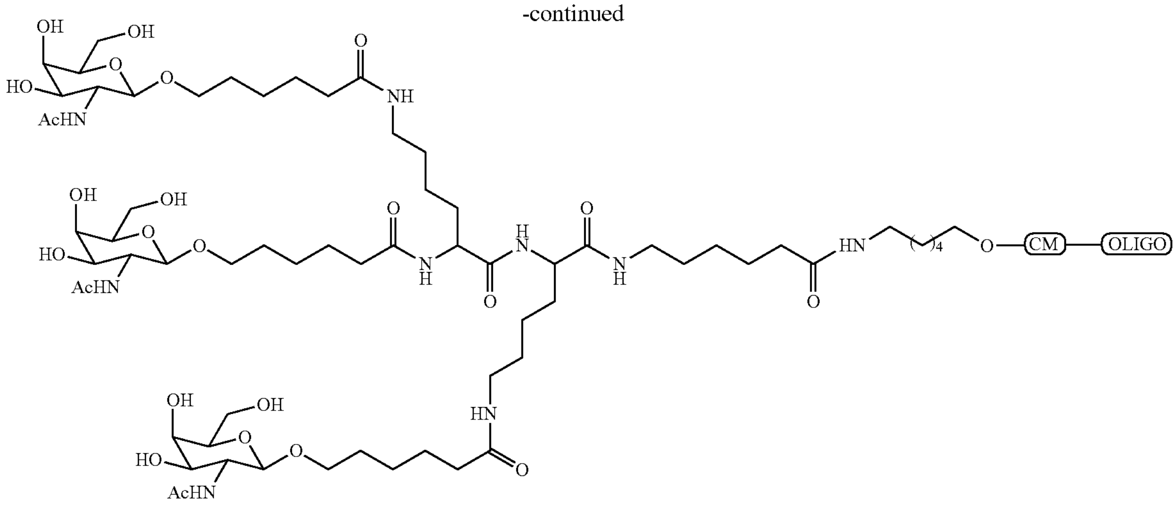

180

Compound 176 was prepared using the general procedure shown in Example 2. Oligomeric compound 180, comprising a $GalNAc_3$-13 conjugate group, was prepared from compound 177 using the general procedures illustrated in Example 49. The $GalNAc_3$ cluster portion of the conjugate group $GalNAc_3$-13 ($GalNAc_3$-$13_a$) can be combined with any cleavable moiety to provide a variety of conjugate groups. In a certainembodiments, the cleavable moiety is -P(═O)(OH)-$A_d$-P(═O)(OH)—. The structure of $GalNAc_3$-13 ($GalNAc_3$-$13_a$-CM-) is shown below:

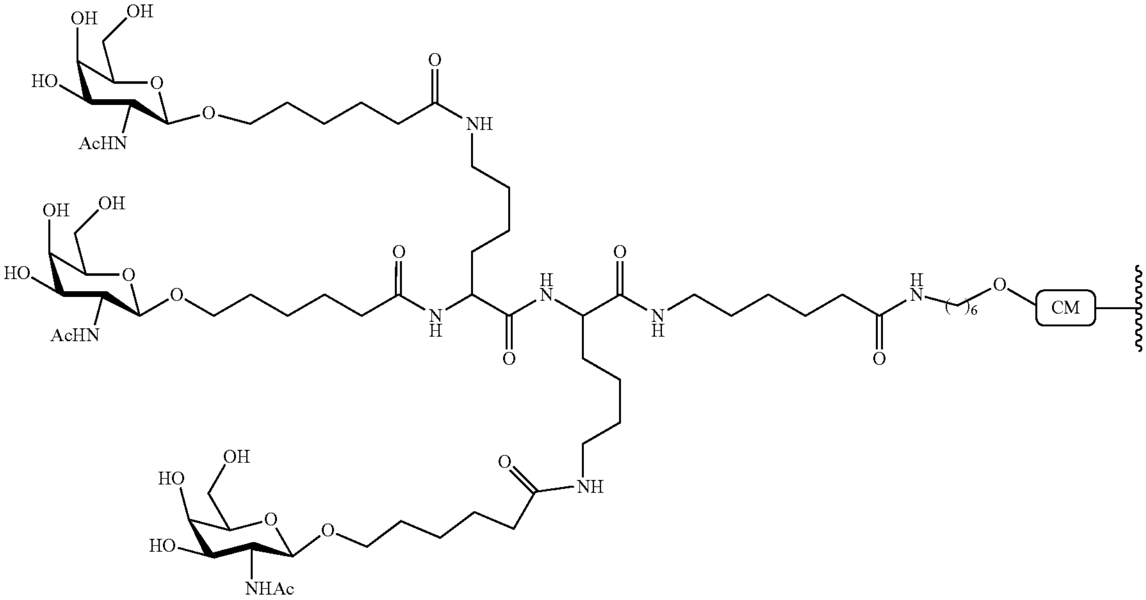

Example 63: Preparation of Oligomeric Compound 188 Comprising $GalNAc_3$-14
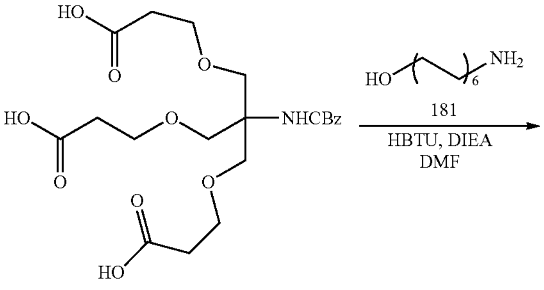
13
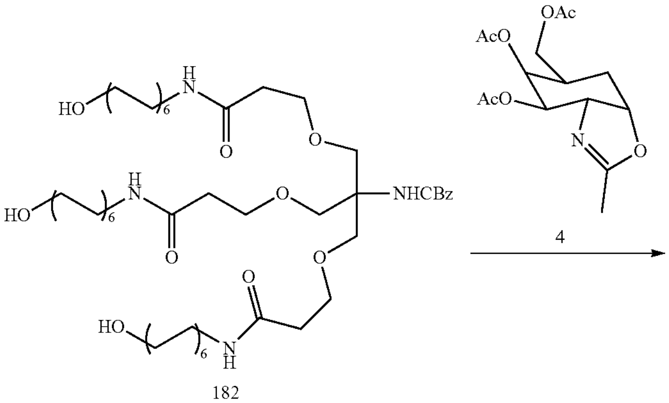
182
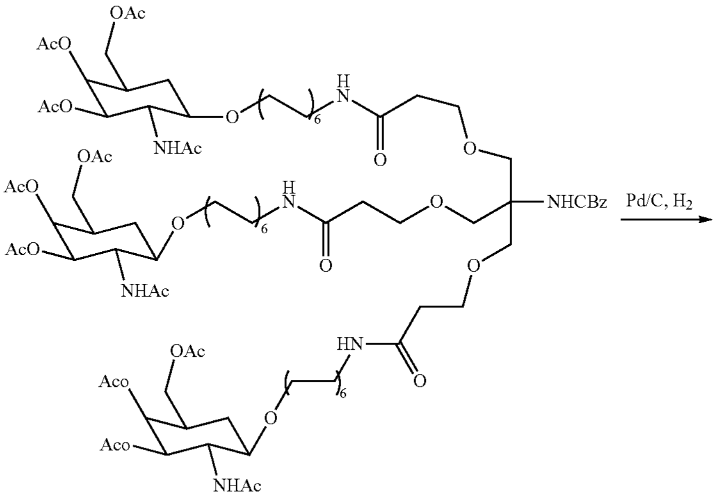
183

-continued
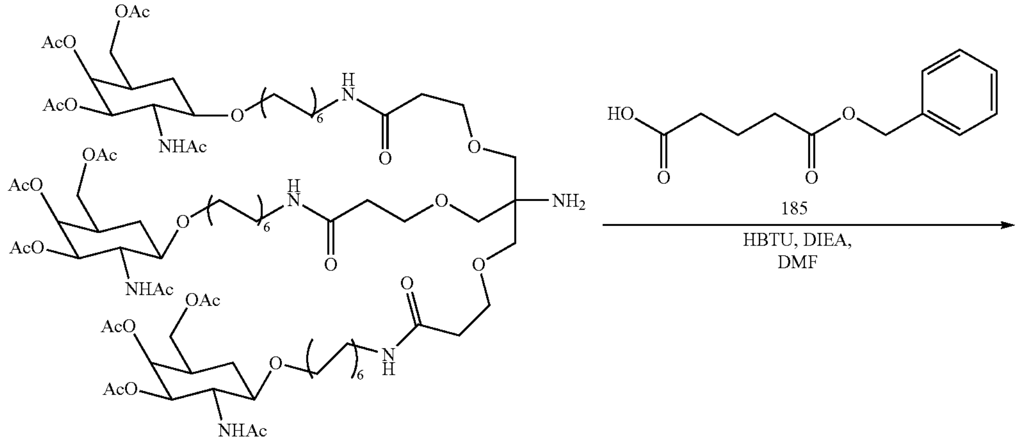
184
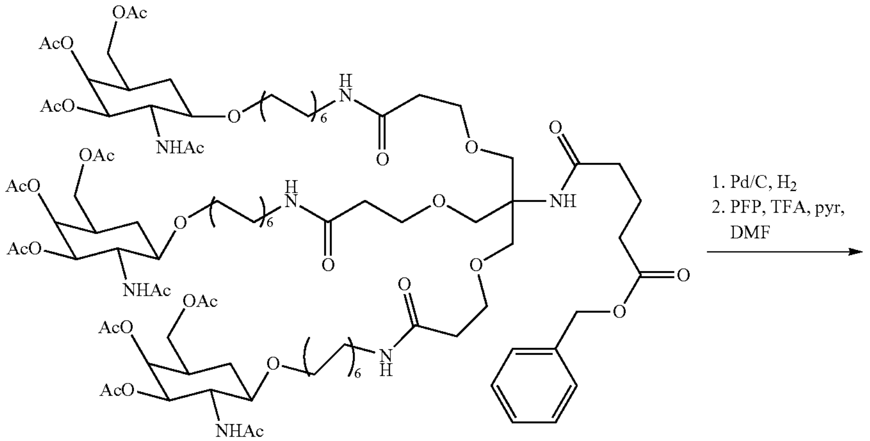
186
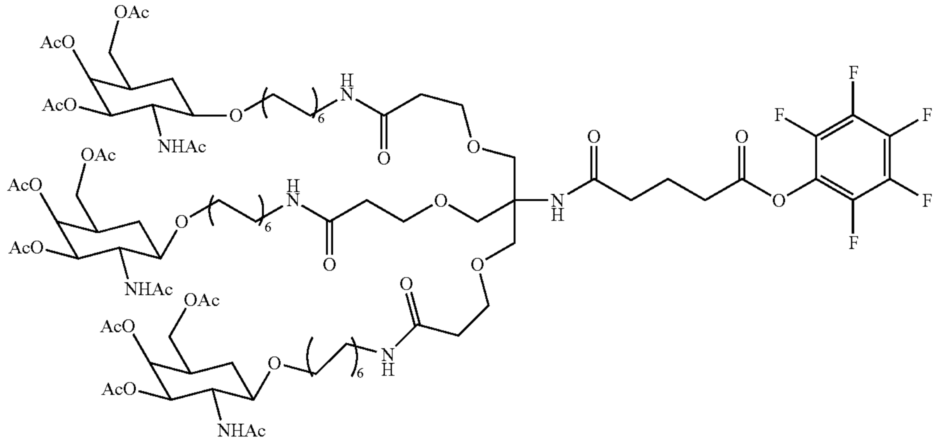
187
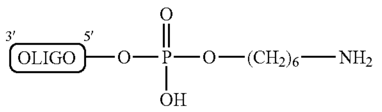
83e
187
1. Borate buffer, DMSO, pH 8.5, rt
2. aq. ammonia, rt -continued

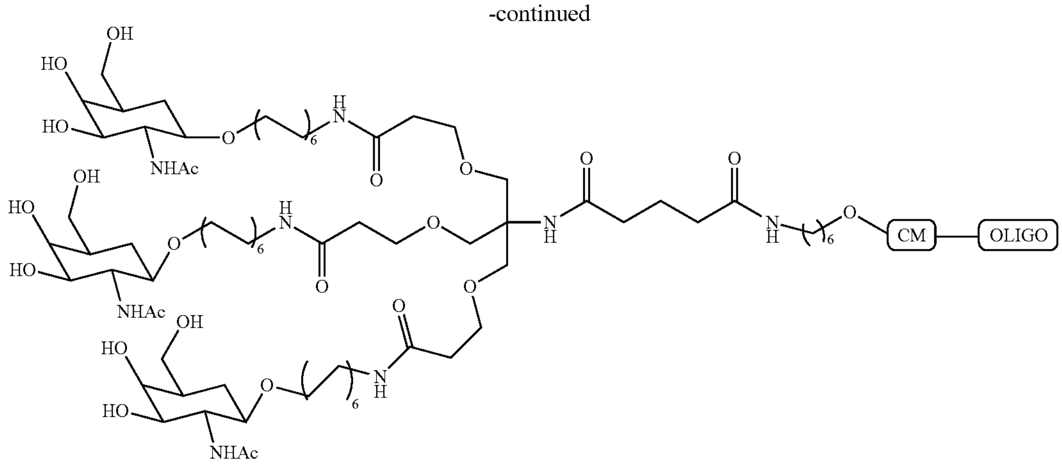

188

Compounds 181 and 185 are commercially available. Oligomeric compound 188, comprising a $GalNAc_3$-14 conjugate group, was prepared from compound 187 using the general procedures illustrated in Example 46. The $GalNAc_3$ cluster portion of the conjugate group $GalNAc_3$-14 ($GalNAc_3$-$14_a$) can be combined with any cleavable moiety to provide a variety of conjugate groups. In certain embodiments, the cleavable moiety is —P(═O)(OH)-$A_a$-P(═O)(OH)—. The structure of $GalNAc_3$-14 ($GalNAc_3$-$14_a$—CM-) is shown below:

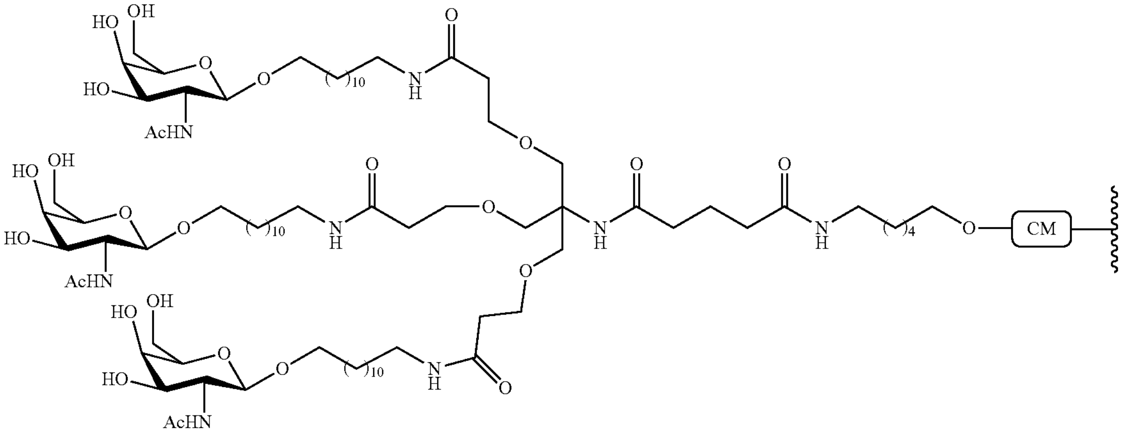

Example 64: Preparation of oligomeric compound 197 comprising $GalNAc_3$-15

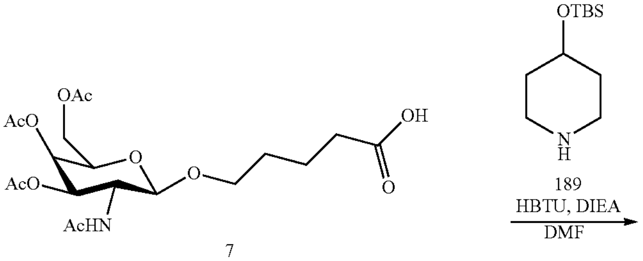

7

-continued
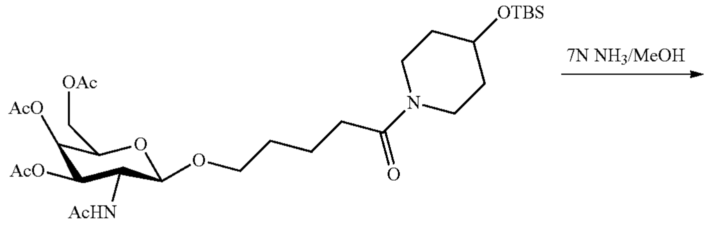
190
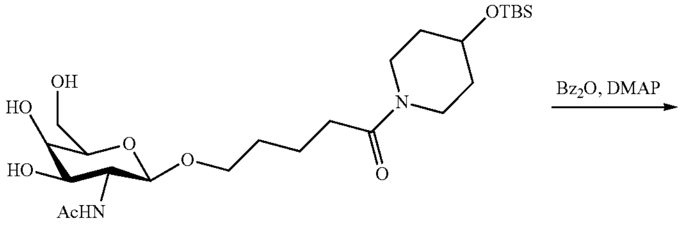
191
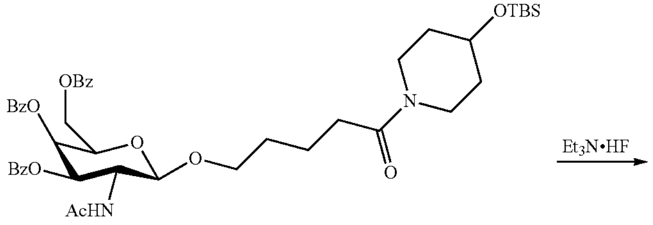
192
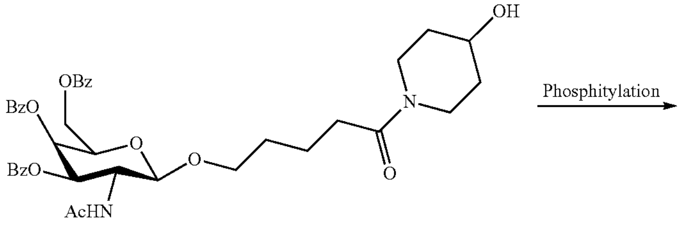
193
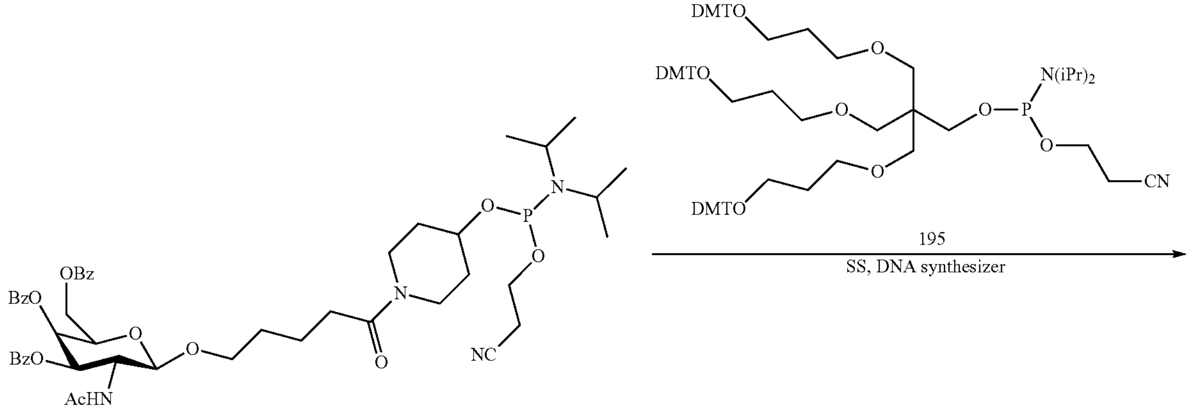
194
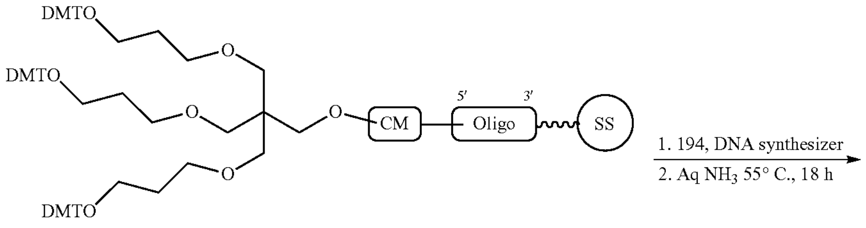
196

-continued

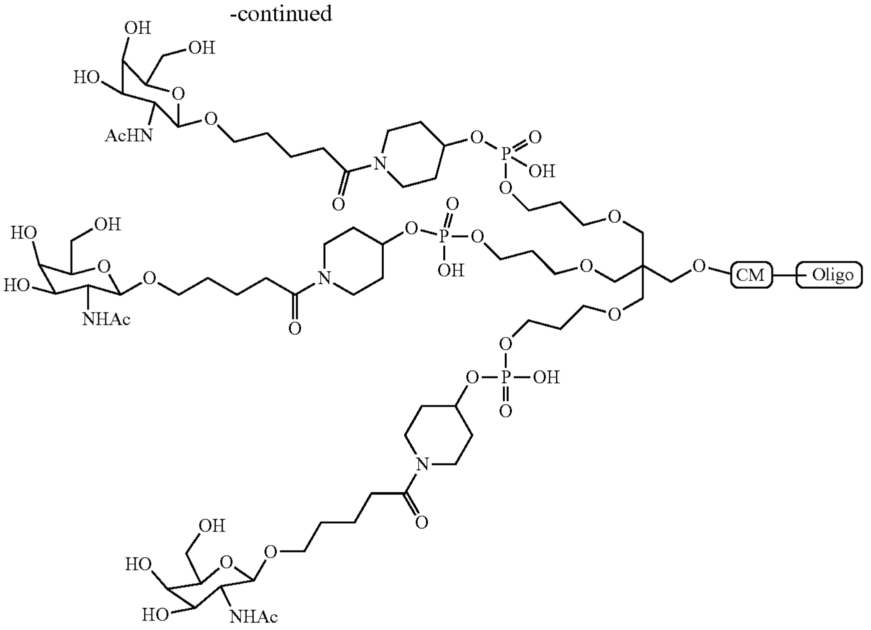

197

Compound 189 is commercially available. Compound 195 was prepared using the general procedure shown in Example 31. Oligomeric compound 197, comprising a GalNAc$_3$-15 conjugate group, was prepared from compounds 194 and 195 using standard oligonucleotide synthesis procedures. The GalNAc$_3$ cluster portion of the conjugate group GalNAc$_3$-15 (GalNAc$_3$-15$_a$) can be combined with any cleavable moiety to provide a variety of conjugate groups. In certain embodiments, the cleavable moiety is —P(═O)(OH)-A$_a$-P(═O)(OH)—. The structure of GalNAc$_3$-15 (GalNAc$_3$-15$_a$-CM-) is shown below:

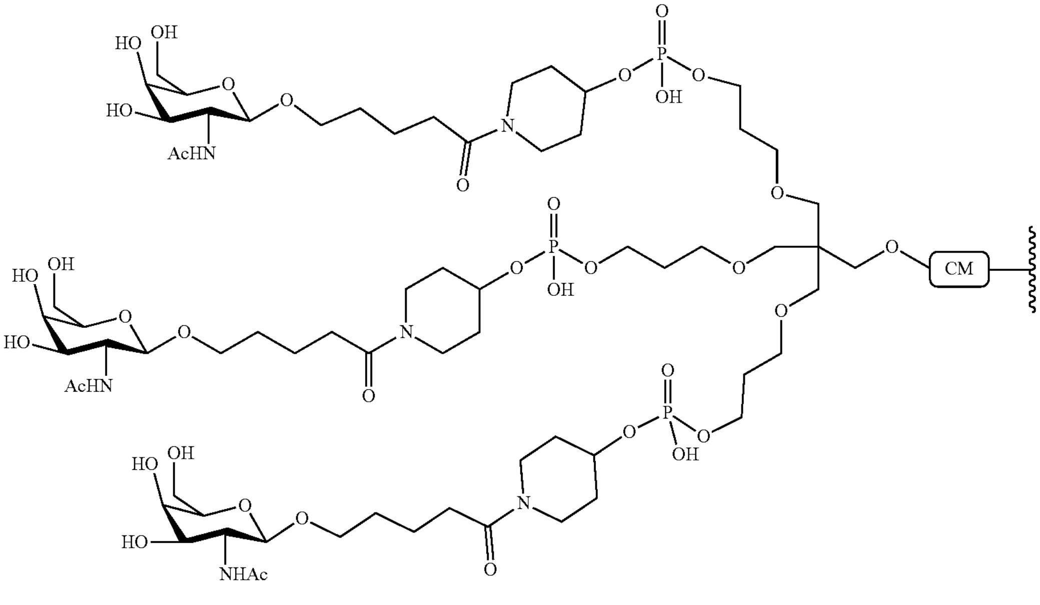

Example 65: Dose-Dependent Study of Oligonucleotides Comprising a 5'-Conjugate Group (Comparison of $GalNAc_3$-3, 12, 13, 14, and 15) Targeting SRB-1 In Vivo The oligonucleotides listed below were tested in a dose-dependent study for antisense inhibition of SRB-1 in mice. Unconjugated ISIS 353382 was included as a standard. Each of the $GalNAc_3$ conjugate groups was attached at the 5' terminus of the respective oligonucleotide by a phosphodiester linked 2'-deoxyadenosine nucleoside (cleavable moiety).

TABLE 41

Modified ASOs targeting SRB-1

| ISIS No. | Sequences (5' to 3') | Conjugate | SEQ ID No. |
|---|---|---|---|
| 353382 | $G_{es}{}^{m}C_{es}T_{es}T_{es}{}^{m}C_{es}A_{ds}G_{ds}$<br>$T_{ds}{}^{m}C_{ds}A_{ds}T_{ds}\ G_{ds}A_{ds}{}^{m}C_{ds}$<br>$T_{ds}T_{es}{}^{m}C_{es}{}^{m}C_{es}T_{es}T_{e}$ | none | 28 |
| 661161 | **$GalNAc_3$-3**$_{a}$-$_{o'}$**A**$_{do}G_{es}{}^{m}C_{es}$<br>$T_{es}T_{es}{}^{m}C_{es}A_{ds}G_{ds}T_{ds}$<br>${}^{m}C_{ds}A_{ds}T_{ds}G_{ds}A_{ds}{}^{m}C_{ds}$<br>$T_{ds}T_{es}{}^{m}C_{es}{}^{m}C_{es}T_{es}T_{e}$ | $GalNAC_3$-3 | 30 |
| 671144 | **$GalNAc_3$-12**$_{a}$-$_{o'}$**A**$_{do}G_{es}{}^{m}C_{es}$<br>$T_{es}T_{es}{}^{m}C_{es}A_{ds}G_{ds}T_{ds}$<br>${}^{m}C_{ds}A_{ds}T_{ds}G_{ds}A_{ds}{}^{m}C_{ds}$<br>$T_{ds}T_{es}{}^{m}C_{es}{}^{m}C_{es}T_{es}T_{e}$ | $GalNAC_3$-12 | 30 |
| 670061 | **$GalNAc_3$-13**$_{a}$-$_{o'}$**A**$_{do}G_{es}{}^{m}C_{es}$<br>$T_{es}T_{es}{}^{m}C_{es}A_{ds}G_{ds}T_{ds}$<br>${}^{m}C_{ds}A_{ds}T_{ds}G_{ds}A_{ds}{}^{m}C_{ds}$<br>$T_{ds}T_{es}{}^{m}C_{es}{}^{m}C_{es}T_{es}T_{e}$ | $GalNAC_3$-13 | 30 |
| 671261 | **$GalNAc_3$-14**$_{a}$-$_{o'}$**A**$_{do}G_{es}{}^{m}C_{es}$<br>$T_{es}T_{es}{}^{m}C_{es}A_{ds}G_{ds}T_{ds}$<br>${}^{m}C_{ds}A_{ds}T_{ds}G_{ds}A_{ds}{}^{m}C_{ds}$<br>$T_{ds}T_{es}{}^{m}C_{es}{}^{m}C_{es}T_{es}T_{e}$ | $GalNAC_3$-14 | 30 |
| 671262 | **$GalNAc_3$-15**$_{a}$-$_{o'}$**A**$_{do}G_{es}{}^{m}C_{es}$<br>$T_{es}T_{es}{}^{m}C_{es}A_{ds}G_{ds}T_{ds}$<br>${}^{m}C_{ds}A_{ds}T_{ds}G_{ds}A_{ds}{}^{m}C_{ds}$<br>$T_{ds}T_{es}{}^{m}C_{es}{}^{m}C_{es}T_{es}T_{e}$ | $GalNAC_3$-15 | 30 |

Capital letters indicate the nucleobase for each nucleoside and ${}^{m}C$ indicates a 5-methyl cytosine.
Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—.
Conjugate groups are in bold.

The structure of $GalNAc_3$-$3_a$ was shown previously in Example 39. The structure of $GalNAc_3$-$12_a$ was shown previously in Example 61. The structure of $GalNAc_3$-$13_a$ was shown previously in Example 62. The structure of $GalNAc_3$-$14_a$ was shown previously in Example 63. The structure of $GalNAc_3$-$15_a$ was shown previously in Example 64.

Treatment

Six to eight week old C57b16 mice (Jackson Laboratory, Bar Harbor, ME) were injected subcutaneously once or twice at the dosage shown below with ISIS 353382, 661161, 671144, 670061, 671261, 671262, or with saline. Mice that were dosed twice received the second dose three days after the first dose. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 42, treatment with antisense oligonucleotides lowered SRB-1 mRNA levels in a dose-dependent manner. No significant differences in target knockdown were observed between animals that received a single dose and animals that received two doses (see ISIS 353382 dosages 30 and 2×15 mg/kg; and ISIS 661161 dosages 5 and 2×2.5 mg/kg). The antisense oligonucleotides comprising the phosphodiester linked $GalNAc_3$-3, 12, 13, 14, and 15 conjugates showed substantial improvement in potency compared to the unconjugated antisense oligonucleotide (ISIS 335382).

TABLE 42

SRB-1 mRNA (% Saline)

| ISIS No. | Dosage (mg/kg) | SRB-1 mRNA (% Saline) | $ED_{50}$ (mg/kg) | Conjugate |
|---|---|---|---|---|
| Saline | n/a | 100.0 | n/a | n/a |
| 353382 | 3 | 85.0 | 22.4 | none |
| | 10 | 69.2 | | |
| | 30 | 34.2 | | |
| | 2 × 15 | 36.0 | | |
| 661161 | 0.5 | 87.4 | 2.2 | $GalNAc_3$-3 |
| | 1.5 | 59.0 | | |
| | 5 | 25.6 | | |
| | 2 × 2.5 | 27.5 | | |
| | 15 | 17.4 | | |
| 671144 | 0.5 | 101.2 | 3.4 | $GalNAc_3$-12 |
| | 1.5 | 76.1 | | |
| | 5 | 32.0 | | |
| | 15 | 17.6 | | |
| 670061 | 0.5 | 94.8 | 2.1 | $GalNAc_3$-13 |
| | 1.5 | 57.8 | | |
| | 5 | 20.7 | | |
| | 15 | 13.3 | | |
| 671261 | 0.5 | 110.7 | 4.1 | $GalNAc_3$-14 |
| | 1.5 | 81.9 | | |
| | 5 | 39.8 | | |
| | 15 | 14.1 | | |
| 671262 | 0.5 | 109.4 | 9.8 | $GalNAc_3$-15 |
| | 1.5 | 99.5 | | |
| | 5 | 69.2 | | |
| | 15 | 36.1 | | |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 43 below.

TABLE 43

| ISIS No. | Dosage (mg/kg) | ALT (U/L) | AST (U/L) | Total Bilirubin (mg/dL) | BUN (mg/dL) | Conjugate |
|---|---|---|---|---|---|---|
| Saline | n/a | 28 | 60 | 0.1 | 39 | n/a |
| 353382 | 3 | 30 | 77 | 0.2 | 36 | none |
| | 10 | 25 | 78 | 0.2 | 36 | |
| | 30 | 28 | 62 | 0.2 | 35 | |
| | 2 × 15 | 22 | 59 | 0.2 | 33 | |
| 661161 | 0.5 | 39 | 72 | 0.2 | 34 | $GalNAc_3$-3 |
| | 1.5 | 26 | 50 | 0.2 | 33 | |
| | 5 | 41 | 80 | 0.2 | 32 | |
| | 2 × 2.5 | 24 | 72 | 0.2 | 28 | |
| | 15 | 32 | 69 | 0.2 | 36 | |

TABLE 43-continued

| ISIS No. | Dosage (mg/kg) | ALT (U/L) | AST (U/L) | Total Bilirubin (mg/dL) | BUN (mg/dL) | Conjugate |
|---|---|---|---|---|---|---|
| 671144 | 0.5 | 25 | 39 | 0.2 | 34 | $GalNAc_3$-12 |
| | 1.5 | 26 | 55 | 0.2 | 28 | |
| | 5 | 48 | 82 | 0.2 | 34 | |
| | 15 | 23 | 46 | 0.2 | 32 | |
| 670061 | 0.5 | 27 | 53 | 0.2 | 33 | $GalNAc_3$-13 |
| | 1.5 | 24 | 45 | 0.2 | 35 | |
| | 5 | 23 | 58 | 0.1 | 34 | |
| | 15 | 24 | 72 | 0.1 | 31 | |
| 671261 | 0.5 | 69 | 99 | 0.1 | 33 | $GalNAc_3$-14 |
| | 1.5 | 34 | 62 | 0.1 | 33 | |
| | 5 | 43 | 73 | 0.1 | 32 | |
| | 15 | 32 | 53 | 0.2 | 30 | |
| 671262 | 0.5 | 24 | 51 | 0.2 | 29 | $GalNAc_3$-15 |
| | 1.5 | 32 | 62 | 0.1 | 31 | |
| | 5 | 30 | 76 | 0.2 | 32 | |
| | 15 | 31 | 64 | 0.1 | 32 | |

Example 66: Effect of Various Cleavable Moieties on Antisense Inhibition In Vivo by Oligonucleotides Targeting SRB-1 Comprising a 5'-$GalNAc_3$ Cluster The oligonucleotides listed below were tested in a dose-dependent study for antisense inhibition of SRB-1 in mice. Each of the $GalNAc_3$ conjugate groups was attached at the 5' terminus of the respective oligonucleotide by a phosphodiester linked nucleoside (cleavable moiety (CM)).

TABLE 44

Modified ASOs targeting SRB-I

| ISIS No. | Sequences (5' to 3') | $GalNAc_3$ Cluster | CM | SEQ ID No. |
|---|---|---|---|---|
| 661161 | $\mathbf{GalNAc_3\text{-}3}_{a}\text{-}_{o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | $A_d$ | 30 |
| 670699 | $\mathbf{GalNAc_3\text{-}3}_{a}\text{-}_{o'}\mathbf{T}_{do}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}G_{ds}T_{eo}{}^{m}C_{eo}{}^{m}C_{es}T_{es}T_{e}$ | $GalNAc_3$-3a | $T_d$ | 33 |
| 670700 | $\mathbf{GalNAc_3\text{-}3}_{a}\text{-}_{o'}\mathbf{A}_{eo}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}G_{ds}T_{eo}{}^{m}C_{eo}{}^{m}C_{es}T_{es}T_{e}$ | $GalNAc_3$-3a | $A_e$ | 30 |
| 670701 | $\mathbf{GalNAc_3\text{-}3}_{a}\text{-}_{o'}\mathbf{T}_{eo}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}G_{ds}T_{eo}{}^{m}C_{eo}{}^{m}C_{es}T_{es}T_{e}$ | $GalNAc_3$-3a | $T_c$ | 33 |
| 671165 | $\mathbf{GalNAc_3\text{-}13}_{a}\text{-}_{o'}\mathbf{A}_{do}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}G_{ds}T_{eo}{}^{m}C_{eo}{}^{m}C_{es}T_{es}T_{e}$ | $GalNAc_3$-13a | $A_d$ | 30 |

Capital letters indicate the nucleobase for each nucleoside and ${}^{m}C$ indicates a 5-methyl cytosine.
Subscripts: "e" indicates a 2'-MOE modified nucleoside; "d" indicates a β-D-2"-deoxyribonucleoside; "s" indicates a phosphorothioate internucleoside linkage (PS); "o" indicates a phosphodiester internucleoside linkage (PO); and "o'" indicates —O—P(=O)(OH)—.
Conjugate groups are in bold.

The structure of $GalNAc_3$-$3_a$ was shown previously in Example 39. The structure of $GalNAc_3$-$13_a$ was shown previously in Example 62.

Treatment

Six to eight week old $C_{57}$b16 mice (Jackson Laboratory, Bar Harbor, ME) were injected subcutaneously once at the dosage shown below with ISIS 661161, 670699, 670700, 670701, 671165, or with saline. Each treatment group consisted of 4 animals. The mice were sacrificed 72 hours following the final administration to determine the liver SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 45, treatment with antisense oligonucleotides lowered SRB-1 mRNA levels in a dose-dependent manner. The antisense oligonucleotides comprising various cleavable moieties all showed similar potencies.

TABLE 45

SRB-1 mRNA (% Saline)

| ISIS No. | Dosage (mg/kg) | SRB-1 mRNA (% Saline) | $GalNAc_3$ Cluster | CM |
|---|---|---|---|---|
| Saline | n/a | 100.0 | n/a | n/a |
| 661161 | 0.5 | 87.8 | $GalNAc_3$-3a | $A_d$ |
| | 1.5 | 61.3 | | |
| | 5 | 33.8 | | |
| | 15 | 14.0 | | |
| 670699 | 0.5 | 89.4 | $GalNAc_3$-3a | $T_d$ |
| | 1.5 | 59.4 | | |
| | 5 | 31.3 | | |
| | 15 | 17.1 | | |
| 670700 | 0.5 | 79.0 | $GalNAc_3$-3a | $A_e$ |
| | 1.5 | 63.3 | | |
| | 5 | 32.8 | | |
| | 15 | 17.9 | | |
| 670701 | 0.5 | 79.1 | $GalNAc_3$-3a | $T_e$ |
| | 1.5 | 59.2 | | |
| | 5 | 35.8 | | |
| | 15 | 17.7 | | |
| 671165 | 0.5 | 76.4 | $GalNAc_3$-13a | $A_d$ |
| | 1.5 | 43.2 | | |
| | 5 | 22.6 | | |
| | 15 | 10.0 | | |

Liver transaminase levels, alanine aminotransferase (ALT) and aspartate aminotransferase (AST), in serum were measured relative to saline injected mice using standard protocols. Total bilirubin and BUN were also evaluated. The changes in body weights were evaluated with no significant differences from the saline group (data not shown). ALTs, ASTs, total bilirubin and BUN values are shown in Table 46 below.

TABLE 46

| ISIS No. | Dosage (mg/kg) | ALT (U/L) | AST (U/L) | Total Bilirubin (mg/dL) | BUN (mg/dL) | $GalNAc_3$ Cluster | CM |
|---|---|---|---|---|---|---|---|
| Saline | n/a | 24 | 64 | 0.2 | 31 | n/a | n/a |
| 661161 | 0.5 | 25 | 64 | 0.2 | 31 | $GalNAc_3$-3a | $A_d$ |
| | 1.5 | 24 | 50 | 0.2 | 32 | | |
| | 5 | 26 | 55 | 0.2 | 28 | | |
| | 15 | 27 | 52 | 0.2 | 31 | | |
| 670699 | 0.5 | 42 | 83 | 0.2 | 31 | $GalNAc_3$-3a | $T_d$ |
| | 1.5 | 33 | 58 | 0.2 | 32 | | |
| | 5 | 26 | 70 | 0.2 | 29 | | |
| | 15 | 25 | 67 | 0.2 | 29 | | |

TABLE 46-continued
| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| 670700 | 0.5 | 40 | 74 | 0.2 | 27 | GalNAc$_3$-3a | $A_e$ |
| | 1.5 | 23 | 62 | 0.2 | 27 | | |
| | 5 | 24 | 49 | 0.2 | 29 | | |
| | 15 | 25 | 87 | 0.1 | 25 | | |
| 670701 | 0.5 | 30 | 77 | 0.2 | 27 | GalNAc$_3$-3a | $T_e$ |
| | 1.5 | 22 | 55 | 0.2 | 30 | | |
| | 5 | 81 | 101 | 0.2 | 25 | | |
| | 15 | 31 | 82 | 0.2 | 24 | | |
TABLE 46-continued
| ISIS No. | Dosage (mg/kg) | ALT (U/L) | AST (U/L) | Total Bilirubin (mg/dL) | BUN (mg/dL) | GalNAc$_3$ Cluster | CM |
|---|---|---|---|---|---|---|---|
| 671165 | 0.5 | 44 | 84 | 0.2 | 26 | GalNAc$_3$-13a | $A_d$ |
| | 1.5 | 47 | 71 | 0.1 | 24 | | |
| | 5 | 33 | 91 | 0.2 | 26 | | |
| | 15 | 33 | 56 | 0.2 | 29 | | |
Example 67: Preparation of Oligomeric Compound 199 Comprising GalNAc$_3$-16
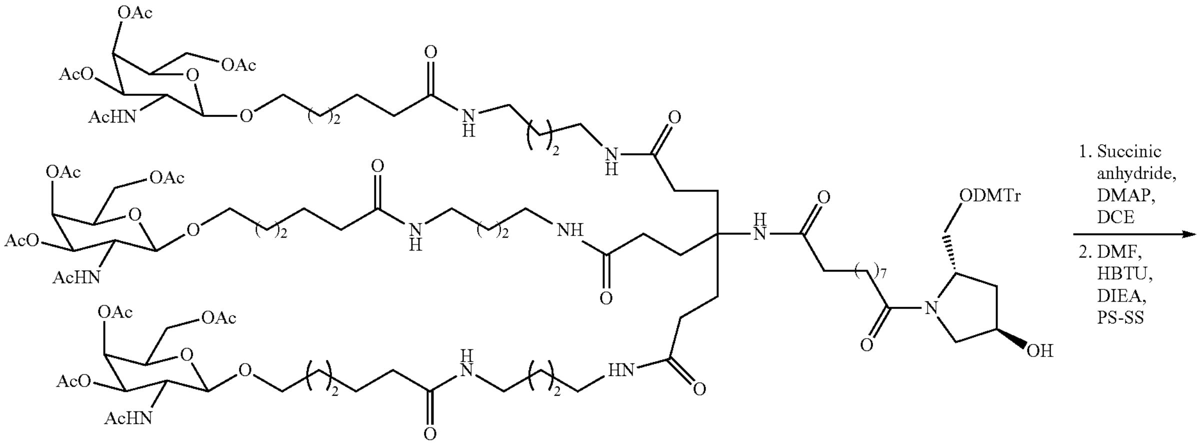
98d
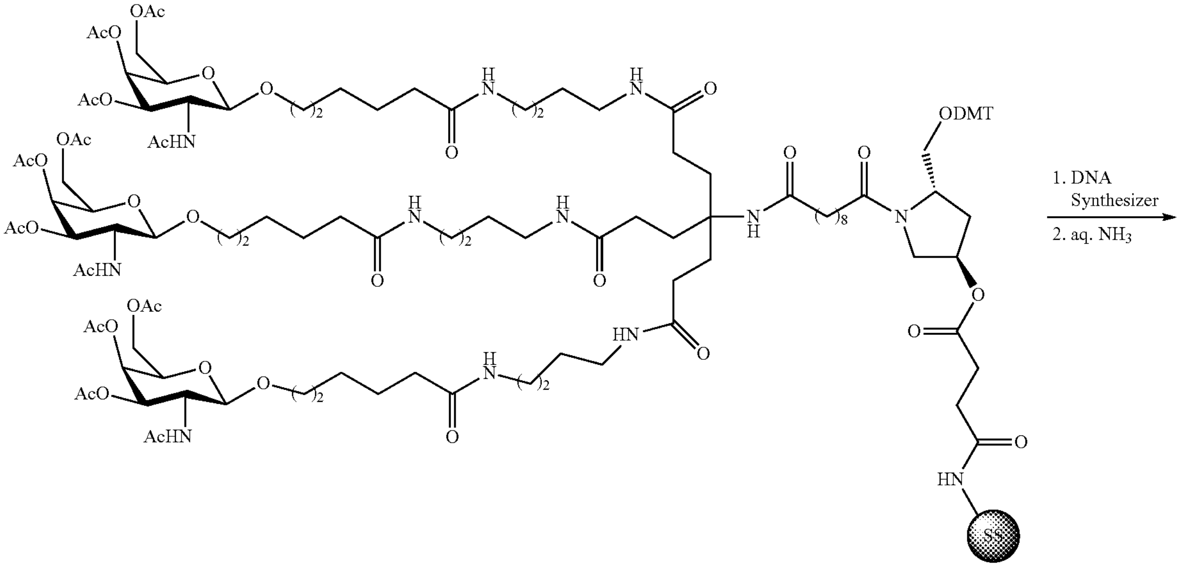
198

-continued

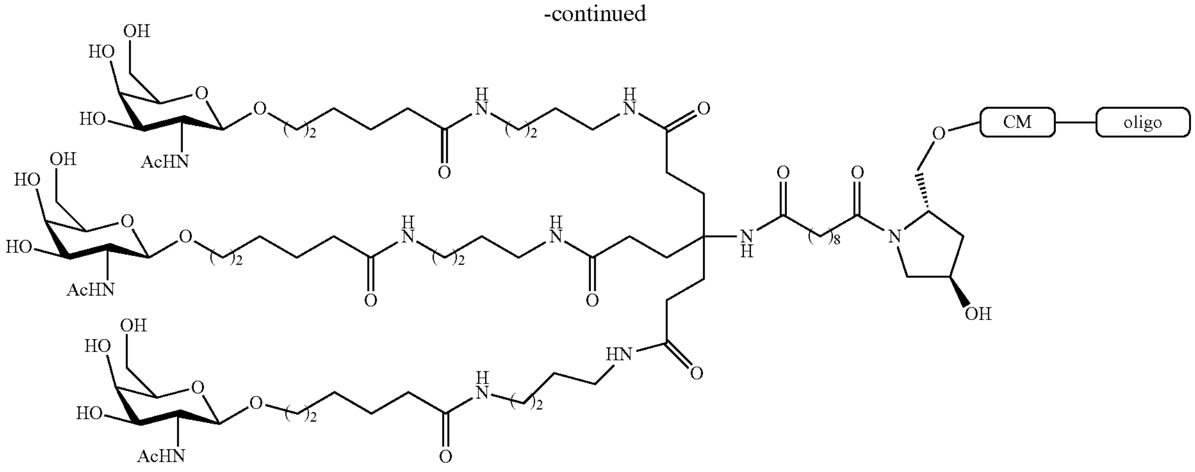

199

Oligomeric compound 199, comprising a $GalNAc_3$-16 conjugate group, is prepared using the general procedures illustrated in Examples 7 and 9. The $GalNAc_3$ cluster portion of the conjugate group $GalNAc_3$-16 ($GalNAc_3$-$16_a$) can be combined with any cleavable moiety to provide a variety of conjugate groups. In certain embodiments, the cleavable moiety is —P(═O)(OH)-$A_a$-P(═O)(OH)—. The structure of $GalNAc_3$-16 ($GalNAc_3$-$16_a$-CM-) is shown below:

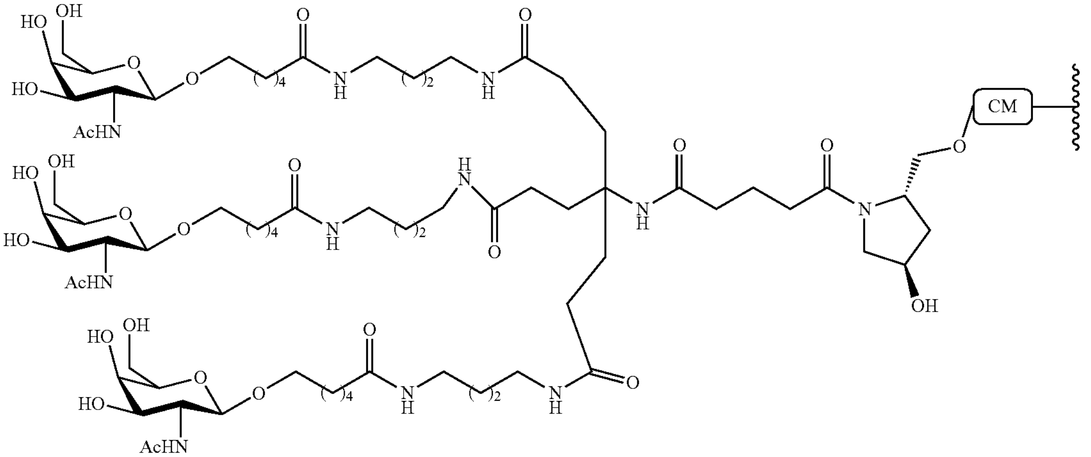

Example 68: Preparation of Oligomeric Compound 200 Comprising $GalNAc_3$-17

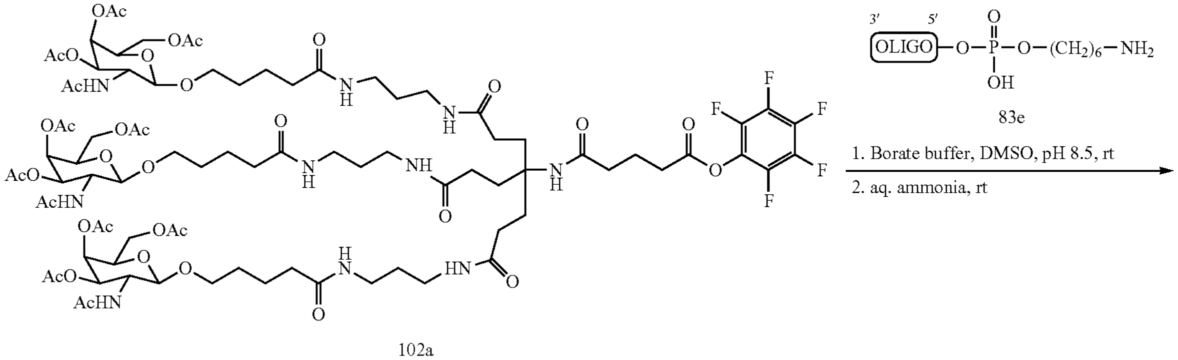

102a

-continued

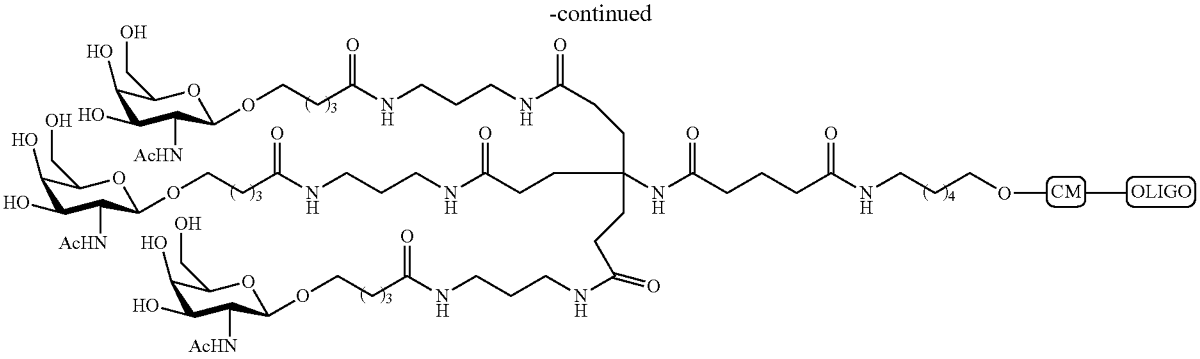

200

Oligomeric compound 200, comprising a GalNAc$_3$-17 conjugate group, was prepared using the general procedures illustrated in Example 46. The GalNAc$_3$ cluster portion of the conjugate group GalNAc$_3$-17 (GalNAc$_3$-17$_a$) can be combined with any cleavable moiety to provide a variety of conjugate groups. In certain embodiments, the cleavable moiety is —P(═O)(OH)-A$_a$-P(═O)(OH)—. The structure of GalNAc$_3$-17 (GalNAc$_3$-17$_a$-CM-) is shown below:

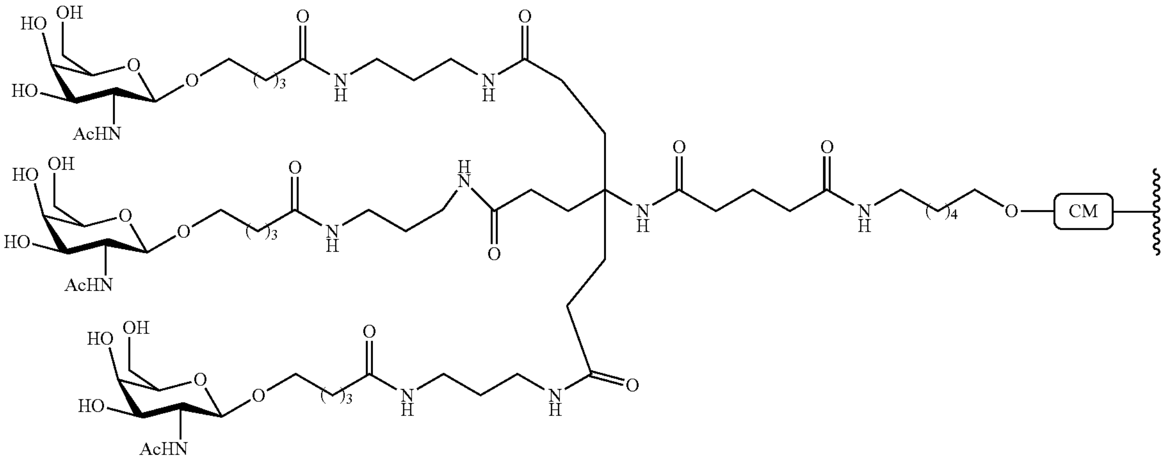

Example 69: Preparation of Oligomeric Compound 201 Comprising GalNAc$_3$-18

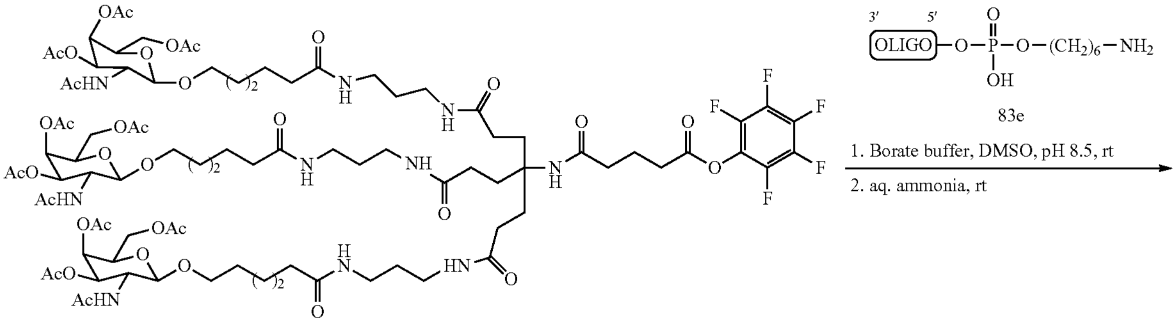

102b

-continued

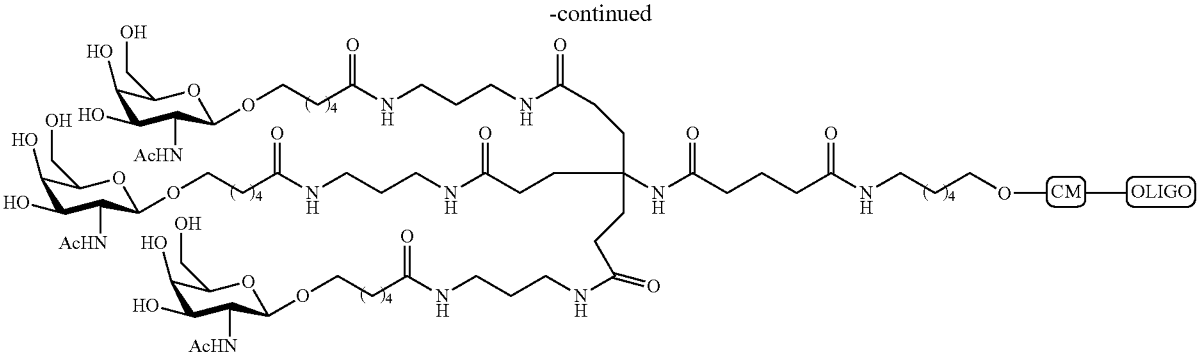

201

Oligomeric compound 201, comprising a $GalNAc_3$-18 conjugate group, was prepared using the general procedures illustrated in Example 46. The $GalNAc_3$ cluster portion of the conjugate group $GalNAc_3$-18 ($GalNAc_3$-$18_a$) can be combined with any cleavable moiety to provide a variety of conjugate groups. In certain embodiments, the cleavable moiety is —P(═O)(OH)-$A_a$-P(═O)(OH)—. The structure of $GalNAc_3$-18 ($GalNAc_3$-$18_a$-CM-) is shown below:

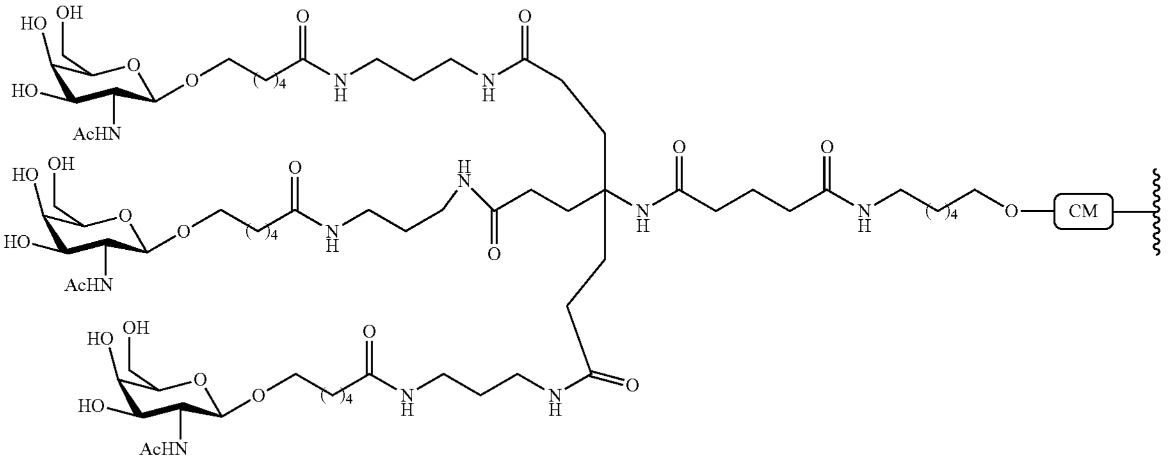

Example 70: Preparation of oligomeric compound 204 comprising $GalNAc_3$-19

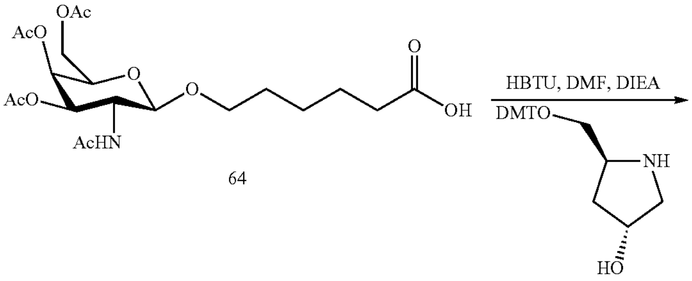

64

47

-continued

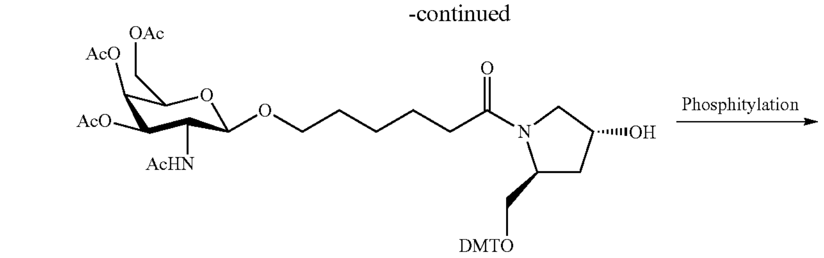

202

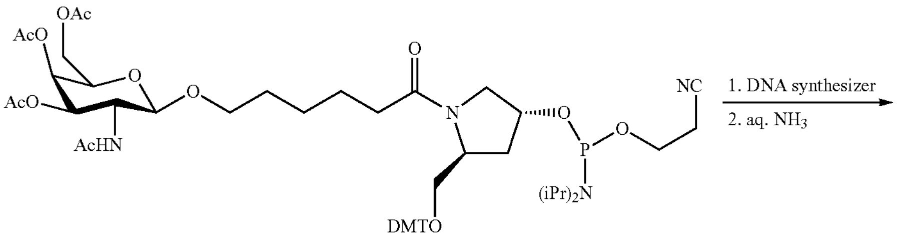

203

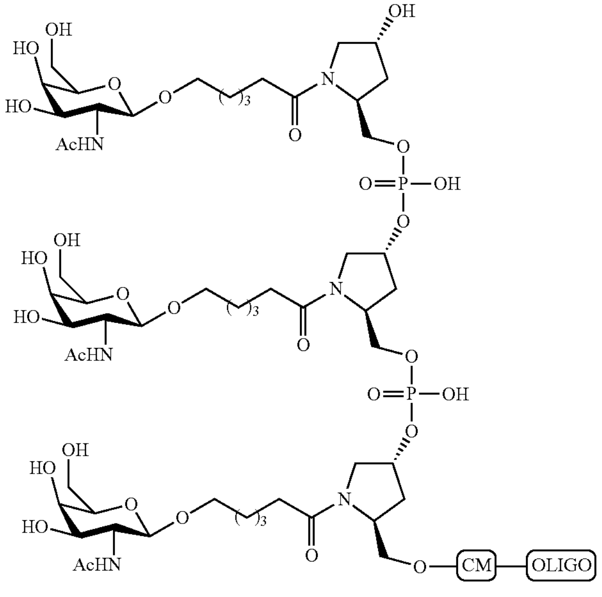

204

Oligomeric compound 204, comprising a $GalNAc_3$-19 conjugate group, was prepared from compound 64 using the general procedures illustrated in Example 52. The $GalNAc_3$ cluster portion of the conjugate group $GalNAc_3$-19 ($GalNAc_3$-$19_a$) can be combined with any cleavable moiety to provide a variety of conjugate groups. In certain embodiments, the cleavable moiety is —P(═O)(OH)-$A_a$-P(═O)(OH)—. The structure of $GalNAc_3$-19 ($GalNAc_3$-$19_a$-CM-) is shown below:

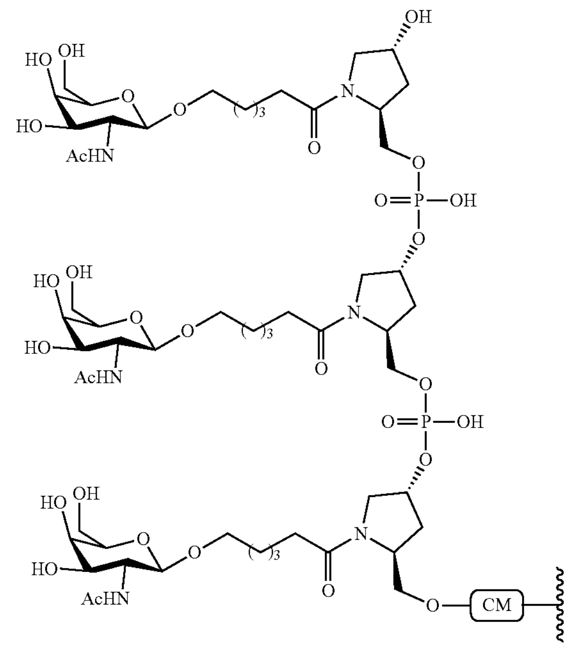
Example 71: Preparation of Oligomeric Compound 210 Comprising $GalNAc_3$-20
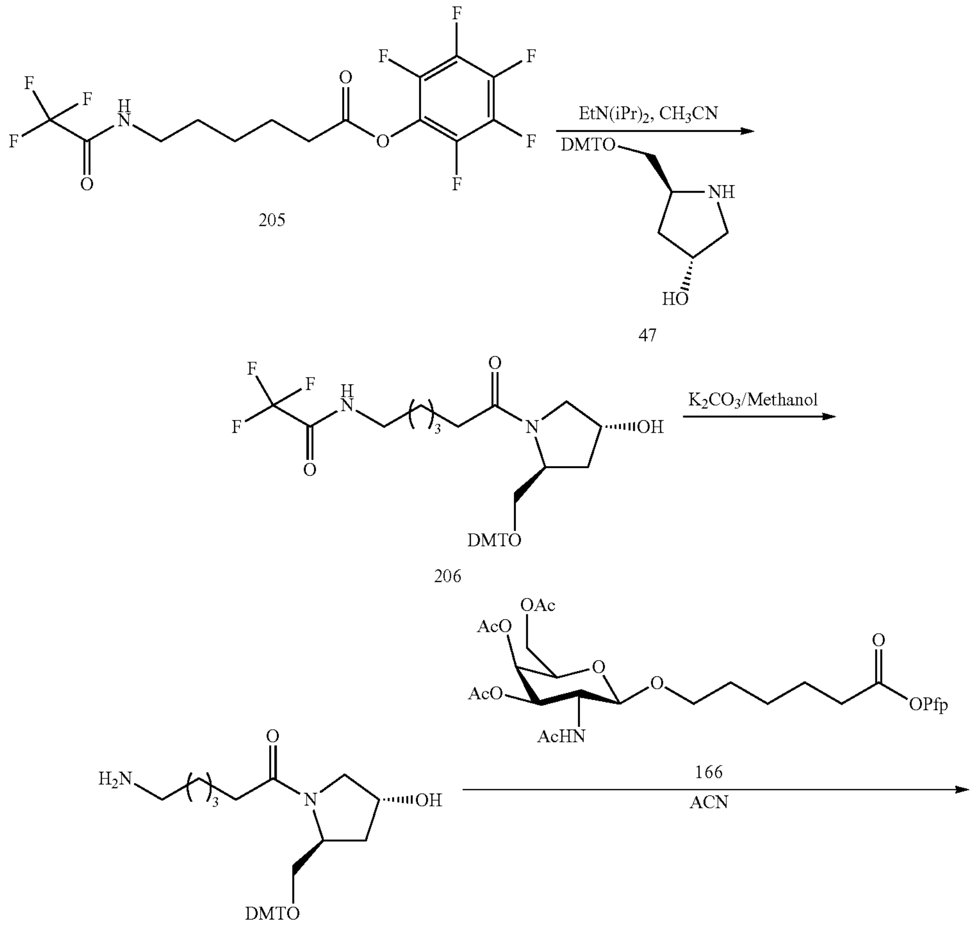
205
47
206
207

-continued

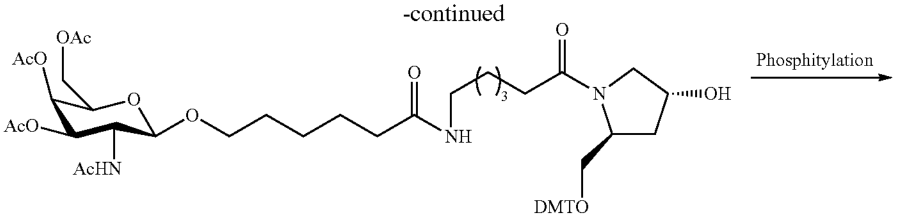

208

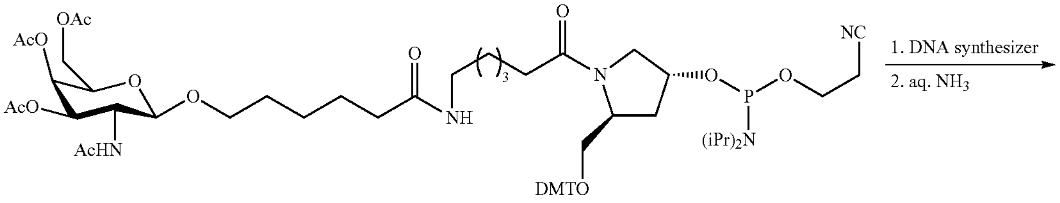

209

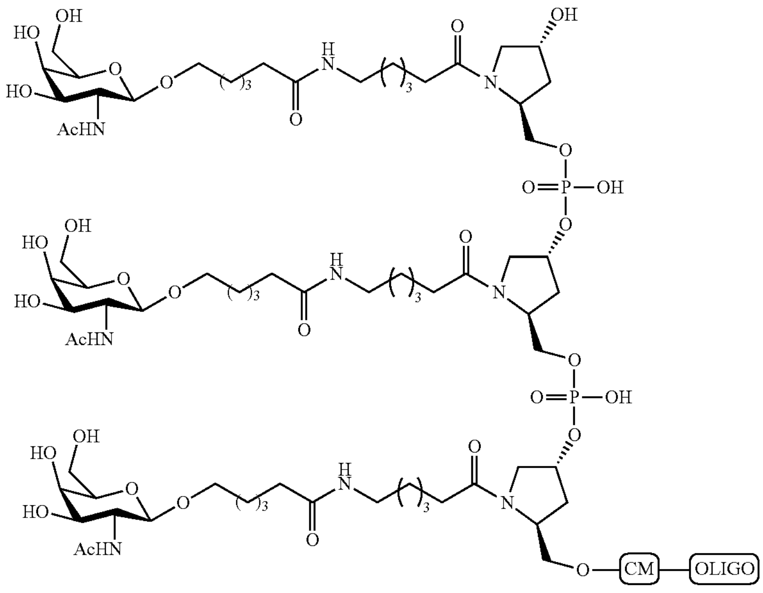

210

Compound 205 was prepared by adding PFP-TFA and DIEA to 6-(2,2,2-trifluoroacetamido) hexanoic acid in acetonitrile, which was prepared by adding triflic anhydride to 6-aminohexanoic acid. The reaction mixture was heated to 80° C., then lowered to rt. Oligomeric compound 210, comprising a $GalNAc_3$-20 conjugate group, was prepared from compound 208 using the general procedures illustrated in Example 52. The $GalNAc_3$ cluster portion of the conjugate group $GalNAc_3$-20 ($GalNAc_3$-$20_a$) can be combined with any cleavable moiety to provide a variety of conjugate groups. In certain embodiments, the cleavable moiety is —P(═O)(OH)-$A_d$-P(═O)(OH)—. The structure of $GalNAc_3$-20 ($GalNAc_3$-202-CM-) is shown below:

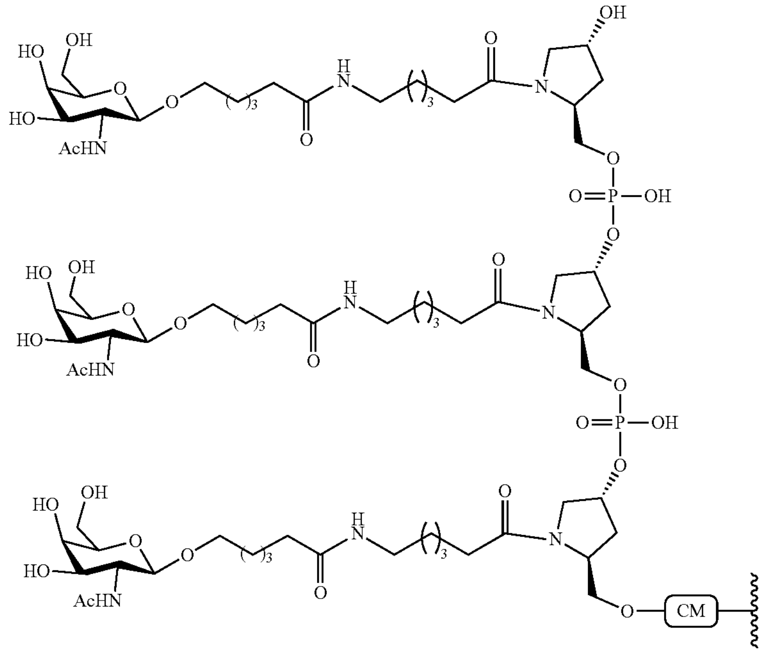
Example 72: Preparation of Oligomeric Compound 215 Comprising GalNAc$_3$-21
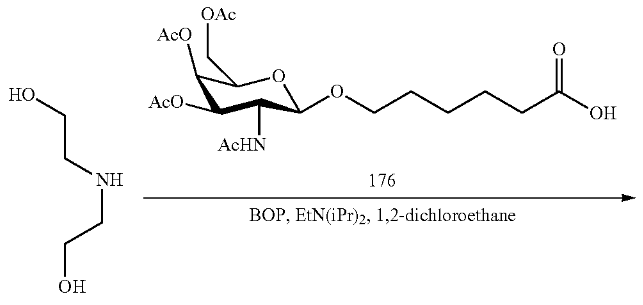
211
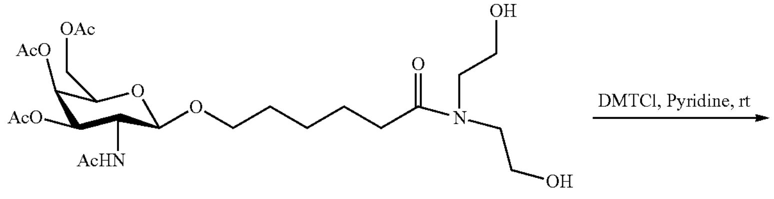
212
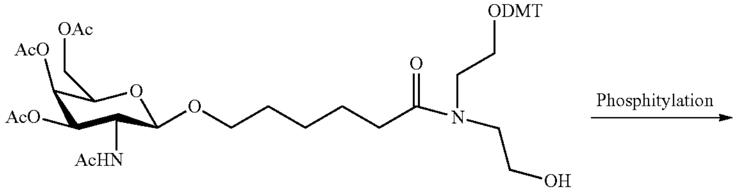
213

-continued

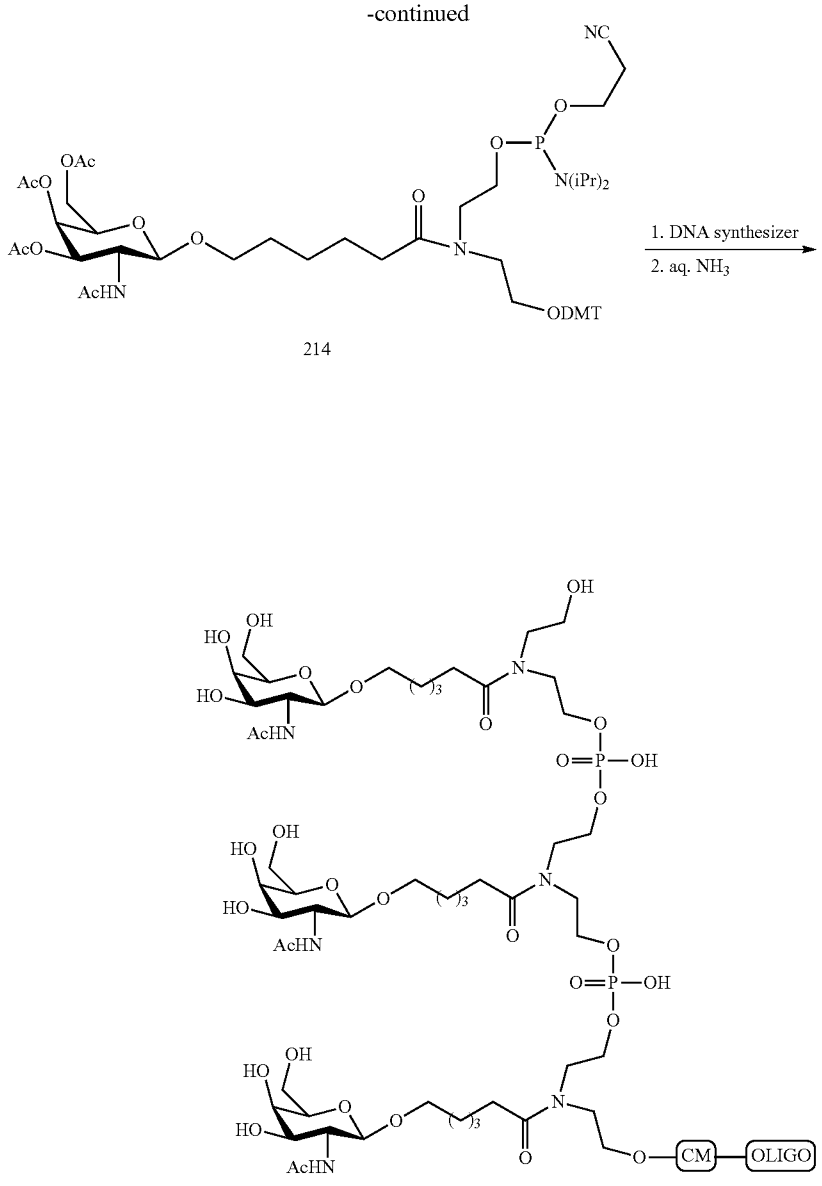

214

215

Compound 211 is commercially available. Oligomeric compound 215, comprising a $GalNAc_3$-21 conjugate group, was prepared from compound 213 using the general procedures illustrated in Example 52. The $GalNAc_3$ cluster portion of the conjugate group $GalNAc_3$-21 ($GalNAc_3$-$21_a$) can be combined with any cleavable moiety to provide a variety of conjugate groups. In certain embodiments, the cleavable moiety is —P(═O)(OH)-$A_d$-P(═O)(OH)—. The structure of $GalNAc_3$-21 ($GalNAc_3$-$21_a$-CM-) is shown below:

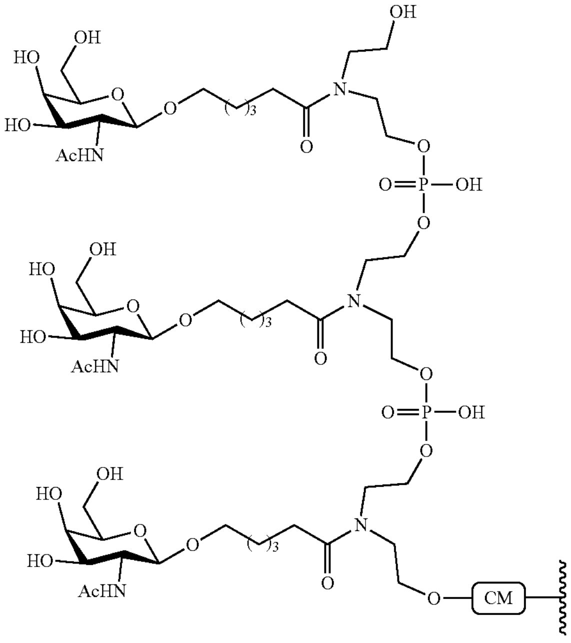
Example 73: Preparation of Oligomeric Compound 221 Comprising $GalNAc_3$-22
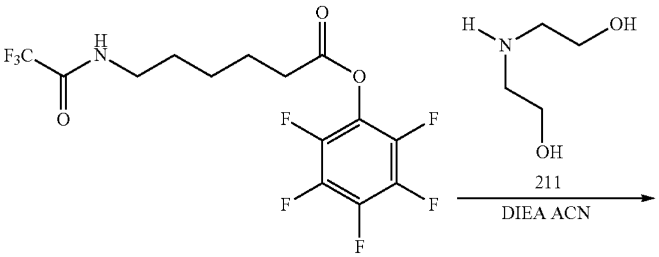
205
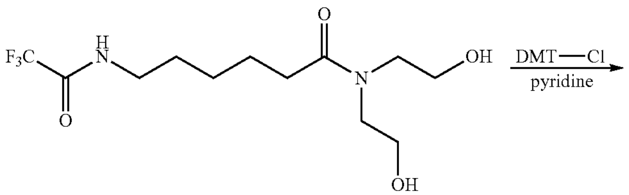
216
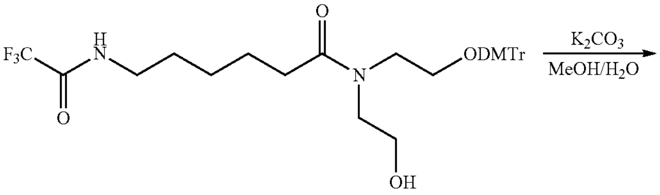
217

-continued

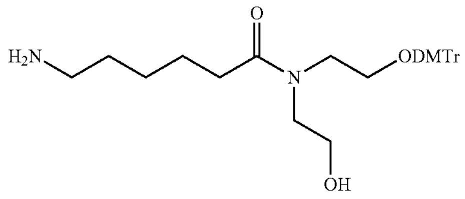

218

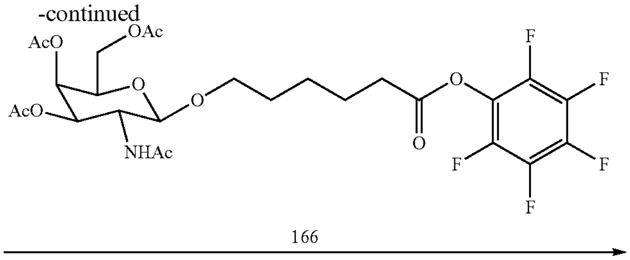

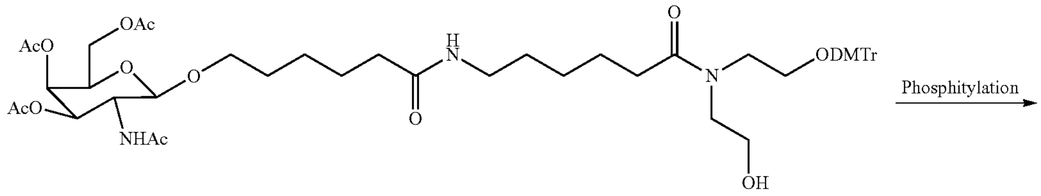

219

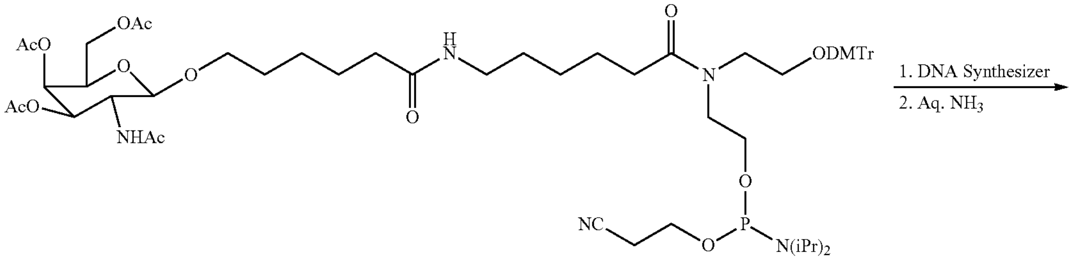

220

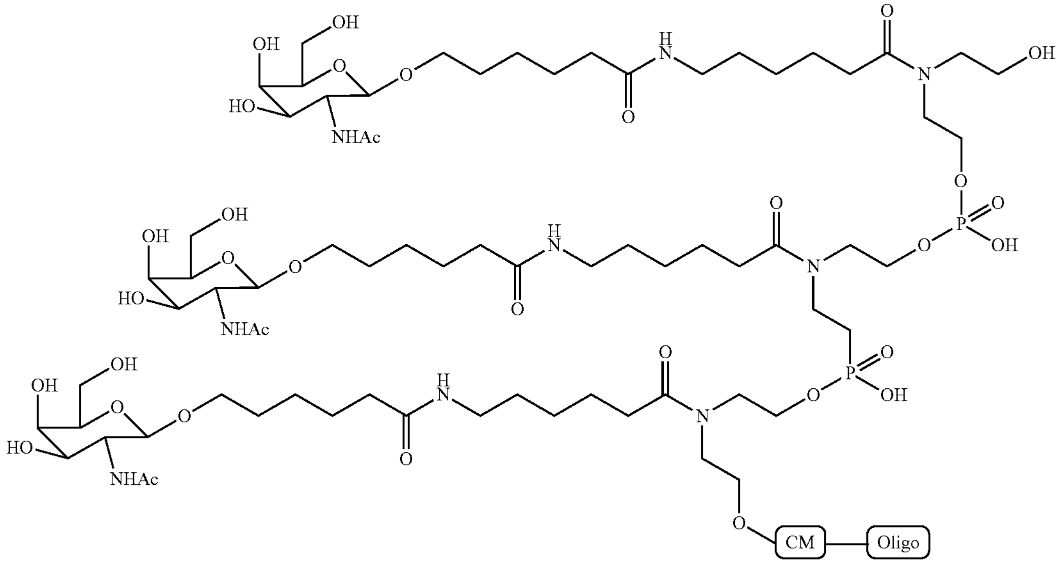

221

Compound 220 was prepared from compound 219 using diisopropylammonium tetrazolide. Oligomeric compound 221, comprising a $GalNAc_3$-21 conjugate group, is prepared from compound 220 using the general procedure illustrated in Example 52. The $GalNAc_3$ cluster portion of the conjugate group $GalNAc_3$-22 ($GalNAc_3$-$22_a$) can be combined with any cleavable moiety to provide a variety of conjugate groups. In certain embodiments, the cleavable moiety is —P(═O)(OH)-$A_a$-P(═O)(OH)—. The structure of $GalNAc_3$-22 ($GalNAc_3$-$22_a$-CM-) is shown below:

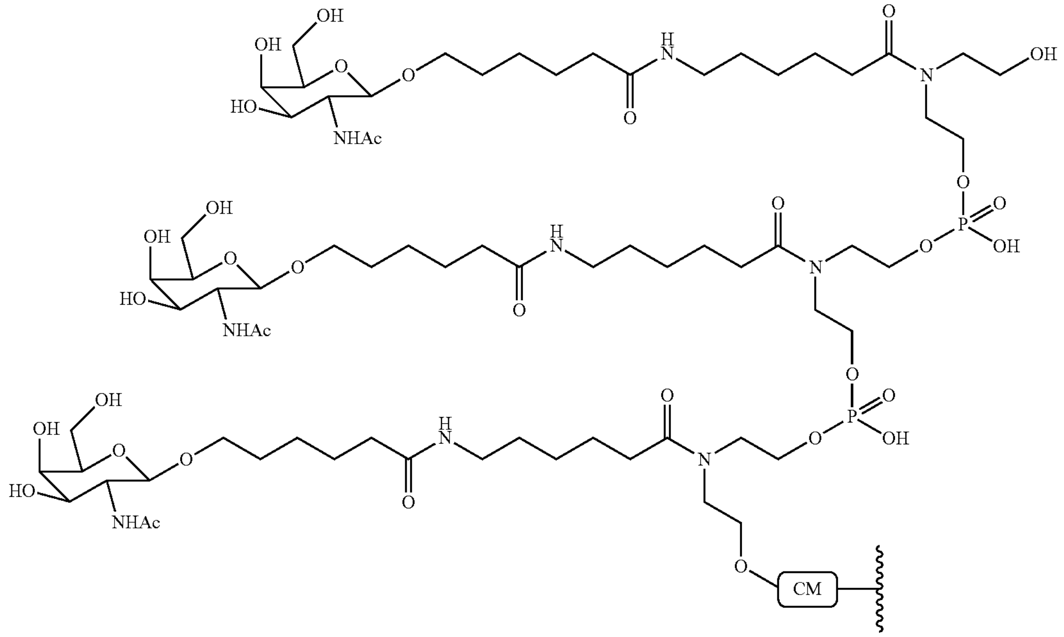

Example 74: Effect of Various Cleavable Moieties on Antisense Inhibition In Vivo by Oligonucleotides Targeting SRB-1 Comprising a 5'-GalNAc$_3$ Conjugate The oligonucleotides listed below were tested in a dose-dependent study for antisense inhibition of SRB-1 in mice. Each of the GalNAc$_3$ conjugate groups was attached at the 5' terminus of the respective oligonucleotide.

TABLE 47

| Modified ASOs targeting SRB-1 | | | | |
|---|---|---|---|---|
| ISIS No. | Sequences (5' to 3') | GalNAc$_3$ Cluster | CM | SEQ ID No. |
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{es}$ | n/a | n/a | 28 |
| 661161 | **GalNAc$_3$-3$_{a}$-$_{o'}$A$_{do}$** $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-3a | $A_d$ | 30 |
| 666904 | **GalNAc$_3$-3$_{a}$-$_{o'}$** $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-3a | PO | 28 |
| 675441 | **GalNAc$_3$-17$_{a}$-$_{o'}$A$_{do}$** $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-17a | $A_d$ | 30 |
| 675442 | **GalNAc$_3$-18$_{a}$-$_{o'}$A$_{do}$** $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | GalNAc$_3$-18a | $A_d$ | 30 |

In all tables, capital letters indicate the nucleobase for each nucleoside and "C indicates a 5-methyl cytosine. Subscripts: "e" indicates a 2'-MOE modified nucleoside; "d" indicates a β-D-2'-deoxyribonucleoside; "s" indicates a phosphorothioate internucleoside linkage (PS); "o" indicates a phosphodiester internucleoside linkage (PO); and "o'" indicates —O—P(═O)(OH)—. Conjugate groups are in bold.

The structure of GalNAc$_3$-3$_a$ was shown previously in Example 39. The structure of GalNAc$_3$-17$_a$ was shown previously in Example 68, and the structure of GalNAc$_3$-18$_a$ was shown in Example 69.

Treatment

Six to eight week old C57BL/6 mice (Jackson Laboratory, Bar Harbor, ME) were injected subcutaneously once at the dosage shown below with an oligonucleotide listed in Table 47 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 48, treatment with antisense oligonucleotides lowered SRB-1 mRNA levels in a dose-dependent manner. The antisense oligonucleotides comprising a GalNAc conjugate showed similar potencies and were significantly more potent than the parent oligonucleotide lacking a GalNAc conjugate.

TABLE 48

| SRB-1 mRNA (% Saline) | | | | |
|---|---|---|---|---|
| ISIS No. | Dosage (mg/kg) | SRB-1 mRNA (% Saline) | GalNAc$_3$ Cluster | CM |
| Saline | n/a | 100.0 | n/a | n/a |
| 353382 | 3 | 79.38 | n/a | n/a |
| | 10 | 68.67 | | |
| | 30 | 40.70 | | |
| 661161 | 0.5 | 79.18 | GalNAc$_3$-3a | $A_d$ |
| | 1.5 | 75.96 | | |

TABLE 48-continued

| SRB-1 mRNA (% Saline) | | | | |
|---|---|---|---|---|
| ISIS No. | Dosage (mg/kg) | SRB-1 mRNA (% Saline) | $GalNAc_3$ Cluster | CM |
| | 5 | 30.53 | | |
| | 15 | 12.52 | | |
| 666904 | 0.5 | 91.30 | $GalNAc_3$-3a | PO |
| | 1.5 | 57.88 | | |
| | 5 | 21.22 | | |
| | 15 | 16.49 | | |
| 675441 | 0.5 | 76.71 | $GalNAc_3$-17a | $A_d$ |
| | 1.5 | 63.63 | | |
| | 5 | 29.57 | | |
| | 15 | 13.49 | | |
| 675442 | 0.5 | 95.03 | $GalNAc_3$-18a | $A_d$ |
| | 1.5 | 60.06 | | |
| | 5 | 31.04 | | |
| | 15 | 19.40 | | |

Liver transaminase levels, alanine aminotransferase (ALT) and aspartate aminotransferase (AST), in serum were measured relative to saline injected mice using standard protocols. Total bilirubin and BUN were also evaluated. The change in body weights was evaluated with no significant change from the saline group (data not shown). ALTs, ASTs, total bilirubin and BUN values are shown in Table 49 below.

TABLE 49

| ISIS No. | Dosage (mg/kg) | ALT (U/L) | AST (U/L) | Total Bilirubin (mg/dL) | BUN (mg/dL) | $GalNAc_3$ Cluster | CM |
|---|---|---|---|---|---|---|---|
| Saline | n/a | 26 | 59 | 0.16 | 42 | n/a | n/a |
| 353382 | 3 | 23 | 58 | 0.18 | 39 | n/a | n/a |
| | 10 | 28 | 58 | 0.16 | 43 | | |
| | 30 | 20 | 48 | 0.12 | 34 | | |
| 661161 | 0.5 | 30 | 47 | 0.13 | 35 | $GalNAc_3$-3a | $A_d$ |
| | 1.5 | 23 | 53 | 0.14 | 37 | | |
| | 5 | 26 | 48 | 0.15 | 39 | | |
| | 15 | 32 | 57 | 0.15 | 42 | | |
| 666904 | 0.5 | 24 | 73 | 0.13 | 36 | $GalNAc_3$-3a | PO |
| | 1.5 | 21 | 48 | 0.12 | 32 | | |
| | 5 | 19 | 49 | 0.14 | 33 | | |
| | 15 | 20 | 52 | 0.15 | 26 | | |
| 675441 | 0.5 | 42 | 148 | 0.21 | 36 | $GalNAc_3$-17a | $A_d$ |
| | 1.5 | 60 | 95 | 0.16 | 34 | | |
| | 5 | 27 | 75 | 0.14 | 37 | | |
| | 15 | 24 | 61 | 0.14 | 36 | | |
| 675442 | 0.5 | 26 | 65 | 0.15 | 37 | $GalNAc_3$-18a | $A_d$ |
| | 1.5 | 25 | 64 | 0.15 | 43 | | |
| | 5 | 27 | 69 | 0.15 | 37 | | |
| | 15 | 30 | 84 | 0.14 | 37 | | |

Example 75: Pharmacokinetic Analysis of Oligonucleotides Comprising a 5'-Conjugate Group The PK of the ASOs in Tables 41, 44 and 47 above was evaluated using liver samples that were obtained following the treatment procedures described in Examples 65, 66, and 74. The liver samples were minced and extracted using standard protocols and analyzed by IP-HPLC-MS alongside an internal standard. The combined tissue level (μg/g) of all metabolites was measured by integrating the appropriate UV peaks, and the tissue level of the full-length ASO missing the conjugate ("parent," which is Isis No. 353382 in this case) was measured using the appropriate extracted ion chromatograms (EIC).

TABLE 50

| PK Analysis in Liver | | | | | |
|---|---|---|---|---|---|
| ISIS No. | Dosage (mg/kg) | Total Tissue Level by UV (μg/g) | Parent ASO Tissue Level by EIC (μg/g) | $GalNAc_3$ Cluster | CM |
| 353382 | 3 | 8.9 | 8.6 | n/a | n/a |
| | 10 | 22.4 | 21.0 | | |
| | 30 | 54.2 | 44.2 | | |
| 661161 | 5 | 32.4 | 20.7 | $GalNAc_3$-3a | $A_d$ |
| | 15 | 63.2 | 44.1 | | |
| 671144 | 5 | 20.5 | 19.2 | $GalNAc_3$-12a | $A_d$ |
| | 15 | 48.6 | 41.5 | | |
| 670061 | 5 | 31.6 | 28.0 | $GalNAc_3$-13a | $A_d$ |
| | 15 | 67.6 | 55.5 | | |
| 671261 | 5 | 19.8 | 16.8 | $GalNAc_3$-14a | $A_d$ |
| | 15 | 64.7 | 49.1 | | |
| 671262 | 5 | 18.5 | 7.4 | $GalNAc_3$-15a | $A_d$ |
| | 15 | 52.3 | 24.2 | | |
| 670699 | 5 | 16.4 | 10.4 | $GalNAc_3$-3a | $T_d$ |
| | 15 | 31.5 | 22.5 | | |
| 670700 | 5 | 19.3 | 10.9 | $GalNAc_3$-3a | $A_e$ |
| | 15 | 38.1 | 20.0 | | |
| 670701 | 5 | 21.8 | 8.8 | $GalNAc_3$-3a | $T_e$ |
| | 15 | 35.2 | 16.1 | | |
| 671165 | 5 | 27.1 | 26.5 | $GalNAc_3$-13a | $A_d$ |
| | 15 | 48.3 | 44.3 | | |
| 666904 | 5 | 30.8 | 24.0 | $GalNAc_3$-3a | PO |
| | 15 | 52.6 | 37.6 | | |
| 675441 | 5 | 25.4 | 19.0 | $GalNAc_3$-17a | $A_d$ |
| | 15 | 54.2 | 42.1 | | |
| 675442 | 5 | 22.2 | 20.7 | $GalNAc_3$-18a | $A_d$ |
| | 15 | 39.6 | 29.0 | | |

The results in Table 50 above show that there were greater liver tissue levels of the oligonucleotides comprising a $GalNAc_3$ conjugate group than of the parent oligonucleotide that does not comprise a $GalNAc_3$ conjugate group (ISIS 353382) 72 hours following oligonucleotide administration, particularly when taking into consideration the differences in dosing between the oligonucleotides with and without a $GalNAc_3$ conjugate group. Furthermore, by 72 hours, 40-98% of each oligonucleotide comprising a $GalNAc_3$ conjugate group was metabolized to the parent compound, indicating that the $GalNAc_3$ conjugate groups were cleaved from the oligonucleotides.

Example 76: Preparation of Oligomeric Compound 230 Comprising $GalNAc_3$-23

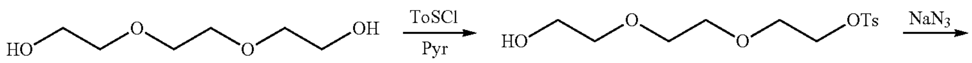

222

223

-continued
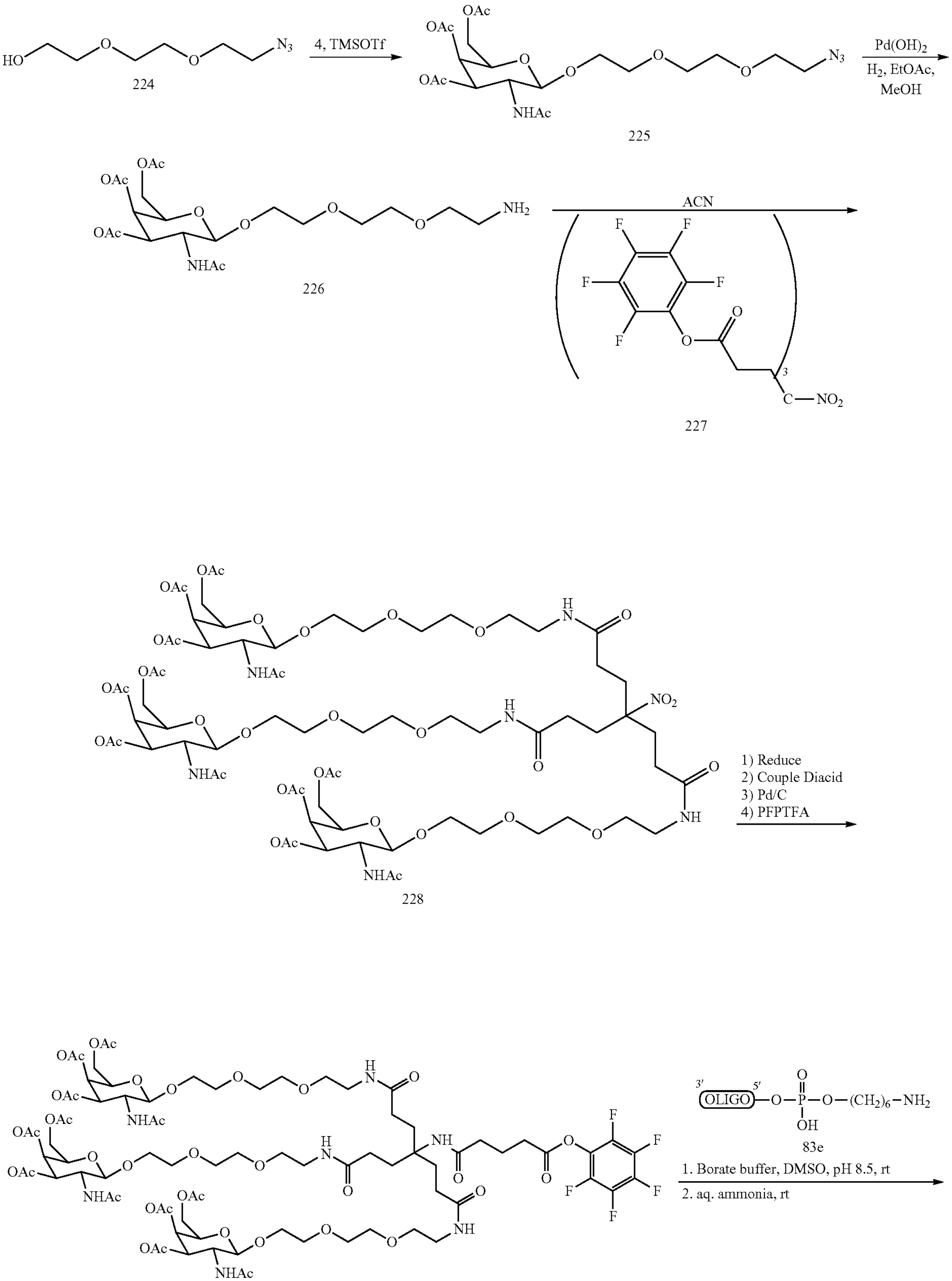
224
225
226
227
228
229
83e

-continued

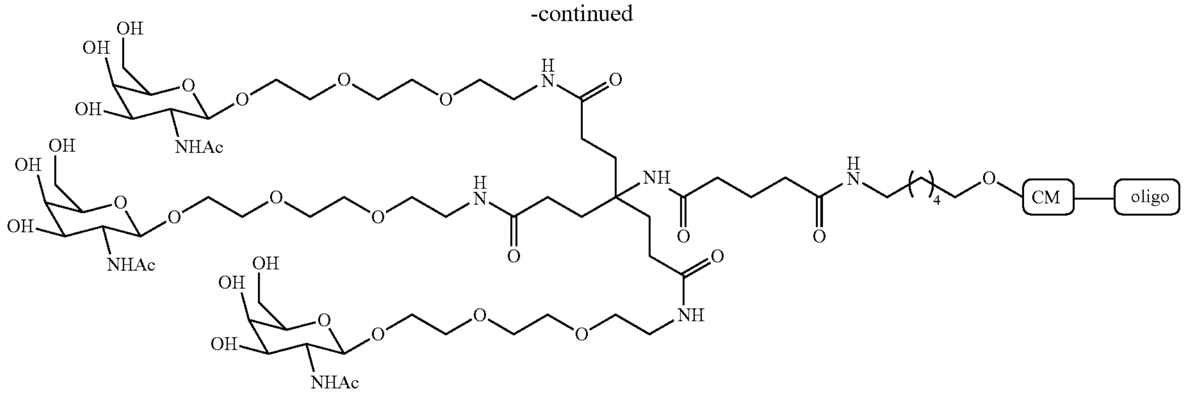

230

Compound 222 is commercially available. 44.48 ml (0.33 mol) of compound 222 was treated with tosyl chloride (25.39 g, 0.13 mol) in pyridine (500 mL) for 16 hours. The reaction was then evaporated to an oil, dissolved in EtOAc and washed with water, sat. $NaHCO_3$, brine, and dried over $Na_2SO_4$. The ethyl acetate was concentrated to dryness and purified by column chromatography, eluted with EtOAc/hexanes (1:1) followed by 10% methanol in $CH_2Cl_2$ to give compound 223 as a colorless oil. LCMS and NMR were consistent with the structure. 10 g (32.86 mmol) of 1-Tosyltriethylene glycol (compound 223) was treated with sodium azide (10.68 g, 164.28 mmol) in DMSO(100 mL) at room temperature for 17 hours. The reaction mixture was then poured onto water, and extracted with EtOAc. The organic layer was washed with water three times and dried over $Na_2SO_4$. The organic layer was concentrated to dryness to give 5.3 g of compound 224 (92%). LCMS and NMR were consistent with the structure. 1-Azidotriethylene glycol (compound 224, 5.53 g, 23.69 mmol) and compound 4 (6 g, 18.22 mmol) were treated with 4A molecular sieves (5 g), and TMSOTf (1.65 ml, 9.11 mmol) in dichloromethane (100 mL) under an inert atmosphere. After 14 hours, the reaction was filtered to remove the sieves, and the organic layer was washed with sat. $NaHCO_3$, water, brine, and dried over $Na_2SO_4$. The organic layer was concentrated to dryness and purified by column chromatography, eluted with a gradient of 2 to 4% methanol in dichloromethane to give compound 225. LCMS and NMR were consistent with the structure. Compound 225 (11.9 g, 23.59 mmol) was hydrogenated in EtOAc/Methanol (4:1, 250 mL) over Pearlman's catalyst. After 8 hours, the catalyst was removed by filtration and the solvents removed to dryness to give compound 226. LCMS and NMR were consistent with the structure.

In order to generate compound 227, a solution of nitromethanetrispropionic acid (4.17 g, 15.04 mmol) and Hunig's base (10.3 ml, 60.17 mmol) in DMF (100 mL) were treated dropwise with pentaflourotrifluoro acetate (9.05 ml, 52.65 mmol). After 30 minutes, the reaction was poured onto ice water and extracted with EtOAc. The organic layer was washed with water, brine, and dried over $Na_2SO_4$. The organic layer was concentrated to dryness and then recrystallized from heptane to give compound 227 as a white solid. LCMS and NMR were consistent with the structure. Compound 227 (1.5 g, 1.93 mmol) and compound 226 (3.7 g, 7.74 mmol) were stirred at room temperature in acetonitrile (15 mL) for 2 hours. The reaction was then evaporated to dryness and purified by column chromatography, eluting with a gradient of 2 to 10% methanol in dichloromethane to give compound 228. LCMS and NMR were consistent with the structure. Compound 228 (1.7 g, 1.02 mmol) was treated with Raney Nickel (about 2 g wet) in ethanol (100 mL) in an atmosphere of hydrogen. After 12 hours, the catalyst was removed by filtration and the organic layer was evaporated to a solid that was used directly in the next step. LCMS and NMR were consistent with the structure. This solid (0.87 g, 0.53 mmol) was treated with benzylglutaric acid (0.18 g, 0.8 mmol), HBTU (0.3 g, 0.8 mmol) and DIEA (273.7 μl, 1.6 mmol) in DMF (5 mL). After 16 hours, the DMF was removed under reduced pressure at 65° C. to an oil, and the oil was dissolved in dichloromethane. The organic layer was washed with sat. $NaHCO_3$, brine, and dried over $Na_2SO_4$. After evaporation of the organic layer, the compound was purified by column chromatography and eluted with a gradient of 2 to 20% methanol in dichloromethane to give the coupled product. LCMS and NMR were consistent with the structure. The benzyl ester was deprotected with Pearlman's catalyst under a hydrogen atmosphere for 1 hour. The catalyst was them removed by filtration and the solvents removed to dryness to give the acid. LCMS and NMR were consistent with the structure. The acid (486 mg, 0.27 mmol) was dissolved in dry DMF (3 mL). Pyridine (53.61 μl, 0.66 mmol) was added and the reaction was purged with argon. Pentaflourotriflouro acetate (46.39 μl, 0.4 mmol) was slowly added to the reaction mixture. The color of the reaction changed from pale yellow to burgundy, and gave off a light smoke which was blown away with a stream of argon. The reaction was allowed to stir at room temperature for one hour (completion of reaction was confirmed by LCMS). The solvent was removed under reduced pressure (rotovap) at 70° C. The residue was diluted with DCM and washed with IN $NaHSO_4$, brine, saturated sodium bicarbonate and brine again. The organics were dried over $Na_2SO_4$, filtered, and were concentrated to dryness to give 225 mg of compound 229 as a brittle yellow foam. LCMS and NMR were consistent with the structure.

Oligomeric compound 230, comprising a $GalNAc_3$-23 conjugate group, was prepared from compound 229 using the general procedure illustrated in Example 46. The $GalNAc_3$ cluster portion of the $GalNAc_3$-23 conjugate group ($GalNAc_3$-$23_a$) can be combined with any cleavable moiety to provide a variety of conjugate groups. The structure of $GalNAc_3$-23 ($GalNAc_3$-$23_a$-CM) is shown below:

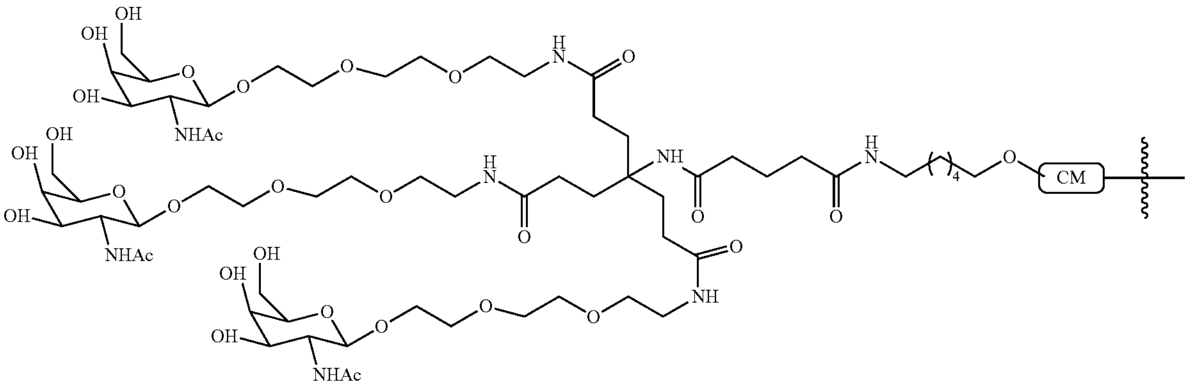

Example 77: Antisense Inhibition In Vivo by Oligonucleotides Targeting SRB-1 Comprising a $GalNAc_3$ Conjugate The oligonucleotides listed below were tested in a dose-dependent study for antisense inhibition of SRB-1 in mice.

TABLE 51

Modified ASOs targeting SRB-1

| ISIS No. | Sequences (5' to 3') | $GalNAc_3$ Cluster | CM | SEQ ID No. |
|---|---|---|---|---|
| 661161 | $\mathbf{GalNAc_3\text{-}3_a\text{-}_{o'}A_{do}}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | $A_d$ | 30 |
| 666904 | $\mathbf{GalNAc_3\text{-}3_a\text{-}_{o'}}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | PO | 28 |
| 673502 | $\mathbf{GalNAc_3\text{-}10_a\text{-}_{o'}A_{do}}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | $GalNAc_3$-10a | $A_d$ | 30 |
| 677844 | $\mathbf{GalNAc_3\text{-}9_a\text{-}_{o'}A_{do}}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-9a | $A_d$ | 30 |
| 677843 | $\mathbf{GalNAc_3\text{-}23_a\text{-}_{o'}A_{do}}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-23a | $A_d$ | 30 |
| 655861 | $G_{es}{}^{m}C_{es}T_{es}T_{es}{}^{m}C_{es}A_{ds}G_{ds}T_{ds}{}^{m}C_{ds}GA_{ds}T_{dsds}A_{ds}{}^{m}C_{ds}T_{ds}T_{es}{}^{m}C_{es}{}^{m}C_{es}T_{es}T_{eo}\mathbf{A_{do'}\text{-}GalNAc_3\text{-}1_a}$ | $GalNAc_3$-1a | $A_d$ | 29 |
| 677841 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}\mathbf{A_{do'}\text{-}GalNAc_3\text{-}19_a}$ | $GalNAc_3$-19a | $A_d$ | 29 |
| 677842 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}\mathbf{A_{do'}\text{-}GalNAc_3\text{-}20_a}$ | $GalNAc_3$-20a | $A_d$ | 29 |

The structure of $GalNAc_3$-$1_a$ was shown previously in Example 9, $GalNAc_3$-$3_a$ was shown in Example 39, $GalNAc_3$-$9_a$ was shown in Example 52, $GalNAc_3$-$10_a$ was shown in Example 46, $GalNAc_3$-$19_a$ was shown in Example 70, $GalNAc_3$-$20_a$ was shown in Example 71, and $GalNAc_3$-$23_a$ was shown in Example 76.

Treatment

Six to eight week old C57BL/6 mice (Jackson Laboratory, Bar Harbor, ME) were each injected subcutaneously once at a dosage shown below with an oligonucleotide listed in Table 51 or with saline. Each treatment group consisted of 4 animals. The mice were sacrificed 72 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of SRB-1 mRNA levels for each treatment group, normalized to the saline control.

As illustrated in Table 52, treatment with antisense oligonucleotides lowered SRB-1 mRNA levels in a dose-dependent manner.

TABLE 52

SRB-1 mRNA (% Saline)

| ISIS No. | Dosage (mg/kg) | SRB-1 mRNA (% Saline) | $GalNAc_3$ Cluster | CM |
|---|---|---|---|---|
| Saline | n/a | 100.0 | n/a | n/a |
| 661161 | 0.5 | 89.18 | $GalNAc_3$-3a | $A_d$ |
| | 1.5 | 77.02 | | |
| | 5 | 29.10 | | |
| | 15 | 12.64 | | |
| 666904 | 0.5 | 93.11 | $GalNAc_3$-3a | PO |
| | 1.5 | 55.85 | | |
| | 5 | 21.29 | | |
| | 15 | 13.43 | | |
| 673502 | 0.5 | 77.75 | $GalNAc_3$-10a | $A_d$ |
| | 1.5 | 41.05 | | |
| | 5 | 19.27 | | |
| | 15 | 14.41 | | |
| 677844 | 0.5 | 87.65 | $GalNAc_3$-9a | $A_d$ |
| | 1.5 | 93.04 | | |
| | 5 | 40.77 | | |
| | 15 | 16.95 | | |
| 677843 | 0.5 | 102.28 | $GalNAc_3$-23a | $A_d$ |
| | 1.5 | 70.51 | | |
| | 5 | 30.68 | | |
| | 15 | 13.26 | | |
| 655861 | 0.5 | 79.72 | $GalNAc_3$-1a | $A_d$ |
| | 1.5 | 55.48 | | |
| | 5 | 26.99 | | |
| | 15 | 17.58 | | |
| 677841 | 0.5 | 67.43 | $GalNAc_3$-19a | $A_d$ |
| | 1.5 | 45.13 | | |
| | 5 | 27.02 | | |
| | 15 | 12.41 | | |
| 677842 | 0.5 | 64.13 | $GalNAc_3$-20a | $A_d$ |
| | 1.5 | 53.56 | | |
| | 5 | 20.47 | | |
| | 15 | 10.23 | | |

Liver transaminase levels, alanine aminotransferase (ALT) and aspartate aminotransferase (AST), in serum were also measured using standard protocols. Total bilirubin and BUN were also evaluated. Changes in body weights were evaluated, with no significant change from the saline group (data not shown). ALTs, ASTs, total bilirubin and BUN values are shown in Table 53 below.

TABLE 53

| ISIS No. | Dosage (mg/kg) | ALT (U/L) | AST (U/L) | Total Bilirubin (mg/dL) | BUN (mg/dL) | $GalNAc_3$ Cluster | CM |
|---|---|---|---|---|---|---|---|
| Saline | n/a | 21 | 45 | 0.13 | 34 | n/a | n/a |
| 661161 | 0.5 | 28 | 51 | 0.14 | 39 | $GalNAc_3$-3a | $A_d$ |
| | 1.5 | 23 | 42 | 0.13 | 39 | | |
| | 5 | 22 | 59 | 0.13 | 37 | | |
| | 15 | 21 | 56 | 0.15 | 35 | | |
| 666904 | 0.5 | 24 | 56 | 0.14 | 37 | $GalNAc_3$-3a | PO |
| | 1.5 | 26 | 68 | 0.15 | 35 | | |
| | 5 | 23 | 77 | 0.14 | 34 | | |
| | 15 | 24 | 60 | 0.13 | 35 | | |
| 673502 | 0.5 | 24 | 59 | 0.16 | 34 | $GalNAc_3$-10a | $A_d$ |
| | 1.5 | 20 | 46 | 0.17 | 32 | | |
| | 5 | 24 | 45 | 0.12 | 31 | | |
| | 15 | 24 | 47 | 0.13 | 34 | | |
| 677844 | 0.5 | 25 | 61 | 0.14 | 37 | $GalNAc_3$-9a | $A_d$ |
| | 1.5 | 23 | 64 | 0.17 | 33 | | |
| | 5 | 25 | 58 | 0.13 | 35 | | |
| | 15 | 22 | 65 | 0.14 | 34 | | |
| 677843 | 0.5 | 53 | 53 | 0.13 | 35 | $GalNAc_3$-23a | $A_d$ |
| | 1.5 | 25 | 54 | 0.13 | 34 | | |
| | 5 | 21 | 60 | 0.15 | 34 | | |
| | 15 | 22 | 43 | 0.12 | 38 | | |
| 655861 | 0.5 | 21 | 48 | 0.15 | 33 | $GalNAc_3$-1a | $A_d$ |
| | 1.5 | 28 | 54 | 0.12 | 35 | | |
| | 5 | 22 | 60 | 0.13 | 36 | | |
| | 15 | 21 | 55 | 0.17 | 30 | | |
| 677841 | 0.5 | 32 | 54 | 0.13 | 34 | $GalNAc_3$-19a | $A_d$ |
| | 1.5 | 24 | 56 | 0.14 | 34 | | |
| | 5 | 23 | 92 | 0.18 | 31 | | |
| | 15 | 24 | 58 | 0.15 | 31 | | |
| 677842 | 0.5 | 23 | 61 | 0.15 | 35 | $GalNAc_3$-20a | $A_d$ |
| | 1.5 | 24 | 57 | 0.14 | 34 | | |
| | 5 | 41 | 62 | 0.15 | 35 | | |
| | 15 | 24 | 37 | 0.14 | 32 | | |

Example 78: Antisense Inhibition In Vivo by Oligonucleotides Targeting Angiotensinogen Comprising a $GalNAc_3$ Conjugate The oligonucleotides listed below were tested in a dose-dependent study for antisense inhibition of Angiotensinogen (AGT) in normotensive Sprague Dawley rats.

TABLE 54

Modified ASOs targeting AGT

| ISIS No. | Sequences (5' to 3') | $GalNAc_3$ Cluster | CM | SEQ ID No. |
|---|---|---|---|---|
| 552668 | $^{m}C_{es}A_{es}{}^{m}C_{es}T_{es}G_{es}A_{ds}T_{ds}T_{ds}T_{ds}T_{ds}T_{ds}G_{ds}{}^{m}C_{ds}{}^{m}C_{ds}{}^{m}C_{ds}A_{es}G_{es}G_{es}A_{es}T_{e}$ | n/a | n/a | 34 |
| 669509 | $^{m}C_{es}A_{es}{}^{m}C_{es}T_{es}G_{es}A_{ds}T_{ds}T_{ds}T_{ds}T_{ds}T_{ds}G_{ds}{}^{m}C_{ds}{}^{m}C_{ds}{}^{m}C_{ds}A_{es}G_{es}G_{es}A_{es}T_{eo}A_{do'}$**-GalNAc$_3$-1$_a$** | $GalNAc_3$-$1_a$ | Ad | 35 |

The structure of $GalNAc_3$-$1_a$ was shown previously in Example 9.

Treatment

Six week old, male Sprague Dawley rats were each injected subcutaneously once per week at a dosage shown below, for a total of three doses, with an oligonucleotide listed in Table 54 or with PBS. Each treatment group consisted of 4 animals. The rats were sacrificed 72 hours following the final dose. AGT liver mRNA levels were measured using real-time PCR and RIBOGREEN® RNA quantification reagent (Molecular Probes, Inc. Eugene, OR) according to standard protocols. AGT plasma protein levels were measured using the Total Angiotensinogen ELISA (Catalog #JP27412, IBL International, Toronto, ON) with plasma diluted 1:20,000. The results below are presented as the average percent of AGT mRNA levels in liver or AGT protein levels in plasma for each treatment group, normalized to the PBS control.

As illustrated in Table 55, treatment with antisense oligonucleotides lowered AGT liver mRNA and plasma protein levels in a dose-dependent manner, and the oligonucleotide comprising a GalNAc conjugate was significantly more potent than the parent oligonucleotide lacking a GalNAc conjugate.

TABLE 55

AGT liver mRNA and plasma protein levels

| ISIS No. | Dosage | AGT liver mRNA (% PBS) | AGT plasma protein (% PBS) | $GalNAc_3$ Cluster | CM |
|---|---|---|---|---|---|
| PBS | n/a | 100 | 100 | n/a | n/a |
| 552668 | 3 | 95 | 122 | n/a | n/a |
| | 10 | 85 | 97 | | |
| | 30 | 46 | 79 | | |
| | 90 | 8 | 11 | | |
| 669509 | 0.3 | 95 | 70 | $GalNAc_3$-1a | $A_d$ |
| | 1 | 95 | 129 | | |
| | 3 | 62 | 97 | | |
| | 10 | 9 | 23 | | |

Liver transaminase levels, alanine aminotransferase (ALT) and aspartate aminotransferase (AST), in plasma and body weights were also measured at time of sacrifice using standard protocols. The results are shown in Table 56 below.

TABLE 56

Liver transaminase levels and rat body weights

| ISIS No. | Dosage (mg/kg) | ALT (U/L) | AST (U/L) | Body Weight (% of baseline) | $GalNAc_3$ Cluster | CM |
|---|---|---|---|---|---|---|
| PBS | n/a | 51 | 81 | 186 | n/a | n/a |
| 552668 | 3 | 54 | 93 | 183 | n/a | n/a |
| | 10 | 51 | 93 | 194 | | |
| | 30 | 59 | 99 | 182 | | |
| | 90 | 56 | 78 | 170 | | |
| 669509 | 0.3 | 53 | 90 | 190 | $GalNAc_3$-1a | $A_d$ |
| | 1 | 51 | 93 | 192 | | |
| | 3 | 48 | 85 | 189 | | |
| | 10 | 56 | 95 | 189 | | |

Example 79: Duration of Action In Vivo of Oligonucleotides Targeting APOC-III Comprising a $GalNAc_3$ Conjugate The oligonucleotides listed in Table 57 below were tested in a single dose study for duration of action in mice

TABLE 57

| Modified ASOs targeting APOC-III | | | | |
|---|---|---|---|---|
| ISIS No. | Sequences (5' to 3') | $GalNAc_3$ Cluster | CM | SEQ ID No. |
| 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | n/a | n/a | 20 |
| 647535 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{eo}A_{do'}$-**$GalNAc_3$-1**$_a$ | $GalNAc_3$-1a | $A_d$ | 21 |
| 663083 | **$GalNAc_3$-3**$_a$-$_{o'}$**A**$_{do}A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-3a | $A_d$ | 36 |
| 674449 | **$GalNAc_3$-7**$_a$-$_{o'}$**A**$_{do}A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-7a | $A_d$ | 36 |
| 674450 | **$GalNAc_3$-10**$_a$-$_{o'}$**A**$_{do}A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-10a | $A_d$ | 36 |

TABLE 57-continued

| Modified ASOs targeting APOC-III | | | | |
|---|---|---|---|---|
| ISIS No. | Sequences (5' to 3') | $GalNAc_3$ Cluster | CM | SEQ ID No. |
| 674451 | **$GalNAc_3$-13**$_a$-$_{o'}$**A**$_{do}A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | $GalNAc_3$-13a | $A_d$ | 36 |

The structure of $GalNAc_3$-1a was shown previously in Example 9, $GalNAc_3$-$3_a$ was shown in Example 39, $GalNAc_3$-$7_a$ was shown in Example 48, $GalNAc_3$-$10_a$ was shown in Example 46, and $GalNAc_3$-$13_a$ was shown in Example 62.

Treatment

Six to eight week old transgenic mice that express human APOC-III were each injected subcutaneously once with an oligonucleotide listed in Table 57 or with PBS. Each treatment group consisted of 3 animals. Blood was drawn before dosing to determine baseline and at 72 hours, 1 week, 2 weeks, 3 weeks, 4 weeks, 5 weeks, and 6 weeks following the dose. Plasma triglyceride and APOC-III protein levels were measured as described in Example 20. The results below are presented as the average percent of plasma triglyceride and APOC-III levels for each treatment group, normalized to baseline levels, showing that the oligonucleotides comprising a GalNAc conjugate group exhibited a longer duration of action than the parent oligonucleotide without a conjugate group (ISIS 304801) even though the dosage of the parent was three times the dosage of the oligonucleotides comprising a GalNAc conjugate group.

TABLE 58

| Plasma triglyceride and APOC-III protein levels in transgenic mice | | | | | | |
|---|---|---|---|---|---|---|
| ISIS No. | Dosage (mg/kg) | Time point (days post-dose) | Tri-glycerides (% baseline) | APOC-III protein (% baseline) | $GalNAc_3$ Cluster | CM |
| PBS | n/a | 3 | 97 | 102 | n/a | n/a |
| | | 7 | 101 | 98 | | |
| | | 14 | 108 | 98 | | |
| | | 21 | 107 | 107 | | |
| | | 28 | 94 | 91 | | |
| | | 35 | 88 | 90 | | |
| | | 42 | 91 | 105 | | |
| 304801 | 30 | 3 | 40 | 34 | n/a | n/a |
| | | 7 | 41 | 37 | | |
| | | 14 | 50 | 57 | | |
| | | 21 | 50 | 50 | | |
| | | 28 | 57 | 73 | | |
| | | 35 | 68 | 70 | | |
| | | 42 | 75 | 93 | | |
| 647535 | 10 | 3 | 36 | 37 | $GalNAc_3$-1a | $A_d$ |
| | | 7 | 39 | 47 | | |
| | | 14 | 40 | 45 | | |
| | | 21 | 41 | 41 | | |
| | | 28 | 42 | 62 | | |
| | | 35 | 69 | 69 | | |
| | | 42 | 85 | 102 | | |
| 663083 | 10 | 3 | 24 | 18 | $GalNAc_3$-3a | $A_d$ |
| | | 7 | 28 | 23 | | |
| | | 14 | 25 | 27 | | |
| | | 21 | 28 | 28 | | |
| | | 28 | 37 | 44 | | |
| | | 35 | 55 | 57 | | |
| | | 42 | 60 | 78 | | |
| 674449 | 10 | 3 | 29 | 26 | $GalNAc_3$-7a | $A_d$ |
| | | 7 | 32 | 31 | | |
| | | 14 | 38 | 41 | | |
| | | 21 | 44 | 44 | | |
| | | 28 | 53 | 63 | | |
| | | 35 | 69 | 77 | | |

TABLE 58-continued

| Plasma triglyceride and APOC-III protein levels in transgenic mice | | | | | | |
|---|---|---|---|---|---|---|
| ISIS No. | Dosage (mg/kg) | Time point (days post-dose) | Tri-glycerides (% baseline) | APOC-III protein (% baseline) | $GalNAc_3$ Cluster | CM |
| | | 42 | 78 | 99 | | |
| 674450 | 10 | 3 | 33 | 30 | $GalNAc_3$-10a | $A_d$ |
| | | 7 | 35 | 34 | | |
| | | 14 | 31 | 34 | | |
| | | 21 | 44 | 44 | | |
| | | 28 | 56 | 61 | | |
| | | 35 | 68 | 70 | | |
| | | 42 | 83 | 95 | | |
| 674451 | 10 | 3 | 35 | 33 | $GalNAc_3$-13a | $A_d$ |
| | | 7 | 24 | 32 | | |
| | | 14 | 40 | 34 | | |
| | | 21 | 48 | 48 | | |
| | | 28 | 54 | 67 | | |
| | | 35 | 65 | 75 | | |
| | | 42 | 74 | 97 | | |

Example 80: Antisense Inhibition In Vivo by Oligonucleotides Targeting Alpha-1 Antitrypsin (A1AT) Comprising a $GalNAc_3$ Conjugate The oligonucleotides listed in Table 59 below were tested in a study for dose-dependent inhibition of A1AT in mice.

TABLE 59

| Modified ASOs targeting A1AT | | | | |
|---|---|---|---|---|
| ISIS No. | Sequences (5' to 3') | $GalNAc_3$ Cluster | CM | SEQ ID No. |
| 476366 | $A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | n/a | n/a | 37 |
| 656326 | $A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{eo}\mathbf{A_{do'}}$**-GalNAc$_3$-1$_a$** | $GalNAC_3$-1a | $A_d$ | 38 |
| 678381 | **GalNAc$_3$-3$_a$-$_{o'}$A$_{do}$**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | $GalNAC_3$-3a | $A_d$ | 39 |
| 678382 | **GalNAc$_3$-7$_a$-$_{o'}$A$_{do}$**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | $GalNAC_3$-7a | $A_d$ | 39 |
| 678383 | **GalNAc$_3$-10$_a$-$_{o'}$A$_{do}$**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | $GalNAC_3$-10a | $A_d$ | 39 |
| 678384 | **GalNAc$_3$-13$_a$-$_{o'}$A$_{do}$**$A_{es}{}^{m}C_{es}{}^{m}C_{es}{}^{m}C_{es}A_{es}A_{ds}T_{ds}T_{ds}{}^{m}C_{ds}A_{ds}G_{ds}A_{ds}A_{ds}G_{ds}G_{ds}A_{es}A_{es}G_{es}G_{es}A_{e}$ | $GalNAC_3$-13a | $A_d$ | 39 |

The structure of $GalNAc_3$-1a was shown previously in Example 9, $GalNAc_3$-$3_a$ was shown in Example 39, $GalNAc_3$-$7_a$ was shown in Example 48, $GalNAc_3$-$10_a$ was shown in Example 46, and $GalNAc_3$-$13_a$ was shown in Example 62.

Treatment

Six week old, male C57BL/6 mice (Jackson Laboratory, Bar Harbor, ME) were each injected subcutaneously once per week at a dosage shown below, for a total of three doses, with an oligonucleotide listed in Table 59 or with PBS. Each treatment group consisted of 4 animals. The mice were sacrificed 72 hours following the final administration. A1AT liver mRNA levels were determined using real-time PCR and RIBOGREEN® RNA quantification reagent (Molecular Probes, Inc. Eugene, OR) according to standard protocols. A1AT plasma protein levels were determined using the Mouse Alpha 1-Antitrypsin ELISA (catalog #41-$A_1$AMS-E01, Alpco, Salem, NH). The results below are presented as the average percent of A1AT liver mRNA and plasma protein levels for each treatment group, normalized to the PBS control.

As illustrated in Table 60, treatment with antisense oligonucleotides lowered A1AT liver mRNA and A1AT plasma protein levels in a dose-dependent manner. The oligonucleotides comprising a GalNAc conjugate were significantly more potent than the parent (ISIS 476366).

TABLE 60

| A1AT liver mRNA and plasma protein levels | | | | | |
|---|---|---|---|---|---|
| ISIS No. | Dosage (mg/kg) | A1AT liver mRNA (% PBS) | A1AT plasma protein (% PBS) | $GalNAc_3$ Cluster | CM |
| PBS | n/a | 100 | 100 | n/a | n/a |
| 476366 | 5 | 86 | 78 | n/a | n/a |
| | 15 | 73 | 61 | | |
| | 45 | 30 | 38 | | |
| 656326 | 0.6 | 99 | 90 | $GalNAc_3$-1a | $A_d$ |
| | 2 | 61 | 70 | | |
| | 6 | 15 | 30 | | |
| | 18 | 6 | 10 | | |
| 678381 | 0.6 | 105 | 90 | $GalNAc_3$-3a | $A_d$ |
| | 2 | 53 | 60 | | |
| | 6 | 16 | 20 | | |
| | 18 | 7 | 13 | | |
| 678382 | 0.6 | 90 | 79 | $GalNAc_3$-7a | $A_d$ |
| | 2 | 49 | 57 | | |
| | 6 | 21 | 27 | | |
| | 18 | 8 | 11 | | |
| 678383 | 0.6 | 94 | 84 | $GalNAc_3$-10a | $A_d$ |
| | 2 | 44 | 53 | | |
| | 6 | 13 | 24 | | |
| | 18 | 6 | 10 | | |
| 678384 | 0.6 | 106 | 91 | $GalNAc_3$-13a | $A_d$ |
| | 2 | 65 | 59 | | |
| | 6 | 26 | 31 | | |
| | 18 | 11 | 15 | | |

Liver transaminase and BUN levels in plasma were measured at time of sacrifice using standard protocols. Body weights and organ weights were also measured. The results are shown in Table 61 below. Body weight is shown as % relative to baseline. Organ weights are shown as % of body weight relative to the PBS control group.

TABLE 61

| ISIS No. | Dosage (mg/kg) | ALT (U/L) | AST (U/L) | BUN (mg/dL) | Body weight (% baseline) | Liver weight (Rel % BW) | Kidney weight (Rel % BW) | Spleen weight (Rel % BW) |
|---|---|---|---|---|---|---|---|---|
| PBS | n/a | 25 | 51 | 37 | 119 | 100 | 100 | 100 |
| 476366 | 5 | 34 | 68 | 35 | 116 | 91 | 98 | 106 |
| | 15 | 37 | 74 | 30 | 122 | 92 | 101 | 128 |
| | 45 | 30 | 47 | 31 | 118 | 99 | 108 | 123 |
| 656326 | 0.6 | 29 | 57 | 40 | 123 | 100 | 103 | 119 |
| | 2 | 36 | 75 | 39 | 114 | 98 | 111 | 106 |
| | 6 | 32 | 67 | 39 | 125 | 99 | 97 | 122 |
| | 18 | 46 | 77 | 36 | 116 | 102 | 109 | 101 |
| 678381 | 0.6 | 26 | 57 | 32 | 117 | 93 | 109 | 110 |
| | 2 | 26 | 52 | 33 | 121 | 96 | 106 | 125 |
| | 6 | 40 | 78 | 32 | 124 | 92 | 106 | 126 |
| | 18 | 31 | 54 | 28 | 118 | 94 | 103 | 120 |
| 678382 | 0.6 | 26 | 42 | 35 | 114 | 100 | 103 | 103 |
| | 2 | 25 | 50 | 31 | 117 | 91 | 104 | 117 |
| | 6 | 30 | 79 | 29 | 117 | 89 | 102 | 107 |
| | 18 | 65 | 112 | 31 | 120 | 89 | 104 | 113 |
| 678383 | 0.6 | 30 | 67 | 38 | 121 | 91 | 100 | 123 |
| | 2 | 33 | 53 | 33 | 118 | 98 | 102 | 121 |
| | 6 | 32 | 63 | 32 | 117 | 97 | 105 | 105 |
| | 18 | 36 | 68 | 31 | 118 | 99 | 103 | 108 |
| 678384 | 0.6 | 36 | 63 | 31 | 118 | 98 | 103 | 98 |
| | 2 | 32 | 61 | 32 | 119 | 93 | 102 | 114 |
| | 6 | 34 | 69 | 34 | 122 | 100 | 100 | 96 |
| | 18 | 28 | 54 | 30 | 117 | 98 | 101 | 104 |

Example 81: Duration of Action In Vivo of Oligonucleotides Targeting A1AT Comprising a $GalNAc_3$ Cluster The oligonucleotides listed in Table 59 were tested in a single dose study for duration of action in mice.

Treatment

Six week old, male C57BL/6 mice were each injected subcutaneously once with an oligonucleotide listed in Table 59 or with PBS. Each treatment group consisted of 4 animals. Blood was drawn the day before dosing to determine baseline and at 5, 12, 19, and 25 days following the dose. Plasma A1AT protein levels were measured via ELISA (see Example 80). The results below are presented as the average percent of plasma A1AT protein levels for each treatment group, normalized to baseline levels. The results show that the oligonucleotides comprising a GalNAc conjugate were more potent and had longer duration of action than the parent lacking a GalNAc conjugate (ISIS 476366). Furthermore, the oligonucleotides comprising a 5'-GalNAc conjugate (ISIS 678381, 678382, 678383, and 678384) were generally even more potent with even longer duration of action than the oligonucleotide comprising a 3'-GalNAc conjugate (ISIS 656326).

TABLE 62

Plasma A1AT protein levels in mice

| ISIS No. | Dosage (mg/kg) | Time point (days post-dose) | A1AT (% baseline) | $GalNAc_3$ Cluster | CM |
|---|---|---|---|---|---|
| PBS | n/a | 5 | 93 | n/a | n/a |
| | | 12 | 93 | | |
| | | 19 | 90 | | |
| | | 25 | 97 | | |
| 476366 | 100 | 5 | 38 | n/a | n/a |
| | | 12 | 46 | | |
| | | 19 | 62 | | |
| | | 25 | 77 | | |
| 656326 | 18 | 5 | 33 | $GalNAc_3$-1a | $A_d$ |
| | | 12 | 36 | | |
| | | 19 | 51 | | |
| | | 25 | 72 | | |
| 678381 | 18 | 5 | 21 | $GalNAc_3$-3a | $A_d$ |
| | | 12 | 21 | | |
| | | 19 | 35 | | |
| | | 25 | 48 | | |
| 678382 | 18 | 5 | 21 | $GalNAc_3$-7a | $A_d$ |
| | | 12 | 21 | | |
| | | 19 | 39 | | |
| | | 25 | 60 | | |
| 678383 | 18 | 5 | 24 | $GalNAc_3$-10a | $A_d$ |
| | | 12 | 21 | | |
| | | 19 | 45 | | |
| | | 25 | 73 | | |
| 678384 | 18 | 5 | 29 | $GalNAc_3$-13a | $A_d$ |
| | | 12 | 34 | | |
| | | 19 | 57 | | |
| | | 25 | 76 | | |

Example 82: Antisense Inhibition In Vitro by Oligonucleotides Targeting SRB-1 Comprising a $GalNAc_3$ Conjugate Primary mouse liver hepatocytes were seeded in 96 well plates at 15,000 cells/well 2 hours prior to treatment. The oligonucleotides listed in Table 63 were added at 2, 10, 50, or 250 nM in Williams E medium and cells were incubated overnight at 37° C. in 5% $CO_2$. Cells were lysed 16 hours following oligonucleotide addition, and total RNA was purified using RNease 3000 BioRobot (Qiagen). SRB-1 mRNA levels were determined using real-time PCR and RIBOGREEN® RNA quantification reagent (Molecular Probes, Inc. Eugene, OR) according to standard protocols. $IC_{50}$ values were determined using Prism 4 software (GraphPad). The results show that oligonucleotides comprising a variety of different GalNAc conjugate groups and a variety of different cleavable moieties are significantly more potent in an in vitro free uptake experiment than the parent oligonucleotides lacking a GalNAc conjugate group (ISIS 353382 and 666841).

TABLE 63

Inhibition of SRB-1 expression in vitro

| ISIS No. | Sequence (5′ to 3′) | Linkages | GalNAc cluster | CM | $IC_{50}$ (nM) | SEQ ID No. |
|---|---|---|---|---|---|---|
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | n/a | n/a | 250 | 28 |
| 655861 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}\mathbf{A}_{do'}\mathbf{\text{-}GalNAc_3\text{-}1}_{a}$ | PS | $GalNAc_3$-$1_a$ | $A_d$ | 40 | 29 |
| 661161 | $\mathbf{GalNAc_3\text{-}3}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$3_a$ | $A_d$ | 40 | 30 |
| 661162 | $\mathbf{GalNAc_3\text{-}3}_{a\text{-}o'}\mathbf{A}_{do}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | $GalNAc_3$-$3_a$ | $A_d$ | 8 | 30 |
| 664078 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}\mathbf{A}_{do'}\mathbf{\text{-}GalNAc_3\text{-}9}_{a}$ | PS | $GalNAc_3$-$9_a$ | $A_d$ | 20 | 29 |
| 665001 | $\mathbf{GalNAc_3\text{-}8}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$8_a$ | $A_d$ | 70 | 30 |
| 666224 | $\mathbf{GalNAc_3\text{-}5}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$5_a$ | $A_d$ | 80 | 30 |
| 666841 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | n/a | n/a | >250 | 28 |
| 666881 | $\mathbf{GalNAc_3\text{-}10}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$10_a$ | $A_d$ | 30 | 30 |
| 666904 | $\mathbf{GalNAc_3\text{-}3}_{a\text{-}o'}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$3_a$ | PO | 9 | 28 |
| 666924 | $\mathbf{GalNAc_3\text{-}3}_{a\text{-}o'}\mathbf{Tdo}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$3_a$ | $T_d$ | 15 | 33 |
| 666961 | $\mathbf{GalNAc_3\text{-}6}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$6_a$ | $A_d$ | 150 | 30 |
| 666981 | $\mathbf{GalNAc_3\text{-}7}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$7_a$ | $A_d$ | 20 | 30 |
| 670061 | $\mathbf{GalNAc_3\text{-}13}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$13_a$ | $A_d$ | 30 | 30 |
| 670699 | $\mathbf{GalNAc_3\text{-}3}_{a\text{-}o'}\mathbf{T}_{do}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | $GalNAc_3$-$3_a$ | $T_d$ | 15 | 33 |
| 670700 | $\mathbf{GalNAc_3\text{-}3}_{a\text{-}o'}\mathbf{A}_{eo}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | $GalNAc_3$-$3_a$ | $A_d$ | 30 | 30 |
| 670701 | $\mathbf{GalNAc_3\text{-}3}_{a\text{-}o'}\mathbf{T}_{eo}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | $GalNAc_3$-$3_a$ | $T_d$ | 25 | 33 |
| 671144 | $\mathbf{GalNAc_3\text{-}12}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$12_a$ | $A_d$ | 40 | 30 |
| 671165 | $\mathbf{GalNAc_3\text{-}13}_{a\text{-}o'}\mathbf{A}_{do}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | $GalNAc_3$-$13_a$ | $A_d$ | 8 | 30 |
| 671261 | $\mathbf{GalNAc_3\text{-}14}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$14_a$ | $A_d$ | >250 | 30 |
| 671262 | $\mathbf{GalNAc_3\text{-}15}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | PS | $GalNAc_3$-$15_a$ | $A_d$ | >250 | 30 |
| 673501 | $\mathbf{GalNAc_3\text{-}7}_{a\text{-}o'}\mathbf{A}_{do}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | $GalNAc_3$-$7_a$ | $A_d$ | 30 | 30 |
| 673502 | $\mathbf{GalNAc_3\text{-}10}_{a\text{-}o'}\mathbf{A}_{do}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | PO/PS | $GalNAc_3$-$10_a$ | $A_d$ | 8 | 30 |

TABLE 63-continued

| Inhibition of SRB-1 expression in vitro | | | | | | |
|---|---|---|---|---|---|---|
| ISIS No. | Sequence (5' to 3') | Linkages | GalNAc cluster | CM | $IC_{50}$ (nM) | SEQ ID No. |
| 675441 | $\mathbf{GalNAc_3\text{-}17}_a\text{-}_{o'}\mathbf{A}_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc$_3$-17$_a$ | $A_d$ | 30 | 30 |
| 675442 | $\mathbf{GalNAc_3\text{-}18}_a\text{-}_{o'}\mathbf{A}_{do}G_{es}{}^mC_{es}T_{es}T_{es}{}^mC_{es}A_{ds}G_{ds}{}^mT_{ds}{}^mC_{ds}A_{ds}T_{ds}G_{ds}A_{ds}C_{ds}T_{ds}T_{es}{}^mC_{es}{}^mC_{es}T_{es}T_e$ | PS | GalNAc$_3$-18$_a$ | $A_d$ | 20 | 30 |
| 677841 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}\mathbf{A}_{do'}\text{-}\mathbf{GalNAc_3\text{-}19}_a$ | PS | GalNAc$_3$-19$_a$ | $A_d$ | 40 | 29 |
| 677842 | $G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_{eo}\mathbf{A}_{do'}\text{-}\mathbf{GalNAc_3\text{-}20}_a$ | PS | GalNAc$_3$-20$_a$ | $A_d$ | 30 | 29 |
| 677843 | $\mathbf{GalNAc_3\text{-}23}_a\text{-}_{o'}\mathbf{A}_{do}G_{es}{}^mC_{es}T_{es}T_{es}{}^mC_{es}A_{ds}G_{ds}T_{ds}{}^mC_{ds}A_{ds}T_{ds}G_{ds}A_{ds}{}^mC_{ds}T_{ds}T_{es}{}^mC_{es}{}^mC_{es}T_{es}T_e$ | PS | GalNAc$_3$-23$_a$ | $A_d$ | 40 | 30 |

The structure of GalNAc$_3$-1a was shown previously in Example 9, GalNAc$_3$-3$_a$ was shown in Example 39, GalNAc$_3$-5$_a$ was shown in Example 49, GalNAc$_3$-6$_a$ was shown in Example 51, GalNAc$_3$-7$_a$ was shown in Example 48, GalNAc$_3$-8$_a$ was shown in Example 47, GalNAc$_3$-9$_a$ was shown in Example 52, GalNAc$_3$-10$_a$ was shown in Example 46, GalNAc$_3$-12$_a$ was shown in Example 61, GalNAc$_3$-13$_a$ was shown in Example 62, GalNAc$_3$-14$_a$ was shown in Example 63, GalNAc$_3$-15$_a$ was shown in Example 64, GalNAc$_3$-17$_a$ was shown in Example 68, GalNAc$_3$-18$_a$ was shown in Example 69, GalNAc$_3$-19$_a$ was shown in Example 70, GalNAc$_3$-20$_a$ was shown in Example 71, and GalNAc$_3$-23$_a$ was shown in Example 76.

Example 83: Antisense Inhibition In Vivo by Oligonucleotides Targeting Factor XI Comprising a GalNAc$_3$ Cluster The oligonucleotides listed in Table 64 below were tested in a study for dose-dependent inhibition of Factor XI in mice.

TABLE 64

| Modified Oligonucleotides targeting Factor XI | | | | |
|---|---|---|---|---|
| ISIS No. | Sequence (5' to 3') | GalNAc cluster | CM | SEQ ID No. |
| 404071 | $T_{es}G_{es}G_{es}T_{es}A_{es}A_{ds}T_{ds}{}^mC_{ds}{}^mC_{ds}A_{ds}{}^mC_{ds}T_{ds}T_{ds}T_{ds}{}^mC_{ds}A_{es}G_{es}A_{es}G_{es}G_e$ | n/a | n/a | 31 |
| 656173 | $T_{es}G_{eo}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_{eo}\mathbf{A}_{do'}\text{-}\mathbf{GalNAc_3\text{-}1}_a$ | GalNAc$_3$-1$_a$ | $A_d$ | 32 |
| 663086 | $\mathbf{GalNAc_3\text{-}3}_a\text{-}_{o'}\mathbf{A}_{do}T_{es}G_{eo}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_{eo}$ | GalNAc$_3$-3$_a$ | $A_d$ | 40 |
| 678347 | $\mathbf{GalNAc_3\text{-}7}_a\text{-}_{o'}\mathbf{A}_{do}T_{es}G_{eo}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_{eo}$ | GalNAc$_3$-7$_a$ | $A_d$ | 40 |
| 678348 | $\mathbf{GalNAc_3\text{-}10}_a\text{-}_{o'}\mathbf{A}_{do}T_{es}G_{eo}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_{eo}$ | GalNAc$_3$-10$_a$ | $A_d$ | 40 |
| 678349 | $\mathbf{GalNAc_3\text{-}13}_a\text{-}_{o'}\mathbf{A}_{do}T_{es}G_{eo}G_{eo}T_{eo}A_{eo}A_{ds}T_{ds}{}^mC_{ds}{}^mC_{ds}A_{ds}{}^mC_{ds}T_{ds}T_{ds}T_{ds}{}^mC_{ds}A_{eo}G_{eo}A_{es}G_{es}G_e$ | GalNAc$_3$-13$_a$ | $A_d$ | 40 |

The structure of GalNAc$_3$-1a was shown previously in Example 9, GalNAc$_3$-3$_a$ was shown in Example 39, GalNAc$_3$-7$_a$ was shown in Example 48, GalNAc$_3$-10$_a$ was shown in Example 46, and GalNAc$_3$-13$_a$ was shown in Example 62.

Treatment

Six to eight week old mice were each injected subcutaneously once per week at a dosage shown below, for a total of three doses, with an oligonucleotide listed below or with PBS. Each treatment group consisted of 4 animals. The mice were sacrificed 72 hours following the final dose. Factor XI liver mRNA levels were measured using real-time PCR and normalized to cyclophilin according to standard protocols. Liver transaminases, BUN, and bilirubin were also measured. The results below are presented as the average percent for each treatment group, normalized to the PBS control.

As illustrated in Table 65, treatment with antisense oligonucleotides lowered Factor XI liver mRNA in a dose-dependent manner. The results show that the oligonucleotides comprising a GalNAc conjugate were more potent than the parent lacking a GalNAc conjugate (ISIS 404071). Furthermore, the oligonucleotides comprising a 5'-GalNAc conjugate (ISIS 663086, 678347, 678348, and 678349) were even more potent than the oligonucleotide comprising a 3'-GalNAc conjugate (ISIS 656173).

TABLE 65

| Factor XI liver mRNA, liver transaminase, BUN, and bilirubin levels | | | | | | | | |
|---|---|---|---|---|---|---|---|---|
| ISIS No. | Dosage (mg/kg) | Factor XI mRNA (% PBS) | ALT (U/L) | AST (U/L) | BUN (mg/dL) | Bilirubin (mg/dL) | $GalNAc_3$ Cluster | SEQ ID No. |
| PBS | n/a | 100 | 63 | 70 | 21 | 0.18 | n/a | n/a |
| 404071 | 3 | 65 | 41 | 58 | 21 | 0.15 | | |
| | 10 | 33 | 49 | 53 | 23 | 0.15 | n/a | 31 |
| | 30 | 17 | 43 | 57 | 22 | 0.14 | | |
| 656173 | 0.7 | 43 | 90 | 89 | 21 | 0.16 | $GalNAc_3$-1a | 32 |
| | 2 | 9 | 36 | 58 | 26 | 0.17 | | |
| | 6 | 3 | 50 | 63 | 25 | 0.15 | | |
| 663086 | 0.7 | 33 | 91 | 169 | 25 | 0.16 | $GalNAc_3$-3a | 40 |
| | 2 | 7 | 38 | 55 | 21 | 0.16 | | |
| | 6 | 1 | 34 | 40 | 23 | 0.14 | | |
| 678347 | 0.7 | 35 | 28 | 49 | 20 | 0.14 | $GalNAc_3$-7a | 40 |
| | 2 | 10 | 180 | 149 | 21 | 0.18 | | |
| | 6 | 1 | 44 | 76 | 19 | 0.15 | | |
| 678348 | 0.7 | 39 | 43 | 54 | 21 | 0.16 | $GalNAc_3$-10a | 40 |
| | 2 | 5 | 38 | 55 | 22 | 0.17 | | |
| | 6 | 2 | 25 | 38 | 20 | 0.14 | | |
| 678349 | 0.7 | 34 | 39 | 46 | 20 | 0.16 | $GalNAc_3$-13a | 40 |
| | 2 | 8 | 43 | 63 | 21 | 0.14 | | |
| | 6 | 2 | 28 | 41 | 20 | 0.14 | | |

Example 84: Duration of Action In Vivo of Oligonucleotides Targeting Factor XI Comprising a $GalNAc_3$ Conjugate The oligonucleotides listed in Table 64 were tested in a single dose study for duration of action in mice.

Treatment

Six to eight week old mice were each injected subcutaneously once with an oligonucleotide listed in Table 64 or with PBS. Each treatment group consisted of 4 animals. Blood was drawn by tail bleeds the day before dosing to determine baseline and at 3, 10, and 17 days following the dose. Plasma Factor XI protein levels were measured by ELISA using Factor XI capture and biotinylated detection antibodies from R & D Systems, Minneapolis, MN (catalog #AF2460 and #BAF2460, respectively) and the OptEIA Reagent Set B (Catalog #550534, BD Biosciences, San Jose, CA). The results below are presented as the average percent of plasma Factor XI protein levels for each treatment group, normalized to baseline levels. The results show that the oligonucleotides comprising a GalNAc conjugate were more potent with longer duration of action than the parent lacking a GalNAc conjugate (ISIS 404071). Furthermore, the oligonucleotides comprising a 5'-GalNAc conjugate (ISIS 663086, 678347, 678348, and 678349) were even more potent with an even longer duration of action than the oligonucleotide comprising a 3'-GalNAc conjugate (ISIS 656173).

TABLE 66

| Plasma Factor XI protein levels in mice | | | | | | |
|---|---|---|---|---|---|---|
| ISIS No. | Dosage (mg/kg) | Time point (days post-dose) | Factor XI (% baseline) | $GalNAc_3$ Cluster | CM | SEQ ID No. |
| PBS | n/a | 3 | 123 | n/a | n/a | n/a |
| | | 10 | 56 | | | |
| | | 17 | 100 | | | |
| 404071 | 30 | 3 | 11 | n/a | n/a | 31 |
| | | 10 | 47 | | | |
| | | 17 | 52 | | | |
| 656173 | 6 | 3 | 1 | $GalNAc_3$-1a | $A_d$ | 32 |
| | | 10 | 3 | | | |
| | | 17 | 21 | | | |
| 663086 | 6 | 3 | 1 | $GalNAc_3$-3a | $A_d$ | 40 |
| | | 10 | 2 | | | |
| | | 17 | 9 | | | |
| 678347 | 6 | 3 | 1 | $GalNAc_3$-7a | $A_d$ | 40 |
| | | 10 | 1 | | | |
| | | 17 | 8 | | | |
| 678348 | 6 | 3 | 1 | $GalNAc_3$-10a | $A_d$ | 40 |
| | | 10 | 1 | | | |
| | | 17 | 6 | | | |
| 678349 | 6 | 3 | 1 | $GalNAc_3$-13a | $A_d$ | 40 |
| | | 10 | 1 | | | |
| | | 17 | 5 | | | |

Example 85: Antisense Inhibition In Vivo by Oligonucleotides Targeting SRB-1 Comprising a $GalNAc_3$ Conjugate Oligonucleotides listed in Table 63 were tested in a dose-dependent study for antisense inhibition of SRB-1 in mice.

Treatment

Six to eight week old C57BL/6 mice were each injected subcutaneously once per week at a dosage shown below, for a total of three doses, with an oligonucleotide listed in Table 63 or with saline. Each treatment group consisted of 4 animals. The mice were sacrificed 48 hours following the final administration to determine the SRB-1 mRNA levels using real-time PCR and RIBOGREEN® RNA quantification reagent (Molecular Probes, Inc. Eugene, OR) according to standard protocols. The results below are presented as the average percent of liver SRB-1 mRNA levels for each treatment group, normalized to the saline control.

As illustrated in Tables 67 and 68, treatment with antisense oligonucleotides lowered SRB-1 mRNA levels in a dose-dependent manner.

TABLE 67

SRB-1 mRNA in liver

| ISIS No. | Dosage (mg/kg) | SRB-1 mRNA (% Saline) | $GalNAc_3$ Cluster | CM |
|---|---|---|---|---|
| Saline | n/a | 100 | n/a | n/a |
| 655861 | 0.1 | 94 | $GalNAc_3$-1a | $A_d$ |
| | 0.3 | 119 | | |
| | 1 | 68 | | |
| | 3 | 32 | | |
| 661161 | 0.1 | 120 | $GalNAc_3$-3a | $A_d$ |
| | 0.3 | 107 | | |
| | 1 | 68 | | |
| | 3 | 26 | | |
| 666881 | 0.1 | 107 | $GalNAc_3$-10a | $A_d$ |
| | 0.3 | 107 | | |
| | 1 | 69 | | |
| | 3 | 27 | | |
| 666981 | 0.1 | 120 | $GalNAc_3$-7a | $A_d$ |
| | 0.3 | 103 | | |
| | 1 | 54 | | |
| | 3 | 21 | | |
| 670061 | 0.1 | 118 | $GalNAc_3$-13a | $A_d$ |
| | 0.3 | 89 | | |
| | 1 | 52 | | |
| | 3 | 18 | | |
| 677842 | 0.1 | 119 | $GalNAc_3$-20a | $A_d$ |
| | 0.3 | 96 | | |
| | 1 | 65 | | |
| | 3 | 23 | | |

TABLE 68

SRB-1 mRNA in liver

| ISIS No. | Dosage (mg/kg) | SRB-1 mRNA (% Saline) | $GalNAc_3$ Cluster | CM |
|---|---|---|---|---|
| 661161 | 0.1 | 107 | $GalNAc_3$-3a | $A_d$ |
| | 0. 3 | 95 | | |
| | 1 | 53 | | |
| | 3 | 18 | | |
| 677841 | 0.1 | 110 | $GalNAc_3$-19a | $A_d$ |
| | 0.3 | 88 | | |
| | 1 | 52 | | |
| | 3 | 25 | | |

Liver transaminase levels, total bilirubin, BUN, and body weights were also measured using standard protocols. Average values for each treatment group are shown in Table 69 below.

TABLE 69

| ISIS No. | Dosage (mg/kg) | ALT (U/L) | AST (U/L) | Bilirubin (mg/dL) | BUN (mg/dL) | Body Weight (% baseline) | $GalNAc_3$ Cluster | CM |
|---|---|---|---|---|---|---|---|---|
| Saline | n/a | 19 | 39 | 0.17 | 26 | 118 | n/a | n/a |
| 655861 | 0.1 | 25 | 47 | 0.17 | 27 | 114 | $GalNAc_3$-la | $A_d$ |
| | 0.3 | 29 | 56 | 0.15 | 27 | 118 | | |
| | 1 | 20 | 32 | 0.14 | 24 | 112 | | |
| | 3 | 27 | 54 | 0.14 | 24 | 115 | | |
| 661161 | 0.1 | 35 | 83 | 0.13 | 24 | 113 | $GalNAc_3$-3a | $A_d$ |
| | 0.3 | 42 | 61 | 0.15 | 23 | 117 | | |
| | 1 | 34 | 60 | 0.18 | 22 | 116 | | |
| | 3 | 29 | 52 | 0.13 | 25 | 117 | | |
| 666881 | 0.1 | 30 | 51 | 0.15 | 23 | 118 | $GalNAc_3$-10a | $A_d$ |
| | 0.3 | 49 | 82 | 0.16 | 25 | 119 | | |
| | 1 | 23 | 45 | 0.14 | 24 | 117 | | |
| | 3 | 20 | 38 | 0.15 | 21 | 112 | | |
| 666981 | 0.1 | 21 | 41 | 0.14 | 22 | 113 | $GalNAc_3$-7a | $A_d$ |
| | 0.3 | 29 | 49 | 0.16 | 24 | 112 | | |
| | 1 | 19 | 34 | 0.15 | 22 | 111 | | |
| | 3 | 77 | 78 | 0.18 | 25 | 115 | | |
| 670061 | 0.1 | 20 | 63 | 0.18 | 24 | 111 | $GalNAc_3$-13a | $A_d$ |
| | 0.3 | 20 | 57 | 0.15 | 21 | 115 | | |
| | 1 | 20 | 35 | 0.14 | 20 | 115 | | |
| | 3 | 27 | 42 | 0.12 | 20 | 116 | | |
| 677842 | 0.1 | 20 | 38 | 0.17 | 24 | 114 | $GalNAc_3$-20a | $A_d$ |
| | 0.3 | 31 | 46 | 0.17 | 21 | 117 | | |
| | 1 | 22 | 34 | 0.15 | 21 | 119 | | |
| | 3 | 41 | 57 | 0.14 | 23 | 118 | | |

Example 86: Antisense Inhibition In Vivo by Oligonucleotides Targeting TTR Comprising a $GalNAc_3$ Cluster Oligonucleotides listed in Table 70 below were tested in a dose-dependent study for antisense inhibition of human transthyretin (TTR) in transgenic mice that express the human TTR gene.

Treatment

Eight week old TTR transgenic mice were each injected subcutaneously once per week for three weeks, for a total of three doses, with an oligonucleotide and dosage listed in the tables below or with PBS. Each treatment group consisted of 4 animals. The mice were sacrificed 72 hours following the final administration. Tail bleeds were performed at various time points throughout the experiment, and plasma TTR protein, ALT, and AST levels were measured and reported in Tables 72-74. After the animals were sacrificed, plasma ALT, AST, and human TTR levels were measured, as were body weights, organ weights, and liver human TTR mRNA levels. TTR protein levels were measured using a clinical analyzer (AU480, Beckman Coulter, CA). Real-time PCR and RIBOGREEN® RNA quantification reagent (Molecular Probes, Inc. Eugene, OR) were used according to standard protocols to determine liver human TTR mRNA levels. The results presented in Tables 71-74 are the average values for each treatment group. The mRNA levels are the average values relative to the average for the PBS group. Plasma protein levels are the average values relative to the average value for the PBS group at baseline. Body weights are the average percent weight change from baseline until sacrifice for each individual treatment group. Organ weights shown are normalized to the animal's body weight, and the average normalized organ weight for each treatment group is then presented relative to the average normalized organ weight for the PBS group.

In Tables 71-74, "BL" indicates baseline, measurements that were taken just prior to the first dose. As illustrated in Tables 71 and 72, treatment with antisense oligonucleotides lowered TTR expression levels in a dose-dependent manner. The oligonucleotides comprising a GalNAc conjugate were more potent than the parent lacking a GalNAc conjugate (ISIS 420915). Furthermore, the oligonucleotides comprising a GalNAc conjugate and mixed PS/PO internucleoside linkages were even more potent than the oligonucleotide comprising a GalNAc conjugate and full PS linkages.

TABLE 70

Oligonucleotides targeting human TTR

| Isis No. | Sequence 5' to 3' | Linkages | GalNAc cluster | CM | SEQ ID No. |
|---|---|---|---|---|---|
| 420915 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | PS | n/a | n/a | 41 |
| 660261 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{eo}$ **$A_{do'}$-$GalNAc_3$-$1_a$** | PS | $GalNAc_3$-1a | Ad | 42 |
| 682883 | **$GalNAc_3$-$3_{a-o'}$** $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{eo}$ | PS/PO | $GalNAc_3$-3a | PO | 74 |
| 682884 | **$GalNAc_3$-$7_{a-o'}$** $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{eo}$ | PS/PO | $GalNAc_3$-7a | PO | 55 |
| 682885 | **$GalNAc_3$-$10_{a-o'}$** $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{eo}$ | PS/PO | $GalNAc_3$-10a | PO | 41 |
| 682886 | **$GalNAc_3$-$13_{a-o'}$** $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | $GalNAc_3$-13a | PO | 41 |
| 684057 | $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{eo}$ **$A_{do'}$-$GalNAc_3$-$19_a$** | PS/PO | $GalNAc_3$-19a | $A_d$ | 42 |

The legend for Table 72 can be found in Example 74. The structure of $GalNAc_3$-1 was shown in Example 9. The structure of $GalNAc_3$-$3_a$ was shown in Example 39. The structure of $GalNAc_3$-$7_a$ was shown in Example 48. The structure of $GalNAc_3$-$10_a$ was shown in Example 46. The structure of $GalNAc_3$-$13_a$ was shown in Example 62. The structure of $GalNAc_3$-$19_a$ was shown in Example 70.

TABLE 71

Antisense inhibition of human TTR in vivo

| Isis No. | Dosage (mg/kg) | TTR mRNA (% PBS) | Plasma TTR protein (% PBS) | GalNAc cluster | CM | SEQ ID No. |
|---|---|---|---|---|---|---|
| PBS | n/a | 100 | 100 | n/a | n/a | |
| 420915 | 6 | 99 | 95 | n/a | n/a | 41 |
| | 20 | 48 | 65 | | | |
| | 60 | 18 | 28 | | | |
| 660261 | 0.6 | 113 | 87 | $GalNAc_3$-1a | $A_d$ | 42 |
| | 2 | 40 | 56 | | | |
| | 6 | 20 | 27 | | | |
| | 20 | 9 | 11 | | | |

TABLE 72

Antisense inhibition of human TTR in vivo

| Isis No. | Dosage (mg/kg) | TTR mRNA (% PBS) | Plasma TTR protein (% PBS at BL) | | | | GalNAc cluster | CM | SEQ ID No. |
|---|---|---|---|---|---|---|---|---|---|
| | | | BL | Day 3 | Day 10 | Day 17 (After sac) | | | |
| PBS | n/a | 100 | 100 | 96 | 90 | 114 | n/a | n/a | |
| 420915 | 6 | 74 | 106 | 86 | 76 | 83 | n/a | n/a | 41 |
| | 20 | 43 | 102 | 66 | 61 | 58 | | | |

TABLE 72-continued

Antisense inhibition of human TTR in vivo

| Isis No. | Dosage (mg/kg) | TTR mRNA (% PBS) | Plasma TTR protein (% PBS at BL) BL | Day 3 | Day 10 | Day 17 (After sac) | GalNAc cluster | CM | SEQ ID No. |
|---|---|---|---|---|---|---|---|---|---|
| | 60 | 24 | 92 | 43 | 29 | 32 | | | |
| 682883 | 0.6 | 60 | 88 | 73 | 63 | 68 | $GalNAc_3$-3a | PO | 41 |
| | 2 | 18 | 75 | 38 | 23 | 23 | | | |
| | 6 | 10 | 80 | 35 | 11 | 9 | | | |
| 682884 | 0.6 | 56 | 88 | 78 | 63 | 67 | $GalNAc_3$-7a | PO | 55 |
| | 2 | 19 | 76 | 44 | 25 | 23 | | | |
| | 6 | 15 | 82 | 35 | 21 | 24 | | | |
| 682885 | 0.6 | 60 | 92 | 77 | 68 | 76 | $GalNAc_3$-10a | PO | 41 |
| | 2 | 22 | 93 | 58 | 32 | 32 | | | |
| | 6 | 17 | 85 | 37 | 25 | 20 | | | |
| 682886 | 0.6 | 57 | 91 | 70 | 64 | 69 | $GalNAc_3$-13a | PO | 41 |
| | 2 | 21 | 89 | 50 | 31 | 30 | | | |
| | 6 | 18 | 102 | 41 | 24 | 27 | | | |
| 684057 | 0.6 | 53 | 80 | 69 | 56 | 62 | $GalNAc_3$-19a | $A_d$ | 42 |
| | 2 | 21 | 92 | 55 | 34 | 30 | | | |
| | 6 | 11 | 82 | 50 | 18 | 13 | | | |

TABLE 73

Transaminase levels, body weight changes, and relative organ weights

| Isis No. | Dosage (mg/kg) | ALT (U/L) BL | ALT Day 3 | ALT Day 10 | ALT Day 17 | AST (U/L) BL | AST Day 3 | AST Day 10 | AST Day 17 | Body (% BL) | Liver (% PBS) | Spleen (% PBS) | Kidney (% PBS) | SEQ ID No. |
|---|---|---|---|---|---|---|---|---|---|---|---|---|---|---|
| PBS | n/a | 33 | 34 | 33 | 24 | 58 | 62 | 67 | 52 | 105 | 100 | 100 | 100 | n/a |
| 420915 | 6 | 34 | 33 | 27 | 21 | 64 | 59 | 73 | 47 | 115 | 99 | 89 | 91 | 41 |
| | 20 | 34 | 30 | 28 | 19 | 64 | 54 | 56 | 42 | 111 | 97 | 83 | 89 | |
| | 60 | 34 | 35 | 31 | 24 | 61 | 58 | 71 | 58 | 113 | 102 | 98 | 95 | |
| 660261 | 0.6 | 33 | 38 | 28 | 26 | 70 | 71 | 63 | 59 | 111 | 96 | 99 | 92 | 42 |
| | 2 | 29 | 32 | 31 | 34 | 61 | 60 | 68 | 61 | 118 | 100 | 92 | 90 | |
| | 6 | 29 | 29 | 28 | 34 | 58 | 59 | 70 | 90 | 114 | 99 | 97 | 95 | |
| | 20 | 33 | 32 | 28 | 33 | 64 | 54 | 68 | 95 | 114 | 101 | 106 | 92 | |

TABLE 74

Transaminase levels, body weight changes, and relative organ weights

| Isis No. | Dosage (mg/kg) | ALT (U/L) BL | ALT Day 3 | ALT Day 10 | ALT Day 17 | AST (U/L) BL | AST Day 3 | AST Day 10 | AST Day 17 | Body (% BL) | Liver (% PBS) | Spleen (% PBS) | Kidney (% PBS) | SEQ ID No. |
|---|---|---|---|---|---|---|---|---|---|---|---|---|---|---|
| PBS | n/a | 32 | 34 | 37 | 41 | 62 | 78 | 76 | 77 | 104 | 100 | 100 | 100 | n/a |
| 420915 | 6 | 32 | 30 | 34 | 34 | 61 | 71 | 72 | 66 | 102 | 103 | 102 | 105 | 41 |
| | 20 | 41 | 34 | 37 | 33 | 80 | 76 | 63 | 54 | 106 | 107 | 135 | 101 | |
| | 60 | 36 | 30 | 32 | 34 | 58 | 81 | 57 | 60 | 106 | 105 | 104 | 99 | |
| 682883 | 0.6 | 32 | 35 | 38 | 40 | 53 | 81 | 74 | 76 | 104 | 101 | 112 | 95 | 41 |
| | 2 | 38 | 39 | 42 | 43 | 71 | 84 | 70 | 77 | 107 | 98 | 116 | 99 | |
| | 6 | 35 | 35 | 41 | 38 | 62 | 79 | 103 | 65 | 105 | 103 | 143 | 97 | |
| 682884 | 0.6 | 33 | 32 | 35 | 34 | 70 | 74 | 75 | 67 | 101 | 100 | 130 | 99 | 55 |
| | 2 | 31 | 32 | 38 | 38 | 63 | 77 | 66 | 55 | 104 | 103 | 122 | 100 | |
| | 6 | 38 | 32 | 36 | 34 | 65 | 85 | 80 | 62 | 99 | 105 | 129 | 95 | |
| 682885 | 0.6 | 39 | 26 | 37 | 35 | 63 | 63 | 77 | 59 | 100 | 109 | 109 | 112 | 41 |
| | 2 | 30 | 26 | 38 | 40 | 54 | 56 | 71 | 72 | 102 | 98 | 111 | 102 | |
| | 6 | 27 | 27 | 34 | 35 | 46 | 52 | 56 | 64 | 102 | 98 | 113 | 96 | |
| 682886 | 0.6 | 30 | 40 | 34 | 36 | 58 | 87 | 54 | 61 | 104 | 99 | 120 | 101 | 41 |
| | 2 | 27 | 26 | 34 | 36 | 51 | 55 | 55 | 69 | 103 | 91 | 105 | 92 | |
| | 6 | 40 | 28 | 34 | 37 | 107 | 54 | 61 | 69 | 109 | 100 | 102 | 99 | |
| 684057 | 0.6 | 35 | 26 | 33 | 39 | 56 | 51 | 51 | 69 | 104 | 99 | 110 | 102 | 42 |
| | 2 | 33 | 32 | 31 | 40 | 54 | 57 | 56 | 87 | 103 | 100 | 112 | 97 | |
| | 6 | 39 | 33 | 35 | 40 | 67 | 52 | 55 | 92 | 98 | 104 | 121 | 108 | |

Example 87: Duration of Action In Vivo by Single Doses of Oligonucleotides Targeting TTR Comprising a $GalNAc_3$ Cluster ISIS numbers 420915 and 660261 (see Table 70) were tested in a single dose study for duration of action in mice. ISIS numbers 420915, 682883, and 682885 (see Table 70) were also tested in a single dose study for duration of action in mice.

Treatment

Eight week old, male transgenic mice that express human TTR were each injected subcutaneously once with 100 mg/kg ISIS No. 420915 or 13.5 mg/kg ISIS No. 660261. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 75

Plasma TTR protein levels

| ISIS No. | Dosage (mg/kg) | Time point (days post-dose) | TTR (% baseline) | $GalNAc_3$ Cluster | CM | SEQ ID No. |
|---|---|---|---|---|---|---|
| 420915 | 100 | 3 | 30 | n/a | n/a | 41 |
| | | 7 | 23 | | | |
| | | 10 | 35 | | | |
| | | 17 | 53 | | | |
| | | 24 | 75 | | | |
| | | 39 | 100 | | | |
| 660261 | 13.5 | 3 | 27 | $GalNAc_3$-1a | $A_d$ | 42 |
| | | 7 | 21 | | | |
| | | 10 | 22 | | | |
| | | 17 | 36 | | | |
| | | 24 | 48 | | | |
| | | 39 | 69 | | | |

Treatment

Female transgenic mice that express human TTR were each injected subcutaneously once with 100 mg/kg ISIS No. 420915, 10.0 mg/kg ISIS No. 682883, or 10.0 mg/kg 682885. Each treatment group consisted of 4 animals. Tail bleeds were performed before dosing to determine baseline and at days 3, 7, 10, 17, 24, and 39 following the dose. Plasma TTR protein levels were measured as described in Example 86. The results below are presented as the average percent of plasma TTR levels for each treatment group, normalized to baseline levels.

TABLE 76

Plasma TTR protein levels

| ISIS No. | Dosage (mg/kg) | Time point (days post-dose) | TTR (% baseline) | $GalNAc_3$ Cluster | CM | SEQ ID No. |
|---|---|---|---|---|---|---|
| 420915 | 100 | 3 | 48 | n/a | n/a | 41 |
| | | 7 | 48 | | | |
| | | 10 | 48 | | | |
| | | 17 | 66 | | | |
| | | 31 | 80 | | | |
| 682883 | 10.0 | 3 | 45 | $GalNAc_3$-3a | PO | 41 |
| | | 7 | 37 | | | |
| | | 10 | 38 | | | |
| | | 17 | 42 | | | |
| | | 31 | 65 | | | |
| 682885 | 10.0 | 3 | 40 | $GalNAc_3$-10a | PO | 41 |
| | | 7 | 33 | | | |
| | | 10 | 34 | | | |
| | | 17 | 40 | | | |
| | | 31 | 64 | | | |

The results in Tables 75 and 76 show that the oligonucleotides comprising a GalNAc conjugate are more potent with a longer duration of action than the parent oligonucleotide lacking a conjugate (ISIS 420915).

Example 88: Splicing Modulation In Vivo by Oligonucleotides Targeting SMN Comprising a $GalNAc_3$ Conjugate The oligonucleotides listed in Table 77 were tested for splicing modulation of human survival of motor neuron (SMN) in mice.

TABLE 77

Modified ASOs targeting SMN

| ISIS No. | Sequences (5' to 3') | GalNAC3 Cluster | CM | SEQ ID No. |
|---|---|---|---|---|
| 387954 | $A_{es}T_{es}T_{es}{}^{m}C_{es}A_{es}{}^{m}C_{es}T_{es}T_{es}T_{es}{}^{m}C_{es}A_{es}T_{es}A_{es}A_{es}T_{es}G_{es}{}^{m}C_{es}T_{es}G_{es}G_{e}$ | n/a | n/a | 43 |
| 699819 | **$GalNAc_3$-$7_a$-$_{o'}$** $A_{es}T_{es}T_{es}{}^{m}C_{es}A_{es}{}^{m}C_{es}T_{es}T_{es}T_{es}{}^{m}C_{es}A_{es}T_{es}A_{es}A_{es}T_{es}G_{es}{}^{m}C_{es}T_{es}G_{es}G_{e}$ | $GalNAc_3$-7a | PO | 43 |
| 699821 | **$GalNAc_3$-$7_a$-$_{o'}$** $A_{es}T_{eo}T_{eo}{}^{m}C_{eo}A_{es}{}^{m}C_{es}T_{es}$7a $T_{es}T_{es}{}^{m}C_{es}A_{es}T_{es}A_{es}A_{es}T_{es}G_{es}{}^{m}C_{es}T_{es}G_{es}G_{e}$ | $GalNAc_3$-7a | PO | 43 |
| 700000 | $A_{es}T_{es}T_{es}{}^{m}C_{es}A_{es}{}^{m}C_{es}T_{es}T_{es}T_{es}{}^{m}C_{es}A_{es}T_{es}A_{es}A_{es}T_{es}G_{es}{}^{m}C_{es}T_{es}G_{es}G_{eo}$ **$A_{do'}$-$GalNAc_3$-$1_a$** | $GalNAc_3$-1a | $A_d$ | 44 |
| 703421 | X-ATT$^m$CA$^m$CTTT$^m$CATAATG$^m$CTGG | n/a | n/a | 43 |
| 703422 | **$GalNAc_3$-$7_b$-** X-ATT$^m$CA$^m$CTTT$^m$CATAATG$^m$CTGG | $GalNAc_3$-7b | n/a | 43 |

The structure of $GalNAc_3$-$7_a$ was shown previously in Example 48. "X" indicates a 5' primary amine generated by Gene Tools (Philomath, OR), and $GalNAc_3$-7, indicates the structure of $GalNAc_3$-$7_a$ lacking the—NH—$C_6$-O portion of the linker as shown below:

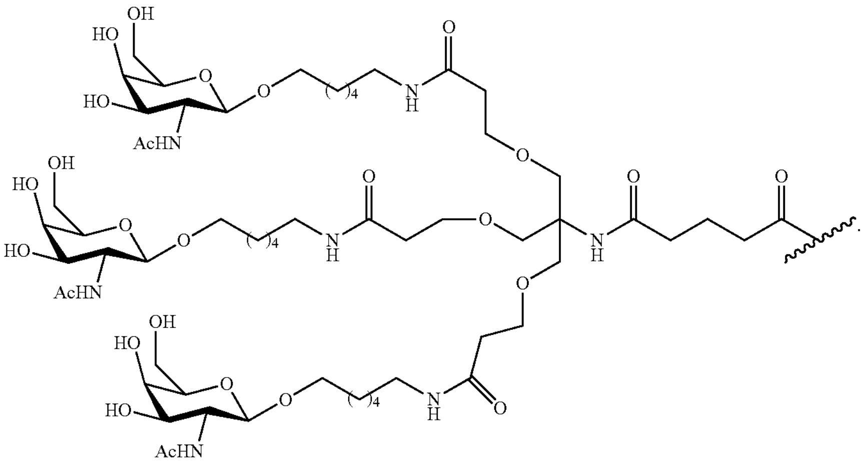

ISIS numbers 703421 and 703422 are morphlino oligonucleotides, wherein each nucleotide of the two oligonucleotides is a morpholino nucleotide.

Treatment

Six week old transgenic mice that express human SMN were injected subcutaneously once with an oligonucleotide listed in Table 78 or with saline. Each treatment group consisted of 2 males and 2 females. The mice were sacrificed 3 days following the dose to determine the liver human SMN mRNA levels both with and without exon 7 using real-time PCR according to standard protocols. Total RNA was measured using Ribogreen reagent. The SMN mRNA levels were normalized to total mRNA, and further normalized to the averages for the saline treatment group. The resulting average ratios of SMN mRNA including exon 7 to SMN mRNA missing exon 7 are shown in Table 78. The results show that fully modified oligonucleotides that modulate splicing and comprise a GalNAc conjugate are significantly more potent in altering splicing in the liver than the parent oligonucleotides lacking a GlaNAc conjugate. Furthermore, this trend is maintained for multiple modification chemistries, including 2'-MOE and morpholino modified oligonucleotides.

TABLE 78

Effect of oligonucleotides targeting human SMN in vivo

| ISIS No. | Dose (mg/kg) | +Exon 7/ −Exon 7 | $GalNAc_3$ Cluster | CM | SEQ ID No. |
|---|---|---|---|---|---|
| Saline | n/a | 1.00 | n/a | n/a | n/a |
| 387954 | 32 | 1.65 | n/a | n/a | 43 |
| 387954 | 288 | 5.00 | n/a | n/a | 43 |
| 699819 | 32 | 7.84 | $GalNAc_3$-7a | PO | 43 |
| 699821 | 32 | 7.22 | $GalNAc_3$-7a | PO | 43 |
| 700000 | 32 | 6.91 | $GalNAc_3$-1a | $A_d$ | 44 |
| 703421 | 32 | 1.27 | n/a | n/a | 43 |
| 703422 | 32 | 4.12 | $GalNAc_3$-7b | n/a | 43 |

Example 89: Antisense Inhibition In Vivo by Oligonucleotides Targeting Apolipoprotein a (Apo (a)) Comprising a $GalNAc_3$ Conjugate The oligonucleotides listed in Table 79 below were tested in a study for dose-dependent inhibition of Apo (a) in transgenic mice.

TABLE 79

| Modified ASOs targeting Apo(a) | | | | |
|---|---|---|---|---|
| ISIS No. | Sequences (5' to 3') | $GalNAc_3$ Cluster | CM | SEQ ID No. |
| 494372 | $T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | n/a | n/a | 53 |
| 681257 | **$GalNAc_3$-$7_a$-$_{o'}$** $T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-7a | PO | 53 |

Treatment

Eight week old, female C57BL/6 mice (Jackson Laboratory, Bar Harbor, ME) were each injected subcutaneously once per week at a dosage shown below, for a total of six doses, with an oligonucleotide listed in Table 79 or with PBS. Each treatment group consisted of 3-4 animals. Tail bleeds were performed the day before the first dose and weekly following each dose to determine plasma Apo (a) protein levels. The mice were sacrificed two days following the final administration. Apo (a) liver mRNA levels were determined using real-time PCR and RIBOGREEN® RNA quantification reagent (Molecular Probes, Inc. Eugene, OR) according to standard protocols. Apo (a) plasma protein levels were determined using ELISA, and liver transaminase levels were determined. The mRNA and plasma protein results in Table 80 are presented as the treatment group average percent relative to the PBS treated group. Plasma protein levels were further normalized to the baseline (BL) value for the PBS group. Average absolute transaminase levels and body weights (% relative to baseline averages) are reported in Table 81.

As illustrated in Table 80, treatment with the oligonucleotides lowered Apo (a) liver mRNA and plasma protein levels in a dose-dependent manner. Furthermore, the oligonucleotide comprising the GalNAc conjugate was significantly more potent with a longer duration of action than the parent oligonucleotide lacking a GalNAc conjugate. As illustrated in Table 81, transaminase levels and body weights were unaffected by the oligonucleotides, indicating that the oligonucleotides were well tolerated.

TABLE 80

| Apo(a) liver mRNA and plasma protein levels | | | | | | | | | |
|---|---|---|---|---|---|---|---|---|---|
| ISIS | Dosage | Apo(a) mRNA | Apo(a) plasma protein (% PBS) | | | | | | |
| No. | (mg/kg) | (% PBS) | BL | Week 1 | Week 2 | Week 3 | Week 4 | Week 5 | Week 6 |
| PBS | n/a | 100 | 100 | 120 | 119 | 113 | 88 | 121 | 97 |
| 494372 | 3 | 80 | 84 | 89 | 91 | 98 | 87 | 87 | 79 |
| | 10 | 30 | 87 | 72 | 76 | 71 | 57 | 59 | 46 |
| | 30 | 5 | 92 | 54 | 28 | 10 | 7 | 9 | 7 |
| 681257 | 0.3 | 75 | 79 | 76 | 89 | 98 | 71 | 94 | 78 |
| | 1 | 19 | 79 | 88 | 66 | 60 | 54 | 32 | 24 |
| | 3 | 2 | 82 | 52 | 17 | 7 | 4 | 6 | 5 |
| | 10 | 2 | 79 | 17 | 6 | 3 | 2 | 4 | 5 |

TABLE 81

| ISIS No. | Dosage (mg/kg) | ALT (U/L) | AST (U/L) | Body weight (% baseline) |
|---|---|---|---|---|
| PBS | n/a | 37 | 54 | 103 |
| 494372 | 3 | 28 | 68 | 106 |

TABLE 81-continued

| ISIS No. | Dosage (mg/kg) | ALT (U/L) | AST (U/L) | Body weight (% baseline) |
|---|---|---|---|---|
| | 10 | 22 | 55 | 102 |
| | 30 | 19 | 48 | 103 |
| 681257 | 0.3 | 30 | 80 | 104 |
| | 1 | 26 | 47 | 105 |
| | 3 | 29 | 62 | 102 |
| | 10 | 21 | 52 | 107 |

Example 90: Antisense Inhibition In Vivo by Oligonucleotides Targeting TTR Comprising a $GalNAc_3$ Cluster Oligonucleotides listed in Table 82 below were tested in a dose-dependent study for antisense inhibition of human transthyretin (TTR) in transgenic mice that express the human TTR gene.

Treatment

TTR transgenic mice were each injected subcutaneously once per week for three weeks, for a total of three doses, with an oligonucleotide and dosage listed in Table 83 or with PBS. Each treatment group consisted of 4 animals. Prior to the first dose, a tail bleed was performed to determine plasma TTR protein levels at baseline (BL). The mice were sacrificed 72 hours following the final administration. TTR protein levels were measured using a clinical analyzer (AU480, Beckman Coulter, CA). Real-time PCR and RIBOGREEN® RNA quantification reagent (Molecular Probes, Inc. Eugene, OR) were used according to standard protocols to determine liver human TTR mRNA levels. The results presented in Table 83 are the average values for each treatment group. The mRNA levels are the average values relative to the average for the PBS group. Plasma protein levels are the average values relative to the average value for the PBS group at baseline. "BL" indicates baseline, measurements that were taken just prior to the first dose. As illustrated in Table 83, treatment with antisense oligonucleotides lowered TTR expression levels in a dose-dependent manner. The oligonucleotides comprising a GalNAc conjugate were more potent than the parent lacking a GalNAc conjugate (ISIS 420915), and oligonucleotides comprising a phosphodiester or deoxyadenosine cleavable moiety showed significant improvements in potency compared to the parent lacking a conjugate (see ISIS numbers 682883 and 666943 vs 420915 and see Examples 86 and 87).

TABLE 82

| Oligonucleotides targeting human TTR | | | | | |
|---|---|---|---|---|---|
| Isis No. | Sequence 5' to 3' | Link-ages | GalNAC cluster | CM | SEQ ID No. |
| 420915 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | PS | n/a | n/a | 41 |
| 682883 | **GalNAc$_3$-3$_{a-o'}$** $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | GalNAC$_3$-3a | PO | 41 |
| 666943 | **GalNAc$_3$-3$_{a-o'}$A$_{do}$** $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | GalNAC$_3$-3a | $A_d$ | 45 |
| 682887 | **GalNAc$_3$-7$_{a-o'}$A$_{do}$** $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | GalNAC$_3$-7a | $A_d$ | 45 |
| 682888 | **GalNAc$_3$-10$_{a-o'}$A$_{do}$** $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | GalNAC$_3$-10a | $A_d$ | 45 |
| 682889 | **GalNAc$_3$-13$_{a-o'}$A$_{do}$** $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{e}$ | PS/PO | GalNAC$_3$-13a | $A_d$ | 45 |

The legend for Table 82 can be found in Example 74. The structure of GalNAc$_3$-3$_a$ was shown in Example 39. The structure of GalNAc$_3$-7$_a$ was shown in Example 48. The structure of GalNAc$_3$-10$_a$ was shown in Example 46. The structure of GalNAc$_3$-13$_a$ was shown in Example 62.

TABLE 83

| Antisense inhibition of human TTR in vivo | | | | | |
|---|---|---|---|---|---|
| Isis No. | Dosage (mg/kg) | TTR mRNA (% PBS) | TTR protein (% BL) | GalNAc cluster | CM |
| PBS | n/a | 100 | 124 | n/a | n/a |
| 420915 | 6 | 69 | 114 | n/a | n/a |
| | 20 | 71 | 86 | | |
| | 60 | 21 | 36 | | |
| 682883 | 0.6 | 61 | 73 | GalNAc$_3$-3a | PO |
| | 2 | 23 | 36 | | |
| | 6 | 18 | 23 | | |
| 666943 | 0.6 | 74 | 93 | GalNAc$_3$-3a | $A_d$ |
| | 2 | 33 | 57 | | |
| | 6 | 17 | 22 | | |
| 682887 | 0.6 | 60 | 97 | GalNAc$_3$-7a | $A_d$ |
| | 2 | 36 | 49 | | |
| | 6 | 12 | 19 | | |
| 682888 | 0.6 | 65 | 92 | GalNAc$_3$-10a | $A_d$ |
| | 2 | 32 | 46 | | |
| | 6 | 17 | 22 | | |
| 682889 | 0.6 | 72 | 74 | GalNAc$_3$-13a | $A_d$ |
| | 2 | 38 | 45 | | |
| | 6 | 16 | 18 | | |

Example 91: Antisense Inhibition In Vivo by Oligonucleotides Targeting Factor VII Comprising a GalNAc$_3$ Conjugate in Non-Human Primates Oligonucleotides listed in Table 84 below were tested in a non-terminal, dose escalation study for antisense inhibition of Factor VII in monkeys.

Treatment

Non-naïve monkeys were each injected subcutaneously on days 0, 15, and 29 with escalating doses of an oligonucleotide listed in Table 84 or with PBS. Each treatment group consisted of 4 males and 1 female. Prior to the first dose and at various time points thereafter, blood draws were performed to determine plasma Factor VII protein levels. Factor VII protein levels were measured by ELISA. The results presented in Table 85 are the average values for each treatment group relative to the average value for the PBS group at baseline (BL), the measurements taken just prior to the first dose. As illustrated in Table 85, treatment with antisense oligonucleotides lowered Factor VII expression levels in a dose-dependent manner, and the oligonucleotide comprising the GalNAc conjugate was significantly more potent in monkeys compared to the oligonucleotide lacking a GalNAc conjugate.

TABLE 84

| Oligonucleotides targeting Factor VII | | | | | |
|---|---|---|---|---|---|
| Isis No. | Sequence 5' to 3' | Linkages | GalNAc cluster | CM | SEQ ID No. |
| 407935 | $A_{es}T_{es}G_{es}{}^{m}C_{es}A_{es}T_{ds}G_{ds}G_{ds}T_{ds}G_{ds}A_{ds}T_{ds}G_{ds}{}^{m}C_{ds}T_{ds}T_{es}{}^{m}C_{es}T_{es}G_{es}A_{e}$ | PS | n/a | n/a | 46 |
| 686892 | **GalNAc$_3$-10$_{a-o'}$** $A_{es}T_{es}G_{es}{}^{m}C_{es}A_{es}T_{ds}G_{ds}G_{ds}T_{ds}G_{ds}A_{ds}T_{ds}G_{ds}{}^{m}C_{ds}T_{ds}T_{es}{}^{m}C_{es}T_{es}G_{es}A_{e}$ | PS | GalNAc$_3$-10a | PO | 46 |

The legend for Table 84 can be found in Example 74. The structure of $GalNAc_3$-$10_a$ was shown in Example 46.

TABLE 85

| Factor VII plasma protein levels | | | |
|---|---|---|---|
| ISIS No. | Day | Dose (mg/kg) | Factor VII (% BL) |
| 407935 | 0 | n/a | 100 |
| | 15 | 10 | 87 |
| | 22 | n/a | 92 |
| | 29 | 30 | 77 |
| | 36 | n/a | 46 |
| | 43 | n/a | 43 |
| 686892 | 0 | 3 | 100 |
| | 15 | 10 | 56 |
| | 22 | n/a | 29 |
| | 29 | 30 | 19 |
| | 36 | n/a | 15 |
| | 43 | n/a | 11 |

Example 92: Antisense Inhibition in Primary Hepatocytes by Antisense Oligonucleotides Targeting Apo-CIII Comprising a $GalNAc_3$ Conjugate Primary mouse hepatocytes were seeded in 96-well plates at 15,000 cells per well, and the oligonucleotides listed in Table 86, targeting mouse ApoC-III, were added at 0.46, 1.37, 4.12, or 12.35, 37.04, 111.11, or 333.33 nM or 1.00 µM. After incubation with the oligonucleotides for 24 hours, the cells were lysed and total RNA was purified using RNeasy (Qiagen). ApoC-III mRNA levels were determined using real-time PCR and RIBOGREEN® RNA quantification reagent (Molecular Probes, Inc.) according to standard protocols. $IC_{50}$ values were determined using Prism 4 software (GraphPad). The results show that regardless of whether the cleavable moiety was a phosphodiester or a phosphodiester-linked deoxyadensoine, the oligonucleotides comprising a GalNAc conjugate were significantly more potent than the parent oligonucleotide lacking a conjugate.

TABLE 86

| Inhibition of mouse APOC-III expression in mouse primary hepatocytes | | | | |
|---|---|---|---|---|
| ISIS No. | Sequence (5' to 3') | CM | $IC_{50}$ (nM) | SEQ ID No. |
| 440670 | ${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}A_{es}G_{es}{}^{m}C_{es}A_{e}$ | n/a | 13.20 | 47 |
| 661180 | ${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{eo}\mathbf{A}_{do'}$**-GalNAc**$_3$**-1**$_a$ | $A_d$ | 1.40 | 48 |
| 680771 | **GalNAc**$_3$**-3**$_{a\text{-}o'}{}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{e}$ | PO | 0.70 | 47 |
| 680772 | **GalNAc**$_3$**-7**$_{a\text{-}o'}{}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{e}$ | PO | 1.70 | 47 |
| 680773 | **GalNAc**$_3$**-10**$_{a\text{-}o'}{}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{e}$ | PO | 2.00 | 47 |
| 680774 | **GalNAc**$_3$**-13**$_{a\text{-}o'}{}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{e}$ | PO | 1.50 | 47 |
| 681272 | **GalNAc**$_3$**-3**$_{a\text{-}o'}{}^{m}C_{es}A_{eo}G_{eo}{}^{m}C_{eo}T_{eo}T_{ds}T_{ds}A_{ds}T_{ds}T_{ds}A_{ds}G_{ds}G_{ds}G_{ds}A_{ds}{}^{m}C_{eo}$ $A_{eo}G_{es}{}^{m}C_{es}A_{e}$ | PO | <0.46 | 47 |
| 681273 | **GalNAc**$_3$**-3**$_{a\text{-}o'}\mathbf{A}_{do}{}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}$ ${}^{m}C_{es}A_{es}G_{es}{}^{m}C_{es}A_{e}$ | $A_d$ | 1.10 | 49 |
| 683733 | ${}^{m}C_{es}A_{es}G_{es}{}^{m}C_{es}T_{es}T_{ds}T_{ds}A_{ds}T_{ds}T_{ds}A_{ds}G_{ds}G_{ds}G_{ds}A_{ds}{}^{m}C_{es}$ $A_{es}G_{es}{}^{m}C_{es}A_{eo}\mathbf{A}_{do'}$**-GalNAc**$_3$**-19**$_a$ | $A_d$ | 2.50 | 48 |

The structure of $GalNAc_3$-1a was shown previously in Example 9, $GalNAc_3$-$3_a$ was shown in Example 39, $GalNAc_3$-$7_a$ was shown in Example 48, $GalNAc_3$-$10_a$ was shown in Example 46, $GalNAc_3$-$13_a$ was shown in Example 62, and $GalNAc_3$-$19_a$ was shown in Example 70.

Example 93: Antisense Inhibition In Vivo by Oligonucleotides Targeting SRB-1 Comprising Mixed Wings and a 5'-$GalNAc_3$ Conjugate The oligonucleotides listed in Table 87 were tested in a dose-dependent study for antisense inhibition of SRB-1 in mice.

TABLE 87

| Modified ASOs targeting SRB-1 | | | | |
|---|---|---|---|---|
| ISIS No. | Sequences (5' to 3') | GalNAc$_3$ Cluster | CM | SEQ ID No. |
| 449093 | $T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | n/a | n/a | 50 |
| 699806 | **GalNAc$_3$-3$_a$**-$_{o'}$$T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | GalNAc$_3$-3a | PO | 50 |
| 699807 | **GalNAc$_3$-7$_a$**-$_{o'}$$T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | GalNAc$_3$-7a | PO | 50 |
| 699809 | **GalNAc$_3$-7$_a$**-$_{o'}$$T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{e}$ | GalNAc$_3$-7a | PO | 50 |
| 699811 | **GalNAc$_3$-7$_a$**-$_{o'}$$T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | GalNAc$_3$-7a | PO | 50 |
| 699813 | **GalNAc$_3$-7$_a$**-$_{o'}$$T_{ks}T_{ds}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ds}{}^{m}C_{k}$ | GalNAc$_3$-7a | PO | 50 |
| 699815 | **GalNAc$_3$-7$_a$**-$_{o'}$$T_{es}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{e}$ | GalNAc$_3$-7a | PO | 50 |

The structure of GalNAc$_3$-3$_a$ was shown previously in Example 39, and the structure of GalNAc$_3$-7$_a$ was shown previously in Example 48. Subscripts: "e" indicates 2'-MOE modified nucleoside; "d" indicates β-D-2'-deoxyribonucleoside; "k" indicates 6'-(S)—$CH_3$ bicyclic nucleoside (cEt); "s" indicates phosphorothioate internucleoside linkages (PS); "o" indicates phosphodiester internucleoside linkages (PO). Supersript "m" indicates 5-methylcytosines.

Treatment

Six to eight week old C57BL/6 mice (Jackson Laboratory, Bar Harbor, ME) were injected subcutaneously once at the dosage shown below with an oligonucleotide listed in Table 87 or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The results are presented as the average percent of SRB-1 mRNA levels for each treatment group relative to the saline control group. As illustrated in Table 88, treatment with antisense oligonucleotides lowered SRB-1 mRNA levels in a dose-dependent manner, and the gapmer oligonucleotides comprising a GalNAc conjugate and having wings that were either full cEt or mixed sugar modifications were significantly more potent than the parent oligonucleotide lacking a conjugate and comprising full cEt modified wings.

Body weights, liver transaminases, total bilirubin, and BUN were also measured, and the average values for each treatment group are shown in Table 88. Body weight is shown as the average percent body weight relative to the baseline body weight (% BL) measured just prior to the oligonucleotide dose.

TABLE 88

| SRB-1 mRNA, ALT, AST, BUN, and total bilirubin levels and body weights | | | | | | | |
|---|---|---|---|---|---|---|---|
| ISIS No. | Dosage (mg/kg) | SRB-1 mRNA (% PBS) | ALT (U/L) | AST (U/L) | Bil | BUN | Body weight (% BL) |
| PBS | n/a | 100 | 31 | 84 | 0.15 | 28 | 102 |
| 449093 | 1 | 111 | 18 | 48 | 0.17 | 31 | 104 |
| | 3 | 94 | 20 | 43 | 0.15 | 26 | 103 |
| | 10 | 36 | 19 | 50 | 0.12 | 29 | 104 |
| 699806 | 0.1 | 114 | 23 | 58 | 0.13 | 26 | 107 |
| | 0.3 | 59 | 21 | 45 | 0.12 | 27 | 108 |
| | 1 | 25 | 30 | 61 | 0.12 | 30 | 104 |
| 699807 | 0.1 | 121 | 19 | 41 | 0.14 | 25 | 100 |
| | 0.3 | 73 | 23 | 56 | 0.13 | 26 | 105 |
| | 1 | 24 | 22 | 69 | 0.14 | 25 | 102 |
| 699809 | 0.1 | 125 | 23 | 57 | 0.14 | 26 | 104 |
| | 0.3 | 70 | 20 | 49 | 0.10 | 25 | 105 |
| | 1 | 33 | 34 | 62 | 0.17 | 25 | 107 |
| 699811 | 0.1 | 123 | 48 | 77 | 0.14 | 24 | 106 |
| | 0.3 | 94 | 20 | 45 | 0.13 | 25 | 101 |
| | 1 | 66 | 57 | 104 | 0.14 | 24 | 107 |
| 699813 | 0.1 | 95 | 20 | 58 | 0.13 | 28 | 104 |
| | 0.3 | 98 | 22 | 61 | 0.17 | 28 | 105 |
| | 1 | 49 | 19 | 47 | 0.11 | 27 | 106 |
| 699815 | 0.1 | 93 | 30 | 79 | 0.17 | 25 | 105 |
| | 0.3 | 64 | 30 | 61 | 0.12 | 26 | 105 |
| | 1 | 24 | 18 | 41 | 0.14 | 25 | 106 |

Example 94: Antisense Inhibition In Vivo by Oligonucleotides Targeting SRB-1 Comprising 2'-Sugar Modifications and a 5'-GalNAc$_3$ Conjugate The oligonucleotides listed in Table 89 were tested in a dose-dependent study for antisense inhibition of SRB-1 in mice.

TABLE 89

| Modified ASOs targeting SRB-1 | | | | |
|---|---|---|---|---|
| ISIS No. | Sequences (5' to 3') | GalNAc$_3$ Cluster | CM | SEQ ID No. |
| 353382 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | n/a | n/a | 28 |

TABLE 89-continued

| Modified ASOs targeting SRB-1 | | | | |
|---|---|---|---|---|
| ISIS No. | Sequences (5' to 3') | $GalNAc_3$ Cluster | CM | SEQ ID No. |
| 700989 | $G_{ms}C_{ms}U_{ms}U_{ms}C_{ms}A_{ds}G_{ds}T_{ds}{}^{m}C_{ds}A_{ds}T_{ds}G_{ds}A_{ds}{}^{m}C_{ds}T_{ds}U_{ms}C_{ms}C_{ms}U_{ms}U_{m}$ | n/a | n/a | 51 |
| 666904 | **$GalNAc_3$-3**$_{a}$-$_{o'}$$G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_3$-3a | PO | 28 |
| 700991 | **$GalNAc_3$-7**$_{a}$-$_{o'}$$G_{ms}C_{ms}U_{ms}U_{ms}C_{ms}A_{ds}G_{ds}T_{ds}{}^{m}C_{ds}A_{ds}T_{ds}G_{ds}A_{ds}{}^{m}C_{ds}T_{ds}U_{ms}C_{ms}C_{ms}U_{ms}$Um | $GalNAc_3$-7a | PO | 51 |

Subscript "m" indicates a 2'-O-methyl modified nucleoside. See Example 74 for complete table legend. The structure of $GalNAc_3$-$3_a$ was shown previously in Example 39, and the structure of $GalNAc_3$-$7_a$ was shown previously in Example 48.

Treatment

The study was completed using the protocol described in Example 93. Results are shown in Table 90 below and show that both the 2'-MOE and 2'-OMe modified oligonucleotides comprising a GalNAc conjugate were significantly more potent than the respective parent oligonucleotides lacking a conjugate. The results of the body weights, liver transaminases, total bilirubin, and BUN measurements indicated that the compounds were all well tolerated.

TABLE 90

| SRB-1 mRNA | | |
|---|---|---|
| ISIS No. | Dosage (mg/kg) | SRB-1 mRNA (% PBS) |
| PBS | n/a | 100 |
| 353382 | 5 | 116 |
| | 15 | 58 |
| | 45 | 27 |
| 700989 | 5 | 120 |
| | 15 | 92 |
| | 45 | 46 |
| 666904 | 1 | 98 |
| | 3 | 45 |
| | 10 | 17 |
| 700991 | 1 | 118 |
| | 3 | 63 |
| | 10 | 14 |

Example 95: Antisense Inhibition In Vivo by Oligonucleotides Targeting SRB-1 Comprising Bicyclic Nucleosides and a 5'-$GalNAc_3$ Conjugate The oligonucleotides listed in Table 91 were tested in a dose-dependent study for antisense inhibition of SRB-1 in mice.

TABLE 91

| Modified ASOs targeting SRB-1 | | | | |
|---|---|---|---|---|
| ISIS No. | Sequenc$_{es}$(5' to 3') | GalNAc3 Cluster | CM | SEQ ID No |
| 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | n/a | n/a | 22 |
| 666905 | **$GalNAc_3$-3**$_{a}$-$_{o'}$$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | $GalNAc_3$-$3_a$ | PO | 22 |
| 699782 | **$GalNAc_3$-7**$_{a}$-$_{o'}$$T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | $GalNAc_3$-$7_a$ | PO | 22 |
| 699783 | **$GalNAc_3$-3**$_{a}$-$_{o'}$$T_{ls}{}^{m}C_{ls}A_{ds}G_{ds}T_{ds}{}^{m}C_{ds}A_{ds}T_{ds}G_{ds}A_{ds}{}^{m}C_{ds}T_{ds}T_{ls}{}^{m}C_{l}$ | $GalNAc_3$-$3_a$ | PO | 22 |
| 653621 | $T_{ls}{}^{m}C_{ls}A_{ds}G_{ds}T_{ds}{}^{m}C_{ds}A_{ds}T_{ds}G_{ds}A_{ds}{}^{m}C_{ds}T_{ds}T_{ls}{}^{m}C_{10}$**$A_{do'}$-$GalNAc_3$-1**$_{a}$ | $GalNAc_3$-$1_a$ | $A_d$ | 23 |
| 439879 | $T_{gs}{}^{m}C_{gs}A_{ds}G_{ds}T_{ds}{}^{m}C_{ds}A_{ds}$Td$G_{ds}A_{ds}{}^{m}C_{ds}T_{ds}T_{gs}{}^{m}C_{g}$ | n/a | n/a | 22 |
| 699789 | **$GalNAc_3$-3**$_{a}$-$_{o'}$$T_{gs}{}^{m}C_{gs}A_{ds}G_{ds}T_{ds}{}^{m}C_{ds}A_{ds}$Td$G_{ds}A_{ds}{}^{m}C_{ds}T_{ds}T_{gs}{}^{m}C_{g}$ | $GalNAc_3$-$3_a$ | PO | 22 |

Subscript “g” indicates a fluoro-HNA nucleoside, subscript “1” indicates a locked nucleoside comprising a 2'-O—$CH_2$-4' bridge. See the Example 74 table legend for other abbreviations. The structure of GalNAc$_3$-1$_a$ was shown previously in Example 9, the structure of GalNAc$_3$-3$_a$ was shown previously in Example 39, and the structure of GalNAc$_3$-7$_a$ was shown previously in Example 48.

Treatment

The study was completed using the protocol described in Example 93. Results are shown in Table 92 below and show that oligonucleotides comprising a GalNAc conjugate and various bicyclic nucleoside modifications were significantly more potent than the parent oligonucleotide lacking a conjugate and comprising bicyclic nucleoside modifications. Furthermore, the oligonucleotide comprising a GalNAc conjugate and fluoro-HNA modifications was significantly more potent than the parent lacking a conjugate and comprising fluoro-HNA modifications. The results of the body weights, liver transaminases, total bilirubin, and BUN measurements indicated that the compounds were all well tolerated.

TABLE 92

| SRB-1 mRNA, ALT, AST, BUN, and total bilirubin levels and body weights | | |
|---|---|---|
| ISIS No. | Dosage (mg/kg) | SRB-1 mRNA (% PBS) |
| PBS | n/a | 100 |
| 440762 | 1 | 104 |
| | 3 | 65 |
| | 10 | 35 |
| 666905 | 0.1 | 105 |
| | 0.3 | 56 |
| | 1 | 18 |
| 699782 | 0.1 | 93 |
| | 0.3 | 63 |
| | 1 | 15 |
| 699783 | 0.1 | 105 |
| | 0.3 | 53 |
| | 1 | 12 |
| 653621 | 0.1 | 109 |
| | 0.3 | 82 |
| | 1 | 27 |
| 439879 | 1 | 96 |
| | 3 | 77 |
| | 10 | 37 |
| 699789 | 0.1 | 82 |
| | 0.3 | 69 |
| | 1 | 26 |

Example 96: Plasma Protein Binding of Antisense Oligonucleotides Comprising a GalNAc$_3$ Conjugate Group Oligonucleotides listed in Table 57 targeting ApoC-III and oligonucleotides in Table 93 targeting Apo (a) were tested in an ultra-filtration assay in order to assess plasma protein binding.

TABLE 93

| Modified oligonucl$_{eo}$tid$_{es}$targeting Apo(a) | | | | |
|---|---|---|---|---|
| ISIS No. | Sequenc$_{es}$(5' to 3') | GalNAc$_3$ Cluster | CM | SEQ ID No |
| 494372 | $T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}$Ce | n/a | n/a | 53 |
| 693401 | $T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}$Ce | n/a | n/a | 53 |
| 681251 | **GalNAc$_3$-7$_a$-$_{o'}$**$T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | GalNAc$_3$-7$_a$ | PO | 53 |
| 681257 | **GalNAc$_3$-7$_a$-$_{o'}$**$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | GalNAc$_3$-7$_a$ | PO | 53 |

See the Example 74 for table legend. The structure of GalNAc$_3$-7$_a$ was shown previously in Example 48.

Ultrafree-MC ultrafiltration units (30,000 NMWL, low-binding regenerated cellulose membrane, Millipore, Bedford, MA) were pre-conditioned with 300 μL of 0.5% Tween 80 and centrifuged at 2000 g for minutes, then with 300 μL of a 300 μg/mL solution of a control oligonucleotide in $H_2O$ and centrifuged at 2000 g for 16 minutes. In order to assess non-specific binding to the filters of each test oligonucleotide from Tables 57 and 93 to be used in the studies, 300 μL of a 250 ng/mL solution of oligonucleotide in $H_2O$ at pH 7.4 was placed in the pre-conditioned filters and centrifuged at 2000 g for 16 minutes. The unfiltered and filtered samples were analyzed by an ELISA assay to determine the oligonucleotide concentrations. Three replicates were used to obtain an average concentration for each sample. The average concentration of the filtered sample relative to the unfiltered sample is used to determine the percent of oligonucleotide that is recovered through the filter in the absence of plasma (% recovery).

Frozen whole plasma samples collected in K3-EDTA from normal, drug-free human volunteers, cynomolgus monkeys, and CD-1 mice, were purchased from Bioreclamation LLC(Westbury, NY). The test oligonucleotides were added to 1.2 mL aliquots of plasma at two concentrations (5 and 150 μg/mL). An aliquot (300 μL) of each spiked plasma sample was placed in a pre-conditioned filter unit and incubated at 37° C. for 30 minutes, immediately followed by centrifugation at 2000 g for 16 minutes. Aliquots of filtered and unfiltered spiked plasma samples were analyzed by an ELISA to determine the oligonucleotide concentration in each sample. Three replicates per concentration were used to determine the average percentage of bound and unbound oligonucleotide in each sample. The average concentration of the filtered sample relative to the concentration of the unfiltered sample is used to determine the percent of oligonucleotide in the plasma that is not bound to plasma proteins (% unbound). The final unbound oligonucleotide values are corrected for non-specific binding by dividing the % unbound by the % recovery for each oligonucleotide. The final % bound oligonucleotide values are determined by subtracting the final % unbound values from 100. The results are shown in Table 94 for the two concentrations of oligonucleotide tested (5 and 150 μg/mL) in each species of plasma. The results show that GalNAc conjugate groups do not have a significant impact on plasma protein binding. Furthermore, oligonucleotides with full PS internucleoside linkages and mixed PO/PS linkages both bind plasma proteins, and those with full PS linkages bind plasma proteins to a somewhat greater extent than those with mixed PO/PS linkages.

TABLE 94

Percent of modified oligonucleotide bound to plasma proteins

| ISIS No. | Human plasma 5 μg/mL | Human plasma 150 μg/mL | Monkey plasma 5 μg/mL | Monkey plasma 150 μg/mL | Mouse plasma 5 μg/mL | Mouse plasma 150 μg/mL |
|---|---|---|---|---|---|---|
| 304801 | 99.2 | 98.0 | 99.8 | 99.5 | 98.1 | 97.2 |
| 663083 | 97.8 | 90.9 | 99.3 | 99.3 | 96.5 | 93.0 |
| 674450 | 96.2 | 97.0 | 98.6 | 94.4 | 94.6 | 89.3 |
| 494372 | 94.1 | 89.3 | 98.9 | 97.5 | 97.2 | 93.6 |
| 693401 | 93.6 | 89.9 | 96.7 | 92.0 | 94.6 | 90.2 |
| 681251 | 95.4 | 93.9 | 99.1 | 98.2 | 97.8 | 96.1 |
| 681257 | 93.4 | 90.5 | 97.6 | 93.7 | 95.6 | 92.7 |

Example 97: Modified Oligonucleotides Targeting TTR Comprising a $GalNAc_3$ Conjugate Group The oligonucleotides shown in Table 95 comprising a GalNAc conjugate were designed to target TTR.

TABLE 95

Modified oligonucleotides targeting TTR

| ISIS No. | Sequences (5' to 3') | $GalNAc_3$ Cluster | CM | SEQ ID No |
|---|---|---|---|---|
| 666941 | $\mathbf{GalNAc_3\text{-}3}_{a\text{-}o'}\mathbf{A}_{do}T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-3 | $A_d$ | 45 |
| 666942 | $T_{es}{}^{m}C_{eo}T_{eo}T_{eo}G_{eo}G_{ds}T_{ds}T_{ds}A_{ds}{}^{m}C_{ds}A_{ds}T_{ds}G_{ds}A_{ds}A_{ds}A_{eo}T_{eo}{}^{m}C_{es}{}^{m}C_{es}{}^{m}C_{eo}\mathbf{A}_{do'}\text{-}\mathbf{GalNAc_3\text{-}3}_{a}$ | $GalNAc_3$-1 | $A_d$ | 42 |
| 682876 | $\mathbf{GalNAc_3\text{-}3}_{a\text{-}o'}T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-3 | PO | 41 |
| 682877 | $\mathbf{GalNAc_3\text{-}7}_{a\text{-}o'}T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}Ce$ | $GalNAc_{3\text{-}7}$ | PO | 41 |
| 682878 | $\mathbf{GalNAc_3\text{-}10}_{a\text{-}o'}T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-10 | PO | 41 |
| 682879 | $\mathbf{GalNAc_3\text{-}13}_{a\text{-}o'}T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-13 | PO | 41 |
| 682880 | $\mathbf{GalNAc_3\text{-}7}_{a\text{-}o'}T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}ik_{es}T_{es}{}^{m}C_{es}{}^{m}C_{es}{}^{m}C_{e}$ | $GalNAc_3$-7 | $A_d$ | 45 |
| 682881 | $\mathbf{GalNAc_3\text{-}10}_{a\text{-}o'}\mathbf{A}_{do}T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-10 | $A_d$ | 45 |
| 682882 | $\mathbf{GalNAc_3\text{-}13}_{a\text{-}o'}\mathbf{A}_{do}T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{e}$ | $GalNAc_3$-13 | $A_d$ | 45 |
| 684056 | $T_{es}{}^{m}C_{es}T_{es}T_{es}G_{es}G_{ds}T_{ds}T_{ds}A_{ds}{}^{m}C_{ds}A_{ds}T_{ds}G_{ds}A_{ds}A_{ds}A_{es}T_{es}{}^{m}C_{es}{}^{m}C_{es}{}^{m}C_{eo}\mathbf{A}_{do'}\text{-}\mathbf{GalNAc_3\text{-}19}_{a}$ | $GalNAc_3$-19 | $A_d$ | 42 |

The legend for Table 95 can be found in Example 74. The structure of $GalNAc_3$-1 was shown in Example 9. The structure of $GalNAc_3$-$3_a$ was shown in Example 39. The structure of $GalNAc_3$-$7_a$ was shown in Example 48. The structure of $GalNAc_3$-$10_a$ was shown in Example 46. The structure of $GalNAc_3$-$13_a$ was shown in Example 62. The structure of $GalNAc_3$-$19_a$ was shown in Example 70.

Example 98: Evaluation of Pro-Inflammatory Effects of Oligonucleotides Comprising a GalNAc Conjugate in hPMBC Assay The oligonucleotides listed in Table 96 and were tested for pro-inflammatory effects in an hPMBC assay as described in Examples 23 and 24. (See Tables 17, 70, 82, and 95 for descriptions of the oligonucleotides.) ISIS 353512 is a high responder used as a positive control, and the other oligonucleotides are described in Tables 70, 82, and 95. The results shown in Table 96 were obtained using blood from one volunteer donor. The results show that the oligonucleotides comprising mixed PO/PS internucleoside linkages produced significantly lower pro-inflammatory responses compared to the same oligonucleotides having full PS linkages. Furthermore, the GalNAc conjugate group did not have a significant effect in this assay.

TABLE 96

| ISIS No. | $E_{max}/EC_{50}$ | $GalNAc_3$ cluster | Linkages | CM |
|---|---|---|---|---|
| 353512 | 3630 | n/a | PS | n/a |
| 420915 | 802 | n/a | PS | n/a |
| 682881 | 1311 | $GalNAc_3$-10 | PS | $A_d$ |
| 682888 | 0.26 | $GalNAc_3$-10 | PO/PS | $A_d$ |
| 684057 | 1.03 | $GalNAc_3$-19 | PO/PS | $A_d$ |

Example 99: Binding Affinities of Oligonucleotides Comprising a GalNAc Conjugate for the Asialoglycoprotein Receptor The binding affinities of the oligonucleotides listed in Table 97 (see Table 63 for descriptions of the oligonucleotides) for the asialoglycoprotein receptor were tested in a competitive receptor binding assay. The competitor ligand, al-acid glycoprotein (AGP), was incubated in 50 mM sodium acetate buffer (pH 5) with 1 U neuraminidase-agarose for 16 hours at 37° C., and >90% desialylation was confirmed by either sialic acid assay or size exclusion chromatography (SEC). Iodine monochloride was used to iodinate the AGP according to the procedure by Atsma et al. (see J Lipid Res. 1991 January; 32 (1): 173-81.) In this method, desialylated al-acid glycoprotein (de-AGP) was added to 10 mM iodine chloride, $Na125^I$, and 1 M glycine in 0.25 M NaOH. After incubation for 10 minutes at room temperature, $125^I$-labeled de-AGP was separated from free 125I by concentrating the mixture twice utilizing a 3 KDMWCO spin column. The protein was tested for labeling efficiency and purity on a HPLC system equipped with an Agilent SEC-3 column (7.8×300 mm) and a β-RAM counter. Competition experiments utilizing $125^I$-labeled de-AGP and various GalNAc-cluster containing ASOs were performed as follows. Human HepG2 cells ($10^6$ cells/ml) were plated on 6-well plates in 2 ml of appropriate growth media. MEM media supplemented with 10% fetal bovine serum (FBS), 2 mM L-Glutamine and 10 mM HEPES was used. Cells were incubated 16-20 hours @ 37° C. with 5% and 10% $CO_2$ respectively. Cells were washed with media without FBS prior to the experiment. Cells were incubated for 30 min @37° C. with 1 ml competition mix containing appropriate growth media with 2% FBS, 10-8 M 125I-labeled de-AGP and GalNAc-cluster containing ASOs at concentrations ranging from 10-11 to 10-5 M. Non-specific binding was determined in the presence of 102 M GalNAc sugar. Cells were washed twice with media without FBS to remove unbound $125^I$-labeled de-AGP and competitor GalNAc ASO. Cells were lysed using Qiagen's RLT buffer containing 1% β-mercaptoethanol. Lysates were transferred to round bottom assay tubes after a brief 10 min freeze/thaw cycle and assayed on a y-counter. Non-specific binding was subtracted before dividing $125^I$ protein counts by the value of the lowest GalNAc-ASO concentration counts. The inhibition curves were fitted according to a single site competition binding equation using a nonlinear regression algorithm to calculate the binding affinities ($K_D$'s).

The results in Table 97 were obtained from experiments performed on five different days. Results for oligonucleotides marked with superscript "a" are the average of experiments run on two different days. The results show that the oligonucleotides comprising a GalNAc conjugate group on the 5'-end bound the asialoglycoprotein receptor on human HepG2 cells with 1.5 to 16-fold greater affinity than the oligonucleotides comprising a GalNAc conjugate group on the 3'-end.

TABLE 97

Asialoglycoprotein receptor binding assay results

| ISIS No. | GalNAc conjugate | Oligonucleotide end to which GalNAc conjugate is attached | $K_D$ (nM) |
|---|---|---|---|
| 661161[a] | $GalNAc_3$-3 | 5' | 3.7 |
| 666881[a] | $GalNAc_3$-10 | 5' | 7.6 |
| 666981 | $GalNAc_3$-7 | 5' | 6.0 |
| 670061 | $GalNAc_3$-13 | 5' | 7.4 |
| 655861[a] | $GalNAc_3$-1 | 3' | 11.6 |
| 677841[a] | $GalNAc_3$-19 | 3' | 60.8 |

Example 100: Antisense Inhibition In Vivo by Oligonucleotides Comprising a GalNAc Conjugate Group Targeting Apo (a) In Vivo The oligonucleotides listed in Table 98a below were tested in a single dose study for duration of action in mice.

TABLE 98a

Modified ASOs targeting APO(a)

| ISIS No. | Sequences (5' to 3') | $GalNAc_3$ Cluster | CM | SEQ ID No. |
|---|---|---|---|---|
| 681251 | **$GalNAc_3$-$7_a$-$_{o'}$**$T_{es}G_{es}{}^mC_{es}T_{es}{}^mC_{es}{}^mC_{ds}G_{ds}T_{ds}T_{ds}G_{ds}G_{ds}T_{ds}G_{ds}{}^mC_{ds}T_{ds}T_{es}G_{es}T_{es}T_{es}{}^mC_e$ | $GalNAc_3$-7a | PO | 53 |

TABLE 98a-continued

Modified ASOs targeting APO(a)

| ISIS No. | Sequences (5' to 3') | GalNAc3 Cluster | CM | SEQ ID No. |
|---|---|---|---|---|
| 681257 | **GalNAc$_3$-7$_a$**-$_{o'}T_{es}G_{eo}{}^mC_{eo}T_{eo}{}^mC_{eo}{}^mC_{ds}G_{ds}T_{ds}T_{ds}G_{ds}G_{ds}T_{ds}G_{ds}{}^mC_{ds}T_{ds}T_{eo}G_{eo}T_{es}T_{es}{}^mC_e$ | GalNAc$_3$-7a | PO | 53 |

The structure of GalNAc$_3$-7$_a$ was shown in Example 48.

Treatment

Female transgenic mice that express human Apo (a) were each injected subcutaneously once per week, for a total of 6 doses, with an oligonucleotide and dosage listed in Table 98b or with PBS. Each treatment group consisted of 3 animals. Blood was drawn the day before dosing to determine baseline levels of Apo (a) protein in plasma and at 72 hours, 1 week, and 2 weeks following the first dose. Additional blood draws will occur at 3 weeks, 4 weeks, 5 weeks, and 6 weeks following the first dose. Plasma Apo (a) protein levels were measured using an ELISA. The results in Table 98b are presented as the average percent of plasma Apo (a) protein levels for each treatment group, normalized to baseline levels (% BL), The results show that the oligonucleotides comprising a GalNAc conjugate group exhibited potent reduction in Apo (a) expression. This potent effect was observed for the oligonucleotide that comprises full PS internucleoside linkages and the oligonucleotide that comprises mixed PO and PS linkages.

TABLE 98b

Apo(a) plasma protein levels

| ISIS No. | Dosage (mg/kg) | Apo(a) at 72 hours (% BL) | Apo(a) at 1 week (% BL) | Apo(a) at 3 weeks (% BL) |
|---|---|---|---|---|
| PBS | n/a | 116 | 104 | 107 |
| 681251 | 0.3 | 97 | 108 | 93 |
| | 1.0 | 85 | 77 | 57 |
| | 3.0 | 54 | 49 | 11 |
| | 10.0 | 23 | 15 | 4 |
| 681257 | 0.3 | 114 | 138 | 104 |
| | 1.0 | 91 | 98 | 54 |
| | 3.0 | 69 | 40 | 6 |
| | 10.0 | 30 | 21 | 4 |

Example 101: Antisense Inhibition by Oligonucleotides Comprising a GalNAc Cluster Linked Via a Stable Moiety The oligonucleotides listed in Table 99 were tested for inhibition of mouse APOC-III expression in vivo. C57B1/6 mice were each injected subcutaneously once with an oligonucleotide listed in Table 99 or with PBS. Each treatment group consisted of 4 animals. Each mouse treated with ISIS 440670 received a dose of 2, 6, 20, or 60 mg/kg. Each mouse treated with ISIS 680772 or 696847 received 0.6, 2, 6, or 20 mg/kg. The GalNAc conjugate group of ISIS 696847 is linked via a stable moiety, a phosphorothioate linkage instead of a readily cleavable phosphodiester containing linkage. The animals were sacrificed 72 hours after the dose. Liver APOC-III mRNA levels were measured using real-time PCR. APOC-III mRNA levels were normalized to cyclophilin mRNA levels according to standard protocols. The results are presented in Table 99 as the average percent of APOC-III mRNA levels for each treatment group relative to the saline control group. The results show that the oligonucleotides comprising a GalNAc conjugate group were significantly more potent than the oligonucleotide lacking a conjugate group. Furthermore, the oligonucleotide comprising a GalNAc conjugate group linked to the oligonucleotide via a cleavable moiety (ISIS 680772) was even more potent than the oligonucleotide comprising a GalNAc conjugate group linked to the oligonucleotide via a stable moiety (ISIS 696847).

TABLE 99

Modified oligonucleotides targeting mouse APOC-III

| ISIS No. | Sequences (5' to 3') | CM | Dosage (mg/kg) | APOC-III mRNA (% PBS) | SEQ ID No. |
|---|---|---|---|---|---|
| 440670 | ${}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}Ae$ | n/a | 2 | 92 | 47 |
| | | | 6 | 86 | |
| | | | 20 | 59 | |
| | | | 60 | 37 | |
| 680772 | **GalNAc$_3$-7**$_{a-o'}{}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}Ae$ | PO | 0.6 | 79 | 47 |
| | | | 2 | 58 | |
| | | | 6 | 31 | |
| | | | 20 | 13 | |
| 696847 | **GalNAc$_3$-7**$_{a-s'}{}^mC_{es}A_{es}G_{es}{}^mC_{es}T_{es}T_{ds}T_{ds}A_{ds}T_{ds}T_{ds}A_{ds}G_{ds}G_{ds}G_{ds}A_{ds}{}^mC_{es}A_{es}G_{es}{}^mC_{es}Ae$ | n/a (PS) | 0.6 | 83 | 47 |
| | | | 2 | 73 | |
| | | | 6 | 40 | |
| | | | 20 | 28 | |

The structure of $GalNAc_3$-$7_a$ was shown in Example 48.

Example 102: Distribution in Liver of Antisense Oligonucleotides Comprising a GalNAc Conjugate The liver distribution of ISIS 353382 (see Table 23) that does not comprise a GalNAc conjugate and ISIS 655861 (see Table 23) that does comprise a GalNAc conjugate was evaluated. Male balb/c mice were subcutaneously injected once with ISIS 353382 or 655861 at a dosage listed in Table 100. Each treatment group consisted of 3 animals except for the 18 mg/kg group for ISIS 655861, which consisted of 2 animals. The animals were sacrificed 48 hours following the dose to determine the liver distribution of the oligonucleotides. In order to measure the number of antisense oligonucleotide molecules per cell, a Ruthenium (II) tris-bipyridine tag (MSD TAG, Meso Scale Discovery) was conjugated to an oligonucleotide probe used to detect the antisense oligonucleotides. The results presented in Table 100 are the average concentrations of oligonucleotide for each treatment group in units of millions of oligonucleotide molecules per cell. The results show that at equivalent doses, the oligonucleotide comprising a GalNAc conjugate was present at higher concentrations in the total liver and in hepatocytes than the oligonucleotide that does not comprise a GalNAc conjugate. Furthermore, the oligonucleotide comprising a GalNAc conjugate was present at lower concentrations in non-parenchymal liver cells than the oligonucleotide that does not comprise a GalNAc conjugate. And while the concentrations of ISIS 655861 in hepatocytes and non-parenchymal liver cells were similar per cell, the liver is approximately 80% hepatocytes by volume. Thus, the majority of the ISIS 655861 oligonucleotide that was present in the liver was found in hepatocytes, whereas the majority of the ISIS 353382 oligonucleotide that was present in the liver was found in non-parenchymal liver cells.

TABLE 100

| ISIS No. | Dosage (mg/kg) | Concentration in whole liver (molecules* 10^6 per cell) | Concentration in hepatocytes (molecules* 10^6 per cell) | Concentration in non-parenchymal liver cells (molecules* 10^6 per cell) |
|---|---|---|---|---|
| 353382 | 3 | 9.7 | 1.2 | 37.2 |
| | 10 | 17.3 | 4.5 | 34.0 |
| | 20 | 23.6 | 6.6 | 65.6 |
| | 30 | 29.1 | 11.7 | 80.0 |
| | 60 | 73.4 | 14.8 | 98.0 |
| | 90 | 89.6 | 18.5 | 119.9 |
| 655861 | 0.5 | 2.6 | 2.9 | 3.2 |
| | 1 | 6.2 | 7.0 | 8.8 |
| | 3 | 19.1 | 25.1 | 28.5 |
| | 6 | 44.1 | 48.7 | 55.0 |
| | 18 | 76.6 | 82.3 | 77.1 |

Example 103: Duration of Action In Vivo of Oligonucleotides Targeting APOC-III Comprising a $GalNAc_3$ Conjugate The oligonucleotides listed in Table 101 below were tested in a single dose study for duration of action in mice.

TABLE 101

Modified ASOs targeting APOC-III

| ISIS No. | Sequences (5' to 3') | $GalNAc_3$ Cluster | CM | SEQ ID No. |
|---|---|---|---|---|
| 304801 | $A_{es}G_{es}{}^{m}C_{es}T_{es}T_{es}{}^{m}C_{ds}T_{ds}T_{ds}G_{ds}T_{ds}{}^{m}C_{ds}{}^{m}C_{ds}A_{ds}G_{ds}{}^{m}C_{ds}T_{es}T_{es}T_{es}A_{es}T_{e}$ | n/a | n/a | 20 |
| 663084 | $\mathbf{GalNAc_3\text{-}3_a\text{-}_{o'}Ado}A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{e}$ | GalNAc3-3a | $A_d$ | 36 |
| 679241 | $A_{es}G_{eo}{}^{m}C_{eo}T_{eo}T_{eo}{}^{m}C_{ds}T_{ds}T_{ds}G_{ds}T_{ds}{}^{m}C_{ds}{}^{m}C_{ds}A_{ds}G_{ds}{}^{m}C_{ds}T_{eo}T_{eo}T_{es}A_{es}T_{eo}\mathbf{Ado'\text{-}GalNAc_3\text{-}19_a}$ | GalNAc3-19a | $A_d$ | 21 |

The structure of $GalNAc_3$-$3_a$ was shown in Example 39, and $GalNAc_3$-$19_a$ was shown in Example 70.

Treatment

Female transgenic mice that express human APOC-III were each injected subcutaneously once with an oligonucleotide listed in Table 101 or with PBS. Each treatment group consisted of 3 animals. Blood was drawn before dosing to determine baseline and at 3, 7, 14, 21, 28, 35, and 42 days following the dose. Plasma triglyceride and APOC-III protein levels were measured as described in Example 20. The results in Table 102 are presented as the average percent of plasma triglyceride and APOC-III levels for each treatment group, normalized to baseline levels. A comparison of the results in Table 58 of example 79 with the results in Table 102 below show that oligonucleotides comprising a mixture of phosphodiester and phosphorothioate internucleoside linkages exhibited increased duration of action than equivalent oligonucleotides comprising only phosphorothioate internucleoside linkages.

TABLE 102
Plasma triglyceride and APOC-III protein levels in transgenic mice
| ISIS No. | Dosage (mg/kg) | Time point (days post- dose) | Triglycerides (% baseline) | APOC-III protein (% baseline) | GalNAcj Cluster | CM |
|---|---|---|---|---|---|---|
| PBS | n/a | 3 | 96 | 101 | n/a | n/a |
| | | 7 | 88 | 98 | | |
| | | 14 | 91 | 103 | | |
| | | 21 | 69 | 92 | | |
| | | 28 | 83 | 81 | | |
| | | 35 | 65 | 86 | | |
| | | 42 | 72 | 88 | | |
| 304801 | 30 | 3 | 42 | 46 | n/a | n/a |
| | | 7 | 42 | 51 | | |
| | | 14 | 59 | 69 | | |
| | | 21 | 67 | 81 | | |
| | | 28 | 79 | 76 | | |
| | | 35 | 72 | 95 | | |
| | | 42 | 82 | 92 | | |
| 663084 | 10 | 3 | 35 | 28 | GalNAc3-3a | A<j |
| | | 7 | 23 | 24 | | |
| | | 14 | 23 | 26 | | |
| | | 21 | 23 | 29 | | |
| | | 28 | 30 | 22 | | |
| | | 35 | 32 | 36 | | |
| | | 42 | 37 | 47 | | |
| 679241 | 10 | 3 | 38 | 30 | GalNAc.i- 19a | Aa |
| | | 7 | 31 | 28 | | |
| | | 14 | 30 | 22 | | |
| | | 21 | 36 | 34 | | |
| | | 28 | 48 | 34 | | |
| | | 35 | 50 | 45 | | |
| | | 42 | 72 | 64 | | |
Example 104: Synthesis of oligonucleotides comprising a 5'-GalNAc$_2$ conjugate
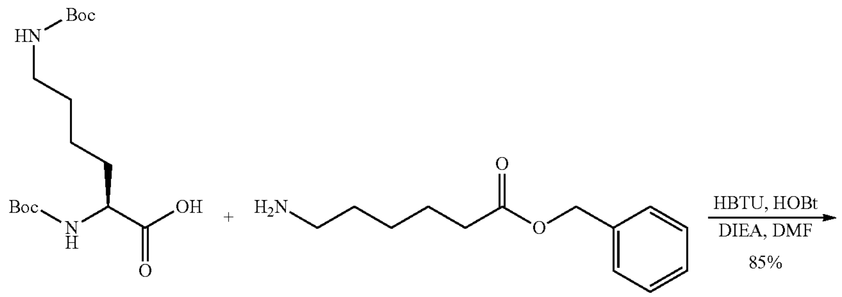
120
126
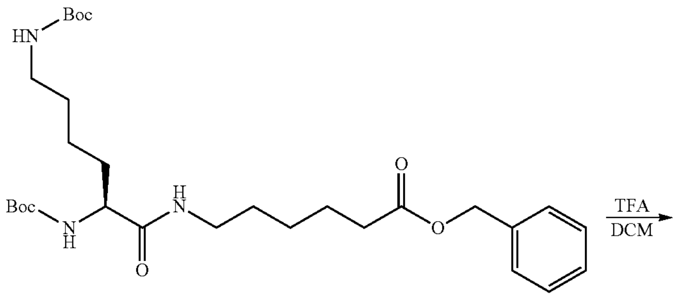
231

-continued
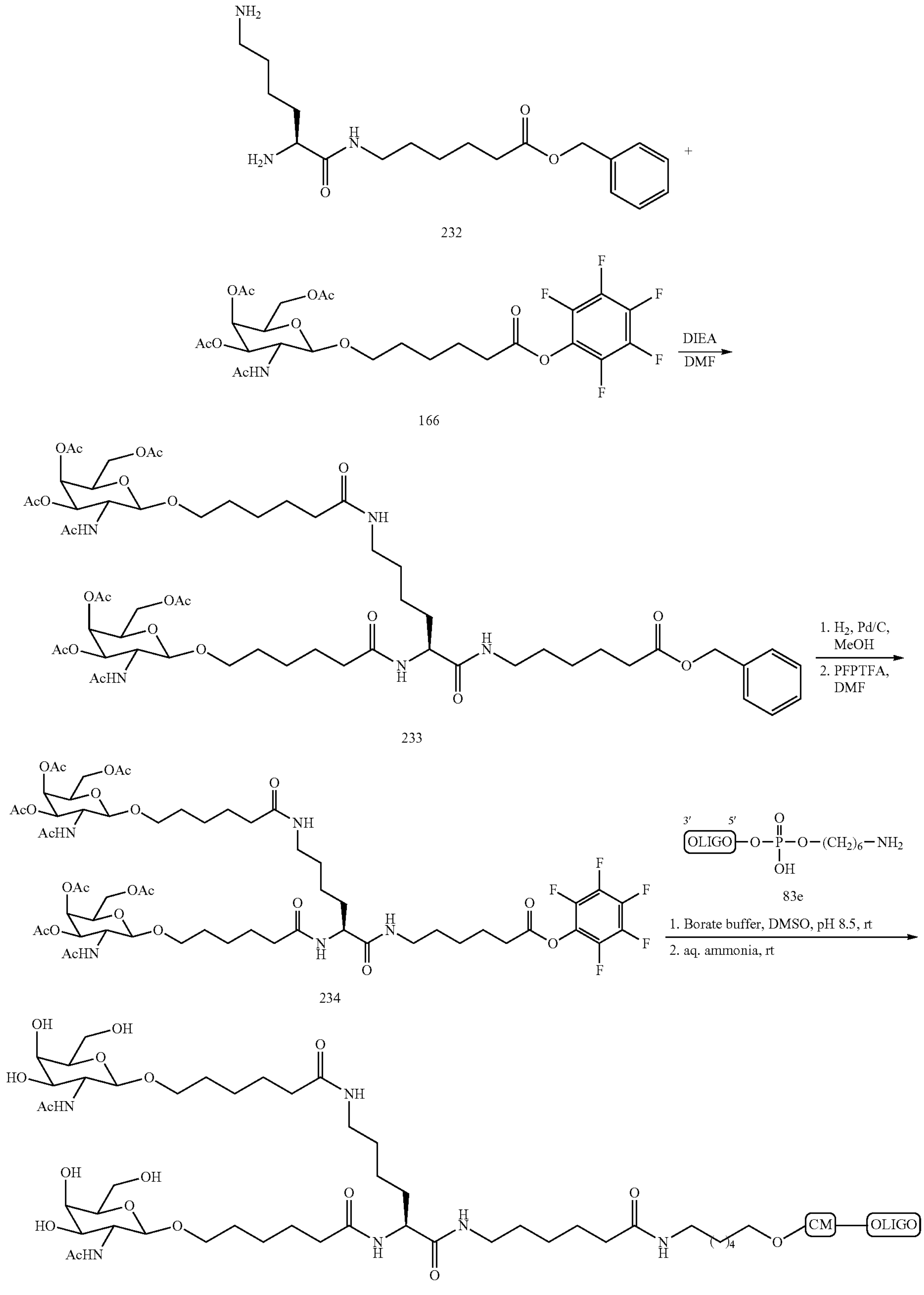
232
166
233
234
83e
235

Compound 120 is commercially available, and the synthesis of compound 126 is described in Example 49. Compound 120 (1 g, 2.89 mmol), HBTU (0.39 g, 2.89 mmol), and HOBt (1.64 g, 4.33 mmol) were dissolved in DMF (10 mL. and N,N-diisopropylethylamine (1.75 mL, 10.1 mmol) were added. After about 5 min, aminohexanoic acid benzyl ester (1.36 g, 3.46 mmol) was added to the reaction. After 3 h, the reaction mixture was poured into 100 mL of 1 M $NaHSO_4$ and extracted with 2×50 mL ethyl acetate. Organic layers were combined and washed with 3×40 mL sat $NaHCO_3$ and 2× brine, dried with $Na_2SO_4$, filtered and concentrated. The product was purified by silica gel column chromatography (DCM: EA: Hex, 1:1:1) to yield compound 231. LCMS and NMR were consistent with the structure. Compounds 231 (1.34 g, 2.438 mmol) was dissolved in dichloromethane (10 mL) and trifluoracetic acid (10 mL) was added. After stirring at room temperature for 2 h, the reaction mixture was concentrated under reduced pressure and co-evaporated with toluene (3×10 mL). The residue was dried under reduced pressure to yield compound 232 as the trifuloracetate salt. The synthesis of compound 166 is described in Example 54. Compound 166 (3.39 g, 5.40 mmol) was dissolved in DMF (3 mL). A solution of compound 232 (1.3 g, 2.25 mmol) was dissolved in DMF (3 mL) and N,N-diisopropylethylamine (1.55 mL) was added. The reaction was stirred at room temperature for 30 minutes, then poured into water (80 mL) and the aqueous layer was extracted with EtOAc (2×$10^0$ mL). The organic phase was separated and washed with sat. aqueous $NaHCO_3$ (3×80 mL), 1 M $NaHSO_4$ (3×80 mL) and brine (2×80 mL), then dried ($Na_2SO_4$), filtered, and concentrated. The residue was purified by silica gel column chromatography to yield compound 233. LCMS and NMR were consistent with the structure. Compound 233 (0.59 g, 0.48 mmol) was dissolved in methanol (2.2 mL) and ethyl acetate (2.2 mL). Palladium on carbon (10 wt % Pd/C, wet, 0.07 g) was added, and the reaction mixture was stirred under hydrogen atmosphere for 3 h. The reaction mixture was filtered through a pad of Celite and concentrated to yield the carboxylic acid. The carboxylic acid (1.32 g, 1.15 mmol, cluster free acid) was dissolved in DMF (3.2 mL). To this N,N-diisopropylehtylamine (0.3 mL, 1.73 mmol) and PFPTFA (0.30 mL, 1.73 mmol) were added. After 30 min stirring at room temperature the reaction mixture was poured into water (40 mL) and extracted with EtOAc (2×50 mL). A standard work-up was completed as described above to yield compound 234. LCMS and NMR were consistent with the structure. Oligonucleotide 235 was prepared using the general procedure described in Example 46. The $GalNAc_2$ cluster portion ($GalNAc_2$-$24_a$) of the conjugate group $GalNAc_2$-24 can be combined with any cleavable moiety present on the oligonucleotide to provide a variety of conjugate groups. The structure of $GalNAc_2$-24 ($GalNAc_2$-$24_a$-CM) is shown below:

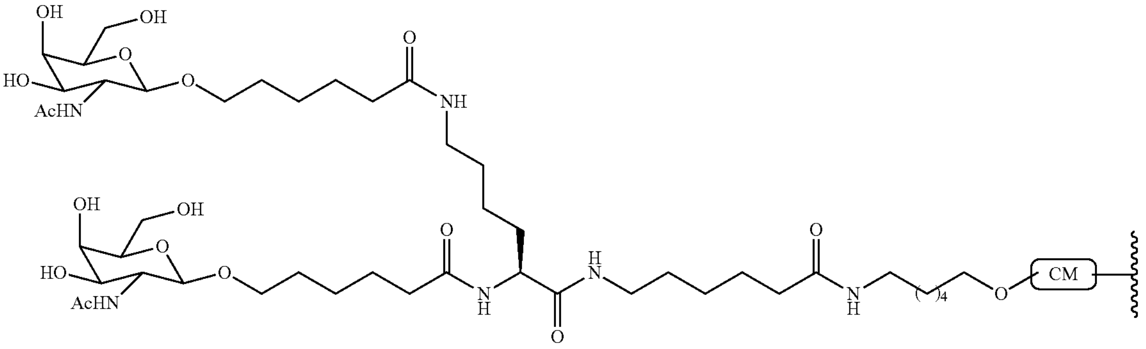

Example 105: Synthesis of oligonucleotides comprising a $GalNAc_1$-25 conjugate

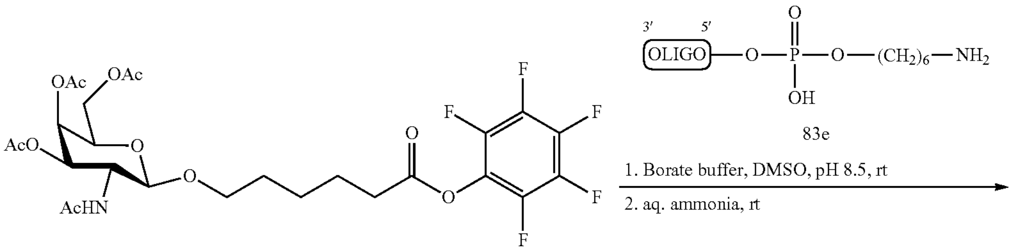

166

83e

-continued

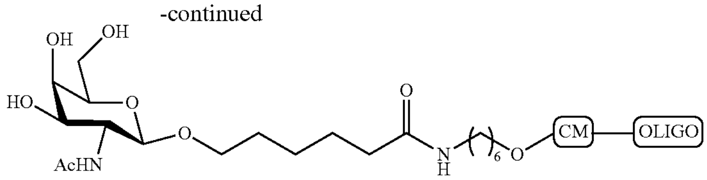

236

The synthesis of compound 166 is described in Example 54. Oligonucleotide 236 was prepared using the general procedure described in Example 46.

Alternatively, oligonucleotide 236 was synthesized using the scheme shown below, and compound 238 was used to form the oligonucleotide 236 using procedures described in Example 10.

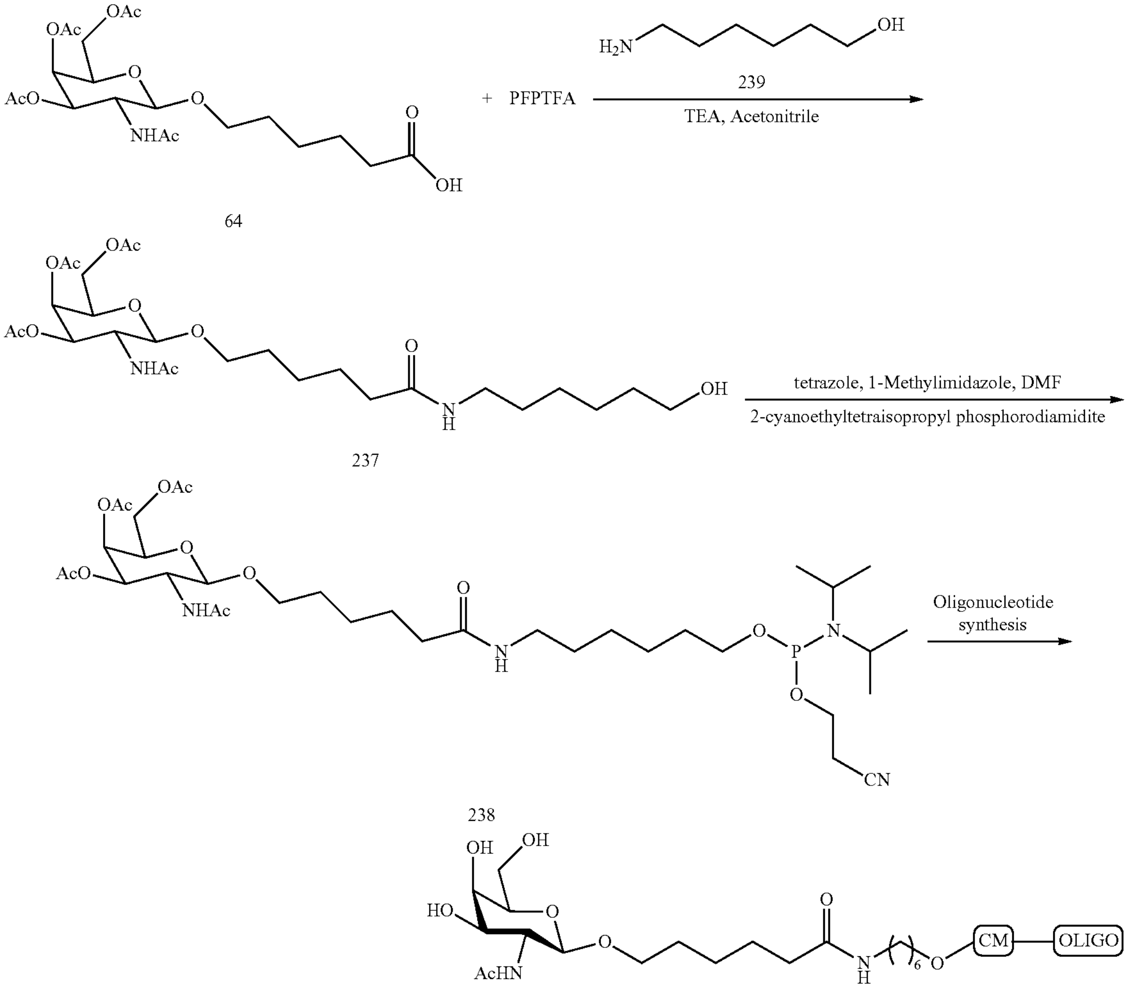

64

237

238

236

The GalNAc$_1$ cluster portion (GalNAc$_1$-25$_a$) of the conjugate group GalNAc$_1$-25 can be combined with any cleavable moiety present on the oligonucleotide to provide a variety of conjugate groups. The structure of GalNAc$_1$-25 (GalNAc$_1$-25$_a$-CM) is shown below:

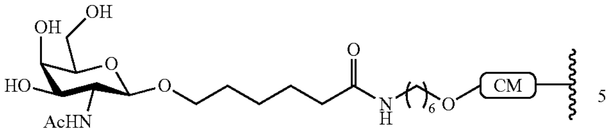

Example 106: Antisense inhibition in vivo by oligonucleotides targeting SRB-1 comprising a 5'-GalNAc$_2$ or a 5'-GalNAc$_3$ conjugate Oligonucleotides listed in Tables 103 and 104 were tested in dose-dependent studies for antisense inhibition of SRB-1 in mice.

Treatment

Six to week old, male C57BL/6 mice (Jackson Laboratory, Bar Harbor, ME) were injected subcutaneously once with 2, 7, or 20 mg/kg of ISIS No. 440762; or with 0.2, 0.6, 2, 6, or 20 mg/kg of ISIS No. 686221, 686222, or 708561; or with saline. Each treatment group consisted of 4 animals. The mice were sacrificed 72 hours following the final administration. Liver SRB-1 mRNA levels were measured using real-time PCR. SRB-1 mRNA levels were normalized to cyclophilin mRNA levels according to standard protocols. The antisense oligonucleotides lowered SRB-1 mRNA levels in a dose-dependent manner, and the ED50 results are presented in Tables 103 and 104. Although previous studies showed that trivalent GalNAc-conjugated oligonucleotides were significantly more potent than divalent GalNAc-conjugated oligonucleotides, which were in turn significantly more potent than monovalent GalNAc conjugated oligonucleotides (see, e.g., Khorev et al., *Bioorg. & Med. Chem.*, Vol. 16, 5216-5231 (2008)), treatment with antisense oligonucleotides comprising monovalent, divalent, and trivalent GalNAc clusters lowered SRB-1 mRNA levels with similar potencies as shown in Tables 103 and 104.

TABLE 103

Modified oligonucleotides targeting SRB-1

| ISIS No. | Sequences (5' to 3') | GalNAc Cluster | $ED_{50}$ (mg/kg) | SEQ ID No |
|---|---|---|---|---|
| 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | n/a | 4.7 | 22 |
| 686221 | $\mathbf{GalNAc_2\text{-}23_a\text{-}_{o'}A_{do}}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | GalNAc$_2$-24$_a$ | 0.39 | 26 |
| 686222 | $\mathbf{GalNAc_3\text{-}13_a\text{-}_{o'}A_{do}}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | GalNAc$_3$-13$_a$ | 0.41 | 26 |

See Example 93 for table legend. The structure of GalNAc$_3$-13$_a$ was shown in Example 62, and the structure of GalNAc$_2$-24$_a$ was shown in Example 104.

TABLE 104

Modified oligonucleotides targeting SRB-1

| ISIS No. | Sequences (5' to 3') | GalNAc Cluster | ED50 (mg/kg) | SEQ ID No |
|---|---|---|---|---|
| 440762 | $T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | n/a | 5 | 22 |
| 708561 | $\mathbf{GalNAc_1\text{-}23_a\text{-}_{o'}}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{k}$ | GalNAc$_1$-25$_a$ | 0.4 | 22 |

See Example 93 for table legend. The structure of GalNAc$_1$-25$_a$ was shown in Example 105.

The concentrations of the oligonucleotides in Tables 103 and 104 in liver were also assessed, using procedures described in Example 75. The results shown in Tables 104$_a$ and 104b below are the average total antisense oligonucleotide tissues levels for each treatment group, as measured by UV in units of μg oligonucleotide per gram of liver tissue. The results show that the oligonucleotides comprising a GalNAc conjugate group accumulated in the liver at significantly higher levels than the same dose of the oligonucleotide lacking a GalNAc conjugate group. Furthermore, the antisense oligonucleotides comprising one, two, or three GalNAc ligands in their respective conjugate groups all accumulated in the liver at similar levels. This result is surprising in view of the Khorev et al. literature reference cited above and is consistent with the activity data shown in Tables 103 and 104 above.

TABLE 104a

Liver concentrations of oligonucleotides comprising a GalNAc$_2$ or GalNAc$_3$ conjugate group

| ISIS No. | Dosage (mg/kg) | [Antisense oligonucleotide] (μg/g) | GalNAc cluster | CM |
|---|---|---|---|---|
| 440762 | 2 | 2.1 | n/a | n/a |
| | 7 | 13.1 | | |
| | 20 | 31.1 | | |
| 686221 | 0.2 | 0.9 | GalNAc$_2$-24$_a$ | $A_d$ |
| | 0.6 | 2.7 | | |
| | 2 | 12.0 | | |
| | 6 | 26.5 | | |
| 686222 | 0.2 | 0.5 | GalNAc$_3$-13$_a$ | $A_d$ |
| | 0.6 | 1.6 | | |
| | 2 | 11.6 | | |
| | 6 | 19.8 | | |

TABLE 104b

| Liver concentrations of oligonucleotides comprising a GalNAc$_1$ conjugate group | | | | |
|---|---|---|---|---|
| ISIS No. | Dosage (mg/kg) | [Antisense oligonucleotide] (μg/g) | GalNAc cluster | CM |
| 440762 | 2 | 2.3 | n/a | n/a |
| | 7 | 8.9 | | |
| | 20 | 23.7 | | |
| 708561 | 0.2 | 0.4 | GalNAc$_1$-25$_a$ | PO |
| | 0.6 | 1.1 | | |
| | 2 | 5.9 | | |
| | 6 | 23.7 | | |
| | 20 | 53.9 | | |

Example 107: Synthesis of Oligonucleotides Comprising a GalNAc$_1$-26 or GalNAc$_1$-27 Conjugate

239

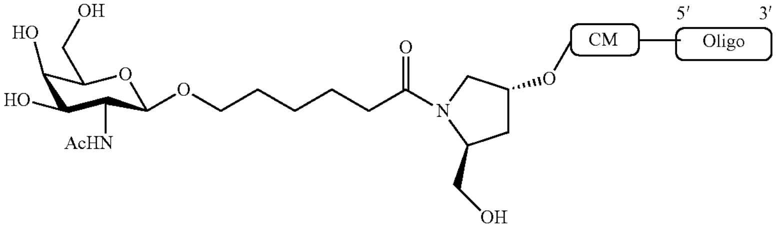

Oligonucleotide 239 is synthesized via coupling of compound 47 (see Example 15) to acid 64 (see Example 32) using HBTU and DIEA in DMF. The resulting amide containing compound is phosphitylated, then added to the 5'-end of an oligonucleotide using procedures described in Example 10. The GalNAc cluster portion (GalNAc$_1$-26$_a$) of the conjugate group GalNAc$_1$-26 can be combined with any cleavable moiety present on the oligonucleotide to provide a variety of conjugate groups. The structure of GalNAc$_1$-26 (GalNAc$_1$-26$_a$-CM) is shown below:

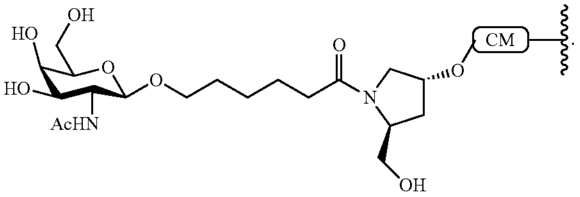

In order to add the GalNAc$_1$ conjugate group to the 3'-end of an oligonucleotide, the amide formed from the reaction of compounds 47 and 64 is added to a solid support using procedures described in Example 7. The oligonucleotide synthesis is then completed using procedures described in Example 9 in order to form oligonucleotide 240.

240

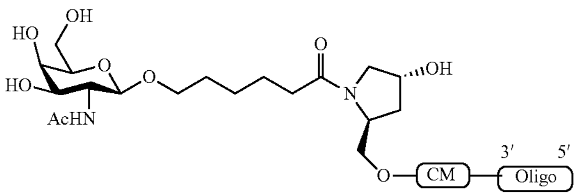

The GalNAc$_1$ cluster portion (GalNAc$_1$-27$_a$) of the conjugate group GalNAc$_1$-27 can be combined with any cleavable moiety present on the oligonucleotide to provide a variety of conjugate groups. The structure of GalNAc$_1$-27 (GalNAc$_1$-27$_a$-CM) is shown below:

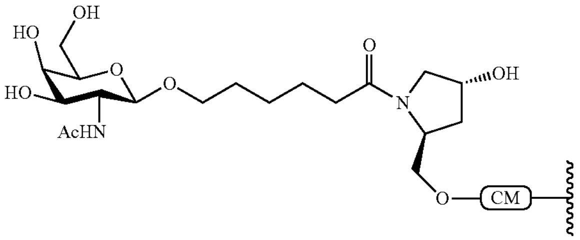

Example 108: Antisense Inhibition In Vivo by Oligonucleotides Comprising a GalNAc Conjugate Group Targeting Apo (a) In Vivo The oligonucleotides listed in Table 105 below were tested in a single dose study in mice.

TABLE 105

| Modified ASOs targeting APO(a) | | | | |
|---|---|---|---|---|
| ISIS No. | Sequences (5' to 3') Cluster | $GalNAc_3$ ID No. | CM | SEQ |
| 494372 | $T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | n/a | n/a | 53 |
| 681251 | **$GalNAc_3$-7**$_{a}$-$_{o'}$$T_{es}G_{es}{}^{m}C_{es}T_{es}{}^{m}C_{es}{}^{m}C_{ds}G_{ds}T_{ds}T_{ds}G_{ds}G_{ds}T_{ds}G_{ds}{}^{m}C_{ds}T_{ds}T_{es}G_{es}T_{es}T_{es}{}^{m}C_{e}$ | $GalNAc_3$-7a | PO | 53 |
| 681255 | **$GalNAc_3$-3**$_{a}$-$_{o'}$$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-3a | PO | 53 |
| 681256 | **$GalNAc_3$-10**$_{a}$-$_{o'}$$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-10a | PO | 53 |
| 681257 | **$GalNAc_3$-7**$_{a}$-$_{o'}$$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-7a | PO | 53 |
| 681258 | **$GalNAc_3$-13**$_{a}$-$_{o'}$$T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{e}$ | $GalNAc_3$-13a | PO | 53 |
| 681260 | $T_{es}G_{eo}{}^{m}C_{eo}T_{eo}{}^{m}C_{eo}{}^{m}C_{ds}G_{ds}T_{ds}T_{ds}G_{ds}G_{ds}T_{ds}G_{ds}{}^{m}C_{ds}T_{ds}T_{eo}G_{eo}T_{es}T_{es}{}^{m}C_{eo}$**A**$_{do'}$-**$GalNAc_3$-19** | $GalNAc_3$-19a | $A_d$ | 52 |

The structure of $GalNAc_3$-$7_a$ was shown in Example 48.

Treatment

Male transgenic mice that express human Apo (a) were each injected subcutaneously once with an oligonucleotide and dosage listed in Table 106 or with PBS. Each treatment group consisted of 4 animals. Blood was drawn the day before dosing to determine baseline levels of Apo (a) protein in plasma and at 1 week following the first dose. Additional blood draws will occur weekly for approximately 8 weeks. Plasma Apo (a) protein levels were measured using an ELISA. The results in Table 106 are presented as the average percent of plasma Apo (a) protein levels for each treatment group, normalized to baseline levels (% BL), The results show that the antisense oligonucleotides reduced Apo (a) protein expression. Furthermore, the oligonucleotides comprising a GalNAc conjugate group exhibited even more potent reduction in Apo (a) expression than the oligonucleotide that does not comprise a conjugate group.

TABLE 106

| Apo(a) plasma protein levels | | |
|---|---|---|
| ISIS No. | Dosage (mg/kg) | Apo(a) at 1 week (% BL) |
| PBS | n/a | 143 |
| 494372 | 50 | 58 |
| 681251 | 10 | 15 |
| 681255 | 10 | 14 |
| 681256 | 10 | 17 |
| 681257 | 10 | 24 |
| 681258 | 10 | 22 |
| 681260 | 10 | 26 |

Example 109: Synthesis of Oligonucleotides Comprising a $GalNAc_1$-28 or $GalNAc_1$-29 Conjugate

241

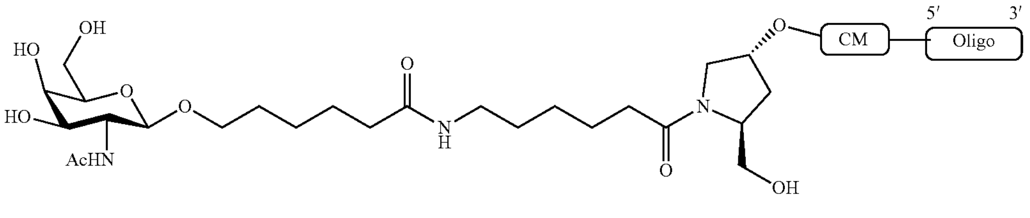

Oligonucleotide 241 is synthesized using procedures similar to those described in Example 71 to form the phosphoramidite intermediate, followed by procedures described in Example 10 to synthesize the oligonucleotide. The $GalNAc_1$ cluster portion ($GalNAc_1$-$28_a$) of the conjugate group $GalNAc_1$-28 can be combined with any cleavable moiety present on the oligonucleotide to provide a variety of conjugate groups. The structure of $GalNAc_1$-28 ($GalNAc_1$-$28_a$-CM) is shown below:

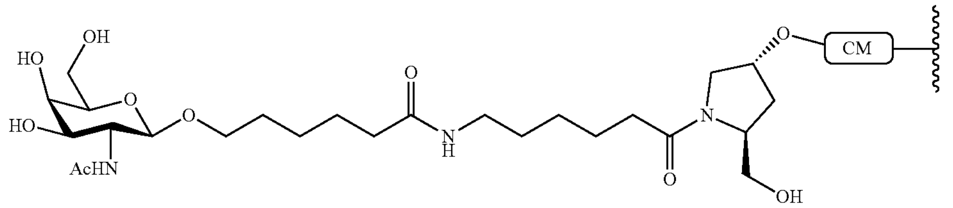

In order to add the $GalNAc_1$ conjugate group to the 3'-end of an oligonucleotide, procedures similar to those described in Example 71 are used to form the hydroxyl intermediate, which is then added to the solid support using procedures described in Example 7. The oligonucleotide synthesis is then completed using procedures described in Example 9 in order to form oligonucleotide 242.

242

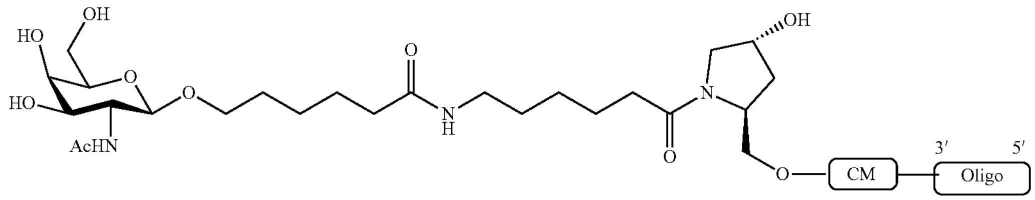

The $GalNAc_1$ cluster portion ($GalNAc_1$-$29_a$) of the conjugate group $GalNAc_1$-29 can be combined with any cleavable moiety present on the oligonucleotide to provide a variety of conjugate groups. The structure of $GalNAc_1$-29 ($GalNAc_1$-$29_a$-CM) is shown below:

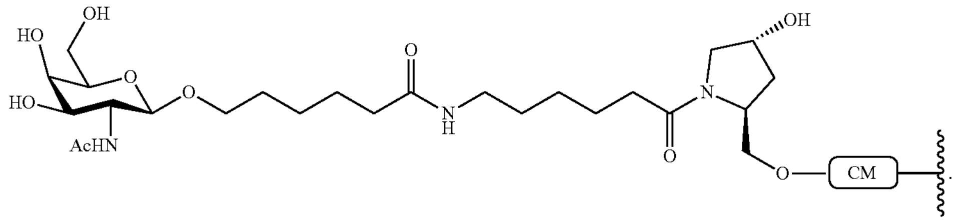

Example 110: Synthesis of Oligonucleotides Comprising a $GalNAc_1$-30 Conjugate

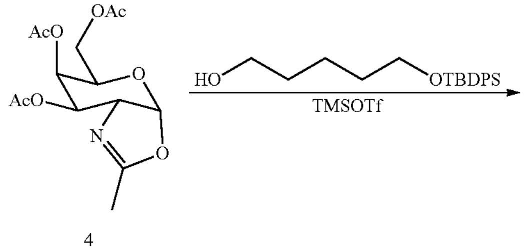

4

-continued

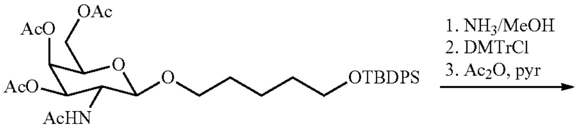

243

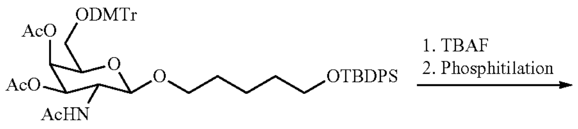

244

-continued

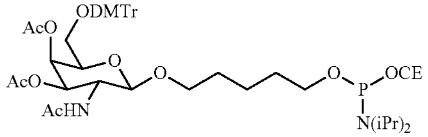

245

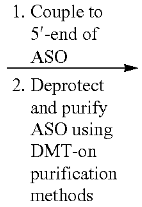

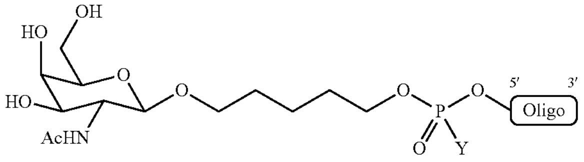

246

Oligonucleotide 246 comprising a $GalNAc_1$-30 conjugate group, wherein Y is selected from O, S, a substituted or unsubstituted $C_1$-$C_{10}$ alkyl, amino, substituted amino, azido, alkenyl or alkynyl, is synthesized as shown above. The $GalNAc_1$ cluster portion ($GalNAc_1$-$30_a$) of the conjugate group $GalNAc_1$-30 can be combined with any cleavable moiety to provide a variety of conjugate groups. In certain embodiments, Y is part of the cleavable moiety. In certain embodiments, Y is part of a stable moiety, and the cleavable moiety is present on the oligonucleotide. The structure of $GalNAc_1$-$30_a$ is shown below:

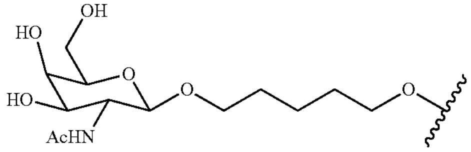 [SMILES: *OCCCCCOC1OC(CO)C(O)C(O)C1NC(C)=O]

Example 111: Synthesis of Oligonucleotides Comprising a GalINAc2-31 or $GalNAc_2$-32 Conjugate

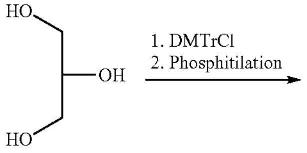

247

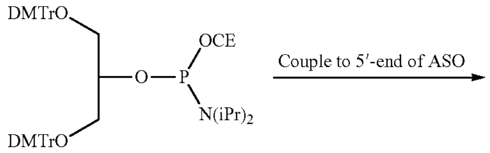

248

-continued

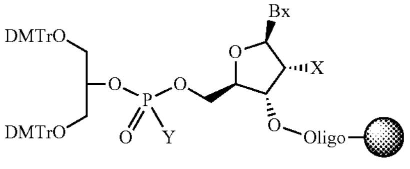

249

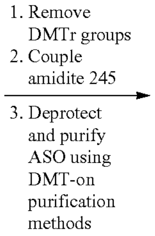

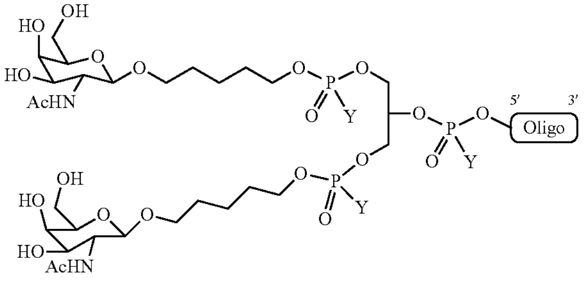

250

Oligonucleotide 250 comprising a $GalNAc_2$-31 conjugate group, wherein Y is selected from O, S, a substituted or unsubstituted $C_1$-$C_{10}$ alkyl, amino, substituted amino, azido, alkenyl or alkynyl, is synthesized as shown above. The $GalNAc_2$ cluster portion ($GalNAc_2$-$31_a$) of the conjugate group $GalNAc_2$-31 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of $GalNAc_2$-$31_a$ is shown below:

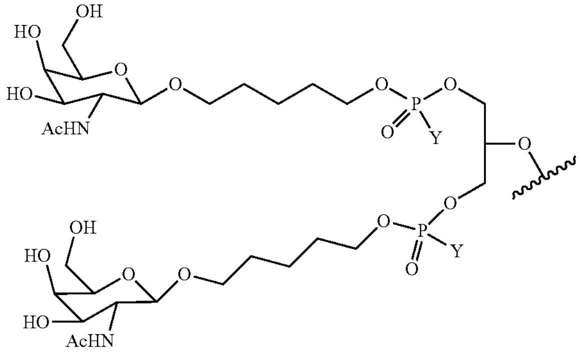

The synthesis of an oligonucleotide comprising a $GalNAc_2$-32 conjugate is shown below.

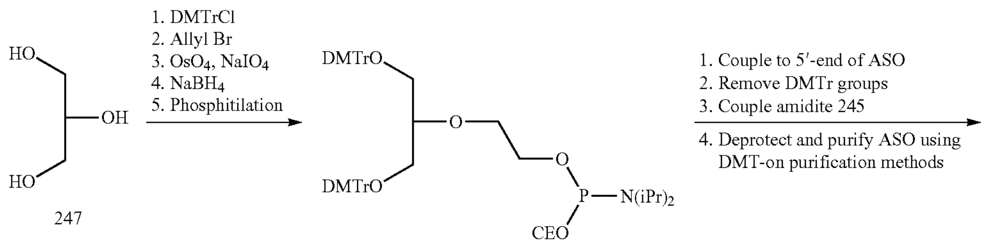

247

251

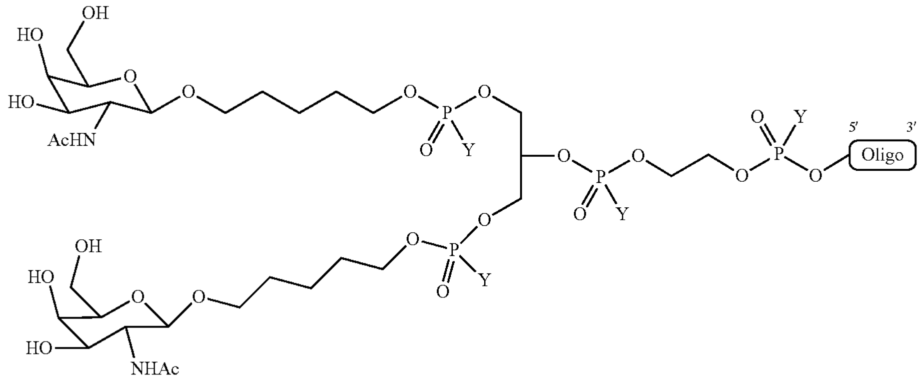

252

Oligonucleotide 252 comprising a $GalNAc_2$-32 conjugate group, wherein Y is selected from O, S, a substituted or unsubstituted $C_1$-$C_{10}$ alkyl, amino, substituted amino, azido, alkenyl or alkynyl, is synthesized as shown above. The $GalNAc_2$ cluster portion ($GalNAc_2$-$32_a$) of the conjugate group $GalNAc_2$-32 can be combined with any cleavable moiety to provide a variety of conjugate groups. In certain embodiments, the Y-containing group directly adjacent to the 5'-end of the oligonucleotide is part of the cleavable moiety. In certain embodiments, the Y-containing group directly adjacent to the 5'-end of the oligonucleotide is part of a stable moiety, and the cleavable moiety is present on the oligonucleotide. The structure of $GalNAc_2$-$32_a$ is shown below:

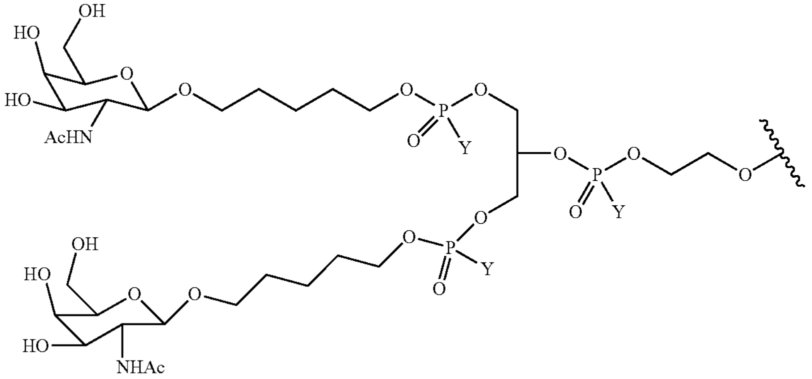

Example 112: Modified oligonucleotides comprising a $GalNAc_1$ conjugate

The oligonucleotides in Table 107 targeting SRB-1 were synthesized with a $GalNAc_1$ conjugate group in order to further test the potency of oligonucleotides comprising conjugate groups that contain one GalNAc ligand.

TABLE 107

| ISIS No. | Sequence (5' to 3') | GalNAc cluster | CM | SEQ ID NO. |
|---|---|---|---|---|
| 711461 | $\mathbf{GalNAc_1\text{-}25}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_1\text{-}25_a$ | $A_d$ | 30 |
| 711462 | $\mathbf{GalNAc_1\text{-}25}_{a\text{-}o'}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_1\text{-}25_a$ | PO | 28 |
| 711463 | $\mathbf{GalNAc_1\text{-}25}_{a\text{-}o'}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | $GalNAc_1\text{-}25_a$ | PO | 28 |
| 711465 | $\mathbf{GalNAc_1\text{-}26}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_1\text{-}26_a$ | $A_d$ | 30 |
| 711466 | $\mathbf{GalNAc_1\text{-}26}_{a\text{-}o'}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_1\text{-}26_a$ | PO | 28 |
| 711467 | $\mathbf{GalNAc_1\text{-}26}_{a\text{-}o'}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | $GalNAc_1\text{-}26_a$ | PO | 28 |
| 711468 | $\mathbf{GalNAc_1\text{-}28}_{a\text{-}o'}\mathbf{A}_{do}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_1\text{-}28_a$ | $A_d$ | 30 |
| 711469 | $\mathbf{GalNAc_1\text{-}28}_{a\text{-}o'}G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{e}$ | $GalNAc_1\text{-}28_a$ | PO | 28 |
| 711470 | $\mathbf{GalNAc_1\text{-}28}_{a\text{-}o'}G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{e}$ | $GalNAc_1\text{-}28_a$ | PO | 28 |
| 713844 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo'}\text{-}\mathbf{GalNAc_1\text{-}27}_{a}$ | $GalNAc_1\text{-}27_a$ | PO | 28 |
| 713845 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo'}\text{-}\mathbf{GalNAc_1\text{-}27}_{a}$ | $GalNAc_1\text{-}27_a$ | PO | 28 |
| 713846 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo}\mathbf{A}_{do'}\text{-}\mathbf{GalNAc_1\text{-}27}_{a}$ | $GalNAc_1\text{-}27_a$ | $A_d$ | 29 |
| 713847 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo'}\text{-}\mathbf{GalNAc_1\text{-}29}_{a}$ | $GalNAc_1\text{-}29_a$ | PO | 28 |
| 713848 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo'}\text{-}\mathbf{GalNAc_1\text{-}29}_{a}$ | $GalNAc_1\text{-}29_a$ | PO | 28 |
| 713849 | $G_{es}{}^{m}C_{es}T_{es}T_{es}{}^{m}C_{es}A_{ds}G_{ds}T_{ds}{}^{m}C_{ds}A_{ds}T_{ds}G_{ds}A_{ds}{}^{m}C_{ds}T_{ds}T_{es}{}^{m}C_{es}{}^{m}C_{es}T_{es}T_{eo}\mathbf{A}_{do'}\text{-}\mathbf{GalNAc_1\text{-}29}_{a}$ | $GalNAc_1\text{-}29_a$ | $A_d$ | 29 |
| 713850 | $G_{es}{}^{m}C_{eo}T_{eo}T_{eo}{}^{m}C_{eo}A_{ds}G_{ds}T_{ds}{}^{m}C_{ds}A_{ds}T_{ds}G_{ds}A_{ds}{}^{m}C_{ds}T_{ds}T_{eo}{}^{m}C_{eo}{}^{m}C_{es}T_{es}T_{eo}\mathbf{A}_{do'}\text{-}\mathbf{GalNAc_1\text{-}29}_{a}$ | $GalNAc_1\text{-}29_a$ | $A_d$ | 29 |

Example 113: Modified oligonucleotides comprising a GalNAc conjugate group targeting Hepatits B Virus (HBV)

The oligonucleotides listed in Table 108 below were designed to target HBV. In certain embodiments, the cleavable moiety is a phosphodiester linkage.

TABLE 108

| Sequences (5' to 3') | SEQ ID No. |
|---|---|
| $\mathbf{GalNAc_3\text{-}3}\text{-}G_{es}{}^{m}C_{es}A_{es}G_{es}A_{es}G_{ds}G_{ds}T_{ds}G_{ds}A_{ds}A_{ds}G_{ds}{}^{m}C_{ds}G_{ds}A_{ds}A_{es}G_{es}T_{es}G_{es}{}^{m}C_{e}$ | 3 |
| $\mathbf{GalNAc_3\text{-}3}\text{-}G_{es}{}^{m}C_{eo}A_{eo}G_{eo}A_{eo}G_{ds}G_{ds}T_{ds}G_{ds}A_{ds}A_{ds}G_{ds}{}^{m}C_{ds}G_{ds}A_{ds}A_{eo}G_{eo}T_{es}G_{es}{}^{m}C_{e}$ | 3 |

TABLE 108-continued

| Sequences (5' to 3') | SEQ ID No. |
| --- | --- |
| **GalNAc$_3$-7**-$G_{es}{}^{m}C_{es}A_{es}G_{es}A_{es}G_{ds}G_{ds}T_{ds}G_{ds}A_{ds}A_{ds}G_{ds}{}^{m}C_{ds}G_{ds}A_{ds}A_{es}G_{es}T_{es}G_{es}{}^{m}C_{e}$ | 3 |
| **GalNAc$_3$-7**-$G_{es}{}^{m}C_{eo}A_{eo}G_{eo}A_{eo}G_{ds}G_{ds}T_{ds}G_{ds}A_{ds}A_{ds}G_{ds}{}^{m}C_{ds}G_{ds}A_{ds}A_{eo}G_{eo}T_{es}G_{es}{}^{m}C_{e}$ | 3 |
| **GalNAc$_3$-10**-$G_{es}{}^{m}C_{es}A_{es}G_{es}A_{es}G_{ds}G_{ds}T_{ds}G_{ds}A_{ds}A_{ds}G_{ds}{}^{m}C_{ds}G_{ds}A_{ds}A_{es}G_{es}T_{es}G_{es}{}^{m}C_{e}$ | 3 |
| **GalNAc$_3$-10**-$G_{es}{}^{m}C_{eo}A_{eo}G_{eo}A_{eo}G_{ds}G_{ds}T_{ds}G_{ds}A_{ds}A_{ds}G_{ds}{}^{m}C_{ds}G_{ds}A_{ds}A_{eo}G_{eo}T_{es}G_{es}{}^{m}C_{e}$ | 3 |
| **GalNAc$_3$-13**-$G_{es}{}^{m}C_{es}A_{es}G_{es}A_{es}G_{ds}G_{ds}T_{ds}G_{ds}A_{ds}A_{ds}G_{ds}{}^{m}C_{ds}G_{ds}A_{ds}A_{es}G_{es}T_{es}G_{es}{}^{m}C_{e}$ | 3 |
| **GalNAc$_3$-13**-$G_{es}{}^{m}C_{eo}A_{eo}G_{eo}A_{eo}G_{ds}G_{ds}T_{ds}G_{ds}A_{ds}A_{ds}G_{ds}{}^{m}C_{ds}G_{ds}A_{ds}A_{eo}G_{eo}T_{es}G_{es}{}^{m}C_{e}$ | 3 |
| $G_{es}{}^{m}C_{es}A_{es}G_{es}A_{es}G_{ds}G_{ds}T_{ds}G_{ds}A_{ds}A_{ds}G_{ds}{}^{m}C_{ds}G_{ds}A_{ds}A_{es}G_{es}T_{es}G_{es}{}^{m}C_{e}$-**GalNAc$_3$-19** | 3 |
| $G_{es}{}^{m}C_{eo}A_{eo}G_{eo}A_{eo}G_{ds}G_{ds}T_{ds}G_{ds}A_{ds}A_{ds}G_{ds}{}^{m}C_{ds}G_{ds}A_{ds}A_{eo}G_{eo}T_{es}G_{es}{}^{m}C_{e}$-**GalNAc$_3$-19** | 3 |
| **GalNAc$_3$-24**-$G_{es}{}^{m}C_{es}A_{es}G_{es}A_{es}G_{ds}G_{ds}T_{ds}G_{ds}A_{ds}A_{ds}G_{ds}{}^{m}C_{ds}G_{ds}A_{ds}A_{es}G_{es}T_{es}G_{es}{}^{m}C_{e}$ | 3 |
| **GalNAc$_3$-24**-$G_{es}{}^{m}C_{eo}A_{eo}G_{eo}A_{eo}G_{ds}G_{ds}T_{ds}G_{ds}A_{ds}A_{ds}G_{ds}{}^{m}C_{ds}G_{ds}A_{ds}A_{eo}G_{eo}T_{es}G_{es}{}^{m}C_{e}$ | 3 |
| **GalNAc$_3$-25**-$G_{es}{}^{m}C_{es}A_{es}G_{es}A_{es}G_{ds}G_{ds}T_{ds}G_{ds}A_{ds}A_{ds}G_{ds}{}^{m}C_{ds}G_{ds}A_{ds}A_{es}G_{es}T_{es}G_{es}{}^{m}C_{e}$ | 3 |
| **GalNAc$_3$-25**-$G_{es}{}^{m}C_{eo}A_{eo}G_{eo}A_{eo}G_{ds}G_{ds}T_{ds}G_{ds}A_{ds}A_{ds}G_{ds}{}^{m}C_{ds}G_{ds}A_{ds}A_{eo}G_{eo}T_{es}G_{es}{}^{m}C_{e}$ | 3 |

The invention claimed is:

1. A compound comprising a modified oligonucleotide and a conjugate group, wherein the modified oligonucleotide consists of 12 to 30 linked nucleosides, and is at least 95% complementary to an equal length portion of nucleobases of SEQ ID NO: 2 over the entire length, wherein the nucleobase sequence of the modified oligonucleotide comprises at least 8 contiguous nucleobases of SEQ ID NO: 12; and wherein the conjugate group is linked to the modified oligonucleotide by a conjugate linker; wherein the conjugate group comprises:

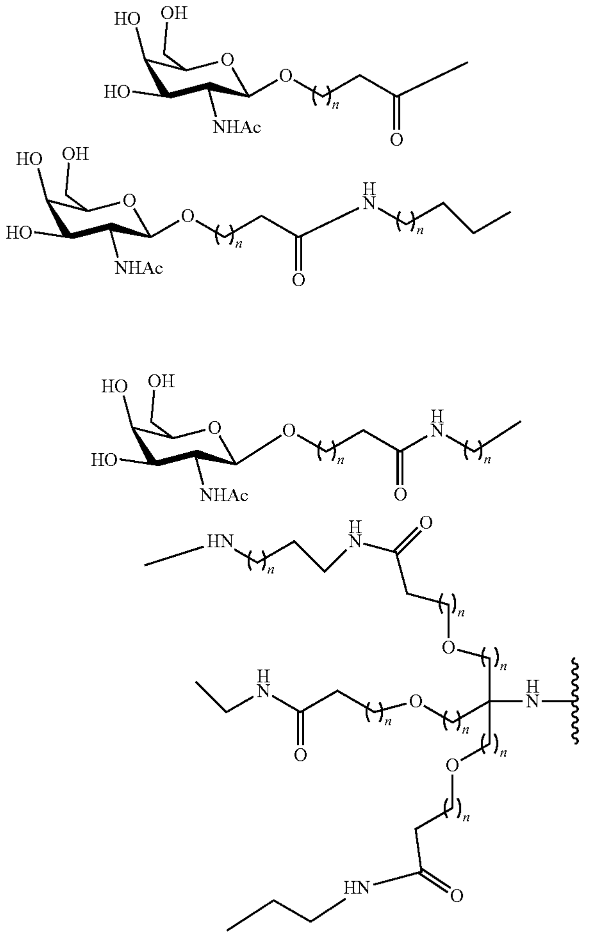

wherein each n is, independently, from 1 to 20; and wherein the conjugate linker comprises:

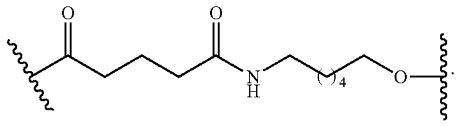 [SMILES: *OCCCNC(=O)CCCC(*)=O]

2. The compound of claim 1, wherein the nucleobase sequence of the modified oligonucleotide is 100% complementary to SEQ ID NO: 2.

3. The compound of claim 1, wherein the modified oligonucleotide comprises at least one modified internucleoside linkage.

4. The compound of claim 3, wherein the modified internucleoside linkage is a phosphorothioate internucleoside linkage.

5. The compound of claim 1, wherein the modified oligonucleotide comprises at least one modified sugar.

6. The compound of claim 5, wherein at least one modified sugar is selected from a bicyclic sugar, a 2'-O-methoxyethyl modified sugar, a constrained ethyl modified sugar, a 3'-fluoro-HNA or a 4'-($CH_2$)n-O-2' bridge, wherein n is 1 or 2.

7. The compound of claim 1, wherein at least one nucleoside comprises a modified nucleobase.

8. The compound of claim 7, wherein the modified nucleobase is a 5-methylcytosine.

9. The compound claim 1, wherein the modified oligonucleotide consists of 20 linked nucleosides having a nucleobase sequence consisting of SEQ ID NO: 12, and wherein the modified oligonucleotide comprises:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment, wherein each nucleoside of each wing segment comprises a 2'-O-methoxyethyl sugar, and wherein each cytosine residue is a 5-methylcytosine.

10. The compound of claim 9, wherein each internucleoside linkage in the gap segment of the modified oligonucleotide is a phosphorothioate linkage.

11. The compound of claim 1, wherein the conjugate group comprises:

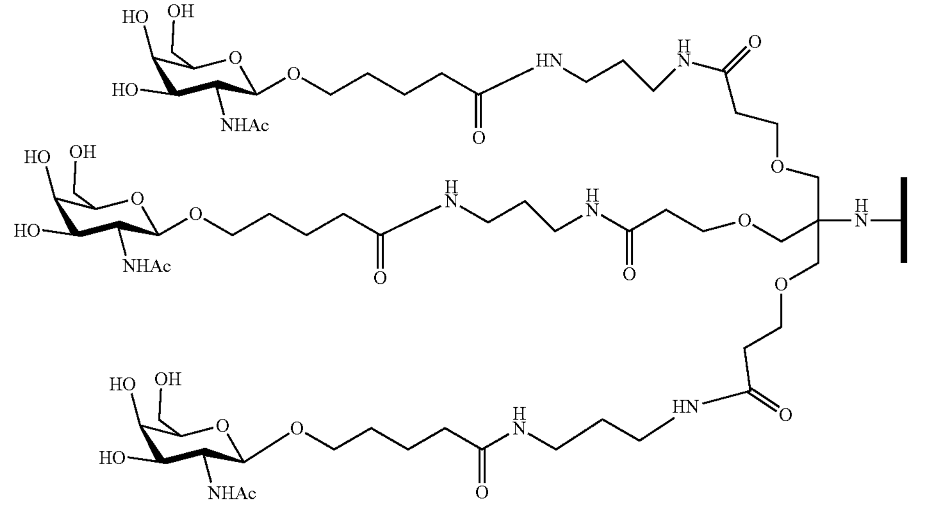

and the conjugate linker has the following structure:

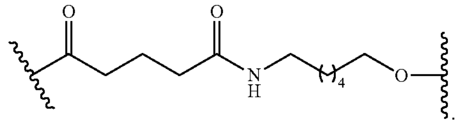

12. The compound of claim 1, wherein the conjugate group comprises a cleavable moiety selected from a phosphodiester, an amide, and an ester.

13. The compound of claim 1, wherein the conjugate group together with the linker comprise:

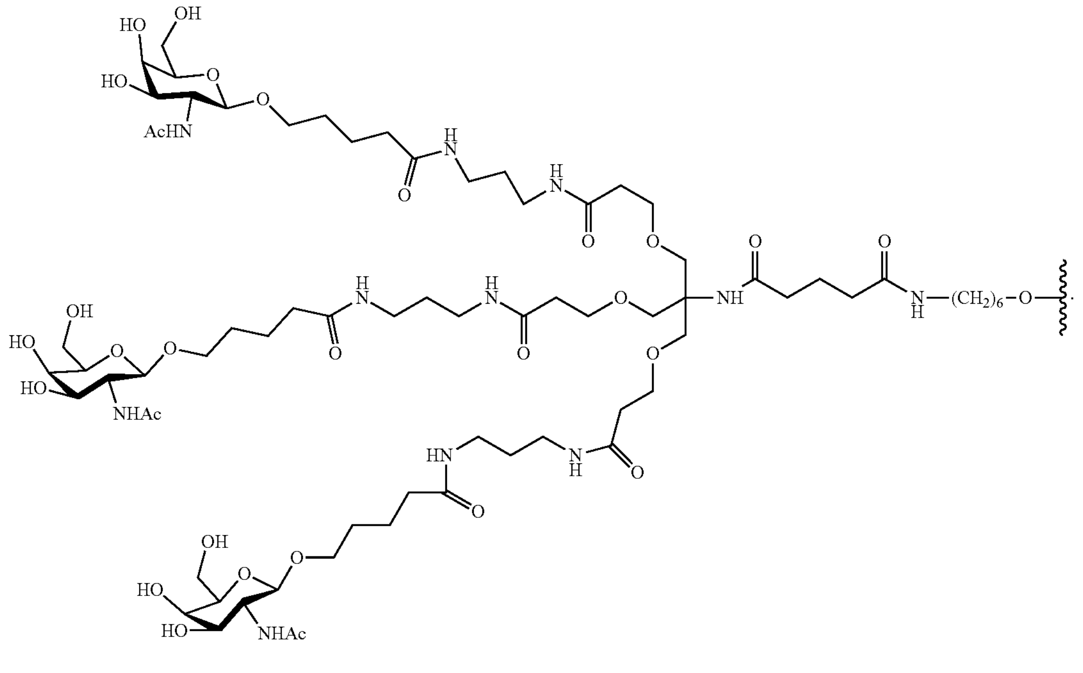

14. A pharmaceutical composition comprising the compound of claim 1 and a pharmaceutically acceptable carrier or diluent.

* * * * *